(12) United States Patent
Lu et al.

(10) Patent No.: US 7,459,308 B2
(45) Date of Patent: Dec. 2, 2008

(54) NUCLEIC ACID MOLECULE ENCODING A CLASP-2 TRANSMEMBRANE PROTEIN

(75) Inventors: Peter S. Lu, Mountain View, CA (US); Jonathan David Garman, San Jose, CA (US); Albert Frederick Candia, III, Menlo Park, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 303 days.

(21) Appl. No.: 10/663,538

(22) Filed: Sep. 15, 2003

(65) Prior Publication Data

US 2006/0153851 A1    Jul. 13, 2006

Related U.S. Application Data

(63) Continuation-in-part of application No. 09/687,837, filed on Oct. 13, 2000, now abandoned, which is a continuation-in-part of application No. 09/547,276, filed on Apr. 11, 2000, now abandoned, application No. 10/663,538, which is a continuation-in-part of application No. 09/978,244, filed on Oct. 15, 2001, now abandoned, and a continuation-in-part of application No. 09/736,969, filed on May 7, 2001, now abandoned, and a continuation-in-part of application No. 09/737,246, filed on Dec. 13, 2000, now abandoned, and a continuation-in-part of application No. 09/736,968, filed on Dec. 13, 2000, now abandoned, and a continuation-in-part of application No. 09/736,960, filed on Dec. 13, 2000, now abandoned.

(60) Provisional application No. 60/310,028, filed on Aug. 3, 2001, provisional application No. 60/240,545, filed on Oct. 13, 2000, provisional application No. 60/196,528, filed on Apr. 11, 2000, provisional application No. 60/196,527, filed on Apr. 11, 2000, provisional application No. 60/196,460, filed on Apr. 11, 2000, provisional application No. 60/196,267, filed on Apr. 11, 2000, provisional application No. 60/182,296, filed on Feb. 14, 2000, provisional application No. 60/176,195, filed on Jan. 14, 2000, provisional application No. 60/170,453, filed on Dec. 13, 1999, provisional application No. 60/162,498, filed on Oct. 29, 1999, provisional application No. 60/160,860, filed on Oct. 21, 1999.

(51) Int. Cl.
C07K 14/435 (2006.01)
C07H 21/04 (2006.01)
C12P 21/02 (2006.01)
C12N 1/16 (2006.01)
C12N 1/20 (2006.01)
C12N 5/06 (2006.01)
C12N 15/09 (2006.01)

(52) U.S. Cl. ............... 435/325; 435/69.1; 435/70.1; 435/252.3; 435/320.1; 536/23.1; 536/23.5; 530/350

(58) Field of Classification Search ............... None
See application file for complete search history.

(56) References Cited

U.S. PATENT DOCUMENTS

| | | | | |
|---|---|---|---|---|
| 5,194,596 A | * | 3/1993 | Tischer et al. | 530/399 |
| 5,350,836 A | * | 9/1994 | Kopchick et al. | 530/399 |
| 5,965,397 A | * | 10/1999 | Jacobs et al. | 435/69.1 |

FOREIGN PATENT DOCUMENTS

WO    WO 00/20434    4/2000

OTHER PUBLICATIONS

Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Campbell et al. Totipotency of multipotentiality of cultured cells: applications and progress Theriogenology 47: 63-72, 1997.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Wigley et al. Site-specific transgene insertion: an approach. Reprod Fertil Dev 6: 585-588, 1994.*
Phillips, A., The challenge of gene therapy and DNA delivery. J Pharm Pharmacology 53: 1169-1174, 2001.*
Benjamin et al. A plasticity window for blood vessel remodelling is defined by pericyte coverage of the preformed endothelial network and is regulated by PDGF-B and VEGF. Development 125: 1591-1598, 1998.*

(Continued)

*Primary Examiner*—Bridget E Bunner
(74) *Attorney, Agent, or Firm*—Townsend and Townsend and Crew, LLP

(57) ABSTRACT

The present invention relates to a cell surface molecules, designated cadherin-like asymmetry proteins ("CLASPs"). In particular, it relates to CLASP-2 polynucleotides, polypeptides, fusion proteins, and antibodies. The invention also relates to methods of modulating an immune response by interfering with CLASP function.

13 Claims, 88 Drawing Sheets

OTHER PUBLICATIONS

Vukicevic et al. Induction of nephrogenic mesenchyme by osteogenic protein 1 (bone morphogenetic protein 7). Proc Natl Acad Sci USA 93: 9021-9026, 1996.*

Massague et al. The TGF-beta family of growth and differentiation factors. Cell 49: 437-438, 1987.*

Pilbeam et al. Comparison of the effects of various lengths of synthetic human parathyroid hormone-related peptide (hPTHrP) of malignancy on resorption and formation in organ culture. Bone 14: 717-720, 1993.*

Skolnick et al. From genes to protein structure and function: novel applications of computational approaches in the genomic era. Trends in Biotech 18(1): 34-39, 2000.*

Bork, A. Powers and pitfalls in sequence analysis: the 70% hurdle. Genome Res 10: 398-400, 2000.*

Doerks et al. Protein annotation: detective work for function prediction. Trends in Genetics 14(6): 248-250, 1998.*

Smith et al. The challenges of genome sequence annotation or "The devil is in the details". Nature Biotech 15: 1222-1223, 1997.*

Bork et al. "Go hunting in sequence databases but watch out for traps," *Trends in Genetics*, 12(10):425-427, 1996.

Bork et al. "Powers and pitfalls in sequence analysis: the 70% hurdle," *Genomic Research*, 10:398-400, 2000.

Brenner et al. "Errors in genome function," *Trends in Genetics*, 15(4): 132-133, 1999.

Chan et al. *Annual Review of Immunology*, 12:555-592, 1994.

Clements et al. *Annual Review of Immunology*, 17:89-108, 1999.

Database EMBL, Accession No. AW959926, Jun. 8, 2000.

Database EMBL, Accession No. AI770179, Dec. 24, 1999.

Database EMBL, Accession No. AW023994, Sep. 14, 1999.

Doyle et al. "Crystal structures of a complexed and peptide-free membrane protein-binding domain: molecular basis of peptide recognition by PDZ," *Cell*, (1996), 85: 1067.

Doerks et al. "Protein annotation: detective work for function prediction," *Trends in Genetics*, 14(6): 248-250, 1998.

Drubin et al., "Origins of Cell Polarity," *Cell*, (1996), vol. 84:335-344.

Dustin et al. *Journal of Immunology*, 157:2014, 1996.

Dustin et al. *Cell*, 94:667, 1998.

Dustin et al. *Science*. 283:649-650, 1999.

Erickson et al. *J. Cell Biol.*, 138:589, 1997.

Geiger et al., "Spatial Relationships of Microtubule-organizing Centers and the Contact Area of Cytotoxic T Lymphocytes and Target Cells," *J. of Cell Biol.*, (1982), vol. 95:137-143.

Genbank Accession No. AB002297, Oct. 6, 2001.

Genbank Accession No. AB028981, Aug. 4, 1999.

Genbank Accession No. AI653716, Dec. 17, 1999.

Genbank Accession No. AF085864, Aug. 24, 1998.

Genbank Accession No. AF188523, Mar. 2, 2000.

Genbank Accession No. AI677957, Dec. 17, 1999.

Genbank Accession No. AI913163, Dec. 16, 1999.

Genbank Accession No. AL133724, Feb. 25, 2000.

Genbank Accession No. AW162535, Nov. 9, 1999.

Genbank Accession No. BE296956, Jul. 20, 2000.

Genbank Accession No. BE301939, Jul. 14, 2000.

Genbank Accession No. BE311583, Oct. 26, 2000.

Genbank Accession No. BE763461, Sep. 19, 2000.

Genbank Accession No. D86964, Oct. 6, 2001.

Genbank Accession No. X68101, Pianese et al., Feb. 24, 1999.

Genbank Accession No. Z28708, Dec. 14, 1993.

Genbank Identification No. 815795, May 18, 1995.

Genbank Identification No. 3876525, Jan. 14, 2003.

Genbank Identification No. 3882152, Jun. 16, 1999.

Genbank Identification No. 5836219, Sep. 30, 2000.

Genbank Identification No. 7243170, Mar. 14, 2000.

Genbank Identification No. 7331559, Mar. 28, 2000.

Genbank Identification No. 7711509, May 6, 2000.

Genbank Identification No. 8158664, Jun. 1, 2001.

Genbank Identification No. 9212047, Jun. 12, 2000.

Genbank Identification No. 9864498, Aug. 19, 2000.

Genbank Identification No. 9884693, Aug. 21, 2000.

Genbank Identification No. 9926440, Aug. 24, 2000.

Genbank Identification No. 9944141, Aug. 28, 2000.

Genbank Identification No. 9988160, Sep. 5, 2000.

Gergely et al., "Immunoreceptor tyrosine-based inhibition motif-bearing receptors regulate the immunoreceptor tyrosine-based activation motif-induced activation of immune competent cells," *Immunol Lett*. (1999), 68: 3-15.

Gregorio et al., "Dynamic Properties of Ankyrin in T Lymphocytes: Colocalization with Spectrin and Protein Kinase Cβ," *J. Cell Biol.*, (1982), vol. 125:345-358.

Gruzca et al., 1999, *Biochemistry* 38: 5024-5033.

Hanada et al., "Human homologue of the Drosophila discs large tumor suppressor binds to p56lck tyrosine kinase and Shaker type Kv1.3 potassium channel in T lymphocytes," *J Biol Chem*, (1997), 272: 26899-26904.

Hung et al. "PDZ domains: structural modules for protein complex assembly," *J. Biol. Chem.*, 277(8): 5699-5702, 2002.

Isakov, "Immunoreceptor tyrosine-based activation motif (ITAM), a unique module linking antigen and Fc receptors to their signaling cascades," *J Leukoc Biol*, (1997), 61: 6-16.

Jackson et al., "The serine protease inhibitor canonical loop conformation: examples found in extracellular hydrolases, toxins, cytokines and viral proteins," *J Mol Biol*, (2000), 296: 325-34.

Kikuno et al., 1999, *DNA Res*. 6: 197-205.

Knudsen et al., "Four Proline-rich Sequences of the Guanine-nucleotide Exchange Factor C3G bind with Unique Specificity to the First Src Homology 3 Domain of Crk," *J. of Biol. Chem.*, (1994), vol. 269(52):32781-32787.

Kozak, M., 1996, *Mamm. Genome* 7(8): 563-74.

Kupfer et al., "Small Splenic B Cells That Bind to Antigen-Specific T Helper (Th) Cells and Face the Site of Cytokine Production in the Th Cells Selectively Proliferate: Immunofluorescence Microscopic Studies of Th-B Antigen-presenting Cell Interactions," *J. Exp. Med.*, (1994), vol. 179:1507-1515.

Lee et al. "Activation Induces a Rapid Reorganization of Spectrin Lymphocytes," *Cell*, (1988), vol. 55:807-816.

Lienard, H., 1999, *J. Biol. Chem* 274: 32493-9.

Lupas et al., "Predicting coiled coils from protein sequences," *Science*, (1991), 252: 1162-64.

Lupas et al., "Prediction and analysis of coiled-coil structures," *Methods Enzymol*. 1996;266:513-25.

Mano, H., "Tec family of protein-tyrosine kinases: an overview of their structure and function," *Cytokine Growth Factor Rev.*, (1999), 10:267-80.

Matsui et al., "Kinetics of T-cell receptor binding to peptide/I-Ek complexes: correlation of the dissociation rate with T-cell responsiveness," Proc Natl Acad Sci, (1994), 91(26): 12862-6.

Miki, H. et al., "Induction of filopodium formation by a WASP-related actin-depolymerizing protein N-WASP," Nature, (1998), 391: 93-6.

Monks et al., 1998, Nature 395: 82-86.

NCI-CGAP http//www.ncbi.nlm.nih.gov/ncicgap; Accession No. AA281512, "National Cancer Institute, Cancer Genome Anatomy Project Tumor Gene Index", Aug. 14, 1997.

NCI-CGAP. Accession No. AA484945, EST database, Aug. 15, 1997.

Negulescu et al. *Immunity*, 4:421-430, 1996.

Ngo et al. "Computational complexity, protein structure prediction, and the Levinthal paradox," *The Protein Folding Problem and Tertiary Structure Prediction*, pp. 492-495, 1994.

Nishihara, H. et al., Analysis of hematopoietic cell specific protein, M-DOCK. Hokkaido Igaku Zasshi, (1999), 74(2): 157-66.

Paul et al., 1994, Cell 76: 241-251.

Pianese et al. (May 29, 1998) Database PIR-62, No. I60486, "A Novel Thyroid transcript Negatively Regulated by TSH."

Rozdzial, MM, Tyrosine-Phosphorylated T Cell Receptor Chain Associates with the Actin Cytoskeleton upon Activation of Mature T Lymphocytes, *Immunity*, (1995), 3: 623-633.

Songyang et al., 1997, Science 275: 73-77.

Skolnick et al. "From genes to protein structure and function: novel applications of computational approaches in the genomic era," *Trends in Biotech*, 18(1): 34-39, 2000.

Smith et al. The challenges of genome sequence annotation or 'the devil is in the details', *Nature Biotech*, 15:1222-1223, 1997.

Takai et al., "Chromosomal mapping of the gene encoding DOCK180, a major Crk-binding protein, to 10q26.13-q26.3 by fluorescence in situ hybridization," Genomics, (1996), 15;35(2):403-403.

Viola et al., 1999, Science 283: 680-82.

Watson et al. *Immunology Today*, 19:260-264, 1998.

Wells, J.A., "Additivity of mutational effects in proteins," *Biochemistry* 29(37): 8509-8517, 1990.

Wu et al., 1998, Nature 392: 501-504.

* cited by examiner

1
A

```
2                                   32
GTT TTA CAC CAT CAC CAA AAC CCA GAA TTT TAT GAT GAG ATT AAA ATA GAG TTG CCC ACT
val leu his his his gln asn pro glu phe tyr asp glu ile lys ile glu leu pro thr 62                                  92
CAG CTG CAT GAA AAG CAC CAC CTG TTG CTC ACA TTC TTC CAT GTC AGC TGT GAC AAC TCA
gln leu his glu lys his his leu leu leu thr phe phe his val ser cys asp asn ser 122                                 152
AGT AAA GGA AGC ACG AAG AAG AGG GAT GTC GTT GAA ACC CAA GTT GGC TAC TCC TGG CTT
ser lys gly ser thr lys lys arg asp val val glu thr gln val gly tyr ser trp leu 182                                 212
CCC CTC CTG AAA GAC GGA AGG GTG GTG ACA AGC GAG CAG CAC ATC CCG GTC TCG GCG AAC
pro leu leu lys asp gly arg val val thr ser glu gln his ile pro val ser ala asn 242                                 272
CTT CCT TCG GGC TAT CTT GGC TAC CAA GAG CTT GGG ATG GGC AGG CAT TAT GGT CCG GAA
leu pro ser gly tyr leu gly tyr gln glu leu gly met gly arg his tyr gly pro glu 302                                 332
ATT AAA TGG GTA GAT GGA GGC AAG CCA CTG CTG AAA ATT TCC ACT CAT CTG GTT TCT ACA
ile lys trp val asp gly gly lys pro leu leu lys ile ser thr his leu val ser thr 362                                 392
GTG TAT ACT CAG GAT CAG CAT TTA CAT AAT TTT TTC CAG TAC TGT CAG AAA ACC GAA TCT
val tyr thr gln asp gln his leu his asn phe phe gln tyr cys gln lys thr glu ser 422                                 452
GGA GCC CAA GCC TTA GGA AAC GAA CTT GTA AAG TAC CTT AAG AGT CTG CAT GCG ATG GAA
gly ala gln ala leu gly asn glu leu val lys tyr leu lys ser leu his ala met glu 482                                 512
GGC CAC GTG ATG ATC GCC TTC TTG CCC ACT ATC CTA AAC CAG CTG TTC CGA GTC CTC ACC
gly his val met ile ala phe leu pro thr ile leu asn gln leu phe arg val leu thr 542                                 572
AGA GCC ACA CAG GAA GAA GTC GCG GTT AAC GTG ACT CGG GTC ATT ATT CAT GTG GTT GCC
arg ala thr gln glu glu val ala val asn val thr arg val ile ile his val val ala 602                                 632
CAG TGC CAT GAG GAA GGA TTG GAG AGC CAC TTG AGG TCA TAT GTT AAG TAC GCG TAT AAG
gln cys his glu glu gly leu glu ser his leu arg ser tyr val lys tyr ala tyr lys 662                                 692
GCT GAG CCA TAT GTT GCC TCT GAA TAC AAG ACA GTG CAT GAA GAA CTG ACC AAA TCC ATG
ala glu pro tyr val ala ser glu tyr lys thr val his glu glu leu thr lys ser met
```

FIG. 1

```
722                                      752
ACC ACG ATT CTC AAG CCT TCT GCC GAT TTC CTC ACC AGC AAC AAA CTA CTG AGG TAC TCA
thr thr ile leu lys pro ser ala asp phe leu thr ser asn lys leu leu arg tyr ser 782                                      812
TGG TTT TTC TTT GAT GTA CTG ATC AAA TCT ATG GCT CAG CAT TTG ATA GAG AAC TCC AAA
trp phe phe phe asp val leu ile lys ser met ala gln his leu ile glu asn ser lys 842              |Cadherin Cleavage|     872
GTT AAG TTG CTG CGA AAC CAG AGA TTT CCT GCA TCC TAT CAT CAT GCA GCG GAA ACC GTT
val lys leu leu arg asn gln arg phe pro ala ser tyr his his ala ala glu thr val 902                                      932
GTA AAT ATG CTG ATG CCA CAC ATC ACT CAG AAG TTT GGA GAT AAT CCA GAG GCA TCT AAG
val asn met leu met pro his ile thr gln lys phe gly asp asn pro glu ala ser lys 962                                      992
AAC GCG AAT CAT AGC CTT GCT GTC TTC ATC AAG AGA TGT TTC ACC TTC ATG GAC AGG GGC
asn ala asn his ser leu ala val phe ile lys arg cys phe thr phe met asp arg gly 1022                                     1052
TTT GTC TTC AAG CAG ATC AAC AAC TAC ATT AGC TGT TTT GCT CCT GGA GAC CCA AAG ACC
phe val phe lys gln ile asn asn tyr ile ser cys phe ala pro gly asp pro lys thr 1082                                     1112
CTC TTT GAA TAC AAG TTT GAA TTT CTC CGT GTA GTG TGC AAC CAT GAA CAT TAT ATT CCG
leu phe glu tyr lys phe glu phe leu arg val val cys asn his glu his tyr ile pro 1142                                     1172
TTG AAC TTA CCA ATG CCA TTT GGA AAA GGC AGG ATT CAA AGA TAC CAA GAC CTC CAG CTT
leu asn leu pro met pro phe gly lys gly arg ile gln arg tyr gln asp leu gln leu 1202                                     1232              |Cadherin EC
GAC TAC TCA TTA ACA GAT GAG TTC TGC AGA AAC CAC TTC TTG GTG GGA CTG TTA CTG AGG
asp tyr ser leu thr asp glu phe cys arg asn his phe leu val gly leu leu leu arg xxx|                                     1292
GAG GTG GGG ACA GCC CTC CAG GAG TTC CGG GAG GTC CGT CTG ATC GCC ATC AGT GTG CTC
glu val gly thr ala leu gln glu phe arg glu val arg leu ile ala ile ser val leu 1322                                     1352
AAG AAC CTG CTG ATA AAG CAT TCT TTT GAT GAC AGA TAT GCT TCA AGG AGC CAT CAG GCA
lys asn leu leu ile lys his ser phe asp asp arg tyr ala ser arg ser his gln ala 1382                                     1412/471
AGG ATA GCC ACC CTC TAC CTG CCT CTG TTT GGT CTG CTG ATT GAA AAC GTC CAG CGG ATC
arg ile ala thr leu tyr leu pro leu phe gly leu leu ile glu asn val gln arg ile 1442                                     1472
AAT GTG AGG GAT GTG TCA CCC TTC CCT GTG AAC GCG GGC ATG ACC GTG AAG GAT GAA TCC
asn val arg asp val ser pro phe pro val asn ala gly met thr val lys asp glu ser
```

FIG. 1 (cont.)

```
1502                                    1532
CTG GCT CTA CCA GCT GTG AAT CCG CTG GTG ACG CCG CAG AAG GGA AGC ACC CTG GAC AAC
leu ala leu pro ala val asn pro leu val thr pro gln lys gly ser thr leu asp asn 1562                                    1592
AGC CTG CAC AAG GAC CTG CTG GGC GCC ATC TCC GGC ATT GCT TCT CCA TAT ACA ACC TCA
ser leu his lys asp leu leu gly ala ile ser gly ile ala ser pro tyr thr thr ser 1622                                    1652
ACT CCA AAC ATC AAC AGT GTG AGA AAT GCT GAT TCG AGA GGA TCT CTC ATA AGC ACA GAT
thr pro asn ile asn ser val arg asn ala asp ser arg gly ser leu ile ser thr asp 1682                                    1712
TCG GGT AAC AGC CTT CCA GAA AGG AAT AGT GAG AAG AGC AAT TCC CTG GAT AAG CAC CAA
ser gly asn ser leu pro glu arg asn ser glu lys ser asn ser leu asp lys his gln 1742                                    1772
CAA AGT AGC ACA TTG GGA AAT TCC GTG GTT CGC TGT GAT AAA CTT GAC CAG TCT GAG ATT
gln ser ser thr leu gly asn ser val val arg cys asp lys leu asp gln ser glu ile 1802                                    1832
AAG AGC CTA CTG ATG TGT TTC CTC TAC ATC TTA AAG AGC ATG TCT GAT GAT GCT TTG TTT
lys ser leu leu met cys phe leu tyr ile leu lys ser met ser asp asp ala leu phe 1862                                    1892
ACA TAT TGG AAC AAG GCT TCA ACA TCT GAA CTT ATG GAT TTT TTT ACA ATA TCT GAA GTC
thr tyr trp asn lys ala ser thr ser glu leu met asp phe phe thr ile ser glu val 1922                                    1952
TGC CTG CAC CAG TTC CAG TAC ATG GGG AAG CGA TAC ATA GCC AGG AAC CAG GAG GGG TTG
cys leu his gln phe gln tyr met gly lys arg tyr ile ala arg asn gln glu gly leu 1982                                    2012
GGA CCC ATA GTT CAT GAT CGA AAG TCT CAG ACA TTG CCT GTT TCC CGT AAC AGA ACA GGA
gly pro ile val his asp arg lys ser gln thr leu pro val ser arg asn arg thr gly 2042                                    2072
ATG ATG CAT GCC AGA TTG CAG CAG CTG GGC AGC CTG GAT AAC TCT CTC ACT TTT AAC CAC
met met his ala arg leu gln gln leu gly ser leu asp asn ser leu thr phe asn his 2102                                    2132
AGC TAT GGC CAC TCG GAC GCA GAT GTT CTG CAC CAG TCA TTA CTT GAA GCC AAC ATT GCT
ser tyr gly his ser asp ala asp val leu his gln ser leu leu glu ala asn ile ala 2162                                    2192
ACT GAG GTT TGC CTG ACA GCT CTG GAC ACG CTT TCT CTA TTT ACA TTG GCG TTT AAG AAC
thr glu val cys leu thr ala leu asp thr leu ser leu phe thr leu ala phe lys asn 2222                                    2252
CAG CTC CTG GCC GAC CAT GGA CAT AAT CCT CTC ATG AAA AAA GTT TTT GAT GTC TAC CTG
gln leu leu ala asp his gly his asn pro leu met lys lys val phe asp val tyr leu
```

FIG. 1 (cont.)

```
2282                                    2312
TGT TTT CTT CAA AAA CAT CAG TCT GAA ACG GCT TTA AAA AAT GTC TTC ACT GCC TTA AGG
cys phe leu gln lys his gln ser glu thr ala leu lys asn val phe thr ala leu arg 2342                                    2372
TCC TTA ATT TAT AAG TTT CCC TCA ACA TTC TAT GAA GGG AGA GCG GAC ATG TGT GCG GCT
ser leu ile tyr lys phe pro ser thr phe tyr glu gly arg ala asp met cys ala ala 2402                                    2432
CTG TGT TAC GAG ATT CTC AAG TGC TGT AAC TCC AAG CTG AGC TCC ATC AGG ACG GAG GCC
leu cys tyr glu ile leu lys cys cys asn ser lys leu ser ser ile arg thr glu ala 2462                                    2492
TCC CAG CTG CTC TAC TTC CTG ATG AGG AAC AAC TTT GAT TAC ACT GGA AAG AAG TCC TTT
ser gln leu leu tyr phe leu met arg asn asn phe asp tyr thr gly lys lys ser phe 2522                                    2552
GTC CGG ACA CAT TTG CAA GTC ATC ATA TCT GTC AGC CAG CTG ATA GCA GAC GTT GTT GGC
val arg thr his leu gln val ile ile ser val ser gln leu ile ala asp val val gly 2582                                    2612
ATT GGG GAA ACC AGA TTC CAG CAG TCC CTG TCC ATC ATC AAC AAC TGT GCC AAC AGT GAC
ile gly glu thr arg phe gln gln ser leu ser ile ile asn asn cys ala asn ser asp 2642                                    2672
CGG CTT ATT AAG CAC ACC AGC TTC TCC TCT GAT GTG AAG GAC TTA ACC AAA AGG ATA CGC
arg leu ile lys his thr ser phe ser ser asp val lys asp leu thr lys arg ile arg 2702                                    2732
ACG GTG CTA ATG GCC ACC GCC CAG ATG AAG GAG CAT GAG AAC GAC CCA GAG ATG CTG GTG
thr val leu met ala thr ala gln met lys glu his glu asn asp pro glu met leu val 2762                                    2792
GAC CTC CAG TAC AGC CTG GCC AAA TCC TAT GCC AGC ACG CCC GAG CTC AGG AAG ACG TGG
asp leu gln tyr ser leu ala lys ser tyr ala ser thr pro glu leu arg lys thr trp 2822                                    2852        |xxxxxxxxxxxxxxxx Predicted
CTC GAC AGC ATG GCC AGG ATC CAT GTC AAA AAT GGC GAT CTC TCA GAG GCA GCA ATG TGC
leu asp ser met ala arg ile his val lys asn gly asp leu ser glu ala ala met cys Transmembrane Domain xxxxxxxxxxxxxxxxxxxxxxxxxxxxxxx|
TAT GTC CAC GTA ACA GCC CTA GTG GCA GAA TAT CTC ACA CGG AAA GGC GTG TTT AGA CAA
tyr val his val thr ala leu val ala glu tyr leu thr arg lys gly val phe arg gln 2942                                    2972
GGA TGC ACC GCC TTC AGG GTC ATT ACC CCA AAC ATC GAC GAG GAG GCC TCC ATG ATG GAA
gly cys thr ala phe arg val ile thr pro asn ile asp glu glu ala ser met met glu 3002                                    3032
GAC GTG GGG ATG CAG GAT GTC CAT TTC AAC GAG GAT GTG CTG ATG GAG CTC CTT GAG CAG
asp val gly met gln asp val his phe asn glu asp val leu met glu leu leu glu gln 3062                                    3092
TGC GCA GAT GGA CTC TGG AAA GCC GAG CGC TAC GAG CTC ATC GCC GAC ATC TAC AAA CTT
cys ala asp gly leu trp lys ala glu arg tyr glu leu ile ala asp ile tyr lys leu
```

FIG. 1 (cont.)

```
3122                                    3155
ATC ATC CCC ATT TAT GAG AAG CGG AGG GAT TTC TTT GAA GAT GAA GAT GGA AAG GAG TAT
ile ile pro ile tyr glu lys arg arg asp phe phe glu asp glu asp gly lys glu tyr 3182                                3212
ATT TAC AAG GAA CCC AAA CTC ACA CCG CTG TCG GAA ATT TCT CAG AGA CTC CTT AAA CTG
ile tyr lys glu pro lys leu thr pro leu ser glu ile ser gln arg leu leu lys leu 3242                                    3272
TAC TCG GAT AAA TTT GGT TCT GAA AAT GTC AAA ATG ATA CAG GAT TCT GGC AAG GTC AAC
tyr ser asp lys phe gly ser glu asn val lys met ile gln asp ser gly lys val asn 3302                                        3332
CCT AAG GAT CTG GAT TCT AAG TAT GCA TAC ATC CAG GTG ACT CAC GTC ATC CCC TTC TTT
pro lys asp leu asp ser lys tyr ala tyr ile gln val thr his val ile pro phe phe 3362                                    3392
GAC GAA AAA GAG TTG CAA GAA AGG AAA ACA GAG TTT GAG AGA TCC CAC AAC ATC CGC CGC
asp glu lys glu leu gln glu arg lys thr glu phe glu arg ser his asn ile arg arg 3422                                    3452
TTC ATG TTT GAG ATG CCA TTT ACG CAG ACC GGG AAG AGG CAG GGC GGG GTG GAA GAG CAG
phe met phe glu met pro phe thr gln thr gly lys arg gln gly gly val glu glu gln 3482                                3512
TGC AAA CGG CGC ACC ATC CTG ACA GCC ATA CAC TGC TTC CCT TAT GTG AAG AAG CGC ATC
cys lys arg arg thr ile leu thr ala ile his cys phe pro tyr val lys lys arg ile 3542                            3572    |xxxxxxxxxxxxxxxxxxxxxxxxxxxxxxx
CCT GTC ATG TAC CAG CAC CAC ACT GAC CTG AAC CCC ATC GAG GTG GCC ATT GAC GAG ATG
pro val met tyr gln his his thr asp leu asn pro ile glu val ala ile asp glu met 3602 xxx  Coiled-Coil 1  xxxxxxxxxxxx 3632 xxxx  Coiled-Coil 1  xxxxxxxxxxxxxx
AGT AAG AAG GTG GCG GAG CTC CGG CAG CTG TGC TCC TCG GCC GAG GTG GAC ATG ATC AAA
ser lys lys val ala glu leu arg gln leu cys ser ser ala glu val asp met ile lys 3662 xxxxxxxxxxxxxxxxxxxxxxxxxxx|       3692
CTG CAG CTC AAA CTC CAG GGC AGC GTG AGT GTT CAG GTC AAT GCT GGC CCA CTA GCA TAT
leu gln leu lys leu gln gly ser val ser val gln val asn ala gly pro leu ala tyr 3722                                3752
GCG CGA GCT TTC TTA GAT GAT ACA AAC ACA AAG CGA TAT CCT GAC AAT AAA GTG AAG CTG
ala arg ala phe leu asp asp thr asn thr lys arg tyr pro asp asn lys val lys leu 3782                                3812    |xxxxxxxxxxxxxxxxxxxxxxx
CTT AAG GAA GTT TTC AGG CAA TTT GTG GAA GCT TGC GGT CAA GCC TTA GCG GTA AAC GAA
leu lys glu val phe arg gln phe val glu ala cys gly gln ala leu ala val asn glu
```

FIG. 1 (cont.)

```
3842 xxx Coiled-Coil 2 xxxxxxxxxxxx 3872 xxxxxxxxxxxxxxxxxxxxxxxxxxxxxx
CGT CTG ATT AAA GAA GAC CAG CTC GAG TAT CAG GAA GAA ATG AAA GCC AAC TAC AGG GAA
arg leu ile lys glu asp gln leu glu tyr gln glu glu met lys ala asn tyr arg glu 3902 xxx Coiled-Coil 2 xxxxxxxxxxxx 3932 xxxxx|
ATG GCG AAG GAG CTT TCT GAA ATC ATG CAT GAG CAG ATC TGC CCC CTG GAG GAG AAG ACG
met ala lys glu leu ser glu ile met his glu gln ile cys pro leu glu glu lys thr 3962                                          3992
AGC GTC TTA CCG AAT TCC CTT CAC ATC TTC AAC GCC ATC AGT GGG ACT CCA ACA AGC ACA
ser val leu pro asn ser leu his ile phe asn ala ile ser gly thr pro thr ser thr 4022                       |xxxx PBM xxxx|
ATG GTT CAC GGG ATG ACC AGC TCG TCT TCG GTC GTG TGA TTA CAT CTC ATG CCC GTG GTG
met val his gly met thr ser ser ser ser val val STP 4082                                         4112
TGG GGA CTT GCT TTG TCA TTT GCA AAC TCA GGA TGC TTT CCA AAG CCA ATC ACT GGG GAG 4142                                         4172
ACC GAG CAC AGG GAG GAC CAA GGG GAA GGG GAG AGA AAG GAA ATA AAG AAC AAC GTT ATT 4202                                         4232
TCT TAA CAG ACT TTC TAT AGG AGT TGT AAG AAG GTG CAC ATA TTT TTT TAA ATC TCA CTG 4262                                         4292
GCA ATA TTC AAA GTT TTC ATT GTG TCT TAA CAA AGG TGT GGT AGA CAC TCT TGA GCT GGA 4322                                         4352
CTT AGA TTT TAT TCT TCC TTG CAG AGT AGT GTT AGA ATA GAT GGC CTA CAG AAA AAA AAG 4382                                         4412
GTT CTG GGA TCT ACA TGG CAG GGA GGG CTG CAC TGA CAT TGA TGC CTG GGG GAC CTT TTG 4442                                         4472
CCT CGA CTC GTG CCG GAA ATC TGA TCG TAA TCA GGG TAC AGA ACT TAC TAG TTT TGT CTA 4502                                         4532
GGA GTA TGT TGT ATG ACT AGG ATT TGT GCT ATT ATC TCA TTC AAC AAC ATA GAG CAA GAA 4562                                         4592
TAG TGA GCT AAC TGA GCT AGA CAC TCA ATT AAT CCG CTA CTG GCT TCA AGT CAG AAC TTT 4622                                         4652
GTC ATT AAT CAT CGA CTC CGG GAC GGT CAT ATA TGT ATT ACA TTT CTA CAT TTT TAA TAC 4682                                         4712
TCA CAT GGG CTT ATG CAT TAA GTT TAA TTG TGA TAA ATT TGT GCT GGT CCA GTA TAT GCA 4742                                         4772
ATA CAC TTT AAT GGT TTA TTC TTG TCA TAA AAA TGT GCA ATA TGG AGA TGT ATA CAA GTC

4802
TTT ACT
```

FIG. 1 (cont.)

```
                                                                            1
                                                                            A
2                                              32
GTT TTA CAC CAT CAC CAA AAC CCA GAA TTT TAT GAT GAG ATT AAA ATA GAG TTG CCC ACT
val leu his his his gln asn pro glu phe tyr asp glu ile lys ile glu leu pro thr 62                                             92
CAG CTG CAT GAA AAG CAC CAC CTG TTG CTC ACA TTC TTC CAT GTC AGC TGT GAC AAC TCA
gln leu his glu lys his his leu leu leu thr phe phe his val ser cys asp asn ser 122                                            152
AGT AAA GGA AGC ACG AAG AAG AGG GAT GTC GTT GAA ACC CAA GTT GGC TAC TCC TGG CTT
ser lys gly ser thr lys lys arg asp val val glu thr gln val gly tyr ser trp leu 182                                            212
CCC CTC CTG AAA GAC GGA AGG GTG GTG ACA AGC GAG CAG CAC ATC CCG GTC TCG GCG AAC
pro leu leu lys asp gly arg val val thr ser glu gln his ile pro val ser ala asn 242                                            272
CTT CCT TCG GGC TAT CTT GGC TAC CAA GAG CTT GGG ATG GGC AGG CAT TAT GGT CCG GAA
leu pro ser gly tyr leu gly tyr gln glu leu gly met gly arg his tyr gly pro glu 302                                            332
ATT AAA TGG GTA GAT GGA GGC AAG CCA CTG CTG AAA ATT TCC ACT CAT CTG GTT TCT ACA
ile lys trp val asp gly gly lys pro leu leu lys ile ser thr his leu val ser thr 362                                            392
GTG TAT ACT CAG GAT CAG CAT TTA CAT AAT TTT TTC CAG TAC TGT CAG AAA ACC GAA TCT
val tyr thr gln asp gln his leu his asn phe phe gln tyr cys gln lys thr glu ser 422                                            452
GGA GCC CAA GCC TTA GGA AAC GAA CTT GTA AAG TAC CTT AAG AGT CTG CAT GCG ATG GAA
gly ala gln ala leu gly asn glu leu val lys tyr leu lys ser leu his ala met glu 482                                            512
GGC CAC GTG ATG ATC GCC TTC TTG CCC ACT ATC CTA AAC CAG CTG TTC CGA GTC CTC ACC
gly his val met ile ala phe leu pro thr ile leu asn gln leu phe arg val leu thr 542                                            572
AGA GCC ACA CAG GAA GAA GTC GCG GTT AAC GTG ACT CGG GTC ATT ATT CAT GTG GTT GCC
arg ala thr gln glu glu val ala val asn val thr arg val ile ile his val val ala 602                                            632
CAG TGC CAT GAG GAA GGA TTG GAG AGC CAC TTG AGG TCA TAT GTT AAG TAC GCG TAT AAG
gln cys his glu glu gly leu glu ser his leu arg ser tyr val lys tyr ala tyr lys 662                                            692
GCT GAG CCA TAT GTT GCC TCT GAA TAC AAG ACA GTG CAT GAA GAA CTG ACC AAA TCC ATG
ala glu pro tyr val ala ser glu tyr lys thr val his glu glu leu thr lys ser met
```

FIG. 2B

```
722                                               752
ACC ACG ATT CTC AAG CCT TCT GCC GAT TTC CTC ACC AGC AAC AAA CTA CTG AGG TAC TCA
thr thr ile leu lys pro ser ala asp phe leu thr ser asn lys leu leu arg tyr ser 782                                               812
TGG TTT TTC TTT GAT GTA CTG ATC AAA TCT ATG GCT CAG CAT TTG ATA GAG AAC TCC AAA
trp phe phe phe asp val leu ile lys ser met ala gln his leu ile glu asn ser lys 842              |Cadherin Cleavage|    872
GTT AAG TTG CTG CGA AAC CAG AGA TTT CCT GCA TCC TAT CAT CAT GCA GCG GAA ACC GTT
val lys leu leu arg asn gln arg phe pro ala ser tyr his his ala ala glu thr val 902                                               932
GTA AAT ATG CTG ATG CCA CAC ATC ACT CAG AAG TTT GGA GAT AAT CCA GAG GCA TCT AAG
val asn met leu met pro his ile thr gln lys phe gly asp asn pro glu ala ser lys 962                                               992
AAC GCG AAT CAT AGC CTT GCT GTC TTC ATC AAG AGA TGT TTC ACC TTC ATG GAC AGG GGC
asn ala asn his ser leu ala val phe ile lys arg cys phe thr phe met asp arg gly 1022                                              1052
TTT GTC TTC AAG CAG ATC AAC AAC TAC ATT AGC TGT TTT GCT CCT GGA GAC CCA AAG ACC
phe val phe lys gln ile asn asn tyr ile ser cys phe ala pro gly asp pro lys thr 1082                                              1112
CTC TTT GAA TAC AAG TTT GAA TTT CTC CGT GTA GTG TGC AAC CAT GAA CAT TAT ATT CCG
leu phe glu tyr lys phe glu phe leu arg val val cys asn his glu his tyr ile pro 1142                                              1172
TTG AAC TTA CCA ATG CCA TTT GGA AAA GGC AGG ATT CAA AGA TAC CAA GAC CTC CAG CTT
leu asn leu pro met pro phe gly lys gly arg ile gln arg tyr gln asp leu gln leu 1202                                   1232                    |Cadherin EC
GAC TAC TCA TTA ACA GAT GAG TTC TGC AGA AAC CAC TTC TTG GTG GGA CTG TTA CTG AGG
asp tyr ser leu thr asp glu phe cys arg asn his phe leu val gly leu leu leu arg xxx|                                   1292
GAG GTG GGG ACA GCC CTC CAG GAG TTC CGG GAG GTC CGT CTG ATC GCC ATC AGT GTG CTC
glu val gly thr ala leu gln glu phe arg glu val arg leu ile ala ile ser val leu 1322                                              1352
AAG AAC CTG CTG ATA AAG CAT TCT TTT GAT GAC AGA TAT GCT TCA AGG AGC CAT CAG GCA
lys asn leu leu ile lys his ser phe asp asp arg tyr ala ser arg ser his gln ala 1382                                              1412
AGG ATA GCC ACC CTC TAC CTG CCT CTG TTT GGT CTG CTG ATT GAA AAC GTC CAG CGG ATC
arg ile ala thr leu tyr leu pro leu phe gly leu leu ile glu asn val gln arg ile 1442                                              1472
AAT GTG AGG GAT GTG TCA CCC TTC CCT GTG AAC GCG GGC ATG ACC GTG AAG GAT GAA TCC
asn val arg asp val ser pro phe pro val asn ala gly met thr val lys asp glu ser
```

FIG. 2B (cont.)

```
1502                                      1532
CTG GCT CTA CCA GCT GTG AAT CCG CTG GTG ACG CCG CAG AAG GGA AGC ACC CTG GAC AAC
leu ala leu pro ala val asn pro leu val thr pro gln lys gly ser thr leu asp asn 1562                                      1592
AGC CTG CAC AAG GAC CTG CTG GGC GCC ATC TCC GGC ATT GCT TCT CCA TAT ACA ACC TCA
ser leu his lys asp leu leu gly ala ile ser gly ile ala ser pro tyr thr thr ser 1622                                      1652
ACT CCA AAC ATC AAC AGT GTG AGA AAT GCT GAT TCG AGA GGA TCT CTC ATA AGC ACA GAT
thr pro asn ile asn ser val arg asn ala asp ser arg gly ser leu ile ser thr asp 1682                                      1712
TCG GGT AAC AGC CTT CCA GAA AGG AAT AGT GAG AAG AGC AAT TCC CTG GAT AAG CAC CAA
ser gly asn ser leu pro glu arg asn ser glu lys ser asn ser leu asp lys his gln 1742                                      1772
CAA AGT AGC ACA TTG GGA AAT TCC GTG GTT CGC TGT GAT AAA CTT GAC CAG TCT GAG ATT
gln ser ser thr leu gly asn ser val val arg cys asp lys leu asp gln ser glu ile 1802                                      1832
AAG AGC CTA CTG ATG TGT TTC CTC TAC ATC TTA AAG AGC ATG TCT GAT GAT GCT TTG TTT
lys ser leu leu met cys phe leu tyr ile leu lys ser met ser asp asp ala leu phe 1862                                      1892
ACA TAT TGG AAC AAG GCT TCA ACA TCT GAA CTT ATG GAT TTT TTT ACA ATA TCT GAA GTC
thr tyr trp asn lys ala ser thr ser glu leu met asp phe phe thr ile ser glu val 1922                                      1952          |xxxxxxxxxxxxxxxxxxxxxx
TGC CTG CAC CAG TTC CAG TAC ATG GGG AAG CGA TAC ATA GCC AGG AAC CAG GAG GGG TTG
cys leu his gln phe gln tyr met gly lys arg tyr ile ala arg asn gln glu gly leu 1982 xxxxxxxxxx  deleted in CLASP-2D(KIAA1058) xxxxxxxxxxxxxxxxxxxxxxxx|
GGA CCC ATA GTT CAT GAT CGA AAG TCT CAG ACA TTG CCT GTT TCC CGT AAC AGA ACA GGA
gly pro ile val his asp arg lys ser gln thr leu pro val ser arg asn arg thr gly 2042                                      2072
ATG ATG CAT GCC AGA TTG CAG CAG CTG GGC AGC CTG GAT AAC TCT CTC ACT TTT AAC CAC
met met his ala arg leu gln gln leu gly ser leu asp asn ser leu thr phe asn his 2102                                      2132
AGC TAT GGC CAC TCG GAC GCA GAT GTT CTG CAC CAG TCA TTA CTT GAA GCC AAC ATT GCT
ser tyr gly his ser asp ala asp val leu his gln ser leu leu glu ala asn ile ala Deleted
2162                                      2192                          |xxx
ACT GAG GTT TGC CTG ACA GCT CTG GAC ACG CTT TCT CTA TTT ACA TTG GCG TTT AAG AAC
thr glu val cys leu thr ala leu asp thr leu ser leu phe thr leu ala phe lys asn in HC2B
xxx|                                      2252
CAG CTC CTG GCC GAC CAT GGA CAT AAT CCT CTC ATG AAA AAA GTT TTT GAT GTC TAC CTG
gln leu leu ala asp his gly his asn pro leu met lys lys val phe asp val tyr leu
```

FIG. 2B (cont.)

```
2282                                    2312
TGT TTT CTT CAA AAA CAT CAG TCT GAA ACG GCT TTA AAA AAT GTC TTC ACT GCC TTA AGG
cys phe leu gln lys his gln ser glu thr ala leu lys asn val phe thr ala leu arg 2342                                    2372
TCC TTA ATT TAT AAG TTT CCC TCA ACA TTC TAT GAA GGG AGA GCG GAC ATG TGT GCG GCT
ser leu ile tyr lys phe pro ser thr phe tyr glu gly arg ala asp met cys ala ala 2402                                    2432
CTG TGT TAC GAG ATT CTC AAG TGC TGT AAC TCC AAG CTG AGC TCC ATC AGG ACG GAG GCC
leu cys tyr glu ile leu lys cys cys asn ser lys leu ser ser ile arg thr glu ala 2462                                    2492
TCC CAG CTG CTC TAC TTC CTG ATG AGG AAC AAC TTT GAT TAC ACT GGA AAG AAG TCC TTT
ser gln leu leu tyr phe leu met arg asn asn phe asp tyr thr gly lys lys ser phe 2522                                    2552
GTC CGG ACA CAT TTG CAA GTC ATC ATA TCT GTC AGC CAG CTG ATA GCA GAC GTT GTT GGC
val arg thr his leu gln val ile ile ser val ser gln leu ile ala asp val val gly 2582                                    2612
ATT GGG GAA ACC AGA TTC CAG CAG TCC CTG TCC ATC ATC AAC AAC TGT GCC AAC AGT GAC
ile gly glu thr arg phe gln gln ser leu ser ile ile asn asn cys ala asn ser asp 2642                                    2672
CGG CTT ATT AAG CAC ACC AGC TTC TCC TCT GAT GTG AAG GAC TTA ACC AAA AGG ATA CGC
arg leu ile lys his thr ser phe ser ser asp val lys asp leu thr lys arg ile arg 2702                                    2732
ACG GTG CTA ATG GCC ACC GCC CAG ATG AAG GAG CAT GAG AAC GAC CCA GAG ATG CTG GTG
thr val leu met ala thr ala gln met lys glu his glu asn asp pro glu met leu val 2762                                    2792
GAC CTC CAG TAC AGC CTG GCC AAA TCC TAT GCC AGC ACG CCC GAG CTC AGG AAG ACG TGG
asp leu gln tyr ser leu ala lys ser tyr ala ser thr pro glu leu arg lys thr trp 2822                                    2852        |xxxxxxxxxxxxxxxx Predicted
CTC GAC AGC ATG GCC AGG ATC CAT GTC AAA AAT GGC GAT CTC TCA GAG GCA GCA ATG TGC
leu asp ser met ala arg ile his val lys asn gly asp leu ser glu ala ala met cys

[Additional and differential exon usage found at position 2927 consisting
        of 69 nucleotides. This entire sequence is found in Human CLASP-2D
        (KIAA1058) and not other isoforms of CLASP-2. It has a sequence of:
        AAGCAGTCCAGTGGGAGCCGCCCCTTCTCCCCCACAGCCATAGCGCCTGCCTGAGGAGGAGCCGGGGAG]

Transmembrane Domain xxxxxxxxxxxxxxxxxxxxxxxxxxxxx|
TAT GTC CAC GTA ACA GCC CTA GTG GCA GAA TAT CTC ACA CGG AAA GGC GTG TTT AGA CAA
tyr val his val thr ala leu val ala glu tyr leu thr arg lys gly val phe arg gln 2942                                    2972
GGA TGC ACC GCC TTC AGG GTC ATT ACC CCA AAC ATC GAC GAG GAG GCC TCC ATG ATG GAA
gly cys thr ala phe arg val ile thr pro asn ile asp glu glu ala ser met met glu
```

FIG. 2B (cont.)

3002       |xxxxxxxxxxxxxxxxxxxxxxxxxxxxxxxxx Sequence deleted in CLASP-2E xxxxx
GAC GTG GGG ATG CAG GAT GTC CAT TTC AAC GAG GAT GTG CTG ATG GAG CTC CTT GAG CAG
asp val gly met gln asp val his phe asn glu asp val leu met glu leu leu glu gln 3062 xxxxxxxxxxxxxxxxxxxx|            3092
TGC GCA GAT GGA CTC TGG AAA GCC GAG CGC TAC GAG CTC ATC GCC GAC ATC TAC AAA CTT
cys ala asp gly leu trp lys ala glu arg tyr glu leu ile ala asp ile tyr lys leu

[Additional and differential exon usage found at position 3153. The
    entire sequence below is found in Human CLASP-2D. Underlined sequence is
    found in Human CLASP-2B, 2C and 2E.
    TGAGAGGCTGGCCCATCTGTATGACACGCTGCACCGGGCCTACAGCAAAGTGACCGAGGTCAT
    GCACTCGGGCCGCAGGCTTCTGGGGACCTACTTCCGGGTAGCCTTCTTCGGGCAGGCAGCGCAATACCAGTTT
    ACAGACAGTGAAACAGATGTGGAGGG<u>GATT</u>]

3122                                   ↓ 3155
ATC ATC CCC ATT TAT GAG AAG CGG AGG GAT TTC TTT GAA GAT GAA GAT GGA AAG GAG TAT
ile ile pro ile tyr glu lys arg arg asp phe phe glu asp glu asp gly lys glu tyr 3182                                3212
ATT TAC AAG GAA CCC AAA CTC ACA CCG CTG TCG GAA ATT TCT CAG AGA CTC CTT AAA CTG
ile tyr lys glu pro lys leu thr pro leu ser glu ile ser gln arg leu leu lys leu 3242                                3272
TAC TCG GAT AAA TTT GGT TCT GAA AAT GTC AAA ATG ATA CAG GAT TCT GGC AAG GTC AAC
tyr ser asp lys phe gly ser glu asn val lys met ile gln asp ser gly lys val asn 3302                                3332
CCT AAG GAT CTG GAT TCT AAG TAT GCA TAC ATC CAG GTG ACT CAC GTC ATC CCC TTC TTT
pro lys asp leu asp ser lys tyr ala tyr ile gln val thr his val ile pro phe phe 3362                                3392
GAC GAA AAA GAG TTG CAA GAA AGG AAA ACA GAG TTT GAG AGA TCC CAC AAC ATC CGC CGC
asp glu lys glu leu gln glu arg lys thr glu phe glu arg ser his asn ile arg arg 3422                                3452
TTC ATG TTT GAG ATG CCA TTT ACG CAG ACC GGG AAG AGG CAG GGC GGG GTG GAA GAG CAG
phe met phe glu met pro phe thr gln thr gly lys arg gln gly gly val glu glu gln 3482                                3512
TGC AAA CGG CGC ACC ATC CTG ACA GCC ATA CAC TGC TTC CCT TAT GTG AAG AAG CGC ATC
cys lys arg arg thr ile leu thr ala ile his cys phe pro tyr val lys lys arg ile Two nucleotide deletion (nts 3586 and 3587) found in Human CLASP-2C
                                                    ↓
3542                                3572           |xxx|
CCT GTC ATG TAC CAG CAC CAC ACT GAC CTG AAC CCC ATC GAG GTG GCC ATT GAC GAG ATG
pro val met tyr gln his his thr asp leu asn pro ile glu val ala ile asp glu met

FIG. 2B (cont.)

```
3602                                    3632
AGT AAG AAG GTG GCG GAG CTC CGG CAG CTG TGC TCC TCG GCC GAG GTG GAC ATG ATC AAA
ser lys lys val ala glu leu arg gln leu cys ser ser ala glu val asp met ile lys 3662                                    3692
CTG CAG CTC AAA CTC CAG GGC AGC GTG AGT GTT CAG GTC AAT GCT GGC CCA CTA GCA TAT
leu gln leu lys leu gln gly ser val ser val gln val asn ala gly pro leu ala tyr 3722                                    3752
GCG CGA GCT TTC TTA GAT GAT ACA AAC ACA AAG CGA TAT CCT GAC AAT AAA GTG AAG CTG
ala arg ala phe leu asp asp thr asn thr lys arg tyr pro asp asn lys val lys leu 3782                                    3812
CTT AAG GAA GTT TTC AGG CAA TTT GTG GAA GCT TGC GGT CAA GCC TTA GCG GTA AAC GAA
leu lys glu val phe arg gln phe val glu ala cys gly gln ala leu ala val asn glu 3842                                    3872
CGT CTG ATT AAA GAA GAC CAG CTC GAG TAT CAG GAA GAA ATG AAA GCC AAC TAC AGG GAA
arg leu ile lys glu asp gln leu glu tyr gln glu glu met lys ala asn tyr arg glu Insertion of 8 nucleotides found only in Human CLASP-2D with sequence: CTGGGATG 3902                                    3932         ⇓
ATG GCG AAG GAG CTT TCT GAA ATC ATG CAT GAG CAG ATC TGC CCC CTG GAG GAG AAG ACG
met ala lys glu leu ser glu ile met his glu gln ile cys pro leu glu glu lys thr 3962                                    3992
AGC GTC TTA CCG AAT TCC CTT CAC ATC TTC AAC GCC ATC AGT GGG ACT CCA ACA AGC ACA
ser val leu pro asn ser leu his ile phe asn ala ile ser gly thr pro thr ser thr 4022                              |xxxx PBM xxxx|
ATG GTT CAC GGG ATG ACC AGC TCG TCT TCG GTC GTG TGA TTA CAT CTC ATG GCC CGT GTG
met val his gly met thr ser ser ser ser val val STP 4082                                    4112
TGG GGA CTT GCT TTG TCA TTT GCA AAC TCA GGA TGC TTT CCA AAG CCA ATC ACT GGG GAG 4142                                    4172
ACC GAG CAC AGG GAG GAC CAA GGG GAA GGG GAG AGA AAG GAA ATA AAG AAC AAC GTT ATT 4202                                    4232
TCT TAA CAG ACT TTC TAT AGG AGT TGT AAG AAG GTG CAC ATA TTT TTT AAA TCA CTG 4262                                    4292
GCA ATA TTC AAA GTT TTC ATT GTG TCT TAA CAA AGG TGT GGT AGA CAC TCT TGA GCT GGA 4322                                    4352
CTT AGA TTT TAT TCT TCC TTG CAG AGT AGT GTT AGA ATA GAT GGC CTA CAG AAA AAA AAG 4382                                    4412
GTT CTG GGA TCT ACA TGG CAG GGA GGG CTG CAC TGA CAT TGA TGC CTG GGG GAC CTT TTG
```

FIG. 2B (cont.)

```
4442                                    4472
CCT CGA CTC GTG CCG GAA ATC TGA TCG TAA TCA GGG TAC AGA ACT TAC TAG TTT TGT CTA 4502                                    4532
GGA GTA TGT TGT ATG ACT AGG ATT TGT GCT ATT ATC TCA TTC AAC AAC ATA GAG CAA GAA 4562                                    4592
TAG TGA GCT AAC TGA GCT AGA CAC TCA ATT AAT CCG CTA CTG GCT TCA AGT CAG AAC TTT 4622                                    4652
GTC ATT AAT CAT CGA CTC CGG GAC GGT CAT ATA TGT ATT ACA TTT CTA CAT TTT TAA TAC 4682                                    4712
TCA CAT GGG CTT ATG CAT TAA GTT TAA TTG TGA TAA ATT TGT GCT GGT CCA GTA TAT GCA 4742                                    4772
ATA CAC TTT AAT GGT TTA TTC TTG TCA TAA AAA TGT GCA ATA TGG AGA TGT ATA CAA GTC

4802
TTT ACT
```

FIG. 2B (cont.)

```
HC2A              ----------------------------------------------------------------
HC2-80            ----------------------------------------------------------------
HC2B              ----------------------------------------------------------------
HC2C              ----------------------------------------------------------------
HC2D-KIAA1058     GCATCTGGAAATCTTGACAAAAATGCCAGATTTTCTGCCATCTACAGGCAAGACAGCAAT
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     AAGCTATCCAATGATGACATGCTCAAGTTACTTGCAGACTTTCGGAAACCTGAGAAGATG
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     GCTAAGCTCCCAGTGATTTTAGGCAATCTAGACATTACAATTGATAATGTTTCCTCAGAC
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     TTCCCTAATTATGTTAATTCATCATACATTCCCACAAAACAATTTGAAACCTGCAGTAAA
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     ACTCCCATCACGTTTGAAGTGGAGGAATTTGTGCCCTGCATACCAAAACACACTCAGCCT
HC2E              ----------------------------------------------------------------
HC2F              ----------------------------------------------------------------
```

FIG. 3A

| | |
|---|---|
| HC2A | ---------------------------------------------------------- |
| HC2-80 | ---------------------------------------------------------- |
| HC2B | ---------------------------------------------------------- |
| HC2C | ---------------------------------------------------------- |
| HC2D-KIAA1058 | TACACCATCTACACCAATCACCTTTACGTTTATCCTAAGTACTTGAAATACGACAGTCAG |
| HC2E | ---------------------------------------------------------- |
| HC2F | ---------------------------------------------------------- |

| | |
|---|---|
| HC2A | ---------------------------------------------------------- |
| HC2-80 | ---------------------------------------------------------- |
| HC2B | ---------------------------------------------------------- |
| HC2C | ---------------------------------------------------------- |
| HC2D-KIAA1058 | AAGTCTTTTGCCAAGGCTAGAAATATTGCGATTTGCATTGAATTCAAAGATTCAGATGAG |
| HC2E | ---------------------------------------------------------- |
| HC2F | ---------------------------------------------------------- |

| | |
|---|---|
| HC2A | ---------------------------------------------------------- |
| HC2-80 | ---------------------------------------------------------- |
| HC2B | ---------------------------------------------------------- |
| HC2C | ---------------------------------------------------------- |
| HC2D-KIAA1058 | GAAGACTCTCAGCCCCTTAAGTGCATTTATGGCAGACCTGGTGGGCCAGTTTTCACAAGA |
| HC2E | ---------------------------------------------------------- |
| HC2F | ---------------------------------------------------------- |

| | |
|---|---|
| HC2A | --------------AGTTTTACACCATCACCAAAACCCAGAATTTTATGATGAGATTAAA |
| HC2-80 | ---------------------------------------------------------- |
| HC2B | ---------------------------------------------------------- |
| HC2C | ---------------------------------------------------------- |
| HC2D-KIAA1058 | AGCGCCTTTGCTGCAGTTTTACACCATCACCAAAACCCAGAATTTTATGATGAGATTAAA |
| HC2E | ---------------------------------------------------------- |
| HC2F | ---------------------------------------------------------- |

| | |
|---|---|
| HC2A | ATAGAGTTGCCCACTCAGCTGCATGAAAAGCACCACCTGTTGCTCACATTCTTCCATGTC |
| HC2-80 | ---------------------------------------------------------- |
| HC2B | ---------------------------------------------------------- |
| HC2C | ---------------------------------------------------------- |
| HC2D-KIAA1058 | ATAGAGTTGCCCACTCAGCTGCATGAAAAGCACCACCTGTTGCTCACATTCTTCCATGTC |
| HC2E | ---------------------------------------------------------- |
| HC2F | ---------------------------------------------------------- |

| | |
|---|---|
| HC2A | AGCTGTGACAACTCAAGTAAAGGAAGCACGAAGAAGAGGGATGTCGTTGAAACCCAAGTT |
| HC2-80 | ---------------------------------------------------------- |
| HC2B | ---------------------------------------------------------- |
| HC2C | ---------------------------------------------------------- |
| HC2D-KIAA1058 | AGCTGTGACAACTCAAGTAAAGGAAGCACGAAGAAGAGGGATGTCGTTGAAACCCAAGTT |
| HC2E | ---------------------------------------------------------- |
| HC2F | ---------------------------------------------------------- |

FIG. 3A (cont.)

```
HC2A           GGCTACTCCTGGCTTCCCCTCCTGAAAGACGGAAGGGTGGTGACAAGCGAGCAGCACATC
HC2-80         ------------------------------------------------------------
HC2B           ------------------------------------------------------------
HC2C           ------------------------------------------------------------
HC2D-KIAA1058  GGCTACTCCTGGCTTCCCCTCCTGAAAGACGGAAGGGTGGTGACAAGCGAGCAGCACATC
HC2E           ------------------------------------------------------------
HC2F           ------------------------------------------------------------

HC2A           CCGGTCTCGGCGAACCTTCCTTCGGGCTATCTTGGCTACCAAGAGCTTGGGATGGGCAGG
HC2-80         ------------------------------------------------------------
HC2B           ------------------------------------------------------------
HC2C           ------------------------------------------------------------
HC2D-KIAA1058  CCGGTCTCGGCGAACCTTCCTTCGGGCTATCTTGGCTACCAGGAGCTTGGGATGGGCAGG
HC2E           ------------------------------------------------------------
HC2F           ------------------------------------------------------------

HC2A           CATTATGGTCCGGAAATTAAATGGGTAGATGGAGGCAAGCCACTGCTGAAAATTTCCACT
HC2-80         ------------------------------------------------------------
HC2B           ------------------------------------------------------------
HC2C           ------------------------------------------------------------
HC2D-KIAA1058  CATTATGGTCCGGAAATTAAATGGGTAGATGGAGGCAAGCCACTGCTGAAAATTTCCACT
HC2E           ------------------------------------------------------------
HC2F           ------------------------------------------------------------

HC2A           CATCTGGTTTCTACAGTGTATACTCAGGATCAGCATTTACATAATTTTTTCCAGTACTGT
HC2-80         ------------------------------------------------------------
HC2B           ------------------------------------------------------------
HC2C           ------------------------------------------------------------
HC2D-KIAA1058  CATCTGGTTTCTACAGTGTATACTCAGGATCAGCATTTACATAATTTTTTCCAGTACTGT
HC2E           ------------------------------------------------------------
HC2F           ------------------------------------------------------------

HC2A           CAGAAAACCGAATCTGGAGCCCAAGCCTTAGGAAACGAACTTGTAAAGTACCTTAAGAGT
HC2-80         ------------------------------------------------------------
HC2B           ------------------------------------------------------------
HC2C           ------------------------------------------------------------
HC2D-KIAA1058  CAGAAAACCGAATCTGGAGCCCAAGCCTTAGGAAACGAACTTGTAAAGTACCTTAAGAGT
HC2E           ------------------------------------------------------------
HC2F           ------------------------------------------------------------

HC2A           CTGCATGCGATGGAAGGCCACGTGATGATCGCCTTCTTGCCCACTATCCTAAACCAGCTG
HC2-80         ------------------------------------------------------------
HC2B           ------GCGATGGAAGGCCACGTGATGATCGCCTTCTTGCCCACTATCCTAAACCAGCTG
HC2C           ------------------------------------------------------------
HC2D-KIAA1058  CTGCATGCGATGGAAGGCCACGTGATGATCGCCTTCTTGCCCACTATCCTAAACCAGCTG
HC2E           ------GCGATGGAAGGCCACGTGATGATCGCCTTCTTGCCCACTATCCTAAACCAGCTG
HC2F           ------------------------------------------------------------
```

FIG. 3A (cont.)

| | |
|---|---|
| HC2A | TTCCGAGTCCTCACCAGAGCCACACAGGAAGAAGTCGCGGTTAACGTGACTCGGGTCATT |
| HC2-80 | ------------------------------------------------------------ |
| HC2B | TTCCGAGTCCTCACCAGAGCCACACAGGAAGAAGTCGCGGTTAACGTGACTCGGGTCATT |
| HC2C | ------------------------------------------------------------ |
| HC2D-KIAA1058 | TTCCGAGTCCTCACCAGAGCCACACAGGAAGAAGTCGCGGTTAACGTGACTCGGGTCATT |
| HC2E | TTCCGAGTCCTCACCAGAGCCACACAGGAAGAAGTCGCGGTTAACGTGACTCGGGTCATT |
| HC2F | ------------------------------------------------------------ |
| | |
| HC2A | ATTCATGTGGTTGCCCAGTGCCATGAGGAAGGATTGGAGAGCCACTTGAGGTCATATGTT |
| HC2-80 | ------------------------------------------------------------ |
| HC2B | ATTCATGTGGTTGCCCAGTGCCATGAGGAAGGATTGGAGAGCCACTTGAGGTCATATGTT |
| HC2C | ------------------------------------------------------------ |
| HC2D-KIAA1058 | ATTCATGTGGTTGCCCAGTGCCATGAGGAAGGATTGGAGAGCCACTTGAGGTCATATGTT |
| HC2E | ATTCATGTGGTTGCCCAGTGCCATGAGGAAGGATTGGAGAGCCACTTGAGGTCATATGTT |
| HC2F | ------------------------------------------------------------ |
| | |
| HC2A | AAGTACGCGTATAAGGCTGAGCCATATGTTGCCTCTGAATACAAGACAGTGCATGAAGAA |
| HC2-80 | ------------------------------------------------------------ |
| HC2B | AAGTACGCGTATAAGGCTGAGCCATATGTTGCCTCTGAATACAAGACAGTGCATGAAGAA |
| HC2C | ------------------------------------------------------------ |
| HC2D-KIAA1058 | AAGTACGCGTATAAGGCTGAGCCATATGTTGCCTCTGAATACAAGACAGTGCATGAAGAA |
| HC2E | AAGTACGCGTATAAGGCTGAGCCATATGTTGCCTCTGAATACAAGACAGTGCATGAAGAA |
| HC2F | ------------------------------------------------------------ |
| | |
| HC2A | CTGACCAAATCCATGACCACGATTCTCAAGCCTTCTGCCGATTTCCTCACCAGCAACAAA |
| HC2-80 | ------------------------------------------------------------ |
| HC2B | CTGACCAAATCCATGACCACGATTCTCAAGCCTTCTGCCGATTTCCTCACCAGCAACAAA |
| HC2C | ------------------------------------------------------------ |
| HC2D-KIAA1058 | CTGACCAAATCCATGACCACGATTCTCAAGCCTTCTGCCGATTTCCTCACCAGCAACAAA |
| HC2E | CTGACCAAATCCATGACCACGATTCTCAAGCCTTCTGCCGATTTCCTCACCAGCAACAAA |
| HC2F | ------------------------------------------------------------ |
| | |
| HC2A | CTACTGAGGTACTCATGGTTTTTCTTTGATGTACTGATCAAATCTATGGCTCAGCATTTG |
| HC2-80 | ------------------------------------------------------------ |
| HC2B | CTACTGAGGTACTCATGGTTTTTCTTTGATGTACTGATCAAATCTATGGCTCAGCATTTG |
| HC2C | ------------------------------------------------------------ |
| HC2D-KIAA1058 | CTACTGAAGTACTCATGGTTTTTCTTTGATGTACTGATCAAATCTATGGCTCAGCATTTG |
| HC2E | CTACTGAGGTACTCATGGTTTTTCTTTGATGTACTGATCAAATCTATGGCTCAGCATTTG |
| HC2F | ------------------------------------------------------------ |
| | |
| HC2A | ATAGAGAACTCCAAAGTTAAGTTGCTGCGAAACCAGAGATTTCCTGCATCCTATCATCAT |
| HC2-80 | ------------------------------------------------------------ |
| HC2B | ATAGAGAACTCCAAAGTTAAGTTGCTGCGAAACCAGAGATTTCCTGCATCCTATCATCAT |
| HC2C | ------------------------------------------------------------ |
| HC2D-KIAA1058 | ATAGAGAACTCCAAAGTTAAGTTGCTGCGAAACCAGAGATTTCCTGCATCCTATCATCAT |
| HC2E | ATAGAGAACTCCAAAGTTAAGTTGCTGCGAAACCAGAGATTTCCTGCATCCTATCATCAT |
| HC2F | ------------------------------------------------------------ |

FIG. 3A (cont.)

| | |
|---|---|
| HC2A | GCAGCGGAAACCGTTGTAAATATGCTGATGCCACACATCACTCAGAAGTTTGGAGATAAT |
| HC2-80 | ------------------------------------------------------------ |
| HC2B | GCAGCGGAAACCGTTGTAAATATGCTGATGCCACACATCACTCAGAAGTTTGGAGATAAT |
| HC2C | ------------------------------------------------------------ |
| HC2D-KIAA1058 | GCAGTGGAAACCGTTGTAAATATGCTGATGCCACACATCACTCAGAAGTTTCGAGATAAT |
| HC2E | GCAGCGGAAACCGTTGTAAATATGCTGATGCCACACATCACTCAGAAGTTTGGAGATAAT |
| HC2F | ------------------------------------------------------------ |
| | |
| HC2A | CCAGAGGCATCTAAGAACGCGAATCATAGCCTTGCTGTCTTCATCAAGAGATGTTTCACC |
| HC2-80 | ------------------------------------------------------------ |
| HC2B | CCAGAGGCATCTAAGAACGCGAATCATAGCCTTGCTGTCTTCATCAAGAGATGTTTCACC |
| HC2C | ------------------------------------------------------------ |
| HC2D-KIAA1058 | CCAGAGGCATCTAAGAACGCGAATCATAGCCTTGCTGTCTTCATCAAGAGATGTTTCACC |
| HC2E | CCAGAGGCATCTAAGAACGCGAATCATAGCCTTGCTGTCTTCATCAAGAGATGTTTCACC |
| HC2F | ------------------------------------------------------------ |
| | |
| HC2A | TTCATGGACAGGGGCTTTGTCTTCAAGCAGATCAACAACTACATTAGCTGTTTTGCTCCT |
| HC2-80 | ------------------------------------------------------------ |
| HC2B | TTCATGGACAGGGGCTTTGTCTTCAAGCAGATCAACAACTACATTAGCTGTTTTGCTCCT |
| HC2C | ------------------------------------------------------------ |
| HC2D-KIAA1058 | TTCATGGACAGGGGCTTTGTCTTCAAGCAGATCAACAACTACATTAGCTGTTTTGCTCCT |
| HC2E | TTCATGGACAGGGGCTTTGTCTTCAAGCAGATCAACAACTACATTAGCTGTTTTGCTCCT |
| HC2F | ------------------------------------------------------------ |
| | |
| HC2A | GGAGACCCAAAGACCCTCTTTGAATACAAGTTTGAATTTCTCCGTGTAGTGTGCAACCAT |
| HC2-80 | ------------------------------------------------------------ |
| HC2B | GGAGACCCAAAGACCCTCTTTGAATACAAGTTTGAATTTCTCCGTGTAGTGTGCAACCAT |
| HC2C | ------------------------------------------------------------ |
| HC2D-KIAA1058 | GGAGACCCAAAGACCCTCTTTGAATACAAGTTTGAATTTCTCCGTGTAGTGTGCAACCAT |
| HC2E | GGAGACCCAAAGACCCTCTTTGAATACAAGTTTGAATTTCTCCGTGTAGTGTGCAACCAT |
| HC2F | ------------------------------------------------------------ |
| | |
| HC2A | GAACATTATATTCCGTTGAACTTACCAATGCCATTTGGAAAAGGCAGGATTCAAAGATAC |
| HC2-80 | ------------------------------------------------------------ |
| HC2B | GAACATTATATTCCGTTGAACTTACCAATGCCATTTGGAAAAGGCAGGATTCAAAGATAC |
| HC2C | ------------------------------------------------------------ |
| HC2D-KIAA1058 | GAACATTATATTCCGTTGAACTTACCAATGCCATTTGGAAAAGGCAGGATTCAAAGATAC |
| HC2E | GAACATTATATTCCGTTGAACTTACCAATGCCATTTGGAAAAGGCAGGATTCAAAGATAC |
| HC2F | ------------------------------------------------------------ |
| | |
| HC2A | CAAGACCTCCAGCTTGACTACTCATTAACAGATGAGTTCTGCAGAAACCACTTCTTGGTG |
| HC2-80 | -------TCCAGCTTGACTACTCATTAACAGATGAGTTCTGCAGAAACCACTTCTTGGTG |
| HC2B | CAAGACCTCCAGCTTGACTACTCATTAACAGATGAGTTCTGCAGAAACCACTTCTTGGTG |
| HC2C | ------------------------------------------------------------ |
| HC2D-KIAA1058 | CAAGACCTCCAGCTTGACTACTCATTAACAGATGAGTTCTGCAGAAACCACTTCTTGGTG |
| HC2E | CAAGACCTCCAGCTTGACTACTCATTAACAGATGAGTTCTGCAGAAACCACTTCTTGGTG |
| HC2F | ------------------------------------------------------------ |

FIG. 3A (cont.)

| | |
|---|---|
| HC2A | GGACTGTTACTGAGGGAGGTGGGGACAGCCCTCCAGGAGTTCCGGGAGGTCCGTCTGATC |
| HC2-80 | GGACTGTTACTGAGGGAGGTGGGGACAGCCCTCCAGGAGTTCCGGGAGGTCCGTCTGATC |
| HC2B | GGACTGTTACTGAGGGAGGTGGGGACAGCCCTCCAGGAGTTCCGGGAGGTCCGTCTGATC |
| HC2C | ------------------------------------------------------------ |
| HC2D-KIAA1058 | GGACTGTTACTGAGGGAGGTGGGGACAGCCCTCCAGGAGTTCCGGGAGGTCCGTCTGATC |
| HC2E | GGACTGTTACTGAGGGAGGTGGGGACAGCCCTCCAGGAGTTCCGGGAGGTCCGTCTGATC |
| HC2F | ------------------------------------------------------------ |
| | |
| HC2A | GCCATCAGTGTGCTCAAGAACCTGCTGATAAAGCATTCTTTTGATGACAGATATGCTTCA |
| HC2-80 | GCCATCAGTGTGCTCAAGAACCTGCTGATAAAGCATTCTTTTGATGACAGATATGCTTCA |
| HC2B | GCCATCAGTGTGCTCAAGAACCTGCTGATAAAGCATTCTTTTGATGACAGATATGCTTCA |
| HC2C | ------------------------------------------------------------ |
| HC2D-KIAA1058 | GCCATCAGTGTGCTCAAGAACCTGCTGATAAAGCATTCTTTTGATGACAGATATGCTTCA |
| HC2E | GCCATCAGTGTGCTCAAGAACCTGCTGATAAAGCATTCTTTTGATGACAGATATGCTTCA |
| HC2F | ------------------------------------------------------------ |
| | |
| HC2A | AGGAGCCATCAGGCAAGGATAGCCACCCTCTACCTGCCTCTGTTTGGTCTGCTGATTGAA |
| HC2-80 | AGGAGCCATCAGGCAAGGATAGCCACCCTCTACCTGCCTCTGTTTGGTCTGCTGATTGAA |
| HC2B | AGGAGCCATCAGGCAAGGATAGCCACCCTCTACCTGCCTCTGTTTGGTCTGCTGATTGAA |
| HC2C | ------------------------------------------------------------ |
| HC2D-KIAA1058 | AGGAGCCATCAGGCAAGGATAGCCACCCTCTACCTGCCTCTGTTTGGTCTGCTGATTGAA |
| HC2E | AGGAGCCATCAGGCAAGGATAGCCACCCTCTACCTGCCTCTGTTTGGTCTGCTGATTGAA |
| HC2F | ------------------------------------------------------------ |
| | |
| HC2A | AACGTCCAGCGGATCAATGTGAGGGATGTGTCACCCTTCCCTGTGAACGCGGGCATGACC |
| HC2-80 | AACGTCCAGCGGATCAATGTGAGGGATGTGTCACCCTTCCCTGTGAACGCGGGCATGACC |
| HC2B | AACGTCCAGCGGATCAATGTGAGGGATGTGTCACCCTTCCCTGTGAACGCGGGCATGACC |
| HC2C | ------------------------------------------------------------ |
| HC2D-KIAA1058 | AACGTCCAGCGGATCAATGTGAGGGATGTGTCACCCTTCCCTGTGAACGCGGGCATGACT |
| HC2E | AACGTCCAGCGGATCAATGTGAGGGATGTGTCACCCTTCCCTGTGAACGCGGGCATGACC |
| HC2F | ------------------------------------------------------------ |
| | |
| HC2A | GTGAAGGATGAATCCCTGGCTCTACCAGCTGTGAATCCGCTGGTGACGCCGCAGAAGGGA |
| HC2-80 | GTGAAGGATGAATCCCTGGCTCTACCAGCTGTGAATCCGCTGGTGACGCCGCAGAAGGGA |
| HC2B | GTGAAGGATGAATCCCTGGCTCTACCAGCTGTGAATCCGCTGGTGACGCCGCAGAAGGGA |
| HC2C | ------------------------------------------------------------ |
| HC2D-KIAA1058 | GTGAAGGATGAATCCCTGGCTCTACCAGCTGTGAATCCGCTGGTGACGCCGCAGAAGGGA |
| HC2E | GTGAAGGATGAATCCCTGGCTCTACCAGCTGTGAATCCGCTGGTGACGCCGCAGAAGGGA |
| HC2F | ------------------------------------------------------------ |
| | |
| HC2A | AGCACCCTGGACAACAGCCTGCACAAGGACCTGCTGGGCGCCATCTCCGGCATTGCTTCT |
| HC2-80 | AGCACCCTGGACAACAGCCTGCACAAGGACCTGCTGGGCGCCATCTCCGGCATTGCTTCT |
| HC2B | AGCACCCTGGACAACAGCCTGCACAAGGACCTGCTGGGCGCCATCTCCGGCATTGCTTCT |
| HC2C | ------------------------------------------------------------ |
| HC2D-KIAA1058 | AGCACCCTGGACAACAGCCTGCACAAGGACCTGCTGGGCGCCATCTCCGGCATTGCTTCT |
| HC2E | AGCACCCTGGACAACAGCCTGCACAAGGACCTGCTGGGCGCCATCTCCGGCATTGCTTCT |
| HC2F | ------------------------------------------------------------ |

FIG. 3A (cont.)

| | |
|---|---|
| HC2A | CCATATACAACCTCAACTCCAAACATCAACAGTGTGAGAAATGCTGATTCGAGAGGATCT |
| HC2-80 | CCATATACAACCTCAACTCCAAACATCAACAGTGTGAGAAATGCTGATTCGAGAGGATCT |
| HC2B | CCATATACAACCTCAACTCCAAACATCAACAGTGTGAGAAATGCTGATTCGAGAGGATCT |
| HC2C | ------------------------------------------------------------ |
| HC2D-KIAA1058 | CCATATACAACCTCAACTCCAAACATCAACAGTGTGAGAAATGCTGATTCGAGAGGATCT |
| HC2E | CCATATACAACCTCAACTCCAAACATCAACAGTGTGAGAAATGCTGATTCGAGAGGATCT |
| HC2F | ----------------------------------------GCTGATTCGAGAGGATCT |
| | |
| HC2A | CTCATAAGCACAGATTCGGGTAACAGCCTTCCAGAAAGGAATAGTGAGAAGAGCAATTCC |
| HC2-80 | CTCATAAGCACAGATTCGGGTAACAGCCTTCCAGAAAGGAATAGTGAGAAGAGCAATTCC |
| HC2B | CTCATAAGCACAGATTCGGGTAACAGCCTTCCAGAAAGGAATAGTGAGAAGAGCAATTCC |
| HC2C | ------------------------------------------------------------ |
| HC2D-KIAA1058 | CTCATAAGCACAGATTCGGGTAACAGCCTTCCAGAAAGGAATAGTGAGAAGAGCAATTCC |
| HC2E | CTCATAAGCACAGATTCGGGTAACAGCCTTCCAGAAAGGAATAGTGAGAAGAGCAATTCC |
| HC2F | CTCATAAGCACAGATTCGGGTAACAGCCTTCCAGAAAGGAATAGTGAGAAGAGCAATTCC |
| | |
| HC2A | CTGGATAAGCACCAACAAAGTAGCACATTGGGAAATTCCGTGGTTCGCTGTGATAAACTT |
| HC2-80 | CTGGATAAGCACCAACAAAGTAGCACATTGGGAAATTCCGTGGTTCGCTGTGATAAACTT |
| HC2B | CTGGATAAGCACCAACAAAGTAGCACATTGGGAAATTCCGTGGTTCGCTGTGATAAACTT |
| HC2C | ------------------------------------------------------------ |
| HC2D-KIAA1058 | CTGGATAAGCACCAACAAAGTAGCACATTGGGAAATTCCGTGGTTCGCTGTGATAAACTT |
| HC2E | CTGGATAAGCACCAACAAAGTAGCACATTGGGAAATTCCGTGGTTCGCTGTGATAAACTT |
| HC2F | CTGGATAAGCACCAACAAAGTAGCACATTGGGAAATTCCGTGGTTCGCTGTGATAAACTT |
| | |
| HC2A | GACCAGTCTGAGATTAAGAGCCTACTGATGTGTTTCCTCTACATCTTAAAGAGCATGTCT |
| HC2-80 | GACCAGTCTGAGATTAAGAGCCTACTGATGTGTTTCCTCTACATCTTAAAGAGCATGTCT |
| HC2B | GACCAGTCTGAGATTAAGAGCCTACTGATGTGTTTCCTCTACATCTTAAAGAGCATGTCT |
| HC2C | ------------------------------------------------------------ |
| HC2D-KIAA1058 | GACCAGTCTGAGATTAAGAGCCTACTGATGTGTTTCCTCTACATCTTAAAGAGCATGTCT |
| HC2E | GACCAGTCTGAGATTAAGAGCCTACTGATGTGTTTCCTCTACATCTTAAAGAGCATGTCT |
| HC2F | GACCAGTCTGAGATTAAGAGCCTACTGATGTGTTTCCTCTACATCTTAAAGAGCATGTCT |
| | |
| HC2A | GATGATGCTTTGTTTACATATTGGAACAAGGCTTCAACATCTGAACTTATGGATTTTTTT |
| HC2-80 | GATGATGCTTTGTTTACATATTGGAACAAGGCTTCAACATCTGAACTTATGGATTTTTTT |
| HC2B | GATGATGCTTTGTTTACATATTGGAACAAGGCTTCAACATCTGAACTTATGGATTTTTTT |
| HC2C | ------------------------------------------------------------ |
| HC2D-KIAA1058 | GATGATGCTTTGTTTACATATTGGAACAAGGCTTCAACATCTGAACTTATGGATTTTTTT |
| HC2E | GATGATGCTTTGTTTACATATTGGAACAAGGCTTCAACATCTGAACTTATGGATTTTTTT |
| HC2F | GATGATGCTTTGTTTACATATTGGAACAAGGCTTCAACATCTGAACTTATGGATTTTTTT |
| | |
| HC2A | ACAATATCTGAAGTCTGCCTGCACCAGTTCCAGTACATGGGGAAGCGATACATAGCCAGG |
| HC2-80 | ACAATATCTGAAGTCTGCCTGCACCAGTTCCAGTACATGGGGAAGCGATACATAGCCAGG |
| HC2B | ACAATATCTGAAGTCTGCCTGCACCAGTTCCAGTACATGGGGAAGCGATACATAGCCAGG |
| HC2C | ------------------------------------------------------------ |
| HC2D-KIAA1058 | ACAATATCTGAAGTCTGCCTGCACCAGTTCCAGTACATGGGGAAGCGATACATAGCCAG- |
| HC2E | ACAATATCTGAAGTCTGCCTGCACCAGTTCCAGTACATGGGGAAGCGATACATAGCCAGG |
| HC2F | ACAATATCTGAAGTCTGCCTGCACCAGTTCCAGTACATGGGGAAGCGATACATAGCCAG- |

FIG. 3A (cont.)

```
HC2A           AACCAGGAGGGGTTGGGACCCATAGTTCATGATCGAAAGTCTCAGACATTGCCTGTTTCC
HC2-80         AACCAGGAGGGGTTGGGACCCATAGTTCATGATCGAAAGTCTCAGACATTGCCTGTTTCC
HC2B           AACCAGGAGGGGTTGGGACCCATAGTTCATGATCGAAAGTCTCAGACATTGCCTGTTTCC
HC2C           ------------------------------------------------------------
HC2D-KIAA1058  ------------------------------------AA----------------------
HC2E           AACCAGGAGGGGTTGGGACCCATAGTTCATGATCGAAAGTCTCAGACATTGCCTGTTTCC
HC2F           -------------TGTGA---------------GAAAG------ATATCAAGTGT----

HC2A           CGTAACAGAACAGGAATGATGCATGCCAGATTGCAGCAGCTGGGCAGCCTGGATAACTCT
HC2-80         CGTAACAGAACAGGAATGATGCATGCCAGATTGCAGCAGCTGGGCAGCCTGGATAACTCT
HC2B           CGTAACAGAACAGGAATGATGCATGCCAGATTGCAGCAGCTGGGCAGCCTGGATAACTCT
HC2C           ------------------------------------------------------------
HC2D-KIAA1058  ----------CAGGAATGATGCATGCCAGATTGCAGCAGCTGGGCAGCCTGGATAACTCT
HC2E           CGTAACAGAACAGGAATGATGCATGCCAGATTGCAGCAGCTGGGCAGCCTGGATAACTCT
HC2F           ----------------------------------------GCTTGGAA------------

HC2A           CTCACTTTTAACCACAGCTATGGCCACTCGGACGCAGATGTTCTGCACCAGTCATTACTT
HC2-80         CTCACTTTTAACCACAGCTATGGCCACTCGGACGCAGATGTTCTGCACCAGTCATTACTT
HC2B           CTCACTTTTAACCACAGCTATGGCCACTCGGACGCAGATGTTCTGCACCAGTCATTACTT
HC2C           ------------------------------------------------------------
HC2D-KIAA1058  CTCACTTTTAACCACAGCTATGGCCACTCGGACGCAGATGTTCTGCACCAGTCATTACTT
HC2E           CTCACTTTTAACCACAGCTATGGCCACTCGGACGCAGATGTTCTGCACCAGTCATTACTT
HC2F           -TTTCTGTAGACAATGGCTATGGCCACTCGGACGCAGATGTTCTGCACCAGTCATTACTT

HC2A           GAAGCCAACATTGCTACTGAGGTTTGCCTGACAGCTCTGGACACGCTTTCTCTATTTACA
HC2-80         GAAGCCAACATTGCTACTGAGGTTTGCCTGACAGCTCTGGACACGCTTTCTCTATTTACA
HC2B           GAAGCCAACATTGCTACTGAGGTTTGCCTGACAGCTCTGGACACGCTTTCTCTATTTACA
HC2C           ------------------------------------------------------------
HC2D-KIAA1058  GAAGCCAACATTGCTACTGAGGTTTGCCTGACAGCTCTGGACACGCTTTCTCTATTTACA
HC2E           GAAGCCAACATTGCTACTGAGGTTTGCCTGACAGCTCTGGACACGCTTTCTCTATTTACA
HC2F           GAAGCCAACATTGCTACTGAGGTTTGCCTGACAGCTCTGGACACGCTTTCTCTATTTACA

HC2A           TTGGCGTTTAAGAACCAGCTCCTGGCCGACCATGGACATAATCCTCTCATGAAAAAAGTT
HC2-80         TTGGCGTTTAAGAACCAGCTCCTGGCCGACCATGGACATAATCCTCTCATGAAAAAAGTT
HC2B           TTGGCGTTTAAG------CTCCTGGCCGACCATGGACATAATCCTCTCATGAAAAAAGTT
HC2C           ------------------------------------------------------------
HC2D-KIAA1058  TTGGCGTTTAAGAACCAGCTCCTGGCCGACCATGGACATAATCCTCTCATGAAAAAAGTT
HC2E           TTGGCGTTTAAGAACCAGCTCCTGGCCGACCATGGACATAATCCTCTCATGAAAAAAGTT
HC2F           TTGGCGTTTAAGAACCAGCTCCTGGCCGACCATGGACATAATCCTCTCATGAAAAAAAAA

HC2A           TTTGATGTCTACCTGTGTTTTCTTCAAAAACATCAGTCTGAAACGGCTTTAAAAAATGTC
HC2-80         TTTGATGTCTACCTGTGTTTTCTTCAAAAACATCAGTCTGAAACGGCTTTAAAAAATGTC
HC2B           TTTGATGTCTACCTGTGTTTTCTTCAAAAACATCAGTCTGAAACGGCTTTAAAAAATGTC
HC2C           ------------------------------------------------------------
HC2D-KIAA1058  TTTGATGTCTACCTGTGTTTTCTTCAAAAACATCAGTCTGAAACGGCTTTAAAAAATGTC
HC2E           TTTGATGTCTACCTGTGTTTTCTTCAAAAACATCAGTCTGAAACGGCTTTAAAAAATGTC
HC2F           A-----------------------------------------------------------
```

FIG. 3A (cont.)

```
HC2A          TTCACTGCCTTAAGGTCCTTAATTTATAAGTTTCCCTCAACATTCTATGAAGGGAGAGCG
HC2-80        TTCACTGCCTTAAGGTCCTTAATTTATAAGTTTCCCTCAACATTCTATGAAGGGAGAGCG
HC2B          TTCACTGCCTTAAGGTCCTTAATTTATAAGTTTCCCTCAACATTCTATGAAGGGAGAGCG
HC2C          ------------------------------------------------------------
HC2D-KIAA1058 TTCACTGCCTTAAGGTCCTTAATTTATAAGTTTCCCTCAACATTCTATGAAGGGAGAGCG
HC2E          TTCACTGCCTTAAGGTCCTTAATTTATAAGTTTCCCTCAACATTCTATGAAGGGAGAGCG
HC2F          ------------------------------------------------------------

HC2A          GACATGTGTGCGGCTCTGTGTTACGAGATTCTCAAGTGCTGTAACTCCAAGCTGAGCTCC
HC2-80        GACATGTGTGCGGCTCTGTGTTACGAGATTCTCAAGTGCTGTAACTCCAAGCTGAGCTCC
HC2B          GACATGTGTGCGGCTCTGTGTTACGAGATTCTCAAGTGCTGTAACTCCAAGCTGAGCTCC
HC2C          ------------------------------------------------------------
HC2D-KIAA1058 GACATGTGTGCGGCTCTGTGTTACGAGATTCTCAAGTGCTGTAACTCCAAGCTGAGCTCC
HC2E          GACATGTGTGCGGCTCTGTGTTACGAGATTCTCAAGTGCTGTAACTCCAAGCTGAGCTCC
HC2F          ------------------------------------------------------------

HC2A          ATCAGGACGGAGGCCTCCCAGCTGCTCTACTTCCTGATGAGGAACAACTTTGATTACACT
HC2-80        ATCAGGACGGAGGCCTCCCAGCTGCTCTACTTCCTGATGAGGAACAACTTTGATTACACT
HC2B          ATCAGGACGGAGGCCTCCCAGCTGCTCTACTTCCTGATGAGGAACAACTTTGATTACACT
HC2C          ------------------------------------------------------------
HC2D-KIAA1058 ATCAGGACGGAGGCCTCCCAGCTGCTCTACTTCCTGATGAGGAACAACTTTGATTACACT
HC2E          ATCAGGACGGAGGCCTCCCAGCTGCTCTACTTCCTGATGAGGAACAACTTTGATTACACT
HC2F          ------------------------------------------------------------

HC2A          GGAAAGAAGTCCTTTGTCCGGACACATTTGCAAGTCATCATATCTGTCAGCCAGCTGATA
HC2-80        GGAAAGAAGTCCTTTGTCCGGACACATTTGCAAGTCATCATATCTGTCAGCCAGCTGATA
HC2B          GGAAAGAAGTCCTTTGTCCGGACACATTTGCAAGTCATCATATCTGTCAGCCAGCTGATA
HC2C          ------------------------------------------------------------
HC2D-KIAA1058 GGAAAGAAGTCCTTTGTCCGGACACATTTGCAAGTCATCATATCTGTCAGCCAGCTGATA
HC2E          GGAAAGAAGTCCTTTGTCCGGACACATTTGCAAGTCATCATATCTGTCAGCCAGCTGATA
HC2F          ------------------------------------------------------------

HC2A          GCAGACGTTGTTGGCATTGGGGAAACCAGATTCCAGCAGTCCCTGTCCATCATCAACAAC
HC2-80        GCAGACGTTGTTGGCATTGGGGAAACCAGATTCCAGCAGTCCCTGTCCATCATCAACAAC
HC2B.         GCAGACGTTGTTGGCATTGGGGAAACCAGATTCCAGCAGTCCCTGTCCATCATCAACAAC
HC2C          ------------------------------------------------------------
HC2D-KIAA1058 GCAGACGTTGTTGGCATTGGGGAAACCAGATTCCAGCAGTCCCTGTCCATCATCAACAAC
HC2E          GCAGACGTTGTTGGCATTGGGGAAACCAGATTCCAGCAGTCCCTGTCCATCATCAACAAC
HC2F          ------------------------------------------------------------

HC2A          TGTGCCAACAGTGACCGGCTTATTAAGCACACCAGCTTCTCCTCTGATGTGAAGGACTTA
HC2-80        TGTGCCAACAGTGACCGGCTTATTAAGCACACCAGCTTCTCCTCTGATGTGAAGGACTTA
HC2B          TGTGCCAACAGTGACCGGCTTATTAAGCACACCAGCTTCTCCTCTGATGTGAAGGACTTA
HC2C          ------------------------------------------------------------
HC2D-KIAA1058 TGTGCCAACAGTGACCGGCTTATTAAGCACACCAGCTTCTCCTCTGATGTGAAGGACTTA
HC2E          TGTGCCAACAGTGACCGGCTTATTAAGCACACCAGCTTCTCCTCTGATGTGAAGGACTTA
HC2F          ------------------------------------------------------------
```

FIG. 3A (cont.)

```
HC2A           ACCAAAAGGATACGCACGGTGCTAATGGCCACCGCCCAGATGAAGGAGCATGAGAACGAC
HC2-80         ACCAAAAGGATACGCACGGTGCTAATGGCCACCGCCCAGATGAAGGAGCATGAGAACGAC
HC2B           ACCAAAAGGATACGCACGGTGCTAATGGCCACCGCCCAGATGAAGGAGCATGAGAACGAC
HC2C           ------------------------------------------------------------
HC2D-KIAA1058  ACCAAAAGGATACGCACGGTGCTAATGGCCACCGCCCAGATGAAGGAGCATGAGAACGAC
HC2E           ACCAAAAGGATACGCACGGTGCTAATGGCCACCGCCCAGATGAAGGAGCATGAGAACGAC
HC2F           ------------------------------------------------------------

HC2A           CCAGAGATGCTGGTGGACCTCCAGTACAGCCTGGCCAAATCCTATGCCAGCACGCCCGAG
HC2-80         CCAGAGATGCTGGTGGACCTCCAGTACAGCCTGGCCAAATCCTATGCCAGCACGCCCGAG
HC2B           CCAGAGATGCTGGTGGACCTCCAGTACAGCCTGGCCAAATCCTATGCCAGCACGCCCGAG
HC2C           ------------------------------------------------------------
HC2D-KIAA1058  CCAGAGATGCTGGTGGACCTCCAGTACAGCCTGGCCAAATCCTATGCCAGCACGCCCGAG
HC2E           CCAGAGATGCTGGTGGACCTCCAGTACAGCCTGGCCAAATCCTATGCCAGCACGCCCGAG
HC2F           ------------------------------------------------------------

HC2A           CTCAGGAAGACGTGGCTCGACAGCATGGCCAGGATCCATGTCAAAAATGGCGATCTCTCA
HC2-80         CTCAGGAAGACGTGGCTCGACAGCATGGCCAGGATCCATGTCAAAAATGGCGATCTCTCA
HC2B           CTCAGGAAGACGTGGCTCGACAGCATGGCCAGGATCCATGTCAAAAATGGCGATCTCTCA
HC2C           ------------------------------------------------------------
HC2D-KIAA1058  CTCAGGAAGACGTGGCTCGACAGCATGGCCAGGATCCATGTCAAAAATGGCGATCTCTCA
HC2E           CTCAGGAAGACGTGGCTCGACAGCATGGCCAGGATCCATGTCAAAAATGGCGATCTCTCA
HC2F           ------------------------------------------------------------

HC2A           GAGGCAGCAATGTGCTATGTCCACGTAACAGCCCTAGTGGCAGAATATCTCACACGGAAA
HC2-80         GAGGCAGCAATGTGCTATGTCCACGTAACAGCCCTAGTGGCAGAATATCTCACACGGAAA
HC2B           GAGGCAGCAATGTGCTATGTCCACGTAACAGCCCTAGTGGCAGAATATCTCACACGGAAA
HC2C           ------------------------------------------------------------
HC2D-KIAA1058  GAGGCAGCAATGTGCTATGTCCACGTAACAGCCCTAGTGGCAGAATATCTCACACGGAAA
HC2E           GAGGCAGCAATGTGCTATGTCCACGTAACAGCCCTAGTGGCAGAATATCTCACACGGAAA
HC2F           ------------------------------------------------------------

HC2A           G-----------------------------------------------------------
HC2-80         G-----------------------------------------------------------
HC2B           G-----------------------------------------------------------
HC2C           ------------------------------------------------------------
HC2D-KIAA1058  GAAGCAGTCCAGTGGGAGCCGCCCCTTCTCCCCCACAGCCATAGCGCCTGCCTGAGGAGG
HC2E           G-----------------------------------------------------------
HC2F           ------------------------------------------------------------

HC2A           ---------GCGTGTTTAGACAAGGATGCACCGCCTTCAGGGTCATTACCCCAAACATC
HC2-80         ---------GCGTGTTTAGACAAGGATGCACCGCCTTCAGGGTCATTACCCCAAACATC
HC2B           ---------GCGTGTTTAGACAAGGATGCACCGCCTTCAGGGTCATTACCCCAAACATC
HC2C           --------------GTTTAGACAAGGATGCACCGCCTTCAGGGTCATTACCCCAAACATC
HC2D-KIAA1058  AGCCGGGGAGGCGTGTTTAGACAAGGATGCACCGCCTTCAGGGTCATTACCCCAAACATC
HC2E           ---------GCGTGTTTAGACAAGGATGCACCGCCTTCAGGGTCATTACCCCAAACATC
HC2F           ------------------------------------------------------------
```

FIG. 3A (cont.)

```
HC2A            GACGAGGAGGCCTCCATGATGGAAGACGTGGGGATGCAGGATGTCCATTTCAACGAGGAT
HC2-80          GACGAGGAGGCCTCCATGATGGAAGACGTGGGGATGCAGGATGTCCATTTCAACGAGGAT
HC2B            GACGAGGAGGCCTCCATGATGGAAGACGTGGGGATGCAGGATGTCCATTTCAACGAGGAT
HC2C            GACGAGGAGGCCTCCATGATGGAAGACGTGGGGATGCAGGATGTCCATTTCAACGAGGAT
HC2D-KIAA1058   GACGAGGAGGCCTCCATGATGGAAGACGTGGGGATGCAGGATGTCCATTTCAACGAGGAT
HC2E            GACGAGGAGGCCTCCATGATGGAAGACGTGGGGA--------------------------
HC2F            ------------------------------------------------------------

HC2A            GTGCTGATGGAGCTCCTTGAGCAGTGCGCAGATGGACTCTGGAAAGCCGAGCGCTACGAG
HC2-80          GTGCTGATGGAGCTCCTTGAGCAGTGCGCAGATGGACTCTGGAAAGCCGAGCGCTACGAG
HC2B            GTGCTGATGGAGCTCCTTGAGCAGTGCGCAGATGGACTCTGGAAAGCCGAGCGCTACGAG
HC2C            GTGCTGATGGAGCTCCTTGAGCAGTGCGCAGATGGACTCTGGAAAGCCGAGCGCTACGAG
HC2D-KIAA1058   GTGCTGATGGAGCTCCTTGAGCAGTGCGCAGATGGACTCTGGAAAGCCGAGCGCTACGAG
HC2E            ------------------------------------AAGCCGAGCGCTACGAG
HC2F            ------------------------------------------------------------

HC2A            CTCATCGCCGACATCTACAAACTTATCATCCCCATTTATGAGAAGCGGAGGGATTT----
HC2-80          CTCATCGCCGACATCTACAAACTTATCATCCCCATTTATGAGAAGCGGAGGGATTT----
HC2B            CTCATCGCCGACATCTACAAACTTATCATCCCCATTTATGAGAAGCGGAGGGATTTTGAG
HC2C            CTCATCGCCGACATCTACAAACTTATCATCCCCATTTATGAGAAGCGGAGGGATTTTGAG
HC2D-KIAA1058   CTCATTGCCGACATCTACAAACTTATCATCCCCATTTATGAGAAGCGGAGGGATTTTGAG
HC2E            CTCATCGCCGACATCTACAAACTTATCATCCCCATTTATGAGAAGCGGAGGGATTTTGAG
HC2F            ------------------------------------------------------------

HC2A            ------------------------------------------------------------
HC2-80          ------------------------------------------------------------
HC2B            AGGCTGGCCCATCTGTATGACACGCTGCACCGGGCCTACAGCAAAGTGACCGAGGTCATG
HC2C            AGGCTGGCCCATCTGTATGACACGCTGCACCGGGCCTACAGCAAAGTGACCGAGGTCATG
HC2D-KIAA1058   AGGCTGGCCCATCTGTATGACACGCTGCACCGGGCCTACAGCAAAGTGACCGAGGTCATG
HC2E            AGGCTGGCCCATCTGTATGACACGCTGCACCGGGCCTACAGCAAAGTGACCGAGGTCATG
HC2F            ------------------------------------------------------------

HC2A            ------------------------------------------------------------
HC2-80          ------------------------------------------------------------
HC2B            CACTCGGGCCGCAGGCTTCTGGGGACCTACTTCCGGGTAGCCTTCTTCGGGCAGG-----
HC2C            CACTCGGGCCGCAGGCTTCTGGGGACCTACTTCCGGGTAGCCTTCTTCGGGCAGG-----
HC2D-KIAA1058   CACTCGGGCCGCAGGCTTCTGGGGACCTACTTCCGGGTAGCCTTCTTCGGGCAGGCAGCG
HC2E            CACTCGGGCCGCAGGCTTCTGGGGACCTACTTCCGGGTAGCCTTCTTCGGGCAGG-----
HC2F            ------------------------------------------------------------

HC2A            -------------------------------------CTTTGAAGATGAAGATGGA
HC2-80          -------------------------------------CTTTGAAGATGAAGATGGA
HC2B            ----------------------------------GATTCTTTGAAGATGAAGATGGA
HC2C            ----------------------------------GATTCTTTGAAGATGAAGATGGA
HC2D-KIAA1058   CAATACCAGTTTACAGACAGTGAAACAGATGTGGAGGGATTCTTTGAAGATGAAGATGGA
HC2E            ----------------------------------GATTCTTTGAAGATGAAGATGGA
HC2F            ------------------------------------------------------------
```

FIG. 3A (cont.)

| | |
|---|---|
| HC2A | AAGGAGTATATTTACAAGGAACCCAAACTCACACCGCTGTCGGAAATTTCTCAGAGACTC |
| HC2-80 | AAGGAGTATATTTACAAGGAACCCAAACTCACACCGCTGTCGGAAATTTCTCAGAGACTC |
| HC2B | AAGGAGTATATTTACAAGGAACCCAAACTCACACCGCTGTCGGAAATTTCTCAGAGACTC |
| HC2C | AAGGAGTATATTTACAAGGAACCCAAACTCACACCGCTGTCGGAAATTTCTCAGAGACTC |
| HC2D-KIAA1058 | AAGGAGTATATTTACAAGGAACCCAAACTCACACCGCTGTCGGAAATTTCTCAGAGACTC |
| HC2E | AAGGAGTATATTTACAAGGAACCCAAACTCACACCGCTGTCGGAAATTTCTCAGAGACTC |
| HC2F | ------------------------------------------------------------ |
| | |
| HC2A | CTTAAACTGTACTCGGATAAATTTGGTTCTGAAAATGTCAAAATGATACAGGATTCTGGC |
| HC2-80 | CTTAAACTGTACTCGGATAAATTTGGTTCTGAAAATGTCAAAATGATACAGGATTCTGGC |
| HC2B | CTTAAACTGTACTCGGATAAATTTGGTTCTGAAAATGTCAAAATGATACAGGATTCTGGC |
| HC2C | CTTAAACTGTACTCGGATAAATTTGGTTCTGAAAATGTCAAAATGACACAGGATTCTGGC |
| HC2D-KIAA1058 | CTTAAACTGTACTCGGATAAATTTGGTTCTGAAAATGTCAAAATGATACAGGATTCTGGC |
| HC2E | CTTAAACTGTACTCGGATAAATTTGGTTCTGAAAATGTCAAAATGATACAGGATTCTGGC |
| HC2F | ------------------------------------------------------------ |
| | |
| HC2A | AAGGTCAACCCTAAGGATCTGGATTCTAAGTATGCATACATCCAGGTGACTCACGTCATC |
| HC2-80 | AAGGTCAACCCTAAGGATCTGGATTCTAAGTATGCATACATCCAGGTGACTCACGTCATC |
| HC2B | AAGGTCAACCCTAAGGATCTGGATTCTAAGTATGCATACATCCAGGTGACTCACGTCATC |
| HC2C | AAGGTCAACCCTAAGGATCTGGATTCTAAGTATGCATACATCCAGGTGACTCACGTCATC |
| HC2D-KIAA1058 | AAGGTCAACCCTAAGGATCTGGATTCTAAGTATGCCTACATCCAGGTGACTCACGTCATC |
| HC2E | AAGGTCAACCCTAAGGATCTGGATTCTAAGTATGCATACATCCAGGTGACTCACGTCATC |
| HC2F | ------------------------------------------------------------ |
| | |
| HC2A | CCCTTCTTTGACGAAAAAGAGTTGCAAGAAAGGAAAACAGAGTTTGAGAGATCCCACAAC |
| HC2-80 | CCCTTCTTTGACGAAAAAGAGTTGCAAGAAAGGAAAACAGAGTTTGAGAGATCCCACAAC |
| HC2B | CCCTTCTTTGACGAAAAAGAGTTGCAAGAAAGGAAAACAGAGTTTGAGAGATCCCACAAC |
| HC2C | CCCTTCTTTGACGAAAAAGAGTTGCAAGAAAGGAAAACAGAGTTTGAGAGATCCCACAAC |
| HC2D-KIAA1058 | CCCTTCTTTGACGAAAAAGAGTTGCAAGAAAGGAAAACAGAGTTTGAGAGATCCCACAAC |
| HC2E | CCCTTCTTTGACGAAAAAGAGTTGCAAGAAAGGAAAACAGAGTTTGAGAGATCCCACAAC |
| HC2F | ------------------------------------------------------------ |
| | |
| HC2A | ATCCGCCGCTTCATGTTTGAGATGCCATTTACGCAGACCGGGAAGAGGCAGGGCGGGGTG |
| HC2-80 | ATCCGCCGCTTCATGTTTGAGATGCCATTTACGCAGACCGGGAAGAGGCAGGGCGGGGTG |
| HC2B | ATCCGCCGCTTCATGTTTGAGATGCCATTTACGCAGACCGGGAAGAGGCAGGGCGGGGTG |
| HC2C | ATCCGCCGCTTCATGTTTGAGATGCCATTTACGCAGACCGGGAAGAGGCAGGGCGGGGTG |
| HC2D-KIAA1058 | ATCCGCCGCTTCATGTTTGAGATGCCATTTACGCAGACCGGGAAGAGGCAGGGCGGGGTG |
| HC2E | ATCCGCCGCTTCATGTTTGAGATGCCATTTACGCAGACCGGGAAGAGGCAGGGCGGGGTG |
| HC2F | ------------------------------------------------------------ |
| | |
| HC2A | GAAGAGCAGTGCAAACGGCGCACCATCCTGACAGCCATACACTGCTTCCCTTATGTGAAG |
| HC2-80 | GAAGAGCAGTGCAAACGGCGCACCATCCTGACAGCCATACACTGCTTCCCTTATGTGAAG |
| HC2B | GAAGAGCAGTGCAAACGGCGCACCATCCTGACAGCCATACACTGCTTCCCTTATGTGAAG |
| HC2C | GAAGAGCAGTGCAAACGGCGCACCATCCTGACAGCCATACACTGCTTCCCTTATGTGAAG |
| HC2D-KIAA1058 | GAAGAGCAGTGCAAACGGCGCACCATCCTGACAGCCATACACTGCTTCCCTTATGTGAAG |
| HC2E | GAAGAGCAGTGCAAACGGCGCACCATCCTGACAGCCATACACTGCTTCCCTTATGTGAAG |
| HC2F | ------------------------------------------------------------ |

FIG. 3A (cont.)

| | |
|---|---|
| HC2A | AAGCGCATCCCTGTCATGTACCAGCACCACACTGACCTGAACCCCATCGAGGTGGCCATT |
| HC2-80 | AAGCGCATCCCTGTCATGTACCAGCACCACACTGACCTGAACCCCATCGAGGTGGCCATT |
| HC2B | AAGCGCATCCCTGTCATGTACCAGCACCACACTGACCTGAACCCCATCGAGGTGGCCATT |
| HC2C | AAGCGCATCCCTTTCATGTACCAGCACCACACTGACCTGAACCCCATCGAGGT--CCATT |
| HC2D-KIAA1058 | AAGCGCATCCCTGTCATGTACCAGCACCACACTGACCTGAACCCCATCGAGGTGGCCATT |
| HC2E | AAGCGCATCCCTGTCATGTACCAGCACCACACTGACCTGAACCCCATCGAGGTGGCCATT |
| HC2F | ------------------------------------------------------------ |
| | |
| HC2A | GACGAGATGAGTAAGAAGGTGGCGGAGCTCCGGCAGCTGTGCTCCTCGGCCGAGGTGGAC |
| HC2-80 | GACGAGATGAGTAAGAAGGTGGCGGAGCTCCGGCAGCTGTGCTCCTCGGCCGAGGTGGAC |
| HC2B | GACGAGATGAGTAAGAAGGTGGCGGAGCTCCGGCAGCTGTGCTCCTCGGCCGAGGTGGAC |
| HC2C | GACGAGATGAGTAAGAAGGTGGCGGAGCTCCGGCAGCTGTGCTCCTCGGCCGAGGTGGAC |
| HC2D-KIAA1058 | GACGAGATGAGTAAGAAGGTGGCGGAGCTCCGGCAGCTGTGCTCCTCGGCCGAGGTGGAC |
| HC2E | GACGAGATGAGTAAGAAGGTGGCGGAGCTCCGGCAGCTGTGCTCCTCGGCCGAGGTGGAC |
| HC2F | ------------------------------------------------------------ |
| | |
| HC2A | ATGATCAAACTGCAGCTCAAACTCCAGGGCAGCGTGAGTGTTCAGGTCAATGCTGGCCCA |
| HC2-80 | ATGATCAAACTGCAGCTCAAACTCCAGGGCAGCGTGAGTGTTCAGGTCAATGCTGGCCCA |
| HC2B | ATGATCAAACTGCAGCTCAAACTCCAGGGCAGCGTGAGTGTTCAGGTCAATGCTGGCCCA |
| HC2C | ATGATCAAACTGCAGCTCAAACTCCAGGGCAGCGTGAGTGTTCAGGTCAATGCTGGCCCA |
| HC2D-KIAA1058 | ATGATCAAACTGCAGCTCAAACTCCAGGGCAGCGTGAGTGTTCAGGTCAATGCTGGCCCA |
| HC2E | ATGATCAAACTGCAGCTCAAACTCCAGGGCAGCGTGAGTGTTCAGGTCAATGCTGGCCCA |
| HC2F | ------------------------------------------------------------ |
| | |
| HC2A | CTAGCATATGCGCGAGCTTTCTTAGATGATACAAACACAAAGCGATATCCTGACAATAAA |
| HC2-80 | CTAGCATATGCGCGAGCTTTCTTAGATGATACAAACACAAAGCGATATCCTGACAATAAA |
| HC2B | CTAGCATATGCGCGAGCTTTCTTAGATGATACAAACACAAAGCGATATCCTGACAATAAA |
| HC2C | CTAGCATATGCGCGAGCTTTCTTAGATGATACAAACACAAAGCGATATCCTGACAATAAA |
| HC2D-KIAA1058 | CTAGCATATGCGCGAGCTTTCTTAGATGATACAAACACAAAGCGATATCCTGACAATAAA |
| HC2E | CTAGCATATGCGCGAGCTTTCTTAGATGATACAAACACAAAGCGATATCCTGACAATAAA |
| HC2F | ------------------------------------------------------------ |
| | |
| HC2A | GTGAAGCTGCTTAAGGAAGTTTTCAGGCAATTTGTGGAAGCTTGCGGTCAAGCCTTAGCG |
| HC2-80 | GTGAAGCTGCTTAAGGAAGTTTTCAGGCAATTTGTGGAAGCTTGCGGTCAAGCCTTAGCG |
| HC2B | GTGAAGCTGCTTAAGGAAGTTTTCAGGCAATTTGTGGAAGCTTGCGGTCAAGCCTTAGCG |
| HC2C | GTGAAGCTGCTTAAGGAAGTTTTCAGGCAATTTGTGGAAGCTTGCGGTCAAGCCTTAGCG |
| HC2D-KIAA1058 | GTGAAGCTGCTTAAGGAAGTTTTCAGGCAATTTGTGGAAGCTTGCGGTCAAGCCTTAGCG |
| HC2E | GTGAAGCTGCTTAAGGAAGTTTTCAGGCAATTTGTGGAAGCTTGCGGTCAAGCCTTAGCG |
| HC2F | ------------------------------------------------------------ |
| | |
| HC2A | GTAAACGAACGTCTGATTAAAGAAGACCAGCTCGAGTATCAGGAAGAAATGAAAGCCAAC |
| HC2-80 | GTAAACGAACGTCTGATTAAAGAAGACCAGCTCGAGTATCAGGAAGAAATGAAAGCCAAC |
| HC2B | GTAAACGAACGTCTGATTAAAGAAGACCAGCTCGAGTATCAGGAAGAAATGAAAGCCAAC |
| HC2C | GTAAACGAACGTCTGATTAAAGAAGACCAGCTCGAGTATCAGGAAGAAATGAAAGCCAAC |
| HC2D-KIAA1058 | GTAAACGAACGTCTGATTAAAGAAGACCAGCTCGAGTATCAGGAAGAAATGAAAGCCAAC |
| HC2E | GTAAACGAACGTCTGATTAAAGAAGACCAGCTCGAGTATCAGGAAGAAATGAAAGCCAAC |
| HC2F | ------------------------------------------------------------ |

FIG. 3A (cont.)

| | |
|---|---|
| HC2A | TACAGGGAAATGGCGAAGGAGCTTTCTGAAATCATGCATGAGCAG--------ATCTGCC |
| HC2-80 | TACAGGGAAATGGCGAAGGAGCTTTCTGAAATCATGCATGAGCAG--------ATCTGCC |
| HC2B | TACAGGGAAATGGCGAAGGAGCTTTCTGAAATCATGCATGAGCAG--------ATCTGCC |
| HC2C | TACAGGGAAATGGCGAAGGAGCTTTCTGAAATCATGCATGAGCAG--------ATCTGCC |
| HC2D-KIAA1058 | TACAGGGAAATGGCGAAGGAGCTTTCTGAAATCATGCATGAGCAGCTGGGATGATCTGCC |
| HC2E | TACAGGGAAATGGCGAAGGAGCTTTCTGAAATCATGCATGAGCAG--------ATCTGCC |
| HC2F | ------------------------------------------------------------ |

| | |
|---|---|
| HC2A | CCCTGGAGGAGAAGACGAGCGTCTTACCGAATTCCCTTCACATCTTCAACGCCATCAGTG |
| HC2-80 | CCCTGGAGGAGAAGACGAGCGTCTTACCGAATTCCCTTCACATCTTCAACGCCATCAGTG |
| HC2B | CCCTGGAGGAGAAGACGAGCGTCTTACCGAATTCCCTTCACATCTTCAACGCCATCAGTG |
| HC2C | CCCTGGAGGAGAAGACGAGCGTCTTACCGAATTCCCTTCACATCTTCAACGCCATCAGTG |
| HC2D-KIAA1058 | CCCTGGAGGAGAAGACGAGCGTCTTACCGAATTCCCTTCACATCTTCAACGCCATCAGTG |
| HC2E | CCCTGGAGGAGAAGACGAGCGTCTTACCGAATTCCCTTCACATCTTCAACGCCATCAGTG |
| HC2F | ------------------------------------------------------------ |

| | |
|---|---|
| HC2A | GGACTCCAACAAGCACAATGGTTCACGGGATGACCAGCTCGTCTTCGGTCGTGTGATTAC |
| HC2-80 | GGACTCCAACAAGCACAATGGTTCACGGGATGACCAGCTCGTCTTCGGTCGTGTGATTAC |
| HC2B | GGACTCCAACAAGCACAATGGTTCACGGGATGACCAGCTCGTCTTCGGTCGTGTGA---- |
| HC2C | GGACTCCAACAAGCACAATGGTTCACGGGATGACCAGCTCGTCTTCGGTCGTGTGA---- |
| HC2D-KIAA1058 | GGACTCCAACAAGCACAATGGTTCACGGGATGACCAGCTCGTCTTCGGTCGTGTGATTAC |
| HC2E | GGACTCCAACAAGCACAATGGTTCACGGGATGACCAGCTCGTCTCTCGGTCGTGTGA---- |
| HC2F | ------------------------------------------------------------ |

| | |
|---|---|
| HC2A | ATCTCATGGCCCGTGTGTGGGGACTTGCTTTGTCATTTGCAAACTCAGGATGCTTTCCAA |
| HC2-80 | ATCTCATGGCCCGTGTGTGGGGACTTGCTTTGTCATTTGCAAACTCAGGATGCTTTCCAA |
| HC2B | ------------------------------------------------------------ |
| HC2C | ------------------------------------------------------------ |
| HC2D-KIAA1058 | ATCTCATGGCCCGTGTGTGGGGACTTGCTTTGTCATTTGCAAACTCAGGATGCTTTCCAA |
| HC2E | ------------------------------------------------------------ |
| HC2F | ------------------------------------------------------------ |

| | |
|---|---|
| HC2A | AGCCAATCACTGGGGAGACCGAGCACAGGGAGGACCAAGGGGAAGGGGAGAGAAAGGAAA |
| HC2-80 | AGCCAATCACTGGGGAGACCGAGCACAGGGAGGACCAAGGGGAAGGGGAGAGAAAGGAAA |
| HC2B | ------------------------------------------------------------ |
| HC2C | ------------------------------------------------------------ |
| HC2D-KIAA1058 | AGCCAATCACTGGGGAGACCGAGCACAGGGAGGACCA-GGGGAAGGGGAGAGAAAGGAAA |
| HC2E | ------------------------------------------------------------ |
| HC2F | ------------------------------------------------------------ |

| | |
|---|---|
| HC2A | TAAAGAACAACGTTATTTCTTAACAGACTTTCTATAGGAGTTGTAAGAAGGTGCACATAT |
| HC2-80 | TAAAGAACAACGTTATTTCTTAACAGACTTTCTATAGGAGTTGTAAGAAGGTGCACATAT |
| HC2B | ------------------------------------------------------------ |
| HC2C | ------------------------------------------------------------ |
| HC2D-KIAA1058 | TAAAGAACAACGTTATTTCTTAACAGACTTTCTATAGGAGTTGTAAGAAGGTGCACATAT |
| HC2E | ------------------------------------------------------------ |
| HC2F | ------------------------------------------------------------ |

FIG. 3A (cont.)

```
HC2A           TTTTTTAAATCTCACTGGCAATATTCAAAGTTTTCATTGTGTCTTAACAAAGGTGTGGTA
HC2-80         TTTTTTAAATCTCACTGGCAATATTCAAAGTTTTCATTGTGTCTTAACAAAGGTGTGGTA
HC2B           ------------------------------------------------------------
HC2C           ------------------------------------------------------------
HC2D-KIAA1058  TTTTTTAAATCTCACTGGCAATATTCAAAGTTTTCATTGTGTCTTAACAAAGGTGTGGTA
HC2E           ------------------------------------------------------------
HC2F           ------------------------------------------------------------

HC2A           GACACTCTTGAGCTGGACTTAGATTTTATTCTTCCTTGCAGAGTAGTGTTAGAATAGATG
HC2-80         GACACTCTTGAGCTGGACTTAGATTTTATTCTTCCTTGCAGAGTAGTGTTAGAATAGATG
HC2B           ------------------------------------------------------------
HC2C           ------------------------------------------------------------
HC2D-KIAA1058  GACACTCTTGAGCTGGACTTAGATTTTATTCTTCCTTGCAGAGTAGTGTTAGAATAGATG
HC2E           ------------------------------------------------------------
HC2F           ------------------------------------------------------------

HC2A           GCCTACAGAAAAAAAAGGTTCTGGGATCTACATGGCAGGGAGGGCTGCACTGACATTGAT
HC2-80         GCCTACAGAAAAAAAAGGTTCTGGGATCTACATGGCAGGGAGGGCTGCACTGACATTGAT
HC2B           ------------------------------------------------------------
HC2C           ------------------------------------------------------------
HC2D-KIAA1058  GCCTACAGAAAAAAAAGGTTCTGGGATCTACATGGCAGGGAGGGCTGCACTGACATTGAT
HC2E           ------------------------------------------------------------
HC2F           ------------------------------------------------------------

HC2A           GCCTGGGGGACCTTTTGCCTCGACTCGTGCCGGAAATCTGATCGTAATCAGGGTACAGAA
HC2-80         GCCTGGGGGACCTTTTGCCTCGACTCGTGCCGGAAATCTGATCGTAATCAGGGTACAGAA
HC2B           ------------------------------------------------------------
HC2C           ------------------------------------------------------------
HC2D-KIAA1058  GCCTGGGGGACCTTTTGCCTCGAGGCTGAGCTGGAAAATCTTGAAAATATTTTTT----T
HC2E           ------------------------------------------------------------
HC2F           ------------------------------------------------------------

HC2A           CTTACTAGTTTTGTCTAGGAGTATGTTGTATGACTAGGATTTGTGCTATTATCTCATTCA
HC2-80         CTTACTAGTTTTGTCTAGGAGTATGTTGTATGACTAGGATTTGTGCTATTATCTCATTCA
HC2B           ------------------------------------------------------------
HC2C           ------------------------------------------------------------
HC2D-KIAA1058  TTTCCTGTGGCACATTCAGGTTGAATACAAGAACTATTTTTGTGACTAGTTTTTGATGAC
HC2E           ------------------------------------------------------------
HC2F           ------------------------------------------------------------

HC2A           ACAACATAGAGCAAGAATAGTGAGCTAACTGAGCTAGACACTCAATTAATCCGCTACTGG
HC2-80         ACAACATAGAGCAAGAATAGTGAGCTAACTGAGCTAGACACTCAATTAATCCGCTACTGG
HC2B           ------------------------------------------------------------
HC2C           ------------------------------------------------------------
HC2D-KIAA1058  CTAAGGGAACTGACCATTGTAATTTTTGTACCAGTGAACCAGGAGATTTAGTGCTTTTAT
HC2E           ------------------------------------------------------------
HC2F           ------------------------------------------------------------
```

FIG. 3A (cont.)

```
HC2A          CTTCAAGTCAGAACTTTGTCATTAATCATCGACTCCGGGACGGTCATATATGTATTACAT
HC2-80        CTTCAAGTCAGAACTTTGTCATTAATCATCGACTCCGGGACGGTCATATATGTATTACAT
HC2B          ------------------------------------------------------------
HC2C          ------------------------------------------------------------
HC2D-KIAA1058 ATTCATTTCCTTGCATTTAAGAAAATATGAAAGCTTAAGGAATTATGTGAGCTTAAAACT
HC2E          ------------------------------------------------------------
HC2F          ------------------------------------------------------------

HC2A          TTCTACATTTTTAATACTCACATGGGCTTATGCATTAAGTTTAATTGTGATAAATTTGTG
HC2-80        TTCTACATTTTTAATACTCACATGGGCTTATGCATTAAGTTTAATTGTGATAAATTTGTG
HC2B          ------------------------------------------------------------
HC2C          ------------------------------------------------------------
HC2D-KIAA1058 AGTCAAGCAGTTTAGAACCAAAGGCCTATATTAATAACCGCAACTATGCTGAAAAGTACA
HC2E          ------------------------------------------------------------
HC2F          ------------------------------------------------------------

HC2A          CTGGTCCAGTATATGCAATACACTTTAATGGTTTATTCTTGTCATAAAAATGTGCAATAT
HC2-80        CTGGTCCAGTATATGCAATACACTTTAATGGTTTATTCTTGTCATAAAAATGTGCAATAT
HC2B          ------------------------------------------------------------
HC2C          ------------------------------------------------------------
HC2D-KIAA1058 AAGTAGTACAGTATATTGTTATGTACATATCATTGTTAATACAGTCCTGGCATTCTGTAC
HC2E          ------------------------------------------------------------
HC2F          ------------------------------------------------------------

HC2A          GGAGATGTATACAAGTCTTTACT-------------------------------------
HC2-80        GGAGATGTATACAAGTCTTTACT-------------------------------------
HC2B          ------------------------------------------------------------
HC2C          ------------------------------------------------------------
HC2D-KIAA1058 ATATATGTATTACATTTCTACATTTTTAATACTCACATGGGCTTATGCATTAAGTTTAAT
HC2E          ------------------------------------------------------------
HC2F          ------------------------------------------------------------

HC2A          ------------------------------------------------------------
HC2-80        ------------------------------------------------------------
HC2B          ------------------------------------------------------------
HC2C          ------------------------------------------------------------
HC2D-KIAA1058 TGTGATAAATTTGTGCTGTTCCAGTATATGCAATACACTTTAATGTTTTATTCTTGTACA
HC2E          ------------------------------------------------------------
HC2F          ------------------------------------------------------------

HC2A          ------------------------------------------------------------
HC2-80        ------------------------------------------------------------
HC2B          ------------------------------------------------------------
HC2C          ------------------------------------------------------------
HC2D-KIAA1058 TAAAAATGTGCAATATGGAGATGTATACAGTCTTTACTATATTAGGTTTATAAACAGTTT
HC2E          ------------------------------------------------------------
HC2F          ------------------------------------------------------------
```

FIG. 3A (cont.)

```
HC2A              ----------------------------------------------------------------
HC2-80            ----------------------------------------------------------------
HC2B              ----------------------------------------------------------------
HC2C              ----------------------------------------------------------------
HC2D-KIAA1058     TAAGAATTTCATCCTTTTGCCAAAATGGTGGAGTATGTAATTGGTAAATCATAAATCCTG
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     TGGTGAATGGTGGTGTACTTTAAAGCTGTCACCATGTTATATTTTCTTTTAAGACATTAA
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     TTTAGTAATTTTATATTTGGGAAAATAAAGGTTTTTAATTTTATTTAACTGGAATCACTG
HC2E              ----------------------------------------------------------------
HC2F              ----------------------------------------------------------------

HC2A              ----------------------------------------------------------------
HC2-80            ----------------------------------------------------------------
HC2B              ----------------------------------------------------------------
HC2C              ----------------------------------------------------------------
HC2D-KIAA1058     CCCTGCTGTAATTAAACATTCTGTACCACATCTGTATTAAAAAGACATTGCTGACC
HC2E              ----------------------------------------------------------------
HC2F              ----------------------------------------------------------------
```

FIG. 3A (cont.)

| | |
|---|---|
| HC2A | CTTCAAGTCAGAACTTTGTCATTAATCATCGACTCCGGGACGGTCATATATGTATTACAT |
| HC2-80 | CTTCAAGTCAGAACTTTGTCATTAATCATCGACTCCGGGACGGTCATATATGTATTACAT |
| HC2B | ------------------------------------------------------------ |
| HC2C | ------------------------------------------------------------ |
| HC2D-KIAA1058 | ATTCATTTCCTTGCATTTAAGAAAATATGAAAGCTTAAGGAATTATGTGAGCTTAAAACT |
| HC2E | ------------------------------------------------------------ |
| HC2F | ------------------------------------------------------------ |
| | |
| HC2A | TTCTACATTTTTAATACTCACATGGGCTTATGCATTAAGTTTAATTGTGATAAATTTGTG |
| HC2-80 | TTCTACATTTTTAATACTCACATGGGCTTATGCATTAAGTTTAATTGTGATAAATTTGTG |
| HC2B | ------------------------------------------------------------ |
| HC2C | ------------------------------------------------------------ |
| HC2D-KIAA1058 | AGTCAAGCAGTTTAGAACCAAAGGCCTATATTAATAACCGCAACTATGCTGAAAAGTACA |
| HC2E | ------------------------------------------------------------ |
| HC2F | ------------------------------------------------------------ |
| | |
| HC2A | CTGGTCCAGTATATGCAATACACTTTAATGGTTTATTCTTGTCATAAAAATGTGCAATAT |
| HC2-80 | CTGGTCCAGTATATGCAATACACTTTAATGGTTTATTCTTGTCATAAAAATGTGCAATAT |
| HC2B | ------------------------------------------------------------ |
| HC2C | ------------------------------------------------------------ |
| HC2D-KIAA1058 | AAGTAGTACAGTATATTGTTATGTACATATCATTGTTAATACAGTCCTGGCATTCTGTAC |
| HC2E | ------------------------------------------------------------ |
| HC2F | ------------------------------------------------------------ |
| | |
| HC2A | GGAGATGTATACAAGTCTTTACT------------------------------------- |
| HC2-80 | GGAGATGTATACAAGTCTTTACT------------------------------------- |
| HC2B | ------------------------------------------------------------ |
| HC2C | ------------------------------------------------------------ |
| HC2D-KIAA1058 | ATATATGTATTACATTTCTACATTTTTAATACTCACATGGGCTTATGCATTAAGTTTAAT |
| HC2E | ------------------------------------------------------------ |
| HC2F | ------------------------------------------------------------ |
| | |
| HC2A | ------------------------------------------------------------ |
| HC2-80 | ------------------------------------------------------------ |
| HC2B | ------------------------------------------------------------ |
| HC2C | ------------------------------------------------------------ |
| HC2D-KIAA1058 | TGTGATAAATTTGTGCTGTTCCAGTATATGCAATACACTTTAATGTTTTATTCTTGTACA |
| HC2E | ------------------------------------------------------------ |
| HC2F | ------------------------------------------------------------ |
| | |
| HC2A | ------------------------------------------------------------ |
| HC2-80 | ------------------------------------------------------------ |
| HC2B | ------------------------------------------------------------ |
| HC2C | ------------------------------------------------------------ |
| HC2D-KIAA1058 | TAAAAATGTGCAATATGGAGATGTATACAGTCTTTACTATATTAGGTTTATAAACAGTTT |
| HC2E | ------------------------------------------------------------ |
| HC2F | ------------------------------------------------------------ |

FIG. 3A (cont.)

```
HC2A              ------------------------------------------------------------
HC2-80            ------------------------------------------------------------
HC2B              ------------------------------------------------------------
HC2C              ------------------------------------------------------------
HC2D-KIAA1058     TAAGAATTTCATCCTTTTGCCAAAATGGTGGAGTATGTAATTGGTAAATCATAAATCCTG
HC2E              ------------------------------------------------------------
HC2F              ------------------------------------------------------------

HC2A              ------------------------------------------------------------
HC2-80            ------------------------------------------------------------
HC2B              ------------------------------------------------------------
HC2C              ------------------------------------------------------------
HC2D-KIAA1058     TGGTGAATGGTGGTGTACTTTAAAGCTGTCACCATGTTATATTTTCTTTTAAGACATTAA
HC2E              ------------------------------------------------------------
HC2F              ------------------------------------------------------------

HC2A              ------------------------------------------------------------
HC2-80            ------------------------------------------------------------
HC2B              ------------------------------------------------------------
HC2C              ------------------------------------------------------------
HC2D-KIAA1058     TTTAGTAATTTTATATTTGGGAAAATAAAGGTTTTTAATTTTATTTAACTGGAATCACTG
HC2E              ------------------------------------------------------------
HC2F              ------------------------------------------------------------

HC2A              ------------------------------------------------------------
HC2-80            ------------------------------------------------------------
HC2B              ------------------------------------------------------------
HC2C              ------------------------------------------------------------
HC2D-KIAA1058     CCCTGCTGTAATTAAACATTCTGTACCACATCTGTATTAAAAAGACATTGCTGACC
HC2E              ------------------------------------------------------------
HC2F              ------------------------------------------------------
```

FIG. 3A (cont.)

```
HC2A       ----------------------------------------------------------
HC2A-80    ----------------------------------------------------------
HC2B       ----------------------------------------------------------
HC2C       ----------------------------------------------------------
HC2D       ASGNLDKNARFSAIYRQDSNKLSNDDMLKLLADFRKPEKMAKLPVILGNLDITIDNVSSD
HC2E       ----------------------------------------------------------
HC2F       ----------------------------------------------------------

HC2A       ----------------------------------------------------------
HC2A-80    ----------------------------------------------------------
HC2B       ----------------------------------------------------------
HC2C       ----------------------------------------------------------
HC2D       FPNYVNSSYIPTKQFETCSKTPITFEVEEFVPCIPKHTQPYTIYTNHLYVYPKYLKYDSQ
HC2E       ----------------------------------------------------------
HC2F       ----------------------------------------------------------

HC2A       -----------------------------------------VLHHHQNPEFYDEIK
HC2A-80    --------------------------------------------------------
HC2B       --------------------------------------------------------
HC2C       --------------------------------------------------------
HC2D       KSFAKARNIAICIEFKDSDEEDSQPLKCIYGRPGGPVFTRSAFAAVLHHHQNPEFYDEIK
HC2E       --------------------------------------------------------
HC2F       --------------------------------------------------------

HC2A       IELPTQLHEKHHLLLTFFHVSCDNSSKGSTKKRDVVETQVGYSWLPLLKDGRVVTSEQHI
HC2A-80    ----------------------------------------------------------
HC2B       ----------------------------------------------------------
HC2C       ----------------------------------------------------------
HC2D       IELPTQLHEKHHLLLTFFHVSCDNSSKGSTKKRDVVETQVGYSWLPLLKDGRVVTSEQHI
HC2E       ----------------------------------------------------------
HC2F       ----------------------------------------------------------

HC2A       PVSANLPSGYLGYQELGMGRHYGPEIKWVDGGKPLLKISTHLVSTVYTQDQHLHNFFQYC
HC2A-80    ----------------------------------------------------------
HC2B       ----------------------------------------------------------
HC2C       ----------------------------------------------------------
HC2D       PVSANLPSGYLGYQELGMGRHYGPEIKWVDGGKPLLKISTHLVSTVYTQDQHLHNFFQYC
HC2E       ----------------------------------------------------------
HC2F       ----------------------------------------------------------

HC2A       QKTESGAQALGNELVKYLKSLHAMEGHVMIAFLPTILNQLFRVLTRATQEEVAVNVTRVI
HC2A-80    ----------------------------------------------------------
HC2B       -------------------AMEGHVMIAFLPTILNQLFRVLTRATQEEVAVNVTRVI
HC2C       ----------------------------------------------------------
HC2D       QKTESGAQALGNELVKYLKSLHAMEGHVMIAFLPTILNQLFRVLTRATQEEVAVNVTRVI
HC2E       -------------------AMEGHVMIAFLPTILNQLFRVLTRATQEEVAVNVTRVI
HC2F       ----------------------------------------------------------
```

Fig. 3B

| | |
|---|---|
| HC2A | IHVVAQCHEEGLESHLRSYVKYAYKAEPYVASEYKTVHEELTKSMTTILKPSADFLTSNK |
| HC2A-80 | ------------------------------------------------------------ |
| HC2B | IHVVAQCHEEGLESHLRSYVKYAYKAEPYVASEYKTVHEELTKSMTTILKPSADFLTSNK |
| HC2C | ------------------------------------------------------------ |
| HC2D | IHVVAQCHEEGLESHLRSYVKYAYKAEPYVASEYKTVHEELTKSMTTILKPSADFLTSNK |
| HC2E | IHVVAQCHEEGLESHLRSYVKYAYKAEPYVASEYKTVHEELTKSMTTILKPSADFLTSNK |
| HC2F | ------------------------------------------------------------ |
| | |
| HC2A | LLRYSWFFFDVLIKSMAQHLIENSKVKLLRNQRFPASYHHAAETVVNMLMPHITQKFGDN |
| HC2A-80 | ------------------------------------------------------------ |
| HC2B | LLRYSWFFFDVLIKSMAQHLIENSKVKLLRNQRFPASYHHAAETVVNMLMPHITQKFGDN |
| HC2C | ------------------------------------------------------------ |
| HC2D | LLKYSWFFFDVLIKSMAQHLIENSKVKLLRNQRFPASYHHAVETVVNMLMPHITQKFRDN |
| HC2E | LLRYSWFFFDVLIKSMAQHLIENSKVKLLRNQRFPASYHHAAETVVNMLMPHITQKFGDN |
| HC2F | ------------------------------------------------------------ |
| | |
| HC2A | PEASKNANHSLAVFIKRCFTFMDRGFVFKQINNYISCFAPGDPKTLFEYKFEFLRVVCNH |
| HC2A-80 | ------------------------------------------------------------ |
| HC2B | PEASKNANHSLAVFIKRCFTFMDRGFVFKQINNYISCFAPGDPKTLFEYKFEFLRVVCNH |
| HC2C | ------------------------------------------------------------ |
| HC2D | PEASKNANHSLAVFIKRCFTFMDRGFVFKQINNYISCFAPGDPKTLFEYKFEFLRVVCNH |
| HC2E | PEASKNANHSLAVFIKRCFTFMDRGFVFKQINNYISCFAPGDPKTLFEYKFEFLRVVCNH |
| HC2F | ------------------------------------------------------------ |
| | |
| HC2A | EHYIPLNLPMPFGKGRIQRYQDLQLDYSLTDEFCRNHFLVGLLLREVGTALQEFREVRLI |
| HC2A-80 | ---------------------QLDYSLTDEFCRNHFLVGLLLREVGTALQEFREVRLI |
| HC2B | EHYIPLNLPMPFGKGRIQRYQDLQLDYSLTDEFCRNHFLVGLLLREVGTALQEFREVRLI |
| HC2C | ------------------------------------------------------------ |
| HC2D | EHYIPLNLPMPFGKGRIQRYQDLQLDYSLTDEFCRNHFLVGLLLREVGTALQEFREVRLI |
| HC2E | EHYIPLNLPMPFGKGRIQRYQDLQLDYSLTDEFCRNHFLVGLLLREVGTALQEFREVRLI |
| HC2F | ------------------------------------------------------------ |
| | |
| HC2A | AISVLKNLLIKHSFDDRYASRSHQARIATLYLPLFGLLIENVQRINVRDVSPFPVNAGMT |
| HC2A-80 | AISVLKNLLIKHSFDDRYASRSHQARIATLYLPLFGLLIENVQRINVRDVSPFPVNAGMT |
| HC2B | AISVLKNLLIKHSFDDRYASRSHQARIATLYLPLFGLLIENVQRINVRDVSPFPVNAGMT |
| HC2C | ------------------------------------------------------------ |
| HC2D | AISVLKNLLIKHSFDDRYASRSHQARIATLYLPLFGLLIENVQRINVRDVSPFPVNAGMT |
| HC2E | AISVLKNLLIKHSFDDRYASRSHQARIATLYLPLFGLLIENVQRINVRDVSPFPVNAGMT |
| HC2F | ------------------------------------------------------------ |
| | |
| HC2A | VKDESLALPAVNPLVTPQKGSTLDNSLHKDLLGAISGIASPYTTSTPNINSVRNADSRGS |
| HC2A-80 | VKDESLALPAVNPLVTPQKGSTLDNSLHKDLLGAISGIASPYTTSTPNINSVRNADSRGS |
| HC2B | VKDESLALPAVNPLVTPQKGSTLDNSLHKDLLGAISGIASPYTTSTPNINSVRNADSRGS |
| HC2C | ------------------------------------------------------------ |
| HC2D | VKDESLALPAVNPLVTPQKGSTLDNSLHKDLLGAISGIASPYTTSTPNINSVRNADSRGS |
| HC2E | VKDESLALPAVNPLVTPQKGSTLDNSLHKDLLGAISGIASPYTTSTPNINSVRNADSRGS |
| HC2F | ---------------------------------------------------ADSRGS |

FIG. 3B (cont.)

```
HC2A       LISTDSGNSLPERNSEKSNSLDKHQQSSTLGNSVVRCDKLDQSEIKSLLMCFLYILKSMS
HC2A-80    LISTDSGNSLPERNSEKSNSLDKHQQSSTLGNSVVRCDKLDQSEIKSLLMCFLYILKSMS
HC2B       LISTDSGNSLPERNSEKSNSLDKHQQSSTLGNSVVRCDKLDQSEIKSLLMCFLYILKSMS
HC2C       ------------------------------------------------------------
HC2D       LISTDSGNSLPERNSEKSNSLDKHQQSSTLGNSVVRCDKLDQSEIKSLLMCFLYILKSMS
HC2E       LISTDSGNSLPERNSEKSNSLDKHQQSSTLGNSVVRCDKLDQSEIKSLLMCFLYILKSMS
HC2F       LISTDSGNSLPERNSEKSNSLDKHQQSSTLGNSVVRCDKLDQSEIKSLLMCFLYILKSMS

HC2A       DDALFTYWNKASTSELMDFFTISEVCLHQFQYMGKRYIARNQEGLGPIVHDRKSQTLPVS
HC2A-80    DDALFTYWNKASTSELMDFFTISEVCLHQFQYMGKRYIARNQEGLGPIVHDRKSQTLPVS
HC2B       DDALFTYWNKASTSELMDFFTISEVCLHQFQYMGKRYIARNQEGLGPIVHDRKSQTLPVS
HC2C       ------------------------------------------------------------
HC2D       DDALFTYWNKASTSELMDFFTISEVCLHQFQYMGKRYIAR--------------------
HC2E       DDALFTYWNKASTSELMDFFTISEVCLHQFQYMGKRYIARNQEGLGPIVHDRKSQTLPVS
HC2F       DDALFTYWNKASTSELMDFFTISEVCLHQFQYMGKRYIAS-------VR--KISSVLGIS

HC2A       RNRTGMMHARLQQLGSLDNSLTFNHSYGHSDADVLHQSLLEANIATEVCLTALDTLSLFT
HC2A-80    RNRTGMMHARLQQLGSLDNSLTFNHSYGHSDADVLHQSLLEANIATEVCLTALDTLSLFT
HC2B       RNRTGMMHARLQQLGSLDNSLTFNHSYGHSDADVLHQSLLEANIATEVCLTALDTLSLFT
HC2C       ------------------------------------------------------------
HC2D       ---TGMMHARLQQLGSLDNSLTFNHSYGHSDADVLHQSLLEANIATEVCLTALDTLSLFT
HC2E       RNRTGMMHARLQQLGSLDNSLTFNHSYGHSDADVLHQSLLEANIATEVCLTALDTLSLFT
HC2F       V--------------D-NG-----YGHSDADVLHQSLLEANIATEVCLTALDTLSLFT

HC2A       LAFKNQLLADHGHNPLMKKVFDVYLCFLQKHQSETALKNVFTALRSLIYKFPSTFYEGRA
HC2A-80    LAFKNQLLADHGHNPLMKKVFDVYLCFLQKHQSETALKNVFTALRSLIYKFPSTFYEGRA
HC2B       LAFK--LLADHGHNPLMKKVFDVYLCFLQKHQSETALKNVFTALRSLIYKFPSTFYEGRA
HC2C       ------------------------------------------------------------
HC2D       LAFKNQLLADHGHNPLMKKVFDVYLCFLQKHQSETALKNVFTALRSLIYKFPSTFYEGRA
HC2E       LAFKNQLLADHGHNPLMKKVFDVYLCFLQKHQSETALKNVFTALRSLIYKFPSTFYEGRA
HC2F       LAFKNQLLADHGHNPLMKKK----------------------------------------

HC2A       DMCAALCYEILKCCNSKLSSIRTEASQLLYFLMRNNFDYTGKKSFVRTHLQVIISVSQLI
HC2A-80    DMCAALCYEILKCCNSKLSSIRTEASQLLYFLMRNNFDYTGKKSFVRTHLQVIISVSQLI
HC2B       DMCAALCYEILKCCNSKLSSIRTEASQLLYFLMRNNFDYTGKKSFVRTHLQVIISVSQLI
HC2C       ------------------------------------------------------------
HC2D       DMCAALCYEILKCCNSKLSSIRTEASQLLYFLMRNNFDYTGKKSFVRTHLQVIISVSQLI
HC2E       DMCAALCYEILKCCNSKLSSIRTEASQLLYFLMRNNFDYTGKKSFVRTHLQVIISVSQLI
HC2F       ------------------------------------------------------------

HC2A       ADVVGIGETRFQQSLSIINNCANSDRLIKHTSFSSDVKDLTKRIRTVLMATAQMKEHEND
HC2A-80    ADVVGIGETRFQQSLSIINNCANSDRLIKHTSFSSDVKDLTKRIRTVLMATAQMKEHEND
HC2B       ADVVGIGETRFQQSLSIINNCANSDRLIKHTSFSSDVKDLTKRIRTVLMATAQMKEHEND
HC2C       ------------------------------------------------------------
HC2D       ADVVGIGGTRFQQSLSIINNCANSDRLIKHTSFSSDVKDLTKRIRTVLMATAQMKEHEND
HC2E       ADVVGIGETRFQQSLSIINNCANSDRLIKHTSFSSDVKDLTKRIRTVLMATAQMKEHEND
HC2F       ------------------------------------------------------------
```

FIG. 3B (cont.)

```
HC2A      PEMLVDLQYSLAKSYASTPELRKTWLDSMARIHVKNGDLSEAAMCYVHVTALVAEYLTRK
HC2A-80   PEMLVDLQYSLAKSYASTPELRKTWLDSMARIHVKNGDLSEAAMCYVHVTALVAEYLTRK
HC2B      PEMLVDLQYSLAKSYASTPELRKTWLDSMARIHVKNGDLSEAAMCYVHVTALVAEYLTRK
HC2C      ------------------------------------------------------------
HC2D      PEMLVDLQYSLAKSYASTPELRKTWLDSMARIHVKNGDLSEAAMCYVHVTALVAEYLTRK
HC2E      PEMLVDLQYSLAKSYASTPELRKTWLDSMARIHVKNGDLSEAAMCYVHVTALVAEYLTRK
HC2F      ------------------------------------------------------------

HC2A      -------------------GVFRQGCTAFRVITPNIDEEASMMEDVGMQDVHFNE
HC2A-80   -------------------GVFRQGCTAFRVITPNIDEEASMMEDVGMQDVHFNE
HC2B      -------------------GVFRQGCTAFRVITPNIDEEASMMEDVGMQDVHFNE
HC2C      ----------------------FRQGCTAFRVITPNIDEEASMMEDVGMQDVHFNE
HC2D      EAVQWEPPLLPHSHSACLRRSRGGVFRQGCTAFRVITPNIDEEASMMEDVGMQDVHFNE
HC2E      -------------------GVFRQGCTAFRVITPNIDEEASMMEDVG--------
HC2F      ------------------------------------------------------------

HC2A      DVLMELLEQCADGLWKAERYELIADIYKLIIPIYEKRR-----------------
HC2A-80   DVLMELLEQCADGLWKAERYELIADIYKLIIPIYEKRR-----------------
HC2B      DVLMELLEQCADGLWKAERYELIADIYKLIIPIYEKRRDFERLAHLYDTLHRAYSK
HC2C      DVLMELLEQCADGLWKAERYELIADIYKLIIPIYEKRRDFERLAHLYDTLHRAYSK
HC2D      DVLMELLEQCADGLWKAERYELIADIYKLIIPIYEKRRDFERLAHLYDTLHRAYSK
HC2E      ---------------KAERYELIADIYKLIIPIYEKRRDFERLAHLYDTLHRAYSK
HC2F      ------------------------------------------------------------

HC2A      ------------------------------------DFFEDEDGKEYIYKEPKLTPLSE
HC2A-80   ------------------------------------DFFEDEDGKEYIYKEPKLTPLSE
HC2B      VTEVMHSGRRLLGTYFRVAFFG-------------QGFFEDEDGKEYIYKEPKLTPLSE
HC2C      VTEVMHSGRRLLGTYFRVAFFG-------------QGFFEDEDGKEYIYKEPKLTPLSE
HC2D      VTEVMHSGRRLLGTYFRVAFFGQAAQYQFTDSETDVEGFFEDEDGKEYIYKEPKLTPLSE
HC2E      VTEVMHSGRRLLGTYFRVAFFG-------------QGFFEDEDGKEYIYKEPKLTPLSE
HC2F      ------------------------------------------------------------

HC2A      ISQRLLKLYSDKFGSENVKMIQDSGKVNPKDLDSKYAYIQVTHVIPFFDEKELQERKTEF
HC2A-80   ISQRLLKLYSDKFGSENVKMIQDSGKVNPKDLDSKYAYIQVTHVIPFFDEKELQERKTEF
HC2B      ISQRLLKLYSDKFGSENVKMIQDSGKVNPKDLDSKYAYIQVTHVIPFFDEKELQERKTEF
HC2C      ISQRLLKLYSDKFGSENVKMTQDSGKVNPKDLDSKYAYIQVTHVIPFFDEKELQERKTEF
HC2D      ISQRLLKLYSDKFGSENVKMIQDSGKVNPKDLDSKYAYIQVTHVIPFFDEKELQERKTEF
HC2E      ISQRLLKLYSDKFGSENVKMIQDSGKVNPKDLDSKYAYIQVTHVIPFFDEKELQERKTEF
HC2F      ------------------------------------------------------------

HC2A      ERSHNIRRFMFEMPFTQTGKRQGGVEEQCKRRTILTAIHCFPYVKKRIPVMYQHHTDLNP
HC2A-80   ERSHNIRRFMFEMPFTQTGKRQGGVEEQCKRRTILTAIHCFPYVKKRIPVMYQHHTDLNP
HC2B      ERSHNIRRFMFEMPFTQTGKRQGGVEEQCKRRTILTAIHCFPYVKKRIPVMYQHHTDLNP
HC2C      ERSHNIRRFMFEMPFTQTGKRQGGVEEQCKRRTILTAIHCFPYVKKRIPFMYQHHTDLNP
HC2D      ERSHNIRRFMFEMPFTQTGKRQGGVEEQCKRRTILTAIHCFPYVKKRIPVMYQHHTDLNP
HC2E      ERSHNIRRFMFEMPFTQTGKRQGGVEEQCKRRTILTAIHCFPYVKKRIPVMYQHHTDLNP
HC2F      ------------------------------------------------------------
```

FIG. 3B (cont.)

```
HC2A      IEVAIDEMSKKVAELRQLCSSAEVDMIKLQLKLQGSVSVQVNAGPLAYARAFLDDTNTKR
HC2A-80   IEVAIDEMSKKVAELRQLCSSAEVDMIKLQLKLQGSVSVQVNAGPLAYARAFLDDTNTKR
HC2B      IEVAIDEMSKKVAELRQLCSSAEVDMIKLQLKLQGSVSVQVNAGPLAYARAFLDDTNTKR
HC2C      IEVHZ-------------------------------------------------------
HC2D      IEVAIDEMSKKVAELRQLCSSAEVDMIKLQLKLQGSVSVQVNAGPLAYARAFLDDTNTKR
HC2E      IEVAIDEMSKKVAELRQLCSSAEVDMIKLQLKLQGSVSVQVNAGPLAYARAFLDDTNTKR
HC2F      ------------------------------------------------------------

HC2A      YPDNKVKLLKEVFRQFVEACGQALAVNERLIKEDQLEYQEEMKANYREMAKELSEIMHEQ
HC2A-80   YPDNKVKLLKEVFRQFVEACGQALAVNERLIKEDQLEYQEEMKANYREMAKELSEIMHEQ
HC2B      YPDNKVKLLKEVFRQFVEACGQALAVNERLIKEDQLEYQEEMKANYREMAKELSEIMHEQ
HC2C      ------------------------------------------------------------
HC2D      YPDNKVKLLKEVFRQFVEACGQALAVNERLIKEDQLEYQEEMKANYREMAKELSEIMHEQ
HC2E      YPDNKVKLLKEVFRQFVEACGQALAVNERLIKEDQLEYQEEMKANYREMAKELSEIMHEQ
HC2F      ------------------------------------------------------------

HC2A      ICPLEEKTSVLPNSLHIFNAISGTPTSTMVHGMTSSSSVVZ----
HC2A-80   ICPLEEKTSVLPNSLHIFNAISGTPTSTMVHGMTSSSSVVZ----
HC2B      ICPLEEKTSVLPNSLHIFNAISGTPTSTMVHGMTSSSSVVZ----
HC2C      ---------------------------------------------
HC2D      LG-------------------------------------------
HC2E      ICPLEEKTSVLPNSLHIFNAISGTPTSTMVHGMTSSSSVVZ----
HC2F      ---------------------------------------------
```

FIG. 3B (cont.)

```
HC2A    ------------------------------------------------------------
KIAA    ASGNLDKNARFSAIYRQDSNKLSNDDMLKLLADFRKPEKMAKLPVILGNLDITIDNVSSD
rat     ------------------------------------------------------------
HC4     ------------------------------------------------------------
HC1     ------------------------------------------------------------
HC3     ------------------------------------------------------------
HC5     ------------------------------------------------------------

HC2A    ------------------------------------------------------------
KIAA    FPNYVNSSYIPTKQFETCSKTPITFEVEEFVPCIPKHTQPYTIYTNHLYVYPKYLKYDSQ
rat     ------------------------------------------------------------
HC4     ------------------------------------------------------------
HC1     ------------------------------------------------------------
HC3     ------------------------------------------------------------
HC5     ------------------------------------------------------------

HC2A    ---------------------------------------------VLHHHQNPEFYDEIK
KIAA    KSFAKARNIAICIEFKDSDEEDSQPLKCIYGRPGGPVFTRSAFAAVLHHHQNPEFYDEIK
rat     ------------------------------------------------------------
HC4     ------------------------------------------------------------
HC1     ------------------------------------------------------------
HC3     ------------------------------------------------------------
HC5     ------------------------------------------------------------

HC2A    IELPTQLHEKHHLLLTFFHVSCDNSSKGSTKKRDVVETQVGYSWLPLLKDGRVVTSEQHI
KIAA    IELPTQLHEKHHLLLTFFHVSCDNSSKGSTKKRDVVETQVGYSWLPLLKDGRVVTSEQHI
rat     ------------------------------------------------------------
HC4     ------------------------------------------------------------
HC1     ------------------------------------------------------------
HC3     ------------------------------------------------------------
HC5     ------------------------------------------------------------

HC2A    PVSANLPSGYLGYQELGMGRHYGPEIKWVDGGKPLLKISTHLVSTVYTQDQHLHNFFQYC
KIAA    PVSANLPSGYLGYQELGMGRHYGPEIKWVDGGKPLLKISTHLVSTVYTQDQHLHNFFQYC
rat     ------------------------------------------------------------
HC4     ------------------------------------------------------------
HC1     ------------------------------------------------------------
HC3     ---------------------------------------GPGPARSTVSISLISNSARV
HC5     ------------------------------------------------------------

HC2A    QKTESGAQALGNELVKYLKSLHAMEGHVMIAFLPTILNQLFRVLT-RATQEEVAVNVTRV
KIAA    QKTESGAQALGNELVKYLKSLHAMEGHVMIAFLPTILNQLFRVLT-RATQEEVAVNVTRV
rat     ------------------------------------------------------------
HC4     ---------------------MEIQVLIRFLSVILMQLFWVLPNMIHEDDVPISCPMV
HC1     ------------------------MSFLPIILNQLFKVLV-QNEEDEITTTVTRV
HC3     NRSRSLSNSNPDISGTPTSPDDEVRSIIGSKGLDRSNSWVNTGGPKAAPWGSNPSPSAES
HC5     ------------------------------------------------------------
```

FIG.5A

```
HC2A   IIHVVAQCHEEGLESHLRSYVKYAYKAEPYVASEYKTVHEELTKSMTTILKPSADFLTSN
KIAA   IIHVVAQCHEEGLESHLRSYVKYAYKAEPYVASEYKTVHEELTKSMTTILKPSADFLTSN
rat    ------------------------------------------------------------
HC4    LFHIVSKCHEEGLDSYLSSFIKYSFRPGKPSAPQAPLIHETLATMMIALLKQSADFLAIN
HC1    LPDIVAKCHEEQLDHSVQSYIKFVFKTR---ACKERPVHEDLAKNVTGLLK-SNDSPTVK
HC3    TQAMDRSCNRMSSHTETSSFLQTLTGRLP----TKKLFHEELALQWVVCSG--SVR---E
HC5    ------------------------------------------------------------
                                          Cadherin
                                          Cleavage
HC2A   KLLRYSWFFFDVLIKSMAQHLIENSKVKLI|RNQR|FPASYHHAAETVVNMLMPHITQKFGD
KIAA   KLLKYSWFFFDVLIKSMAQHLIENSKVKLI|RNQR|FPASYHHAVETVVNMLMPHITQKFRD
rat    -----------------------------|----|-------------------------
HC4    KLLKYSWFFFEIIAKSMATYLLEENKIKLT|HGQR|FPKAYHHALHSLFLAIT-IVESQYAE
HC1    HVLKHSWFFFAIILKSMAQHLIDTNKIQLE|RPQR|FPESYQNELDNLVMVLSDHVIWKYKD
HC3    SALQQAWFFFELMVKSMVHHLYFNDKLEAH|RKSR|FPERFMDDIAALVSTIASDIVSRFQK
HC5    ------------------------------|----|-------------------------

HC2A   NPEASKNANHSLAVFIKRCFTFMDRGFVFKQIN---NYIS--CFAPGDPKTLFEYKFEFL
KIAA   NPEASKNANHSLAVFIKRCFTFMDRGFVFKQIN---NYIS--CFAPGDPKTLFEYKFEFL
rat    ------------------------------------------------------------
HC4    IPKESRNVNYSLASFLKCCLTLMDRGFVFNLIN---DYIS--GFSPKDPKVLAEYKFEFL
HC1    ALEETRRATHSVARFLKRCFTFMDRGCVFKMVN---NYIS--MFSSGDLKTILCQYKFDFL
HC3    DTEMVERLNTSLAFFLNDLLSVMDRGFVFSLIKSCYKQVSSKLYSLPNPSVLVSLRLDFL
HC5    ------------------------------------------------------------

HC2A   RVVCNHEHYIPLNLPM-----PFGKGRIQR-----------YQDLQL----DYSLTDEF
KIAA   RVVCNHEHYIPLNLPM-----PFGKGRIQR-----------YQDLQL----DYSLTDEF
rat    ------------------------------------------------------------
HC4    QTICNHEHYIPLNLPM-----AFAKPKLQR-----------VQDSNL----EYSLSDEY
HC1    QEVCQHEHFIPLCLPIRSANIPDPLTPSES-----------TQELHASDMPEYSVTNEF
HC3    RIICSHEHYVTLNLPCSLLTPPASPSPSVSSATSQSSGFSTNVQDQKIANMFELS--VPF
HC5    ---------------MNADTAPTSPCPSIS---SQNSSSCSSFQDQKIASMFDRTSRVPA HC2A   CRNHFLVGLLLREVGTALQEFRE----VRLIAISVLKNLLIKHSFDDRYASRSHQARIAT
KIAA   CRNHFLVGLLLREVGTALQEFRE----VRLIAISVLKNLLIKHSFDDRYASRSHQARIAT
rat    ------------------------------------------------------------
HC4    CKHHFLVGLLLRETSIALQDNYE----IRYTAISVIKNLLIKHAFDTRYQHKNQQAKIAQ
HC1    CRKHFLIGILLREVGFALQEDQD----VRHLALAVLKNLMAKHSFDDRYREPRKQAQIAS
HC3    RQQHYLAGLVLTELAVILDPDAEGLFGLHKKVINMVHNLLSSHDSDPRYSDPQIKARVAM
HC5    SSTS-SPGLLFTELAAALDAEGEGISEVQRKAVSAIHSLLSSHDLDPRCVKPEVKVKIAA HC2A   LYLPLFGLLIENVQRINVRDVSPFPVNAG-MTVKDESLALPAVNPLVTPQKGSTLDNSLH
KIAA   LYLPLFGLLIENVQRINVRDVSPFPVNAG-MTVKDESLALPAVNPLVTPQKGSTLDNSLH
rat    ------------------------------------------------------------
HC4    LYLPFVGLLLENIQRLAGRDTLYSCAAMPNSASRDEFPCG-----FTSP--AN--RGSLS
HC1    LYMPLYGMLLDNMPRIYLKDLYPFTVNTSNQGSRDDLSTNGGFQSQTAIKHANSVDTSFS
HC3    LYLPLIGIIMETVPQLYDFTETHNQRGRPICIATDDYESE----------SG---SMIS
HC5    LYLPLVGIILDALPQLCDFTVADTRRYR---TSGSDEEQE----------GA---GAIT HC2A   KDLLGAISGIASPYTTSTPNINSVRNADSRGSLISTDSGNSLPERNSEKSNSLDKHQQSS
KIAA   KDLLGAISGIASPYTTSTPNINSVRNADSRGSLISTDSGNSLPERNSEKSNSLDKHQQSS
rat    ------------------------------------------------------------
HC4    TDKDTAYGSFQNG--------HGIKREDSRGSLIP-EGATGFPDQGNTGEN-----TRQS
HC1    KDVLNSIAAFSS------IAISTVNHADSRASLASLDSNPSTNEKSSEKTDNCEKIPRPL
HC3    QTVAMAIAGTSVPQ-------------------LTRPGSFLLTSTSGRQHT---------
HC5    QNVALAIAGNNFN-------------------LKTSG-IVLSSLPYKQYN---------
```

FIG. 5A (cont.)

```
HC2A    TLGNSVVRCDKLDQSEIKSLLMCFLYILKSMSDDALFTYWN-KASTSELMDFFTISEVCL
KIAA    TLGNSVVRCDKLDQSEIKSLLMCFLYILKSMSDDALFTYWN-KASTSELMDFFTISEVCL
rat     ------------------------------------------------------------
HC4     STRSSVSQYNRLDQYEIRSLLMCYLYIVKMISEDTLLTYWN-KVSPQELINILILLEVCL
HC1     ALIGSTLRFDRLDQAETRSLLMCFLHIMKTISYETLIAYWQ-RAPSPEVSDFFSILDVCL
HC3     ----------TFSAESSRSLLICLLWVLKN-ADETVLQKWFTDLSVLQLNRLLDLLYLCV
HC5     ----------MLNADTTRNLMICFLWIMKN-ADQSLIRKWIADLPSTQLNRILDLLFICV HC2A    HQFQYMGKRYIARNQEGLG--PIVHDRKS-----------------QTLPVSRNRTGMM
KIAA    HQFQYMGKRYIAR----------------------------------TGMM
rat     ------------------------------------------------------------
HC4     FHFRYMGKRNIARVHDAWLSKHFGIDRKS-----------------QTMPALRNRSGVM
HC1     QNFRYLGKRNIIRKIAAAF--KFVQSTQNNGTLKGSNPSCQTSGLLAQWMHSTSRHEGHK
HC3     SCFEYKGKKVFERMNSLTFK--KSKDMRAK---------------LEEAILGSIGARQEMV
HC5     LCFEYKGKQSSDKVSTQVLQ--KSRDVKAR---------------LEEALLRGEGARGEMM HC2A    HARLQQL---------GSLDNS---------LTFNHSYGHSDADVLHQSLLEANIATEVC
KIAA    HARLQQL---------GSLDNS---------LTFNHSYGHSDADVLHQSLLEANIATEVC
rat     ------------------------------------------------------------
HC4     QARLQHL---------SSLESS---------FTLNHSSTTTEADIFHQALLEGNTATEVS
HC1     QHRSQTLPIIRGK---NALSNPKL----LQMLDNTMTSNSNEIDIVHHVDTEANIATEGC
HC3     RRSRGQLERSPSGSAFGSQENLRWRKDMTHWRQNTEKLDKSRAEIEHEALIDGNLATEAN
HC5     RRRAPGNDRFP-----GLNENLRWKKEQTHWRQANEKLDKTKAELDQEALISGNLATEAH HC2A    LTALDTLSLFTLAFKNQLLADHGHNPLMKKVFDVYLCFLQKHQSETALKNVFTALRSLIY
KIAA    LTALDTLSLFTLAFKNQLLADHGHNPLMKKVFDVYLCFLQKHQSETALKNVFTALRSLIY
rat     ------------------KLSRGHSPLMKKVFDVYLCFLQKHQSEMALKNVFTALRSLIY
HC4     LTVLDTISFFTQCFKTHFLNNDGHNPLMKKVFDIHLAFLKNGQSEVSLKHVFASLRAFIS
HC1     LTILDLVSLFTQTHQRQLQQCDCQNSLMKRGFDTYMLFFQVNQSATALKHVFASLRLFVC
HC3     LIILDTLEIVVQTVS--VTES--KESILGGVLKVLLHSMACNQSAVYLQHCFATQRALVS
HC5     LIILDMQENIIQASS--ALDC--KDSLLGGVLRVLVNSLNCDQSTTYLTHCFATLRALIA HC2A    KFPSTFYEGRADMCAALCYEILKCCNSKLSSIRTEASQLLYFLMRNNFDYTGKKSFVRTH
KIAA    KFPSTFYEGRADMCAALCYEILKCCNSKLSSIRTEASQLLYFLMRNNFDYTGKKSFVRTH
rat     KFPSTFYEGRADMCASLCYEVLKCCNSKLSSIRTEASQLLYFLMRNNFDYTGKKSFVRTH
HC4     KFPSAFFKGRVNMCAAFCYEVLKCCTSKISSTRNEASALLYLLMRNNFEYTKRKTFLRTH
HC1     KFPSAFFQGPADLCGSFCYEVLKCCNHRSRSTQTEASALLYLFMRKNFEFNKQKSIVRSH
HC3     KFPELLFEEETEQCADLCLRLLRHCSSSIGTIRSHPSASLYLLMRQNFEIGN--NFARVK
HC5     KFGDLLFEEEVEQCFDLCHQVLHHCSSSMDVTRSQACATLYLIMRFSFGATS--NFARVK HC2A    LQVIISVSQLIADVVGIGETRFQQSLSIINNCANSDRLIKHTSFSSDVKDLTKRIRTVLM
KIAA    LQVIISVSQLIADVVGIGGTRFQQSLSIINNCANSDRLIKHTSFSSDVKDLTKRIRTVLM
rat     LQVIISLSQLIADVVGIGGTRFQQSLSIINNCANSDRLIKHTSFSSDVKDLTKRIRTVLM
HC4     LQIIIAVSQLIADVALSGGSRFQESLFIINNFANSDRPMLARAFPAEVKDLTKRIRTVLM
HC1     LQLIKAVSQLIAD-AGIGGSRFQHSLAITNNFANGDKQMKNSNFPAEVKDLTKRIRTVLM
HC3     MQVPMSLSSLVGTSQNFNEEFLRRSLKTILTYAEEDLELRETTFPDQVQDLVFNLHMILS
HC5     MQVTMSLASLVGRAPDFNEEHLRRSLRTILAYSEEDTAMQMTPFPTQVEELLCNLNSILY
```

FIG. 5A (cont.)

```
                                                                            Transmembrane
HC2A    ATAQMKEHENDPEMLVDLQYSLAKSYASTPELRKTWLDSMARIHVKNGD LSEAAMCYVHV
KIAA    ATAQMKEHENDPEMLVDLQYSLAKSYASTPELRKTWLDSMARIHVKNGD LSEAAMCYVHV
rat     ATAQMKEHENDPEMLVDLQYSLAKSYASTPELRKTWLDSMARIHVKNGD LSEAAMCYVHV
HC4     ATAQMKEHEKDPEMLIDLQYSLAKSYASTPELRKTWLDSMAKIHVKNGD FSEAAMCYVHV
HC1     ATAQMKEHEKDPEMLVDLQYSLANSYASTPELRRTWLESMAKIHARNGD LSEAAMCYIHI
HC3     DTVKMKEHQEDPEMLIDLMYRIAKGYQTSPDLRLTWLQNMAGKHSERSN HAEAAQCLVHS
HC5     DTVKMREFQEDPEMLMDLMYRIAKSYQASPDLRLTWLQNMAEKHTKKKQ YTEAAMCLVHA SH3
HC2A    TALVAEYI TRKGV------  ------------------  --FRQGCTAFRVITPN
KIAA    TALVAEYI TRKEA------  ---VQWEPPLLPHSHSACLRRSR GGVFRQGCTAFRVITPN
rat     TALVAEYI TRKEAD-----  -LALQREPPVFPYSHTSCQRKSR GGMFRQGCTAFRVITPN
HC4     AALVAEFI HRKKL------  ------------------  ---FPNGCSAFKKITPN
HC1     AALIAEYL KRKGYWKVEKIQ TASLLSEDTHPCDSNSLLTTPSG GSMFSMGWPAFLSITPN
HC3     AALVAEYI SMLED------  ------------------  RKYLPVGCVTFQNISSN
HC5     AALVAEYI SMLED------  ------------------  HSYLPVGSVSFQNISSN HC2A    IDEEASMMEDVGMQD-------VHFNEDVLMELLEQCADGLWKAERYELIADIYKLIIPI
KIAA    IDEEASMMEDVGMQD-------VHFNEDVLMELLEQCADGLWKAERYELIADIYKLIIPI
rat     IDEEASMMEDVGMQD-------VHFNEDVLMELLEQCADGLWKAERLRAGLLTSINSSSP
HC4     IDEEGAMKEDAGMMD-------VHYSEEVLLELLEQCVNGLWKAERYEIISEISKLIGPI
HC1     IKEEGAAKEDSGMHD-------TPYNENILVEQLYMCGEFLWKSERYELIADVNKPIIAV
HC3     VLEESAVSDDVVSPDEEGICSGKYFTESGLVGLLEQAAASFSMAGMYEAVNEVYKVLIPI
HC5     VLEESVVSEDTLSPDEDGVCAGQYFTESGLVGLLEQAAELFSTGGLYETVNEVYKLVIPI ITAM     ITAM              ITAM              ITAM
HC2A    YEKRRD----- ----  ---  ------------------------------
KIAA    YEKRRDFERLAHI YDTI HRAY SKV TEVMHSGRRLLGT YFRV AFFGQAAQYQFTDSETDVE
rat     SMKSGGTLETTHI YDTI HREY SKV TEVITR-----------A----AGSWDLLPGGLFGQ
HC4     YENRREFENLTQV YRTI HGAY TKI LEVMHTKKRLLG-------------TFFRVAFYGQ
HC1     FEKQRDFKKLSDI YYD I HRSY LKV AEVVNSEKRLFG-------------R YYRV AFYGQ
HC3     HEANRDAKKLSTI HGKI QEAF SKI VHQSTGWERMFG-------------T YFRV GFYG-
HC5     LEAHREFRKLTLT HSKI QRAF DSI VNKDH--KRMFG-------------T YFRV GFFG- ITAM              ITAM
HC2A    -FFEDEDGKE YIYKEP KLTPLSEISQRLLKL YSDKF GSENVKMIQDSGKVNPKDLDSK YA
KIAA    GFFEDEDGKE YIYKEP KLTPLSEISQRLLKL YSDKF GSENVKMIQDSGKVNPKDLDSK YA
rat     GFFEDEDGKE YIYKEP KLTPLSEISQRLLKL YSDKF GSENVKMIQDSGKVNPKDLDSK FA
HC4     SFFEEEDGKE YIYKEP KLTGLSEISLRLVKL YGEKF GTENVKIIQDSDKVNAKELDPK YA
HC1     GFFEEEEGKE YIYKEP KLTGLSEISQRLLKL YADKF GADNVKIIQDSNKVNPKDLDPK YA
HC3     TKFGDLDEQE FVYKEP AITKLAEISHRLEGF YGERF GEDVVEVIKDSNPVDKCKLDPN KA
HC5     SKFGDLDEQE FVYKEP AITKLPEISHRLEAF YGQCF GAEFVEVIKDSTPVDKTKLDPN KA ITAM
HC2A    YIQV THVIPFFDEKELQERKTEFERSHNIRRFMFEMPFTQTGKRQGGVEEQCKRRTILTA
KIAA    YIQV THVIPFFDEKELQERKTEFERSHNIRRFMFEMPFTQTGKRQGGVEEQCKRRTILTA
rat     YIQV THVTPFFDEKELQERKTEFERCHNIRRFMFEMPFTQTGKRQGGVEEQCKRRTILTA
HC4     HIQV TYVKPYFDDKELTERKTEFERNHNISRFVFEAPYTLSGKKQGCIEEQCKRRTILTT
HC1     YIQV TYVTPFFEEKEIEDRKTDFEMHHNINRFVFETPFTLSGKKHGGVAEQCKRRTILTT
HC3     YIQI TYVEPYFDTYEMKDRITYFDKNYNLRRFMYCTPFTLDGRAHGELHEQFKRKTILTT
HC5     YIQI TFVEPYFDEYEMKDRVTYFEKNFNLRRFMYTTPFTLEGRPRGELHEQYRRNTVLTT
```

FIG. 5A (cont.)

```
                                          Coiled-Coil 1
HC2A    IHCFPYVKKRIPVMYQHHTDINPIEVAIDEMSKKVAELRQLCSSAEVDMIKLQLKLQGSV
KIAA    IHCFPYVKKRIPVMYQHHTDINPIEVAIDEMSKKVAELRQLCSSAEVDMIKLQLKLQGSV
rat     IHCFPYVKKRIPVMYQHHTDINPIEVAIDEMSKKVAELRQLCSSAEVDMIKLQLKLQGSV
HC4     SNSFPYVKKRIPINCEQQINLKPIDGATDEIKDKTAELQKLCSSTDVDMIQLQLKLQGWV
HC1     SHLFPYVKKRIQVISQSSTEINPIEVAIDEMSRKVSELNQLCTMEEVDMISLQLKLQGSV
HC3     SHAFPYIKTRVNVTHKEEIILTPIEVAIEDMQKKTQELAFATHQDPADPKMLQMVLQGSV
HC5     MHAFPYIKTRISVIQKEEFVLTPIEVAIEDMKKKTLQLAVAINQEPPDAKMLQMVLQGSV Coled-Coil 2
HC2A    SVQVNAGPLAYARAFLDDTNTKRYPDNKVKLLKEVFRQFVEACGQALAVNERLIKEDQLE
KIAA    SVQVNAGPLAYARAFLDDTNTKRYPDNKVKLLKEVFRQFVEACGQALAVNERLIKEDQLE
rat     SVQVNAGPLAYARAFLDDTNTKRYPDNKVKLLKEVFRQFVEACGQALAVNERLIKEDQLE
HC4     SVQVNAGPLAYARAFLNDSQASKYPPKKVSELKDMFRKFIQACSIALELNERLIKEDQVE
HC1     SVKVNAGPMAYARAFLEETNAKKYPDNQVKLLKEIFRQFADACGQALDVNERLIKEDQLE
HC3     GTTVNQGPLEVAQVFLSEIPSDPKLFRHHNKLRLCFKDFTKRCEDALRKNKSLIGPVQKE
HC5     GATVNQGPLEVAQVFLAEIPADPKLYRHHNKLRLCFKEFIMRCGEAVEKNKRLITADQRE Coiled-Coil 2
HC2A    YQEEMKANYREMAKELSEIMHEQICPLEEKTS-VLPNSLHIFNAISGTPTSTMVHGMTSS
KIAA    YQEEMKANYREMAKELSEIMHEQLG-----------------------------------
rat     YQEEMKANYREIRKELSDIIVPRICPGEDKRATKFPAHLQRHQRDTNKHSGSRVDQFILS
HC4     YHEGLKSNFRDMVKELSDIIHEQILQEDTMHSPWMSNTLHVFCAISGTSSDRGYGSPRYA
HC1     YQEELRSHYKDMLSELSTVMNEQITGRDDLSK---RGVDQTCTRVISKATPALPTVSISS
HC3     YQRELG----KLSS---------PZ-----------------------------------
HC5     YQQELKKNYNKLKENLRPMIERKIPELYKPIFRVESQKRDSFHRSSFRKCETQLSQGSZ- PBM
HC2A    SSVVZ-------------------------------------------------------
KIAA    ------------------------------------------------------------
rat     CVTLPHEPHVGTCFVMCKLRTTFRANHWFCQAQEEAMGNGREKEPWTVIFNSRFYRSWGK
HC4     EVZ---------------------------------------------------------
HC1     SAEVZ-------------------------------------------------------
HC3     ------------------------------------------------------------
HC5     ------------------------------------------------------------

HC2A    -----
KIAA    -----
rat     VHIFF
HC4     -----
HC1     -----
HC3     -----
HC5     -----
```

FIG. 5A (cont.)

```
                        A                              B
CLASP-1      YRVAFYGQ::::::::::::::GFFEEEEGKEYIYKEP
KIAA1058     FRVAFFGQAAQYQFTDSETDVEGFFEDEDGKEYIYKEP
CLASP-2                           FEDEDGKEYIYKEP
CLASP-6      FRVAFFGQ::::::::::::::GFFEDEDGKEYIYKEP
CLASP-4      FRVAFYGQ::::::::::::::SFFEEEDGKEYIYKEP
DOCK180      FAVGYYGQ::::::GFPTFLRGKVFIYRGKEYERRED
DOCK2        FAVGYYGQ::::::GFPSFLRNKVFIYRGKEYERRED
DOCK3        FRVGFYGR::::::::::::::KFPFFLRNKEYVCRGH
KIAA0716     FRVGFYGK::::::::::::::KFPFFLRNKEFVCRGH
CLASP-3      FRVGFYGT::::::::::::::KFGDLDEQEFVYKEP
CONSENSUS    F  V FYG                KEY  K
                YF                    Q F  R

C
TRG       PKLTPLSEISQRLLKLYSDKFGSENVKMIQDSGKVNPKDLDSKFAYIQVTHVTPFFDEKE
CLASP-1   PKLTGLSEISQRLLKLYADKFGADNVKIIQDSNKVNPKDLDPKYAYIQVTYVTPFFEEKE
CLASP-2   PKLTPLSEISQRLLKLYSDKFGSENVKMTQDSGKVNPKDLDSKYAYIQVTHVIPFFDEKE
CLASP-4   PKLTGLSEISLRLVKLYGEKFGTENVKIIQDSDKVNAKELDPKYAHIQVTYVKPYFDDKE
CLASP-3   PAITKLAEISHRLEGFYGERFGEDVVEVIKDSNPVDKCKLDPNKAYIQITYVEPYFDTYE
KIAA0716  HDYERLEAFQQRMLNEFPHAIA------MQHANQPDETIFQAEAQYLQIYAVTPIPESQE
DOCK3     HDYERLEAFQQRMLSEFPQAVA------MQHPNHPDDAILQCDAQYLQIYAVTPIPDYVD
DOCK2         FQMQLMTQFPNAEK------MNTTSAPGDDVKNAPGQYIQCFTVPVLDEHP
DOCK180   EYERREDFQMQLMTQFPNAEK-------MNTTSAPGDDVKNAPGQYIQCFTVPVLDEHP
CONSENSUS             L       Y                            YIQ+  V P D
                      M       F                             L         E

D                    E
CLASP-1   RTILTTSHLFPYVKKRIQVISQSSTELNPIEVAIDEMSRKVSELN
TRG       RTILTAIHCFPYVKKRIPVMYQHHTDLNPIEVAIDEMSKKVAELH
KIAA1058  RTILTAIHCFPYVKKRIPVMYQHHTDLNPIEVAIDEMSKKVAELR
CLASP-2   RTILTAIHCFPYVKKRIPVMYQHHTDLNPIEVAIDEMSKKVAELR
CLASP-6   RTILTAIHCFPYVKKRIPFMYQHHTDLNPIEV:HDEMSKKVAELR
CLASP-4   RTILTTSNSFPYVKKRIPINCEQQINLKPIDVATDEIKDKTAELQ
CLASP-3   KTILTTSHAFPYIKTRVNVTHKEEIILTPIEVAIEDMQKKTQELA
CLASP-5   NTVLTTMHAFPYIKTRISVIQKEEFVLTPIEVAIEDMKKKTLQLA
KIAA0716  RTSLYLVQSLPGISRWFEVEKREVVEMSPLENAIEVLNKNQQLK
DOCK2     RTSFVTAYKLPGILRWFEVVHMSQTTISPLENAIETMSTANEKIL
DOCK3     RTTLTLTHSLPGISRWFEVERRELVEVSPLENAIQVVNKNQELR
DOCK180   RTSFVTAYKLPGILRWFEVVHMSQTTISPLENAIETMSTANEKIL
CONSENSUS RT L      FP V     + V        P+E AI+ M    +L
               F    L L                          +     I
```

FIG. 5B

```
                      F                    G
CLASP-1    SLQLKLQGSVSVKVNAG PMAYARAFLEE TNAKKY PDNQV--KLL KEIFRQFADACGQALD
TRG        KLQLKLQGSVSVQVNAG PLAYARAFLDD TNTKRY PDNKV--KIL KEVFRQFVEACGQALA
KIAA1058   KLQLKLQGSVSVQVNAG PLAYARAFLDD TNTKRY PDNKV--KIL KEVFRQFVEACGQALA
CLASP-2    KLQLKLQGSVSVQVNAG PLAYARAFLDD TNTKRY PDNKV--KIL KEVFRQFVEACGQALA
CLASP-6    KLQLKLQGSVSVQVNAG PLAYARAFLDD TNTKRY PDNKV--KIL KEVFRQFVEACGQALA
CLASP-3    MLQMVLQGSVGTTVNQG PLEVAQVFLSE --IPSD PKLFRHHNK LRLCFKDFTKRCEDALR
CLASP-4    QLQLKLQGCVSVQVNAG PLAYARAFLND SQASKY PPKVSELKD MFRKFI--QACSIALE
CLASP-5    MLQMVLQGSVGATVNQG PLEVAQVFLAE --IPAD PKLYRHHNK LRLCFKEFIMRCGEAVE
KIAA0716   PLTMCLNGVIDAAVNGG VSRYQEAFFVK EYILSH PEDGEKIAR LRELMLEQAQILEFGLA
DOCK2      PLSMLLNGIVDPAVMGG FAKYEKAFFTE EYVRDH PEDQDKLTH LKDLIAWQIPFLGAGIK
DOCK3      LLSMCLNGVIDAAVNGG IARYQEAFFDK DYINKH PGDAEKITQ LKELMQEQVHVLGVGLA
DOCK180    PLSMLLNGIVDPAVMGG FAKYEKAFFTE EYVRDH PEAHEKIEK LKDLIAWQIPFLAEGIR
CONSENSUS  L M L+G V    VN G   Y  AFL +   +    P         L+              L
             L   I               V  V F                                  I
```

DOCK2=KIAA0209
DOCK3=KIAA0299
CLASP2variant=KIAA1058

FIG. 5B (cont.)

1
A 2                                                    32
GTT TTA CAC CAT CAC CAA AAC CCA GAA TTT TAT GAT GAG ATT AAA ATA GAG TTG CCC ACT
val leu his his his gln asn pro glu phe tyr asp glu ile lys ile glu leu pro thr 62                                                   92
CAG CTG CAT GAA AAG CAC CAC CTG TTG CTC ACA TTC TTC CAT GTC AGC TGT GAC AAC TCA
gln leu his glu lys his his leu leu leu thr phe phe his val ser cys asp asn ser 122                                                  152
AGT AAA GGA AGC ACG AAG AAG AGG GAT GTC GTT GAA ACC CAA GTT GGC TAC TCC TGG CTT
ser lys gly ser thr lys lys arg asp val val glu thr gln val gly tyr ser trp leu 182                                                  212
CCC CTC CTG AAA GAC GGA AGG GTG GTG ACA AGC GAG CAG CAC ATC CCG GTC TCG GCG AAC
pro leu leu lys asp gly arg val val thr ser glu gln his ile pro val ser ala asn 242                                                  272
CTT CCT TCG GGC TAT CTT GGC TAC CAA GAG CTT GGG ATG GGC AGG CAT TAT GGT CCG GAA
leu pro ser gly tyr leu gly tyr gln glu leu gly met gly arg his tyr gly pro glu 302                                                  332
ATT AAA TGG GTA GAT GGA GGC AAG CCA CTG CTG AAA ATT TCC ACT CAT CTG GTT TCT ACA
ile lys trp val asp gly gly lys pro leu leu lys ile ser thr his leu val ser thr
                         ref 1.1, 1.2 and 1.3
362                                                  392
GTG TAT ACT CAG GAT CAG CAT TTA CAT AAT TTT TTC CAG TAC TGT CAG AAA ACC GAA TCT
val tyr thr gln asp gln his leu his asn phe phe gln tyr cys gln lys thr glu ser 422                                                  452
GGA GCC CAA GCC TTA GGA AAC GAA CTT GTA AAG TAC CTT AAG AGT CTG CAT GCG ATG GAA
gly ala gln ala leu gly asn glu leu val lys tyr leu lys ser leu his ala met glu 482                                                  512
GGC CAC GTG ATG ATC GCC TTC TTG CCC ACT ATC CTA AAC CAG CTG TTC CGA GTC CTC ACC
gly his val met ile ala phe leu pro thr ile leu asn gln leu phe arg val leu thr 542                                                  572
AGA GCC ACA CAG GAA GAA GTC GCG GTT AAC GTG ACT CGG GTC ATT ATT CAT GTG GTT GCC
arg ala thr gln glu glu val ala val asn val thr arg val ile ile his val val ala 602                                                  632
CAG TGC CAT GAG GAA GGA TTG GAG AGC CAC TTG AGG TCA TAT GTT AAG TAC GCG TAT AAG
gln cys his glu glu gly leu glu ser his leu arg ser tyr val lys tyr ala tyr lys 662                                                  692
GCT GAG CCA TAT GTT GCC TCT GAA TAC AAG ACA GTG CAT GAA GAA CTG ACC AAA TCC ATG
ala glu pro tyr val ala ser glu tyr lys thr val his glu glu leu thr lys ser met

FIG. 6A

```
722                             752
ACC ACG ATT CTC AAG CCT TCT GCC GAT TTC CTC ACC AGC AAC AAA CTA CTG AGG TAC TCA
thr thr ile leu lys pro ser ala asp phe leu thr ser asn lys leu leu arg tyr ser 782                             812
TGG TTT TTC TTT GAT GTA CTG ATC AAA TCT ATG GCT CAG CAT TTG ATA GAG AAC TCC AAA
trp phe phe phe asp val leu ile lys ser met ala gln his leu ile glu asn ser lys 842          |Cadherin Cleavage|    872
GTT AAG TTG CTG CGA AAC CAG AGA TTT CCT GCA TCC TAT CAT CAT GCA GCG GAA ACC GTT
val lys leu leu arg asn gln arg phe pro ala ser tyr his his ala ala glu thr val 902                             932
GTA AAT ATG CTG ATG CCA CAC ATC ACT CAG AAG TTT GGA GAT AAT CCA GAG GCA TCT AAG
val asn met leu met pro his ile thr gln lys phe gly asp asn pro glu ala ser lys 962                             992
AAC GCG AAT CAT AGC CTT GCT GTC TTC ATC AAG AGA TGT TTC ACC TTC ATG GAC AGG GGC
asn ala asn his ser leu ala val phe ile lys arg cys phe thr phe met asp arg gly
                                                                    ref 2.1↓
1022                            1052
TTT GTC TTC AAG CAG ATC AAC AAC TAC ATT AGC TGT TTT GCT CCT GGA GAC CCA AAG ACC
phe val phe lys gln ile asn asn tyr ile ser cys phe ala pro gly asp pro lys thr 1082                            1112
CTC TTT GAA TAC AAG TTT GAA TTT CTC CGT GTA GTG TGC AAC CAT GAA CAT TAT ATT CCG
leu phe glu tyr lys phe glu phe leu arg val val cys asn his glu his tyr ile pro 1142                            1172
TTG AAC TTA CCA ATG CCA TTT GGA AAA GGC AGG ATT CAA AGA TAC CAA GAC CTC CAG CTT
leu asn leu pro met pro phe gly lys gly arg ile gln arg tyr gln asp leu gln leu 1202                            1232
GAC TAC TCA TTA ACA GAT GAG TTC TGC AGA AAC CAC TTC TTG GTG GGA CTG TTA CTG AGG
asp tyr ser leu thr asp glu phe cys arg asn his phe leu val gly leu leu leu arg 1262                            1292
GAG GTG GGG ACA GCC CTC CAG GAG TTC CGG GAG GTC CGT CTG ATC GCC ATC AGT GTG CTC
glu val gly thr ala leu gln glu phe arg glu val arg leu ile ala ile ser val leu
                                                              ref 3.1↓
1322                            1352
AAG AAC CTG CTG ATA AAG CAT TCT TTT GAT GAC AGA TAT GCT TCA AGG AGC CAT CAG GCA
lys asn leu leu ile lys his ser phe asp asp arg tyr ala ser arg ser his gln ala 1382                            1412/471
AGG ATA GCC ACC CTC TAC CTG CCT CTG TTT GGT CTG CTG ATT GAA AAC GTC CAG CGG ATC
arg ile ala thr leu tyr leu pro leu phe gly leu leu ile glu asn val gln arg ile 1442                            1472
AAT GTG AGG GAT GTG TCA CCC TTC CCT GTG AAC GCG GGC ATG ACC GTG AAG GAT GAA TCC
asn val arg asp val ser pro phe pro val asn ala gly met thr val lys asp glu ser
```

FIG. 6A (cont.)

```
1502                                    1532
CTG GCT CTA CCA GCT GTG AAT CCG CTG GTG ACG CCG CAG AAG GGA AGC ACC CTG GAC AAC
leu ala leu pro ala val asn pro leu val thr pro gln lys gly ser thr leu asp asn
                                                    ⇓ ref 4.1 and 4.2
1562                                    1592
AGC CTG CAC AAG GAC CTG CTG GGC GCC ATC TCC GGC ATT GCT TCT CCA TAT ACA ACC TCA
ser leu his lys asp leu leu gly ala ile ser gly ile ala ser pro tyr thr thr ser 1622                                    1652
ACT CCA AAC ATC AAC AGT GTG AGA AAT GCT GAT TCG AGA GGA TCT CTC ATA AGC ACA GAT
thr pro asn ile asn ser val arg asn ala asp ser arg gly ser leu ile ser thr asp
                                                    ref 5.1 and 5.2 ⇓
1682                                    1712
TCG GGT AAC AGC CTT CCA GAA AGG AAT AGT GAG AAG AGC AAT TCC CTG GAT AAG CAC CAA
ser gly asn ser leu pro glu arg asn ser glu lys ser asn ser leu asp lys his gln 1742                                    1772
CAA AGT AGC ACA TTG GGA AAT TCC GTG GTT CGC TGT GAT AAA CTT GAC CAG TCT GAG ATT
gln ser ser thr leu gly asn ser val val arg cys asp lys leu asp gln ser glu ile 1802                                    1832
AAG AGC CTA CTG ATG TGT TTC CTC TAC ATC TTA AAG AGC ATG TCT GAT GAT GCT TTG TTT
lys ser leu leu met cys phe leu tyr ile leu lys ser met ser asp asp ala leu phe 1862                                    1892
ACA TAT TGG AAC AAG GCT TCA ACA TCT GAA CTT ATG GAT TTT TTT ACA ATA TCT GAA GTC
thr tyr trp asn lys ala ser thr ser glu leu met asp phe phe thr ile ser glu val
                        ⇓ ref 6.1
1922                                    1952
TGC CTG CAC CAG TTC CAG TAC ATG GGG AAG CGA TAC ATA GCC AGG AAC CAG GAG GGG TTG
cys leu his gln phe gln tyr met gly lys arg tyr ile ala arg asn gln glu gly leu 1982                                    2012
GGA CCC ATA GTT CAT GAT CGA AAG TCT CAG ACA TTG CCT GTT TCC CGT AAC AGA ACA GGA
gly pro ile val his asp arg lys ser gln thr leu pro val ser arg asn arg thr gly 2042                                    2072
ATG ATG CAT GCC AGA TTG CAG CAG CTG GGC AGC CTG GAT AAC TCT CTC ACT TTT AAC CAC
met met his ala arg leu gln gln leu gly ser leu asp asn ser leu thr phe asn his 2102                                    2132
AGC TAT GGC CAC TCG GAC GCA GAT GTT CTG CAC CAG TCA TTA CTT GAA GCC AAC ATT GCT
ser tyr gly his ser asp ala asp val leu his gln ser leu leu glu ala asn ile ala ref 7.1 ⇓
2162                                    2192
ACT GAG GTT TGC CTG ACA GCT CTG GAC ACG CTT TCT CTA TTT ACA TTG GCG TTT AAG AAC
thr glu val cys leu thr ala leu asp thr leu ser leu phe thr leu ala phe lys asn 2222                                    2252
CAG CTC CTG GCC GAC CAT GGA CAT AAT CCT CTC ATG AAA AAA GTT TTT GAT GTC TAC CTG
gln leu leu ala asp his gly his asn pro leu met lys lys val phe asp val tyr leu

```
TGT TTT CTT CAA AAA CAT CAG TCT GAA ACG GCT TTA AAA AAT GTC TTC ACT GCC TTA AGG
cys phe leu gln lys his gln ser glu thr ala leu lys asn val phe thr ala leu arg 2342                                2372
TCC TTA ATT TAT AAG TTT CCC TCA ACA TTC TAT GAA GGG AGA GCG GAC ATG TGT GCG GCT
ser leu ile tyr lys phe pro ser thr phe tyr glu gly arg ala asp met cys ala ala 2402                                2432
CTG TGT TAC GAG ATT CTC AAG TGC TGT AAC TCC AAG CTG AGC TCC ATC AGG ACG GAG GCC
leu cys tyr glu ile leu lys cys cys asn ser lys leu ser ser ile arg thr glu ala 2462                                2492
TCC CAG CTG CTC TAC TTC CTG ATG AGG AAC AAC TTT GAT TAC ACT GGA AAG AAG TCC TTT
ser gln leu leu tyr phe leu met arg asn asn phe asp tyr thr gly lys lys ser phe 2522                                2552
GTC CGG ACA CAT TTG CAA GTC ATC ATA TCT GTC AGC CAG CTG ATA GCA GAC GTT GTT GGC
val arg thr his leu gln val ile ile ser val ser gln leu ile ala asp val val gly 2582                                2612
ATT GGG AAA ACC AGA TTC CAG CAG TCC CTG TCC ATC ATC AAC AAC TGT GCC AAC AGT GAC
ile gly glu thr arg phe gln gln ser leu ser ile ile asn asn cys ala asn ser asp 2642                                2672
CGG CTT ATT AAG CAC ACC AGC TTC TCC TCT GAT GTG AAG GAC TTA ACC AAA AGG ATA CGC
arg leu ile lys his thr ser phe ser ser asp val lys asp leu thr lys arg ile arg 2702                                2732
ACG GTG CTA ATG GCC ACC GCC CAG ATG AAG GAG CAT GAG AAC GAC CCA GAG ATG CTG GTG
thr val leu met ala thr ala gln met lys glu his glu asn asp pro glu met leu val 2762                                2792
GAC CTC CAG TAC AGC CTG GCC AAA TCC TAT GCC AGC ACG CCC GAG CTC AGG AAG ACG TGG
asp leu gln tyr ser leu ala lys ser tyr ala ser thr pro glu leu arg lys thr trp 2822                                2852        |xxxxxxxxxxxxxx Predicted
CTC GAC AGC ATG GCC AGG ATC CAT GTC AAA AAT GGC GAT CTC TCA GAG GCA GCA ATG TGC
leu asp ser met ala arg ile his val lys asn gly asp leu ser glu ala ala met cys Transmembrane Domain xxxxxxxxxxxxxxxxxxxxxxxxxxxxxxx|
TAT GTC CAC GTA ACA GCC CTA GTG GCA GAA TAT CTC ACA CGG AAA GGC GTG TTT AGA CAA
tyr val his val thr ala leu val ala glu tyr leu thr arg lys gly val phe arg gln 2942                                2972
GGA TGC ACC GCC TTC AGG GTC ATT ACC CCA AAC ATC GAC GAG GAG GCC TCC ATG ATG GAA
gly cys thr ala phe arg val ile thr pro asn ile asp glu glu ala ser met met glu
        ref 8.1
3002              ⇓                 3032
GAC GTG GGG ATG CAG GAT GTC CAT TTC AAC GAG GAT GTG CTG ATG GAG CTC CTT GAG CAG
asp val gly met gln asp val his phe asn glu asp val leu met glu leu leu glu gln 3062                                3092
TGC GCA GAT GGA CTC TGG AAA GCC GAG CGC TAC GAG CTC ATC GCC GAC ATC TAC AAA CTT
cys ala asp gly leu trp lys ala glu arg tyr glu leu ile ala asp ile tyr lys leu
```

FIG. 6A (cont.)

```
                              ┌ ref 9.1
3122                          ⇓         3152
ATC ATC CCC ATT TAT GAG AAG CGG AGG GAT TTC TTT GAA GAT GAA GAT GGA AAG GAG TAT
ile ile pro ile tyr glu lys arg arg asp phe phe glu asp glu asp gly lys glu tyr 3182                                    3212
ATT TAC AAG GAA CCC AAA CTC ACA CCG CTG TCG GAA ATT TCT CAG AGA CTC CTT AAA CTG
ile tyr lys glu pro lys leu thr pro leu ser glu ile ser gln arg leu leu lys leu
                                                                  ref 10.1 ┌
3242                                    3272                               ⇓
TAC TCG GAT AAA TTT GGT TCT GAA AAT GTC AAA ATG ATA CAG GAT TCT GGC AAG GTC AAC
tyr ser asp lys phe gly ser glu asn val lys met ile gln asp ser gly lys val asn 3302                                    3332
CCT AAG GAT CTG GAT TCT AAG TAT GCA TAC ATC CAG GTG ACT CAC GTC ATC CCC TTC TTT
pro lys asp leu asp ser lys tyr ala tyr ile gln val thr his val ile pro phe phe 3362                                    3392
GAC GAA AAA GAG TTG CAA GAA AGG AAA ACA GAG TTT GAG AGA TCC CAC AAC ATC CGC CGC
asp glu lys glu leu gln glu arg lys thr glu phe glu arg ser his asn ile arg arg 3422                                    3452
TTC ATG TTT GAG ATG CCA TTT ACG CAG ACC GGG AAG AGG CAG GGC GGG GTG GAA GAG CAG
phe met phe glu met pro phe thr gln thr gly lys arg gln gly gly val glu glu gln
                     ┌ ref 11.1
3482                 ⇓                  3512
TGC AAA CGG CGC ACC ATC CTG ACA GCC ATA CAC TGC TTC CCT TAT GTG AAG AAG CGC ATC
cys lys arg arg thr ile leu thr ala ile his cys phe pro tyr val lys lys arg ile 3542                                    3572     |xxxxxxxx Coiled-coil 1 xxxxxx
CCT GTC ATG TAC CAG CAC CAC ACT GAC CTG AAC CCC ATC GAG GTG GCC ATT GAC GAG ATG
pro val met tyr gln his his thr asp leu asn pro ile glu val ala ile asp glu met 3602 xxxxxxxx Coiled coil 1 cont'd xxxx 3632 xxxxxxxxxxxxxxxxxxxxxxxxxxxxxxxxxx
AGT AAG AAG GTG GCC GAG CTC CGG CAG CTG TGC TCC TCG GCC GAG GTG GAC ATG ATC AAA
ser lys lys val ala glu leu arg gln leu cys ser ser ala glu val asp met ile lys
                                                          ┌ ref 12.1
3662 xxxxxxxxxxxxxxxxxxxxxxxx |         3692              ⇓
CTG CAG CTC AAA CTC AGG GGC AGC GTG AGT GTT CAG GTC AAT GCT GGC CCA CTA GCA TAT
leu gln leu lys leu gln gly ser val ser val gln val asn ala gly pro leu ala tyr 3722                                    3752
GCG CGA GCT TTC TTA GAT GAT ACA AAC ACA AAG CGA TAT CCT GAC AAT AAA GTG AAG CTG
ala arg ala phe leu asp asp thr asn thr lys arg tyr pro asp asn lys val lys leu 3782                                    3812     |xxxxxxxxxxxxxxxxxxxx
CTT AAG GAA GTT TTC AGG CAA TTT GTG GAA GCT TGC GGT CAA GCC TTA GCG GTA AAC GAA
leu lys glu val phe arg gln phe val glu ala cys gly gln ala leu ala val asn glu 3842 xxxxxxx Coiled coil 2 xxxxxxxxx 3872 xxxxxxxxxxxxxxxxxxxxxxxxxxxxxxxxxx
CGT CTG ATT AAA GAA GAC CAG CTC GAG TAT CAG GAA GAA ATG AAA GCC AAC TAC AGG GAA
arg leu ile lys glu asp gln leu glu tyr gln glu glu met lys ala asn tyr arg glu 3902 xxxxxxxxxxxxxxxxxxxxxxxxxxxxxxxxxxx 3932 xxx|
```

FIG. 6A (cont.)

```
ATG GCG AAG GAG CTT TCT GAA ATC ATG CAT GAG CAG ATC TGC CCC CTG GAG GAG AAG ACG
met ala lys glu leu ser glu ile met his glu gln ile cys pro leu glu glu lys thr 3962                                    3992
AGC GTC TTA CCG AAT TCC CTT CAC ATC TTC AAC GCC ATC AGT GGG ACT CCA ACA AGC ACA
ser val leu pro asn ser leu his ile phe asn ala ile ser gly thr pro thr ser thr 4022                          |xxxx PBM xxxxx|
ATG GTT CAC GGG ATG ACC AGC TCG TCT TCG GTC GTG TGA TTA CAT CTC ATG GCC CGT GTG
met val his gly met thr ser ser ser ser val val STP 4082                                    4112
TGG GGA CTT GCT TTG TCA TTT GCA AAC TCA GGA TGC TTT CCA AAG CCA ATC ACT GGG GAG 4142                                    4172
ACC GAG CAC AGG GAG GAC CAA GGG GAA GGG GAG AGA AAG GAA ATA AAG AAC AAC GTT ATT 4202                                    4232
TCT TAA CAG ACT TTC TAT AGG AGT TGT AAG AAG GTG CAC ATA TTT TTT TAA ATC TCA CTG 4262                                    4292
GCA ATA TTC AAA GTT TTC ATT GTG TCT TAA CAA AGG TGT GGT AGA CAC TCT TGA GCT GGA 4322                                    4352
CTT AGA TTT TAT TCT TCC TTG CAG AGT AGT GTT AGA ATA GAT GGC CTA CAG AAA AAA AAG 4382                                    4412
GTT CTG GGA TCT ACA TGG CAG GGA GGG CTG CAC TGA CAT TGA TGC CTG GGG GAC CTT TTG ⇓ ref 13.1
4442    ⇓                               4472
CCT CGA CTC GTG CCG GAA ATC TGA TCG TAA TCA GGG TAC AGA ACT TAC TAG TTT TGT CTA 4502                                    4532
GGA GTA TGT TGT ATG ACT AGG ATT TGT GCT ATT ATC TCA TTC AAC AAC ATA GAG CAA GAA 4562                                    4592
TAG TGA GCT AAC TGA GCT AGA CAC TCA ATT AAT CCG CTA CTG GCT TCA AGT CAG AAC TTT
                                              ⇓ ref 14.1
4622                                    4652  ⇓
GTC ATT AAT CAT CGA CTC CGG GAC GGT CAT ATA TGT ATT ACA TTT CTA CAT TTT TAA TAC 4682                                    4712
TCA CAT GGG CTT ATG CAT TAA GTT TAA TTG TGA TAA ATT TGT GCT GGT CCA GTA TAT GCA 4742                                    4772
ATA CAC TTT AAT GGT TTA TTC TTG TCA TAA AAA TGT GCA ATA TGG AGA TGT ATA CAA GTC

4802
TTT ACT
```

FIG. 6A (cont.)

BAC sequences of Human CLASP 2

Ref 1.1
Sequence of BAC4 using primer HC2AS2, which spans nucleotides 327-346 of the cDNA. Exon sequence is underlined and represents nucleotides 356-375.
<u>TTTCTACAGNGTNTACTCAG</u>GTATGTGCTCCTTCAACAAAATTAGCAGTTGCTGCTCT
GTGACAAAGTTTGCACCATTTTGCAAGAAGAAAAAAATCCTAATGTGTTATATTACTA
TATTTTTACTCTATAGATCTTTTTCTAAAGAAAGAAAGTACAACTGAAGTGCTTATAT
GTATTCATATAAATGACTAGTACAAGCATCATTTTGCAACAGATTTCCCCTTTCATTG
GAGGATCTTCTTGATGTTATTTGTACACGATCAATTTTTAGTCTTAATAAGATGAGGC
TGGGTGTGGTGGCTCACACCTGTAATCCTAGCATTTTGGAGGCCAAGGTGGGCAGAT
CACTTTAGCCCAGGGGTTTGAGACCAGCCTGGCCAACATGGCAAAACCTTGTCTCTA
CAAAAATACNAAAATTATCCAGGCATGGTGATGTGTGCCTGTAGTCCCAACTNCCTAG
GAGGCTAGGGGTAGGGGGATTTGCAAGAGGCTGGGAGGGTCAAAGCCCNAANTGAG
CCATTGGTNCATGTCACTTGGACCCCAAGCNNGGGGNGANCAAGAGCAAAGGACTNN
TGTNNTTTANAAAAAAAACCGGGCTACCATACNNACCAACCCNCNNACCTACCCNACC
TTTCCANNTTAAAANAAGGCTTTGNCTTGCANAGGAAAANCAAAATNNCC Ref 1.2
Sequence of BAC26 using primer HC2AS2, which spans nucleotides 327-346 of the cDNA. Exon sequence is underlined and represents nucleotides 351-375.
<u>TCTGGTTTCTACAGTGTATACTNAG</u>GTATGTGCTCCTTNAACAAAATTAGCAGTTGCT
GCTCTGTGACAAAGTTTGCACCATTTTGCAAGAAGAAAAAAATCCTAATGTGTTATAT
TACTATATTTTTACTCTATAGATCTTTTTCTAAAGAAAGAAAGTACAACTGAAGTGCTT
ATATGTATTCATATAAATGACTAGTACAAGCATCATTTTGCAACAGATTTCCCCTTTC
ATTGGAGGATCTTCTTGATGTTATTTGTACACGATCAATTTTTAGTCTTAATAAGATG
AGGCTGGGTGTGGTGGCTCACACCTGTAATCCTAGCATTTTGGAGGCCAAGGTGGGC
AGATCACTTTAGCCCAGGGGTTTGAGACCAGCCTGGCCAACATGGCAAAACCTTGTC
TCTACAAAAATACAAAAATTATCCAGGCATGGTGATGTGTGCCTGTAGTCCCAGCTAC
CTAGGAGGCTAGGGTAGGGGGATTGCAAGAGGCTNGGAGGTCAAGGCCCGCAGTGA
GCCATGGTCATGTCACTGCACCCCCAGCCAGGGCCGACAGGAGCAAGACTNTTGTNT
CAAAAAAAAACAGNAACCAACANCCAACAACAACAACNACCTTTCNGCAAAANAAGC
TTGCTNCAANGAAACCAAAATGNCTTCTTNTTTTCCCCCN Ref 1.3
Sequence of BAC26 using primer HC2AS2, which spans nucleotides 327-346 of the cDNA. Exon sequence is not found within this sequence. This sequence most likely represent intron sequence since this sequence matches the intron sequence found in the previous two BAC sequences.
AGNNNNNCCCNCTACNCCACTTTTAACCTTTTGAAAACACAGTGTTTNCTCAANTATG
CGCTCCTTCACATATTAGCAGTTGCTGCTCTGTGACATAGTTGCACCATTNTGCAAGA
AGAAAAAATCCTAAGTGTNATATCACTATATNNNTACTCTATAGATCTTNTCTAAAGA
AAGAAAGTCAACTGATGTGCTTATATGTATNCATATAAATGACTAGTACATGCATCAT
TTTGCAACAGATNTCTCCTCACATTGGAGGATCTTCTNGANGNATTCGACACGATNAN
TATTAGTCTNAATAAGATGANGCTGGTGTGGNGGTACACTGNATCTAGCATNTGGAN
GCATGTGGCAGACACTTANCCNCGGTNGAGACAGCTGTCACTGNCNAACTGTCTCTN
TAAANCAAANNCTCCGCNGGNGATGGGCTGAGCCAGTCCTAGNNGCTAGNTAGNGAT

FIG. 6A (cont.)

GNNGAGNTGTNGCACGNCGAGNGAGCATGNTCTGTACTGACTCATCAGGCGNCNACA
CGNTCTGTTCNAAAACATACCACACACACTCNCACCTNCGCAAAATTGCTCTNNAAAN
ATGCTTNTTTCACACNGNTNCAATCNCTATATNNTCTTCTATTCTNCACGTNTNATTA
NNATCTTNCNCTGCANAACNATNCGNCCACCTNNANNACCTTANGCTTNGTTTCACGC
TTATAGCTCCCCTACACNTNNCAGCNNTTNCNNGTGAAGGGCCNCCCGAATCTACGA
NCATACTCTCTCCGTATATNGCCTCGGTCANCGCCATCTGCTGTNTNCTCNTCNCTNG
CNNTTNANCNGTNCGCTATCTCTNNNCCGGATCCNCNCCATATNNTNNCTCTACTTAN
AGCGTAANNTNTNCNCNCACTANTCACAACTTNTNCNTNNAACTCTATCTNCTCCTCT
CTACCACCTCACTTACTACCTNTTCACNCANTCTCCTTCNCTNTCCACTGATCTCCACA
TAGCTGCTNTACTCGCCANTTTATCATATNCACACNCTCTACGCTNNNTNT

Ref 2.1
Sequence of BAC4 using primer HC2S1, which spans nucleotides 1107-1126 of the cDNA. Exon
sequence is underlined and represents nucleotides 1079-1097.
<u>CTTGTATTNAAAGAGGGTCTGCAGGAAGAAGTGTGT</u>AGTCATAAATACCTCACTGGA
TATTTTATACAGGATTCTAAAAAACCTATTAGCAATAGTATGCTAGAAATAGTCATTA
GCTTCTTGACCTTCTTAGAACTGCACACTCTATTGCACTGTACAGATTTCAGGATGGC
TGCAGGGATTGATTTGAAAACTAAGGACACATTTCAATAAACAATGTCTTCAATTGAT
TTTTAGGGCTCCTCCTACTTCAATGAAGGACTTCAGGTAGCTTATAATTACAGACACA
GGCTCAATACAATAAAAAAATTAGTAAGGCAGAGCTTTAAAAAAAAAAAAGGAAAAA
GATAATTCTACCAGAGAAAGGCTACATGGTGACTTCTGTTACCAGTAACAACCCCCG
CACTACCTTTGGGTCTCCAGGAGCAAAACAGCTAATGTAGTTGTTGATCTGCTTGAAG
ACAAAGCCCCTGTCCATGAAGGTGAAACATCTCTGTGGAGGAAAACAAGCAAAAAG
TTATTTCAGGTCCAAACATTTCGGAAATTTGGATTCAAAGCAGGCATTTATTGCTAAT
AAGTTTATCCACTGACATAAAAAACATGCCTTCAACATTGCCAGAGCACCTACTCTAT
TNTAGTCNCN Ref 3.1
Sequence of BAC4 using primer C96AS, which spans nucleotides 1443-1452 of the cDNA. Exon
sequence is underlined and represents nucleotides 1370-1422.
<u>AATCAGCAGACCAAACAGAGGCAGGTAGAGGGTGGCTATCCTTGCCTGATGGCTCTG</u>
AAAAGAAGACACACATGGTAAGTTTGACCCAGGATTCTGAGAACCGAACTAAGTTGG
TGCTGACCATCTCCTTTATTTGGATCCTTCCTATAAAGACAGATATTTGATTTTAGTCC
CAAAATAGAGCAAAATCTTAGTGCTGTTACCATGAATTTTCTAACTGATTACTTTCTTT
ACACCACTTAAAATAAAGGACATTATCAATGCACATTCCTTCCATTGGGGACCACTCA
CCCTTGAAGCATATCTGTCATCAAAAGAATGCTTTATCAGCAGGTTCTTGAGCACACT
GATGGCGATCAGACGGACCTCCCGGAACTCCTGGAGGGCTGTCCCCACCTCCCTNAG
TAACAGTCCCACCAAGAAGTGGTTTCTGCAGAACTCATCTGTTAATGAGTAGTCAAGC
TGGGAGGTCTGAAATGAGGATAGAAACTACTTTGNGTTAGGAAAGATGCAATGCTCT
TTTGAATAAAACAAACAAACCAAACNAACAAAAAAAAAAACTAAGACCCATCCTTNTGN
ATTTCAAGCCCACCCTGGGGTNGGTCAAAGAGATGATCAGNANTTTGGCNTTNAAAT
GAAGAAAGAAATNAATTNTCCAGGGGNTGTTCTNCTTTTTAGCACANGGAGGGATNT
TAANTGAAAACCAATTTAAATCCAATTNAGGNG

FIG. 6A (cont.)

Ref 4.1
Sequence of BAC4 using primer C2AS5, which spans nucleotides 1716-1735 of the cDNA. Exon sequence is underlined and represents nucleotides 1602-1703.

<u>TTCCTTTCTGCAAGGCTGTTCCCGAATCTGTGCTTATGAGAGATCCTCTCGAATCAGC
ATTTCTCACACTGTTGATGTTTGGAGTTGAGGTTGTATATGGAGAAGCTAAATGGAAA</u>
TCAAGCCAACAATAAAGTTTTATTAAGACAGAACAAAATAAAGATGAGTACTGAACTT
TAAGGGAAATTGCTTTTATTGCACTTATTTTTCTGTTAGGAAGTTGGCTCAAGAGTT
GCATTCCATTACTTCACCTTTAAAGAACCAGGTCATATACAATGAGATAAAAAGAAAC
TAGTCTGAAACATTCAGATGTAAACATCAATTCACTTGTTAGAAACCACCTTTGATCG
CTAAAGACTAAATGCATACCTGTTTCAGAATGTGATAGAATGAAGACTTAAAAAAATT
AAAAGATAAATCCACCTACAACTATCAAATCACAAAATTAAACCACACAACAAACTTG
TAGCATTCAAACTGGTAATAAACACTGAGGAGCCTACCCAACTCTGAGGGGTGTCAT
GGGGTATTTTAAATTTTCGAGGAGAACACAGTGATATGTGACCTCAGCCAGAAGCTG
CTGTTTNAGCAGCAGGTTGGTGCTATGCTCCTTTTTGAAGACATATTTGTGAAGCTGG
GTATTTTGGGGGGCCTGCTTATGATAAAANGGCAAGGTNTTCAATGNAGGGGN

Ref 4.2
Sequence of BAC26 using primer C2AS5, which spans nucleotides 1716-1735 of the cDNA. Exon sequence is underlined and represents nucleotides 1602-1703.

<u>TTCCTTTCTGGAAGGCTGTTACCCGAATCTGTGCTTATGAGAGATCCTCTCGAATCAG
CATTTCTCACACTGTTGATGTTTGGAGTTGAGGTTGTATATGGAGAAGCTAAATGGAA</u>
ATCAAGCCAACAATAAAGTTTTATTAAGACAGAACAAAATAAAGATGAGTACTGAACT
TTAAGGGAAATTGCTTTTATTGCACTTATTTTTCTGTTAGGAAGTTGGCTCAAGAGT
TGCATTCCATTACTTCACCTTTAAAGAACCAGGTCATATACAATGAGATAAAAAGAAA
CTAGTCTGAAACATTCAGATGTAAACATCAATTCACTTGTTAGAAACCACCTTTGATC
GCTAAAGACTAAATGCATACCTGTTTCAGAATGTGATAGAATGAAGACTTAAAAAAAT
TAAAAGATAAATCCACCTACAACTATCAAATCACAAAATTAAACCNCACAACAAACTT
GTAGCATTCAAACTGGTAATAAAACACTGAGGAGCCTACCCAACTTTGAGGGGTGTC
AATGGGGTNTTTTAAATTTTTCGNGGGANANCCCAGTGNTATGGTGACCTTCACCCA
AGAAGCTTGTTTGTTTNACCAAGCNAGGTTGNNCTNTGCTCCTTTTTAGAANACNNTA
TTTTNNNAAATNCTGGNTTTTTTNNGNGGCCCCCTNCNTTNNT

Ref 5.1
Sequence of BAC4 using primer C2S6, which spans nucleotides 1686-1705 of the cDNA. Exon sequence is underlined and represents nucleotides 1724-1736.

<u>TTCCTGGATAAGG</u>TAATTGCTTTTACCCAACACAAATGTTTCTTATAATCAATGGATT
TAGCCCAAAGTAAACGTACTTCATGTTCTAGTGCCTTTTAAGTGTGACCTTTTGTTTT
TTTCTAAACCACCCGGCTGACCTGGAGTAGGTGATGAGAGCTTTAAGGTTGGGGCCC
ATTCCTTGAAGTGCTCTGATTCCTGTTTCCAGTACCTCAGATCCTGGGCAGGGTTTGC
AGTGGAGCGTCTTGAGTGAATGGCTCTGGTGGGTTGAACGGGGAGGGACTCAAAAT
GCTGCCCATCTCAATTTCCTGTAGTCTTTTTATTTATTTATTTATTTTTTGAGACAGAG
TCTCGCTCTGTCGCCCAGGCTGGAGTACAGCGGCACGATCTCAATTNACTGCAACCT
CCGCCTCC:TGGGTTCAAACGACTCCTCTGCCTCAGCCTCCCCAGCAGC:TGGGACCA
CAGGCACAAGCCACCACCGCCCGGCTAATTTTTTGTNTTTTTAGTA:GAGAT:GGGGTT
TCACCATATTTGGCCAGGCTGGGCTCAAACTCCTGACC:TCGTCATCCGCNCCCTCGG
NCTNCCAAAGTGCTTGGGATTNCAGGCNGTGAGCCCACTTACACCTNGGGCAATTCC
CTGTNAGTCTTTTTTACCAGAGACACCATCATTCAACACAGCTTTTCCACCCACAA

FIG. 6A (cont.)

Ref 5.2
Sequence of BAC26 using primer C2S6, which spans nucleotides 1686-1705 of the cDNA. Exon sequence is underlined and represents nucleotides 1712-1736.
<u>TGAGAAGAGCAATTTCCTGGATAAG</u>GTAATTGCTTTTACCCAACACAAATGTTTCTTA
TAATCAATGGATTTAGCCCAAAGTAAACGTACTTCATGTTCTAGTGCCTTTTAAGTGT
GACCTTTTGTTTTTTTCTAAACCACCCGGCTGACCTGGAGTAGGTGATGAGAGCTTTA
AGGTTGGGGCCCATTCCTTGAAGTGCTCTGATTCCTGTTTCCAGTACCTCAGATCCTG
GGCAGGGTTTGCAGTGGAGCGTCTTGAGTGAATGGCTCTGGTGGGTTGAACGGGGA
GGGACTCAAAATGCTGCCCATCTCAATTTCCTGTAGTCTTTTTATTTATTTATTTATTT
TTTGAGACAGAGTCTCGCTCTGTCGCCCAGGCTGGAGTACAGCGGCACGATCTCAAT
TCACTGCAACCTCCGNCTCCCTGGGTTCAAACGACTCCTCTGNCTNAGNCTCCC:AGC
AGCCTGGGAACCACAGGCTCANGCCACCACGCCCGGCTAATTNTTGTAATTTTNAGT
AANAAATTGGGGGTTCTCACCATNTTGGCCCAAGNCTTGGGCCTAAAAACCTTNCTNA
CCNTCGNCATTCNCNCCCCNACCNTGGGCNCTNCTCAAANGNGCTTGGGGATTTANC
ANNGGCNTTAACCCCCCNTATCACCGTGGNCCTTAATTT Ref 6.1
Sequence of BAC4 using primer C2S7, which spans nucleotides 1918-1937 of the cDNA. Exon sequence is not found within this sequence.Since the primer is directed against exon sequence we presume that sequence derived from C2S7 is intron sequence.
NAGNGNGGGTTTNAGNCGTTTGAAGCCTGNNACGNGGTGNGTGCTNGAACTCTGTGG
GCTTTCAGGTACTGGGGTATCTGGGAGCCTGCTGTTTGCATTGCTAGTGCATCAGAC
CAGGGCTTTTTCCTCCCTGTAGCTGCTACTTATACACATAGCTCTAACTGAGATGATT
CTCCAGACAACTGATGCAGAGCAGCAAAAGCTTCTGCCGTTCTCCCCTTCTAGGAGT
GTCTCCTTTCTTTGGAAAGAGATCATGAGGGGCTAGATTGTAATGAAGTGAGGCTCA
GTGCTTGAGCACATCCGGTAAAAGTTCCAATATATTGGTCATAAAGTTTCTCATTCTT
TATAGCAGTTAATTTCTCTGGCTCATGAGTTTTCTTAGTTTTAATCTGACTTTTAAATT
AATGTCTCCAGCACCAGTCATATCCCCAGGGCAAACTCAAAGGCATGAGAGGCCAGA
CTCGGGTCCTGGTCATAGCAACCCCTGTCTAGGGCCTTGGTCCCTGCCTCCGCTTGT
GTGCTGTGGCGCAGGTCCTATGGGCCCTTAGGAAACAGGACCACCCTGTCGCACCCC
CTACAGAGACCAGCCAAGTTTGACATTAGATCACCGTAGCAATGTNTGCAAATTCCA
GTTTCTTGCTAAAACAGGTTAAGCCTTGCAGCCACTTTATCTGTAACTGGCNGAGGTT
TTGACATAAAA Ref 7.1
Sequence of BAC4 using primer C2S8, which spans nucleotides 2143-2162 of the cDNA. Exon sequence is underlined and represents nucleotides 2182-2219.
<u>CTCTCGACACGCTGTTTCTATTAACATTGGCGTTTAAG</u>GTTTGTATCAATTTGCTGTT
CGNGGTTCTAGTTTTACCTTTCACATTCATTCTGCTTGGTAAGCTCAGTGAGCACAAA
CTTACTATGTTGCATTTTTACTTCAGCAATTATTTTTGTCCCTGTAAGGAAACCATTAA
TCTTTAAATTCCTTTAATGAAATCATTCCACAGTGAATGGCTTGAATGCCCTGAAATA
AAATTTAACTGGTCAGTGTGTGCTGCGCGCTTGGGTATGGTGGAAACACGGTCTCTG
GAGGCAGTTAACTCTTGGCTCGAACCTTGAGGATGGTGAATATAGGCACCTAATCAG

FIG. 6A (cont.)

```
GCATTTCTGCCTTGAATATCTTTAAATATATCCAAATGTTATAGCGTTTAATTAGATTT
TTATGTAGAAAGGAGCAATAAACACAAGACACATGTTTTCAGTTTTTTATCTGTTACT
GCATTAAATGATAAAAACGTTTTGGAGATAGAAAATGAAAGGGGTTTTTTTTTTGTCT
TGTTTTAAAGTTTTAGCAAATAATATTCAAGTAGGTGGAGATGGACTCTTCACCACTC
TCCTGTTTTTAGGAACCCAATACTTTTTCATTCTTGCTAAATGATTACTTCCATTTCTA
GCATAGAAAAGGAGAAAATTGGAATGAGTGTTTATAT
```

Ref 8.1
Sequence of BAC4 using primer C2S9, which spans nucleotides 2992-3011 of the cDNA. Exon sequence is not found within this sequence. Since the primer is directed against exon sequence we presume that sequence derived from C2S9 is intron sequence
```
CGCTTTNAAATNCCAGCCGCTACTGCGGGGCGNTNAATTCGAAACGTGTTGTTNTCT
GTGATGCCTGGCTCTGATTGTGTGGGATTGGTCATCAGTGGCGGTTGGCAGNTGGGG
TTCATGGAAGCGGCCATGGGGACTGATGGCAGGCCCTTGGATTGCCACCGCAGAGCC
TGGCAGTGTCTTTGGTCTGCATTCCTACCGGCGAAGTCTCATTTCACCTACGTGTTA
TCTCTTGGAAAGCATTCCTTTAGCGGGCTGTGTCTACCCTTCCATCCTCTCGTCCAAA
CTCCCCCTCCTTCTCTGTTCTGTCTCCTTCCCATCCTCTTCTCCCCAGTTCTTCTTCCT
ATGTTCCTTCCTCAGTGGTTTCTCTTCCTCTGTTTGACTTTCCAAGGTCATTTTGACTG
TTCCTGCTCCCAACTACAAAGATACTAAAATCTCACCTAACCACTCTTCTTCTTTCTTA
ATGAAAGAATGTTTTCAGTCCATCCCAAATTTGTGTGGACTTCACAAACCTTCTCTAA
AATGGAGCCTTTTCTCTTCCTACTCTTGACTAGNTGGTAAACGCTCCATGTTCTTGGC
CAGAACTCCCTGGTGAGTAGCGTCACTCCCACTTTCCTGTGCAGAACCAAGCCTCCT
AGAAAACTCCTTTGCANCTGAGTGGGTTGGGACACGCCCTTTNTTTGGG
```

Ref 9.1
Sequence of BAC4 using primer C2AS10, which spans nucleotides 3276-3295 of the cDNA. Exon sequence is underlined and represents nucleotides 3147-3234.
<u>TTTANACCNATNTATCCGNGTCAGTTANAGGAGTCTCTGAGAAATTTCCGACAGCGGT
GTGAGTTTGGGTTCCTTGTAAATATACTCCTTTCCATCTTCATCTTCAAAGAATCCCT</u>
GTGACATAAAGCACAATTAGAGCTATCCCTGAACGTAAGCCCAGGGCTTACCACCTA
GGAAGCGTTCTTTTATTACAAGGGGGAAAAAAAGGAATGGGTCTAAAAATCCAGCTG
AAATGGGCTTTCTGAATGAGAAAGAAAATGCTAATAACATGAAGTCTAGGTGCAAAG
GTAAAGGAAAAACACAACATTGCAAACTTATTCAAGAATGCAGTCATTAAGTGTTGAG
TGAAATGAAAGATTTTGGATACAAGACTAAGCTGTCCCAGGGAAGTCTAATGGGAGT
CAAGCCTGTTTCACTTTCCCAAGAAGCAGAACTCACTANAAAATGATGAGCAGCCCA
CGACAGGCAGGCTCAGAAGTGGACATGCCTCCCTTCTCCTGATGGCTNCCATGCACA
CAGGATTTTATGGCATGAACTGAAGCGTTTGGGGGTCTGGAGTAAGTTTAGTAAAAG
TTAGGTAAAGCTTGTATAAATTGTATTTTTGCTTTACCCGATGAGAAAAAAAATATTN
AAGACCTGGTAGCTTCAATATTCAAGAAAAATATTTTTCATNTCACCCG Ref 10.1
Sequence of BAC4 using primer C2S11, which spans nucleotides 3167-3186 of the cDNA. Exon sequence is underlined and represents nucleotides 3231-3296.
NGNANGTGGAGCCNCGANCCAGGGACAATCTNAAC<u>CTNCTTAAACTGTACTCGGATN
AATTTGGTTCTGAAAATGTCAAAATGATACAGGATTCTGGCAAG</u>GTATTGACCATGTT
TGGANAAGTTTCATAGCAATGTAATGTTGTGATNCGATTACATATNATATATTTTAA
ATGTNTATAGAAAAAAACACANGAAAAATATTAAGGATTGTTGGCCCGTGAGTGGCA
GGTGTATNTTCTTNCTGATCCTTTAGNGCTTTCCATTACATGCNTGACATTAAAAAAA
NCTTTATCGCCTAATTTTTGAAACATCTAATTTTACAAAATAATTAACCGTNTGGCCAN
GNATATTNTCATTTTTAGGNCCAGCTATTTAGAAACTCTGACANAAATGAGGGGCTGT
GGCTTNCCTNCCTNNACTTGNCCCTCTTTCNNGNATGTACCACATGAACTTGNCNCCT
CTTTCNNCTNACCGGGTGGCATGTTANAGGACAGGTTGAAACCNCANTNGGGCNGGA
NTTNGGTNNAATTGGGACACAATGGTACNANGCTCTATNGGAATNGAAACTCTCCCN
ACNNNCNGTGNNCCNTGGGGAAAATGNGNCNNATTCATTTTN Ref 11.1
Sequence of BAC4 using primer C2S12, which spans nucleotides 3474-3493 of the cDNA. Exon sequence is not found within this sequence. Since the primer is directed against exon sequence we presume that sequence derived from C2S9 is intron sequence
AGNANNGTTNNGCAGCTGCANNTCTGGACCCANAGGCCGCANGGGCACGAGCCNGG
ACACGCTCGGCAAAGAGCTGTCCAGAGGGATTCAGAAGCTTCAGGACTGGAAGGGTC
TTTCGAGCTCAGTTAGCCACCCCCACACCCATTTCAGTTTCACATTTATCTAGTGCTT
CCTTTTGAATACTTGGGATGTTTTCTGTTGATCTGTTGGCACTTCCTTCTTCCACAA
GACCAGAAGCTCATATCCAATCTAAGGTCACTTACCCTTCTGAGAATCTGATGAAAAT
GGCGTGCCTTATGTGCCTAGATGCTTTTGCACACAGTCTAAGGTGACTTATGGACTCC
AGGTCCAGCAGCCACACCCAGTCCTGGGTCTCCGCACAGGGAGGGACCCGTCTTCAC
ACACCTGTCTCAGGTTCTAGCATTGGGCTGCTTCAGCGGTCTCAGGCTGTGAGTAAA
TGGGATGTGAGCTTGGATCGCCCCACGCTGTTGNCCCCCGGGGGGCTTGGCCAGCTG
GCCACTTNGAAATGCCTCCTTTTGCCCAGGAAAGCTCACTGCATTTCAATGGGGNTTN
TCCACGAAGTTCANCTTTANGGG Ref 12.1
Sequence of BAC4 using primer C2S13, which spans nucleotides 3645-3664 of the cDNA. Exon sequence is underlined and represents nucleotides 3683-3699.
AGNAAGGTNNCTCANTNAANN<u>CAGCGTGAGNGTTCAGG</u>TGAGCCAGGCACAGCAGGC
CGGAGGGCAGCAGGGGACGTCCTTGCCCCTGGGTGACTTGAGAGTCGTTTCCACTAA
CAAGGTCTACTTGAGAGCCTCGGTTTACCAAGTGATCCCTGCTCCCTTCCCCCAACGT
NTGTGACATTTCTCCTGATATCAGAGGGGGAGGAAACCTCATGATCCCTGCCCCCCG
CCCCATGAGGACTGACTGTGGGGACAAAGAGCCAGATCTCATAGACTACCCTGATTT
GTCAGTATTTGGGGAATTCTGGGTGCCTGATTAGAAGCATCAAGACTCTTCTAAATNC
AAAGAAGTGTGGAGAGCAGTAGATTTTCCTATAAAACTGGTGTTGCTGGTTTCTATGA
AAATTGGATCCAAAAAAAGTCCTTAAGTTTACCCTCTTAATGGNATCTTTTGATTAAT
GGAATTCATTATTTTAATATAGCCCAATCAATCCAATTTTTCTTTATTGGTAGCATTTT
TATGTTCTCTTTAAAAAAATCTTGGNCTACCTCCAAAATTTCACAGATGTTCTCCTAG
GGTTTTCCTCCTTTTGGTTCAAGCATCCCATTCAANGTCTTGCAGTCCATTCTGGGG

FIG. 6A (cont.)

Ref 13.1
Sequence of BAC4 using primer C2S14, which spans nucleotides 4289-4308 of the cDNA. Exon sequence is underlined and represents nucleotides 4321-4448.
<u>GACTTANATTTATTCTTCCTTGCAGAGTAGTGTTAGAATAGATGGCCTACAGAAAAAA
AAGGTTCTGGGATCTACATGGCAGGGAGGGCTGCACTGACATTGATGCCTGGGGGAC
CTTTTGCCTCG</u>AGGCTGAGCTGGAAAATCTTGAAAATATTTTTTTTTCCTGTGGCAC
ATTCAGGTTGAATACAAGAACTATTTTTGTGACTATGTTTTTGATGACCTAAGGGAAC
TGACCATTGTAATTTTTGTACCANTGAACCANGAGATTTAAGTGCTTTTATATTCATTT
CCTTGCATTTAAGAAAATATGAAAGCTTAAGGAATTATGTGAGCTTAAAACTAGTCAA
GCANTTTAGAACCAAAGGCCTATNTTNATAACCGCAACTATGCTNAAAAGNACAAAGT
AGTACAGNATATTGNTATGTACATATCATTTGGTAATACACNCCNGGCNTTCTGTACA
TATATGTATTACATTTCTACNTTTTTAATACTCCCNTGGGCTTATGCCNTTAAGGTTAA
NTTGNGATAAATTTNGGCTGTTCCNGTNTATNCNATACNCTTTT

Ref 14.1
Sequence of BAC4 using primer C2AS15, which spans nucleotides 4680-4700 of the cDNA. Exon sequence is underlined and represents nucleotides 4660-4683.
<u>ATGAGAATGTAA</u>TACATATATGTACAGAATGCCAGGACTGTATTAACAATGATATGTA
CATAACAATATACTGTACTACTTTGTACTTTTCAGCATAGTTGCGGTTATTAATATAG
GCCTTTGGTTCTAAACTGCTTGACTAGTTTTAAGCTCACATAATTCCTTAAGCTTTCAT
ATTTTCTTAAATGCAAGGAAATGAATATAAAAGCACTAAATCTCCTGGTTCACTGGTA
CAAAAATTACAATGGTCAGTTCCCTTAGGTCATCAAAAACTAGTCACAAAAATAGTTC
TTGTATTCAACCTGAATGTGCCACAGGAAAAAAAAAATATTTTCAAGATTTTCCAGCT
CAGCCTCGAGGCAAAAGGCCCCCAGGCATCAATGTCAGNGCAGCCCTCCTGCCATGT
AGATCCCAGAACCTTTTTTTTCTGTAGGCCATCTATTCTAACACTACTCTGCAGGGAG
AATAAAATCTAAAGNCCAGCTCAAGAGTGCTACCACACCTTTGTTAAGACACAATGAA
AACTTTGGATATTGGCAGGNGAGATTTAAAAAAAAATGTGCCCTTTCTTACCACTCCT
ATAGNAAAGTCTGGTTAAGAAATAACCGTTGGTCTTTATTTTCCTTTTNTTTCCCCTTC
CCTTGGGNCTTCCTGGGGCTCGG

FIG. 6A (cont.)

```
HC2A   ------------------------------------------------------------
KIAA   ASGNLDKNARFSAIYRQDSNKLSNDDMLKLLADFRKPEKMAKLPVILGNLDITIDNVSSD
rat    ------------------------------------------------------------
HC4    ------------------------------------------------------------
HC1    ------------------------------------------------------------
HC3    ------------------------------------------------------------
HC5    ------------------------------------------------------------

HC2A   ------------------------------------------------------------
KIAA   FPNYVNSSYIPTKQFETCSKTPITFEVEEFVPCIPKHTQPYTIYTNHLYVYPKYLKYDSQ
rat    ------------------------------------------------------------
HC4    ------------------------------------------------------------
HC1    ------------------------------------------------------------
HC3    ------------------------------------------------------------
HC5    ------------------------------------------------------------

HC2A   ------------------------------------VLHHHQNPEFYDEIK
KIAA   KSFAKARNIAICIEFKDSDEEDSQPLKCIYGRPGGPVFTRSAFAAVLHHHQNPEFYDEIK
rat    ------------------------------------------------------------
HC4    ------------------------------------------------------------
HC1    ------------------------------------------------------------
HC3    ------------------------------------------------------------
HC5    ------------------------------------------------------------

HC2A   IELPTQLHEKHHLLLTFFHVSCDNSSKGSTKKRDVVETQVGYSWLPLLKDGRVVTSEQHI
KIAA   IELPTQLHEKHHLLLTFFHVSCDNSSKGSTKKRDVVETQVGYSWLPLLKDGRVVTSEQHI
rat    ------------------------------------------------------------
HC4    ------------------------------------------------------------
HC1    ------------------------------------------------------------
HC3    ------------------------------------------------------------
HC5    ------------------------------------------------------------

HC2A   PVSANLPSGYLGYQELGMGRHYGPEIKWVDGGKPLLKISTHLVSTVYTQDQHLHNFFQYC
KIAA   PVSANLPSGYLGYQELGMGRHYGPEIKWVDGGKPLLKISTHLVSTVYTQDQHLHNFFQYC
rat    ------------------------------------------------------------
HC4    ------------------------------------------------------------
HC1    ------------------------------------------------------------
HC3    -----------------------------------GPGPARSTVSISLISNSARV
HC5    ------------------------------------------------------------

HC2A   QKTESGAQALGNELVKYLKSLHAMEGHVMIAFLPTILNQLFRVLT-RATQEEVAVNVTRV
KIAA   QKTESGAQALGNELVKYLKSLHAMEGHVMIAFLPTILNQLFRVLT-RATQEEVAVNVTRV
rat    ------------------------------------------------------------
HC4    ------------------------MEIQVLIRFLSVILMQLFWVLPNMIHEDDVPISCPMV
HC1    -----------------------MSFLPIILNQLFKVLV-QNEEDEITTTVTRV
HC3    NRSRSLSNSNPDISGTPTSPDDEVRSIIGSKGLDRSNSWVNTGGPKAAPWGSNPSPSAES
HC5    ------------------------------------------------------------
```

FIG. 6B

```
                                                                                            Ref.
HC2A    IIHVVAQCHEEGLESHLRSYVKYAYKAEPYVASEYKTVHEELTKSMTTILKPSADFLTSN
KIAA    IIHVVAQCHEEGLESHLRSYVKYAYKAEPYVASEYKTVHEELTKSMTTILKPSADFLTSN
rat     ------------------------------------------------------------
HC4     LFHIVSKCHEEGLDSYLSSFIKYSFRPGKPSAPQAPLIHETLATMMIALLKQSADFLAIN
HC1     LPDIVAKCHEEQLDHSVQSYIKFVFKTR---ACKERPVHEDLAKNVTGLLK-SNDSPTVK
HC3     TQAMDRSCNRMSSHTETSSFLQTLTGRLP----TKKLFHEELALQWVVCSG--SVR---E
HC5     ------------------------------------------------------------
                                        Cadherin
                                        Cleavage
HC2A    KLLRYSWFFFDVLIKSMAQHLIENSKVKLLRNQRFPASYHHAAETVVNMLMPHITQKFGD
KIAA    KLLKYSWFFFDVLIKSMAQHLIENSKVKLLRNQRFPASYHHAVETVVNMLMPHITQKFRD
rat     ------------------------------------------------------------
HC4     KLLLKYSWFFFEIIAKSMATYLLEENKIKLTHGQRFPKAYHHALHSLFLAIT-IVESQYAE
HC1     HVLKHSWFFFAIILKSMAQHLIDTNKIQLPRPQRFPESYQNELDNLVMVLSDHVIWKYKD    6.1
HC3     SALQQAWFFFELMVKSMVHHLYFNDKLEAPRKSRFPERFMDDIAALVSTIASDIVSRFQK    1.2/1.2/2.1/2
HC5     ------------------------------------------------------------

HC2A    NPEASKNANHSLAVFIKRCFTFMDRGFVFKQIN---NYIS--CFAPGDPKTLFEYKFEFL    2.1
KIAA    NPEASKNANHSLAVFIKRCFTFMDRGFVFKQIN---NYIS--CFAPGDPKTLFEYKFEFL
rat     ------------------------------------------------------------
HC4     IPKESRNVNYSLASFLKCCLTLMDRGFVFNLIN---DYIS--GFSPKDPKVLAEYKFEFL
HC1     ALEETRRATHSVARFLKRCFTFMDRGCVFKMVN---NYIS--MFSSGDLKTLCQYKFDFL    7.1
HC3     DTEMVERLNTSLAFFLNDLLSVMDRGFVFSLIKSCYKQVSSKLYSLPNPSVLVSLRLDFL    3.1/3.2
HC5     ------------------------------------------------------------

HC2A    RVVCNHEHYIPLNLPM-----PFGKGRIQR------------YQDLQL----DYSLTDEF
KIAA    RVVCNHEHYIPLNLPM-----PFGKGRIQR------------YQDLQL----DYSLTDEF
rat     ------------------------------------------------------------
HC4     QTICNHEHYIPLNLPM-----AFAKPKLQR------------VQDSNL----EYSLSDEY
HC1     QEVCQHEHFIPLCLPIRSANIPDPLTPSES------------TQELHASDMPEYSVTNEF
HC3     RIICSHEHYVTLNLPCSLLTPPASPSPSVSSATSQSSGFSTNVQDQKIANMFELS--VPF    4.1/4.2
HC5     ---------------MNADTAPTSPCPSIS---SQNSSSCSSFQDQKIASMFDRTSRVPA HC2A    CRNHFLVGLLLREVGTALQEFRE----VRLIAISVLKNLLIKHSFDDRYASRSHQARIAT    3.1
KIAA    CRNHFLVGLLLREVGTALQEFRE----VRLIAISVLKNLLIKHSFDDRYASRSHQARIAT
rat     ------------------------------------------------------------
HC4     CKHHFLVGLLLRETSIALQDNYE----IRYTAISVIKNLLIKHAFDTRYQHKNQQAKIAQ
HC1     CRKHFLIGILLREVGFALQEDQD----VRHLALAVLKNIMAKHSFDDRYREPRKQAQIAS    8.1
HC3     RQQHYLAGLVLTELAVILDPDAEGLFGLHKKVINMVHNLLSSHDSDPRYSDPQIKARVAM
HC5     SSTS-SPGLLFTELAAALDAEGEGISEVQRKAVSAIHSLLSSHDLDPRCVKPEVKVKIAA HC2A    LYLPLFGLLIENVQRINVRDVSPFPVNAG-MTVKDESLALPAVNPLVTPQKGSTLDNSLH
KIAA    LYLPLFGLLIENVQRINVRDVSPFPVNAG-MTVKDESLALPAVNPLVTPQKGSTLDNSLH
rat     ------------------------------------------------------------
HC4     LYLPFVGLLLENIQRLAGRDTLYSCAAMPNSASRDEFPCG------FTSP--AN---RGSLS
HC1     LYMPLYGMLLDNMPRIYLKDLYPFTVNTSNQGSRDDLSTNGGFQSQTAIKHANSVDTSFS    9.1
HC3     LYLPLIGIIMETVPQLYDFTETHNQRGRPICIATDDYESE-----------SG---SMIS
HC5     LYLPLVGIIILDALPQLCDFTVADTRRYR---TSGSDEEQE-----------GA---GAIT
                4.1/4.2
HC2A    KDLLGAISGIASPYTTSTPNINSVRNADSRGSLISTDSGNSLPERNSEKSNSLDKHQQSS    5.1/5.2
KIAA    KDLLGAISGIASPYTTSTPNINSVRNADSRGSLISTDSGNSLPERNSEKSNSLDKHQQSS
rat     ------------------------------------------------------------
HC4     TDKDTAYGSFQNG--------HGIKREDSRGSLIP-EGATGFPDQGNTGEN-----TRQS
HC1     KDVLNSIAAFSS------IAISTVNHADSRASLASLDSNPSTNEKSSEKTDNCEKIPRPL    10.1
HC3     QTVAMAIAGTSVPQ-----------------LTRPGSFLLTSTSGRQHT---------    3.1
HC5     QNVALAIAGNNFN-----------------LKTSG-IVLSSLPYKQYN---------    2.1
```

FIG. 6B (cont.)

```
                                                                                  Ref.
HC2A    TLGNSVVRCDKLDQSEIKSLLMCFLYILKSMSDDALFTYWN-KASTSEIMDFFTISEVCL
KIAA    TLGNSVVRCDKLDQSEIKSLLMCFLYILKSMSDDALFTYWN-KASTSEIMDFFTISEVCL
rat     ------------------------------------------------------------
HC4     STRSSVSQYNRLDQYEIRSLLMCYLYIVKMISEDTLLTYWN-KVSPQELINILILLEVCL
HC1     ALIGSTLRFDRLDQAETRSLLMCFLHIMKTISYETLIAYWQ-RAPSPEVSDFFSIIDVCL   11.1/11.2
HC3     ----------TFSAESSRSLLICLLWVLKN-ADETVLQKWFTDLSVLQLNRLLDLLYLCV
HC5     ----------MLNADTTRNLMICFLWIMKN-ADQSLIRKWIADLPSTQLNRILDLLFICV HC2A    HQFQYMGKRYIARNQEGLG--PIVHDRKS-----------------QTLPVSRNRTGMM    6.1
KIAA    HQFQYMGKRYIAR-------------------------------------------TGMM
rat     ------------------------------------------------------------
HC4     FHFRYMGKRNIARVHDAWLSKHFGIDRKS-----------------QTMPALRNRSGVM
HC1     QNFRYLGKRNIIRKIAAAF--KFVQSTQNNGTLKGSNPSCQTSGLLAQWMHSTSRHEGHK
HC3     SCFEYKGKKVFERMNSLTFK--KSKDMRAK--------------LEEAILGSIGARQEMV
HC5     LCFEYKGKQSSDKVSTQVLQ--KSRDVKAR--------------LEEALLRGEGARGEMM HC2A    HARLQQL---------GSLDNS---------LTFNHSYGHSDADVLHQSLLEANIATEVC
KIAA    HARLQQL---------GSLDNS---------LTFNHSYGHSDADVLHQSLLEANIATEVC
rat     ------------------------------------------------------------
HC4     QARLQHL---------SSLESS---------FTILNHSSTTTEADIFHQALLEGNTATEVS
HC1     QHRSQTLPIIRGK---NALSNPKL----LQMLDNTMTSNSNEIDIVHHVDTEANIATEGC  12.1/12.2
HC3     RRSRGQLERSPSGSAFGSQENLRWRKDMTHWRQNTEKLDKSRAEIEHEALIDGNLATEAN  6.1/6.2
HC5     RRRAPGNDRFP-----GLNENLRWKKEQTHWRQANEKLDKTKAELDQEALISGNLATEAH HC2A    LTALDTLSLFTLAFKNQLLADHGHNPLMKKVFDVYLCFLQKHQSETALKNVFTALRSLIY  7.1
KIAA    LTALDTLSLFTLAFKNQLLADHGHNPLMKKVFDVYLCFLQKHQSETALKNVFTALRSLIY
rat     ------------------KLSRGHSPLMKKVFDVYLCFLQKHQSEMALKNVFTALRSLIY
HC4     LTVLDTISFFTQCFKTHFLNNDGHNPLMKKVFDIHLAFLKNGQSEVSLKHVFASLRAFIS
HC1     LTILDLVSLFTQTHQRQLQQCDCQNSIMKRGFDTYMLFFQVNQSATALKHVFASLRLFVC  13.1
HC3     LIILDTLEIVVQTVS--VTES--KESILGGVLKVLLHSMACNQSAVYLQHCFATQRALVS
HC5     LIILDMQENIIQASS--ALDC--KDSLLGGVLRVLVNSLNCDQSTTYLTHCFATLRALIA  3.1

HC2A    KFPSTFYEGRADMCAALCYEILKCCNSKLSSIRTEASQLLYFLMRNNFDYTGKKSFVRTH
KIAA    KFPSTFYEGRADMCAALCYEILKCCNSKLSSIRTEASQLLYFLMRNNFDYTGKKSFVRTH
rat     KFPSTFYEGRADMCASLCYEVLKCCNSKLSSIRTEASQLLYFLMRNNFDYTGKKSFVRTH
HC4     KFPSAFFKGRVNMCAAFCYEVLKCCTSKISSTRNEASALLYLLMRNNFEYTKRKTFLRTH
HC1     KFPSAFFQGPADLCGSFCYEVLKCCNHRSRSTQTEASALLYLFMRKNFEFNKQKSIVRSH
HC3     KFPELLFEEETEQCADLCLRLLRHCSSSIGTIRSHPSASLYLLMRQNFEIGN--NFARVK  7.1/7.2
HC5     KFGDLLFEEEVEQCFDLCHQVLHHCSSSMDVTRSQACATLYLLMRFSFGATS--NFARVK HC2A    LQVIISVSQLIADVVGIGETRFQQSLSIINNCANSDRLIKHTSFSSDVKDLTKRIRTVLM
KIAA    LQVIISVSQLIADVVGIGGTRFQQSLSIINNCANSDRLIKHTSFSSDVKDLTKRIRTVLM
rat     LQVIISLSQLIADVVGIGGTRFQQSLSIINNCANSDRLIKHTSFSSDVKDLTKRIRTVLM
HC4     LQIIIAVSQLIADVALSGGSRFQESLFIINNFANSDRPMLARAFPAEVKDLTKRIRTVLM
HC1     LQLIKAVSQLIAD-AGIGGSRFQHSLAITNNFANGDKQMKNSNFPAEVKDLTKRIRTVLM  14.1/14.2/15
HC3     MQVPMSLSSLVGTSQNFNEEFLRRSLKTILTYAEEDLELRETTFPDQVQDLVFNLHMILS
HC5     MQVTMSLASLVGRAPDFNEEHLRRSLRTILAYSEEDTAMQMTPFPTQVEELLCNLNSILY
```

FIG. 6B (cont.)

```
                                                            Transmembrane      Ref.
HC2A   ATAQMKEHENDPEMLVDLQYSLAKSYASTPELRKTWLDSMARIHVKNGD LSEAAMCYVHV
KIAA   ATAQMKEHENDPEMLVDLQYSLAKSYASTPELRKTWLDSMARIHVKNGD LSEAAMCYVHV
rat    ATAQMKEHENDPEMLVDLQYSLAKSYASTPELRKTWLDSMARIHVKNGD LSEAAMCYVHV
HC4    ATAQMKEHEKDPEMLIDLQYSLAKSYASTPELRKTWLDSMAKIHVKNGD FSEAAMCYVHV
HC1    ATAQMKEHEKDPEMLVDLQYSLANSYASTPELRRTWLESMAKIHARNGD LSEAAMCYIHI    16.1/16.2
HC3    DTVKMKEHQEDPEMLIDLMYRIAKGYQTSPDLRLTWLQNMAGKHSERSN HAEAAQCLVHS
HC5    DTVKMREFQEDPEMLMDLMYRIAKSYQASPDLRLTWLQNMAEKHTKKKQ YTEAAMCLVHA SH3
HC2A   TALVAEYL TRKGV-------|---------------------------|-FRQGCTAFRVITPN
KIAA   TALVAEYL TRKEA-------|---VQWEPPLLPHSHSACLRRSRGG  |VFRQGCTAFRVITPN
rat    TALVAEYL TRKEAD------|-LALQREPPVFPYSHTSCQRKSRGG  |MFRQGCTAFRVITPN
HC4    AALVAEFL HRKKL-------|---------------------------|-FPNGCSAFKKITPN
HC1    AALIAEYL KRKGYWKVEKIC |TASLLSEDTHPCDSNSLLTTPSGGS  |MFSMGWPAFLSITPN
HC3    AALVAEYL SMLED-------|------------------------RK |YLPVGCVTFQNISSN
HC5    AALVAEYL SMLED-------|------------------------HS |YLPVGSVSFQNISSN HC2A   IDEEASMMEDVG MQD-------VHFNEDVLMELLEQCADGLWKAERYELIADIYKLIIPI     8.1
KIAA   IDEEASMMEDVG MQD-------VHFNEDVLMELLEQCADGLWKAERYELIADIYKLIIPI
rat    IDEEASMMEDVGMQD-------VHFNEDVLMELLEQCADGLWKAERLRAGLLTSINSSSP
HC4    IDEEGAMKEDAGMMD-------VHYSEEVLLELLEQCVNGLWKAERYEIISEISKLIGPI
HC1    IKEEGAAKEDSGMHD-------TPYNE NILVEQLYMCGEFLWKSERYELIADVNKPIIAV      17.1/17.2
HC3    VLEESAVSDDVVSPDEEGICSGKYFTESGLVGLLEQAAASFSMAGMYEAVNEVYKVLIPI
HC5    VLEESVVSEDTLSPDEDGVCAGQYFTESGLVGLLEQAAELFSTGGLYETVNEVYKLVIPI ITAM    ITAM              ITAM         ITAM
HC2A   YEKR RD------|----|---|----|------------------------------         9.1
KIAA   YEKRRDFERLAH L YDTL HRA YSKV TEVMHSGRRLLGT YFRV AFFGQAAQYQFTDSETDVE
rat    SMKSGGTLETTH I YDTL HRP YSKV TEVITR----------A----AGSWDLLPGGLFGQ
HC4    YENRREFENLTQ V YRTL HGA YTKI LEVMHTKKRLLG--------------TFFRVAFYGQ
HC1    FEKQRDFKKLSD I YYDI HRS YLKV AEVVNSEKRLFG--------------R YYRV AFYGQ
HC3    HEANRDAKKLST I HGKL QEA FSKI VHQ STGWERMFG--------------T YFRV GFYG-    9.1
C5     LEAHREFRKLTLT H SKLQ RAF DSIV NKDH--KRMFG--------------TY FRV GFFG- HC2A   -FFEDEDGKEYIYKEPKLTPLSEISQRLLKLYSDKFGSENVKMIQDSGK VNPKDLDSKYA      10.1
KIAA   GFFEDEDGKEYIYKEPKLTPLSEISQRLLKLYSDKFGSENVKMIQDSGKVNPKDLDSKYA
rat    GFFEDEDGKEYIYKEPKLTPLSEISQRLLKLYSDKFGSENVKMIQDSGKVNPKDLDSKFA
HC4    SFFEEEDGKEYIYKEPKLTGLSEISLRLVKLYGEKFGTENVKIIQDSDKVNAKELDPKYA
HC1    GFFEEEEGKEYIYKEPKLTGLSEISQRLLKLYADKFGADNVKIIQDSNKVNPKDLDPKYA
HC3    TKFGDLDEQEFVYKEPAITKLAEISHRL EGFYGERFGEDVVEVIKDSNPVDKCKLDPNKA    10.1/10.2
HC5    SKFGDLDEQEFVYKEPAITKLPEISHRLEAFYGQCFGAEFVEVIKDSTPVDK TKLDPNKA     4.1

HC2A   YIQVTHVIPFFDEKELQERKTEFERSHNIRRFMFEMPFTQTGKRQGGVEEQCKRR TILTA    11.1/11.2
KIAA   YIQVTHVIPFFDEKELQERKTEFERSHNIRRFMFEMPFTQTGKRQGGVEEQCKRRTILTA
rat    YIQVTHVTPFFDEKELQERKTEFERCHNIRRFMFEMPFTQTGKRQGGVEEQCKRRTILTA
HC4    HIQVTYVKPYFDDKELTERKTEFERNHNISRFVFEAPYTLSGKKQGCIEEQCKRRTILTT
HC1    YIQVTYVTPFFEEKEIEDRKTDFEMHHNINRFVFETPFTLSGKKHGGVAEQCKRRTILT T     18.1
HC3    YIQITYVEPYFDTYEMKDRITYFDKNYNLRRFMYCTPFTLDGRAHGELHEQFKRKTILTT
HC5    YIQITFVEPYFDEYEMKDRVTYFEKNFNLRRFMYTTPFTLEGRPRGELHEQYRRNTVLTT
```

FIG. 6B (cont.)

```
                                              Coiled-Coil 1                    Ref
HC2A    IHCFPYVKKRIPVMYQHHTDLNP EVAIDEMSKKVAELRQLCSSAEVDMIKLQLKLQG SV
KIAA    IHCFPYVKKRIPVMYQHHTDLNP EVAIDEMSKKVAELRQLCSSAEVDMIKLQLKLQG SV
rat     IHCFPYVKKRIPVMYQHHTDLNP EVAIDEMSKKVAELHQLCSSAEVDMIKLQLKLQG SV
HC4     SNSFPYVKKRIPINCEQQINLKP DGATDEIKDKTAELQKLCSSTDVDMIQLQLKLQG WV
HC1     SHLFPYVKKRIQVISQSSTELNP EVAIDEMSRKVSELNQLCTMEEVDMISLQLKLQG SV
HC3     SHAFPYIKTRVNVTHKEEIILTP EVAIEDMQKKTQELAFATHQDPADPKMLQMVLQG SV  11.1
HC5     MHAFPYIKTRISVIQKEEFVLTP EVAIEDMKKKTLQLAVAINQEPPDAKMLQMVLQG SV Coiled-Coil 2
HC2A    SVQVNAGPLAYARAFLDDTNTKRYPDNKVKLLKEVFRQFVEACGQA LAVNERLIKEDQLE 11.1/12.1
KIAA    SVQVNAGPLAYARAFLDDTNTKRYPDNKVKLLKEVFRQFVEACGQA LAVNERLIKEDQLE
rat     SVQVNAGPLAYARAFLDDTNTKRYPDNKVKLLKEVFRQFVEACGQA LAVNERLIKEDQLE
HC4     SVQVNAGPLAYARAFLNDSQASKYPPKKVSELKDMFRKFIQACSIA LELNERLIKEDQVE
HC1     SVKVNAGPMAYARAFLEETNAKKYPDNQVKLLKEIFRQFADACGQA LDVNERLIKEDQLE
HC3     GTTVNQGPLEVAQVFLSEIPSDPKLFRHHNKLRLCFKDFTKRCEDA LRKNKSLIGPVQKE
HC5     GATVNQGPLEVAQVFLAEIPADPKLYRHHNKLRLCFKEFIMRCGEA VEKNKRLITADQRE Coiled-Coil 2
HC2A    YQEEMKANYREMAKELSEIMHEQIC PLEEKTS-VLPNSLHIFNAISGTPTSTMVHGMTSS
KIAA    YQEEMKANYREMAKELSEIMHEQLG--------------------------------------
rat     YQEEMKANYREIRKELSDIIVPRIC PGEDKRATKFPAHLQRHQRDTNKHSGSRVDQFILS
HC4     YHEGLKSNFRDMVKELSDIIHEQIL QEDTMHSPWMSNTLHVFCAISGTSSDRGYGSPRYA
HC1     YQEELRSHYKDMLSELSTVMNEQIT GRDDLSK---RGVDQTCTRVISKATPALPTVSISS  19.1
HC3     YQRELG----KLSS----------PZ--------------------------------
HC5     YQQELKKNYNKLKENLRPMIERKIP ELYKPIFRVESQKRDSFHRSSFRKCETQLSQGSZ- PBM
HC2A    SSVVZ--------------------------------------------------------
KIAA    -------------------------------------------------------------
rat     CVTLPHEPHVGTCFVMCKLRTTFRANHWFCQAQEEAMGNGREKEPWTVIFNSRFYRSWGK
HC4     EVZ----------------------------------------------------------
HC1     SAEVZ--------------------------------------------------------
HC3     -------------------------------------------------------------
HC5     -------------------------------------------------------------

HC2A    -----
KIAA    -----
rat     VHIFF
HC4     -----
HC1     -----
HC3     -----
HC5     -----
```

FIG. 6B (cont.)

```
      |  10        |  20        |  30        |  40         |  50        |  60        |  70        |  80
   1  AATTGTAATA  CGACTCACTA  TAGGGCGAAT  TGGGTACCGG   GCCCCCCCTC  GAGGTCGACG  GTATCGATAA  GCTTGATATC   80
  81  GAATTCGGCA  CGAGTTTTAC  ACCATCACCA  AAACCCAGAA   TTTTATGATG  AGATTAAAAT  AGAGTTGCCC  ACTCAGCTGC  160
 161  ATGAAAAGCA  CCACCTGTTG  CTCACATTCT  TCCATGTCAG   CTGTGACAAC  TCAAGTAAAG  GAAGCACGAA  GAAGAGGGAT  240
 241  GTCGTTGAAA  CCCAAGTTGG  CTACTCCTGG  CTTCCCCTCC   TGAAAGACGG  AAGGGTGGTG  ACAAGCGAGC  AGCACATCCC  320
 321  GGTCTCGGCG  AACCTTCCTT  CGGGCTATCT  TGGCTACCAA   GAGCTTGGGA  TGGGCAGGCA  TTATGGTCCG  GAAATTAAAT  400
 401  GGGTAGATGG  AGGCAAGCCA  CTGCTGAAAA  TTTCCACTCA   TCTGGTTTCT  ACAGGGATAC  TCAGGATCAG  CATTTACATA  480
 481  ATTTTTTCCA  GTACTGTCAG  AAAACCGAAT  CTGGAGCCCA   AGCCTTAGGA  AACGAACTTG  TAAAGTACCT  TAAGAGTCTG  560
 561  CATGCGATGG  AAGGCCACGT  GATGATCGCC  TTCTTGCCCA   CTATCCTAAA  CCAGCTGTTC  CGAGTCCTCA  CCAGAGCCAC  640
 641  ACAGGAAGAA  GTCGCGGTTA  ACGTGACTCG  GGTCATTATT   CATGTGGTTG  CCCAGTGCCA  TGAGGAAGGA  TTGGAGAGCC  720
 721  ACTTGAGGTC  ATATGTTAAG  TACGCGTATA  AGGCTGAGCC   ATATGTTGCC  TCTGAATACA  AGACAGTGCA  TGAAGAACTG  800
 801  ACCAAATCCA  TGACCACGAT  TCTCAAGCCT  TCTGCCGATT   TCCTCACCAG  CAACAAACTA  CTGAGGTACT  CATGGTTTTT  880
 881  CTTTGATGTA  CTGATCAAAT  CTATGGCTCA  GCATTTGATA   GAGAACTCCA  AAGTTAAGTT  GCTGCGAAAC  CAGAGATTTC  960
 961  CTGCATCCTA  TCATCATGCA  GCGGAAACCG  TTGTAAATAT   GCTGATGCCA  CACATCACTC  AGAAGTTTGG  AGATAATCCA 1040
1041  GAGGCATCTA  AGAACGCGAA  TCATGACCTT  GCTGTCTTCA   TCAAGAGATG  TTTCACCTTC  ATGGACAGGG  GCTTTGTCTT 1120
1121  CAAGCAGATC  AACAACTACA  TTAGCTGTTT  TGCTCCTGGA   GACCCAAAGA  CCCTCTTTGA  ATACAAGTTT  GAATTTCTCC 1200
1201  GTGTAGTGTG  CAACCATGAA  CATTATATTC  CGTTGAACTT   ACCAATGCCA  TTTGGAAAAG  GCAGGATTCA  AAGATACCAA 1280
1281  GACCTCCAGC  TTGACTACTC  ATTAACAGAT  GAGTTCTGCA   GAAACCACTT  CTTGGTGGGA  CTGTTACTGA  GGGAGGTGGG 1360
1361  GACAGCCCTC  CAGGAGTTCC  GGGAGGTCCG  TCTGATCGCC   ATCAGTGTGC  TCAAGAACCT  GCTGATAAAG  CATTCTTTTG 1440
1441  ATGACAGATA  TGCTTCAAGG  AGCCATCAGG  CAAGGATAGC   CACCCTCTAC  CTGCCTCTGT  TTGGTCTGCT  GATTGAAAAC 1520
1521  GTCCAGCGGA  TCAATGTGAG  GGATGTGTCA  CCCTTCCCTG   TGAACGCGGA  CATGACCGTG  AAGGATGAAT  CCCTGGCTCT 1600
1601  ACCAGCTGTG  AATCCGCTGG  TGACGCCGCA  GAAGGGAAGC   ACCCTGGACA  ACAGCCTGCA  CAAGGACCTG  CTGGGCGCCA 1680
1681  TCTCCGGCAT  TGCTTCTCCA  TATACAACCT  CAACTCCAAA   CATCAACAGT  GTGAGAAATG  CTGATTCGAG  AGGATCTCTC 1760
1761  ATAAGCACAG  ATTCGGGTAA  CAGCCTTCCA  GAAAGGAATA   GTGAGAAGAG  CAATTCCCTG  GATAAGCACC  AACAAAGTAG 1840
1841  CACATTGGGA  AATTCCGTGG  TTCGCTGTGA  TAAACTTGAC   CAGTCTGAGA  TTAACAGCCT  ACTGATGTGT  TTCCTCTACA 1920
1921  TCTTAAAGAG  CATGTCTGAT  GATGCTTTGT  TTACATATTG   GAACAAGGCT  TCAACATCTG  AACTTATGGA  TTTTTTTACA 2000
2001  ATATCTGAAG  TCTGCCTGCA  CCAGTTCCAG  TACATGGGGA   AGCGATACAT  AGCCAGGAAC  CAGGAGGGGT  TGGGACCCAT 2080
2081  AGTTCATGAT  CGAAAGTCTC  AGACATTGCC  TGTTTCCCGT   AACAGAACAG  GAATGATGCA  TGCCAGATTG  CAGCAGCTGG 2160
2161  GCAGCCTGGA  TAACTCTCTC  ACTTTTAACC  ACAGCTATGG   CCACTCGGAC  GCAGATGTTC  TGCACCAGTC  ATTACTTGAA 2240
2241  GCCAACAGTG  CTACTGAGGT  TTGCCTGACA  GCTCTGGACA   CGCTTCTCT  ATTTACATTG  GCGTTTAAGA  ACCAGCTCCT 2320
2321  GGCCGACCAT  GGACATAATC  CTCTCATGAA  AAAAGTTTTT   GATGTCTACC  TGTGTTTTCT  TCAAAAACAT  CAGTCTGAAA 2400
2401  CGGCTTTAAA  AAATGTCTTC  ACTGCCTTAA  GGTCCTTAAT   TTATAAGTTT  CCCTCAACAT  TCTATGAAGG  GAGAGCGGAC 2480
2481  ATGTGTGCGG  CTCTGTGTTA  CGAGATTCTC  AAGTGCTGTA   ACTCCAAGCT  GAGCTCCATC  AGGACGGAGG  CCTCCCAGCT 2560
2561  GCTCTACTTC  CTGATGAGGA  ACAACTTTGA  TTACACTGGA   AAGAAGTCCT  TTGTCCGGAC  ACATTTGCAA  GTCATCATAT 2640
2641  CTGTCAGCCA  GCTGATAGCA  GACGTTGTTG  GCATTGGGGA   AACCAGATTC  CAGCAGTCCC  TGTCCATCAT  CAACAACTGT 2720
2721  GCCAACAGTG  ACCGGCTTAT  TAAGCACACC  AGCTTCTCCT   CTGATGTGAA  GGACTTAACC  AAAAGGATAC  GCAGGTGCT 2800
2801  AATGCCACC  GCCCAGATGA  AGGAGCATGA  GAACGACCCA   GAGATGCTGG  TGGACCTCCA  GTACAGCCTG  GCCAAATCCT 2880
2881  ATGCCAGCAC  GCCCGAGCTC  AGGAAGACGT  GGCTCGACAG   CATGGCCAGG  ATCCATGTCA  AAATGGCGA  TCTCTCAGAG 2960
2961  GCAGCAATGT  GCTATGTCCA  CGTAACAGCC  CTAGTGGCAG   AATATCTCAC  ACGGAAAGGC  GTGTTTAGAC  AAGGATGCAC 3040
3041  CGCCTTCAGG  GTCATTACCC  CAAACATCGA  CGAGGAGGCC   TCCATGATGG  AAGACGTGGG  GATGCAGGAT  GTCCATTTCA 3120
3121  ACGAGGATGT  GCTGATGGAG  CTCCTTGAGC  AGTGCGCAGA   TGGGACTCTGG  AAAGCCGAGC  GCTACGAGCT  CATCGCCGAC 3200
3201  ATCTACAAAC  TTATCATCCAC  CATTTATGAG  AAGCGGAGGG   ATTTCTTTGA  AGATGAAGAT  GGAAAGGAGT  ATATTTACAA 3280
3281  GGAACCCAAA  CTCACACCGC  TGTCGGAAAT  TTCTCAGAGA   CTCCTTAAAC  TGTACTCGGA  TAAATTTGGT  TCTGAAAATG 3360
3361  TCAAAATGAT  ACAGGATTCT  GCCAAGGTCA  ACCCTAAGGA   TCTGGATTCT  AAGTATGCAT  ACATCCAGGT  GACTCACGTC 3440
3441  ATCCCCTTCT  TTGACGAAAA  AGAGTTGCAA  GAAAGGAAAA   CAGAGTTTGA  GAGATCCCAC  AACATCCGCC  GCTTCATGTT 3520
3521  TGAGATGCCA  TTTACGCAGA  CCGGGAAGAG  GCAGGGCGGG   GTGGAAGAGC  AGTGCAAACG  GCGCACCATC  CTGACAGCCA 3600
3601  TACACCGCTT  CCCTTATGTG  AAGAAGCGCA  TCCCTGTCAT   GTACCAGCAC  CACTGACCC  TGAACCCCAT  CGAGGTGGCC 3680
3681  ATTGACGAGA  TGAGTAAGAA  GGTGGCGGAG  CTCCGGCAGC   TGTGCTCCTC  GGCCGAGGTG  GACATGATCA  AACTGCAGCT 3760
3761  CAAACTCCAG  GGCAGCGTGA  GTGTTCAGGT  CAATGCTGCC   CCACTAGCAT  ATGCGCGAGC  TTTCTTAGAT  GATACAAACA 3840
3841  CAAAGCGATA  TCCTGACAAT  AAAGTGAAGC  TGCTTAAGGA   AGTTTTCAGG  CAATTTGTGG  AAGCTTGCGG  TCAAGCCTTA 3920
3921  GCGGTAAACG  AACGTCTGAT  TAAAGAAGAC  CAGCTCGAGT   ATCAGGAAGA  AATGAAAGCC  AACTACAGGG  AAATGGCGAA 4000
4001  GGAGCTTTCT  GAAATCATGC  ATGAGCAGAT  CTGCCCCCTG   GAGGAGAAGA  CGAGCGTCTT  ACCGAATTCC  CTTCACATCT 4080
4081  TCAACGCCAT  CAGTGGGACT  CCAACAAGCA  CAATGGTTCA   CGGGATGACC  AGCTCGTCTT  CGGTCGTGTG  ATTACATCTC 4160
4161  ATGCCCGTG  TGTGGGGACT  TGCTTTGTCA  TTTGCAAACT   CAGGATGCTT  TCCAAAGCCA  ATCACTGGGG  AGACCGAGCA 4240
4241  CAGGGAGGAC  CAAGGGGAAG  GGGAGAGAAA  GGAAATAAAG   AACAACGTTA  TTTCTTAACA  GACTTTCTAT  AGGAGTTGTA 4320
4321  AGAAGGTGCA  CATATTTTTT  TAAATCTCAC  TGGCAATATT   CAAAGTTTTC  ATTGTGTCTT  AACAAAGGTG  TGGTAGACAC 4400
4401  TCTTGAGCTC  GACTTAGATT  TTATTCTTCC  TTGCAGAGTA   GTGTTAGAAT  AGATGGCCTA  CAGAAAAAAA  AGGTTCTGGG 4480
4481  ATCTACATGG  CAGGGAGGGC  TGCACTGACA  TTGATGCCTG   GGGGACCTTT  TGCCTCGACT  CGTGCCGGAA  ATCTGATCGT 4560
4561  AATCAGGGTA  CAGAACTTAC  TAGTTTTGTC  TAGGAGTATG   TTGTATGACT  AGGATTTGTG  CTATTATCTC  ATTCAACAAC 4640
4641  ATAGAGCAAG  AATAGTGAGC  TAACTGAGCT  AGACACTCAA   TTAATCCGCT  ACTGGCTTCA  AGTCAGAACT  TTGTCATTAA 4720
4721  TCATCGACTC  CGGGACGGTC  ATATATGTAT  TACATTTCTA   CATTTTTAAT  ACTCACATGG  GCTTATGCAT  TAAGTTTAAT 4800
4801  TGTGATAAAT  TTGTGCTGGT  CCAGTATATG  CAATACACTT   TAATGGTTTA  TTCTTGTCAT  AAAAATGTGC  AATATGGAGA 4880
4881  TGTATACAAG  TCTTTACT                                                                          4898
      |  10        |  20        |  30        |  40         |  50        |  60        |  70        |  80
```

FIG.10A

```
      |   10       |   20       |   30       |   40       |   50       |   60       |   70       |   80
   1  MEGHVMIAFL  PTILNQLFRV  LTRATQEEVA  VNVTRVIIHV  VAQCHEEGLE  SHLRSYVKYA  YKAEPYVASE  YKTVHEELTK   80
  81  SMTTILKPSA  DFLTSNKLLR  YSWFFFDVLI  KSMAQHLIEN  SKVKLLRNQR  FPASYHHAAE  TVVNMLMPHI  TQKFGDNPEA  160
 161  SKNANHSLAV  FIKRCFTFMD  RGFVFKQINN  YISCFAPGDP  KTLFEYKFEF  LRVVCNHEHY  IPLNLPMPFG  KGRIQRYQDL  240
 241  QLDYSLTDEF  CRNHFLVGLL  LREVGTALQE  FREVRLIAIS  VLKNLLIKHS  FDDRYASRSH  QARIATLYLP  LFGLLIENVQ  320
 321  RINVRDVSPF  PVNAGMTVKD  ESLALPAVNP  LVTPQKGSTL  DNSLHKDLLG  AISGIASPYT  TSTPNINSVR  NADSRGSLIS  400
 401  TDSGNSLPER  NSEKSNSLDK  HQQSSTLGNS  VVRCDKLDQS  EIKSLLMCFL  YILKSMSDDA  LFTYWNKAST  SELMDFFTIS  480
 481  EVCLHQFQYM  GKRYIARNQE  GLGPIVHDRK  SQTLPVSRNR  TGMMHARLQQ  LGSLDNSLTF  NHSYGHSDAD  VLHQSLLEAN  560
 561  IATEVCLTAL  DTLSLFTLAF  KNQLLADHGH  NPLMKKVFDV  YLCFLQKHQS  ETALKNVFTA  LRSLIYKFPS  TFYEGRADMC  640
 641  AALCYEILKC  CNSKLSSIRT  EASQLLYFLM  RNNFDYTGKK  SFVRTHLQVI  ISVSQLIADV  VGIGETRFQQ  SLSIINNCAN  720
 721  SDRLIKHTSF  SSDVKDLTKR  IRTVLMATAQ  MKEHENDPEM  LVDLQYSLAK  SYASTPELRK  TWLDSMARIH  VKNGDLSEAA  800
 801  MCYVHVTALV  AEYLTRKGVF  RQGCTAFRVI  TPNIDEEASM  MEDVGMQDVH  FNEDVLMELL  EQCADGLWKA  ERYELIADIY  880
 881  KLIIPIYEKR  RDFFEDEDGK  EYIYKEPKLT  PLSEISQRLL  KLYSDKFGSE  NVKMIQDSGK  VNPKDLDSKY  AYIQVTHVIP  960
 961  FFDEKELQER  KTEFERSHNI  RRFMFEMPFT  QTGKRQGGVE  EQCKRRTILT  AIHCFPYVKK  RIPVMYQHHT  DLNPIEVAID 1040
1041  EMSKKVAELR  QLCSSAEVDM  IKLQLKLQGS  VSVQVNAGPL  AYARAFLDDT  NTKRYPDNKV  KLLKEVFRQF  VEACGQALAV 1120
1121  NERLIKEDQL  EYQEEMKANY  REMAKELSEI  MHEQICPLEE  KTSVLPNSLH  IFNAISGTPT  STMVHGMTSS  SSVV        1195
      |   10       |   20       |   30       |   40       |   50       |   60       |   70       |   80
```

FIG. 10A (cont.)

```
       |    10      |    20      |    30      |    40         |    50      |    60      |    70      |    80
    1  AATTGTAATA  CGACTCACTA  TAGGGCGAAT  TGGGTACCGG     GCCCCCCCTC  GAGGTCGACG  GTATCGATAA  GCTTGATATC   80
   81  GAATTCGGCA  CGAGTTTTAC  ACCATCACCA  AAACCCAGAA     TTTTATGATG  AGATTAAAAT  AGAGTTGCCC  ACTCAGCTGC  160
  161  ATCAAAAGCA  CCACCTGTTG  CTCACATTCT  TCCATGTCAG     CTGTGACAAC  TCAAGTAAAG  GAAGCACGAA  GAAGAGGGAT  240
  241  GTCGTTGAAA  CCCAAGTTGG  CTACTCCTGG  CTTCCCCTCC     TGAAAGACGG  AAGGGTGGTG  ACAAGCGAGC  AGCACATCCC  320
  321  GGTCTCGGCG  AACCTTCCTT  CGGGCTATCT  TGGCTACCAA     GAGCTTGGGA  TGGGCAGGCA  TTATGGTCCG  GAAATTAAAT  400
  401  GGGTAGATGG  AGGCAAGCCA  CTGCTGAAAA  TTTCCACTCA     TCTGGTTTCT  ACAGGGATAC  TCAGGATCAG  CATTTACATA  480
  481  ATTTTTTCCA  GTACTGTCAG  AAAACCGAAT  CTGGAGCCCA     AGCCTTAGGA  AACGAACTTG  TAAAGTACCT  TAAGAGTCTG  560
  561  CATGCGATGG  AAGGCCACGT  GATGATCGCC  TTCTTGCCCA     CTATCCTAAA  CCAGCTGTTC  CGAGTCCTCA  CCAGAGCCAC  640
  641  ACAGGAAGAA  GTCGCGGTTA  ACGTGACTCG  GGTCATTATT     CATGTGGTTG  CCCAGTGCCA  TGAGGAAGGA  TTGGAGAGCC  720
  721  ACTTCAGGTC  ATATGTTAAG  TACGCGTATA  AGGCTCAGCC     ATATGTTGCC  TCTGAATACA  AGACAGTGCA  TGAAGAACTG  800
  801  ACCAAATCCA  TGACCACGAT  TCTCAAGCCT  TCTGCCGATT     TCCTCACCAG  CAACAAACTA  CTGAGGTACT  CATGGTTTTT  880
  881  CTTTGATGTA  CTGATCAAAT  CTATGGCTCA  GCATTTGATA     GAGAACTCCA  AAGTTAAGTT  GCTGCGAAAC  CAGAGATTTC  960
  961  CTGCATCCTA  TCATCATGCA  GCGGAAACCG  TTGTAAATAT     GCTGATGCCA  CACATCACTC  AGAAGTTTGG  AGATAATCCA 1040
 1041  GAGGCATCTA  AGAACGCGAA  TCATAGCCTT  GCTGTCTTCA     TCAAGAGATG  TTTCACCTTC  ATGGACAGGG  GCTTTGTCTT 1120
 1121  CAAGCAGATC  AACAACTACA  TTAGCTGTTT  TGCTCCTGGA     GACCCAAAGA  CCCTCTTTGA  ATACAAGTTT  GAATTTCTCC 1200
 1201  GTGTAGTGTG  CAACCATGAA  CATTATATTC  CGTTGAACTT     ACCAATGCCA  TTTGGAAAAG  GCAGGATTCA  AAGATACCAA 1280
 1281  GACCTCCAGC  TTGACTACTC  ATTAACAGAT  GAGTTCTGCA     GAAACCACTT  CTTGGTGGGA  CTGTTACTGA  GGGAGGTGGG 1360
 1361  GACAGCCCTC  CAGGAGTTCC  GGGAGGTCCG  TCTGATCGCC     ATCAGTGTGC  TCAAGAACCT  GCTGATAAAG  CATTCTTTTG 1440
 1441  ATGACAGATA  TGCTTCAAGG  AGCCATCAGG  CAAGGATAGC     CACCCTCTAC  CTGCCTCTGT  TTGGTCTGCT  GATTGAAAAC 1520
 1521  GTCCAGCGGA  TCAATGTGAG  GGATGTGTCA  CCCTTCCCTG     TGAACGCGGG  CATGACCGTG  AAGGATGAAT  CCCTGGCTCT 1600
 1601  ACCAGCTGTG  AATCCGCTGG  TGACGCCGCA  GAAGGGAAGC     ACCCTGGACA  ACAGCCTGCA  CAAGGACCTG  CTGGGCGCCA 1680
 1681  TCTCCGGCAT  TGCTTCTCCA  TATACAACCT  CAACTCCAAA     CATCAACAGT  GTGAGAAATG  CTGATTCGAG  AGGATCTCTC 1760
 1761  ATAAGCACAG  ATTCGGGTAA  CAGCCTTCCA  GAAAGGAATA     GTGAGAAGAG  CAATTCCCTG  GATAAGCACC  AACAAAGTAG 1840
 1841  CACATTGGGA  AATTCCGTGG  TTCGCTGTGA  TAAACTTGAC     CAGTCTGAGA  TTAAGAGCCT  ATGCCAGCTG  TTCCTCTACA 1920
 1921  TCTTAAAGAG  CATGTCTGAT  GATGCTTTGT  TTACATATTG     GAACAAGGCT  TCAACATCTG  AACTTATGGA  TTTTTTTACA 2000
 2001  ATATCTGAAG  TCTGCCTGCA  CCAGTTCCAG  TACATGGGGA     AGCGATACAT  AGCCAGGAAC  CAGGAGGGGT  TGGGACCCAT 2080
 2081  AGTTCATGAT  CGAAAGTCTA  AGACATTGCC  TGTTTCCCGT     AACAGACAGA  GAATGATGCA  TGCCAGGATG  CAGCAGCTGG 2160
 2161  GCAGCCTGGA  TAACTCTCTC  ACTTTTAACC  ACAGCTATGG     CCACTCGGAC  GCAGATGTTC  TGCACCAGTG  ATTACTTGAA 2240
 2241  GCCAACATTG  CTACTGAGGT  TTGCCTGACA  GCTCTGGACA     CGCTTTCTCT  ATTTACATTG  GCGTTTAAGA  ACCAGCTCCT 2320
 2321  GGCCGACCAT  GGACATAATC  CTCTCATGAA  AAAGTTTTT     GATGTCTACC  TGTGTTTTCT  TCAAAAACAT  CAGTCTGAAA 2400
 2401  CGGCTTTAAA  AAATGTCTTC  ACTGCCTTAA  GGTCCTTAAT     TTATAAGTTT  CCCTCAACAT  TCTATGAAGG  GAGAGCGGAC 2480
 2481  ATGTGTGCGG  CTCTGTGTTA  CGAGATTCTC  AAGTGCTGTA     ACTCCAAGCT  GAGCTCCATC  AGGACGGAGG  CCTCCCAGCT 2560
 2561  GCTCTACTTC  CTGATGAGGA  ACACTTTGA  TTACACTGGA     AAGAAGTCCT  TTGTCCGGCA  ACATTTGCAA  GTCATCATAT 2640
 2641  CTGTCAGCCA  GCTGATAGCA  GACGTTGTTG  GCATTGGGGA     AACCAGATTC  CAGCAGTCCC  TGTCCATCAT  CAACAACTGT 2720
 2721  GCCAACAGTG  ACCGGCTTAT  TAAGCACACC  AGCTTCTCCT     CTGATGTGAA  GGACTTAACC  AAAAGGATAC  GCACGGTGCT 2800
 2801  AATGGCACC  GCCCAGATGA  AGGAGCATGA  GAACGACCCA     GAGATGCTGG  TGGACCTCCA  GTACGCCTG  GCCAAATCCT 2880
 2881  ATGCCAGCAC  GCCCGAGCTC  AGGAAGACGT  GGCTCGACAG     CATGGCCAGG  ATCCATGTCA  AAAATGGCGA  TCTCTCAGAG 2960
 2961  GCAGCAATGT  GCTATGTCCA  CGTAACAGCC  CTAGTGGCAG     AATATCTCAC  ACGGAAAGGC  GTGTTTAGAC  AAGGATGCAC 3040
 3041  CGCCTTCAGC  GTCATTACCC  CAAACATCGA  CGAGGAGGCC     TCCATGCAGG  AAGACGTGGG  GATGCAGGAT  GTCCATTTCA 3120
 3121  ACGAGGATGT  GCTGATGGCA  CTCCTTGAGC  AGTGCGCAGA     TGGACTCTGG  AAAGCCGAGC  GCTACGAGCT  CATCGCCGAC 3200
 3201  ATCTACAAAC  TTATCATCCC  CATTTATGAG  AAGCGGAGGG     ATTTCTTTGA  AGATAAGGAT  GGAAAGGAGT  ATATTTACAA 3280
 3281  GGAACCCAAA  CTCACACCGC  TGTCGGAAAT  TTCTCAGAGA     CTCCCTTAAAC  TGTACTCGGA  TAAATTTGGT  TCTGAAAATG 3360
 3361  TCAAAATGAT  ACAGGATTCT  GGCAAGGTCA  ACCCTAAGGA     TCTGGATTCT  AAGTATGCAT  ACATCCAGGT  GACTCACGTC 3440
 3441  ATCCCCTTCT  TTGACGAAAA  AGAGTTGCAA  GAAAGGAAAA     CAGAGTTTGA  GAGATCCCAC  AACATCCGCC  GCTTCATGTT 3520
 3521  TGAGATGCCA  TTTACGCAGA  CCGGGAAGAG  GCAAGGCGGG     GTGGAAGAGC  AGTGCAAAACG  GCGCACCATC  CTGACAGCCA 3600
 3601  TACACTGCTT  CCCTTATGTG  AAGAAGCGCA  TCCCTGTCAT     GTACCAGCAC  CACACTGACC  TGAACCCCAT  CGAGGTGGCC 3680
 3681  ATTGACGAGA  TCAGTAAGAA  GGTGCGCGAG  CTCCGGCAGC     TGTGCTCCTC  GGCCGAGGTG  GACATGATCA  AACTGCAGCT 3760
 3761  CAAACTCCAG  GGCAGCGTGA  GTGTTCAGGT  CAATGCTGGC     CCACTAGCAT  ATGCGCGAC  TTTCTTAGAT  GATACAAACA 3840
 3841  CAAAGCGATA  TCCTGACAAT  AAAGTGAAGC  TGCTTAAGGA     AGTTTTCAGG  CAATTTGTGG  AAGCTTGCGG  TCAAGCCTTA 3920
 3921  GCGGTAAACG  AACGTCTGAT  TAAAGAAGAC  CAGCTCGAGT     ATCAGGAAGA  AATGAAAGCC  AACTACAGGG  AAATGGCGAA 4000
 4001  GGAGCTTTCT  GAAATCATGC  ATGAGCACAT  CTGCCCCCTG     GAGGAGAACA  CGAAGCGTCT  ACCGAATTCC  CTTCACATCT 4080
 4081  TCAACGCCAT  CAGTGGGACT  CCAACAAGCA  CAATGGTTCA     CGGGATGACC  AGCTCGTCTT  CGGTCGTGTG  ATTACATCTC 4160
 4161  ATGGCCCGTG  TGTGGGGACT  TGCTTTGTCA  TTTGCAAACT     CAGGATGCTT  TCCAAAGCCA  ATCACTGGGG  AGACCAGCA 4240
 4241  CAGGGAGGAC  CAAGGGGAAG  GGGAGAGAAA  GGAAATAAAG     AACAAGCTTA  TTTCTTAACA  GACTTTCTAT  AGGAGTTGTA 4320
 4321  AGAAGGTGCA  CATATTTTTT  TAAATCTCAC  TGGCAATATT     CAAAGTTTTC  ATTGTGTCTT  AACAAAGGTG  TGGTAGACAC 4400
 4401  TCTTGAGCTG  GACTTAGATT  TTATTCTTCC  TTGCAGAGTA     GTGTTAGAAT  AGATGGCCTA  CAGAAAAAAA  AGGTTCTGGG 4480
 4481  ATCTACATGG  CAGGGACGGC  TGCACTGACA  TTGATGCCTG     GGGGACCTTT  TGCCTCGACT  CGTGCCGGAA  ATCTGATCGT 4560
 4561  AATCAGGGTA  CAGAACTTAC  TAGTTTTGTC  TAGGAGTATG     TTGTATGACT  AGGATTTGTG  CTATTATCTC  ATTCAACAAC 4640
 4641  ATAGAGCAAG  AATAGTGAGC  TAACTGAGCT  AGACACTCAA     TTAATCCGCT  ACTGGCTTCA  AGTCAGAACT  TTGTCATTAA 4720
 4721  TCATCGACTC  CGGGACGGTC  ATATATGTAT  TACATTTCTA     CATTTTTAAT  ACTCACATGG  GCTTATGCAT  TAAGTTTAAT 4800
 4801  TGTGATAAAT  TTGTCTGGT  CCAGTATATG  CAATACACTT     TAATGGTTTA  TTCTTGTCAT  AAAAATGTGC  AATATGGAGA 4880
 4881  TGTATACAAG  TCTTTACT                                                                             4898
       |    10      |    20      |    30      |    40         |    50      |    60      |    70      |    80
```

FIG.10B

```
      |   10       |   20       |   30       |   40       |   50       |   60       |   70       |   80
   1  MEGHVMIAFL  PTILNQLFRV  LTRATQEEVA  VNVTRVIIHV  VAQCHEEGLE  SHLRSYVKYA  YKAEPYVASE  YKTVHEELTK   80
  81  SMTTILKPSA  DFLTSNKLLR  YSWFFFDVLI  KSMAQHLIEN  SKVKLLRNQR  FPASYHHAAE  TVVNMLMPHI  TQKFGDNPEA  160
 161  SKNANHSLAV  FIKRCFTFMD  RGFVFKQINN  YISCFAPGDP  KTLFEYKFEF  LRVVCNHEHY  IPLNLPMPFG  KGRIQRYQDL  240
 241  QLDYSLTDEF  CRNHFLVGLL  LREVGTALQE  FREVRLIAIS  VLKNLLIKHS  FDDRYASRSH  QARIATLYLP  LFGLLIENVQ  320
 321  RINVRDVSPF  PVNAGMTVKD  FSIALPAVNP  LVTPQKGSTL  DNSLHKDLLG  AISGIASPYT  TSTPNINSVR  NADSRGSLIS  400
 401  TDSGNSLPER  NSEKSNSLDK  HQQSSTLGNS  VVRCDKLDQS  EIKSLIMCFL  YILKSMSDDA  LFTYWNKAST  SEIMDFFTIS  480
 481  EVCLHQFQYM  GKRYIARNQE  GLGPIVHDRK  SQTLPVSRNR  TGMMHARLQQ  LGSLDNSLTF  NHSYGHSDAD  VLHQSLLEAN  560
 561  IATEVCLTAL  DTLSLFTLAF  KNQLLADHGH  NPLMKKVFDV  YLCFLQKHQS  ETALKNVFTA  LRSLIYKFPS  TFYEGRADMC  640
 641  AALCYEILKC  CNSKLSSIRT  EASQLLYFLM  RNNFDYTGKK  SFVRTHLQVI  ISVSQLIADV  VGIGETRFQQ  SLSIINNCAN  720
 721  SDRLIKHTSF  SSDVKDLTKR  IRTVLMATAQ  MKEHENDPEM  LVDLQYSLAK  SYASTPELRK  TWLDSMARIH  VKNGDLSEAA  800
 801  MCYVHVTALV  AEYLTRKGVF  RQGCTAFRVI  TPNIDEEASM  MEDVGMQDVH  FNEDVLMELL  EQCADGLWKA  ERYELIADIY  880
 881  KLIIPIYEKR  RDFFEDEDGK  EYIYKEPKLT  PLSEISQRLL  KLYSDKFGSE  NVKMIQDSGK  VNPKDLDSKY  AYIQVTHVIP  960
 961  FFDEKELQER  KTEFERSHNI  RRFMFEMPFT  QTGKRQGGVE  EQCKRRTILT  AIHCFPYVKK  RIPVMYQHHT  DLNPIEVAID 1040
1041  EMSKKVAELR  QLCSSAEVDM  IKLQLKLQGS  VSVQVNAGPL  AYARAFLDDT  NTKRYPDNKV  KLLKEVFRQF  VEACGQALAV 1120
1121  NERLIKEDQL  EYQEEMKANY  REMAKELSEI  MHEQICPLEE  KTSVLPNSLH  IFNAISGTPT  STMVHGMTSS  SSVV        1195
      |   10       |   20       |   30       |   40       |   50       |   60       |   70       |   80
```

FIG. 10B (cont.)

```
           |   10       |   20       |   30       |   40       |   50       |   60       |   70       |   80
   1 AATTGTAATA CGACTCACTA TAGGGCGAAT TGGGTACCGG GCCCCCCCTC GAGGTCGACG GTATCGATAA GCTTGATATC   80
  81 GAATTCGGCA CGAGTTTTAC ACCATCACCA AAACCCAGAA TTTTATGATG AGATTAAAAT AGAGTTGCCC ACTCAGCTGC  160
 161 ATGAAAAGCA CCACCTGTTG CTCACATTCT TCCATGTCAG CTGTGACAAC TCAAGTAAAG GAAGCACGAA GAAGAGGGAT  240
 241 GTCGTTGAAA CCCAAGTTGG CTACTCCTGG CTTCCCCTCC TGAAAGACGG AAGGGTGGTG ACAAGCGAGC AGCACATCCC  320
 321 GGTCTCGGCG AACCTTCCTT CGGGCTATCT TGGCTACCAA GAGCTTGGGA TGGGCAGGCA TTATGGTCCG GAAATTAAAT  400
 401 GGGTAGATGG AGGCAAGCCA CTGCTGAAAA TTTCCACTCA TCTGGTTTCT ACAGGGATAC TCAGGATCAG CATTTACATA  480
 481 ATTTTTTCCA GTACTGTCAG AAAACCGAAT CTGGAGCCCA AGCCTTAGGA AACGAACTTG TAAAGTACCT TAAGAGTCTG  560
 561 CATGCGATGG AAGGCCACGT GATGATCGCC TTCTTGCCCA CTATCCTAAA CCAGCTGTTC CGAGTCCTCA CCAGAGCCAC  640
 641 ACAGGAAGAA GTCGCGGTTA ACGTGACTCG GGTCATTATT CATGTGGTTG CCCAGTGCCA TGAGGAAGGA TTGGAGAGCC  720
 721 ACTTGAGGTC ATATGTTAAG TACGCGTATA AGGCTGAGCC ATATGTTGCC TCTGAATACA AGACAGTGCA TGAAGAACTG  800
 801 ACCAAATCCA TGCCACGAT TCTCAAGCCT TCTGCCGATT TCCTCACCAG CAACAAACTA CTGAGGTACT CATGGTTTTT  880
 881 CTTTGATGTA CTGATCAAAT CTATGCCTCA GCATTTGATA GAGAACTCCA AAGTTAAGTT GCTGCGAAAC CAGAGATTTC  960
 961 CTGCATCCTA TCATCATGCA GCGGAAACCG TTGTAAATAT GCTGATGCCA CACATCACTC AGAAGTTTGG AGATAATCCA 1040
1041 GAGGCATCTA AGAACGCGAA TCATAGCCTT GCTGTCTTCA TCAAGAGATG TTTCACCTTC ATGGACAGGG GCTTTGTCTT 1120
1121 CAAGCAGATC AACAACTACA TTAGCTGTTT TGCTCCTGGA GACCCAAAGA CCCTCTTTGA ATACAAGTTT GAATTTCTCC 1200
1201 GTGTAGTGTG CAACCATGAA CATTATATTC CGTTGAACTT ACCAATGCCA TTTGGAAAAG GCAGGATTCA AAGATACCAA 1280
1281 GACCTCCAGC TTGACTACTC ATTAACAGAT GAGTTCTGCA GAAACCACTT CTTGGTGGGA CTGTTACTGA GGGAGGTGGG 1360
1361 GACAGCCCTC CAGGAGTTCC GGGAGGTCCG TCTGATCGCC ATCAGTGTGC TCAAGAACCT GCTGATAAAG CATTCTTTTG 1440
1441 ATGACAGATA TGCTTCAAGG AGCCATCAGG CAAGGATAGC CACCCTCTAC CTGCCTCTGT TTGGTCTGCT GATTGAAAAC 1520
1521 GTCCAGCGGA TCAATGTGAG GGATGTGTCA CCCTTCCCTG TGAACGCGGG CATGACCGTG AAGGATGAAT CCCTGGCTCT 1600
1601 ACCAGCTGTG AATCCGCTGG TGACGCCGCA GAAGGGAAGC ACCCTGGACA ACAGCCTGCA CAAGGACCTG CTGGGCGCCA 1680
1681 TCTCCGGCAT TGCTTCTCCA TATACAACCT CAACTCCAAA CATCAACAGT GTGAGAAATG CTGATTCGAG AGGATCTCTC 1760
1761 GTAGCACAG ATTCGGGTAA CAGCCTTCCA GAAAGGAATA GTGAGAAGAG CAATTCCCTG GATAAGCACC AACAAAGTAG 1840
1841 CACATTGGGA AATTCCGTGG TTCGCTGTGA TAAACTTGAC CAGTCTGAGA TTAAGAGCCT ACTGATGTGT TTCCTCTACA 1920
1921 TCTTAAAGAG CATGTCTGAT GATGCTTTGT TTACATATTG GAACAAGGCT TCAACATCTC AACTTATGCA TTTTTTTACA 2000
2001 ATATCTGAAA TGTGCCTGCA CCAGTTCCAG TACATGGGGA AGCGATACAT AGCCAGGAAC CAGGAGGGGT TGGGACCCAT 2080
2081 AGTTCATGAT CGAAAGTCTC AGACATTGCC TGTTTCCCGT AACAGAACAG GAATGATGCA TGCCAGATTG CAGCAGCTGG 2160
2161 GCAGCCTGGA TAACTCTCTC ACTTTTAACC ACAGCTATGG CCACTCGGAC GCAGATGTTC TGCACCAGTG ATTACTTGAA 2240
2241 GAGGCATTG CTACTGAGGT TTGCCTGACA GCTCTGGACA CGCTTTCTCT ATTTACATTG GCGTTTAAGA ACCAGCTCCT 2320
2321 GGCCGACCAT GGACATAATC CTCTCATGAA AAAAGTTTTT GATGTCTACC TGTGTTTTCT TCAAAAACAT CAGTCTGAAA 2400
2401 CGGCTTTAAA AAATGTCTTC ACTGCCTTAA GGTCCTTAAT TTATAAGTTT CCCTCAACAT TCTATGAAGG GAGAGCGGAC 2480
2481 ATGTGTGCGG CTCTGTGTTA CGAGATTCTC AAGTGCTGTA ACTCCAAGCT GAGCTCCATC AGGACGGAGG CCTCCCAGCT 2560
2561 GCTCTACTTC CTGATGAGGA ACAACTTTGA TTACACTGGA AAGAAGTCCT TGTCCGGAC ACATTTGCAA GTCATCATAT 2640
2641 CTGTCAGCCA GCTGATAGCA GACGTTGTTG GCATTGGGGA AACCGATTC CAGCAGTCCC TGTCCATCAT CAACAACTGT 2720
2721 GTCGATGTGAA ACCGGCTTAT TAAGCACACC AGCTTCTCCT CTGATGTGAA GGACTTAACC AAAAGGATAC GCACGGTGCT 2800
2801 AATGGCCACC GCCCAGATGA AGGAGCATGA GAACGACCCA GAGATGCTGG TGGACCTCCA GTACAGCCTG GCCAAATCCT 2880
2881 ATGCCAGCAC GCCCGAGCTC AGGAAGACGT GGCTCGACAG CATGGCCAGG ATCCATGTCA AAATGGCGA TCTCTCAGAG 2960
2961 GCAGCAATGT GCTATGTCCA CGTAACAGCC CTAGTGGCAG ATTTCTTTGA AGATGAAGAT GGAAAGGAGT ATATTTACAA 3040
3041 CGCCTTCAGG GTCATTACCC CAAACATCGA CGAGGAGGCC TCCATGATGG AAGACGTGGG GATGCAGGAT GTCCATTTCA 3120
3121 ACGAGGATGT GCTGATGGAG CTCCTTGAGC AGTGCGCAGA TGGACTCTGG AAAGCCGAGC GCTACGAGCT CATCGCCGAC 3200
3201 ATCTACAAAC TTATCATCCA CATTTATGAG AAGCGGAGGG ATTTCTTTGA AGATGAAGAT GGAAAGGAGT ATATTTACAA 3280
3281 GGAACCCAAA CTCACACCGC TGTCGGAAAT TTCTCAGAGA CTCCTTAAAC TGTACTCGGA TAAATTTGGT TCTGAAAATG 3360
3361 TCAAAATGAT ACAGGATTCT GGCAAGGTCA ACCCTAAGGA TCTGGATTCT AAGTATGCAT ACATCCAGGT GACTCACGTC 3440
3441 ATCCCCTTCT TTGACGAAAA AGAGTTGCAA GAAAGGAAAA CAGAGTTTGA GAGATCCCAC ACAACATCCGCC GCTTCATGTT 3520
3521 TGAGATGCCA TTTACGCAGA CCGGGAAGAG GCAGGGCGGG GTGGAAGAGC AGTGCAAACG GCGCACCATC CTGACAGCCA 3600
3601 TACACTGCTT CCCCTTATGTG AAGAAGCCGA TCCCTGTCAT GTACCAGCAC CACACTGACC TGAACCCCAT CGAGGTGGCC 3680
3681 ATTGCACGAGA GGTAAGCAG GTGGCGGAGC CTCCGGCAGC TGTGCTCCTC GGCCGAGGTG GACATGATCA AACTGCAGCT 3760
3761 CAAACTCCAG GCAGCGTGA GTGTTCAGGT CAATGCTGGC CCACTAGCAT ATGCGCGAGC TTTCTTAGAT GATACAAACA 3840
3841 CAAAGCGATA TCCTAGCAAT AAAGTGAAGC TGCTTAAGGA AGTTTTCAGG CAAGTTGCGG TCAAGCCTTA 3920
3921 GCGGTAAACG AACGTCTGAT TAAAGAAGAC CAGCTCGAGT ATCAGGAAGA AATGAAAGCC AACTACAGGG AAATGGCGAA 4000
4001 GGAGCTTTCT GAAATCATGC ATGAGCAGAT CTGCCCCCTG GAGGAGAAGA CGAGCGTCTT ACCGAATTCC CTTCACATCT 4080
4081 TCAACGCCAT CAGTGGGCAT CCAACAAGCA CAATGGTTCA CGGGATGACC AGCTCGTCTT CGGTCGTGTG ATTACATCTC 4160
4161 ATGCCCGTG TGTGGGACT TGCTTTGTCA TTTGCAAACT CAGGATGCTT TCCAAAGCCA ATCACTGGGG AGACCGAGCA 4240
4241 CAGGGAGGAC CAAGGGGAAG GGGAGAGAAA GGAATAAAG AACAACGTTA TTTCTTAACA GACTTTCTAT AGGAGTTGTA 4320
4321 AGAAAGGTGCA CATATTTTTT TAAATCTCAC TGGCAATATT CAAAGTTTC ATTGTGTCTT AACAAGGTG TGGTAGACAC 4400
4401 TCTTGAGCTG GACTTAGATT TTATTCTTCC TTGCAGAGTA GTGTTAGAAT AGATGGCCTA CAGAAAAAAA AGGTTCTGGG 4480
4481 ATCTACATGG CAGGGAGGGC TGCACTGACA TTGATGCCTG GGGGACCTTT TGCCTCGACT CGTGCCGGAA ATCTGATCGT 4560
4561 AATCAGGGTA CAGAACTTAC TAGTTTTGTC TAGGAGTATG TTGTATGACT AGGATTTGTG CTATTATCTC ATTCAACAAC 4640
4641 ATAGAGCAAG AATAGTGAGC TAACTGAGCT AGACACTCAA TTAATCCGCT ACTGGCTTCA AGTCAGAACT TTGTCATTAA 4720
4721 TCATCGACTC CGGGACGGTC ATATATGTAT TACATTTCTA CATTTTTAAT ACTCACATGG GCTTATGCAT TAAGTTTAAT 4800
4801 TGTGATAAAT TTGTGCTGGT CCAGTATATG CAATACACTT TAATGGTTTA TTCTTGTCAT AAAAATGTGC AATATGGAGA 4880
4881 TGTATACAAG TCTTTACT                                                                    4898
           |   10       |   20       |   30       |   40       |   50       |   60       |   70       |   80
```

FIG.10C

```
        |   10        |   20        |   30        |   40        |   50        |   60        |   70        |   80
   1  MEGHVMIAFL  PTIILNQLFRV  LTRATQEEVA  VNVTRVIIHV  VAQCHEEGLE  SHLRSYVKYA  YKAEPYVASE  YKTVHEELTK   80
  81  SMTTILKPSA  DFLTSNKLLR   YSWFFFDVLI  KSMAQHLIEN  SKVKLLRNQR  FPASYHHAAE  TVVNMLMPHI  TQKFGDNPEA  160
 161  SKNANHSLAV  FIKRCFTFMD   RGFVFKQINN  YISCFAPGDP  KTLFEYKFEF  LRVVCNHEHY  IPLNLPMPFG  KGRIQRYQDL  240
 241  QLDYSLTDEF  CRNHFLVGLL   LREVGTALQE  FREVRLIAIS  VLKNLLIKHS  FDDRYASRSH  QARIATLYLP  LFGLLIENVQ  320
 321  RINVRDVSPF  PVNAGMTVKD   ESLALPAVNP  LVTPQKGSTL  DNSLHKDLLG  AISGIASPYT  TSTPNINSVR  NADSRGSLIS  400
 401  TDSGNSLPER  NSEKSNSLDK   HQQSSTLGNS  VVRCDKLDQS  EIKSLLMCFL  YILKSMSDDA  LFTYWNKAST  SELMDFFTIS  480
 481  EVCLHQFQYM  GKRYIARNQE   GLGPIVHDRK  SQTLPVSRNR  TGMMHARLQQ  LGSLDNSLTF  NHSYGHSDAD  VLHQSLLEAN  560
 561  IATEVCLTAL  DTLSLFTLAF   KNQLLADHGH  NPLMKKVFDV  YLCFLQKHQS  ETALKNVFTA  LRSLIYKFPS  TFYEGRADMC  640
 641  AALCYEILKC  CNSKLSSIRT   EASQLLYFLM  RNNFDYTGKK  SFVRTHLQVI  ISVSQLIADV  VGIGETRFQQ  SLSIINNCAN  720
 721  SDRLIKHTSF  SSDVKDLTKR   IRTVLMATAQ  MKEHENDPEM  LVDLQYSLAK  SYASTPELRK  TWLDSMARIH  VKNGDLSEAA  800
 801  MCYVHVTALV  AEYLTRKGVF   RQGCTAFRVI  TPNIDEEASM  MEDVGMQDVH  FNEDVLMELL  EQCADGLWKA  ERYELIADIY  880
 881  KLIIPIYEKR  RDFFEDEDGK   EYIYKEPKLT  PLSEISQRLL  KLYSDKFGSE  NVKMIQDSGK  VNPKDLDSKY  AYIQVTHVIP  960
 961  FFDEKELQER  KTEFERSHNI   RRFMFEMPFT  QTGKRQGGVE  EQCKRRTILT  AIHCFPYVKK  RIPVMYQHHT  DLNPIEVAID 1040
1041  EMSKKVAELR  QLCSSAEVDM   IKLQLKLQGS  VSVQVNAGFL  AYARAFLDDT  NTKRYPDNKV  KLLKEVFRQF  VEACGQALAV 1120
1121  NERLIKEDQL  EYQEEMKANY   REMAKELSEI  MHEQICPLEE  KTSVLPNSLH  IFNAISGTPT  STMVHGMTSS  SSVV       1195
        |   10        |   20        |   30        |   40        |   50        |   60        |   70        |   80
```

FIG. 10C (cont.)

```
            |  10       |  20       |  30       |  40        |  50       |  60       |  70       |  80
   1 AATTGTAATA CGACTCACTA TAGGGCGAAT TGGGTACCGG  GCCCCCCCTC GAGGTCGACG GTATCGATAA GCTTGATATC 80
  81 GAATTCGGCA CGAGTTTTAC ACCATCACCA AAACCCAGAA  TTTTATGATG AGATTAAAAT AGAGTTGCCC ACTCAGCTGC 160
 161 ATGAAAAGCA CCACCTGTTG CTCACATTCT TCCATGTCAG  CTGTGACAAC TCAAGTAAAG GAAGCACGAA GAACAGGGAT 240
 241 GTCGTTGAAA CCCAAGTTGG CTACTCCTGG CTTCCCCTCC  TGAAAGACGG AAGGGTGGTG ACAAGCGAGC AGCACATCCC 320
 321 GGTCTCGGCG AACCTTCCTT CGGGCTATCT TGGCTACCAA  GAGCTTGGGA TGGGCAGGCA TTATGGTCCG GAAATTAAAT 400
 401 GGGTAGATGG AGGCAAGCCA CTGCTGAAAA TTTCCACTCA  TCTGGTTTCT ACAGGGATAC TCAGGATCAG CATTTACATA 480
 481 ATTTTTTCCA GTACTGTCAG AAAACCGAAT CTGGAGCCCA  AGCCTTAGGA AACGAACTTG TAAAGTACCT TAAGAGTCTG 560
 561 CATGCGATGG AAGGCCACGT GATGATCGCC TTCTTGCCCA  CTATCCTAAA CCAGCTGTTC CGAGTCCTCA CCAGAGCCAC 640
 641 ACAGGAAGAA GTCGCGGTTA ACGTGACTCG GGTCATTATT  CATGTGGTTG CCCAGTGCCA TGAGGAAGGA TTGGAGAGCC 720
 721 ACTTGAGGTC ATATGTTAAG TACGCGTATA AGGCTGAGCC  ATATGTTGCC TCTGAATACA AGACAGTGCA TGAAGAACTG 800
 801 ACCAAATCCA TGACCACGAT TCTCAAGCCT TCTGCCGATT  TCCTCACCAG CAACAAACTA CTGAGGTACT CATGGTTTTT 880
 881 CTTTGATGTA CTGATCAAAT CTATGGCTCA GCATTTGATA  GAGAACTCCA AAGTTAAGTT GCTGCGAAAC CAGAGATTTC 960
 961 CTGCATCCTA TCATCATGCA GCGGAAACCG TTGTAAATAT  GCTGATGCCA CACATCACTC AGAAGTTTGG AGATAATCCA 1040
1041 GAGGCATCTA AGAACGCGAA TCATAGCCTT GCTGTCTTCA  TCAAGAGATG TTTCACCTTC ATGGACAGGG GCTTTGTCTT 1120
1121 CAAGCAGATC AACAACTACA TTAGCTGTTT TGCTCCTGGA  GACCCAAAGA CCCTCTTTGA ATACAAGTTT GAATTTCTCC 1200
1201 GTGTAGTGTG CAACCATGAA CATTATATTC CGTTGAACTT  ACCAATGCCA TTTGGAAAAG GCAGGATTCA AAGATACCAA 1280
1281 GACCTCCAGC TTGACTACTC ATTAACAGAT GAGTTCTGCA  GAAACCACTT CTTGGTGGGA CTGTTACTGA GGGAGGTGGG 1360
1361 GACAGCCCTC CAGGAGTTCC GGGAGGTCCG TCTGATCGCC  ATCAGTGTGC TCAAGAACCT GCTGATAAAG CATTCTTTTG 1440
1441 ATGACAGATA TGCTTCAAGG AGCCATCAGG CAAGGATAGC  CACCCTCTAC CTGCCTCTGT TTGGTCTGCT GATTGAAAAC 1520
1521 GTCCAGCGGA TCAATGTGAG GGATGTGTCA CCCTTCCCTG  TGAACGCGGG CATGACCGTG AAGGATGAAR CCCTGGCTCT 1600
1601 ACCCAGCTGTG AATCCGCTGG TGACGCCGCA GAAGGGAAGC  ACCCTGGACA ACAGCCTGCA CAAGGACCTG CTGGGCGCCA 1680
1681 TCTCCGGCAT TGCTTCTCCA TATACAACCT CAACTCCAAA  CATCAACAGT GTGAGAAATG CTGATTCGAG AGGATCTCTC 1760
1761 ATAAGCACAG ATTCGGGTAA CAGCCTTCCA GAAAGGAATA  GTGAGAAGAC CAATTCCCTG GATAAGCACC AACAAAGTAG 1840
1841 CAGTTGGAA AATTCCGTGG TTCGCTGTGA TAAACTTGAC  CAGTCTGAGA TTAAGAGCCT ACTGATGTGT TTCCTCTACA 1920
1921 TCTTAAAGAG CATGTCTGAT GATGCTTTGT TTACATATTG  GAACAAGGCT TCAACATCTG AACTTATGGA TTTTTTTACA 2000
2001 ATATCTGAAG TCTGCCTGCA CCAGTTCCAG TACATGGGGA  AGCGATACAT AGCCAGGAAC CAGGAGGGGT TGGGACCCAT 2080
2081 AGTTCATGAT CGAAAGTCTC AGACATTCCC TGTTTCCGT  AACAGAACAG GAATGATGCA TGCCAGATTG CAGCAGCTGG 2160
2161 GCAGCCTGGA TAACTCTCTC ACTTTTAACC ACAGCTATGG  CCACTCGGAC GCAGATGTTC TGCCACCAGTC ATTACTTGAA 2240
2241 GCCAACATTG CTACTGAGGT TTGCCTGACA GCTCTGGACA  CGCTTTCTCT ATTTACATTG GCGTTAAGA ACCAGCTCCT 2320
2321 GATGTCTACC TGTGTTTTCT CAAAAACAT CAGTCTGAAA 2400
2401 CGGCTTTAAA AAATGTCTTC ACTGCCTAAG GGTCCTTAAT  TTATAAGTTT CCCTCAACAT TCTATGAAGG GAGACGGAC 2480
2481 ATGTGTGCGG CTCTGTGTTA CGAATTCTC AAGTGCTGTA  ACTCCAAGCT GAGCTCCATC AGGACGGAGG CCTCCCAGCT 2560
2561 GCTCTACTTC CTGATGAGGA ACAACTTTGA TTACACTGGA  AAGAAGTCCT TTGTCCGGAC ACATTTGCAA GTCATCATAT 2640
2641 CTGTCAGCCA GCTGATAGCA GACGTTGTTG GCATTGGGGA  AACCCAGATTC CAGCAGTCCC TGTCCATCAT CAACAACTGT 2720
2721 GCCAACAGTG ACCGGCTTAT TAAGCACACC AGCTTCTCCT  CTGATGTGAA GGACTTAACC AAAGGATAC GCACGGTGCT 2800
2801 AATGCCCACC GCCCAGATGA AGGAGCATGA GAACGACCCA  GAGATGCTGG TGGACCTCCA GTACAGCCTG GCCAAATCCT 2880
2881 ATGCCAGCAC GCCCGAGCTC AGGAAGACGT GGCTCGACAC  CATGGCCAGG ATCCATGTCA AAAATGGCGA TCTCTCAGAG 2960
2961 GCTCTAATGT GCTATGTCCA CGTAACAGCC CTAGTGCACA  AATATCTCAC ACGGAAAGGC GTGTTTAGAC AAGGATGCAC 3040
3041 CGCCTTCAGG GTCATTACCC CAAACATCGA CGAGGAGGCC  TCCATGATGG AAGACGTGGG GATGCAGGAT GTCCATTCA 3120
3121 ACAAGGATGT GCTGATGGAG CTCCTTGAGC AGTGCGCAGA  TGGACTCTGG AAAGCCGAGC GCTACGAGCT CATCGCCGAC 3200
3201 ATTCTAAAC TTATCATCCC CATTTATGAG AAGCGGAGGC  ATTTCTTTGA AGATGAAGAT GGAAAGGAGT ATATTTACAA 3280
3281 GGAACCCAAA CTCACACCGC TGTCGGAAAT TTCTCAGAGA  CTCCTTAAAC TGTACTCGGA TAAATTTGT TCTGAAAATG 3360
3361 TCAAAATGAT ACAGGATTCT GGCAAGGTCA ACCCTAAGGA  TCTGGATTCT AAGTATGCAT ACATCCAGGT GACTCACGTC 3440
3441 ATCCCCTTCT TTGACGAAAA ACAGTTGCAA GAAAGGAAAA  CAGAGTTTGA GAGATCCCAC AACATCCCGCC GCTTCATGTT 3520
3521 TGAGATGCCA TTTACGCAGA CCGGGAAGAG GCAGGCGGG  GTGGAAGAGC AGTCAAACG GCGCACCATC CTGACAGCCA 3600
3601 TACACTGCTT CCCTTATGTG AAGAAGCGCA TCCCTGTCAT  GTACCGCAC CACACTGACC TGAACCCCAT CGAGGTGGCT 3680
3681 ATTGACGAGA TGAGTAAGAA GGTGGCGGAG CTCGGCAGC  TGTGCTCCTC GGCCGAGGTG GACATGATCA AACTGCAGCT 3760
3761 CAAACTCCAG GGCAGCGTGA GTGTTCAGGT CAATGCTGGC  CCACTAGCAT ATGCGCGAGC TTTCTTAGAT GATACAAACA 3840
3841 CAAAGCGATA TCCTGACAAT AAAGTGAAGC TGCTTAAGGA  AGTTTTCAGG CAATTGTGG AAGCTGCCG TCAAGCCTTA 3920
3921 GCGGTAAACG AACGTCTGAT TAAAGAAGAC CAGCTGGAGT  ATCAGGAAGA AATGAAAGCC AACTACAGGG AAATGGCGAA 4000
4001 GGAGCTTTCT GAAATCATGC ATGAGCAGAT CTGCCCCCTG  GAGGAGAAGA CGAGCGTCTT ACCGAATTCC CTTCACATCT 4080
4081 TCAACGCCAT GGCTATGGCT CCAACAAGCA CAATGGTTCA  CGGGATGACC AGCTCGTCTT CGGTCGTGTG ATTACATCTC 4160
4161 ATGCCCCGTG TGTGGGACT TGCTTTGTCA TTTGCAAACT  CAGGATGCTT TCCAAAGCCA ATCACTGGGG AGACCGAGCA 4240
4241 CAGGGAGGAC CAAGGGGAAG GGGAGAGAAA GGAAATAAAG  AACAACGTTA TTTTCTTAACA GACTTCTTAT AGGAGTGTA 4320
4321 AGAAGGTTGCA CATATTTTT TAAATCTCAC TGGCAATATT  CAAAGTTTTC ATTGTGTTCT AACAAAGGTG TGGTAGACAC 4400
4401 TCTTGAGCTG GACTTAGATT TTATTCTTCC TTGCAGAGTA  GTGTTAGAAT AGATGGCCTA CAGAAAAAA AGGTTCTGGG 4480
4481 ATCTACATGG CAGGGAGGGC TGCACTGACA TTGATGCCTG  GGGGACCTTT TGCCTCGACT CGTGCCGGAA ATCTGATCGT 4560
4561 AATCAGGGTA CAGACTTAC TAGTTTTGTC TAGGAGTATG  TTGTATGACT AGGATTTGTG CTATTATCTC ATTCAACAAC 4640
4641 ATAGAGCAAG AATAGTGAGC TAACTGAGCT AGACACTCAA  TTAATCCGCT ACTGGCTTCA AGTCAGAACT TTGTCATTAA 4720
4721 TCATCGACTC CGGGACGGTC ATATATATGT ACATTTCTA  CATTTTAAT ACTCACATGG GCTTATGCAT TAAGTTTAAT 4800
4801 TGTGATAAAT TTGTGCTGGT CCAGTATATG CAATACACTT  TAATGGTTTA TTCTTGTCAT AAAAATGTGC AATATGGAGA 4880
4881 TGTATACAAG TCTTTACT                                                                    4898
            |  10       |  20       |  30       |  40        |  50       |  60       |  70       |  80
```

FIG.10D

```
         |   10       |   20       |   30       |   40       |   50       |   60       |   70       |   80
    1 MEGHVMIAFL PTILNQLFRV LTRATQEEVA VNVTRVIIHV VAQCHEEGLE SHLRSYVKYA YKAEPYVASE YKTVHEELTK  80
   81 SMTTILKPSA DFLTSNKLLR YSWFFFDVLI KSMAQHLIEN SKVKLLRNQR FPASYHHAAE TVVNMLMPHI TQKFGDNPEA 160
  161 SKNANHSLAV FIKRCFTFMD RGFVFKQINN YISCFAPGDP KTLFEYKFEF LRVVCNHEHY IPLNLPMPFG KGRIQRYQDL 240
  241 QLDYSLTDEF CRNHFLVGLL LREVGTALQE FREVRLIAIS VLKNLLIKHS FDDRYASRSH QARIATLYLP LFGLLIENVQ 320
  321 RINVRDVSPF PVNAGMTVKD ESLALPAVNP LVTPQKGSTL DNSLHKDLLG AISGIASPYT TSTPNINSVR NADSRGSLIS 400
  401 TDSGNSLPER NSEKSNSLDK HQQSSTLGNS VVRCDKLDQS EIKSLLMCFL YILKSMSDDA LFTYWNKAST SEIMDFFTIS 480
  481 EVCLHQFQYM GKRYIARNQE GLGPIVHDRK SQTLPVSRNR TGMMHARLQQ LGSLDNSLTF NHSYGHSDAD VLHQSLLEAN 560
  561 IATEVCLTAL DTLSLFTLAF KNQLLADHGH NPLMKKVFDV YLCFLQKHQS ETALKNVFTA LRSLIYKFPS TFYEGRADMC 640
  641 AALCYEILKC CNSKLSSIRT EASQLLYFLM RNNFDYTGKK SFVRTHLQVI ISVSQLIADV VGIGETRFQQ SLSIINNCAN 720
  721 SDRLIKHTSF SSDVKDLTKR IRTVLMATAQ MKEHENDPEM LVDLQYSLAK SYASTPELRK TWLDSMARIH VKNGDLSEAA 800
  801 MCYVHVTALV AEYLTRKGVF RQGCTAFRVI TPNIDEEASM MEDVGMQDVH FNEDVLMELL EQCADGLWKA ERYELIADIY 880
  881 KLIIPIYEKR RDFFEDEDGK EYIYKEPKLT PLSEISQRLL KLYSDKFGSE NVKMIQDSGK VNPKDLDSKY AYIQVTHVIP 960
  961 FFDEKELQER KTEFERSHNI RRFMFEMPFT QTGKRQGGVE EQCKRRTILT AIHCFPYVKK RIPVMYQHHT DLNPIEVAID 1040
 1041 EMSKKVAELR QLCSSAEVDM IKLQLKLQGS VSVQVNAGPL AYARAFLDDT NTKRYPDNKV KLLKEVFRQF VEACGQALAV 1120
 1121 NERLIKEDQL EYQEEMKANY REMAKELSEI MHEQICPLEE KTSVLPNSLH IFNAISGTPT STMVHGMTSS SSVV        1195
         |   10       |   20       |   30       |   40       |   50       |   60       |   70       |   80
```

FIG. 10D(cont.)

```
      |   10       |   20       |   30       |   40       |   50       |   60       |   70       |   80
    1 AATTGTAATA  CGACTCACTA  TAGGGCGAAT  TGGGTACCGG  GCCCCCCCTC  GAGGTCGACG  GTATCGATAA  GCTTGATATC   80
   81 GAATTCGGCA  CGAGTTTTAC  ACCATCACCA  AAACCCAGAA  TTTTATGATG  AGATTAAAAT  AGAGTTGCCC  ACTCAGCTGC  160
  161 ATGAAAAGCA  CCACCTGTTG  CTCACATTCT  TCCATGTCAG  CTGTGACAAC  TCAAGTAAAG  GAAGCACGAA  GAAGAGGGAT  240
  241 GTCGTTGAAA  CCCAAGTTGG  CTACTCCTGG  CTTCCCCTCC  TGAAAGACGG  AAGGGTGGTG  ACAAGCGAGC  AGCACATCCC  320
  321 GGTCTCGGCG  AACCTTCCTT  CGGGCTATCT  TGGCTACCAA  GAGCTTGGGA  TGGGCAGGCA  TTATGGTCCG  GAAATTAAAT  400
  401 GGGTAGATGG  AGGCAAGCCA  CTGCTGAAAA  TTTCCACTCA  TCTGGTTTCT  ACAGGGATAC  TCAGGATCAG  CATTTACATA  480
  481 ATTTTTTCCA  GTACTGTCAG  AAAACCGAAT  CTGGAGCCCA  AGCCTTAGGA  AACGAACTTG  TAAAGTACCT  TAAGAGTCTG  560
  561 CATGCGATGG  AAGGCCACGT  GATGATCGCC  TTCTTGCCCA  CTATCCTAAA  CCAGCTGTTC  CGAGTCCTCA  CCAGAGCCAC  640
  641 ACAGGAACAA  GTCGCGGTTA  ACGTGACTCG  GGTCATTATT  CATGTGGTTG  CCCAGTGCCA  TGAGGAAGGA  TTGGAGAGCC  720
  721 ACTTGAGGTC  ATATGTTAAG  TACGCGTATA  AGGCTGAGCC  ATATGTTGCC  TCTGAATACA  ACACAGTGCA  TGAAGAACTG  800
  801 ACCAAATCCA  TGACCACGAT  TCTCAAGCCT  TCTGCCGATT  TCCTCACCAG  CAACAAACTA  CTGAGGTACT  CATGGTTTTT  880
  881 CTTTGATGTA  CTGATCAAAT  CTATGGCTCA  GCATTTGATA  GAGAACTCCA  AAGTTAAGTT  GCTGCGAAAC  CAGAGATTTC  960
  961 CTGCATCCTA  TCATCATGCA  GCGGAAACCG  TTGTAAATAT  GCTGATGCCA  CACATCACTC  AGAAGTTTGG  AGATAATCCA 1040
 1041 GAGGCATCTA  AGAACGCGAA  TCATAGCCTT  GCTGTCTTCA  TCAAGAGATG  TTTCACCTTC  ATGGACAGGG  GCTTTGTCTT 1120
 1121 CAAGCAGATC  AACAACTACA  TTAGCTGTTT  TGCTCCTGGA  GACCCAAAGA  CCCTCTTTGA  ATACAAGTTT  GAATTTCTCC 1200
 1201 GTGTAGTGTG  CAACCATGAA  CATTATATTC  CGTTGAACTT  ACCAATGCCA  TTTGGAAAAG  GCAGGATTCA  AAGATACCAA 1280
 1281 GACCTCCAGC  TTGACTACTC  ATTAACAGAT  GAGTTCTGCA  GAAACCACTT  CTTGGTGGGA  CTGTTACTGA  GGGAGGTGGG 1360
 1361 GACAGCCGTC  CAGGAGGTCC  GGGAGGTCCG  TCTGATCGCC  ATCAGTGTGC  TCAAGAACCT  GCTGATAAAG  CATTCTTTTG 1440
 1441 ATGACAGATA  TGCTTCAAGG  AGCCATCAGG  CAAGGATAGC  CACCCTCTAC  CTGCCTCTGT  TTGGTCTGCT  GATTGAAAAC 1520
 1521 GTCCAGGCGA  TCAATGTCGA  GGATGTGTCA  CCCCTTCCCTG  TGAACGCGGG  CATGACCGTG  AAGGATGAAT  CCCTGCCTCT 1600
 1601 ACCAGCTGTG  AATCCGCTGG  TGACGCCGCA  GAAGGGAAGC  ACCCTGGACA  ACAGCCTGCA  CAAGGACCTG  CTGGGCGCCA 1680
 1681 TCTCCGGCAT  TGCTTCTCCA  TATACAACCT  CAACTCCAAA  CATCAACAGT  GTGAGAAGAG  CTGATTCGAG  AGGATCTCTC 1760
 1761 ATAAGCACAG  ATTCGGGTAA  CAGCCTTCCA  GAAAGGAATA  GTGAGAAGAG  CAATTCCCTG  GATAAGCACC  AACAAAGTAG 1840
 1841 CACATTGGGA  AATTCCGTGG  TTCCGTCTGT  GT AAACTTGGA  CAGTCTGAGA  TTAAGAGCCT  ACTGATGTGT  TTCCTCTACA 1920
 1921 TCTTAAAGAG  CATGTCTGAT  GATGCTTTGT  TTACATATTG  GAACAAGGCT  TCAACATCTG  AACTTATGGA  TTTTTTTACA 2000
 2001 ATATCTGAAG  TCTGCCTGCA  CCAGTTCCAG  TACATGGGGA  AGCGATACAT  AGCCAGGAAC  CAGGAGGGGT  TGGGACCCAT 2080
 2081 AGTTCATGAT  CGAAAGTCTC  AGACATTGCC  TGTTTCCCGT  AACAGAACGA  GAATGATGCA  TGCCAGATTG  CAGCAGCTGG 2160
 2161 GCAGCCTGGA  TAACTCTCTC  ACTTTTAACC  ACAGCTATGG  CCACTCGGAC  GCAGATGTTC  TGCACCAGTC  ATTACTTGAA 2240
 2241 GCCAACATTG  CTACTGAGGT  TTGCCTGACA  GCTCTGGACA  CGCTTTCTCT  ATTTACATTG  GCGTTTAAGA  ACCAGCTCCT 2320
 2321 GGCCGACCAT  GGACATAATC  CTCTCATGAA  AAAAGTTTTT  GATGATGTACC  TGTGTTTTCT  TCAAAAACAT  CAGTCTGAAA 2400
 2401 CGGCTTTAAA  AAATGTCTTC  ACTGCCTTAA  GGTCCTTAAT  TTATAAGTTT  CCCTCAACAT  TCTATGAAGG  GAGAGCGGAC 2480
 2481 ATGTGTGCGG  CTCTGTGTTA  CGAGATTCTC  AAGTGCTGTA  ACTCCAAGCT  GAGCTCCATC  AGGACGGAGG  CCTCCCAGCT 2560
 2561 GCTCTACTTC  CTGATGAGGA  ACAACTTTGA  TTACACTGGA  AAGAAGTCCT  TTGTCCGGAC  ACATTTGCAA  GTCATCATAT 2640
 2641 CTGTCAGCCA  GCTGATAGCA  GACGTTGTTG  GCATTGGGGA  AACCAGATTC  CAGCAGTCCC  TGTCCATCAT  CAACAACTGT 2720
 2721 GCCAACAGTG  ACCGCTTAT  TAAGCACACC  AGCTTCTCCT  CTGATGTGAA  GGACTTAACC  AAAAGGATAC  GCACGGTGCT 2800
 2801 AATGGCCACC  GCCCAGATGA  AGGAGCATGA  GAACGACCCA  GAGATGCTGG  TGGACCTCCA  GTACAGCCTG  GCCAAATCCT 2880
 2881 ATGCCAGCAC  GCCCGAGCTC  AGGAAGACGT  GGCTCGACAG  CATGGCCAGG  ATCCATGTCA  AAATGGCGA  TCTCTCAGAG 2960
 2961 GCAGCAATGT  GCTATGTCCA  CGTAACAGCC  CTAGTGGCAG  AATATCTCAC  ACGGAAAGGC  GTGTTTAGC  AAGGATGCAC 3040
 3041 CGCCTTCAGG  GTCATTGAAC  CAAACATCGA  CGAGGAGGCC  TCCATGATGG  GATGCAGGAT  GATGCAGGAT  GTCCATTTCA 3120
 3121 ACGAGGATGT  GCTGATGCAG  CTCCTTGAGC  AGTGCGCAGA  TGGACTCTGG  AAAGCCGAGC  GCTACGAGCT  CATCGCCGAC 3200
 3201 ATCTACAAAC  TTATCATCCC  CATTTATGAG  AAGCGGAGGG  ATTTCTTTGA  AGATAAGAT  GGAAAGGAGT  ATATTTACAA 3280
 3281 GGAACCCAAA  CTGCACACGC  TGTCAGAAAT  TTCTCAGAGA  CTCCTTAAAC  TGTACTCGGA  TAAATTTGGT  TCTGAAAATG 3360
 3361 TCAAAATGAT  ACAGGATTCT  GGCAAGGTCA  ACCCTAAGGA  TCTGGATTCT  AAGTATGCAT  ACATCCAGGT  GACTCACGTC 3440
 3441 ATCCCCTTCT  TTGACGAAAA  AGAGTTGCAA  GAAAGGAAAA  CAGAGTTTGA  GAGATCCCAC  AACATCCGCC  GCTTCATGTT 3520
 3521 TGAGATGCCA  CAGGGAGAGA  CCGGGAACAG  GCAGGGCGGG  GTGGAAGCCA  GCAGCTCATC  CTGACAGCCA 3600
 3601 TACACTGCTT  CCCTTATGTG  AAGAAGCGCA  TCCCTGTCAT  GTACCAGCAC  CACACTGACC  TGAACCCCAT  CGAGGTGGCC 3680
 3681 ATTGACGAGA  TGAGTAAGAA  GGTGGCGGAG  CTCCGGCAGC  TGTGCTCCTC  GGCCGAGGTG  GACATGATCA  AACTGCAGCT 3760
 3761 CAAACTCCAG  GGCAGCGTGA  GTGTTCAGGT  CAATGCTGGC  CCACTAGCAT  ATGCGGCAGC  TTTCTTAGAT  GATACAAACA 3840
 3841 CAAAGCGATA  TCCTGACAAT  AAAGTGAAGC  TGCTTAAGGCA  AGTTTTCAGG  CAATTTGTGG  AAGCTTGCGG  TCAAGCCTTA 3920
 3921 GCGGTAAACG  AACGTCTGAT  TAAAGAAGAC  CAGCTCGAGT  ATCAGGAAGA  AATGAAAGCC  AACTACAGGG  AAATGGCGAA 4000
 4001 GGAGCTTTCT  GAAATCATGC  ATGAGCAGAT  CTGCCCCCTG  GAGGAGAAGA  CGAGCGTCTT  ACCGAATTCC  CTTCACATCT 4080
 4081 TCAACGCCAT  CAGTGGGACT  CCAACAAGCA  CAATGGTTCA  CGGGATGACC  AGCTCGTCTT  CGGTCGTGTG  ATTACATCTC 4160
 4161 ATGCCCGTG  TGTGGGACT  TGCTTTGTCA  TTTGCAAACT  CAGGATGCTT  TCCAAAGCCA  ATCACTGGGA  AGACCAGCCA 4240
 4241 CAGGGAGGAC  CAAGGGGAAG  GGGAGACAAA  GGAAATAAAG  AACAACGTTA  TTTCTTAACA  GACTTTCTAT  AGGAGTTGTA 4320
 4321 AGAAGGTGCA  CATATTTTTT  TAAATCTCAC  TGGCAATATT  CAAAGTTTTC  ATTGTGTCTT  AACAAAGGTG  TGGTAGACAC 4400
 4401 TCTTGAGCTG  GACTTAGATT  TTATTCTTCC  TTGCAGAGTA  GTGTTAGAAT  AGATGGCCTA  CAGAAAAAA  AGGTTCTGGG 4480
 4481 ATCTACATGG  CAGGGAGGC  TGCACTGACA  TTGATGCCTG  GGGGACCTTT  TGCCTCGACT  CGTGCCGGAA  ATCTGATCGT 4560
 4561 AATCAGGGTA  CAGAACTTAC  TAGTTTTGTC  TAGGAGTATG  TTGTATGACT  AGGATTGTG  CTATTATCTC  ATTCAACAAC 4640
 4641 ATAGAGCAAG  AATAGTGAGC  TAACTGAGCT  AGACACTCAA  TTAATCCGCT  ACTGGCTTCA  AGTCAGAACT  TTGTCATTAA 4720
 4721 TCATCGACTC  CGGCACGGTC  ATATATGTAT  TACATTTCTA  CATTTTAAT  ACTCACATGG  GCTTATGCAT  TAAGTTTAAT 4800
 4801 TGTGATAAAT  TTGTGCTGGT  CCAGTATATG  CAATACACTT  TAATGGTTTA  TTCTTGTCAT  AAAAATGTGC  AATATGGAGA 4880
 4881 TGTATACAAG  TCTTTACT                                                                          4898
      |   10       |   20       |   30       |   40       |   50       |   60       |   70       |   80
```

FIG.10E

```
        |   10       |   20       |   30       |   40       |   50       |   60       |   70       |   80
    1 MEGHVMIAFL PTIINQLFRV LTRATQEEVA VNVTRVIIHV VAQCHEEGLE SHLRSYVKYA YKAEPYVASE YKTVHEELTK   80
   81 SMTTILKPSA DFLTSNKLLR YSWFFFDVLI KSMAQHLIEN SKVKLLRNQR FPASYHHAAE TVVNMLMPHI TQKFGDNPEA  160
  161 SKNANHSLAV FIKRCFTEMD RGFVFKQINN YISCFAPGDP KTLFEYKFEF LRVVCNHEEY IPLNLPMPFG KGRIQRYQDL  240
  241 QLDYSLTDEF CRNHFLVGLL LREVGTALQE FREVRLIAIS VLKNLLIKHS FDDRYASRSH QARIATLYLP LFGLLIENVQ  320
  321 RINVRDVSPF PVNAGMTVKD ESLALPAVNP LVTPQKGSTL DNSLHKDLLG AISGIASPYT TSTPNINSVR NADSRGSLIS  400
  401 TDSGNSLPER NSEKSNSLDK HQQSSTLGNS VVRCDKLDQS EIKSLLMCFL YILKSMSDDA LFTYWNKAST SELMDFFTIS  480
  481 EVCLHQFQYM GKRYIARNQE GLGPIVHDRK SQTLPVSRNR TGMMHARLQQ LGSLDNSLTF NHSYGHSDAD VLHQSLLEAN  560
  561 IATEVCLTAL DTLSLFTLAF KNQLLADHGH NPLMKKVFDV YLCFLQKHQS ETALKNVFTA LRSLIYKFPS TFYEGRADMC  640
  641 AALCYEILKC CNSKLSSIRT EASQLLYFLM RNNFDYTGKK SFVRTHLQVI ISVSQLIADV VGIGETRFQQ SLSIINNCAN  720
  721 SDRLIKHTSF SSDVKDLTKR IRTVLMATAQ MKEHENDPEM LVDLQYSLAK SYASTPELRK TWLDSMARIH VKNGDLSEAA  800
  801 MCYVHVTALV AEYLTRKGVF RQGCTAFRVI TPNIDEEASM MEDVGMQDVH FNEDVLMELL EQCADGLWKA ERYELIADIY  880
  881 KLIIPIYEKR RDFFEDEDGK EYIYKEPKLT PLSEISQRLL KLYSDKFGSE NVKMIQDSGK VNPKDLDSKY AYIQVTHVIP  960
  961 FFDEKELQER KTEFERSHNI RRFMFEMPFT QTGKRQGGVE EQCKRRTILT AIHCFPYVKK RIPVMYQHHT DLNPIEVAID 1040
 1041 EMSKKVAELR QLCSSAEVDM IKLQLKLQGS VSVQVNAGPL AYARAFLDDT NTKRYPDNKV KLLKEVFRQF VEACGQALAV 1120
 1121 NERLIKEDQL EYQEEMKANY REMAKELSEI MHEQICPLRE KTSVLPNSLH IFNAISGTPT STMVHGMTSS SSVV        1195
        |   10       |   20       |   30       |   40       |   50       |   60       |   70       |   80
```

FIG. 10E (cont.)

```
        |   10      |   20      |   30      |   40      |   50      |   60      |   70      |   80
   1 AATTGTAATA CGACTCACTA TAGGGCGAAT TGGGTACCGG GCCCCCCCTC GAGGTCGACG GTATCGATAA GCTTGATATC   80
  81 GAATTCGGCA CGAGTTTTAC ACCATCACCA AAACCCAGAA TTTTATGATG AGATTAAAAT AGAGTTGCCC ACTCAGCTGC  160
 161 ATGAAAAGCA CCACCTGTTG CTCACATTCT TCCATGTCAG CTGTGACAAC TCAAGTAAAG GAAGCACGAA GAAGAGGGAT  240
 241 GTCGTTGAAA CCCAAGTTGG CTACTCCTGG CTTCCCCTCC TGAAAGACGG AAGGGTGGTG ACAAGCGAGC AGCACATCCC  320
 321 GGTCTCGGCG AACCTTCCTT CGGGCTATCT TGGCTACCAA GAGCTTGGGA TGGGCAGGCA TTATGGTCCG GAAATTAAAT  400
 401 GGGTAGATGG AGGCAAGCCA CTGCTGAAAA TTTCCACTCA TCTGGTTTCT ACAGGGATAC TCAGGATCAG CATTTACATA  480
 481 ATTTTTTCCA GTACTGTCAG AAAACCGAAT CTGGAGCCCA AGCCTTAGGA AACGAACTTG TAAAGTACCT TAAGAGTCTG  560
 561 CATGCGATGG AAGGCCACGT GATGATCGCC TTCTTGCCCA CTATCCTAAA CCAGCTGTTC CGAGTCCTCA CCAGAGCCAC  640
 641 ACAGGAAGAA GTCGCGGTTA ACGTGACTCG GGTCATTATT CATGTGGTTG CCCAGTGCCA TGAGGAAGGA TTGGAGAGCC  720
 721 ACTTGAGGTC ATATGTTAAG TACGCGTATA AGGCTGAGCC ATATGTTGCC TCTGAATACA AGACAGTGCA TGAAGAACTG  800
 801 ACCAAATCCA TGACCACGAT TCTCAAGCCT CTGCCGATT  TCCTCACCAG CAACAAACTA CTGAGGTACT CATGGTTTTT  880
 881 CTTTGATGTA CTGATCAAAT CTATGGCTCA GCATTTGATA GAGAACTCCA AAGTAAGTT GCTGCGAAAC CAGAGATTTC  960
 961 CTGCATCCTA TCATCATGCA GCGGAAACCG TTGTAAATAT GCTGATGCCA CACATCACTC AGAAGTTTGG AGATAATCCA 1040
1041 GAGGCATCTA AGAACGCGAA TCATAGCCTT GCTGTCTTCA TCAAGAGATG TTTCACCTTC ATGGACAGGG GTTTTGTCTT 1120
1121 CAAGCAGATC AACAACTACA TTAGCTGTTT TGCTCCTGGA GACCCAAAGA CCCTCTTTGA ATACAAGTTT GAATTCTCCC 1200
1201 GTGTAGTGTG CAACCATGAA CATTATATTC CGTTGAACTT ACCAATGCCA TTTGAAAAG GCAGGATTCA AAGATACCAA 1280
1281 GACCTCCAGC TTGACTACTC ATTAACAGAT GAGTTCTGCA GAAACCACTT CTTGGTGGGA CTGTTACTGA GGGAGGTGGG 1360
1361 GACAGCCCTC CAGGAGTTCC GGGAGGTCCG TCTGATCGCC ATCAGTGTGC TCAAGAACCT GCTGATAAAG CATTCTTTTG 1440
1441 ATGACAGATA TGCTTCAAGG AGCCATCAGG CAAGGATAGC CACCCTCTAC CTGCCTCTGT TTGGTCTGCT GATTGAAAAC 1520
1521 GTCCAGCGGA TCAATGTGAG GGATGTGTCA CCCTTCCCTG TGAACGCGGG CATGACCGTG AAGGATGAAT CCCTGGCTCT 1600
1601 ACCAGCTGTG AATCCGCTGC TGACGCCGCA GAAGGGAAGC ACCCTGGACA ACAGCCTGCA CAAGGACCTG CTGGGCGCCA 1680
1681 TCTCAACAGT TGCTTCTCCA TATACAACCT CAACTCCAAA CATCAACGCT GTGAGAAATG CTGATTCGAG AGGATCTCTC 1760
1761 ATAAGCACAG ATTCGGGTAA CAGCCTTCCA GAAAGGAATA GTGAGAAGAG CAATTCCCTG GATAAGCACC AACAAAGTAG 1840
1841 CACATTGGGA AATTCCGTGG TTCGCTGTGA TAAACTTGAC CAGTCTGAGA TTAAGCCCT ACTGATGTGT TTCCTCTACA 1920
1921 TCTTAAAGAG CATGTCTGAT GATGCTTTGT TTACATATTG GAACAAGGCT TCAACATCTG AACTTATGGA TTTTTTACA 2000
2001 ATATCTGAAG TCTGCCTGCA CCAGTTCCAG TACATGGGGA AGCGATACAT AGCCAGGAAC CAGGAGGGGT TGGGACCCAT 2080
2081 AGTTCATGAT CGAAAGTCTC AGACATTGCC TGTTTCCCGT AACAGAACGA GAATGATGCA TGCCAGATTG CAGCAGCTGG 2160
2161 GCAGCCTGGA TAACTCTCTC ACTTTTAACC ACAGCTATGG CCACCGACAA GCCGAGCTC TGCACCAGTC ATTACTTGAA 2240
2241 GCCAACATTG CTACTGAGGT TTGCCTGACA GCTCTGACA CGCTTCTCT ATTTACATTG GCGTTTAAGA ACCAGCTCCT 2320
2321 GGCCGACCAT GGACATAATC CTCTCATGAA AAAGTTTTT GATGTCTACC TGTGTTTTCT TCAAAAACAT CAGTCTGAAA 2400
2401 CGGCTTTAAA AAATGTCTTC ACTGCCTTAA GGTCCTTAAT TTATAAGTTT CCCTCAACAT TCTATGAAGG GAGAGCGGAC 2480
2481 ATGTGTGCGG CTCTGTGTTA CGAGATTCTC AAGTGCTGTA ACTCCAAGCT GAGCTCCATC AGGACGGAGG CCTCCCAGCT 2560
2561 GCTCTACTTC CTGATGAGGA ACAACTTTGA TTACACTGGA AAGAAGTCCT TTGTCCGGAC ACATTTGCAA GTCATCATAT 2640
2641 CTGTCAGCCA GCTGATAGCA GACGTTGTTG GCATTGGGGA AACCAGATTC CAGCAGTCCC TGTCCATCAT CAACAACTGT 2720
2721 GCCAACAGTG ACCGGCTTAT TAAGCACACC AGCTTCTCCT CTGATGTGAA GGACTTAACC AAAAGGATAC GCACGGTGCT 2800
2801 AATGGCCACC GCCCAGATGA AGGAGCATGA GAACGACCCA GAGATGCTGG TGGACCTCCA GTACAGCCTG GCCAATCCT 2880
2881 ATGCCAGCAC GCCCGAGCTC CTCCTTGAGC AGTGCGCAGA CATGGCCAGG ATCCATGTCA AAAATGGCGA TCTCTCAGAG 2960
2961 GCAGCAATGT GCTATGTCCA CGTAACAGCC CTAGTGGCAG AATATCTCAC ACGGAAAGGC GTGTTAGAC AAGGATGCAC 3040
3041 CGCCTTCAGG GTCATTACCC CAAACATCGA CGAGGAGGCC TCCATGATGG AAGACGTGGG GATGCAGGAT GTCCATTTCA 3120
3121 ACGAGGATGT GCCCGAGCTC CTCCTTGAGC AGTGCGCAGA TGGACTCTGG AAAGCCGAGC GCTACGAGCT CATCGCCGAC 3200
3201 ATCTACAAAC TTATCATCCC CATTATGAAG AAGCGGAGGG ATTTCTTTGA AGATGAAGAT GGAAAGGAGT ATATTACAA 3280
3281 GGAACCCAAA CTCACACCGC TGTCGGAAAT TTCTCAGAGA CTCCTTAAAC TGTACTCGGA TAAATTTGGT TCTGAAAATG 3360
3361 TCTAAAATGAT ACAGGATTCT GGCAAGGTCA ACCCTAAGGA TCTGGATTCT AAGTATGCAT ACATCCAGGT GACTCACGTC 3440
3441 ATCCCCTTCT TTGACCAAAA AGAGTTGCAA GAAAGGAAAA CAGAGTTTGA GAGATCCCAC AACATCCGCC GCTTCATGTT 3520
3521 TGAGATGCCA TTTACGCAGA CCGGGAAGAG GCAGGGCGGG GTGGAAGAGC AGTGCAAACG GCGCACCATC CTGACAGCCA 3600
3601 TACACTGCTT CCCTTATGTG AAGAAGCGCA TCCCTGTCAT GTACCAGCAC CACACTGACC TGAACCCAT CGAGGTGCCC 3680
3681 ATTGACGAGA TGAGTAAGAA GGTGGCGGAG CTCCGGCAGC TGTGCTCCTC GGCCGAGGTG GACATGATCA AACTGCAGCT 3760
3761 CAAACTCCAG GGCAGCGTGA GTGTTCAGGT CAATGCTGGC CCACTAGCAT ATGCGCGAGC TTTCTTAGAT GATACAAACA 3840
3841 CAAAGCGATA TCCTGACAAT AAAGTGAAGC TGCTTAAGGA AGTTTTCAGG CAATTTGTGG AAGCTTGCGG TCAAGCCTTA 3920
3921 GCGGTAAACG AACGTCTGAT TAAAGAAGAC CAGCTCGAGT ATCAGGAAGA AATGAAAGCC AACTACAGGG AAATGGCGAA 4000
4001 GGAGCTTTCT GAAATCATGC ATGAGCAGAT CTGCCCCCTG GAGGAGAAGA CGAGCGTCTT ACCGAATTCC CTTCACATCT 4080
4081 TCAACGCCAT GCCCGAGCTC CCAACAAGCA CAATGGTTCA CGGGATGACC AGCTCGTCTT CGGTCGTGTG ATTACATCTC 4160
4161 ATGGCCCGTG TGTGGGGACT TGCTTTGTCA TTTGCAAACT CAGGATGCTT TCCAAAGCCA ATCACTGGGG AGACCGAGCA 4240
4241 CAGGGAGGAC CAAGGGGAAG GGGAGAGAA GGAAATAAAG AACAACGTTA TTTCTTAACA GACTTTCTAT AGGAGTTGTA 4320
4321 AGAAGGTGCA CATATTTTTT TAAATCTCAC TGGCAATATT CAAAGTTTTC ATTGTGTCTT AACAAAGGTG TGGTAGACAC 4400
4401 TCTTGAGCTG GACTTAGATT TTATTCTTCC TTGCAGAGTA GTGTTAGAAT AGATGGCCTA CAGAAAAAAA AGGTTCTGGG 4480
4481 ATCTACATGG CAGGGAGGGC TGCACTGACA TTGATGCCTG GGGGACCTTT TGCCTCGACT CGTGCCGGAA ATCTGATCGT 4560
4561 AATCAGGGTA CAGAACTTAC TAGTTTTGTC TAGGAGTATG TTGTATGACT AGGATTTGTG CTATTATCTC ATTCAACAAC 4640
4641 ATAGAGCAAG AATAGTGAGC TAACTGAGCT AGACACTCAA TTAATCGGCT ACTGGCTTCA AGTCAGAACT TTGTCATTAA 4720
4721 TCATCGACTC CGGGACGGTC ATATATGTAT TACATTTCTA CATTTTTAAT ACTCACATGG GCTTATGCAT TAAGTTTAAT 4800
4801 TGTATAAAAT TTGTGCTGGT CCAGTATATG CAATACACTT TAATGGTTTA TTCTTGTCAT AAAAATGTGC AATATGGAGA 4880
4881 TGTATACAAG TCTTTACT                                                                     4898
        |   10      |   20      |   30      |   40      |   50      |   60      |   70      |   80
```

FIG.10F

```
          |   10       |   20       |   30       |   40       |   50       |   60       |   70       |   80
    1 MEGHVMIAFL PTILNQLFRV LTRATQEEVA VNVTRVIIHV VAQCHEEGLE SHLRSYVKYA YKAEPYVASE YKTVHEELTK  80
   81 SMTTILKPSA DFLTSNKLLR YSWFFFDVLI KSMAQHLIEN SKVKLLRNQR FPASYHHAAE TVVRMLMPHI TQKFGDNPEA 160
  161 SKNANHSLAV FIKRCFTFMD RGFVFKQINN YISCFAPGDP KTLFEYKFEF LRVVCNHEHY IPLNLPMPFG KGRIQRYQDL 240
  241 QLDYSLTDEF CRNHFLVGLL LREVGTALQE FREVRLIAIS VLKNLLIKHS FDDRYASRSH QARIATLYLP LFGLLIENVQ 320
  321 RINVRDVSPF PVNAGMTVKD ESLALPAVNP LVTPQKGSTL DNSLHKDLLG AISGIASPYT TSTPNINSVR NADSRGSLIS 400
  401 TDSGNSLPER NSEKSNSLDK HQQSSTLGNS VVRCDKLDQS EIKSLLMCFL YILKSMSDDA LFTYWNKAST SELMDFFTIS 480
  481 EVCLHQFQYM GKRYIARNQE GLGPIVHDRK SQTLPVSRNR TGMMHARLQQ LGSLDNSLTF NHSYGHSDAD VLEQSLLEAN 560
  561 IATEVCLTAL DTLSLFTLAF KNQLLADHGH NPLMKKVFDV YLCFLQKHQS ETALKNVFTA LRSLIYKFPS TFYEGRADMC 640
  641 AALCYEILKC CNSKLSSIRT EASQLLYFLM RNNFDYTGKK SFVRTHLQVI ISVSQLIADV VGIGETRFQQ SLSIINNCAN 720
  721 SDRLIKHTSF SSDVKDLTKR IRTVLMATAQ MKEHENDPEM LVDLQYSLAK SYASTPELRK TWLDSMARIH VKNGDLSEAA 800
  801 MCYVHVTALV AEYLTRKGVF RQGCTAFRVI TPNIDEEASM MEDVGMQDVH FNEDVIMELL EQCADGLWKA ERYELIADIY 880
  881 KLIIPIYEKR RDFFEDEDGK EYIYKEPKLT PLSEISQRLL KLYSDKFGSE NVKMIQDSGK VNPKDLDSKY AYIQVTHVIP 960
  961 FFDEKELQER KTEFERSHNI RRFMFEMPFT QTGKRQGGVE EQCKRRTILT AIHCFPYVKK RIPVMYQHHT DLNPIEVAID 1040
 1041 EMSKRVAELR QLCSSAEVDM IKLQLKLQGS VSVQVNAGPL AYARAFLDDT NTKRYPDNKV KLLKEVFRQF VEACGQALAV 1120
 1121 NERLIKEDQL EYQEEMKANY REMAKELSEI MHEQICPLEE KTSVLPNSLH IFNAISGTPT STMVHGMTSS SSVV        1195
          |   10       |   20       |   30       |   40       |   50       |   60       |   70       |   80
```

FIG. 10F (cont.)

```
         |   10        |   20        |   30        |   40        |   50        |   60        |   70        |   80
   1 AATTGTAATA CGACTCACTA TAGGGCGAAT TGGGTACCGG GCCCCCCCTC GAGGTCGACG GTATCGATAA GCTTGATATC 80
  81 GAATTCGGCA CGAGTTTTAC ACCATCACCA AAACCCAGAA TTTTATGATG AGATTAAAAT AGAGTTGCCC ACTCAGCTGC 160
 161 ATGAAAAGCA CCACCTGTTG CTCACATTCT TCCATGTCAG CTGTGACAAC TCAAGTAAAG GAAGCACGAA GAAGAGGGAT 240
 241 GTCGTTGAAA CCCAAGTTGG CTACTCCTGG CTTCCCCTCC TGAAAGACGG AAGGGTGGTG ACAAGCGAGC AGCACATCCC 320
 321 GGTCTCGGCG AACCTTCCTT CGGGCTATCT TGGCTACCAA GAGCTTGGGA TGGGCAGGCA TTATGGTCCG GAAATTAAAT 400
 401 GGGTAGATGG AGGCAAGCCA CTGCTGAAAA TTTCCACTCA TCTGGTTTCT ACAGGGATAC TCAGGATCAG CATTTACATA 480
 481 ATTTTTTCCA GTACTGTCAG AAAACCGAAT CTGGAGCCCA AGCCTTAGGA AACGAACTTG TAAAGTACCT TAAGAGTCTG 560
 561 CATGCGATGG AAGGCCACGT GATGATCGCC TTCTTGCCCA CTATCCTAAA CCAGCTGTTC CGATCCTCA CCAGAGCCAC 640
 641 ACAGGAAGAA GTCGCGGTTA ACGTGACTCG GGTCATTATT CATGTGGTTG CCCAGTGCCA TGAGGAAGGA TTGGAGAGCC 720
 721 ACTTGAGGTC ATATGTTAAG TACGCGTATA AGGCTGAGCC ATATGTTGCC TCTGAATACA AGACAGTGCA TGAAGAACTG 800
 801 ACCAAATCCA TGACCACGAT TCTCAAGCCT TCTGCCGATT TCCTCACCAG CAACAAACTA CTGAGGTACT CATGGTTTTT 880
 881 CTTTGATGTA CTGATCAAAT CTATGCCTCA GCATTTGATA GAGAACTCCA AAGTTAAGTT GCTGCCAAAC CAGAGATTTC 960
 961 CTGCATCCTA TCATCATGCA GCGGAAACCG TTGTAAATAT GCTGATGCCA CACATCACTC AGAGTTTGG AGATAATCCA 1040
1041 GAGGCATCTA AGAACGCGAA TCATAGCCTT GCTGTCTTCA TCAAGAGATG TTTCACCTTC ATGGACAGGG GCTTTGTCTT 1120
1121 CAAGCAGATC AACAACTACA TTAGCTGTTT TGCTCCTGGA GACCCAAAGA CCCTCTTTGA ATACAAGTTT GAATTTCTCC 1200
1201 GTGTAGTGTG CAACCATGAA CATTATATTC CGTTGAACTT ACCAATGCCA TTTGGAAAAG GCAGGATTCA AAGATACCAA 1280
1281 GACCTCCAGC TTGACTACTC ATTAACAGAT GAGTTCTGCA GAAACCACTT CTTGGTGGGA CTGTTACTGA GGGAGGTGGG 1360
1361 GACAGCCCTC CAGGAGTTCC GGGAGGTCCG TCTGATCGCC ATCAGTGTGC TCAAGACCCT GCTGATAAAG CATTCTTTTG 1440
1441 ATGACAGATA TGCTTCAAGG AGCCATCAGG CAAGGATAGC CACCCTCTAC CTGCCTCTGT TTGGTCTGCT GATTGAAAAC 1520
1521 GTCCAGCGGA TCAATGTGAG GGATGTGTCA CCCTTCCCTG TGAACGCGGG CATGACCGTG AAGGATGAAT CCCTGGCTCT 1600
1601 ACCAGCTGTG AATCCGCTGG TGACGCCGCA GAAGGGAAGC ACCCTGGACA ACAGCCTGCA CAAGGACCTG CTGGGCGCCA 1680
1681 TCTCCGGCAT TGCTTCTCCA TATACAACCT CAACTCCAAA CATCAACAGT GTGAGAAATG CTGATTCGAG AGGATCTCTC 1760
1761 ATAAGCACAG ATTCGGGTAA CAGCCTTCCA GAAAGGAATA GTGAGAAGAG CAATTCCCTG GATAAGCACT AACAAAGTAG 1840
1841 CACATTGGGA AATTCCGTGG TTCGCTGTGA TAAACTTGAC CAGTCTGAGA TTAAGAGCCT ACTGATGTGT TTCCTCTACA 1920
1921 TCTTAAAGAG CATGTCTGAT GATGCTTTGT TTACATATTG GAACAAGGCT TCAACATCTG AACTTATGGA TTTTTTTACA 2000
2001 ATATCTGAAG TCTGCCTGCA CCAGTTCCAG TACATGGGGA AGCAGTACAT AGCCAGCAAC CAGGAGGGT TGGGACCCAT 2080
2081 AGTTCATGAT CGAAAGTCTC AGACATTGCC TGTTTCCCGT AACAGAACGA GAATGATGCA TGCCAGATTG CAGCAGCTGG 2160
2161 GCAGCCTGGA TAACTCTCTC ACTTTTAACC ACAGCTATGG CCACTCGGAC GCAGATGTTC TGCACCAGTC ATTACTTGAA 2240
2241 GCCAACATTG CTACTGAGGT TTGCCTGACA GCTCTGGACA CGCTTTCTCT ATTTACATTG GCGTTTAAGA ACCAGCTCCT 2320
2321 GGCCGACCAT GGACATAATC CTCTCATGAA AAAGTTTTT GATGCTCTACC TGTGTTTTCT TCAAAAACAT CAGTCTGAAA 2400
2401 CGGCTTTAAA AAATGTCTTC ACTGCCTTAA GGTCCTTAAT TTATAAGTTT CCCTCAACAT TCTATGAAGG GAGAGCGGAC 2480
2481 ATGTGTGCGG CTCTGTGTTA CGAGATTCTC AAGTGCTGTA ACTCAAGCT GAGCTCCATC AGGACGGAGG CCTCCCAGCT 2560
2561 GCTCTACTTC CTGATGAGGA ACAACTTTGA TTACACTGGA AAGAAGTCCT TTGTCCGGAC ACATTTGCAA GTCATCATAT 2640
2641 CTGTCAGCCA GCTGATAGCA GACGTTGTTG GCATTGGGGA AACCAGATTC CAGCAGTCCC TGTCCATCAT CAACAACTGT 2720
2721 GCCAACAGTG ACCGGCTTAT TAAGCACACC AGCTTCTCCT CTGATGTGAA GGACTTAACC AAAAGGATAC GCACGGTGCT 2800
2801 AATGGCCACC GCCCAAGCCA AGGAGCATGA GAACGACCCA GATGTGTGG TGGACCTCCA GTACAGCCTG GCCAAATCCT 2880
2881 ATGCCAGCAC GCCCGAGCTC AGGAAGACGT GGCTCGACAG CATGGCCAGG ATCCATGTCA AAAATGGCGA TCTCTCAGAG 2960
2961 GCAGCAATGT GCTATGTCCA CGTAACAGCC CTAGTGGCAG AATATCTCAC ACGGAAAGGC GTGTTTAGAC AAGGATGCAC 3040
3041 CGCCTTCAGG GTCATTACCC CAAACATCGA CAGGAGGCC TCCATGATGG AAGACGTGGG GATGCAGGAT GTCCATTTCA 3120
3121 ACGAGGATGT GCTGATGGAG CTCCTTGAGC AGTGCGCAGA TGGACTCTGA AAAGCGAGC GCTACGAGCT CATGCCGAC 3200
3201 ATCTACAAAC TTATCATCCC CATTTATGAG AAGCGGAGGG ATTTCTTTGA AGATAGAAGAT GGAAAGGAGT ATATTTACAA 3280
3281 GGAACCCAAA CTCACACCGC TGTCGGAAAT TTCTCAGAGA CTCCTTAAAC TGTACTCGGA TAAATTTGGT TCTGAAAATG 3360
3361 TCAAAATGAT ACAGGATTCT GGCAAGGTCA ACCCTAAGGA TCTGGATTCT AAGTATGCAT ACATCCAGGT GACTCACGTC 3440
3441 ATCCCCTTCT TTGACGAAAA AGAGTTGCAA GAAAGGAAAA CAGAGTTTGA GAGATCCCCA AACATCCGCC GCTTCATGTT 3520
3521 TGAGATGCCA TTTACGCAGA CCGGGAAGAG GCAGGGCGGG GTGGAAGAGC AGTGCAAACG GCGCACCATC CTGACAGCCA 3600
3601 TACACTGCTT CCCTTATGTG AAGAAGCGCA TCCCTGTCAT GTACCACAC CACACTGACC TGAACCCCAT GGGTGGCC 3680
3681 ATTGACGAGA TGAGTAAGAA GGTGGCGGAG CTCCGGCAGC TGTGCTCCTC GGCCGAGGTG GACATGATCA AACTGCAGCT 3760
3761 CAAACTCCAG GGCAGCGTGA GTTCAGGT CAATGCTGGC CCACTAGCAT ATGCGCAGC TTTCTTAGAT GATACAAACA 3840
3841 CAAAGCCGATA TCCTGACAAT AAAGTGAAGC TGCTTAAGGA AGTTCAGG CAATTTTGCG GGCAAAAAA AGGTTCTGGG 3920
3921 GCGGTAAACG AACGTCTGAT TAAAGAAGAC CAGCTCGAGT ATCAGGAAGA AATGAAAGCC AACTACAGG AAATGGCGAA 4000
4001 GGAGCTTTCT GAAATCATGC ATGAGCAGAT CTGCCCCCTG GAGGAGAAGA CGAGCGTCTT ACCGAATTCC CTTCACATCT 4080
4081 TCAACGCCAT CAGTGGGACT CCAACAAGCA CAATGGTTCA CGGGATGACC AGCTCGTCTT CGGTCGTGTG ATTACATCTC 4160
4161 ATGGCCCGTG TGTGGGGACT TGCTTTGTCA TTTGCAAACT CAGGATGCTT TCCAAAGCCA ATCACTGGGG AGACCGAGCA 4240
4241 CAGGGAGGAC CAAGGGGAAG GGGAGAGAAA GGAAATAAAG AACAACGTTA TTTCTTAACA GACTTTCTAT AGGAGTTGTA 4320
4321 AGAAGGTGCA CATATTTTTT TAAATCTCAC TGGCAATATT CAAAGTTTTC ATTGTGTCTT AACAAAGGTG TGGTAGACAC 4400
4401 TCTTGAGCTG GACTTAGATT TTATTCTTCC TTGCAGAGTA GTGTTAGAAT AGATGGCCTA CAGAAAAAA AGGTTCTGGG 4480
4481 ATCTACATGG CAGGGAGGGC TGCACTGACA TTGATGCCTG GGGGACCTTT TGCCTCGACT CGTGCCGGAA ATCTGATCGT 4560
4561 AATCAGGGTA CAGAACTTAC TAGTTTTGTC TAGGAGTATG TTGTATGACT AGGATTGTG CTATTATCTC ATTCAACAAC 4640
4641 ATAGAGCAAG AATAGTGAGC TAACTGAGCT AGACACTCAA TTAATCCGCT ACTGCTTCA AGTCAGAACT TTGTCATTAA 4720
4721 TCATCGACTC CGGGACGGTC ATATATGTAT TACATTTCTA CATTTTAAT ACTCACATGG GCTTATGCAT TAAGTTTAAT 4800
4801 TGTGATAAAT TTGTGCTGGT CCAGTATATG CAATACACTT TAATGGTTTA TTCTTGTCAT AAAAATGTGC AATATGGAGA 4880
4881 TGTATACAAG TCTTTACT                                                                    4898
         |   10        |   20        |   30        |   40        |   50        |   60        |   70        |   80
```

FIG.10G

```
         |   10       |   20       |   30       |   40       |   50       |   60       |   70       |   80
   1 MEGHVMIAFL PTILNQLFRV LTRATQEEVA VNVTRVIIHV VAQCHEEGLE SHLRSYVKYA YKAEPYVASE YKTVHEELTK  80
  81 SMTTILKPSA DFLTSNKLLR YSWFFFDVLI KSMAQHLIEN SKVKLLRNQR FPASYHHAAE TVVNMLMPHI TQKFGDNPEA 160
 161 SKNANHSLAV FIKRCFTFMD RGFVFKQINN YISCFAPGDP KTLFEYKFEF LRVVCNHEHY IPLNLPMPFG KGRIQRYQDL 240
 241 QLDYSLTDEF CRNHFLVGLL LREVGTALQE FREVRLIAIS VLKNLLIKHS FDDRYASRSH QARIATLYLP LFGLLIENVQ 320
 321 RINVRDVSPF PVNAGMTVKD ESLALPAVNP LVTPQKGSTL DNSLHKDLLG AISGIASPYT TSTPNINSVR NADSRGSLIS 400
 401 TDSGNSLPER NSEKSNSLDK HQQSSTLGNS VVRCDKLDQS EIKSLLMCFL YILKSMSDDA LFTYWNKAST SEIMDFFTIS 480
 481 EVCLHQFQYM GKRYIARNQE GLGPIVHDRK SQTLPVSRNR TGMMHARIQQ LGSLDNSLTF NHSYGHSDAD VLHQSLLEAN 560
 561 IATEVCLTAL DTLSLFTLAF KNQLLADHGH NPLMKKVFDV YLCFLQKHQS ETALKNVFTA LRSLIYKFPS TFYEGRADMC 640
 641 AALCYEILKC CNSKLSSIRT EASQLLYFLM RNNFDYTGKK SFVRTHLQVI ISVSQLIADV VGIGETRFQQ SLSIINNCAN 720
 721 SDRLIKHTSF SSDVKDLTKR IRTVLMATAQ MKEHENDPEM LVDLQYSLAK SYASTPELRK TWLDSMARIH VKNGDLSEAA 800
 801 MCYVHVTALV AEYLTRKGVF RQGCTAFRVI TPNIDEEASM MEDVGMQDVH FNEDVLMELL EQCADGLWKA ERYELIADIY 880
 881 KLIIPIYEKR RDFFEDEDGK EYIYKEPKLT PLSEISQRLL KLYSDKFGSE NVKMIQDSGK VNPKDLDSKY AYIQVTHVIP 960
 961 FFDEKELQER KTEFERSHNI RRFMFEMPFT QTGKRQGGVE EQCKRRTILT AIHCFPYVKK RIPVMYQHHT DLNPIEVAID 1040
1041 EMSKKVAELR QLCSSAEVDM IKLQLKLQGS VSVQVNAGPL AYARAPLDDT NTKRYPDNKV KLLKEVFRQF VEACGQALAV 1120
1121 NERLIKEDQL EYQEEMKANY REMAKELSEI MHEQICPLEE KTSVLPNSLH IFNAISGTPT STMVHGMTSS SSVV        1195
         |   10       |   20       |   30       |   40       |   50       |   60       |   70       |   80
```

FIG. 10G (cont.)

```
         |   10        |   20        |   30        |   40         |   50        |   60        |   70        |   80
    1 AATTGTAATA CGACTCACTA TAGGGCGAAT TGGGTACCGG GCCCCCCCTC GAGGTCGACG GTATCGATAA GCTTGATATC   80
   81 GAATTCGGCA CGAGTTTTAC ACCATCACCA AAACCCAGAA TTTTATGATG AGATTAAAAT AGAGTTGCCC ACTCAGCTGC  160
  161 ATGAAAGCA CCACCTGTTG CTCACATTCT TCCATGTCAG CTGTGACAAC TCAAGTAAAG GAAGCACGAA GAAGAGGGAT  240
  241 GTCGTTGAAA CCCAAGTTGG CTACTCCTGG CTTCCCCTCC TGAAAGACGG AAGGGTGGTG ACAAGCGAGC AGCACATCCC  320
  321 GGTCTCGGCG AACCTTCCTT CGGGCTATCT TGGCTACCAA GAGCTTGGGA TGGGCAGGCA TTATGGTCCG GAAATTAAAT  400
  401 GGGTAGATGG AGGCAAGCCA CTGCTGAAAA TTTCCACTCA TCTGGTTTCT ACAGGGATAC TCAGGATCAG CATTTACATA  480
  481 ATTTTTTCCA GTACTGTCAG AAAACCGAAT CTGGAGCCCA AGCCTTAGGA AACGAACTTG TAAAGTACCT TAAGAGTCTG  560
  561 CATGCCGATGG AAGGCCACGT GATGATCGCC TTCTTGCCCA CTATCCTAAA CCAGCTGTTC CGAGTCCTCA CCAGAGCCAC  640
  641 ACAGGAAGAA GTCGCGGTTA ACGTGACTCG GGTCATTATT CATGTGGTTG CCCAGTGCCA TGAGGAAGGA TTGGAGAGCC  720
  721 ACTTGAGGTC ATATGTTAAG TACGCGTATA AGGCTGAGCC ATATGTTGCC TCTGAATACA AGACAGTGCA TGAAGAACTG  800
  801 ACCAAATCCA TGACCACGAT TCTCAAGCCT TCTGCCGATT TCCTCACCAG CAACAAACTA CTGAGGTACT CATGGTTTTT  880
  881 CTTTGATGTA CTGATCAAAT CTATGGCTCA GCATTTGATA GAGAACTCCA AAGTTAAGTT GCTGCGAAAC CAGAGATTTC  960
  961 CTGCATCCTA TCATCATGCA GCGGAAACCG TTGTAAATAT GCTGATGCCA CACATCACTC AGAAGTTTGG AGATAATCCA 1040
 1041 GAGGCATCTA AGAACGCGAA TCATAGCCTT GCTGTCTTCA TCAAGAGATG TTTCACCTTC ATGGACAGGG GCTTTGTCTT 1120
 1121 CAAGCAGATC AACAACTACA TTAGCTGTTT TGCTCCTGGA GACCCAAAGA CCCTCTTTGA ATACAAGTTT GAATTTCTCC 1200
 1201 GTGTAGTGTG CAACCATGAA CATTATATTC CGTTGAACTT ACCAATGCCA TTTGGAAAAG GCAGGATTCA AAGATACCAA 1280
 1281 GACCTCCAGC TTGACTACTC ATTAACAGAT GAGTTCTGCA GAAACCACTT CTTGGTGGGA CTGTTACTGA GGGAGGTGGG 1360
 1361 GACAGCCCTC CAGGAGTTCC GGGAGGTCCG TCTGATCGCC ATCAGTGTGC TCAAGAACCT GCTGATAAAG CATTCTTTTG 1440
 1441 ATGACAGATA TGCTTCAAGG AGCCATCAGG CAAGGATAGC CACCCTCTAC CTGCCTCTGT TTGGTCTGCT GATTGAAAAC 1520
 1521 GTCCAGCGGA TCAATGTGAG GGATGTGTCA CCCTTCCCTG TGAACGCGGG CATGACCGTG AAGGATGAAT CCCTGCCTCT 1600
 1601 ACCAGCTGTG AATCCGCTGG TGACGCCGCA GAAGGGAAGC ACCCTGGACA ACAGCCTGCA CAAGGACCTG CTGGGCGCCA 1680
 1681 TCTCCGGCAT TGCTTCTCCA TATACAACCT CAACTCCAAA CATCAACATC GTGAGAAATG CTGATTCGAG AGGATCTCTC 1760
 1761 ATAAGCACAG ATTCGGGTAA CAGCCTTCCA GAAAGGAATA GTGAGAAGAG CAATTCCCTG GATAAGCACC AACAAAGTAG 1840
 1841 CACATTGGGA AATTCCGTGG TTCGCTGTGA TAAACTTGAC CAGTCTGAGA TTAAGAGCCT ACTGATGTGT TTCCTCTACA 1920
 1921 TCTTAAAGAG CATGTCTGAT GATGCTTTGT TTACATATTG GAACAAGGCT TCAACATCTG AACTTATGGA TTTTTTTACA 2000
 2001 ATATCTGAAG TCTGCCTGCA CCAGTTCCAG TACATGGGGA AGCGATACAT AGCCAGGAAC CAGGAGGGGT TGGGACCCAT 2080
 2081 AGTTCATGAT CGAAAGCTCT AGACATTGCC TGTTTCCCGT AACAGAACAG GAATGATGCA TGCCAGATTG CAGCAGCTGG 2160
 2161 GCAGCCTGGA TAACTCTCTC ACTTTTAACC ACAGCTATGG CCACTCGGAC GCAGATGTTC TGCACCAGTC ATTACTTGAA 2240
 2241 GCCAACATTG CTACTGAGGT TTGCCTGACA GCTCTGGACA CGCTTTCTCT ATTTACATTG GCGTTTAAGA ACCAGCTCCT 2320
 2321 GGCCGACCAT GGACATAATC CTCTCATGAA AAAGTTTTT GATGCTACC TGTGTTTTCT TCAAAAACAT CAGTCTGAAA 2400
 2401 CGGCTTTAAA AAATGTCTTC ACTGCCTTAA GGTCCTTAAT TTATAAGTTT CCCTCAACAT TCTATGAAGG GAGAGCGGAC 2480
 2481 ATGTGTGCGG CTCTGTGTTA CGAGATTCTC AAGTGCTGTA ACTCCAAGCT GAGCTCCATC AGGACGGAGG CCTCCCAGCT 2560
 2561 GCTCTACTTC CTGATGAGGA ACAACTTTGA TTACACTGGA AAGAAGTCCT TTGTCCGGAC ACATTTGGAT GTCATCATAT 2640
 2641 CTGTCAGCCA GCTGATAGCA GACGTTGTTG GCATTGGGGA AACCAGATTC CAGCAGTCCC TGTCCATCAT CAACAACTGT 2720
 2721 GCCAACAGTG ACCGGCTTAT TAAGCACACC AGCTTCTCCT CTGATGTGAA GGACTTAACC AAAAGGATAC GCACGGTGCT 2800
 2801 AATGGCCACC GCCAGATGA AGGAGCATGA GAACGACCCA GGATGCTGG TGGACCTCCA GTACAGCCTG GCCAAATCCT 2880
 2881 ATGCCAGCAC GCCCGAGCTC AGGAAGACGT GGCTCGACAG CATGGCCAGG ATCCATGTCA AAAATGGCGA TCTCTCAGAG 2960
 2961 GCAGCAATGT GCTATGTCCA CGTAACAGCC CTAGTGGCAG AATATCTCAC ACGGAAAGGC GTGTTTAGAC AAGGATGCAC 3040
 3041 CGCCTTCAGG GTCATTACCC CAAACATCGA CGAGGAGGCC TCCATGATGG AAGACGTGGG GATGCAGGAT GTCGATTTCA 3120
 3121 ACGAGGATGT GCTGATGGAG CTCCTTGAGC AGTGCGCAGA TGGACTCTGG AAAGCCGAGC GCTACGAGCT CATCGCCGAC 3200
 3201 ATCTACAAAC TTATCATCCC CATTTATGAG AAGCGGAGGG ATTTCTTTGA AGATGAAGAT GGAAAGGAGT ATATTTACAA 3280
 3281 GGAACCCAAA CTCACACCGC TGTCGGAAAT TTCTCAGAAA CTCCTTAAAC TGTACTCGGA TAAATTTGGT TCTGAAAATG 3360
 3361 TCAAAATGAT ACAGGATTCT GGCAAGGTCA ACCCTAAGGA TCTGGATTCT AAGTATGCAT ACATCCAGGT GACTCACGTC 3440
 3441 ATCCCCTTCT TTGACGAAAA AGAGTTGCAA GAAAGGAAAA CAGAGTTTGA GGAGATCCCAC AACATCGCCC GCTTCATGTT 3520
 3521 TGAGATGCCA TTTACGCAGA CCGGGAAGAG GCAGGCGGG GTGGAAGAGC AGTGCAAACG GCGCACCATC CTGACAGCCA 3600
 3601 TACACTGCTT CCCTTATGTG AAGAAGCGCA TCCCTGTCAT GTACCAGCAC CACACTGACC TGAACCCCAC CGAGGTGGCC 3680
 3681 ATTGACAGCA TGAGTAAGAA GGTGGCGAG CTCCGGCAGC TGTGCTCCTC GGGCCAGGTG GACATGATCA AACTGCAGCT 3760
 3761 CAAACTCCAG GGCAGCGTGA GTGTTCAGGT CAATGCTGGC CCACTAGCAT ATGCGGAGC TTTCTTAGAT GATACAAACA 3840
 3841 CAAAGCGATA TCCTGACAAT AAAGTGAAGC TGCTTAAGGA AGTTTTCAGG CAATTTGTGG AAGCTTGCGG TCAAGCCTTA 3920
 3921 GCGGTAAACG AACGTCGAT TAAAGAAGAC CAGCTCGAGT CAGGAGAA AATGAAAGCC AACTACAGGG AAATGGCGAA 4000
 4001 GGAGCTTTCT GAAATCATGC ATGAGCAGAT CTGCCCCCTG GAGGAGAAGA CGAGCGTCTT ACCGAATTCC CTTCACATCT 4080
 4081 TCAACGCCAT CAGTGGGACT CCAACAAGCA CAATGGTTCA CGGGATGACC AGCTCGTCTT CGGTCGTGTG ATTACATCTC 4160
 4161 ATGGCCCGTG TGTGGGGACT TGCTTTGTCA TTTGCAAACT CAGGATGCTT TCCAAAGCCA ATCACTGGGG AGACCGAGCA 4240
 4241 CAGGGAGGAC CAAGGGGAAG GGGAGAGAAA GGAAATAAAG AACAACGTTA TTTCTTAACA GACTTTCTAT AGGAGTTGTA 4320
 4321 AGAAGGTGCA CATATTTTTT TAAATCTCAC TGGCAATATT CAAAGTTTTC ATTGTGTCTT AACAAAGGTG TGGTAGACAC 4400
 4401 TCTTGAGCTG GACTTAGATT TTATTCTTCC TTGCAGAGTA GTGTTAGAAT AGATGGCCTA CAGAAAAAAA ACGTTCTGGG 4480
 4481 ATCTACATGT CAGGGAGGGC TGCACTGACA TTGATGCCTG GGGGACCTTT TGCCTCGACT CGTGCCGGAA ATCTGATCGT 4560
 4561 AATCAGGGTA CAGAACTTAC TAGTTTTGTC TAGGAGTATG TTGTATGACT AGGATTTGTG CTATTATCTC ATTCAACAAC 4640
 4641 ATAGAGCAAG AATAGTGAGC TAACTGAGCT AGACACTCAA TTAATCCGCT ACTGGCTTCA AGTCAGAACT TGTCATTAA 4720
 4721 TCATCGACTC CGGGACGGTC ATATATGTAT TACATTTCTA CATTTTTAAT ACTCACATGG GCTTATGCAT TAAGTTTAAT 4800
 4801 TGTGATAAAT TTGTGCTGGT CCAGTATATG CAATACACTT TAATGGTTTA TTCTTGTCAT AAAAATGTGC AATATGGAGA 4880
 4881 TGTATACAAG TCTTTACT                                                                     4898
         |   10        |   20        |   30        |   40         |   50        |   60        |   70        |   80
```

FIG.10H

```
        |    10      |    20      |    30      |    40      |    50      |    60      |    70      |    80
     1  MEGHVMIAFL  PTIINQLFRV  LTRATQEEVA  VNVTRVIIHV  VAQCHEEGLE  SHLRSYVKYA  YKAEPYVASE  YKTVHEELTK    80
    81  SMTTILKPSA  DFLTSNKLLR  YSWFFFDVLI  KSMAQHLIEN  SKVKLLRNQR  FPASYHHAAE  TVVNMLMPHI  TQKFGDNPEA   160
   161  SKNANHSLAV  FIKRCFTFMD  RGFVFKQINN  YISCFAPGDP  KTLFEYKFEF  LRVVCNHEHY  IPLNLPMPFG  KGRIQRYQDL   240
   241  QLDYSLTDEF  CRNHFLVGLL  LREVGTALQE  FREVRLIAIS  VLKNLLIKHS  FDDRYASRSH  QARIATLYLP  LFGLLIENVQ   320
   321  RINVRDVSPF  PVNAGMTVKD  ESLALPAVNP  LVTPQKGSTL  DNSLHKDLLG  AISGIASPYT  TSTPNINSVR  NADSRGSLIS   400
   401  TDSGNSLPER  NSEKSNSLDK  HQQSSTLGNS  VVRCDKLDQS  EIKSLLMCFL  YILKSMSDDA  LFTYWNKAST  SELMDFFTIS   480
   481  EVCLHQFQYM  GKRYIARNQE  GLGPIVHDRK  SQTLPVSRNR  TGMMHARLQQ  LGSLDNSLTF  NHSYGHSDAD  VLHQSLLEAN   560
   561  IATEVCLTAL  DTLSLFTLAF  KNQLLADHGH  NPLMKKVFDV  YLCFLQKHQS  ETALKNVFTA  LRSLIYKFPS  TFYEGRADMC   640
   641  AALCYEILKC  CNSKLSSIRT  EASQLLYFLM  RNNFDYTGKK  SFVRTHLQVI  ISVSQLIADV  VGIGETRFQQ  SLSIINNCAN   720
   721  SDRLIKHTSF  SSDVKDLTKR  IRTVLMATAQ  MKEHENDPEM  LVDLQYSLAK  SYASTPELRK  TWLDSMARIH  VKNGDLSEAA   800
   801  MCYVHVTALV  AEYLTRKGVF  RQGCTAFRVI  TPNIDEEASM  MEDVGMQDVH  FNEDVLMELL  EQCADGLWKA  ERYELIADIY   880
   881  KLIIPIYEKR  RDFFEDEDGK  EYIYKEPKLT  PLSEISQRLL  KLYSDKFGSE  NVKMIQDSGK  VNPKDLDSKY  AYIQVTHVIP   960
   961  FFDEKELQER  KTEFERSHNI  RRFMFEMPFT  QTGKRQGGVE  EQCKRRTILT  AIHCFPYVKK  RIPVMYQHHT  DLNPIEVAID  1040
  1041  EMSKKVAELR  QLCSSAEVDM  IKLQLKLQGS  VSVQVNAGPL  AYARAFLDDT  NTKRYPDNKV  KLLKEVFRQF  VEACGQALAV  1120
  1121  NERLIKEDQL  EYQEEMKANY  REMAKELSEI  MHEQICPLEE  KTSVLPNSLH  IFNAISGTPT  STMVHGMTSS  SSVV        1195
        |    10      |    20      |    30      |    40      |    50      |    60      |    70      |    80
```

FIG. 10H (cont.)

Human CLASP-2 expression in T cells upon activation

NUCLEIC ACID MOLECULE ENCODING A CLASP-2 TRANSMEMBRANE PROTEIN

0.0 CROSS-REFERENCES TO RELATED APPLICATIONS

This application: a) is a CIP of U.S. Non-Provisional application Ser. No. 09/687,837, filed Oct. 13, 2000, which application claims benefit of U.S. Non-Provisional application Ser. No. 09/547,276, which application claims benefit of U.S. Provisional Application No. 60/182,296, filed Feb. 14, 2000, U.S. Provisional Application No. 60/176,195, filed Jan. 14, 2000, U.S. Provisional Application No. 60/170,453, filed Dec. 13, 1999, U.S. Provisional Application No. 60/162,498, filed Oct. 29, 1999, and U.S. Provisional Application No. 60/160,860, filed Oct. 21, 1999; b) is a CIP of U.S. Non-Provisional application Ser. No. 09/978,244, filed Oct. 15, 2001, which application claims priority to U.S. Provisional Application No. 60/310,028, filed Aug. 3, 2001, and U.S. Provisional Application 60/240,545, filed Oct. 13, 2000; c) is a CIP of U.S. Non-Provisional application Ser. No. 09/737, 246, Filed Dec. 13, 2000, which application claims benefit of U.S. Provisional Application No. 60/196,267, filed Apr. 11, 2000; d) is a CIP of U.S. Non-Provisional application Ser. No. 09/737,246, Filed Dec. 13, 2000, which application claims benefit of U.S. Provisional Application No. 60/196,267, filed Apr. 11, 2000; e) is a CIP of U.S. Non-Provisional application Ser. No. 09/736,969, Filed Dec. 13, 2000, which application claims benefit of U.S. Provisional Application No. 60/196, 527, filed Apr. 11, 2000; f) is a CIP of U.S. Non-Provisional application Ser. No. 09/736,960, Filed Dec. 13, 2000, which application claims benefit of U.S. Provisional Application No. 60/196,528, filed Apr. 11, 2000; g) is a CIP of U.S. Non-Provisional application Ser. No. 09/736,968, Filed Dec. 13, 2000, which application claims benefit of U.S. Provisional Application No. 60/196,460, filed Apr. 11, 2000.

ACKNOWLEDGEMENT OF GOVERNMENT SUPPORT

This invention was made with Government support under Small Business Innovation Research Grant No. 1 R43 AI45724-01A2, awarded by the National Institute of Allergy and Infectious Disease. The Government may have certain rights in this invention.

1.0 FIELD OF THE INVENTION

The present invention relates to molecules expressed in cells of the immune system. In particular, the invention relates to a transmembrane protein that contains certain classical cadherin characteristics.

2.0 BACKGROUND OF THE INVENTION

The generation of an immune response against an antigen is carried out by a number of distinct immune cell types that work in concert within the context of a particular antigen. The helper T cell ($T_H$) plays a pivotal role to coordinate two types of antigen-specific immune response; i.e., cellular and humoral immune response. Recognition of antigen by T cells requires the formation of a specialized junction between the T cell and the antigen-presenting cell (APC) called the "immunological synapse" (Dustin, et al., 1998, Cell 94: 667-677). The immune synapse orchestrates recruitment and exclusion of specific proteins from the contact area by an unknown mechanism and is thought to be initiated by T-cell antigen receptor (TCR) recognition of peptides bound to MHC molecules (antigen) (Monk, et al. 1998, Nature 395: 82). However, the low affinity of the TCR for antigen as well as limited number of ligands makes it unlikely that TCR: antigen interaction alone is sufficient to drive the formation of the immunological synapse (Matsui et al., 1994, Proc. Natl. Acad. Sci. U.S.A. 91: 12861-12866).

Costimulatory molecules such as CD4, ICAM-1, LFA-1, CD28, CD2 have been proposed to stabilize the cell-cell contact (Dustin, et al., 1999, Science 283: 649). However, since these molecules are recruited to the synapse after activation they cannot account for the high specificity and avidity during the early phases of T-cell antigen recognition. Recent work demonstrated that a portion of the T cell surface at the leading edge is specialized to mediate the early phases of synapse formation (Negulescu, et al., 1996, Immunity 4: 421-430). Such a specialization must be a pre-formed structure containing cell surface adhesion proteins (ectodomains) to augment TCR engagement and corresponding cytoplasmic portions (endodomains) to transduce signals and bind cytoskeleton to maintain structural/functional polarity.

The ectodomain of the pre-formed synapse or "immune gateway" was recently discovered and is created in part by CLASP-1 (U.S. Ser. No. 09/411,328, filed Oct. 1, 1999(abandoned); WO00/20434). In addition to cadherin motifs, CLASP-1 also contains a CRK-SH3 binding domain, tyrosine phosphorylation sites, and coiled/coil domains suggesting direct interaction with cytoskeleton and regulation by adaptor molecules such as CRK. The CLASP-1 transcript is present in lymphoid organs and neural tissue, and the protein is expressed by T and B lymphocytes and macrophages in the MOMA-1 subregion of the marginal zone of the spleen, an area known to be important in T: B cell interaction. CLASP-1 staining of individual T and B cells exhibits a preactivation structural polarity, being organized as a "ball" or "cap" structure in B cells, and forming a "ring", "ball" or "cap" structure in T cells. The placement of these structures is adjacent to the microtubule-organizing center ("MTOC"). CLASP-1 antibody staining indicates that CLASP-1 is at the interface of T-B cell conjugates that are fully committed to differentiation. Antibodies to the extracellular domain of CLASP-1 also block T-B cell conjugate formation and T cell activation.

3.0 SUMMARY OF THE INVENTION

The present invention relates to a cell surface molecule, a member of a new multigene family designated cadherin-like asymmetry protein(s) ("CLASP(s)"). In particular, it relates to a polynucleotides comprising a coding sequences for CLASPs, polynucleotides that selectively hybridize to the complement of a CLASP coding sequence, expression vectors containing such polynucleotides, genetically-engineered host cells containing such polynucleotides, CLASP polypeptides, CLASP fusion proteins, therapeutic compositions, CLASP domain mutants, antibodies specific for CLASP polypeptides, methods for detecting the expression of CLASP, and methods of inhibiting an immune response by interfering with CLASP function. A wide variety of uses are encompassed by the invention, including but not limited to, treatment of autoimmune diseases and hypersensitivities, prevention of transplantation rejection responses, and augmentation of immune responsiveness in immunodeficiency states.

The invention therefore relates to methods and compositions relating to CLASP polynucleotides and polypeptides (i.e., full length human or mouse CLASP 1-6 polynucleotides or polypeptides of fragments thereof.

In one aspect, the invention provides an isolated CLASP-2 polynucleotide that is: (a) a polynucleotide that has the sequence of SEQ ID NO: 1, 3, 5 or 9; (b) a polynucleotide that hybridizes under stringent hybridization conditions to (a) and encodes a polypeptide having the sequence of SEQ ID NO: 2, 4, 6 or 10 or an allelic variant or homologue of a polypeptide having the sequence of SEQ ID NO: 2, 4, 6 or 10; or (c) a polynucleotide that hybridizes under stringent hybridization conditions to (a) and encodes a polypeptide with at least 25 contiguous residues of the polypeptide of SEQ ID NO: 2, 4, 6 or 10; or (d) a polynucleotide that hybridizes under stringent hybridization conditions to (a) and has at least 12 contiguous bases identical to or exactly complementary to SEQ ID NO: 1, 3, 5, or 9. In a related aspect, the invention provides a CLASP-2 polynucleotide wherein the polynucleotide encodes a polypeptide that binds to the PDZ domain of PSD95, DLG1 or neDLG. In another related aspect, the invention provides a CLASP-2 polynucleotide wherein the polynucleotide encodes a polypeptide that has a binding affinity of at least $10^4$ $M^{-1}$ for binding PSD95, DLG1 or neDLG.

In one aspect, the invention provides a CLASP-2 polynucleotide that encodes a polypeptide having the full-length sequence of SEQ ID NO: 2, 4, 6, or 10 or the cDNA sequence encoded by the inserts of ATCC Deposit Nos: PTA-1562, PTA-1563 and PTA-1573.

In another aspect, the invention provides a CLASP-2 polynucleotide that encodes a polypeptide having the full-length sequence of Isoform 1, Isoform 2, or Isoform 3 or the cDNA sequence encoded by the inserts of AVC-PD14 (ATCC Deposit No. PTA-2611) and AVC-PD19 (ATCC Deposit No. PTA-2614).

In another aspect, the invention further provides an isolated CLASP-2 polynucleotide comprising a nucleotide sequence that has at least 90% percent identity to SEQ ID NO: 1, 3, 5 or 9 as calculated using FASTA wherein said sequences are aligned so that highest order match between said sequences is obtained.

The invention further provides an isolated polypeptide comprising a nucleotide sequence that has at least 90% sequence identity to SEQ ID NO: 2, 4, 6 or 10 and is immunologically crossreactive with SEQ ID NO: 2, 4, 6 or 10 or shares a biological function with native CLASP-2.

The invention also provides vectors, such as expression vectors, comprising a polynucleotide sequence of the invention. In other embodiments, the invention provides host cells or progeny of the host cells comprising a vector of the invention. In certain embodiments, the host cell is a eukaryote. In other embodiments, the expression vector comprises a CLASP polynucleotide in which the nucleotide sequence of the polynucleotide is operatively linked with a regulatory sequence that controls expression of the polynucleotide in a host cell. In certain embodiments, the invention provides a host cell comprising a CLASP polynucleotide, wherein the nucleotide sequence of the polynucleotide is operatively linked with a regulatory sequence that controls expression of the polynucleotide in a host cell, or progeny of the cell.

In another aspect, the invention further provides a CLASP-2 polynucleotide that is an antisense polynucleotide. In a preferred embodiment, the antisense polynucleotide is less than about 200 bases in length. In other embodiments, the invention provides an antisense oligonucleotide complementary to a messenger RNA comprising SEQ ID NO: 1, 3, 5 or 9 and encoding CLASP-2, wherein the oligonucleotide inhibits the expression of CLASP-2.

In another aspect, the invention provides an isolated DNA that encodes a CLASP-2 protein as shown in SEQ ID NO: 2, 4, 6 or 10. In certain embodiments, the CLASP-2 polynucleotide is RNA.

The invention provides a method for producing a polypeptide comprising: (a) culturing the host cell containing a CLASP-2 polynucleotide under conditions such that the polypeptide is expressed; and (b) recovering the polypeptide from the cultured host cell or its cultured medium.

The invention further provides an isolated CLASP-2 polypeptide encoded by a CLASP-2 polynucleotide. In some embodiments, the CLASP-2 polypeptide has the amino acid sequence of SEQ ID NO: 2, 4, 6 or 10, or a fragment thereof. In some embodiments, the isolated CLASP-2 polypeptide is cell-membrane associated. In other embodiments, the isolated CLASP-2 polypeptide is soluble. In other embodiments, the soluble CLASP-2 polypeptide is fused with a heterologous polypeptide.

The invention further provides an isolated CLASP-2 protein having the sequence as shown in SEQ ID NO: 2, 4, 6 or 10. In some embodiments, the invention provides a CLASP-2 protein comprising the sequence as shown in SEQ. ID. NO: 1 and variants thereof that are at least 95% identical to SEQ ID. NO: 2 and specifically binds a cytoskeletal protein. In certain embodiments the cytoskeletal protein is spectrin.

The invention further provides an isolated antibody that specifically binds to a polypeptide having the amino acid sequence as shown in SEQ ID NO: 2, 4, 6 or 10, or a binding fragment thereof. In some embodiments the antibody is monoclonal. In other embodiments, the invention provides a hybridoma capable of secreting the antibody.

The invention further provides a method of identifying a compound or agent that binds a CLASP-2 polypeptide comprising: i) contacting a CLASP-2 polypeptide with the compound or agent under conditions which allow binding of the compound to the CLASP-2 polypeptide to form a complex and ii) detecting the presence of the complex.

The invention further provides a method of detecting a CLASP-2 polypeptide in a sample, comprising: (a) contacting the sample with a CLASP-2 antibody or binding fragment and (b) determining whether a complex has been formed between the antibody and with CLASP-2 polypeptide.

The invention further provides a method of detecting a CLASP-2 polypeptide in a sample, comprising: (a) contacting the sample with a CLASP-2 polynucleotide or a polynucleotide that comprises a sequence of at least 12 nucleotides and is complementary to a contiguous sequence of the CLASP-2 polynucleotide and (b) determining whether a hybridization complex has been formed.

The invention further provides a method of detecting a CLASP-2 nucleotide in a sample, comprising: (a) using a polynucleotide that comprises a sequence of at least 12 nucleotides and is complementary to a contiguous sequence of a CLASP-2 polynucleotide in an amplification process; and (b) determining whether a specific amplification product has been formed.

The invention further provides pharmaceutical compositions comprising a CLASP-2 polynucleotide, a CLASP-2 polypeptide, or a CLASP-2 antibody and a pharmaceutically acceptable carrier.

In one aspect, the invention provides a method of inhibiting an immune response in a cell comprising: (a) interfering with the expression of a CLASP-2 gene in the cell; (b) interfering with the ability of a CLASP-2 protein to mediate cell-cell interaction (e.g., interfering with a heterotypic and/or homotypic interaction) between CLASP-2 and an extracellular protein; (c) interfering with the ability of a CLASP-2 protein to bind to another protein. In some such methods, the cell is a T cell or a B cell. Some such methods comprise contacting the cell with an effective amount of a polypeptide which comprises the amino acid sequence of SEQ ID NO: 2, 4, 6 or 10 or a fragment thereof.

In another aspect, the invention provides a method of inhibiting an immune response in a subject, comprising administering to the subject a therapeutically effective amount of an antibody which specifically binds a polypeptide having the sequence of SEQ ID NO: 2, 4, 6 or 10.

In another aspect, the invention provides a method of preventing or treating a CLASP-2-mediated disease comprising administering to a subject in need thereof a therapeutically effective amount of a CLASP-2 pharmaceutical composition. In some such methods, the CLASP-2-mediated disease is an autoimmune disease.

The invention further provides a method of treating an autoimmune disease in a subject caused or exacerbated by increased activity of $T_H1$ cells consisting of administering a therapeutically effective amount of a CLASP-2 pharmaceutical composition to the subject.

BRIEF DESCRIPTION OF THE DRAWINGS

FIG. 1. Nucleotide and predicted amino acid sequence of CLASP-2A cDNA. Notable protein motifs are indicated above the nucleotide sequence in bold. Potential initiator methionines are underscored. The notable, predicted protein motifs are: a cadherin cleavage site encoded by nucleotides 854-868, a cadherin ectodomain (EC) encoded by nucleotides 1253-1264, a transmembrane domain encoded by nucleotides 2861-2917, a coiled coil domain encoded by nucleotides 3579-3682, a second coiled coil domain encoded by nucleotides 3827-3937, and a PDZ binding motif (PBM) encoded by nucleotides 4046-4057.

FIG. 3. A. Alignment of nucleotide sequences of the CLASP-2 isoforms. Sequences were aligned using ClustalW B. Alignment of amino acid sequence of the CLASP-2 isoforms. Sequences were aligned using ClustalW. One letter amino acid abbreviation is used.

FIG. 5. A. Amino acid sequence of human and rat CLASP proteins. Sequences were aligned using ClustalW. One letter amino acid abbreviation used. Protein motifs are found within the labeled boxes. A "-" indicates gaps that are placed to acquire a best overall alignment. Other abbreviations: "HC2A" Human CLASP-2 sequence, "KIAA" KIAA1058 sequence (Genbank Accession No. AB028981), "rat" TRG gene (Genbank Accession No. X68101), "HC4" Human CLASP-4 sequence, "HC1" Human CLASP-1 sequence, "HC3" Human CLASP-3 sequence, "HC5" Human CLASP-5 sequence. B. Alignment of DOCK motifs found within the human CLASPs and compared to canonical DOCK motifs. Consensus amino acids found within all DOCK motifs are also indicated.

FIG. 6. A. Nucleotide and predicted amino acid sequence of CLASP-2A cDNA. Notable protein motifs are indicated (see FIG. 1 legend for details). Additionally, boundaries between exons and introns are indicated by arrows. These boundaries were defined by sequencing Bacterial Artificial Chromosomes (BACs) containing genomic DNA corresponding to CLASP-2. BACs were sequenced using primers derived from exon sequences corresponding to the CLASP-2 cDNA. Each exon/intron boundary is noted (as "Ref" with an appropriate reference number) above the cDNA sequence. The references contain exact nucleotide location of introns.

The names and nucleotide numbers of the primers that were used in sequence reactions are also indicated. All nucleotide numbers refer to CLASP-2A cDNA sequence. As shown in the reference, not all of the sequence from sequencing reactions produced sequence matching the cDNA. These nucleotide sequences that did not match the exon sequence for CLASP-2 were considered to be intron sequences. B. Alignment of human and rat CLASP amino acid sequences by ClustalW. Notable protein motifs are indicated (see FIG. 1 Legend for additional details). Additionally, the exon/intron borders described in part A are indicated with vertical lines between appropriate amino acids. Reference numbers are indicted in the right margin and correspond to references in FIGS. 6A and B.

Figure 7:
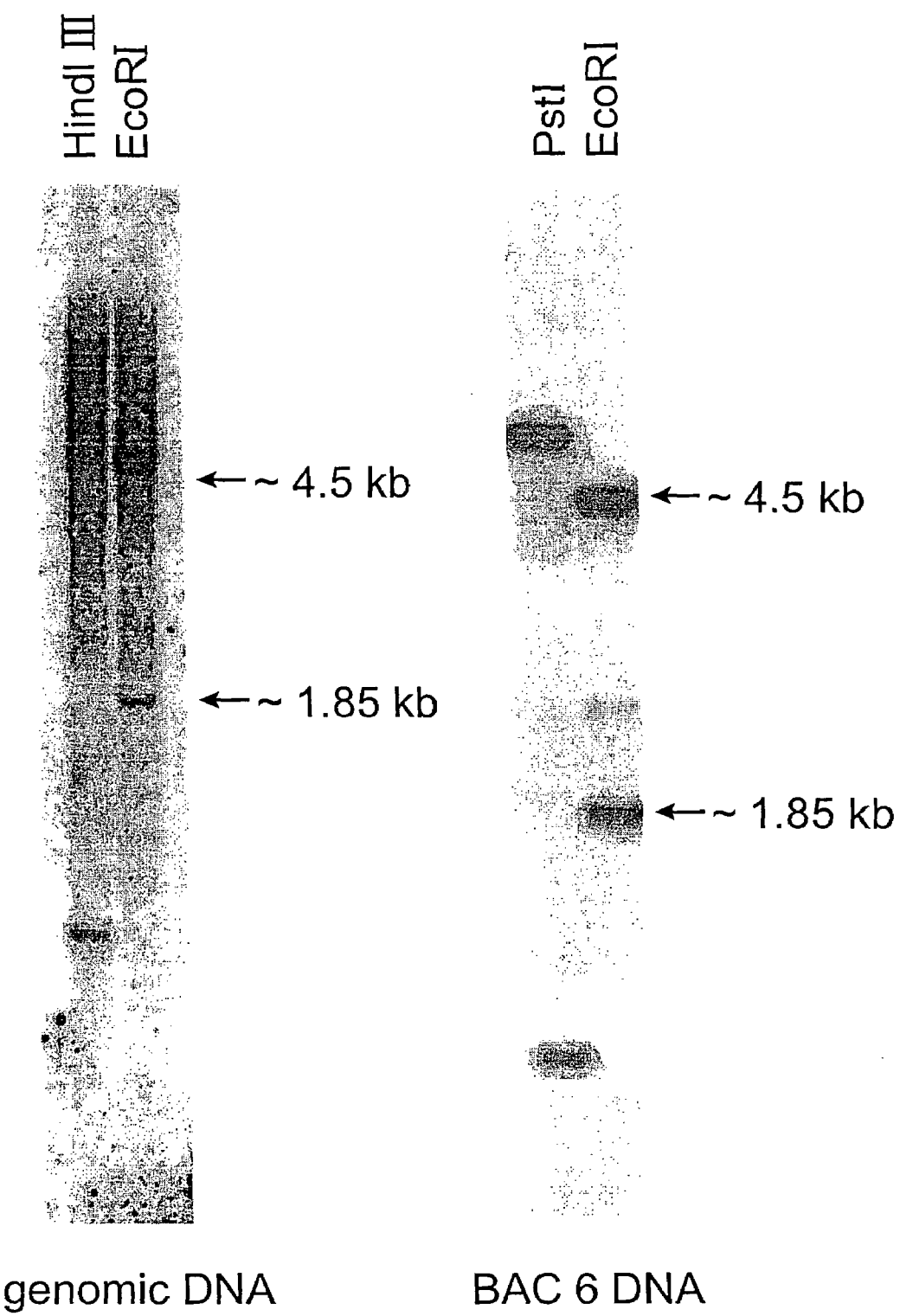

FIG. 7. Southern hybridization analysis of CLASP-2. Genomic DNA from HeLa cells or a BAC DNA clone was digested with EcoRI or HinDIII (genomic DNA) or Pst I (BAC DNA) and eletrophoresed and transferred to nylon membrane by standard methods. For a probe, a CLASP-2-specific DNA fragment was generated by PCR from a CLASP-2 cDNA clone (HC2-5'), using primers HC2AS2 and HC2S1. The fragment was labeled by incorporation of radioactive $^{32}$P dCTP. Probe HC2.1 is 800 bp long and it recognizes two fragments (~4.5 kb and 1.85 kb) on Eco RI digested genomic DNA. Three fragments are revealed by this probe when hybridized to digested DNA of BACs 4 and 6, with the two major ones identical in size to those detected on genomic DNA.

Figure 8:
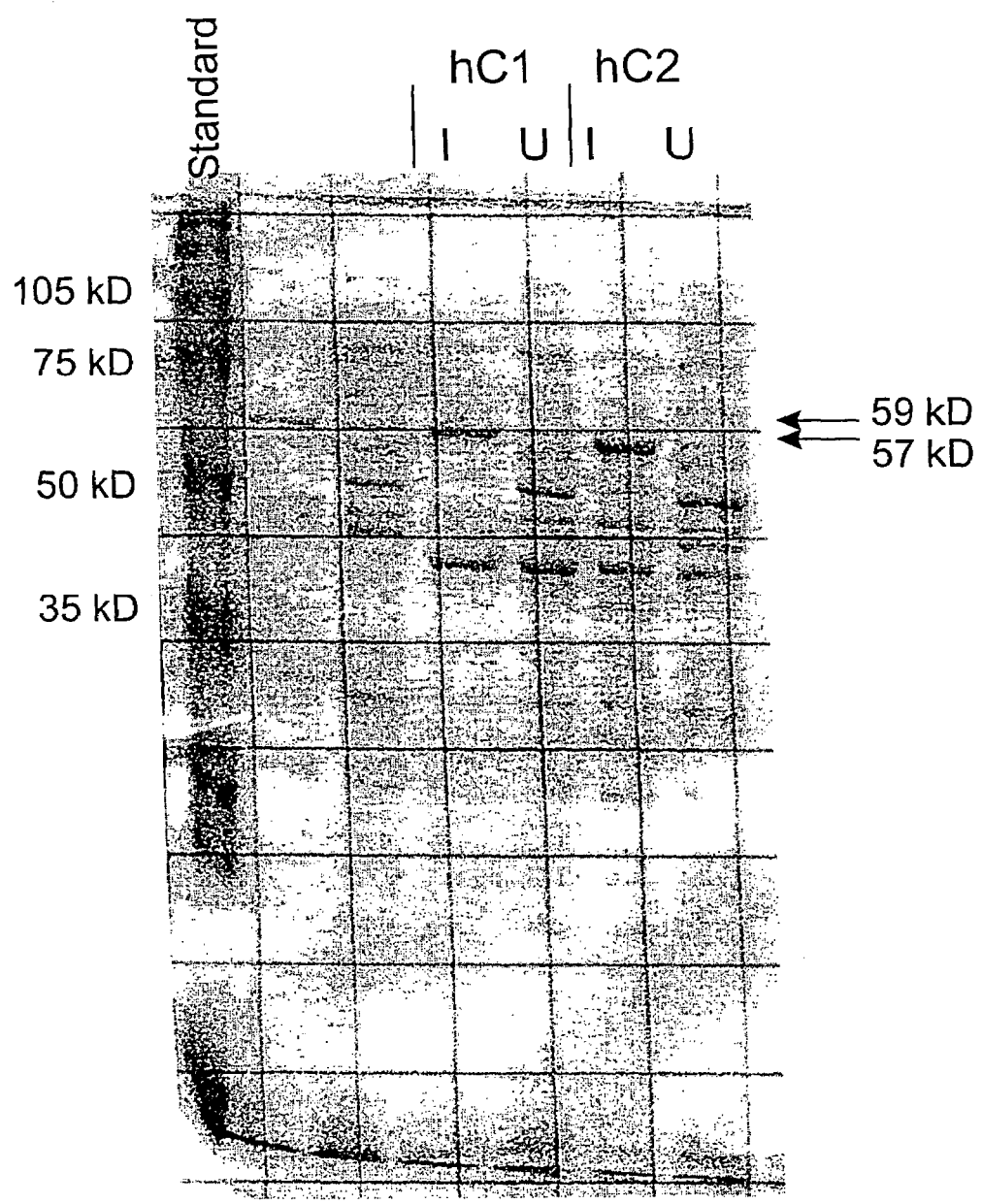

FIG. 8. Expression of human CLASP-1 (hCLASP-1) CLASP-1 and CLASP-2 Glutathion-S-Transferase (GST) fusion proteins. Nucleotides encoding a portion of the hCLASP-2A intracellular domain (nucleotides 3230-4065) were subcloned into pGEX vectors (Pharmacia). Recombinant plasmids were transformed into *E. coli* (strain DH5α), and transformed strains were grown by standard conditions. While in log phase cells were either induced (I) with IPTG (0.1 mM final concentration) or left uninduced (U). After several additional hours of growth cells were harvested and soluble protein lysates generated by standard methods. Aliquots of the protein lysates were eletrophoresed on SDS-PAGE along with molecular mass standards. The gel was stained with Coomassie Blue and shows that fusion proteins migrated with their predicted molecular masses of 59 and 57 kD for hCLASP-1 and hCLASP-2, respectively.

FIG. 9 A. Binding of CLASP-2 C-terminal 20 amino acids to PDZ domains. 20 .mu.M biotinylated synthetic peptide corresponding to the C-terminal 20 amino acids of CLASP-2 was reacted with the indicated plate bound GST fusion proteins (none=no GST fusion protein coated onto plate). Error bars indicate standard deviation of duplicate measurements. FIG.9B. Affinity of CLASP 2-PDZ interactions. Varying concentrations of biotinylated CLASP-2 peptide were reacted with plate bound GST alone, GST-DLG1, GST-NeDLG, and GST-PSD95 fusion proteins. The binding to GST alone (<0.1 OD units) was subtracted from the binding to the fusion proteins and the remaining signal was divided by the signal observed upon addition of 30 μM CLASP-2 peptide to each PDZ domain-containing protein (0.4-1.0 OD units) and plotted. The plotted data was fit to a saturation binding curve, yielding an apparent affinity of 7.5 μM for NeDLG-CLASP-2 interaction, 21 μM for DLG1-CLASP-2 interaction, and 45 μM for PSD95-CLASP-2 interaction. Data are means of duplicate data points, with standard errors between duplicate data points <10%. FIG. 9C. Inhibition of CLASP-2-PDZ binding. 5 μM biotinylated synthetic peptide corresponding to the C-terminal 20 amino acids of CLASP-2 was reacted with the indicated, plate-bound PDZ domain-containing GST fusion proteins in the presence or absence of 100 μM competitor peptide. CLASP-2 Inhibitor refers to a synthetic peptide composed of the eight C-terminal amino acids of CLASP-2. KV1.3 Inhibitor refers to a synthetic peptide composed of the 19 C-terminal amino acids of KV1.3, a lymphocyte potassium channel. The amino acid sequence of the KV1.3 inhibitor is TTNNNPNSAVNIKKIFTDV (SEQ ID NO:86). FIG. 9D. Inhibition of KV1.3-PDZ binding. 5 μM biotinylated synthetic peptide corresponding to the C-terminal 19 amino acids of KV1.3 was reacted with the indicated, plate-bound PDZ-domain containing GST fusion proteins in the presence or absence of 100 μM CLASP-2 Inhibitor (see FIG. 9C legend).

FIG. 10A-H. Preliminary nucleotide sequences of CLASP-2 cDNAs.

Figure 11:
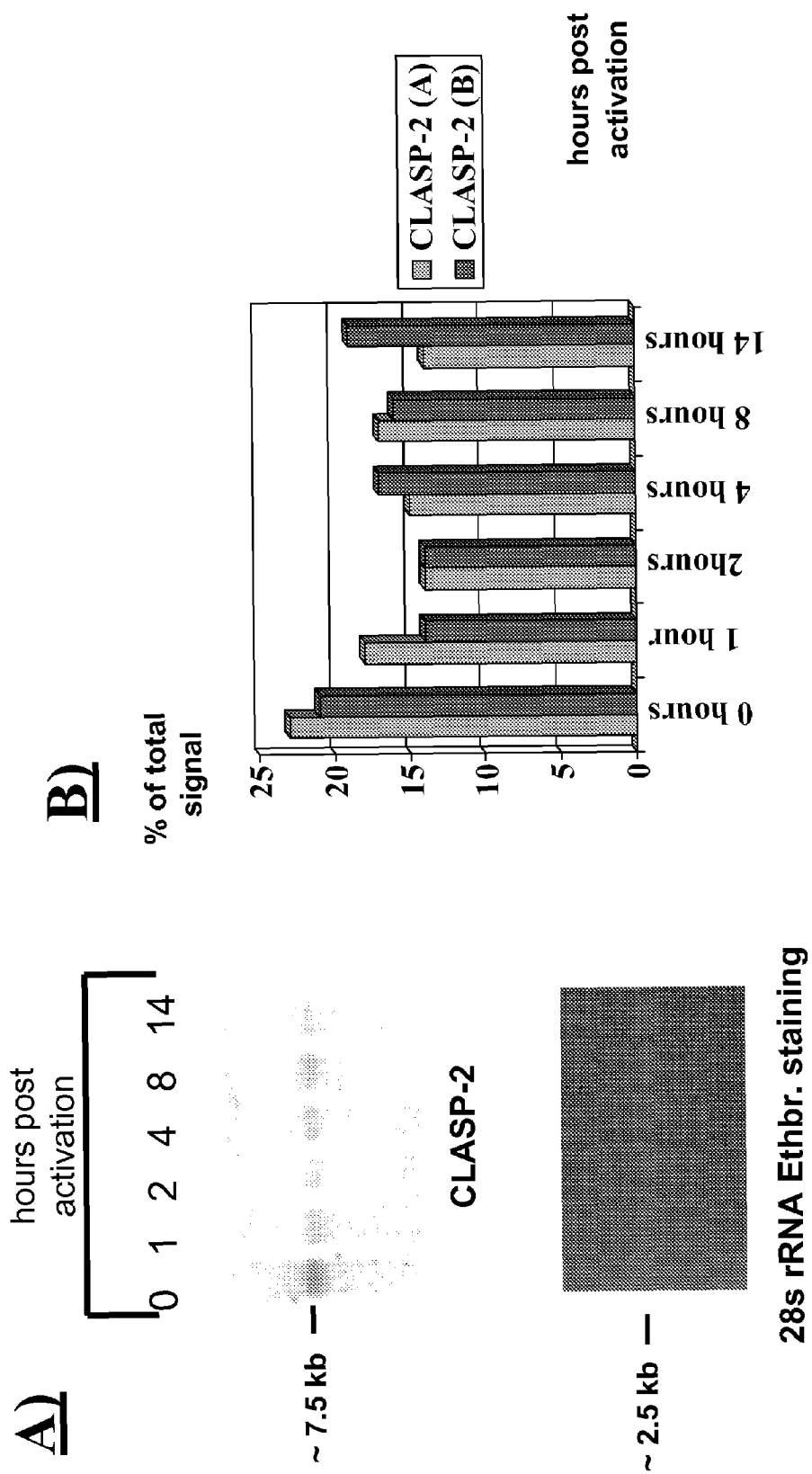

FIG. 11. Expression of CLASP-2 upon T-cell activation as assayed by Northern analysis. Jurkat cells were activated using PMA, Ionomycin, and αCD28. RNA was prepared from cell culture aliquots at 0, 1, 2, 4, 8, 14 hours post activation and Northern analysis was performed (A). Hybridization signals obtained with a CLASP-2-specific probe were quantified using a phosphor imager system. Relative signal intensities (refers to total signal of the specific probe used) are shown in the bar diagram (B). The ethidium staining of the Northern gel (A) demonstrates even RNA loading.

DETAILED DESCRIPTION 5.0 Definitions

Except when noted, the terms "patient" or "subject" are used interchangeably and refer to mammals such as human patients and non-human primates, as well as experimental animals such as rabbits, rats, and mice, and other animals.

The term "biological sample" as used herein is a sample of biological tissue, fluid, or cells that contains CLASPs or nucleic acid encoding CLASP proteins. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

The term "lymphocyte" as used herein has the normal meaning in the art, and refers to any of the mononuclear, nonphagocytic leukocytes, found in the blood, lymph, and lymphoid tissues, i.e., B and T lymphocytes.

The terms "isolated," or "purified," refer to material that is substantially free from components that normally accompany it as found in its native state (e.g., recombinantly produced or purified away from other cell components with which it is naturally associated). Purity and homogeneity are typically determined using analytical chemistry techniques such as polyacrylamide gel electrophoresis or high performance liquid chromatography. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The terms "nucleic acid" and "polynucleotide" are used interchangeably" and refer to refers to DNA, RNA and nucleic acid polymers containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The amino acids may be natural amino acids, or include an artificial chemical mimetic of a corresponding naturally occurring amino acid.

As used herein a "nucleic acid probe" is defined as a nucleic acid capable of specifically binding to a target nucleic acid of complementary sequence (e.g., through complementary base pairing). As used herein, a probe may include natural (i.e., A, G, C, or T) or modified bases (7-deazaguanosine, inosine, and the like). In addition, the bases in a probe may be joined by a linkage other than a phosphodiester bond, so long as it does not interfere with hybridization (e.g., probes may be peptide nucleic acids). The probes can be directly labeled as with isotopes, chromophores, lumiphores, chromogens, or indirectly labeled such as with biotin to which a streptavidin complex may later bind.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or, in the case of cells, to progeny of a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "sequence identity" refers to a measure of similarity between amino acid or nucleotide sequences, and can be measured using methods known in the art, such as those described below:

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region (see, e.g., SEQ ID NO: 1), when compared and aligned for maximum correspondence over a comparison window, or designated region as measured using one of the following sequence comparison algorithms or by manual alignment and visual inspection.

The phrase "substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

The phrase "sequence similarity" in the context of two nucleic acids or polypeptides, refers to two or more sequences that are identitical or in the case of amino acids, have homologous amino acid substitutions at either 50%, often at least 60%, often at least 70%, preferably at least 80%, most preferably at least 90% or at least 95% of the indicated positions.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to CLASP nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2: 482), by the homology alignment algorithm of Needleman & Wunsch, 1970, J. Mol. Biol. 48: 443, by the search for similarity method of Pearson & Lipman, 1988, Proc. Natl. Acad. Sci. U.S.A. 85: 2444, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., 1987 (1999 Suppl.), Current Protocols in Molecular Biology, Greene Publishing Associates and Wiley Interscience, N.Y.)

A preferred example of an algorithm that is suitable for determining percent sequence identity and sequence similarity is the FASTA algorithm, which is described in Pearson, W. R. & Lipman, D. J., 1988, Proc. Natl. Acad. Sci. U.S.A. 85: 2444. See also W. R. Pearson, 1996, Methods Enzymol. 266: 227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another preferred example of algorithm that is suitable for determining percent sequence identity and sequence similarity are the BLAST and BLAST 2.0 algorithms, which are described in Altschul et al., 1977, Nuc. Acids Res. 25: 3389-3402 and Altschul et al., 1990, J. Mol. Biol. 215: 403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence.

T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, Proc. Natl. Acad. Sci. U.S.A. 89: 10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Natl. Acad. Sci. U.S.A. 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, J. Mol. Evol. 35: 351-360. The method used is similar to the method described by Higgins & Sharp, 1989, CABIOS 5: 151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, Nuc. Acids Res. 12: 387-395.

Another preferred example of an algorithm that is suitable for multiple DNA and amino acid sequence alignments is the CLUSTALW program (Thompson, J. D. et al., 1994, Nucl. Acids. Res. 22: 4673-4680). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, 1992, Proc. Natl. Acad. Sci. U.S.A. 89: 10915-10919).

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO: 1 can be made detectable, e.g., by incorporating a radiolabel into the peptide, and used to detect antibodies specifically reactive with the peptide).

The term "sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "specifically (or selectively) binds" to an antibody refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

The phrase "specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore and Western blot are used to identify peptides that specifically react with PDZ domain-containing proteins. Typically a specific or selective reaction will be at least twice background signal or noise and more typically more than 10 times background. Specific binding between a monovalent peptide and a PDZ-containing protein means a binding affinity of at least $10^4$ $M^{-1}$, and preferably $10^5$ or $10^6$ $M^{-1}$.

The phrase "homotypic interaction" refers to the binding of a given protein to another molecule of the same protein (e.g., the binding of hCLASP-2 to hCLASP-2). The phrase "heterotypic interaction" refers to the binding of a given protein to a different protein or other molecule (e.g., the binding of hCLASP to a PDZ domain-containing protein or the binding of a transcription factor to DNA).

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The terms "B lymphocyte response" and "B lymphocyte activity" are used interchangeably to refer to the component of immune response carried out by B lymphocytes (i.e. the proliferation and maturation of B lymphocytes, the binding of antigen to cell surface immunogobulin, the internalization of antigen and presentation of that antigen via MHC molecules to T lymphocytes, and the synthesis and secretion of antibodies).

The terms "T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Components of an immune response may be detected in vitro by various methods that are well known to those of ordinary skill in the art. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen A; et al., 1995, Immunity 2(4): 373-80), (3) antigen presenting cells can be incubated with whole protein antigen and the presentation of that antigen on MHC detected by either T lymphocyte activation assays or biophysical methods (Harding et al., 1989, Proc. Natl. Acad. Sci., 86: 4230-4), (4) mast cells can be incubated with reagents that cross-link their Fc-epsilon receptors and histamine release measured by enzyme immunoassay (Siraganian, et al., 1983, TIPS 4: 432-437).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, Blood 72: 1310-5); (3) the proliferation of peripheral blood mononuclear cells in response to mitogens or mixed lymphocyte reaction can be measured using $^3$H-thymidine; (4) the phagocitic capacity of granulocytes, macrophages, and other phagocytes in PBMCs can be measured by placing PMBCs in wells together with labeled particles (Peters et al., 1988); and (5) the differentation of immune system cells can be measured by labeling PBMCs with antibodies to CD molecules such as CD4 and CD8 and measuring the fraction of the PBMCs expressing these markers.

As used herein, the phrase "signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., an immune response described above.

A signal transduction pathway refers to the biochemical relationship between a variety of signal transduction molecules that play a role in the transmission of a signal from one portion of a cell to another portion of a cell. Signal transduction molecules of the present invention include, for example, CLASP proteins. As used herein, the phrase "cell surface receptor" includes molecules and complexes of molecules capable of receiving a signal and the transmission of such a signal across the plasma membrane of a cell. An example of a "cell surface receptor" of the present invention is the T cell receptor (TCR). As used herein, the phrase "intracellular signal transduction molecule" includes those molecules or complexes of molecules involved in transmitting a signal from the plasma membrane of a cell through the cytoplasm of the cell, and in some instances, into the cell's nucleus. In the present invention, CLASPs can be referred to as "intracellular signal transduction molecules", but can also be referred to as "signal transduction molecules".

A signal transduction pathway in a cell can be initiated by interaction of a cell with a stimulator that is inside or outside of the cell. If an exterior (i.e., outside of the cell) stimulator (e.g., an MHC-antigen complex on an antigen presenting cell) interacts with a cell surface receptor (e.g., a T cell receptor), a signal transduction pathway can transmit a signal across the cell's membrane, through the cytoplasm of the cell, and in some instances into the nucleus. If an interior (e.g., inside the cell) stimulator interacts with an intracellular signal transduction molecule, a signal transduction pathway can result in transmission of a signal through the cell's cytoplasm, and in some instances into the cell's nucleus.

Signal transduction can occur through, e.g., the phosphorylation of a molecule; non-covalent allosteric interactions; complexing of molecules; the conformational change of a molecule; calcium release; inositol phosphate production; proteolytic cleavage; regulation or exchange of nucleotide mono-, di- or tri-phosphates, cyclic nucleotide production and diacylglyceride production. Typically, signal transduction occurs through phosphorylating a signal transduction molecule. According to the present invention, a CLASP signal transduction pathway refers generally to a pathway in which a CLASP protein regulates a pathway that includes engaged-receptors, kinases, PKC-substrates, G proteins, and other molecules.

5.1. Introduction

The present invention relates to novel transmembrane proteins, termed CLASPs. CLASP family members contain an endodomain that displays the appropriate properties to organize the cytoskeleton and interact with signal transduction apparatus of the immune gateway and signaling pathways.

CLASPs function in cells of the immune system, e.g., T cells and B cells, as well as non-immune cells. The CLASP proteins function in a variety of cellular processes, particularly related to immune function, regulation of T cell and B cell interactions, T cell activation, other cellular activation, and in the organization, establishment and maintenance of the "immunological synapse" (see Dustin et al., 1999, Science 283: 680-682; Paul et al., 1994, Cell 76: 241-251; Dustin et al., 1996, J. Immunol. 157: 2014; Dustin et al., 1998, Cell 94: 667), including signal transduction, cytoskeletal interactions, and membrane organization.

Without intending to be bound by a particular mechanism or limited in any way, the CLASP proteins are believed to be a component of the lymphocyte organelle called the "immune gateway" that creates a docking site for cell-cell contact during antigen-presentation. It is believed the cytoplasmic domains of CLASP proteins organize it into a patch at the leading edge of T cells. The carboxy-terminus encoded sequences of some CLASPs may mediate interaction with PDZ domain proteins and with cytoskeletal proteins (e.g., spectrin or ankyrin) to connect CLASPs to the microtubule network and hold receptors or other signaling molecules at a polarized configuration just above the microtubule-organizing center ("MTOC"). Thus, when T cells engages a B cell acting as an APC, the CLASP molecules are organized at the interface of the two cells.

Modulating the expression of the CLASP protein, and interference with, or enhancement of, CLASP protein interactions with other proteins has a number of beneficial physiological effects, e.g., altered signaling in response to antigen, altered T and B cell response to antigen, and modulation of T cell activation. Disorders that can be treated by disrupting CLASP function, include without limitation, multiple sclerosis, juvenile diabetes, rheumatoid arthritis, pemphigus, pemphigoid, epidermolysis bullosa acquista, lupus, endometriosis, toxemia or pregnancy induced hypertension, pruritic urticarial papules and plaques of pregnancy (PUPPP), herpes gestationis, impetigo herpetiformis, pruritus gravidarum, placenta-related disorders, and Rh incompatibility.

In another aspect, the present invention provides methods and reagents for detection of CLASP expression and CLASP-expressing cells. Abnormal expression patterns or expression levels are diagnostic for immune and other disorders. For example, diseases characterized by overproduction or depletion of lymphocytes in blood or other organs may be detected or monitored by monitoring the level of CLASP polypeptide or mRNA in a biological sample (e.g., peripheral blood), e.g., the number or percentage of CLASP expressing cells. Diseases characterized by overproduction of T cells include, e.g., leukemia (both ALL and CLL), lymphoma (including non-Hodgkins lymphoma, Burkitt's lymphoma, mycosis fungoides, and sezary syndrome), EBV, CMV, toxoplasmosis, syphilis, typhoid, brucellosis, tuberculosis, influenza, hepatitis, serum sickness, and thyrotoxicosis. Diseases associated with the depletion of T cells include, e.g., HIV and myelodysplasia. Diseases associated with the overproduction of B cells include, e.g., leukemia (both ALL and CLL), non-Hodgkins lymphoma, Burkitt's lymphoma, myeloma, EBV, CMV, toxoplasmosis, syphilis, typhoid, brucellosis, tuberculosis, influenze, hepatitis, serum sickness, and thyrotoxicosis. Diseases associated with the depletion of B cells include, e.g., myelodysplasia.

In many embodiments described herein, "CLASP-2" is provided solely to provided an example of a CLASP. Any other CLASP molecule, e.g., CLASP-1, -3, -4, -5, -6, from humans or mice may be used in the subject methods, or repace CLASP-2 in the subject compositions.

For Example, if CLASP-2 polynucleotide, polypeptides or antibody thereto is recited herein in a composition, then that CLASP-2 polynucleotide, polypeptides or antibody thereto may be replaced by an equivalent CLASP-1, CLASP-3, or CLASP-4, CLASP-5, or CLASP-6 polynucleotide, polypeptides or antibody thereto or any mouse CLASP polynucleotide, polypeptides or antibody thereto.

Also, if CLASP-2 polynucleotide, polypeptides or antibody thereto is recited herein in a method, then that CLASP-2 polynucleotide, polypeptides or antibody thereto may be replaced by an equivalent CLASP-1, CLASP-3, or CLASP-4, CLASP-5, or CLASP-6 polynucleotide, polypeptides or antibody thereto or any mouse CLASP polynucleotide, polypeptides or antibody thereto.

Further, if "CLASP" is recited herein, any CLASP, e.g., CLASP-1, CLASP-2, CLASP-3, or CLASP-4, CLASP-5, or CLASP-6, from either human or mouse is refered to. In certain embodiments, "CLASP" refers to the human CLASP-2.

5.2. CLASP cDNA and Polypeptide Structure

The cDNA and polypeptide sequences of human and mouse CLASPs is described in the sequence lising and figures.

Figure 2A:
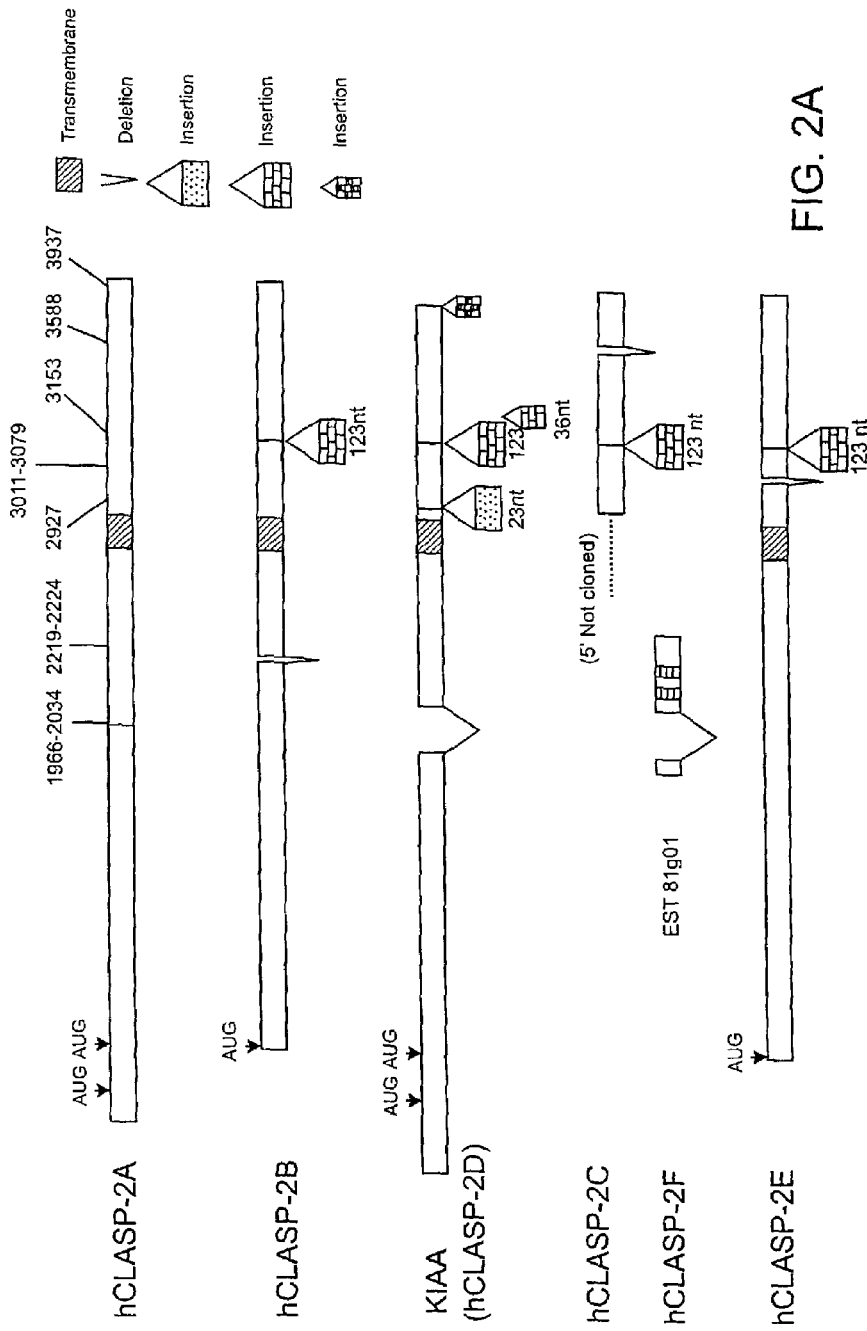
FIG. 2A. Schematic of CLASP-2 splice variants. Splice variants are compared to Human (h) CLASP-2A. Numbers above hCLASP-2A line diagram indicate where splice variations comprising deletions and insertions relative to hCLASP-2A are found. Abbreviations: "KIAA" KIAA1058 sequence (Genbank Accession No. AB028981). 2B. Nucleotide and predicted amino acid sequence of CLASP-2A cDNA. Notable protein motifs are indicated above the nucleotide sequence in bold. Exact position of insertions and deletions are indicated above the CLASP-2A sequence with arrows and "x", respectively. The nucleotide sequence of insertions schematized in FIG. 2A are indicated above the arrow. The insertions and deletions are as follows (numeration refers to Human CLASP-2A nucleotide sequence): Nucleotides 1966-2034 are deleted in CLASP-2D. Nucleotides 2219-2224 are deleted in CLASP-2B. There is an insertion of 69 amino acids at nucleotide 2927 found in CLASP-2D. The nucleotide sequence for this insertion is: AAGCAGTCCAGTGGGAGCCGCCCCT-TCTCCCCCACAGCCATAGCGCCTGCCTGAG GAG-GAGCCGGGGAG (SEQ ID NO:11) and encodes amino acids AVQWEPPLLPHSHSACLRRSRG (SEQ ID NO:12) (one letter amino acid abbreviation). This amino acid sequence encodes a putative SH3 binding domain. There is another deletion at between nucleotides 3011-3079 found in CLASP-2E. CLASPs 2B, 2C, 2D and 2E contain an insertion at nucleotide 3153 with the nucleotide sequence of: TGAGAGGCTGGCCCATCTGTATGA-CACGCTGCACCGGGCCTACAGCAAAGTGAC CGAG-GTCATGCACTCGGGCCGCAGGCT-TCTGGGGACCTACTTCCGGGTAGCCTTC TTCGGGCAGGCAGCGCAATACCAGTTTA- CAGACAGTGAAACAGATGTGGAGGGA TT. (SEQ ID NO:13) The entire sequence is found in CLASP-2D and encodes amino acids ERLAHLYDTLHRAYSKVTEVMHS-GRRLLGTYFRVAFFGQAAQYQFTDSETDVEG (SEQ ID NO:14) while the underline sequence is found in CLASPs 2B, 2C, and 2E and encodes amino Acids ERLAHLYDTLHRAY-SKVTEVMHSGRRLLGTYFRVAFFGQG (SEQ ID NO:15). This amino acid sequence encodes a putative immunoreceptor tyrosine-based activation motif (ITAM). There is a two nucleotide deletion in Human CLASP-2C found at nucleotides 3586 and 3587. There is an insertion of 8 nucleotides found only in Human CLASP-2D with sequence: CTGGGATG at nucleotide 3937. This insertion puts a stop codon into the CLASP-2D nucleotide sequence.

The CLASP-2 protein is characterized by multiple forms produced by alternative exon usage (i.e., production of splice variants). In one naturally occurring form, CLASP-2 has the structure shown in FIG. 1. However, as discussed in detail infra, the CLASP-2 gene encodes a variety of gene product due to alternative splicing of mRNA. FIG. 2 shows the nucleotide sequence and conceptual translation of human CLASP-2 polypeptides:

```
hCLASP-2A cDNA           (SEQ ID NO: 1)
and hCLASP-2A polypeptide.   (SEQ ID NO: 2)

hCLASP-2B cDNA           (SEQ ID NO: 3)
and hCLASP-2B polypeptide.   (SEQ ID NO: 4)

hCLASP-2C cDNA           (SEQ ID NO: 5)
and hCLASP-2C polypeptide.   (SEQ ID NO: 6)

hCLASP-2D cDNA           (SEQ ID NO: 7)
and hCLASP-2D polypeptide.   (SEQ ID NO: 8)
```

-continued

```
hCLASP-2E cDNA          (SEQ ID NO: 9)
and hCLASP-2E polypeptide.  (SEQ ID NO: 10)
```

Unless specifically referred to, the phrase "human CLASP-2 (hCLASP-2)" is used herein refers to hCLASP-2A, hCLASP-2B, hCLASP-2C and hCLASP-2E. "hCLASP-2D" cDNA is also known as KIAA1058, which was described by Kikuno et al., 1999, *DNA Res.* 6, 197-205 as a cDNA from brain encoding a protein of unknown function.

CLASP polypeptides typically include a leader sequence, followed in certain cases by a PH domain that may localize it to the cell membrane, and a long domain that may contain phosphorylation sites, PDZ binding sites, guanine nucleotide binding functions, and coiled-coiled regions. The present invention provides a polynucleotide having the sequence of SEQ. ID. NO: 1, or a fragment thereof, and a polypeptide having the sequence of SEQ. ID NO: 2, or a fragment thereof. In addition, the invention provides polynucleotides comprising CLASP genomic sequences, CLASP homologues from other species, naturally occurring alleles of hCLASPs, and hCLASP variants as described herein, and methods for using CLASP polynucleotides, polypeptides, antibodies and other reagents.

5.2.1. CLASP Polypeptide Domains

As is shown in FIG. 1, one naturally occurring CLASP-2 cDNA encodes a polypeptide characterized by several structural and functional domains and defined sequence motifs. To provide guidance to the practitioner, the structural features are described infra. However, it will be understood that the present invention is not limited to polypeptides that include all, or any particular one of these domains or motifs. For example, a CLASP-2 fusion protein of the invention contains only the putative extracellular domain of CLASP-2. Similarly, the CLASP-2A polypeptide of SEQ ID NO: 2 does not have the ITAM motifs (discussed infra) found in the CLASP-2B and 2C polypeptides.

It will be appreciated that the structurally (and functionally) different domains of CLASP-2 polypeptides (and the corresponding region of the mRNA) are of interest, in part, because they may be separately targeted or modified (e.g., deleted or mutated) to affect the activity or expression of a CLASP-2 gene product (in order to, for example, modulate an immune response). For example, the putative extracellular domain of a CLASP-2 protein can be targeted (e.g., using an anti-CLASP monoclonal antibody to (a) block the interaction of a CLASP-2-expressing cell (e.g., a T cell) and a second cell (e.g., a B cell) displaying a protein that is bound by CLASP-2 (i.e., a CLASP-2 ligand). Similarly, an intracellular domain (e.g., ITAM or DOCK, see infra) can be targeted to interfere with signal transduction without interfering with extracellular ligand binding.

Generally, inhibiting CLASP expression or CLASP polypeptide function will result in modulation of immune function including, for example, changing the threshold for T cell activation by affecting formation of the immune synapse. Modulation of immune function can be screened and quantitated by a number of assays known in the art and described herein (see also § 5.14).

5.2.1.1. Signal Peptide

The human CLASP-2 sequence presented in FIG. 1 encodes two potential start sites for translation. The first predicted methionine appears at nucleotide 278 (ATG). The second methionine appears at nucleotide 476. Both have an acceptable consensus sequence for a translational start (A/GxxATGG; Kozak, M., 1996, Mamm. Genome 7(8): 563-74). A polypeptide beginning at the second methionine is also predicted to encode a signal peptide capable of localizing the protein to the secretory pathway by SignalP, a signal sequence prediction program (Nielsen, H. et al., 1997, Protein Eng. 10(1): 1-6). Polypeptides beginning at the first methionine are not predicted to contain a signal sequence; however, the consensus for signal prediction is only 80-90% accurate for known signal sequences. A third possibility for a translational start is that the cDNA listed in FIG. 1 is incomplete and another methionine is encoded in frame and upstream of the sequence shown in FIG. 1. Further research demonstrated that third possibility was correct.

5.2.1.2. Extracellular Domain

If the predicted membrane spanning stretches do indeed function as transmembrane domains (sec 5.2.1.3), then the putative CLASP extracellular domains are characterized by one cadherin EC-like motif (Pigott, R. and Power, C., 1993, The Adhesion Molecule Factbook. Academic Press, pg. 6; Jackson, R. M. and Russell, R. B., 2000, J, Mol. Biol. 296: 325-34). Several highly conserved cysteines are found in the extracellular domain, as well as various glycosylation signals. Through its putative extracellular domains, CLASP proteins may interact with Uganda in a homotypic and/or heterotypic manner to establish the immunological synapse in conjunction with molecules such as TCR MHC class I, MHC clasp II, CD3 complex and accessory molecules such as 0D4, 0D3, ICAM-1, LFA-1, and others. Many cadherins contain a pro-domain of approximately 50 to 150 amino acids that is removed before localization to the plasma membrane. This cleavage is presumed to be carried out by Furin (Posthaus, H. et at, 1998, FEBS Lot 438: 306-10) at a consensus sequence of R.KQR (SEO ID NO:89). Furin is a protease that is at least partially responsible for the maturation of certain cadherins. CLASP-2 has the sequence RNQR (SEQ ID NO:90) at nucleotides 854 through 865 (FIG. 1). By homology, this region is around 120 amino acids into the predicted protein start site for hCLASP-2A. This region may be a pro-domain and cleavage may be required for CLASP function, or aspects of CLASP function.

Antibodies raised against the extracellular domain can be added to cells expressing CLASPs. These antibodies can either block the interaction of CLASP-2 with potential ligands or stabilize these interactions. Any immunoassay known in the art, e.g., listed and described herein, may be used to assess the modulation of immune function brought about by this approach.

Similarly, portions of the extracellular domain of CLASP can be expressed as soluble protein. This soluble protein can then be added to cells expressing CLASP. These proteins may interact with potential ligands to competitively inhibit their binding to endogenous CLASPs. This could modulate CLASP function via the immunoassays described herein. Recombinant proteins could interfere in a positive or negative fashion with CLASP interactions.

5.2.1.3. Transmembrane Domain

CLASP predicted amino acid sequences were analyzed using the PHDhtm analysis software for prediction of transmembrane helices (Rost, B., et al., 1996, Prot. Science 7: 1704-1718). Using the PPHDhtm analysis software, it was determined that there is a predicted transmembrane domain for CLASP-2 located from nucleotides 2861-2917 (see FIG. 1), as well as three other potential transmembrane domains located near the amino terminal end. These have not been verified experimentally, and are not clearly functioning as membrane spanning regions. The presence of a N-terminal PH domain in certain CLASPs suggest that these proteins are membrane associated through that domain and are less likely to utilize membrane spanning regions.

5.2.1.4. Intracellular Domains

The CLASP intracellular domains contain motifs corresponding to several types of protein domains. Depending on the specific CLASP (i.e., specific family member or splice variant) all or only some of the domains can be present. Listed from amino terminus to carboxy terminus, the domains include: (1) ITAM (Chan et al. 1994, *Annual Review of Immunology* 12: 555-592), (2) a newly discovered DOCK/CLASP motif, (3) one or two coiled-coil motifs, and (4) a C-terminal PDZ binding motif (PBM) (also referred to as PDZ ligand or "PL").

5.2.1.5. ITAM

Immunoreceptor Tyrosine-based Activation Motifs (ITAM motifs; also known as ARAM, or antigen recognition activation motifs) are motifs contained within antigen receptors for T and B cells, and Fc receptors on other leukocytes, and are necessary for proper activation and signal transduction in these cells. They are characterized by the consensus sequence YXXL/I-X7/8-YXXL/I (Grucza et al., 1999, Biochemistry 38: 5024-5033), usually separated by 6-8 amino acids (Watson et al., 1998, Immunol. Today 19: 260-264; Isakov, J. Leukoc. Biol. 61: 6-16). ITAM is used as an intracellular regulatory motif through its ability to be tyrosine phosphorylated by src-family tyrosine kinases such as Lyn that are involved in leukocyte signal transduction. Once phosphorylated, the ITAM acts as a high affinity binding site for SH2 containing proteins. Signal transduction components including ZAP-70, Syk, Lyn, Shc, PI3 kinase, and Grb2 contain SH2 domains and have been shown to bind ITAMs (Clements et al., 1999, Annu. Rev. Immunol. 17: 89-108). This places ITAM-containing molecules in a central role of intracellular signal regulation in leukocytes. ITAM motifs in leukocyte signaling can facilitate signal transduction (e.g., tyrosine kinase signaling) by acting as temporal scaffolds where other transduction components could bind and be properly positioned to mediate transduction. ITAM motifs often appear in multiples in a protein, however, it is known that one set of YXXL/I alone can transduce signals of the PTK pathway, though weakly.

CLASP proteins typically have ITAM YXXL/I motifs (where X is any amino acid) separated by 3 or 13 amino acids. In various embodiments the CLASP-2 polypeptide of the invention is characterized by one or more of the motifs shown in Table 1.

TABLE 1

CLASP-2 ITAM Motifs

| Motif No. | Sequence Motif |
|---|---|
| 1 | YXX(I/L)-$X_3$-YXX(I/L) |
| 2 | YXX(I/L)-$X_{13}$-YXX(I/L) |
| 3 | YXX(I/L)-$X_3$-YXX(I/L)-$X_{13}$-YXX(I/L) |

The presence of multiple ITAM motifs in CLASP proteins indicates that they may be engaged by multiple signal transduction components (e.g., ZAP-70/Syk, Shc, PI3 kinase, and Grb2). In general, the ITAM motif in CLASP proteins match identically to the canonical ITAM motif with some motifs containing a conservative amino acid change (i.e. valine instead of isoleucine or leucine). As previously described for other ITAMs, the ITAMs within CLASPs can bind SH2-containing proteins including ZAP-70, Syk, Shc, PI3 kinase, and Grb2. Since CLASPs have an extracellular domain, CLASPs protein can independently initiate a signal transduction cascade through engagement of its extracellular domain. Otherwise CLASPs may cooperate with an antigen receptor signaling complex (e.g., with CD3/TCR, BCR, FcR), to facilitate tyrosine kinase signal transduction The ITAMs have demonstrated different binding specificity and affinities for SH2 domains (Clements, et al., 1999, Ann. Rev. Immunol. 17: 89-108). For example, Shc, PI3 kinase, and Grb2 bind to dual and mono phosphorylated ITAMs with different affinities. Thus the ITAMs in CLASPs are believed to provide quantitative as well as qualitative differences in signal transduction depending up their phosphorylation state, as well as to inhibit or augment specific protein interactions and hence specific tyrosine kinase-mediated signaling pathways in leukocytes.

Antagonizing the PTK-CLASP interactions (e.g., phosphorylation of CLASP-2) will thus inhibit immune function. In one embodiment, interactions between ITAM-bearing human CLASPs and their binding partners are believed to be antagonized by the alpha subtype (SIRPalpha) of signal regulatory proteins that has been shown to negatively regulate ITAM-dependent lymphocyte activation (Lienard H; 1999, J Biol Chem 274: 32493-9). Also, a recently recognized family of immunoreceptor tyrosine-based inhibition motif (ITIM) receptors are thought to inhibit the ITAM-induced activation of immune competent cells (Gergely, et al., 1999, J. Immunol Lett 68: 3-15) and therefore may block CLASP-partner interactions.

5.2.1.6. DOCK

CLASP polypeptides contain a new "DOCK" motif, not previously described in the scientific literature. The CLASP DOCK motif includes a series of five tyrosines surrounded by conserved sequences in regions A, B, C, D, and G (see FIG. 5B). There are also two highly conserved non-tyrosine containing regions (E and G) separated by nine amino acids (P+EXAI+XM)(SEQ ID NO:91) and (LXMXL+GXVXXX-VNXG)(SEQ ID NO:92) (where X is any amino acid).

The region of CLASP proteins immediately following the ITAM motifs exhibits sequence similarity to the C-terminal third of the so-called "DOCK" proteins. The DOCK gene family includes three molecules that are the human homologues of the *C. elegans* CED proteins known to be involved in apoptosis. CED-5 (DOCK180), a major CRK-binding protein, alters cell morphology upon translocation to the membrane (mediates the membrane motion that scavenger cells exhibit as they surround and engulf dying cells; its function can be partially rescued by the human DOCK180 (Wu et al., 1998, *Nature* 392: 501-504). Myoblast City in *Drosophila* (MBC) is another member of the DOCK protein family and has been found to be involved in myoblast fusion (Erickson, et al., 1997, J. Cell Biol. 138: 589). Since CLASP-2 expression is found in syncytial tissues such as placenta, muscle, and heart, it is believed that CLASP-2 is involved in mediating or inhibiting cell fusion.

The DOCK family has been implicated in the control of cell shape. DOCK1, when transfected into spindle cells, can make them flattened and polygonal (Takai, et al., 1996, Genomics 35: 403-303). DOCK1 expression is ubiquitous except in hematopoetic cells. DOCK2 is expressed in hematopoetic cells and when transfected into spindle cells can make them round up (Nishihara, H., 1999, Hokkaido Igaku Zasshi 74: 157-66). DOCK2 is expressed in peripheral blood lymphocytes, thymus, spleen, and liver.

5.2.1.7. Coiled-Coil

CLASPs have one to two predicted coiled-coil domains (Lupas et al., 1991, *Science* 252: 1162-64; Lupas, A., 1996, Meth. Enzymology 266: 513-525). Coiled-coil domains are known to interact directly with cytoskeleton or other proteins, indicating that that CLASP proteins may interact directly with the cytoskeleton. Thus, it is believed that CLASP proteins may bind cytoskeletal proteins, e.g., spectrin, ankyrin, hsp70, talin, ezrin, tropomyosin, myosin, plectin, syndecans, paralemmin, Band 3 protein, Cytoskeletal protein 4.1, Tyrosine phosphatase PTP36 and other molecules.

5.2.1.8. PDZ Ligand

Some CLASP proteins contain a PDZ-ligand motif ("PBM" or "PL") at the C-terminus of the protein. This short (3-8 amino acid) motif mediates the binding of proteins terminating at their carboxyl terminus in the motif (most commonly S/T-X-V-free carboxyl-terminus) to other proteins containing one or more specific PDZ domains (See Songyang et al., 1997, Science 275: 72 and Doyle et al., 1996, Cell 85: 1067 for a discussion of PDZ-ligand structures).

PDZ domain-containing proteins are involved in the organization of ion channels and receptors at the neurological synapse and in establishing and maintaining polarity in epithelial cells via their binding to the C-termini of transmembrane receptors. It has been shown that PDZ-domain containing proteins can mediate protein-protein interactions in immune system cells (e.g., DLG1 binds to the lymphocyte potassium channel KV1.3 in human T lymphocytes, (Hanada et al., 1997, J. Biol. Chem. 272: 26899).

Figure 9A:
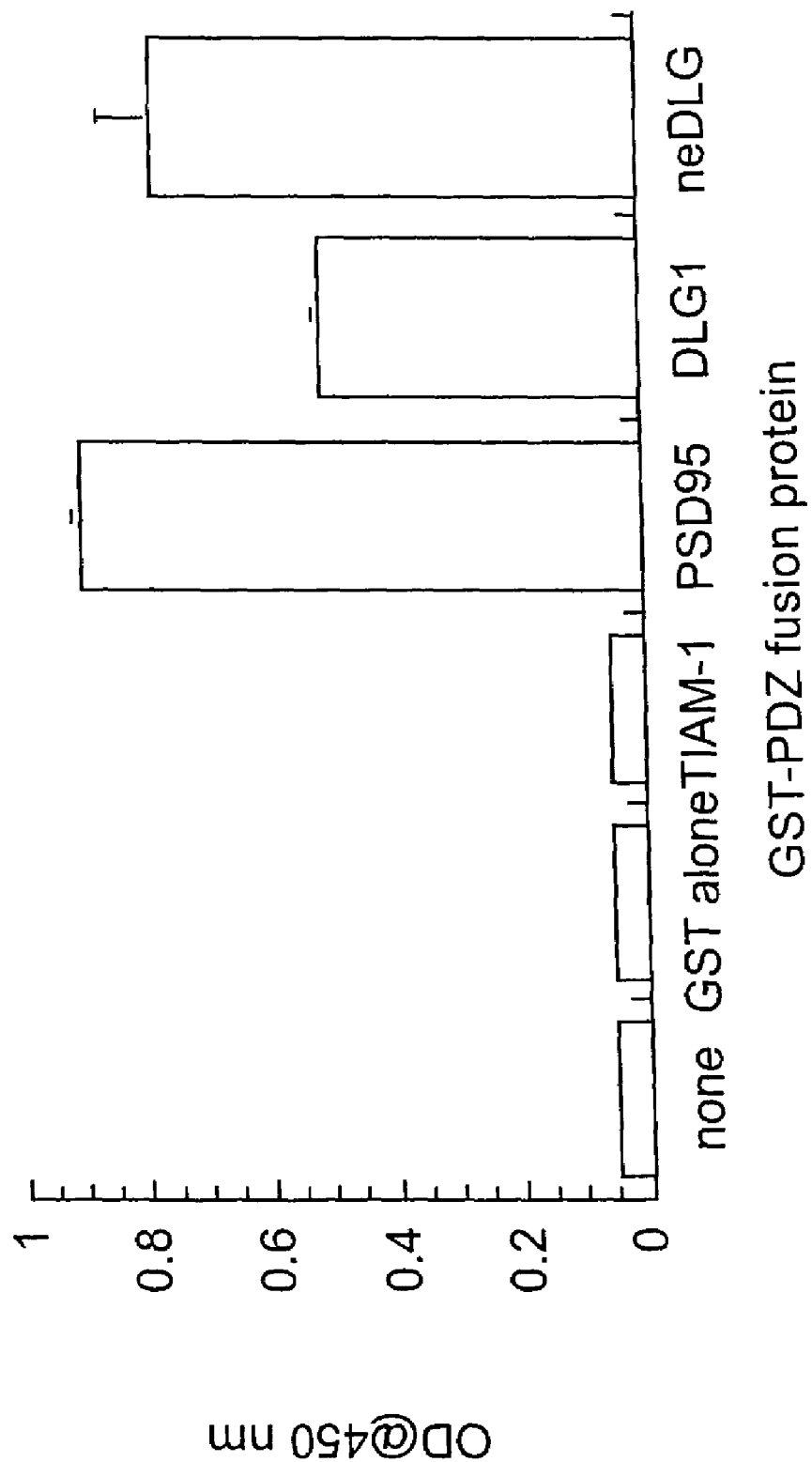
Figure 9B:
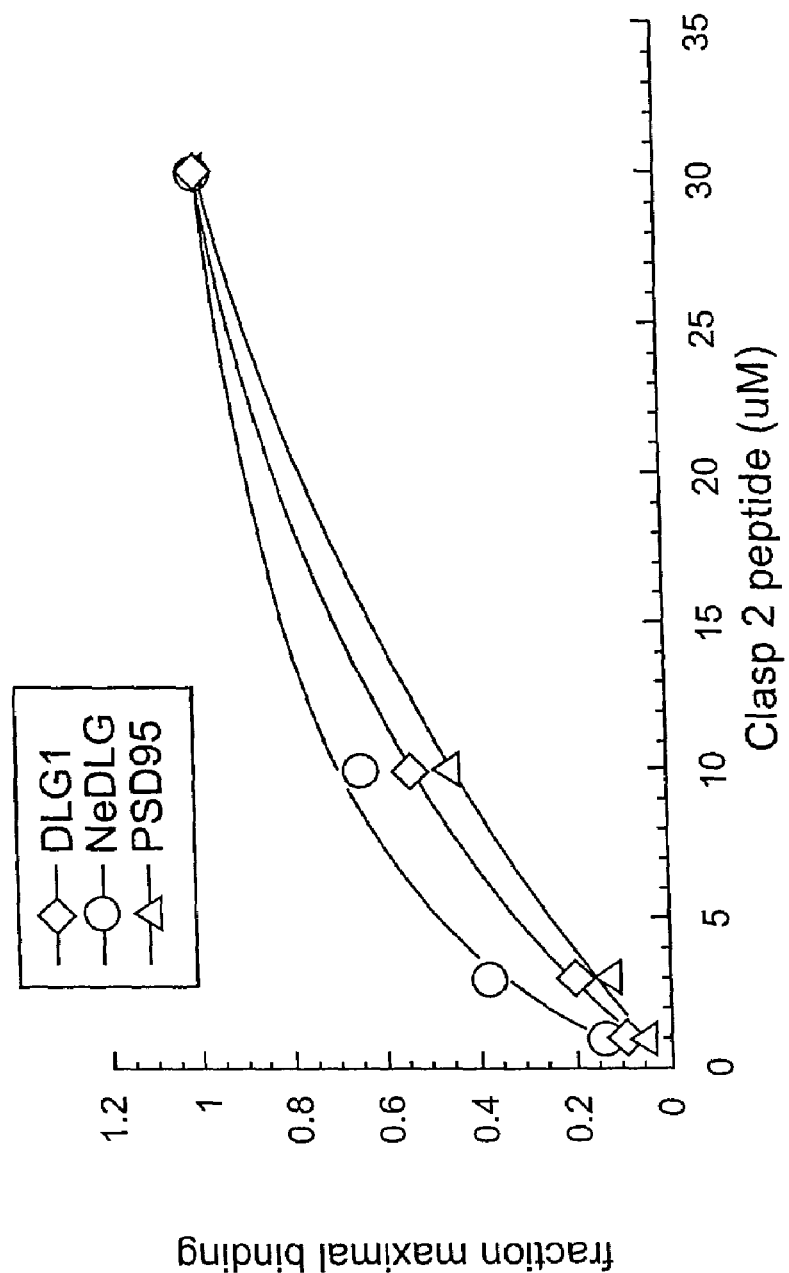
Figure 9C:
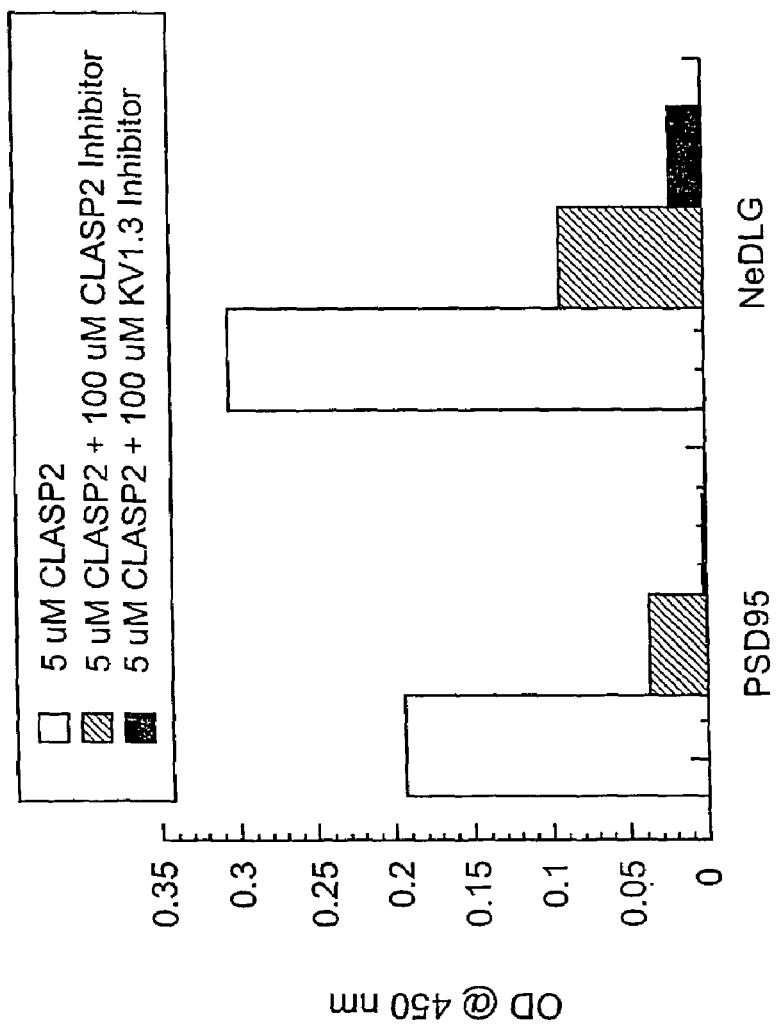
Figure 9D:
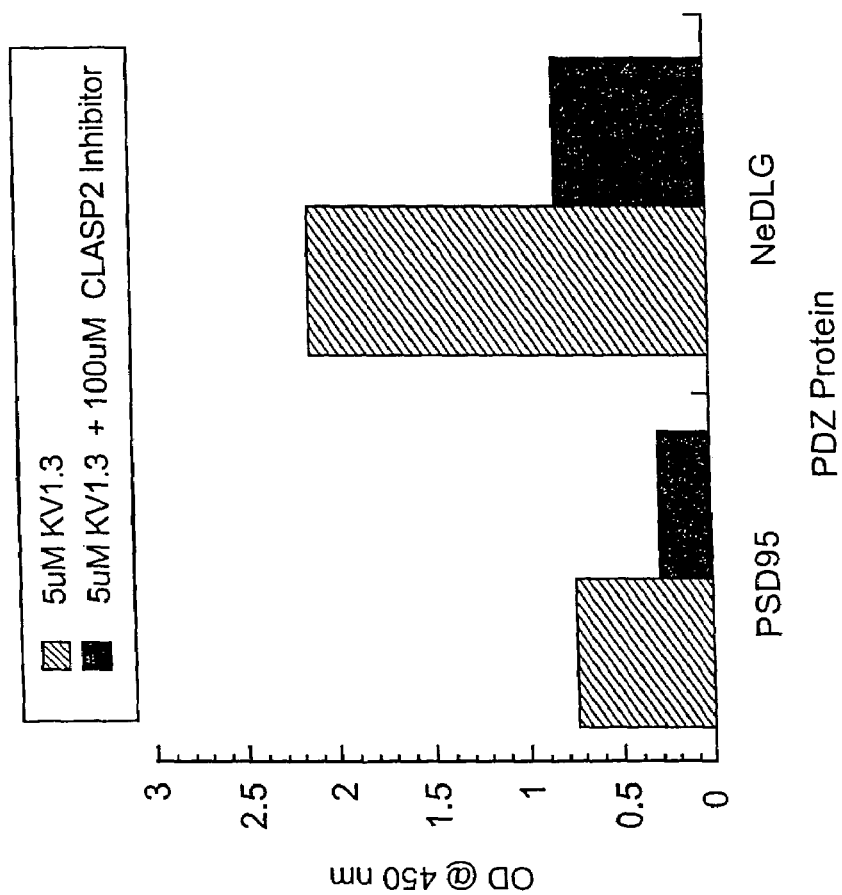

Biochemical evidence that CLASP-2 interacts with the PDZ domains of three closely related proteins is shown in FIG. 9A-D. FIG. 9A demonstrates the specificity of the interaction, as the C-terminal 20 amino acids of CLASP-2 bind PSD-95, NeDLG, and DLG1, but not to the PDZ domains of the TIAM-1 protein. FIG. 9B demonstrates the affinity of the interaction. Notably, the highest affinity interaction occurs between CLASP-2 and NeDLG, with a specific binding affinity of at least $10^4$ $M^{-1}$. Affinities in the micromolar range have been found for other biologically important PDZ-ligand interactions. FIG. 9C demonstrates the ability to inhibit CLASP-2 PDZ interactions using either a short fragment of CLASP-2 (the eight C-terminal amino acids) or the C-terminus of KV1.3. As noted above, KV1.3 is known to bind to DLG1 in live lymphocytes. FIG. 9D demonstrates that CLASP-2 and KV1.3 compete for PDZ binding; i.e., not only does KV1.3 block CLASP-2 binding but CLASP-2 also blocks KV1.3 binding. The ability of the eight C-terminal residues of CLASP-2 to inhibit the interaction of both CLASP-2 and KV1.3 with selected PDZ domains suggests that compounds related to the C-terminal eight-amino acids of CLASP-2, when introduced into cells, will mediate changes in multiple protein-protein interactions involved in the function of lymphoid tissues and other tissues that express these proteins (including heart, lung, and kidney).

Evidence that the C-terminal 8 amino acids of CLASP-2, when introduced into cells, can effect cellular function comes from the experiments in which these amino acids were introduced into cells as a fusion, e.g., with the HIV-derived TAT transporter peptide sequence. Addition of the TAT-CLASP-2 fusion peptide to Jurkat T lymphocytes (compared to controls using the TAT peptide alone) results in subtle, time-dependent alterations in intracellular calcium concentrations as measured using the calcium indicator dye Fluo-4. While these results are consistent with the hypothesis that the TAT-CLASP-2 fusion changes T cell ion fluxes. In particular, the results indicate that the CLASP-2 C-terminal sequence can slightly increase basal intracellular calcium concentrations and can slightly decrease the proportional increase in calcium upon activation of the cells with anti-CD3 antibody. Such changes would be expected for a compound that disrupts localization of the T cell activation-associated CLASP-2 protein and the KV1.3 potassium channel. Small changes in T cell calcium flux can result in large changes in the functional activity of the cells (Wulfing et al., 1997, J. Exp. Med. 185: 1815). Of note, the brain alternatively spliced isoform KIAA1058 lacks the PDZ binding domain due to an alternative splice.

5.2.1.9. Modulation of Immune Responses

CLASP proteins, as described above, modulate immune function in a variety of ways and through a variety of mechanisms (i.e., changing the threshold for T cell activation) by affecting formation of the immunological synapse. Establishment and maintenance of the immunological synapse can involve: (A) signal transduction, (B) cell-cell interactions, and (C) membrane organization.

(A) Signal Transduction

Human CLASP proteins, as discussed above, may contain SH3 domains and tyrosine phosphorylation sites. These regions have been shown to be involved in signal transduction in a variety of cells including lymphocytes. Thus, human CLASP proteins are believed to interact with these regions during signal transduction events which lead to modulation of immune responses.

CLASP proteins can interact with Tec sub-family of non-receptor tyrosine kinases. The Tec sub-family of nonreceptor tyrosine kinases consists of Tec, Btk, Tsk/Itk/Emt Itk, and Bmx, and is defined by the presence of SH3 and SH2 domains adjacent to the catalytic domain and an amino-terminal region containing a pleckstrin homology (PH) domain, a Tec homology (TH) domain, and a proline-rich region (Mano, H.; 1999, Cytokine Growth Factor Rev 10: 267-80). The T cell specific Tsk/Itk/Emt, and Btk expressed in most hematopoietic cells other than T cells are important components of antigen receptor signaling pathways in hematopoietic cells.

Btk has been identified as the gene defective in murine X-linked immunodeficiency (xid) and human X-linked agammaglobulinemia (XLA) (Nisitani, S., 2000, Proc Natl Acad Sci U.S.A. 97: 2737-42). In xid mice, B cell numbers are reduced to one-half of normal and the titers of specific immunoglobulin isotypes are significantly reduced; in addition, xid B cells are insensitive to a number of mitogenic stimuli. The human disorder is much more severe, resulting in nearly complete elimination of the B cell compartment and dramatically reduced immunoglobulin levels. Biochemical studies have supported multiple roles for Btk in B cell activation. Btk kinase activity and tyrosine phosphorylation are increased after cross-linking either the B cell receptor on B cells or the high affinity IgE receptor, FcRI, on mast cells. Interleukin-5 and interleukin-6 treatment have also been shown to lead to the activation of Btk.

Itk, like Btk, is tyrosine-phosphorylated upon antigen receptor cross-linking (Mano, H., 1999, Cytokine Growth Factor Rev, 10: 267-80). In addition, peripheral T cells from mice lacking functional Itk are refractory to stimulation by antibodies to CD3 plus antigen presenting cells. These Itk-deficient T cells can be stimulated by phorbol ester and calcium ionophore, demonstrating that Itk acts in signaling pathways proximal to the TCR.

Unlike the related Src family tyrosine kinases including Lyn, Lck, Fyn, ZAP-70, SyK, and CSK, the Tec family kinases lack the amino-terminal myristylation site crucial for the membrane localization of Src family kinases, suggesting that some adaptor proteins are required for the their membrane localization (Mano, H., 1999, Cytokine Growth Factor Rev 10: 267-80). Since all the Tec family kinases contain a proline-rich region which could be bound by a SH3 domain, and since all the human CLASPs contain a putative SH3 domain, it is believed that human CLASPs could serve as adaptors for the members in the Tec family in different hematopoietic cells.

GTP-binding proteins play an important role in immune response (Mach, B., 1999, Science 285: 1367). A number of biochemical events triggered by TCR/CD3-induced T cell activation are ablated by agents that modulate the action of G proteins. Pertinent to this is the ability of cholera toxin to inhibit the cellular proliferation and intracellular $Ca^{2+}$ mobilization that is mediated by anti-CD3 antibody treatment of T cells. The G protein competitive inhibitor GDPS, can impede the extent of inositol phosphates generated upon stimulation in peripheral T lymphocytes. Nonhydrolyzable analogs of GTP, such as GTPgammaS, or other agents such as ALF that activate G proteins by circumventing the need for receptor engagement, can result in T cell activation.

The $G\alpha q/11$ subfamily (Stanners, J., 1995, J Biol Chem 270: 30635-42) and Rap1 (Lafont, V., 1998, Biochem Pharmacol 55: 319-24) of GTP-binding proteins have been shown to be involved in human T cell receptor/CD3-mediated signal transduction pathway. Also, Cdc42, a Rho family small GTPase, is known to play a critical role in the formation of actin microspikes in response to external stimuli (Miki, H.; 1998, Nature, 391: 93-6). Interestingly, a Cdc42 binding protein, WASP, has a proline-rich domain which could interact with the SH3 domain present in all the human CLASPs. Human CLASPs may interact with these GTP-binding proteins.

Several adaptor proteins including NCK, CBL (Bachmaier, K., 2000 Nature 403: 211-6), SHC, LNK, SLP-76, HS1, SIT, VAV, GrB2, and BRDG1, and two tyrosine phosphotases, EZRIN, SHP-1 and SHP-2 have been shown to interact with ITAM or SH3 domains. These proteins may also interact with CLASPs. Several proteins have been shown to interact with ITAM or SH3 domains and may also interact with CLASP proteins. These include adaptor proteins such as NCK, CBL (Bachmaier, K., 2000, Nature 403: 211-6), SHC, LAT, LNK, SLP-76 (Krause M et al., 2000, J Cell Biol 149: 181-94), HS1, SIT, VAV, GrB2 (Zhang W. and Samelson, L. E., 2000, Semin Immunol 12: 35-41), and BRDG1, kinases such as SYK and LCK, and tyrosine phosphatases such as SHP-1 and SHP-2. These interactions can be defined by a number of different biochemical or cell biological methods including in vitro binding assays, co-immunoprecipitation assays, co-immunostaining (Harlow, E. and Lane, D., 1999, Using Antibodies: A laboratory Manual. Cold Spring Harbor Press) or genetic assays such as yeast the yeast two hybrid system, in which a CLASP protein or fragment can be used as "bait" (Zervos et al., 1993, Cell 72: 223-232; Madura et al., 1993, J. Biol. Chem 268: 12046-12054).

Other assays include in vitro binding assays, co-immunoprecipitation assays, co-immunostaining assays, and yeast two hybrid system screening assays in which a CLASP-2 domain or fragment can be used as "bait" or "trap" protein (Zervos et al. (1993), Cell 72: 223-232; Madura et al. (1993) J. Biol. Chem. 268: 12046-12054).

In other embodiments, CLASP polypeptides are transfected into lymphocytes. After transfection, a variety of standard assays can be used to evaluate, for example, CLASP modulation of T cell activation. These assays include calcium influx assays, NF-AT nuclear translocation assays (e.g., Cell, 1998, 93: 851-61), NF-AT/luciferase reporter assays (e.g., MCB 1996 16: 7151-7160), tyrosine phosphorylation of early response proteins such as HS1, PLC-γ, ZAP-76, and Vav (e.g., J. Biol. Chem. 1997, 272: 14562-14570).

(B) Cell-Cell Interaction

As discussed above, human CLASP proteins display homologous aspects of E-cadherin. As shown in FIG. 1, CLASP-2 contains both a cadherin cleavage domain and a cadherin ectodomain. Therefore CLASP proteins may interact with cadherins through these domains. The cadherins constitute a family of cell surface adhesion molecules that are involved in calcium-dependent cell to cell adhesion. Human cadherins, E-, P- N- and VE-cadherin, have a restricted tissue distribution: E- and P-cadherin are expressed in epithelial tissues, N-cadherin is found mainly on neural cells, and VE-cadherin is found on vascular endothelium. Homophilic binding between cadherins on adjacent cells is vital for the maintenance of strong cell to cell adhesion in these tissues. For example E-cadherin is required for the formation of adherens junctions between mature epithelial cells and is involved in Langerhans cell adhesion to keratinocytes, and VE-cadherin is needed for the maintenance of lateral association between endothelial cells. The extracellular regions of mature mammalian cadherins are comprised of five "CAD" modules of approximately 1110 amino acids. Crystallographic and biochemical studies indicate that cadherins can form dimers on the cell surface, and that interaction with dimeric cadherins on opposing cell surfaces can lead to the formation of "zipper-like" cell junctions.

The integrins are a second family of transmembrane adhesion molecules that are involved in both cell to cell and cell to matrix interactions. At least 15 chains associate with 8 chains to form a large number of heterodimeric integrins that can be classified into several major subfamilies based on their shared use of a particular chain. Members of three subfamilies, the 1, 2, and 7 integrins, are commonly found on leukocytes. The expression of 1 integrins is widespread (for example, 51, CD49e/CD29, is found on T cells, granulocytes, platelets, fibroblasts, endothelium, and epithelium), whereas the 2 and 7 integrins have a restricted pattern of expression.

Interestingly, E-cadherin on human epithelial cells has been found to be a ligand for the mucosal lymphocyte integrin, E7, and a similar interaction has been indicated in the mouse. Monoclonal antibodies to E-cadherin or to E7 block IEL adherence to epithelial cells, and transfection of cells with E7 confers upon them the ability to adhere to cells transfected with E-cadherin.

L929 cells can be transfected with CLASP and Neomycin. G418-resistant clones can be screened for CLASP-expression with anti-CLASP peptide-specific antibodies. CLASP-expressing clones can be used to test for homotypic and/or heterotypic calcium dependent cell adhesion using the "cell aggregation assay" described for cadherin molecules (Murphy-Erdosh, C. et al., 1995, J. Cell Biol. 129: 1379-1390).

Several approaches can be used to identify the amino acids involved in the binding domains. Soluble fusion molecules (e.g., EC12-IgG, ECC-IgG, ECM-IgG, and GST-EC12), peptides, and peptide-specific anti-CLASP antibodies are available for blocking experiments in the above-described assay. Transfectants generated by site-directed mutagenesis can also be used.

(C) Membrane Anchoring/Cytoskeletal Interactions

Interestingly, tyrosine-phosphorylated ITAMs interact with actin cytoskeleton upon activation of mature T lymphocytes (Rozdzial, M. M., 1995, Immunity 3: 623-633). Since human CLASPs contain both ITAMs and coiled-coil domains which have been shown to interact with cytoskeletal proteins, CLASPs are believed to play an important role in modulating cell surface molecule expression by re-organizing cytoskeletal structure.

F-actin microfilament cytoskeletal organization has been known to be involved in the modulation of cell surface molecule expression. WASP, a GTPase-binding protein, plays a critical role in the formation of actin microspikes in response to external stimuli and ectopic expression of WASP induces the formation of F-actin filament clusters that overlap with the expressed WASP itself. Another WASP family protein, N-WASP, has also been shown to play important roles in filopodium formation. Both of these proteins cause actin polymerization, but with different features when they are expressed in cells; WASP mainly localizes at perinuclear areas and causes actin clustering, but most N-WASP is present at plasma membranes and induces filopodium formation (Miki, H.; 1998, Nature 391: 93-6). Both WASP and N-WASP, contain a proline-rich domain which could interact with the SH3 domain present in all the human CLASPs. CLASPs may interact with F-actin filament through CLASP protein binding to WASP or WASP-like proteins.

Standard assays can be used for detecting CLASP protein interaction with cytoskeletal proteins. These assays include co-sedimentation assays, far western blot analysis (Ohba, T., 1998, Anal. Biochem. 262: 185-192), surface pasman resonance, F-actin staining with phalloidin in CLASP-transfected lymphocytes (e.g., Small, J. et al. 1999, Microsc. Res. Tech. 4: 3-17), and immunocytal analysis of subcellular distribution of focal adhesion proteins (such as paxillin, tensin, vinculin, talin, and FAK in CLASP-transfected lymphocytes; see, e.g., Ridyard, M. S., 1998, Biochem. Cell Biol. 76: 45-58).

5.2.2. CLASP-2 Exon Structure and Genomic Domains

Alternative splicing is likely to represent a regulatory switch that governs different functions of CLASP proteins in immune responses. Additionally, alternative splice variants affecting the untranslated regions of an RNA can be a way of regulating RNA stability.

As noted supra, CLASP gene expression is characterized by alternative exon usage. Intron/exon structure can be predicted by computer analysis of genomic DNA, however, splice junctions and alternative splicing can only be elucidated by comparison of genomic clones to cDNA clones. Alternative splicing and RNA editing are mechanisms generate a variety of proteins from the same gene. An example for how alternative splicing is used to generate thousands of different proteins from only a few genes is represented by the Neurexin gene family (for review of Neurexins, see Missler M. and Suedhof, T., 1998, Trends in Genetics, 14: 20-25). Comparative analysis of CLASP-2 genomic clones and cDNA clones revealed that CLASP-2 is composed of numerous exons and that distinct CLASP-2 transcripts are generated by alternative splicing. The protein encoding portion of CLASP-2 is covered by at least 14 exons (FIG. 6A).

Numerous diseases are caused or are thought to be caused by splice site mutations that can cause exon skipping or otherwise result in a truncated protein product Some of these diseases include, e.g., Marfan Syndrome (Liu W, et al., 1997, Nat. Genet. 16: 328-9), Hunter disease (Bonucelli G, et al., 2000, Hum. Mutat. (Online) 2000 15(4): 389, Duchenne muscular dystrophy (Wibawa T, et al., 2000, Brain Dev. 22(2): 107-112), Myelomonocytic leukemia (Wutz D, et al., 1999, Leuk. Lymphoma 35: 491-9.), and Isovaleric acidemia (Vockley J, et al., 2000, Am. J. Hum. Genet. 66: 356-67). This is especially true for genes composed of many exons (such as CLASP genes). The genomic sequence around CLASP exon/intron boundaries is useful for diagnostic approaches towards the identification of diseases caused by splice site mutations. The abundance or presence of CLASP isoforms in cell populations (e.g., hematopoietic cells, lymphocytes) is correlated with a disease state by comparing the abundance of CLASP in cells from subjects suffering from the disease with the level of CLASP in cells from healthy subjects. This can be accomplished by utilizing any number of assays (e.g., PCR).

Alignment of the CLASP-2 intron/exon splice sites with the CLASP-2 protein sequence and the finding of conserved exon/intron boundaries within the CLASP gene family (FIG. 6) suggest that specific CLASP-2 exons encode functionally distinct protein domains (see FIG. 6 and Example 4). ITAM and DOCK motifs 1 and 2 are encompassed by splice sites (amino acid residues 946 and 1063); DOCK motif 3 and COILED-COIL motif 1 and 2 are also encompassed by splice sites (amino acid residues 1102, 1170 and 1246, respectively).

CLASP-2 alternative transcripts are summarized in FIG. 3 and FIG. 11B. Briefly, one alternative exon missing in CLASP-2A is present in CLASP-2B and CLASP-2D. This exon contains the DNA portion encoding the ITAM motif and DOCK motif 1. The CLASP-2D protein product does not contain the C-terminal 38 amino acids of CLASP-2A and CLASP-2B: Thus, a PDZ binding motif (SSVV; amino acid residue 1286 through 1289) that is only present in the CLASP-2A/B-specific C-terminal end is missing in the CLASP-2D gene product. The presence or absence of this PDZ binding motif can be attributed to alternative RNA processing. Additionally, a CLASP-2 alternative transcript has been found that deletes nucleotides 209-291 that results in a premature stop codon. The protein encoded by this transcript appears to be a soluble form of CLASP-2 that may regulate (e.g., is an antagonist or an agonist) the function other CLASP family members and isoforms.

5.2.3. CLASP Superfamily Members

As is illustrated in FIG. 5, CLASP-2 is a member of a superfamily of immune-cell associated proteins with similar motifs. CLASP-1 was described in U.S. Ser. No. 09/411,328, filed Oct. 1, 1999 (abandoned). CLASP-1 uniquely among the known CLASPs contains SH3 binding domain motifs. CLASP-2A, -B, -C, and -E polypeptides have no adaptor binding sites or SH3 binding domains found in CLASP-1. CLASP-3, CLASP-4, CLASP-5 and CLASP-7 are described in U.S. Ser. No. 60/182,296, filed Feb. 14, 2000 (expired), and which is incorporated by reference herein in its entirely for all purposes.

5.3. CLASP mRNA Expression

Figure 4A:
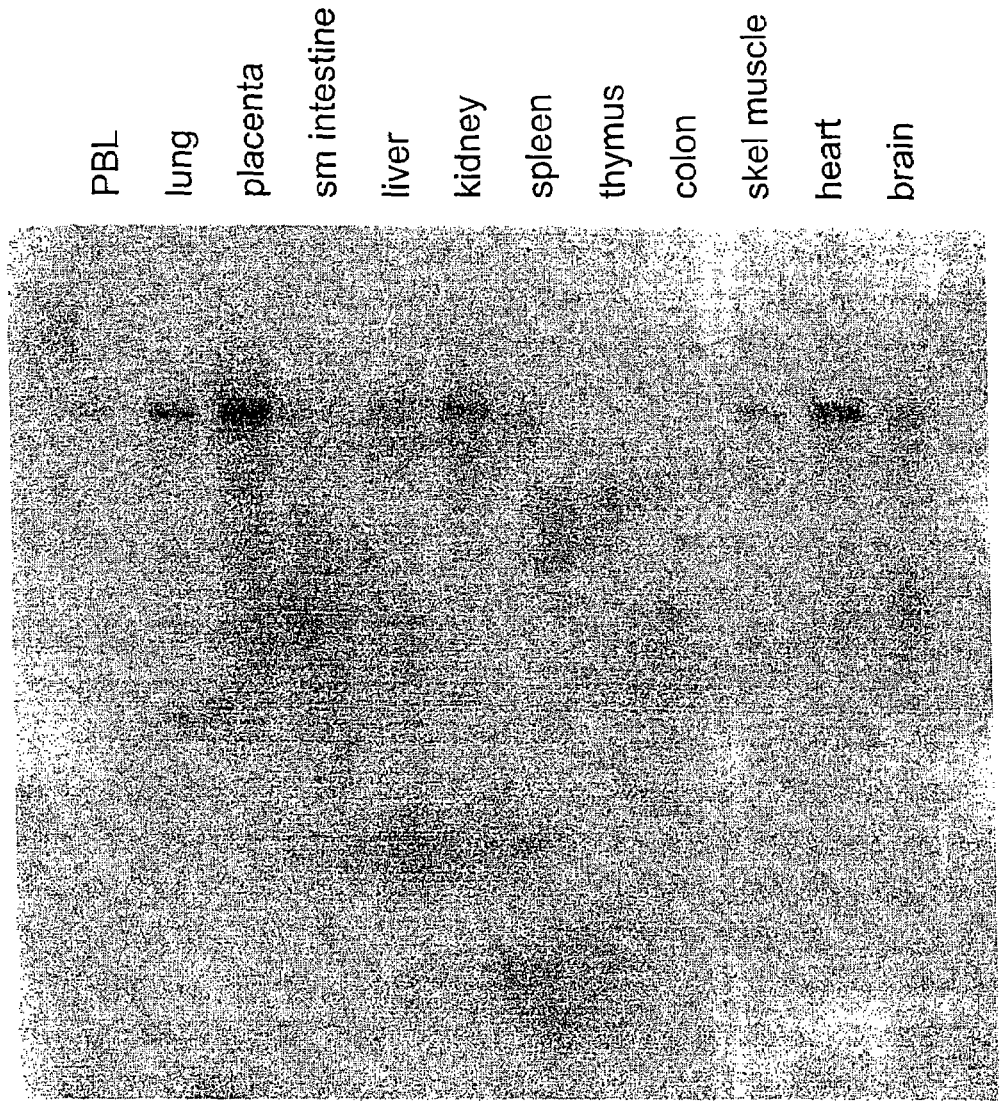
FIG. 4. Expression of CLASP-2 in human cell lines and human tissues as determined by Northern hybridization. A CLASP-2-specific DNA fragment was generated by PCR from a CLASP-2 cDNA clone (HC2-5'), using primers HC2AS2 and HC2S1. The fragment was labeled by incorporation of radioactive $^{32}P$ dCTP. A. Expression in human tissues. The labeled DNA fragment was used as a probe on a human Multiple Tissue Northern (Clonetech MTN Blot, #7780-1). A single band is clearly detect migrating at approximately 7.5 kb in placenta, heart kidney and lung in the Multiple Tissue Northern. Slight expression is detected in liver, skeletal muscle and brain. B. Expression in hematopoietic cell lines. A Northern with RNA from multiple cells lines was hybridized with the same hCLASP-2 probe. A similarly migrating band is detected in Jurkat (T-cell derived), 9D10 (B-cell derived) and 293 (human kidney derived) cell lines. There are multiple weaker bands in the 9D10 lane indicating possible splice variants of hCLASP-2. Weak expression is also detected in the mouse cell lines CH27 (B cell lymphoma) and 3A9 (T-cell hybridoma). Since hybridization and washing were carried out at high stringency, this indicates that the human CLASP-2 probe may cross-react with mouse CLASP mRNA.

As described in Example 2, CLASP-2 mRNA expression was assayed in tissues and cell lines by Northern analysis. The results are shown in FIGS. 4A and B. The results of Northern Analysis of CLASP expression and expression of other members of the CLASP family are summarized in Table 2.

TABLE 2

| Tissue/Cell Line[1] | CLASP | | | | | |
|---|---|---|---|---|---|---|
| | 1 | 2[3,4] | 3 | 4 | 5 | 7 |
| PBL | +[2] | − | − | +++ | ++ | − |
| Lung | − | + | − | − | −/+ | +++ |
| Placenta | −/+ | +++ | + | −/+ | + | + |
| Sm Intestine | −/+ | − | − | − | −/+ | + |
| Liver | −/+ | −/+ | −/+ | − | −/+ | + |
| Kidney | −/+ | + | +++ | −/+ | + | ++ |
| Spleen | ++ | − | − | −/+ | + | −/+ |
| Thymus | ++ | − | − | −/+ | + | − |

TABLE 2-continued

| | CLASP | | | | | |
|---|---|---|---|---|---|---|
| Tissue/Cell Line[1] | 1 | 2[3,4] | 3 | 4 | 5 | 7 |
| Colon | – | – | – | – | – | – |
| Skel Muscle | – | –/+ | ++ | – | – | –/+ |
| Heart | –/+ | ++ | +++ | –/+ | – | +++ |
| Brain | +++ | –/+ | –/+ | – | – | – |
| Jurkat | ++ | ++ | ++ | + | – | – |
| MV411 | ++ | – | ++ | + | + | + |
| THP1 | ++ | – | – | – | – | –/+ |
| HL60 | – | – | – | – | –/+ | – |
| 9D10 | ++ | ++[5] | + | + | + | + |
| 3A9 | + | –/+ | – | – | – | – |
| CH27 | + | –/+ | – | – | – | – |
| 293 | – | ++ | +++ | + | – | + |

[1]Jurkat = human T cell line; MV4-11 = B myelomonocyte; 9D10 = B cell line; THP-1 = monocyte; 3A9 = mouse T cell; CH27 = mouse B cell line; HL60 = human promyelocyte; 293 = embryonic kidney epithelial cells (293)
[2]Table Legend (based on Northern blot results): – = no expression; –/+ = low expression; + = medium expression; ++ medium high expression; +++ high expression.
[3]A CLASP-2 EST (EST 815795) was identified from a bone marrow cDNA library.
[4]The probe used (HC2.2) did not distinguish between CLASP-2A, -2B, -2C and 2D.. This probe encompasses nucleotides 3920 to 4650 (731 bp long) from CLASP-2A cDNA.
[5]In RNA from 9D10, the major transcript runs substantially shorter than the major transcripts seen in Jurkat and 293 cells; however, the longer transcript is also present in 9D10. Hybridization of probe HC2.2 with 9D10 total RNA reveals at least 3 different transcripts. See FIG. 4B As indicated in Table 2 and shown in FIG. 4, CLASP-2 is expressed most strongly in placenta followed by lung, kidney and heart; CLASP-3 is expressed strongly in kidney and heart, and less strongly in placenta and skeletal muscle; CLASP-4 is expressed exclusively in peripheral blood lymphocytes; CLASP-5 is expressed strongly in peripheral blood leukocytes, present in placenta, kidney, spleen and thymus, and weakly in lung, small intestine and liver. It is not expressed in brain, heart, skeletal muscle and large intestine; CLASP-7 is expressed strongly in lung, heart, liver and kidney, but not in PBL, brain or thymus.

Differences in tissue expression patterns for different CLASP proteins indicate different CLASPs have differential roles in immune function and, accordingly, can be separately targeted to achieve different functions. For example, since CLASP proteins are necessary for proper function or signaling by the T cell receptor (TCR), the tissue specific distribution of different CLASPs permits differential modulation of the immune response in different tissues. Since CLASP-2 is present in heart, blocking CLASP-2 function or expression is useful to selectively block immune response in the heart (for example, to selectively stop immune response in the heart compartment, e.g., following cardiac transplant rejection or post-MI inflammation, without compromising immunity elsewhere. Similarly, blocking CLASP-3 can block rejection of the kidney following kidney transplant. Furthermore, by adjusting the level of inhibition, the degree of immune blockage versus response can be modulated in the compartments represented by each CLASP.

5.4. CLASP Polynucleotides and Methods of Use

The present invention provides a variety of CLASP (e.g. CLASP-2) polynucleotides and methods for using them. In one aspect, the polynucleotide of the invention encodes a polypeptide comprising at least a fragment (e.g., an immunogenic fragment) of a CLASP-2 protein (e.g., at least a fragment of SEQ. ID. NO: 2, 4, 6 or 10) or variant thereof. In another aspect, the molecules that comprise a CLASP-2 polynucleotide that, while not necessarily encoding a CLASP-2 protein or fragment, is useful as a probe or primer for detecting CLASP-2 expression, for inhibition of CLASP-2 expression (e.g., antisense or ribozyme-mediated inhibition), for gene knockout, and the like.

5.4.1. CLASP Polynucleotides

The invention also provides isolated or purified nucleic acids having at least 8 nucleotides (i.e., a hybridizable portion) of a CLASP sequence (e.g., CLASP-2) or its complement; in other embodiments, the nucleic acids consist of at least about 25 (continuous) nucleotides, about 50 nucleotides, about 100 nucleotides, about 150 nucleotides, about 200 nucleotides, about 250 nucleotides, about 500 nucleotides, about 550 nucleotides, about 600 nucleotides, or about 650 nucleotides or more of a CLASP sequence, or a full-length CLASP coding sequence. In another embodiment, the nucleic acids are smaller than about 35, about 200 or about 500 nucleotides in length. Polynucleotides can be single or double stranded, and may be DNA, RNA, PNA or a hybrid molecule.

In specific aspects, nucleic acids are provided which comprise a sequence complementary to at least about 10, 25, 50, 100, 150, 200, 250, 500, 550, 600, or 650 nucleotides or the entire coding region of a CLASP coding sequence. Usually, the isolated polynucleotide is less than about 100 kbp, generally less than about 50 kbp, and often less than about 20 kbp, less than about 10 kbp, less than about 5 kbp, or less than about 1000 nucleotides in length.

In a specific embodiment, a nucleic acid that is hybridizable to a CLASP nucleic acid or its complement, or to a nucleic acid encoding a CLASP derivative, under conditions of low stringency is provided. Derivatives of CLASP contemplated include, but are not limited to, splice variants of a gene encoding a CLASP, other members of a CLASP gene family which differ from one of the CLASP nucleotide or amino acid sequences disclosed herein by the insertion or deletion of one or several domains, and the like.

In one embodiment, the CLASP polynucleotide is identical or exactly complementary to SEQ. ID NO: 1, 3, 5 or 9 or selectively hybridizes to an aforementioned sequence. In various embodiments, the polynucleotide is identical or exactly complementary to, or selectively hybridizes to, the nucleotide sequence encoding a particular protein domain or region, or a particular gene exon of the CLASP mRNA or genomic sequence. Such polynucleotides are particularly useful as probes, because they can be selected to identify a defined species of CLASP.

In addition to the polypeptide and polynucleotide sequences specifically exemplified herein, the invention contemplates CLASP homologues from other species, allelic and splice variants, and other variants disclosed herein. The CLASP-2 gene exhibits evidence of alternative splicing of transcripts.

For example, CLASP-2A and CLASP-2C are related to each other as apparent splice variants, with CLASP-2C containing an exon not found in CLASP-2A. The exon sequence is 5'-AGG GAT TTT GAG AGG CTG GCC CAT CTG TAT GAC ACG CTG CAC CGG GCC TAC AGC AAA GTG ACC GAG GTC ATG CAC TCG GGC CGC AGT TNC TGG GGA CCT ACT TCC GGG TAG CCT TCT TCG GGC AG-3' (SEQ ID NO:91)(encoding the peptide sequence: RDFERLAHLYDTLHRAYSKVTEVMHSGRRLLGTYFRVAFFGQGF) (SEQ ID NO:94). It will be apparent to one of skill that, by using polynucleotide probes or primers corresponding to the nucleic acid sequence above, or by using antibodies that specifically recognize the peptide above, or those polynucleotide probes or primers shown in Table 3 below, it is possible to distinguish between different CLASP isoforms (e.g., to detect differential expression).

TABLE 3

| Found in/will detect | Exemplary Probe/Primer (5'-3') | Notes/Comments |
|---|---|---|
| 1 full length hC2A | F1: CCCAGATTTTTATGATGAG (SEQ ID NO:95)<br>R1: GATAATGACAAAGTTCTGAC (SEQ ID NO:96) | |
| 2 full length hC2D | F2: CTGGAAATCTTGACAAAAATGC (SEQ ID NO:97)<br>R2: GTCTTTTTAATACAGATGTGG (SEQ ID NO:98) | |
| 3 hC2B, hC2C, hC2E | F3: GAGAGGCTGGCCCATCTGTATG (SEQ ID NO:99)<br>R3: ATCTTCAAAGAATCCCTGCC (SEQ ID NO:100) | Distinction based upon product size differences following PCR |
| 4 hC2D | F4: GAAGCAGTCCAGTGGGAGCCA (SEQ ID NO:101)<br>R4: GCCTCCCCGGCTCCTCCTCAGG (SEQ ID NO:102) | Recognizes hC2D-specific insertion |
| 5 hC2D | F3: GAGAGGCTGGCCCATCTGTATG (SEQ ID NO:99)<br>R5: CCTCCACATCTGTTTCACTGTC (SEQ ID NO:103) | |
| 6 hC2E | F5: CTCCATGATGGAAGACGTGGG (SEQ ID NO:104)<br>R6: GATGAGCTCGTAGCGCTCGGC (SEQ ID NO:105) | Spans deletion unique to hC2E. Distinction based upon product size differences following PCR |
| 7 hC2B | F6: CATTGGCGTTTAAGCTCCTG (SEQ ID NO:106)<br>R3: ATCTTCAAAGAATCCCTGCC (SEQ ID NO:100) | F6 primer spans deletion unique to hC2E |
| 8 hC2A | F7: GGACCCATAGTTCATGATCG (SEQ ID NO:107)<br>R4: CTTCATCTTCAAGAAATCCCTC (SEQ ID NO:108) | R4 primer spans the region where other CLASPs have an insert |

5.4.1.1. Substantial Identity

In some embodiments, the CLASP polynucleotides of the invention are substantially identical to SEQ ID NOs: 1, 3, 5, or 9, or to a fragment thereof.

An indication that two nucleic acid sequences are substantially identical is that the two polynucleotides have a specified percentage sequence identity e.g., usually at least about 75%, at least about 80%, at least about 85%, at least about 90%, at least about 95%, or at least about 98 identity over a specified region when optimally aligned.

Another indication that two nucleic acid sequences are substantially identical is that a polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

Yet another indication that two nucleic acid sequences are substantially identical (e.g., a naturally occurring allele of the CLASP sequence of SEQ ID NO: 1) is that the same primers can be used to amplify the sequence. For example, CLASP-2 polynucleotides can be PCR amplified from cDNA derived from human lymphocytes using the primer pairs shown in Table 3.

The primers of Table 3 are also useful for amplification of CLASP-2 splice variants. Another indication that two nucleic acid sequences are substantially identical is that they selective hybridize under stringent conditions (i.e., one sequence hybridizes to the complement of the second sequence), as described infra.

5.4.1.2. Selective Hybridization

The invention also relates to nucleic acids that selectively hybridize to exemplified CLASP-2 sequences (including hybridizing to the exact complements of these sequences). Selective hybridization can occur under conditions of high stringency (also called "stringent hybridization conditions"), moderate stringency, or low stringency.

5.4.1.2.1. High Stringency

"Stringent hybridization conditions" are conditions under which a probe will hybridize to its target subsequence, typically in a complex mixture of nucleic acid, but not to other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. In a specific embodiment, a nucleic acid which is hybridizable to a CLASP-2 nucleic acid under the following conditions of high stringency is provided: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 8-16 h at 65° C. in prehybridization mixture containing 100 µg/ml denatured salmon sperm DNA and 5-20×10$^6$ cpm of $^{32}$P-labeled probe. Washing of filters is done at 65° C. for 15-30 h in a solution containing 2×SSC, 0.1% SDS. This is followed by a wash in 0.2×SSC and 0.1% at 50° C. for 15-30 min before autoradiography.

5.4.1.2.2. Moderate Stringency

In another specific embodiment, a nucleic acid, which is hybridizable to a CLASP-2 nucleic acid under conditions of moderate stringency is provided. Examples of procedures using such conditions of moderate stringency are as follows: Filters containing DNA are pretreated for 6 h at 55° C. in a solution containing 6×SSC, 5× Denhart's solution, 0.5% SDS and 100 μg/ml denatured salmon sperm DNA. Hybridizations are carried out in the same solution and 5-20×10$^6$ cpm $^{32}$P-labeled probe is used. Filters are incubated in hybridization mixture for 12-16 h at 55° C., and then washed twice for 30 minutes at 50° C. in a solution containing 1×SSC and 0.1% SDS. Filters are blotted dry and exposed for autoradiography. Other conditions of moderate stringency which can be used are well-known in the art. Washing of filters is done at 45° C. for 1 h in a solution containing 0.2×SSC and 0.1% SDS.

5.4.1.2.3. Low Stringency

By way of example and not limitation, procedures using such conditions of low stringency are as follows (see also Shilo and Weinberg, 1981, Proc. Natl. Acad. Sci. U.S.A. 78: 6789-6792): Filters containing DNA are pretreated for 6 h at 40 C in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 g/ml salmon sperm DNA, 10% (wt/vol) dextran sulfate, and 5-20×10$^6$ cpm $^{32}$P-labeled probe is used. Filters are incubated in hybridization mixture for 18-20 h at 40 C, and then washed for 1.5 h at 55 C in a solution containing 2×SSC and 0.1% SDS. The wash solution is replaced with fresh solution and incubated an additional 30 minutes at 50-55° C. Filters are blotted dry and exposed for autoradiography. If necessary, filters are washed for a third time at 60-65° C. and reexposed to film. Other conditions of low stringency that can be used are well known in the art (e.g., as employed for cross-species hybridizations).

5.4.1.3. CLASP Variants and Fragments

The CLASP variants of the invention can contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. CLASP polynucleotide variants can be produced for a variety of reasons, e.g., to optimize codon expression for a particular host (change codons in the human mRNA to those preferred by a bacterial host such as E. coli).

Exemplary CLASP polynucleotide fragments are preferably at least about 15 nucleotides, and more preferably at least about 20 nucleotides, still more preferably at least about 30 nucleotides, and even more preferably, at least about 40 nucleotides in length, or larger 50, 150, 200, 250, 300, 350, 400, 450, 500, 550, 600, 650 nucleotides. In one embodiment, exemplary fragments include fragments having at least a sequence from about nucleotide number 1-50, 51-100, 101-150, 151-200, 201-250, 251-300, 301-350, 351-400, 401-450, 451-500, 501-550, 551-600 to the end of any sequence shown in the figures or in the sequence listing or comprising the cDNA coding sequence in the deposited clones. In this context "about" includes the particularly recited ranges, larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein.

In other embodiments, CLASP-2 polynucleotides of the invention are other than SEQ ID NO: 1 or fragments of SEQ ID NO: 1.

There are at least three CLASP-2 full length cDNA isoforms (A+Z, B+Z, and C+Z). Each of the isoforms uses a unique first exon (designated exon 1A, (SEQ ID NO: 115, corresponding to −182 to −102), 1B (SEQ ID NO: 116,corresponding to −219 to −102) and 1C (SEQ ID NO: 117, corresponding to −143 to −102), followed by exon 2 and the rest of human CLASP2 DNA, shown in SEQ ID NO: 118, Corresponding to −101 to 6690)(see Table 4 below).

TABLE 4

| CLASP-2 Isoforms | | |
|---|---|---|
| CLASP-2 Isoform | Schematic | Nucleotides |
| Isoform 1 | A + Z | −182 to 6690 |
| Isoform 2 | B + Z | −219 to 6690 |
| Isoform 3 | C + Z | −143 to 6690 |

In one embodiment, the CLASP-2 polynucleotide has the sequence of (Isoform 1, Isoform 2, or Isoform 3 as indicated in Table 4 above) or a fragment of these sequences comprising at least about 1, 5, 10, 25 or 50 or more contiguous nucleotides from nucleotides −182 to 1883 of Isoform 1, nucleotides −219 to 1883 of Isoform 2, or nucleotides −143 to 1883 of Isoform 3.

In another embodiment, CLASP-2 primers or probes comprise at least about 5, 10, 25 or 50 or more contiguous nucleotides from nucleotides −182 to 1883 of Isoform 1, nucleotides −219 to 1883 of Isoform 2, or nucleotides −143 to 1883 of Isoform 3 as shown in Table 4 and Table 4 above alone or in combination with SEQ ID NO: 1 or a fragment of SEQ ID NO:1.

In an aspect, the invention provides antibodies or binding fragments that bind the CLASP. In another embodiment, the invention provides antibodies that specifically bind to the CLASP-2 isoforms in Table 4 but not to the polypeptide encoded by SEQ ID NO:1.

In one embodiment, the CLASP variants differ from those shown in FIG. 1 (SEQ ID NOs 1, 3, 5, 7, 9, 115-118, etc by virtue of incorporating a different combination of exons than found in the exemplified sequences. For example, 81 g01 (Genbank Accession Number AF85864; Locus HUMYN81g01; 526 bp; EST sequence submitted Aug. 29, 1998 by Washington University at St. Louis; see FIG. 3A and FIG. 3B) is a variant of hCLASP-2 on the basis of CLASP-2 identity along certain stretches of the sequence. From 5' to 3', it begins with a 315 nucleotide stretch which is identical to CLASP-2A. It then has a gap relative to CLASP-2A that is identical to the GAP in another CLASP-2 isoform, hCLASP-2D (KIAA1058). In place of that gap, a 16 amino acid insert (48 nucleotides) is present which is not found in other isoforms, followed by another approximately 150 bp stretch of nucleotides once again identical to CLASP-2A. This is characteristic of an alternate splice due to the specific sequence identity on both sides of a differential stretch of nucleotides.

Using known methods of protein engineering and recombinant DNA technology, variants can be generated to improve or alter the characteristics of the CLASP polypeptides. For instance, one or more amino acids can be deleted from the N-terminus or C-terminus of the CLASP-2 protein without substantial loss of biological function.

Furthermore, even if deleting one or more amino acids from the N-terminus or C-terminus of a polypeptide results in modification or loss of one or more biological functions, other biological activities can still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N or C-terminal residues of a protein retains such immunogenic activities can readily be determined by routine methods described herein and otherwise known in the art.

Thus, the invention further includes CLASP polypeptide variants which show biological activity. Such variants include deletions, insertions, inversions, repeats, and substitutions selected according to general rules known in the art so as have little effect on activity. For example, guidance concerning how to make phenotypically silent amino acid substitutions is provided in Bowie, J. U. et al., Science 247: 1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at 30 specific positions of a cloned gene to identify regions critical for protein function. For example, site directed mutagenesis or alanine-scanning mutagenesis (introduction of single alanine mutations at every residue in the molecule) can be used. (Cunningham and Wells, 1989, Science 244: 1081-1085) The resulting mutant molecules can then be tested for biological activity.

In various embodiments, CLASP-2 polynucleotide fragments include coding regions for, or regions hybridizable to, the CLASP-2 structural or functional domains described supra. As set out in the Figures, such preferred regions include the following domains/motifs: ITAM, DOCK, COILED/COILED, and PBM. Thus, for example, polypeptide fragments of CLASP-2 as shown in FIG. 1 and in Table 4(SEQ ID NO: 2, 4, 6, 10, 115, 116, 117, etc.,) falling within conserved domains are specifically contemplated by the present invention (see FIG. 3). Moreover, polynucleotide fragments encoding these domains are also contemplated. Such polypeptide fragments find use, for example, as inhibitors of CLASP-2 function in CLASP-2-expressing cells.

5.4.2. Uses of CLASP-2 Polynucleotides

The CLASP polynucleotides of the invention are useful in a variety of applications. In one aspect of the invention, the polypeptide-encoding CLASP polynucleotides of the invention are used to express CLASP polypeptides (e.g., as described herein) for example to produce anti-CLASP-antibodies or for use as therapeutic polypeptides. In another aspect, the CLASP polynucleotide or fragments thereof can be used for diagnostic purposes (e.g., as probes for CLASP-2 expression). In particular, since CLASPs can be expressed in lymphocytes, a CLASP polynucleotide can be used to detect the expression of CLASP as a lymphocyte marker. For diagnostic purposes, a CLASP polynucleotide can be used to detect CLASP gene expression or aberrant CLASP gene expression in disease states. In another aspect, the CLASP polynucleotide or fragments are used for therapeutic purposes. For example, included in the scope of the invention are methods for inhibiting CLASP expression, e.g., using oligonucleotide sequences, such as antisense RNA and DNA molecules and ribozymes, that function to inhibit expression of CLASP. In another aspect, CLASP polynucleotides can be used to construct transgenic and knockout animals, e.g., for screening of CLASP agonists and antagonists. In another aspect, CLASP polynucleotides can be used for screening of CLASP agonists and antagonists.

5.4.2.1. Use of CLASP-2 Polynucleotides for Detection, Diagnosis, and Treatment

The CLASP polynucleotides of the invention are useful for detection of CLASP expression in cells and in the diagnosis of diseases or disorders (e.g., immunodeficient states) resulting from aberrant expression of the CLASP. For example, aberrant expression of CLASP mRNA or protein means expression in lymphocytes (e.g., T lymphocytes or B lymphocytes) or other CLASP expressing cells of at least 2-fold, preferably at least 5-fold greater or less than expression in control lymphocytes obtained from a healthy subject. CLASP polypeptide expression is easily measured by ELISA using anti-CLASP antibodies of the invention. CLASP mRNA expression (including expression of specific species or splice variants of CLASP) can be measured by quantitative Northern analysis or quantitative PCR, LCR, or other methods, using the probes and primers of the invention.

In one embodiment, the assays of the present invention are amplification-based assays for detection of an CLASP-2 gene product. In an amplification based assay, all or part of a CLASP-2 mRNA or cDNA (hereinafter also referred to as "target") is amplified, and the amplification product is then detected directly or indirectly. When there is no underlying gene product to act as a template, no amplification product is produced (e.g., of the expected size), or amplification is non-specific and typically there is no single amplification product. In contrast, when the underlying gene or gene product is present, the target sequence is amplified, providing an indication of the presence and/or quantity of the underlying gene or mRNA. Target amplification-based assays are well known to those of skill in the art.

The present invention provides a wide variety of primers and probes for detecting CLASP-2 genes and gene products. Such primers and probes are sufficiently complementary to the CLASP-2 gene or gene product to hybridize to the target nucleic acid. Primers are typically at least 6 bases in length, usually between about 10 and about 100 bases, typically between about 12 and about 50 bases, and often between about 14 and about 25 bases in length, often PCR primers of 15-30 (e.g., 18-22 nucleotides) are used. However, the length of primers can be adjusted by one skilled in the art. One of skill, having reviewed the present disclosure, will be able, using routine methods, to select primers to amplify all, or any portion, of the CLASP-2 gene or gene product, or to distinguish between variant gene products, CLASP-2 alleles, and the like. Single oligomers (e.g., U.S. Pat. No. 5,545,522), nested sets of oligomers, or even a degenerate pool of oligomers can be employed for amplification.

It will be appreciated that probes and primers can be selected to distinguish between species and splice variants based on the guidance of this disclosure, by targeting primers or probes to differentially used exons (or exon-exon junctions that differ between variants).

Methods can include the steps of collecting a sample of cells from a patient, isolating nucleic acid (e.g., genomic, mRNA or both) from the cells of the sample, contacting the nucleic acid sample with one or more primers which specifically hybridize to an CLASP-2 gene under conditions such that hybridization and amplification of the CLASP-2-gene (if present) occurs, and detecting the presence or absence of an amplification product, or detecting the size of the amplification product and comparing the length to a control sample. See U.S. Pat. Nos. 4,683,195 and 4,683,202, Landegran et al., 1988, Science 241: 1077-1080; Nakazawa et al., 1994, Proc. Natl. Acad. Sci. U.S.A. 91: 360-364, Abravaya et al., 1995, Nucleic Acids Res. 23: 675-682).

Because CLASP-2 gene products are expressed in the immune system (e.g., T lymphocytes, B lymphocytes and macrophages), expression will be typically assayed in these cells. Methods which are well known to those skilled in the art can be used to isolate lymphocytes, macrophages, and alike (See, e.g., Coligan, J. E., et al. (eds.), 1991, Current Protocols in Immunology, John Wiley & Sons, NY; this reference is incorporated by reference for all purposes). In one embodiment, assays are carried out on biopsy or autopsy-derived tissue.

In various embodiments, CLASP-2 gene expression is detected by hybridization of a detectable probe to mRNA or cDNA obtained from cells (e.g., lymphocytes). A variety of methods for specific DNA and RNA measurement using nucleic acid hybridization techniques are known to those of skill in the art (see Sambrook et al., supra). Hybridization based assays refer to assays in which a probe nucleic acid is hybridized to a target nucleic acid, forming a hybridization complex. Usually the nucleic acid hybridization probes of the invention are entirely or substantially identical to a contiguous sequence of the CLASP-2 gene or RNA sequence. Preferably, nucleic acid probes are at least about 50 bases, often at least about 20 bases, and sometimes at least about 200 bases, at least about 300-500 nucleotides or more in length. Various hybridization techniques are well known in the art, and are in fact the basis of many commercially available diagnostic kits.

Methods of selecting nucleic acid probe sequences for use in nucleic acid hybridization are discussed in Sambrook et al., supra. In some formats, at least one of the target and probe is immobilized. The immobilized nucleic acid can be DNA, RNA, or another oligo- or poly-nucleotide, and can comprise natural or non-naturally occurring nucleotides, nucleotide analogs, or backbones. Such assays can be in any of several formats including: Southern, Northern, dot and slot blots, high-density polynucleotide or oligonucleotide arrays (e.g., GeneChips™ Affymetrix), dip sticks, pins, chips, or beads. All of these techniques are well known in the art and are the basis of many commercially available diagnostic kits. Hybridization techniques are generally described in Hames et al., ed., 1985, Nucleic Acid Hybridization, A Practical Approach IRL Press; Gall and Pardue, 1969, Proc. Natl. Acad. Sci. U.S.A., 63: 378-383; and John et al., 1969, Nature, 223: 582-587.

A variety of nucleic acid hybridization formats are known to those skilled in the art. For example, one common format is direct hybridization, in which a target nucleic acid is hybridized to a labeled, complementary probe. Typically, labeled nucleic acids are used for hybridization, with the label providing the detectable signal. One method for evaluating the presence, absence, or quantity of CLASP-2 mRNA is carrying out a Northern transfer of RNA from a sample and hybridization of a labeled CLASP-2 specific nucleic acid probe. A useful method for evaluating the presence, absence, or quantity of DNA encoding CLASP-2 proteins in a sample involves a Southern transfer of DNA from a sample and hybridization of a labeled CLASP-2 specific nucleic acid probe.

Other common hybridization formats include sandwich assays and competition or displacement assays. Sandwich assays are commercially useful hybridization assays for detecting or isolating nucleic acid sequences. Such assays utilize a "capture" nucleic acid covalently immobilized to a solid support and a labeled "signal" nucleic acid in solution. The biological or clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

In one embodiment, CLASP polypeptides or polynucleotides are useful in treating deficiencies or disorders of the immune system, by activating or inhibiting the activation, differentiation of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders can be genetic, somatic, such as cancer or some autoimmune disorders, acquired (e.g., by chemotherapy or toxins), or infectious.

In another embodiment, CLASP-2 polynucleotides or polypeptides are useful in treating or detecting deficiencies or disorders of hematopoietic cells. CLASP-2 polypeptides or polynucleotides could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g., agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

In one embodiment, CLASP-2 polynucleotides or polypeptides are useful in treating or detecting autoimmune diseases. The term "autoimmune disease" as used herein has the normal meaning in the art and refers to a spontaneous or induced malfunction of the immune system of mammals in which the immune system fails to distinguish between foreign immunogenic substances within the mammal and/or autologous ("self") substances and, as a result, treats autologous ("self") tissues and substances as if they were foreign and mounts an immune response against them. Autoimmune disease is characterized by production of either antibodies that react with self tissue, and/or the activation of immune effector T cells that are autoreactive to endogenous self antigens. Three main immunopathologic mechanisms act to mediate autoimmune diseases: 1) autoantibodies are directed against functional cellular receptors or other cell surface molecules, and either stimulate or inhibit specialized cellular function with or without destruction of cells or tissues; 2) autoantigen—autoantibody immune complexes form in intercellular fluids or in the general circulation and ultimately mediate tissue damage; and 3) lymphocytes produce tissue lesions by release of cytokines or by attracting other destructive inflammatory cell types to the lesions. These inflammatory cells in turn lead to production of lipid mediators and cytokines with associated inflammatory disease.

Since many autoimmune disorders result from inappropriate recognition of self as foreign material by immune cells.

This inappropriate recognition results in an immune response leading to the destruction of the host tissue. Therefore, the administration of CLASP-2 polypeptides or polynucleotides that can inhibit an immune response, particularly the proliferation, or differentiation of T-cells, can be an effective therapy in preventing autoimmune disorders.

Examples of autoimmune disorders that can be treated or detected by CLASP-2 include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, can also be treated by CLASP-2 polypeptides or polynucleotides. Moreover, CLASP-2 can be used to treat anaphylaxis or hypersensitivity to an antigenic molecules.

In one embodiment CLASP-2 polynucleotides or polypeptides are used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of CLASP-2 polypeptides or polynucleotides that inhibits an immune response, particularly the proliferation, differentiation of T-cells, can be an effective therapy in preventing organ rejection or GVHD.

Similarly, in another embodiment, CLASP-2 polypeptides or polynucleotides are used to modulate inflammation. The term "inflammation" refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils.

For example, CLASP-2 polypeptides or polynucleotides can inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.). Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

In another embodiment CLASP-2 polypeptides or polynucleotides are used to treat or detect infectious agents. For example, by increasing the immune response, particularly increasing the proliferation and differentiation of B and/or T cells, infectious diseases can be treated. The immune response can be increased by either enhancing an existing immune response, or by initiating a new immune response. CLASP-2 polypeptides or polynucleotides can be used to treat or detect any of these symptoms or diseases.

5.4.2.2. Use of CLASP Polynucleotides in Screening

The presence or absence of hCLASP nucleotide and amino acid sequences in a biological sample can be used in screening assays as medical diagnostics to aid in clinical decision-making. In one embodiment, bCLASP-based diagnostics involves screening assays for vaginal bleeding of unknown cause. In several examples discussed below, the cause of the bleeding can be in part differentiated by knowledge of whether the vaginal bleeding contains placental components (Hart F D, Ed., 1985, French's Index of Differential Diagnosis, 12th Ed. John Wright & Sons, pp. 561-63). In these cases, the high expression of hCLASP nucleotide sequences in placenta relative to its low expression in blood (FIG. 4A) will allow the detection of the presence of placenta based on the presence of the hCLASP nucleotide or protein. Such detection can be achieved by quantitative RT-PCR, Northern analysis, Western analysis, ELISAs, and fluorescence activated cell sorting (FACS) by using labeled anti-hCLASP-2 antibodies (Sambrook et al., 1989, Molecular Cloning, 2nd Ed., Cold Spring Harbor Lab. Press; Harlow et. al., 1988, Antibodies, a laboratory manual, Cold Spring Harbor Lab. Press).

For example, hCLASP can be used in the following screening assays:

(1) A woman gives birth and presents with post-partum bleeding. In this case the presence of placental tissue indicates a condition called "retained products of conception" that requires surgical evacuation of the uterus (Decherney and Pernol, Eds., 1996, Current Obstetric & Gynecologic Diagnosis & Treatment, 8th Ed. McGraw Hill).

(2) A pregnant woman suffers from vaginal bleeding of unknown origin. In this case the presence of placental tissue indicates a condition called "threatened abortion" that implies a poor prognosis for carrying the fetus to term (Decherney and Pernol, Eds., 1996, Current Obstetric & Gynecologic Diagnosis & Treatment, 8th Ed. McGraw Hill).

(3) A woman of child bearing age presents with vaginal bleeding and is found to have a positive pregnancy test without evidence of an intra-uterine pregnancy. In this case, the most serious of the differential diagnoses is ectopic pregnancy, a medical emergency. However, another common diagnosis is a completed abortion or miscarriage. The presence of products of conception (i.e. placenta) in the vaginal bleeding strongly favors the diagnosis of completed abortion over that of ectopic pregnancy (Decherney and Pernol, Eds., 1996, Current Obstetric & Gynecologic Diagnosis & Treatment, 8th Ed. McGraw Hill).

In another embodiment, hCLASP-2-based diagnostics involve screening assays to determine injury to vital tissues that express hCLASP-2 at high levels. Such tissues include kidney, heart, and lung (FIG. 4A). Injury to these tissues can result in leakage of cells and cellular constituents including hCLASP-2 into surrounding fluids (specified below). Detection of abnormally high levels of hCLASP-2 protein in these surrounding fluids by Western analysis or ELISA, or detection of abnormally high levels of hCLASP-2 RNA in these fluids by RT-PCR or Northern analysis is expected to aid in the diagnosis of tissue injury.

In the case of renal injury, the hCLASP-2 nucleotide or amino acid sequences or fragments thereof would be expected to appear in the urine. Detection of abnormally high levels of hCLASP-2 can aid in the diagnosis of both nephritis and tubular necrosis, and differentiate from non-renal causes of proteinuria. Early diagnosis of nephritis is of particular value in patients with clinical signs and symptoms suggestive of systemic lupus erythematosis in whom early diagnosis and treatment of lupus nephritis can prevent irreversible kidney damage (Cameron J. S., 1999, J Nephrol 12 Suppl 2: S29-41). While tubular necrosis currently cannot be reversed by pharmacotherapy, differentiation of tubular necrosis from pre-renal failure is critical in formulating a treatment plan for oligouric hospitalized patients (Bidani A. and Churchill P. C., 1989, Dis Mon 35: 57-132).

In the case of myocardial injury, the hCLASP-2 nucleic or amino acid sequence or fragments thereof are expected to appear in the blood. This is analogous to current standard practice of monitoring for other elevated levels myocardial proteins (e.g., creatine kinase, troponin) in the blood following myocardial infarction and ischemia by standard ELISA or electrophoretic methodologies (Fauci et al., (eds.), 1998, Harrison's Principles of Internal Medicine, 14th Ed., McGraw Hill, pp. 1352-1375). The presence of hCLASP-2 in cardiac muscle and its absence in skeletal muscle and blood makes hCLASP-2 an ideal marker to diagnose and monitor myocardial injury.

Unlike myocardial injury, pulmonary injury is not routinely diagnosed by assaying serum for lung-specific proteins. By analogy to myocardial infarction, pulmonary infarction also releases lung-specific proteins and cells into systemic circulation. Pulmonary infarction due to pulmonary embolism (PE) or pneumonia is expected to release hCLASP-2-bearing cells or protein/peptides into systemic circulation. Detection of hCLASP-2 protein in serum or RNA in blood can aid in the diagnosis of pulmonary infarction in the appropriate clinical setting. Current methods to diagnose PE are not only expensive but lack specificity and sensitivity, and the misdiagnosis of this condition is a leading cause of preventable death in hospitalized patients (Raskob G. E. and Hull R. D., 1999, Curr Opin Hematol. 6(5): 280-4).

Figure 4B:
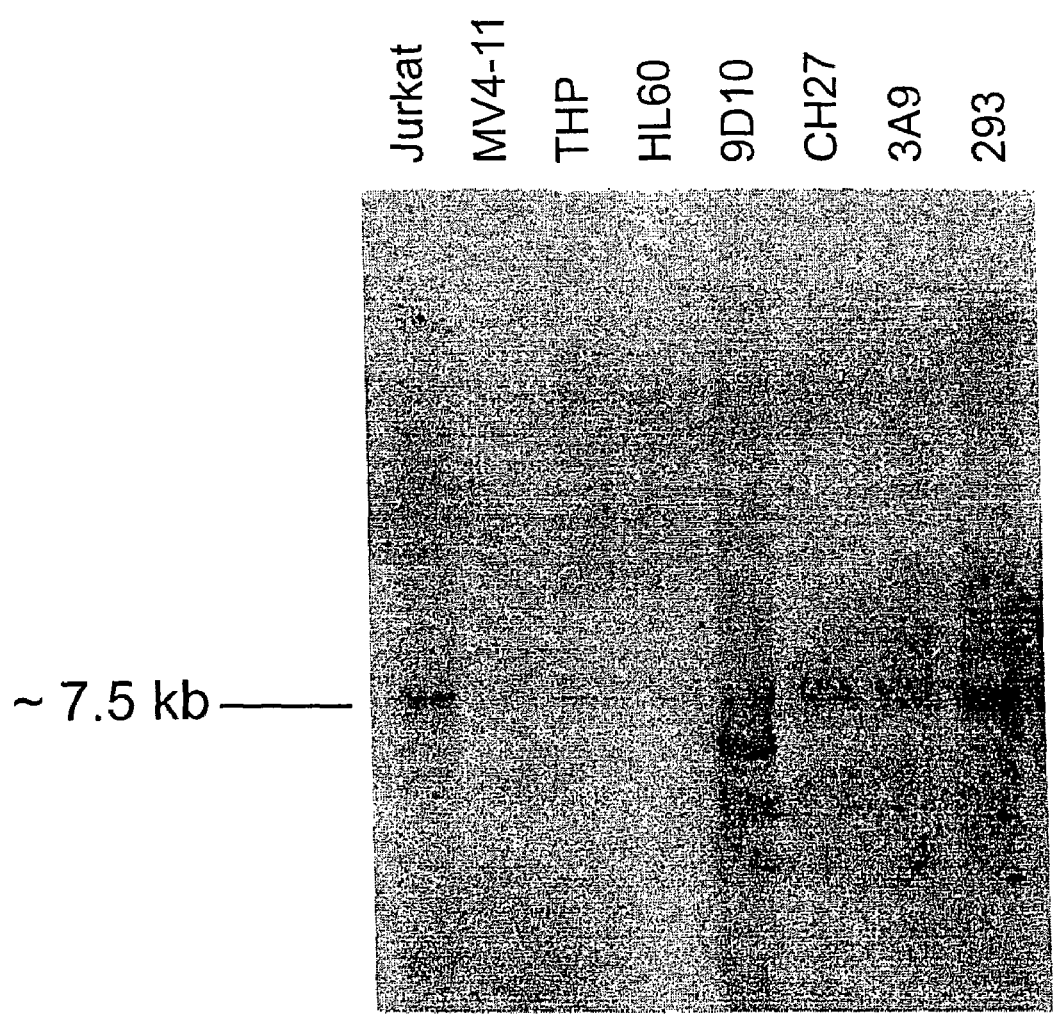

In another embodiment, hCLASP-2-based diagnostics involve screening assays for identifying disorders of cells of hematopoietic lineage. hCLASP-2 is expressed in human T cells, B cells but not cells from the myeloid lineage. Different hCLASP-2 isoforms in T and B cells permit further discrimination between malignancies of T and B lineage (FIG. 4B). Precise identification of hematopoietic cell types is vital to guide chemotherapy and radiation therapy of patients with leukemia and lymphoma (Fauci et al Eds., 1998, Harrison's Principles of Internal Medicine, 14th Ed. McGraw Hill, pp. 695-712). hCLASP-2 expression differences can be detected by using FACS, immunofluorescence, immunoperoxidase staining, RT-PCR, in situ hybridization or RNA blot analysis (Sambrook, Fritsch and Maniatas, Molecular Cloning, 2nd Ed. Cold Spring Harbor Lab. Press, 1989; Ward M S, Pathology 1999 November; 31(4): 382-92).

In another embodiment, hCLASP-2-based diagnostics involve screening assays for identifying activated immune system cells. Although hCLASP-2 is generally expressed at quite low levels in PBMCs (which is critical for some of the above applications), it is known that the surface expression of the closely related mouse CLASP-1 protein is altered during the process of lymphocyte activation. An analogous change in expression is expected for the hCLASP-2 protein. Subtyping lymphocytes specific for a particular antigen, for example, using MHC-based multimeric staining reagents (Altman et. al., 1996, Science 274: 94-6), for separating cell populations into hCLASP-2 high and hCLASP-2 low populations, can aid in determining the nature of the immune response against that antigen. Such understanding is critical, for example, in predicting the course of chronic viral infections such as hepatitis B, hepatitis C, and HIV, and to designing appropriate treatment regimens for patients suffering from these infections.

hCLASP-2 can also serve as a potential therapeutic agent for Wilms' tumor. Wilms tumor is the most common primary renal tumor of childhood (Cotran, Kumar, and Collins, 1999, Robbins Pathologic Basis of Disease, 6th Ed. W.B. Saunders, pp. 487-89). As discussed herein, hCLASP-2 is highly expressed in 293 cells, embryonic kidney epithelial cells. Therefore, hCLASP-2 nucleic or amino acid sequence or fragments can serve as tumor markers for Wilms' tumor. Antibodies directed against a hCLASP-2 variant that is expressed only in Wilms' tumor can serve as novel therapeutic agents for Wilms' tumor, and can also function as delivery vehicles for other targeted therapeutics that may be attached to the anti-hCLASP-2 antibody (e.g., chemotherapeutics or radiolabeling).

5.4.2.2.1. CLASP Antisense, Ribozyme and Triplex Polynucleotides and Methods of Use Oligonucleotide sequences, that include anti-sense RNA and DNA molecules and ribozymes that function to inhibit the translation of a CLASP-2 mRNA are within the scope of the invention. Such molecules are useful in cases where downregulation of CLASP-2 expression is desired. Antisense RNA and DNA molecules act to directly block the translation of mRNA by binding to targeted mRNA and preventing protein translation. The invention provides methods and antisense oligonucleotide or polynucleotide reagents which can be used to reduce expression of CLASP-2 gene products in vitro or in vivo. Administration of the antisense reagents of the invention to a target cell results in reduced CLASP activity. As will be apparent to one of skill and as discussed supra (Table 3), specific CLASP-2 splice variants can be specifically targeted for inhibition. Alternatively, by designing an, e.g., antisense molecule that recognizes a sequence found in several or all CLASP-2 species, a general inhibition can be achieved.

A. Antisense

Without intending to be limited to any particular mechanism, it is believed that antisense oligonucleotides bind to, and interfere with the translation of, the sense CLASP-2 mRNA. Alternatively, the antisense molecule can render the CLASP-2 mRNA susceptible to nuclease digestion, interfere with transcription, interfere with processing, localization or otherwise with RNA precursors ("pre-mRNA"), repress transcription of mRNA from the CLASP-2 gene, or act through some other mechanism. However, the particular mechanism by which the antisense molecule reduces CLASP-2 expression is not critical.

The antisense polynucleotides of the invention comprise an antisense sequence of at least 7 to 10 to typically 20 or more nucleotides that specifically hybridize to a sequence from mRNA encoding CLASP-2 or mRNA transcribed from the CLASP-2 gene. More often, the antisense polynucleotide of the invention is from about 10 to about 50 nucleotides in length or from about 14 to about 35 nucleotides in length. In other embodiments, antisense polynucleotides are polynucleotides of less than about 100 nucleotides or less than about 200 nucleotides. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors. Generally, to assure specific hybridization, the antisense sequence is substantially complementary to the target CLASP-2 mRNA sequence. In certain embodiments, the antisense sequence is exactly complementary to the target sequence. The antisense polynucleotides can also include, however, nucleotide substitutions, additions, deletions, transitions, transpositions, or modifications, or other nucleic acid sequences or non-nucleic acid moieties so long as specific binding to the relevant target sequence corresponding to CLASP-2 RNA or its gene is retained as a functional property of the polynucleotide.

It will be appreciated that the CLASP-2 polynucleotides and oligonucleotides of the invention can be made using nonstandard bases (e.g., other than adenine, cytidine, guanine, thymine, and uridine) or nonstandard backbone structures to provides desirable properties (e.g., increased nuclease-resistance, tighter-binding, stability or a desired TM). Techniques for rendering oligonucleotides nuclease-resistant include those described in PCT publication WO 94/12633. A wide variety of useful modified oligonucleotides may be produced, including oligonucleotides having a peptide-nucleic acid (PNA) backbone (Nielsen et al., 1991, Science 254: 1497) or incorporating 2'-O-methyl ribonucleotides, phosphorothioate nucleotides, methyl phosphonate nucleotides, phosphotriester nucleotides, phosphorothioate nucleotides, phosphoramidates. Still other useful oligonucleotides may contain alkyl and halogen-substituted sugar moieties comprising one of the following at the 2' position: OH, SH, SCH3, F, OCN, OCH3OCH3, OCH3O(CH2)nCH3, O(CH2)nNH2 or O(CH2)nCH3, where n is from 1 to about 10; C1 to C10 lower alkyl, substituted lower alkyl, alkaryl or aralkyl; Cl; Br; CN; CF3; OCF3; O-, S-, or N-alkyl; O-, S-, or N-alkenyl; SOCH3; SO2CH3; ONO2; NO2; N3; NH2; heterocycloalkyl; heterocycloalkaryl; aminoalkylamino; polyalkylamino; substituted silyl; an RNA cleaving group; a cholesteryl group; a folate group; a reporter group; an intercalator; a group for improving the pharmacokinetic properties of an oligonucleotide; or a group for improving the pharmacodynamic properties of an oligonucleotide and other substituents having similar properties. Folate, cholesterol or other groups that facilitate oligonucleotide uptake, such as lipid analogs, may be conjugated directly or via a linker at the 2' position of any nucleoside or at the 3' or 5' position of the 3'-terminal or 5'-terminal nucleoside, respectively. One or more such conjugates may be used. Oligonucleotides may also have sugar mimetics such as cyclobutyls in place of the pentofuranosyl group. Other embodiments may include at least one modified base form or "universal base" such as inosine, or inclusion of other nonstandard bases such as queosine and wybutosine as well as acetyl-, methyl-, thio- and similarly modified forms of adenine, cytidine, guanine, thymine, and uridine which are not as easily recognized by endogenous endonucleases. The antisense oligonucleotide can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The invention further provides oligonucleotides having backbone analogues such as phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or CH2—NH—O—CH2, CH2—N(CH3)—OCH2, CH2—O—N(CH3)—CH2, CH2—N(CH3)—N(CH3)—CH2 and O—N(CH3)—CH2—CH2 backbones (where phosphodiester is O—P—O—CH2), or mixtures of the same. Also useful are oligonucleotides having morpholino backbone structures (U.S. Pat. No. 5,034,506).

Useful references include Oligonucleotides and Analogues, A Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan et al., 9 Jul. 1993, J. Med. Chem. 36(14): 1923-1937; Antisense Research and Applications (1993, CRC Press), in its entirety and specifically Chapter 15, by Sanghvi, entitled "Heterocyclic base modifications in nucleic acids and their applications in antisense oligonucleotides;" and Antisense Therapeutics, ed. Sudhir Agrawal (Humana Press, Totowa, N.J., 1996).

In one embodiment, the antisense sequence is complementary to relatively accessible sequences of the CLASP-2 mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., 1997, Nature Biotechnology 15: 537). Examples of oligonucleotides that can be tested in cells for antisense suppression of CLASP-2 function are those capable of hybridizing to (i.e., substantially complementary to) the following positions from SEQUENCE ID NO: 1:

1) GAAGGCGATCATCACGTGGCCTTCCATCGC (SEQ ID NO:109)

2) GCTTCAAGTAATGACTGGTGCAGAACATCTG (SEQ ID NO:110)

3) GCTCCTCCTCAGGCAGGCGCTATGGCTGTGG (SEQ ID NO:111)

4) GTAGGCCCGGTGCAGCGTGTCATACAGATGG (SEQ ID NO:112)

(See also Example 8)

In some embodiments, administration of antisense oligonucleotides will result in reduction of hCLASP-mRNA expression by at least about 50%, as assessed by Northern analysis after administration of an antisense phosphorothioate oligonucleotide at a concentration of 1 µM, 5 µM, 10 µM or 20 µM.

The invention also provides an antisense polynucleotide that has sequences in addition to the antisense sequence (i.e., in addition to anti-CLASP-2-sense sequence). In this case, the antisense sequence is contained within a polynucleotide of longer sequence. In another embodiment, the sequence of the polynucleotide consists essentially of, or is, the antisense sequence.

The antisense nucleic acids (DNA, RNA, modified, analogues, and the like) can be made using any suitable method for producing a nucleic acid, such as the chemical synthesis and recombinant methods disclosed herein. In one embodiment, for example, antisense RNA molecules of the invention can be prepared by de novo chemical synthesis or by cloning. For example, an antisense RNA that hybridizes to CLASP-2 mRNA can be made by inserting (ligating) an CLASP-2 DNA sequence (e.g., SEQUENCE ID No: 1, or fragment thereof) in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention. The term "operably linked" refers to a functional linkage between a nucleic acid expression control sequence (such as a promoter or enhancer) and a second nucleic acid sequence, wherein the expression control sequence directs transcription of the nucleic acid corresponding to the second sequence.

In one embodiment, antisense DNA oligodeoxyribonucleotides derived from the translation initiation site, e.g., between −10 and +10 regions of a CLASP-2 nucleotide sequence, are used. For general methods relating to antisense polynucleotides, see ANTISENSE RNA AND DNA, 1988, D. A. Melton, Ed., Cold Spring Harbor Laboratory, Cold Spring Harbor, N.Y.). See also, Dagle et al., 1991, Nucleic Acids Research, 19: 1805. For a review of antisense therapy, see, e.g., Uhlmann et al., 1990, Chem. Reviews, 90: 543-584.

B. Ribozyme

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of CLASP-2 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site can be evaluated for predicted structural features such as secondary structure that can render the oligonucleotide sequence unsuitable. The suitability of candidate targets can also be evaluated by testing their accessibility to hybridization with complementary oligonucleotides, using ribonuclease protection assays.

C. Triplex

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6): 569-584; Helene et al., 1992, Ann. N.Y. Acad. Sci., 660: 27-36; and Maher, 1992, Bioassays 14(12): 807-815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizable stretches of either purines or pyrimidines to be present on one strand of a duplex. Nucleotide sequences can be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules can be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

D. General

The anti-sense RNA and DNA molecules, ribozymes and triple helix molecules of the invention can be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules can be introduced as a means of increasing intracellular stability and half-life. Possible modifications include, but are not limited to, the addition of flanking sequences of ribo- or deoxynucleotides to the 5' and/or 3' ends of the molecule or the use of phosphorothioate or 2' O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of a CLASP-2 polynucleotide in a cell ex vivo, the use of a vector such as a virus, (e.g., a retrovirus, adenovirus, adeno-associated virus, and the like), phage or plasmid, and the like or techniques such as electroporation or calcium phosphate precipitation.

5.4.2.2.2. Gene Therapy

By introducing gene sequences into cells, gene therapy can be used to treat conditions in which the cells do not express normal CLASP-2 or express abnormal/inactive CLASP-2. In some instances, the polynucleotide encoding a CLASP-2 is intended to replace or act in the place of a functionally deficient endogenous gene. Alternatively, abnormal conditions characterized by overexpression can be treated using the gene therapy techniques described below.

In a specific embodiment, nucleic acids comprising a sequence encoding a CLASP-2 protein or functional derivative thereof, are administered to promote CLASP-2 function, by way of gene therapy. Gene therapy refers to therapy performed by the administration of a nucleic acid to a subject. In this embodiment of the invention, the nucleic acid produces its encoded protein that mediates a therapeutic effect by promoting CLASP-2 function.

Any of the methods for gene therapy available in the art can be used according to the present invention. Exemplary methods are described below.

For general reviews of the methods of gene therapy, see, Goldspiel et al., 1993, Clinical Pharmacy 12: 488-505; Wu and Wu, 1991, Biotherapy 3: 87-95; Tolstoshev, 1993, Ann. Rev. Pharmacol. Toxicol. 32: 573-596; Mulligan, 1993, Science 260: 926-932; and Morgan and Anderson, 1993, Ann. Rev. Biochem. 62: 191-217; Can, 1993, TIBTECH 11(5): 155-215). Methods commonly known in the art of recombinant DNA technology which can be used are described in Ausubel et al., supra; and Kriegler, 1990, Gene Transfer and Expression, A Laboratory Manual, Stockton Press, NY.

In one aspect, the therapeutic composition comprises a CLASP-2 nucleic acid that is part of an expression vector that encodes a CLASP-2 protein or fragment or chimeric protein thereof in a suitable host. In particular, such a nucleic acid has a promoter operably linked to the CLASP-2 coding region, said promoter being inducible or constitutive, and, optionally, tissue-specific. In another particular embodiment, a nucleic acid molecule is used in which the CLASP-2 coding sequences and any other desired sequences are flanked by regions that promote homologous recombination at a desired site in the genome, thus providing for intrachromosomal expression of the CLASP-2 nucleic acid (Koller and Smithies, 1989, Proc. Natl. Acad. Sci. U.S.A. 86: 8932-8935; Zijlstra et al., 1989, *Nature* 342: 435-438).

Delivery of the nucleic acid into a patient can be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see, e.g., Wu and Wu, 1987, J. Biol. Chem. 262: 4429-4432) (which can be used to target cell types specifically expressing the receptors), and the like. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO 92/20316 dated Nov. 26, 1992; WO 93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. U.S.A. 86: 8932-8935; Zijlstra et al., 1989, Nature 342: 435-438).

In a specific embodiment, a viral vector that contains the CLASP-2 nucleic acid is used. For example, a retroviral vector can be used (see, Miller et al., 1993, Meth. Enzymol. 217: 581-599). These retroviral vectors have been modified to delete retroviral sequences that are not necessary for packaging of the viral genome and integration into host cell DNA. The CLASP-2 nucleic acid to be used in gene therapy is cloned into the vector, which facilitates delivery of the gene into a patient. More detail about retroviral vectors can be found in Boesen et al., 1994, Biotherapy 6: 291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93: 644-651; Kiem et al., 1994, Blood 83: 1467-1473; Salmons and Gunzberg, 1993, Human Gene Therapy 4: 129-141; and Grossman and Wilson, 1993, Curr. Opin. in Genetics and Devel. 3: 110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson 1993, Current Opinion in Genetics and Development 3: 499-503) present a review of adenovirus-based gene therapy. Bout et al., 1994, Human Gene Therapy 5: 3-10, demonstrated the use of adenovirus vectors to transfer genes to the respiratory epithelia of rhesus monkeys. Other instances of the use of adenoviruses in gene therapy can be found in Rosenfeld et al., 1991, Science 252: 431-434; Rosenfeld et al., 1992, Cell 68: 143-155; and Mastrangeli et al., 1993, J. Clin. Invest. 91: 225-234. Adeno-associated virus (AAV) has also been proposed for use in gene therapy (Walsh et al., 1993, Proc. Soc. Exp. Biol. Med. 204: 289-300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, and the like. Numerous techniques are known in the art for the introduction of foreign genes into cells (see, e.g., Loeffler and Behr, 1993, Meth. Enzymol. 217: 599-618; Cohen et al., 1993, Meth. Enzymol. 217: 618-644; Cline, 1985, Pharmac. Ther. 29: 69-92) and can be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells can be applied as a skin graft onto the patient. Recombinant blood cells (e.g., hematopoietic stem or progenitor cells) are preferably administered intravenously. The amount of cells envisioned for use depends on the desired effect, patient state, and the like, and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and the like. In a preferred embodiment, the cell used for gene therapy is autologous to the patient.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.4.2.3. Knockout Cells

In one aspect of the invention, endogenous target gene expression can also be reduced by inactivating or "knocking out" the target gene or its promoter using targeted homologous recombination (see, e.g., Smithies et al., 1985, Nature 317: 230-234; Thomas and Capecchi, 1987, Cell 51: 503-512; Thompson et al., 1989, Cell 5: 313-321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (see, e.g., Thomas and Capecchi, 1987 and Thompson, 1989, supra). However, this approach can be adapted for use in humans provided the recombinant DNA constructs are directly administered or targeted to the required site in vivo using appropriate viral vectors.

5.4.2.4. Transgenic and Knockout Animals

The CLASP-2 gene product can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees can be used to generate CLASP-2 transgenic animals. The term "transgenic," as used herein, refers to animals expressing CLASP-2 gene sequences from a different species (e.g., mice expressing human CLASP-2 gene sequences), as well as animals that have been genetically engineered to overexpress endogenous (i.e., same species) CLASP-2 sequences or animals that have been genetically engineered to no longer express endogenous CLASP-2 gene sequences (i.e., "knock-out" animals), and their progeny.

Any technique known in the art can be used to introduce a CLASP-2 transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten et al., 1985, Proc. Natl. Acad. Sci., U.S.A. 82: 6148-6152); gene targeting in embryonic stem cells (Thompson et al., 1989, Cell 56: 313-321); electroporation of embryos (Lo, 1983, Mol. Cell. Biol. 3: 1803-1814); and sperm-mediated gene transfer (Lavitrano et al., 1989, Cell 57: 717-723) (For a review of such techniques, see Gordon, 1989, Transgenic Animals, Intl. Rev. Cytol. 115, 171-229)

Any technique known in the art can be used to produce transgenic animal clones containing a CLASP-2 transgene, for example, nuclear transfer into enucleated oocytes of nuclei from cultured embryonic, fetal or adult cells induced to quiescence (Campbell et al., 1996, Nature 380: 64-66; Wilmut et al., Nature 385: 810-813).

The present invention provides for transgenic animals that carry a CLASP-2 transgene in all their cells, as well as animals that carry the transgene in some, but not all their cells, i.e., mosaic animals. The transgene can be integrated as a single transgene or in concatamers, e.g., head-to-head tandems or head-to-tail tandems. The transgene can also be selectively introduced into and activated in a particular cell type by following, for example, the teaching of Lasko et al. (1992, Proc. Natl. Acad. Sci. U.S.A. 89: 6232-6236). The regulatory sequences required for such a cell-type specific activation will depend upon the particular cell type of interest, and will be apparent to those of skill in the art. When it is desired that the CLASP-2 transgene be integrated into the chromosomal site of the endogenous CLASP-2 gene, gene targeting is preferred. Briefly, when such a technique is to be utilized, vectors containing some nucleotide sequences homologous to the endogenous CLASP-2 gene are designed for the purpose of integrating, via homologous recombination with chromosomal sequences, into and disrupting the function of the nucleotide sequence of the endogenous CLASP-2 gene. The transgene can also be selectively introduced into a particular cell type, thus inactivating the endogenous CLASP-2 gene in only that cell type, by following, for example, the teaching of Gu et al. (1994, Science 265: 103-106). The regulatory sequences required for such a cell-type specific inactivation will depend upon the particular cell type of interest, and will be apparent to those of skill in the art.

Once transgenic animals have been generated, the expression of the recombinant CLASP-2 gene can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques that include, but are not limited to, Northern blot analysis of tissue samples obtained from the animal, in situ hybridization analysis, and RT-PCR (reverse transcriptase PCR). Samples of CLASP-2 gene-expressing tissue, can also be evaluated immunocytochemically using antibodies specific for the CLASP-2 transgene product.

5.4.2.5. Other Uses of CLASP Polynucleotides

There exists an ongoing need to identify new chromosome marking reagents. Sequences can be mapped to chromosomes by preparing PCR primers from SEQ ID NO: 1, 3, 5, or 9. These primers can be can be less than 50 nucleotides in length, generally less than 46 nucleotides, more generally less than 41 nucleotides, most generally less than 36 nucleotides, preferably less than 31 nucleotides, more preferably less than 26 nucleotides, and most preferably less than 21 nucleotides in length. The probes can also be less than 16 nucleotides, less than 13 nucleotides in length, less than 9 nucleotides in length and less than 7 nucleotides in length. Primers can be selected so that the primers do not span more than one predicted exon in the genomic DNA. These primers are then used for PCR screening of somatic cell hybrids containing individual human chromosomes (i.e., chromosome 13). Only those hybrids containing the human CLASP-2 gene corresponding to SEQ ID NO: 1, 3, 5, or 9 will yield an amplified fragment.

Similarly, somatic hybrids provide a rapid method of PCR mapping the polynucleotides to particular chromosomes. Precise chromosomal location of the CLASP-2 polynucleotides can also be achieved using fluorescence in situ hybridization (FISH) of a metaphase chromosomal spread. See Verma, et al, Human Chromosomes: A Manual of Basic Techniques, Pergamon Press. NY, 1988. Once a polynucleotide has been mapped to a precise chromosomal location, the physical position of the polynucleotide can be used in linkage analysis. Linkage analysis establishes coinheritance between a chromosomal location and presentation of a particular disease. See McKusick, V., 1998, Mendelian Inheritance in Man: A Catalog of Human Genes and Genetic Disorders, 12th Ed, Johns Hopkins University Press.

The CLASP-2 polynucleotides can be used for identifying individuals from minute biological samples as DNA markers for restriction fragment length polymorphism (RFLP). An individual's genomic DNA is digested with one or more restriction enzymes, and probed on a Southern blot with CLASP-2 DNA markers to yield unique bands for identifying the individual.

As described above, upon sequencing of numerous independent cDNA products, single nucleotide polymorphisms (SNPs) have been discovered within CLASP-2. These alterations and differences are presented. They represent missense alterations.

If it is determined that certain SNPs are deleterious or advantageous, SNPs can be used as a diagnostic tool through SNP mapping or direct sequencing of the SNP region to determine which isoform is expressed. Additionally, the SNPs can be used as a general SNP marker for chromosomal defects such as rearrangement and translocations.

CLASP-2 polynucleotides can be also be used as polymorphic markers for forensic analysis. See generally National Research Council, The Evaluation of Forensic DNA Evidence (Eds. 1996, Pollard et al., National Academy Press, Washington D.C.). The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample. The CLASP-2 polynucleotide sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO: 1, 3, 5 or 9 are particularly appropriate for this use as greater numbers of polymorphisms occur in the noncoding regions, making it easier to differentiate individuals using this technique. Examples of polynucleotide reagents include the CLASP-2 nucleotide sequences or portions thereof, e.g., fragments derived from the noncoding regions of SEQ ID NO: 1, 3, 5, or 9 having a length of at least 20 bases, preferably at least 25 bases, and more preferably at least 30 bases.

CLASP-2 polynucleotides can also be used as reagents for paternity testing. The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child. Of course, the present invention can be expanded to the use of this procedure to determine if one individual is related to another. Even more broadly, the present invention can be employed to determine how related one individual is to another, for example, between races or species.

Bacterial infections are a major cause of health-related problems. However, the emergence of drug resistant bacteria is compromising the therapeutic value of the present spectrum of antibiotics. All the currently used antibiotics are small organic molecules, with certain level of structural similarity. This provides an advantage for bacteria to develop drug resistance, since they need to modify a limited number of genes in order to become resistant to a wide variety of antibiotics. The development of antibiotics with different chemical structure and targets can overcome antibiotic resistance, and provide therapeutic superiority in preventing infection by bacterial pathogens. Additionally, most antibiotics are not naturally occurring compounds and cause minor or sometimes serious side effects. For example, antibiotics used to treat TB can cause hearing loss.

The present invention provides new antibacterial agents. Certain CLASP-2 DNA sequences were difficult to clone and subclone (see Example 1). Bacteria harboring certain pieces of CLASP cDNA products were unable to be isolated, indicating that introduction of CLASP sequences compromised bacterial viability. There can be at least two possible reasons why the CLASP cDNA were unable to be cloned, which can reflect a variation of the well-established Modification and Restriction systems found in bacteria (reviewed in Wilson and Murray. (1991) Annu. Rev. Genet. 25:585-627; Bickle and Kruger (1993) Microbiol. Rev. 57:29-67). This well-described system is used by bacteria to prevent deleterious effects caused by the introduction of foreign DNA. Bacteria can recognize foreign DNA since it does not have the same modifications (e.g. methylation) as the native DNA. After recognition, the bacteria then digest and eliminate the foreign DNA (restriction). In the first scenario, the CLASP cDNA can be recognized as foreign DNA, and digested and eliminated as in the Modification and Restriction system. However, this would be unique for CLASP cDNA since the bacteria used for cloning cDNA are compromised in the Modification and Restriction system, which makes cloning of cDNA into bacteria a practice common in the art. If this is the case, the bacterial apparatus that specifically recognizes or eliminates CLASP cDNA can provide a novel target to develop antimicrobial agents. The CLASP DNA sequence would be useful in targeting the apparatus as well as an entry point for designing screens to identify potential targets. The second possibility is that CLASP cDNA behaves as an antimicrobial agent (i.e., antibiotic), and prevents bacterial growth. This, in effect, would create a new type of antibiotic mediated by the presence of foreign DNA (i.e. CLASP cDNA). In the case for the CLASP cDNA, the bacteria can recognize the DNA but instead of digesting and eliminating the DNA, the CLASP cDNA can cause a variation of the restriction and prevent the bacteria from growing, imposing a bacteriacidal effect upon the bacteria.

DNA as an antimicrobial agent has significant advantages over currently available agents. First, it is structurally unrelated to any existing antibiotics, and can overcome the present growing drug-resistance problem to structurally common agents. Second, since DNA antimicrobials composed of naturally-occurring human DNA, are expected to have minimal side effects and immune rejection. Third, DNA sequences can be tailored with sequence variation and numerous chemical modifications to circumvent the problem of resistance. Fourth, the antimicrobial DNA can be delivered specifically to bacterial cells through the use of bacteriophages (i.e., bacterial virus) which specifically infect bacteria and do not infect human cells. Further specificity can be generated to infect certain bacteria and bacterial subpopulations. Finally, this system can be economically robust since the generation of DNA and delivery vehicles are inexpensive.

5.5. Polypeptides Encoded by the CLASP Gene Coding Sequence

In accordance with the invention, a CLASP polynucleotide which encodes the CLASP polypeptides, mutant polypeptides, peptide fragments, CLASP fusion proteins or functional equivalents thereof, can be used to express CLASP proteins in appropriate host cells. In various embodiments, the CLASP-2 polypeptides expressed will be identical or substantially similar to SEQ ID NOs: 2, 4, 6 or 10 or a fragment thereof.

In some embodiments, altered DNA sequences which can be used in accordance with the invention include deletions, additions or substitutions of different nucleotide residues resulting in a sequence that encodes the same or a functionally equivalent gene product. For example, due to the inherent degeneracy of the genetic code, other DNA sequences which encode substantially the same or a functionally equivalent amino acid sequence, can be used in the practice of the invention for the expression of the CLASP protein. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. One of skill will recognize that each codon in a nucleic acid sequence such SEQ ID NO: 1 (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. Thus, for example, due to the degeneracy of the genetic code, a polypeptide having the sequence of SEQ ID NO: 2 or a fragment thereof, can be encoded by numerous polynucleotides other than SEQ ID NO: 1. Typically, the degenerate sequence will hybridize with SEQ ID NO: 1 under high or moderate stringency conditions, but this is not strictly required (e.g., when a copy of a nucleic acid is created using the maximum codon degeneracy permitted by the genetic code. In such cased, the nucleic acids typically hybridize under moderately stringent hybridization conditions.)

The gene product itself can contain deletions, additions or substitutions of amino acid residues within a CLASP sequence, which result in a silent change thus producing a functionally equivalent CLASP protein. Such conservative amino acid substitutions can be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan. Creighton, 1984, PROTEINS, has grouped amino acids that are conservative substitutions for one another as follows: (1) Alanine (A), Glycine (G); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); (6) Phenylalanine (F), Tyrosine (Y), Tryptophan (W); (7) Serine (S), Threonine (T); and (8) Cysteine (C), Methionine (M).

The DNA sequences of the invention can be engineered in order to alter a CLASP coding sequence for a variety of ends, including but not limited to, alterations which modify processing and expression of the gene product. For example, mutations can be introduced using techniques which are well known in the art, e.g., site-directed mutagenesis, to insert new restriction sites, to alter glycosylation patterns, phosphorylation, and the like. Based on the domain organization of the CLASP proteins, a large number of CLASP mutant polypeptides can be constructed by modifying or rearranging the nucleotide sequences that encode the CLASP extracellular, transmembrane and cytoplasmic domains.

In various embodiments, the present invention provides homologues of the CLASP polypeptides which function as either an CLASP agonists or an CLASP-2 antagonist. In a preferred embodiment, the CLASP agonists and antagonists stimulate or inhibit, respectively, a subset of the biological activities of the naturally occurring form of the CLASP-2 polypeptide. Thus, specific biological effects can be elicited by treatment with a homologue of limited function. In one embodiment, treatment of a subject with a homologue having a subset of the biological activities of the naturally occurring form of the polypeptide has fewer side effects in a subject relative to treatment with the naturally occurring form of the CLASP-2 polypeptide.

The invention contemplates both full-length CLASP polypeptides and fragments, e.g., fragments having a length of at least about 10, often 20, frequently 50 or 100 residues substantially identical to the exemplified CLASP polypeptide sequences of the invention. Protein fragments can be "free-standing," or comprised within a larger polypeptide of which the fragment forms a part or region, most preferably as a single continuous region. Representative examples of polypeptide fragments of the invention, include, for example, fragments from about amino acid number 1-20, 21-40, 41-60, 61-80, 81-100, 102-120, 121-140, 141-160, 161-180, 181-200, or 201 to the end of the coding region. Moreover, polypeptide fragments can be about 20, 30, 40, 50, 60, 70, 80, 90, 100, 110, 120, 130, 140, 150, 200 amino acids in length. In this context "about" includes the particularly recited ranges, larger or smaller by several (5, 4, 3, 2, or 1) amino acids, at either extreme or at both extremes.

Preferred polypeptide fragments include the CLASP protein. Further preferred polypeptide fragments include the CLASP-2 protein having a continuous series of deleted residues from the amino or the carboxy terminus, or both. For example, any number of amino acids, ranging from 1-X, can be deleted from the amino terminus of either the CLASP-2 polypeptide. Furthermore, any combination of the above amino and carboxy terminus deletions are preferred. Similarly, polynucleotide fragments encoding these CLASP-2 polypeptide fragments are also preferred.

Even if deletion of one or more amino acids from the N-terminus of a protein results in modification of loss of one or more biological functions of the protein, other biological activities can still be retained. Thus, the ability of shortened CLASP muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that a CLASP-2 mutein with a large number of deleted N-terminal amino acid residues can retain some biological or immunogenic activities. In fact, peptides composed of as few as four CLASP-2 amino acid residues can often evoke an immune response.

Homologues of the CLASP-2 polypeptide can be generated by mutagenesis, e.g., discrete point mutation or truncation of the CLASP-2 polypeptide. As used herein, the term "homologue" refers to a variant form of the CLASP-2 polypeptide which acts as an agonist or antagonist of the activity of the CLASP-2 polypeptide. An agonist of the CLASP-2 polypeptide can retain substantially the same, or a subset, of the biological activities of the CLASP-2 polypeptide. An antagonist of the CLASP-2 polypeptide can inhibit one or more of the activities of the naturally occurring form of the CLASP-2 polypeptide, by, for example, competitively binding to a downstream or upstream member of the CLASP-2 molecular pathway which includes the CLASP-2 polypeptide.

Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, GFP (see, e.g., Mistili & Spector, 1997, Nature Biotechnology 15: 961-964); changes in signal transduction, phosphorylation and dephosphorylation, receptor-ligand interactions, second messenger concentrations (e.g., cGMP, cAMP, $IP_3$, and $Ca^{2+}$), and cell growth. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate ($IP_3$); changes in intracellular calcium levels; cytokine release, and the like.

5.5.1. Synthesis or Expression of CLASP-2 Polypeptide Expression Systems

In order to express a biologically active CLASP, the nucleotide sequence coding for CLASP, or a functional equivalent, is inserted into an appropriate expression vector. The CLASP gene product as well as host cells or cell lines transfected or transformed with recombinant CLASP expression vectors can be used for a variety of purposes. These include, but are not limited to, generating antibodies (i.e., monoclonal or polyclonal) that competitively inhibit activity of CLASP protein and neutralize its activity; antibodies that activate CLASP function and antibodies that detect its presence on the cell surface or in solution. Anti-CLASP antibodies can be used in detecting and quantifying expression of CLASP levels in cells and tissues such as lymphocytes and macrophages, as well as isolating CLASP-positive cells from a cell mixture.

Methods which are well known to those skilled in the art can be used to construct recombinant expression vectors containing the CLASP-2 coding sequence and appropriate transcriptional/translational control signals. These methods include in vitro recombinant DNA techniques, synthetic techniques and in vivo recombination/genetic recombination. (See, e.g., the techniques described in Sambrook et al., 1989, Molecular Cloning A Laboratory Manual, Cold Spring Harbor Laboratory, N.Y. and Ausubel et al., supra). The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. It will be appreciated by those skilled in the art that the design of the expression vector can depend on such factors as the choice of the host cell to be transformed, the level of expression of polypeptide desired, and the like. The expression vectors of the invention can be introduced into host cells to thereby produce polypeptides or peptides, including fusion polypeptides or peptides, encoded by nucleic acids as described herein (e.g., CLASP-2 polypeptides, mutant forms of CLASP-2, fusion polypeptides, and the like).

A variety of host-expression vector systems can be utilized to express a CLASP-2 coding sequence. These include, but are not limited to, microorganisms such as bacteria transformed with recombinant bacteriophage DNA, plasmid DNA, or cosmid DNA expression vectors containing the CLASP-2 coding sequence; yeast transformed with recombinant yeast expression vectors containing the CLASP-2 coding sequence; insect cell systems infected with recombinant virus expression vectors (e.g., baculovirus) containing the CLASP-2 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the CLASP-2 coding sequence; or animal cell systems. The expression elements of these systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage λ, plac, ptrp, ptac (ptrp-lac hybrid promoter; cytomegalovirus promoter) and the like can be used; when cloning in insect cell systems, promoters such as the baculovirus polyhedron promoter can be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the $^{35}$S RNA promoter of CaMV; the coat protein promoter of TMV) can be used; when cloning in mammalian cell systems, promoters derived from the genome of mammalian cells (e.g., metallothionein promoter) or from mammalian viruses (e.g., the adenovirus late promoter; the vaccinia virus 7.5K promoter) can be used; when generating cell lines that contain multiple copies of the CLASP-2 DNA, SV40-, BPV- and EBV-based vectors can be used with an appropriate selectable marker.

In bacterial systems a number of expression vectors can be advantageously selected depending upon the use intended for the expressed CLASP-2 product. For example, when large quantities of CLASP-2 protein are to be produced for the generation of antibodies or to screen peptide libraries, vectors which direct the expression of high levels of fusion protein products that are readily purified can be desirable. Such vectors include, but are not limited to, the E. coli expression vector pUR278 (Ruther et al., 1983, EMBO J. 2: 1791), in which the CLASP-2 coding sequence can be ligated into the vector in frame with the lacZ coding region so that a hybrid protein is produced; pIN vectors (Inouye & Inouye, 1985, Nucleic acids Res. 13: 3101-3109; Van Heeke & Schuster, 1989, J. Biol. Chem. 264: 5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In yeast, a number of vectors containing constitutive or inducible promoters can be used. (Current Protocols in Molecular Biology, Vol. 2, 1988 (Suppl. 1999), Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II.)

In cases where plant expression vectors are used, the expression of the CLASP-2 coding sequence can be driven by any of a number of promoters. For example, viral promoters such as the $^{35}$S RNA and 19S RNA promoters of CaMV (Brisson et al., 1984, Nature 310: 511-514), or the coat protein promoter of TMV (Takamatsu et al., 1987, EMBO J. 6: 307-311) can be used; alternatively, plant promoters such as the small subunit of RUBISCO (Coruzzi et al., 1984, EMBO J. 3: 1671-1680; Broglie et al., 1984, Science 224: 838-843); or heat shock promoters, e.g., soybean hsp17.5-E or hsp17.3-B (Gurley et al., 1986, Mol. Cell. Biol. 6: 559-565) can be used. These constructs can be introduced into plant cells using Ti plasmids, Ri plasmids, plant virus vectors, direct DNA transformation, microinjection, electroporation, and the like. (Weissbach & Weissbach, 1988, Methods for Plant Molecular Biology, Academic Press, NY, Section VIII, pp. 421-463; and Grierson & Corey, 1988, Plant Molecular Biology, 2d Ed., Blackie, London, Ch. 7-9.)

An alternative expression system which could be used to express CLASP-2 is an insect system. In one such system, Autographa californica nuclear polyhedrosis virus (AcNPV) is used as a vector to express foreign genes. The virus grows in Spodoptera frugiperda cells. The CLASP-2 coding sequence can be cloned into non-essential regions (e.g., the polyhedron gene) of the virus and placed under control of an AcNPV promoter (e.g., the polyhedron promoter). Successful insertion of the CLASP-2 coding sequence will result in inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed. (see, e.g., Smith et al., 1983, J. Viol. 46: 584; Smith, U.S. Pat. No. 4,215,051).

In mammalian host cells, a number of viral based expression systems can be utilized. In cases where an adenovirus is used as an expression vector, the CLASP-2 coding sequence can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing CLASP-2 in infected hosts. (See, e.g., Logan & Shenk, 1984, Proc. Natl. Acad. Sci. U.S.A. 81: 3655-3659). Alternatively, the vaccinia 7.5K promoter can be used. (See, e.g., Mackett et al., 1982, Proc. Natl. Acad. Sci. U.S.A. 79: 7415-7419; Mackett et al., 1984, J. Virol. 49: 857-864; Panicali et al., 1982, Proc. Natl. Acad. Sci. U.S.A. 79: 4927-4931). Regulatable expression vectors such as the tetracycline repressible vectors can also be used to express a coding sequence in a controlled fashion.

Specific initiation signals can also be required for efficient translation of inserted CLASP-2 coding sequences. These signals include the ATG initiation codon and adjacent sequences. In cases where the entire CLASP-2 gene, including its own initiation codon and adjacent sequences, is inserted into the appropriate expression vector, no additional translational control signals can be needed. However, in cases where only a portion of the CLASP-2 coding sequence is inserted, exogenous translational control signals, including the ATG initiation codon, must be provided. Furthermore, the initiation codon must be in phase with the reading frame of the CLASP-2 coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, and the like. (see Bittner et al., 1987, Methods in Enzymol. 153: 516-544).

In addition, a host cell strain can be chosen which modulates the expression of the inserted sequences, or modifies and processes the gene product in a specific fashion desired. Such modifications (e.g., glycosylation) and processing (e.g., cleavage) of protein products can be important for the function of the protein. The presence of several consensus N-glycosylation sites in CLASP-2 extracellular domains support the possibility that proper modification can play a role in CLASP-2 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include, but are not limited to, CHO, VERO, BHK, HeLa, COS, MDCK, 293, WI38, and the like.

Host cells transformed with nucleotide sequences encoding CLASP-2 may be cultured under conditions suitable for the expression and recovery of the soluble protein from cell culture. The protein produced by a transformed cell may be secreted or contained intracellularly depending on the sequence and/or the vector used. As will be understood by those of skill in the art, expression vectors containing polynucleotides which encode CLASP-2 may be designed to contain signal sequences which direct secretion of CLASP-2 through a prokaryotic or eukaryotic cell membrane. Other constructions may be used to join sequences encoding CLASP-2 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, For long-term, high-yield production of recombinant proteins, stable expression is preferred. For example, cell lines which stably express CLASP-2 proteins can be engineered. Rather than using expression vectors which contain viral origins of replication, host cells can be transformed with the CLASP-2 DNA controlled by appropriate expression control elements (e.g., promoter, enhancer, sequences, transcription terminators, polyadenylation sites, and the like.), and a selectable marker. Following the introduction of foreign DNA, engineered cells can be allowed to grow for 1-2 days in an enriched medium, and then switched to a selective medium. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the CLASP-2 protein(s) on the cell surface. Such engineered cell lines are particularly useful in screening for molecules or drugs that affect CLASP-2 function.

A number of selection systems can be used, including but not limited to, the herpes simplex virus thymidine kinase (Wigler et al., 1977, Cell 11: 223), hypoxanthine-guanine phosphoribosyltransferase (Szybalska & Szybalski, 1962, Proc. Natl. Acad. Sci. U.S.A. 48: 2026), and adenine phosphoribosyltransferase (Lowy et al., 1980, Cell 22: 817) genes which can be employed in tk⁻, hgprt⁻ or aprt⁻ cells, respectively. Also, antimetabolite resistance can be used as the basis of selection for dhfr, which confers resistance to methotrexate (Wigler et al., 1980, Natl. Acad. Sci. U.S.A. 77: 3567; O'Hare et al., 1981, Proc. Natl. Acad. Sci. U.S.A. 78: 1527); gpt, which confers resistance to mycophenolic acid (Mulligan & Berg, 1981), Proc. Natl. Acad. Sci. U.S.A. 78: 2072); neo, which confers resistance to the aminoglycoside G-418 (Colberre-Garapin et al., 1981, J. Mol. Biol. 150: 1); and hygro, which confers resistance to hygromycin (Santerre et al., 1984, Gene 30: 147). Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. U.S.A. 85: 8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10: 169).

In an alternate embodiment of the invention, the coding sequence of CLASP-2 could be synthesized in whole or in part, using chemical methods well known in the art. (See, e.g., Caruthers et al., 1980, Nuc. Acids Res. Symp. Ser. 7: 215-233; Crea and Horn, 180, Nuc. Acids Res. 9(10): 2331; Matteucci and Caruthers, 1980, Tetrahedron Letter 21: 719; and Chow and Kempe, 1981, Nuc. Acids Res. 9(12): 2807-2817.) Alternatively, the protein itself could be produced using chemical methods to synthesize a CLASP-2 amino acid sequence in whole or in part. For example, peptides can be synthesized by solid phase techniques, cleaved from the resin, and purified by preparative high performance liquid chromatography. (See Creighton, 1983, Proteins Structures And Molecular Principles, W.H. Freeman and Co., N.Y. pp. 50-60). The composition of the synthetic polypeptides can be confirmed by amino acid analysis or sequencing (e.g., the Edman degradation procedure; see Creighton, 1983, Proteins, Structures and Molecular Principles, W.H. Freeman and Co., N.Y., pp. 34-49).

In some embodiments, the CLASP-2 polypeptide contains non-naturally occurring amino acids or amino acid analogs (i.e., compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium).

5.5.2. Identification of Cells that Express CLASP

The recombinant host cells which contain the coding sequence and which express a CLASP gene product or fragments thereof can be identified by at least four general approaches; (a) DNA-DNA or DNA-RNA hybridization; (b) the presence or absence of "marker" gene functions; (c) assessing the level of transcription as measured by the expression of CLASP-2 mRNA transcripts in the host cell; and (d) detection of the gene product as measured by immunoassay or by its biological activity. Prior to the identification of gene expression, the host cells can be first mutagenized in an effort to increase the level of expression of CLASP, especially in cell lines that produce low amounts of CLASP.

In the first approach, the presence of the CLASP-2 coding sequence inserted in the expression vector can be detected by DNA-DNA or DNA-RNA hybridization using probes comprising nucleotide sequences that are homologous to the CLASP-2 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, and the like). For example, if the CLASP-2 coding sequence is inserted within a marker gene sequence of the vector, recombinants containing the CLASP-2 coding sequence can be identified by the absence of the marker gene function. Alternatively, a marker gene can be placed in tandem with the CLASP-2 sequence under the control of the same or different promoter used to control the expression of the CLASP-2 coding sequence. Expression of the marker in response to induction or selection indicates expression of the CLASP-2 coding sequence.

In the third approach, transcriptional activity for the CLASP-2 coding region can be assessed by hybridization assays. For example, RNA can be isolated and analyzed by Northern blot using a probe homologous to the CLASP-2 coding sequence or particular portions thereof. Alternatively, total nucleic acids of the host cell can be extracted and assayed for hybridization to such probes. Additionally, reverse transcription-polymerase chain reactions can be used to detect low levels of gene expression.

In the fourth approach, the expression of the CLASP-2 protein product can be assessed immunologically, for example by Western blots, immunoassays such as radioimmuno-precipitation, enzyme-linked immunoassays, fluorescent activated cell sorting ("FACS"), and the like. This can be achieved by using an anti-CLASP-2 antibody. Alternatively, CLASP-2 protein can be expressed as a fusion protein with green-fluorescent protein to facilitate its detection in cells (U.S. Pat. Nos. 5,491,084; 5,804,387; 5,777,079).

Identification of cells or tissues expressing CLASP protein or mRNA, especially CLASP-2 isoforms, can be useful for determining normal and abnormal CLASP expression in a given cell or tissue. As discussed above, a number of CLASP-2 isoforms have been identified, e.g., in Jurkat cells, peripheral blood, and brain. The identification of mRNA or protein expression in various cell types and tissues can allow for identification of isoforms improperly expressed in either a spatial or temporal manner. Expression of hCLASP-2D isoform in hematopoietic cells may cause problems due to the presence of the SH3 domain not seen in the Jurkat and peripheral blood isoforms.

Other molecules in the immune system may also interact with portions of hCLASP2D. However, the absence of the PBM domain in the hCLASP-2D isoform may be necessary for function in certain cell types or tissues. Similarly, expression of CLASP isoforms 2A, 2B, and 2C in brain may cause problems for different reasons: the PBM present in these isoforms may interfere with a particular function by binding any of the known PDZ domain protein involved in formation of the neurological synapse. Similarly, the lack of an SH3 domain may cause an inappropriate response due to interactions with only a subset of molecules required for CLASP-2 function in the brain.

5.5.3. Uses of CLASP-2 Engineered Host Cells

In one embodiment of the invention, the CLASP-2 protein and/or cell lines that express CLASP-2 can be used to screen for antibodies, peptides, small molecules, natural and synthetic compounds or other cell bound or soluble molecules that bind to the CLASP-2 protein resulting in stimulation or inhibition of CLASP-2 function. For example, anti-CLASP-2 antibodies can be used to inhibit or stimulate CLASP-2 function and to detect its presence. Alternatively, screening of peptide libraries with recombinantly expressed soluble CLASP-2 protein or cell lines expressing CLASP-2 protein can be useful for identification of therapeutic molecules that function by inhibiting or stimulating the biological activity of CLASP-2. The uses of the CLASP-2 protein and engineered cell lines, described in the subsections below, can be employed equally well for homologous CLASP-2 genes in various species.

In a specific embodiment of the invention, cell lines may be engineered to express the extracellular or intracellular domain of CLASP fused to another molecule such as GST. In addition, CLASP, its extracellular domain or its intracellular domain may be fused to an immunoglobulin constant region (Hollenbaugh and Aruffo, 1992, Current Protocols in Immunology, Unit 10.19; Aruffo et al., 1990, Cell 61: 1303) to produce a soluble molecule with increased half life. The soluble protein or fusion protein can be used in binding assays, affinity chromatography, immunoprecipitation, Western blot, and the like. Synthetic compounds, natural products, and other sources of potentially biologically active materials can be screened in assays that are well known in the art.

Random peptide libraries consisting of all possible combinations of amino acids attached to a solid phase support can be used to identify peptides that are able to bind to a specific domain of CLASP-2 (Lam, K. S. et al., 1991, Nature 354: 82-84). The screening of peptide libraries can have therapeutic value in the discovery of pharmaceutical agents that stimulate or inhibit the biological activity of CLASP-2.

Identification of molecules that are able to bind to the CLASP-2 protein can be accomplished by screening a peptide library with recombinant soluble CLASP-2 protein. Methods for expression and purification of CLASP-2 are described in Section 5.7, supra, and can be used to express recombinant full length CLASP-2 or fragments of CLASP-2 depending on the functional domains of interest. Such domains include CLASP-2 extracellular domain, transmembrane domain, CLASP-2 intracellular domain, ITAM containing domain, tyrosine phosphorylation site containing domain, cysteine cluster containing domain, cadherin motif containing domain, and coil/coil domain.

To identify and isolate the peptide/solid phase support that interacts and forms a complex with CLASP-2, it is necessary to label or "tag" the CLASP-2 molecule. The CLASP-2 protein can be conjugated to enzymes such as alkaline phosphatase or horseradish peroxidase or to other reagents such as fluorescent labels which can include fluorescein isothiocyanate (FITC), phycoerythrin (PE) or rhodamine. Conjugation of any given label to CLASP-2 can be performed using techniques that are well known in the art. Alternatively, CLASP-2 expression vectors can be engineered to express a chimeric CLASP-2 protein containing an epitope for which a commercially available antibody exist. The epitope-specific antibody can be tagged with a detectable label using methods well known in the art including an enzyme, a fluorescent dye or colored or magnetic beads.

The "tagged" CLASP-2 conjugate is incubated with the random peptide library for 30 minutes to one hour at 22° C. to allow complex formation between CLASP-2 and peptide species within the library. The library is then washed to remove any unbound protein. If CLASP-2 has been conjugated to alkaline phosphatase or horseradish peroxidase the whole library is poured into a petri dish containing substrates for either alkaline phosphatase or peroxidase, for example, 5-bromo-4-chloro-3-indoyl phosphate (BCIP) or 3,3',4,4"-diaminobenzidine (DAB), respectively. After incubating for several minutes, the peptide/solid phase-CLASP-2 complex changes color, and can be easily identified and isolated physically under a dissecting microscope with a micromanipulator. If a fluorescent tagged CLASP-2 molecule has been used, complexes can be isolated by fluorescence activated sorting. If a chimeric CLASP-2 protein expressing a heterologous epitope has been used, detection of the peptide/CLASP-2 complex can be accomplished by using a labeled epitope-specific antibody. Once isolated, the identity of the peptide attached to the solid phase support can be determined by peptide sequencing.

In addition to using soluble CLASP-2 molecules, in another embodiment, it is possible to detect peptides that bind to cell-associated CLASP-2 using intact cells. The use of intact cells is preferred for use with cell surface molecules. Methods for generating cell lines expressing CLASP-2 are described in Section 5.8. The cells used in this technique can be either live or fixed cells. The cells can be incubated with the random peptide library and bind to certain peptides in the library to form a "rosette" between the target cells and the relevant solid phase support/peptide. The rosette can thereafter be isolated by differential centrifugation or removed physically under a dissecting microscope. Techniques for screening combinatorial libraries are known in the art (Gallop et al., 1994, J. Med. Chem., 37: 1233; Gordon, 1994, J. Med. Chem., 37: 1385).

As an alternative to whole cell assays for membrane bound receptors or receptors that require the lipid domain of the cell membrane to be functional, CLASP-2 molecules can be reconstituted into liposomes where label or "tag" can be attached.

5.5.4. CLASP-2 Fusion Proteins

In another embodiment of the invention, a CLASP or a modified CLASP sequence can be ligated to a heterologous sequence to encode a fusion protein. For example, for screening of peptide libraries for molecules that bind CLASP-2, it can be useful to produce a chimeric CLASP-2 protein expressing a heterologous epitope that is recognized by a commercially available antibody. A fusion protein can also be engineered to contain a cleavage site located between a CLASP-2 sequence and the heterologous protein sequence, so that the CLASP-2 can be cleaved away from the heterologous moiety. In one embodiment, fusion proteins of the invention can contain the CLASP-2 extracellular domain comprising at least about residues 1 through 816 or fragment thereof. In another embodiment, fusion proteins can contain the CLASP-2 intracellular domain comprising at least about residue 843 through the end of the CLASP-2 sequence or fragment thereof.

5.6. Cloning Alleles, Variants, and Species Homologs of CLASP-2

In order to clone the full length cDNA sequence from any species encoding a CLASP-2 cDNA, or to clone variant forms of the molecule, labeled DNA probes made from nucleic acid fragments corresponding to any partial cDNA disclosed herein can be used to screen a cDNA library derived from lymphoid cells or brain cells. More specifically, oligonucleotides corresponding to either the 5' or 3' terminus of the cDNA sequence can be used to obtain longer nucleotide sequences. Briefly, the library can be plated out to yield a maximum of 30,000 pfu for each 150 mm plate. Approximately 40 plates can be screened. The plates are incubated at 37° C. until the plaques reach a diameter of 0.25 mm or are just beginning to make contact with one another (3-8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris-HCl, pH 7.5, before being allowed to air dry. The filters are prehybridized in hybridization buffer such as casein buffer containing 10% dextran sulfate, 0.5M NaCl, 50 mM Tris-HCl, pH 7.5, 0.1% sodium pyrophosphate, 1% casein, 1% SDS, and denatured salmon sperm DNA at 0.5 mg/ml for 6 hours at 60° C. The radiolabeled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage can then be replated and rescreened to obtain single, well isolated positive plaques. Positive plaques can be isolated and the cDNA clones sequenced using primers based on the known cDNA sequence. This step can be repeated until a full length cDNA is obtained.

It can be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique can be used. RACE is a proven PCR-based strategy for amplifying the 5' end of incomplete cDNAs. 5'-RACE-Ready RNA synthesized from human tissues containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence can be translated into amino acid sequence and examined for certain landmarks such as a continuous open reading frame flanked by translation initiation and termination sites, a cadherin-like domain, an ITAM domain, a tyrosine phosphorylation site, a cysteine cluster, a transmembrane domain, and finally overall structural similarity to the CLASP-2 genes disclosed herein. See, Ponassi et al., 1999, Mech. Dev. 80: 207-212; Isakov, 1998, Receptor Channels 5: 243-253; Borroto et al., 1997, Biopolymers 42: 75-88; Dimitratos et al., 1997, Mech. Dev. 63: 127-130; Apperson et al., 1996, J. Neurosci. 16: 6839-6852; Ozawa et al., 1990, Mech. Dev. 33: 49-56, which discuss protein domains and are incorporated herein by reference.

5.7. Modulating Expression of Endogenous CLASP-2 Genes

Alternatively, the expression characteristics of an endogenous CLASP-2 gene within a cell population can be modified by inserting a heterologous DNA regulatory element into the genome of the cell line such that the inserted regulatory element is operatively linked with the endogenous CLASP-2 gene. For example, an endogenous CLASP-2 gene which is normally "transcriptionally silent", i.e., an CLASP-2 gene which is normally not expressed, or is expressed only at very low levels in a cell population, can be activated by inserting a regulatory element which is capable of promoting the expression of a normally expressed gene product in the cells. Alternatively, a transcriptionally silent, endogenous CLASP-2 gene can be activated by insertion of a promiscuous regulatory element that works across cell types.

A heterologous regulatory element can be inserted into a cell line population, such that it is operatively linked with an endogenous CLASP-2 gene, using techniques, such as targeted homologous recombination, which are well known to those of skill in the art, (see e.g., in Chappel, U.S. Pat. No. 5,272,071; PCT publication No. WO 91/06667, published Jan. 16, 1991).

5.8. Anti-CLASP Antibodies

Various procedures known in the art can be used for the production of antibodies to epitopes of the natural and recombinantly produced CLASP protein. Such antibodies include, but are not limited to, polyclonal, monoclonal, chimeric, single chain, human or humanized, IgG, IgM, IgA, IgD or IgE, a complementarity determining region, Fab fragments, F(ab')$_2$ and fragments produced by an Fab expression library as well as anti-idiotypic antibodies. Antibodies which compete for CLASP binding are especially preferred for diagnostics and therapeutics.

Monoclonal antibodies that bind CLASP-2 can be radioactively labeled allowing one to follow their location and distribution in the body after injection. Radioisotope tagged antibodies can be used as a non-invasive diagnostic tool for imaging de novo lymphoid tumors and metastases that express CLASP-2.

Immunotoxins can also be designed which target cytotoxic agents to specific sites in the body. For example, high affinity CLASP-2 specific monoclonal antibodies can be covalently complexed to bacterial or plant toxins, such as diphtheria toxin or ricin. A general method of preparation of antibody/hybrid molecules can involve use of thiol-crosslinking reagents such as SPDP, which attack the primary amino groups on the antibody and by disulfide exchange, attach the toxin to the antibody. The hybrid antibodies can be used to specifically eliminate CLASP-2 expressing lymphocytes.

For the production of antibodies, various host animals can be immunized by injection with the recombinant or naturally purified CLASP-2 protein, fusion protein or peptides, including but not limited to goats, rabbits, mice, rats, hamsters, and the like Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to CLASP-2 can be prepared by using any technique which provides for the production of antibody molecules by continuous cell lines in culture. These include, but are not limited to, the hybridoma technique originally described by Kohler and Milstein, (*Nature*, 1975, 256: 495-497), the human B-cell hybridoma technique (Kosbor et al., 1983, Immunology Today, 4: 72; Cote et al., 1983, Proc. Natl. Acad. Sci. U.S.A., 80: 2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci. U.S.A., 81: 6851-6855; Neuberger et al., 1984, Nature, 312: 604-608; Takeda et al., 1985, Nature, 314: 452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce CLASP-2-specific single chain antibodies. In some embodiments, phage display technology is used to identify antibodies and heteromeric Fab fragments that specifically bind to selected antigens (see, e.g., McCafferty et al., Nature 348: 552-554 (1990); Marks et al., Biotechnology 10: 779-783 (1992)).

Hybridomas can be screened using enzyme-linked immunosorbent assays (ELISA) in order to detect cultures secreting antibodies specific for refolded recombinant CLASP-2. Cultures can also be screened by ELISA to identify those cultures secreting antibodies specific for mammalian-produced CLASP-2. Confirmation of antibody specificity can be obtained by western blot using the same antigens. Subsequent ELISA testing can use recombinant CLASP-2 fragments to identify the specific portion of the CLASP-2 molecule with which a monoclonal antibody binds. Additional testing can be used to identify monoclonal antibodies with desired functional characteristics such as staining of histological sections, immunoprecipitation of CLASP-2, inhibition of CLASP-2 binding or stimulation of CLASP-2 to transmit an intracellular signal. Determination of the monoclonal antibody isotype can be accomplished by ELISA, thus providing additional information concerning purification or function.

Some anti-CLASP-2 monoclonal antibodies of the present invention are humanized, human or chimeric, in order to reduce their potential antigenicity, without reducing their affinity for their target. Humanized antibodies have been described in the art. See, e.g., Queen, et al., 1989, Proc. Natl Acad. Sci. U.S.A. 86: 10029; U.S. Pat. Nos. 5,563,762; 5,693, 761; 5,585,089 and 5,530,101. The human antibody sequences used for humanization can be the sequences of naturally occurring human antibodies or can be consensus sequences of several human antibodies. See Kettleborough et al., 1991, *Protein Engineering* 4: 773; Kolbinger et al., 1993, Protein Engineering 6: 971. Humanized monoclonal antibodies against CLASP-2 peptides can also be produced using transgenic animals having elements of a human immune system (see, e.g., U.S. Pat. Nos. 5,569,825; 5,545,806; 5,693, 762; 5,693,761; and 5,7124,350).

In some embodiments, an anti-CLASP-2 polypeptide monoclonal or polyclonal antiserum is produced that is specifically immunoreactive with a particular CLASP-2 polypeptide and is selected to have low cross-reactivity against other molecules (e.g., other CLASP polypeptides) and any such cross-reactivity is removed by immunoabsorbtion prior to use in the immunoassay. Methods for screening and characterizing monoclonal antibodies for specificity are well known in the art and are described generally in Harlow and Lane, supra. For example, polyclonal antibodies raised to hCLASP-2A, as shown in SEQ ID NO: 1, or splice variants, or immunogenic portions thereof, can be selected to obtain only those polyclonal or monoclonal antibodies that are specifically immunoreactive with the target protein not with other proteins. This selection may be achieved by subtracting out antibodies that cross-react with molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Typically a specific or selective reaction will be at least twice background signal or noise and more typically more than 10 to 100 times background. Alternatively, antibodies that cross-react with a selected set of polypeptides may be prepared.

Antibody fragments which contain specific binding sites of V can be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., 1989, Science, 246: 1275-1281) to allow rapid and easy identification of monoclonal Fab fragments with the desired specificity to CLASP-2.

Anti-CLASP-2 antibodies can also be used to identify, isolate, inhibit or eliminate CLASP-2-expressing cells. In one embodiment, the present invention includes a method of identifying an abnormal T cell profile of an immunocompromised subject relative to the T cell profile of a non-immunocompromised subject. The method includes (i) sorting a sample of peripheral blood mononuclear cells (PBMC) isolated from the immunocompromised subject into sets of T cell types, (ii) determining the ratio of CLASP-2$^+$ cells relative to the total number of cells (CLASP-2$^+$: total) in each set, and identifying an abnormal T cell profile in the immunocompromised subject by comparing the CLASP-2$^+$: total ratios of sets from the immunocompromised subject with the CLASP-2$^+$: total ratios of analogous sets from a non-immunocompromised subject.

In other embodiments, anti-CLASP-2 antibodies can be used for detection of hCLASP-2 protein in assays such as fluorescent activated cell sorting (FACS), ELISA, fluorescent or electron immunomicroscopy, Western blots, gel shift analyses. CLASP-2 expression in various cells, localization within cells, interactions with other proteins, and differentiation between CLASP-2 isoform expression can be determined by use of the techniques listed herein.

5.9. Screening Assays

The invention provides methods for identifying compounds or agents that modulate (i.e., inhibit or enhance) CLASP expression or activity. CLASP expression or activity modulators are useful for treatment of disorders characterized by (or associated with) aberrant or abnormal CLASP expression or activity. Aberrant expression of CLASP mRNA or protein means expression in lymphocytes (e.g., T lymphocytes or B lymphocytes) or other CLASP expressing cells of at least 2-fold, preferably at least 5-fold greater than expression in control lymphocytes obtained from a healthy subject.

The CLASP expression assays can include the steps of contacting a cell expressing CLASP with a compound or agent and assaying CLASP expression. CLASP polypeptide expression is easily measured by ELISA using anti-CLASP-2 antibodies of the invention. CLASP mRNA expression (including expression of specific species or splice variants of CLASP) can be measured by quantitative Northern analysis or quantitative PCR.

CLASP-2 activities include, for example, the CLASP-2 polypeptide binding to PDZ-domain containing molecules and CLASP-2 polypeptide involvement in signal transduction (e.g., leading to T cell activation). Compounds or agents that modulate the interaction of a CLASP-2 polypeptide and a target molecule, modulate CLASP-2 nucleic acid expression, or modulate CLASP-2 polypeptide activity are all contemplated by the methods of the present invention.

Test compounds include, for example, 1) peptides (e.g., soluble peptides, including Ig-tailed fusion peptides and members of random peptide libraries (see, e.g., Lam, K. S. et al, 1991, Nature 354: 82-84; Houghten, R. et al., 1991, Nature 354: 84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al., 1993, Cell 72: 767-778); 3) CLASP-2 antibodies (as described above); 4) small organic and inorganic molecules (e.g., molecules obtained from combinatorial and natural product libraries); 5) antisense RNA and DNA molecules and ribozymes (described above).

The CLASP modulators can be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds.

In one embodiment, the invention provides assays for screening test compounds which bind to CLASP-2 polypeptides. The assays can be recombinant cell based or cell-free assays. These assays can include the steps of combining a cell expressing a CLASP-2 polypeptide or a binding fragment thereof, and a compound or agent under conditions which allow binding of the compound or agent to the CLASP-2 polypeptide to form a complex. Complex formation can then be determined. The ability of the candidate compound or agent to bind to the CLASP-2 polypeptide or fragment thereof is indicated by the presence of the candidate compound in the complex. Formation of complexes between the CLASP-2 polypeptide and the candidate compound can be quantitated, for example, using standard immunoassays.

In another embodiment, the invention provides screening assays to identify test compounds which modulate the interaction (and most likely CLASP-2 activity as well) between a CLASP-2 polypeptide and a molecule (target molecule with which the CLASP-2 polypeptide normally interacts.

In one embodiment, these CLASP-2 target molecules can be tyrosine kinases (e.g., lyn, lck, fyn, ZAP-70m SyK, and CSK). In another embodiment, these CLASP-2 target molecules can be tyrosine phosphatases (e.g., EZRIN, SHP-1, SHP-2 and PTP36). In another embodiment, these CLASP-2 target molecules can be adaptor proteins (e.g., NCK, CBL, SHC, LNK, SLP-76, HS1, SIT, VAV, GrB2, and BRDG1). In another embodiment, these CLASP-2 target molecules can be cytoskeletal associated proteins such as ankyrin, spectrin, talin, ezrin, tropomyosin, myosin, plectin, syndecans, paralemmin, Band 3 protein, cytoskeletal protein 4.1, and PTP36. In a further embodiment, CLASP-2 target molecules can be members of the integrin family.

Typically, the assays are recombinant cell based or cell-free assay. These assays can include the steps of combining a cell expressing a CLASP-2 polypeptide or a binding fragment thereof, a CLASP-2 target molecule (e.g., a CLASP-2 ligand) and a test compound, under conditions where but for the presence of the candidate compound, the CLASP-2 polypeptide or biologically active portion thereof binds to the target molecule. Detecting complex formation between the CLASP-2 polypeptide or the binding fragment thereof, the CLASP-2 target molecule and a test compound detecting the formation of a complex which includes the CLASP-2 polypeptide and the target molecule can be accomplished. Detection of complex formation can include direct quantitation of the complex by, for example, measuring inductive effects, such as T cell activation, of the CLASP-2 polypeptide. A significant change, such as a decrease, in the interaction of the CLASP-2 and target molecule (e.g., in the formation of a complex between the CLASP-2 and the target molecule) in the presence of a candidate compound (relative to what is detected in the absence of the candidate compound) is indicative of a modulation of the interaction between the CLASP-2 polypeptide and the target molecule. Modulation of the formation of complexes between the CLASP-2 polypeptide and the target molecule can be quantitated using, for example, an immunoassay. To perform cell free drug screening assays, it is desirable to immobilize either CLASP-2 or its target molecule to facilitate separation of complexes from uncomplexed forms of one or both of the polypeptides, as well as to accommodate automation of the assay. CLASP-2 binding to a target molecule, in the presence and absence of a candidate compound, can be accomplished in any vessel suitable for containing the reactants. Examples of such vessels include microtitre plates, test tubes, and microcentrifuge tubes.

In one embodiment, a fusion polypeptide can be provided which adds a domain that allows the polypeptide to be bound to a matrix. Alternatively, the complexes can be dissociated from the matrix, separated by SDS-PAGE, and the level of CLASP-2-binding polypeptide found in the bead fraction quantitated from the gel using standard electrophoretic techniques.

Other techniques for immobilizing polypeptides on matrices can also be used in the drug screening assays of the invention. For example, either CLASP-2 or its target molecule can be immobilized utilizing conjugation of biotin and streptavidin. Biotinylated CLASP-2 molecules can be prepared from biotin-NHS(N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with CLASP-2 but which do not interfere with binding of the polypeptide to its target molecule can be derivatized to the wells of the plate, and CLASP-2 trapped in the wells by antibody conjugation. As described above, preparations of a CLASP-2-binding polypeptide and a candidate compound are incubated in the CLASP-2-presenting wells of the plate, and the amount of complex trapped in the well can be quantitated. Methods for detecting such complexes include immunodetection of complexes using antibodies reactive with the CLASP-2 target molecule, or which are reactive with CLASP-2 polypeptide and compete with the target molecule; as well as enzyme-linked assays which rely on detecting an enzymatic activity associated with the target molecule.

One method of drug screening utilizes eukaryotic or prokaryotic host cells which are stably transformed with recombinant DNA molecules expressing the CLASP-2, e.g., the protein having the sequence of SEQ ID NO: 2. Such cells, either in viable or fixed form, can be used for standard ligand/receptor binding assays (see, e.g., Parce et al. (1989) Science 246: 243-247; and Owicki et al. (1990) Proc. Natl Acad. Sci. U.S.A. 87: 4007-4011, which describe sensitive methods to detect cellular responses. A test compound, often labeled, can be assayed for binding or for competition with another ligand for binding. Viable cells could also be used to screen for the effects of drugs on CLASP-2 mediated functions, e.g., T cell activation, second messenger levels, and others).

In another embodiment, the invention provides a method for identifying a compound (e.g., a screening assay) capable of use in the treatment of a disorder characterized by (or associated with) aberrant or abnormal CLASP-2 nucleic acid expression or CLASP-2 polypeptide activity. This method typically includes the step of assaying the ability of the compound or agent to modulate the expression of the CLASP-2 nucleic acid or the activity of the CLASP-2 polypeptide thereby identifying a compound for treating a disorder characterized by aberrant or abnormal CLASP-2 nucleic acid expression or CLASP-2 polypeptide activity.

Methods for assaying the ability of the compound or agent to modulate the expression of the CLASP-2 nucleic acid or activity of the CLASP-2 polypeptide are typically cell-based assays. For example, cells which are sensitive to ligands which transduce signals via a pathway involving CLASP-2 can be induced to overexpress a CLASP-2 polypeptide in the presence and absence of a candidate compound. Candidate compounds which produce a change in CLASP-2-dependent responses can be identified. In one embodiment, expression of the CLASP-2 nucleic acid or activity of a CLASP-2 polypeptide is modulated in cells and the effects of candidate compounds on the readout of interest (such as T cell activation) are measured. For example, the expression of genes which are up- or down-regulated in response to a CLASP-2-dependent signal cascade can be assayed.

Alternatively, modulators of CLASP-2 expression can be identified in a method where a cell is contacted with a candidate compound and the expression of CLASP-2 mRNA or polypeptide in the cell is determined. The level of expression of CLASP-2 mRNA or polypeptide in the presence of the candidate compound is compared to the level of expression of CLASP-2 mRNA or polypeptide in the absence of the candidate compound. The candidate compound can then be identified as a modulator of CLASP-2 nucleic acid expression based on this comparison. For example, when expression of CLASP-2 mRNA or polypeptide is greater in the presence of the candidate compound than in its absence, the candidate compound is identified as a stimulator of CLASP-2 nucleic acid expression. Alternatively, when CLASP-2 nucleic acid expression is less in the presence of the candidate compound than in its absence, the candidate compound is identified as an inhibitor of CLASP-2 nucleic acid expression. The level of CLASP-2 nucleic acid expression in the cells can be determined by methods described herein for detecting CLASP-2 mRNA or polypeptide.

Modulators of CLASP-2 polypeptide activity and CLASP-2 nucleic acid expression identified according to these drug screening assays can be used to treat, for example, immune disorders. These methods of treatment include the steps of administering the modulators of CLASP-2 polypeptide activity or nucleic acid expression, e.g., in a pharmaceutical composition as described in §5.10.1 below, to a subject in need of such treatment, e.g., a subject with a disorder described herein.

5.10. Therapeutic Administration of CLASP-2 Modulators

The CLASP-2 protein is expressed in lymphocytes and, as noted supra, play a role in regulating T cell and B cell interactions, thus making CLASP-2 activity (e.g., CLASP-2 binding of regulatory proteins) a target for diagnostic and treatment of immune disorders and for modulation of immune function (e.g., T cell activation). Additionally, since CLASP-2 contains domains capable of transducing an intracellular signal, cell surface CLASP-2 can be triggered by an anti-CLASP-2 antibody or soluble CLASP-2 or a fragment thereof in order to enhance the activation state of a lymphocyte.

5.10.1. Formulation and Route of Administration

A CLASP-2 polypeptide, a fragment thereof, anti-CLASP-2 antibody, CLASP-2 polynucleotide (e.g., antisense or ribozyme), or small molecule agonists or antagonists can be administered to a subject per se or in the form of a pharmaceutical or therapeutic composition. Pharmaceutical compositions comprising the proteins of the invention can be manufactured by means of conventional mixing, dissolving, granulating, dragee-making, levigating, emulsifying, encapsulating, entrapping or lyophilizing processes. Pharmaceutical compositions can be formulated in conventional manner using one or more physiologically acceptable carriers, diluents, excipients or auxiliaries which facilitate processing of the protein or active peptides into preparations which can be used pharmaceutically. Proper formulation is dependent upon the route of administration chosen.

Currently, there are three major classes of protein-derived cell-penetrating peptides that have been used for delivering of proteins into cells and animals (Lindgren, M.; et al., 2000, Trends Pharmacol Sci. 21: 99-103). In one embodiment, the CLASP-2 protein or fragment (encoding a functional domain of CLASP-2) can be introduced into the cell as a fusion protein tied to a transporter protein derived from homeoprotein transcription factors such as ANTP. In another embodiment, the CLASP-2 protein or fragment (encoding a functional domain of CLASP-2) can be introduced into the cell as a fusion protein tied to other transcription factors such as the HIV Tat protein and the herpes simplex virus type 1 (HSV-1) VP22 protein. Members in this family have been widely used in different cellular and animal systems (Schwarze, S.; et al.; 2000, Trends Pharmacol Sci. 21: 45-48). In another embodiment, the CLASP-2 protein or fragment (encoding a functional domain of CLASP-2) can be introduced into the cell as a fusion protein tied to peptides derived from signal-sequences present in several proteins such as HIV-1 gp41. In other embodiments, there are several synthetic and/or chemeric cell-penetrating peptides such as transportan and Amphiphiloc model peptide (Lindgren, M.; et al., 2000, Trends Pharmacol Sci. 21: 99-103) that can be used. In another embodiment, the CLASP-2 protein or fragment can be introduced by using anti-DNA antibodies (see, e.g., Zack, D. J., et al., 1996, J. Immunol. 157: 2082-8

For topical administration the proteins of the invention can be formulated as solutions, gels, ointments, creams, suspensions, and the like. as are well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration.

For injection, the proteins of the invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents. Alternatively, the proteins can be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as the cross-linked polyvinylpyrrolidone, agar, or alginic acid or a salt thereof such as sodium alginate.

If desired, solid dosage forms can be sugar-coated or enteric-coated using standard techniques.

For oral liquid preparations such as, for example, suspensions, elixirs and solutions, suitable carriers, excipients or diluents include water, glycols, oils, alcohols, and the like. Additionally, flavoring agents, preservatives, coloring agents and the like can be added.

For buccal administration, the proteins can take the form of tablets, lozenges, and the like. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The proteins can also be formulated in rectal or vaginal compositions such as suppositories or retention enemas, e.g., containing conventional suppository bases such as cocoa butter or other glycerides.

In addition to the formulations described previously, the proteins can also be formulated as a depot preparation. Such long acting formulations can be administered by implantation (for example subcutaneously or intramuscularly) or by intramuscular injection. Thus, for example, the proteins can be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver the proteins or peptides of the invention. Certain organic solvents such as dimethylsulfoxide also can be employed, although usually at the cost of greater toxicity. Additionally, the proteins can be delivered using a sustained-release system, such as semipermeable matrices of solid polymers containing the therapeutic agent. Various sustained-release materials have been established and are well known by those skilled in the art. Sustained-release capsules can, depending on their chemical nature, release the proteins for a few weeks up to over 100 days. Depending on the chemical nature and the biological stability of the therapeutic reagent, additional strategies for protein stabilization can be employed.

As the proteins and peptides of the invention can contain charged side chains or termini, they can be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

5.10.2. Effective Dosages

CLASP-2 polypeptides, CLASP-2 fragments and anti-CLASP-2 antibodies will generally be used in an amount effective to achieve the intended purpose. For use to inhibit an immune response, the proteins of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of CLASP-2 binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval can be adjusted individually to provide plasma levels of the proteins which are sufficient to maintain therapeutic effect. Usual patient dosages for administration by injection range from about 0.1 to 5 mg/kg/day, preferably from about 0.5 to 1 mg/kg/day. Therapeutically effective serum levels can be achieved by administering multiple doses each day.

In cases of local administration or selective uptake, the effective local concentration of the proteins can not be related to plasma concentration. One having skill in the art will be able to optimize therapeutically effective local dosages without undue experimentation.

The amount of CLASP-2 administered will, of course, be dependent on the subject being treated, on the subject's weight, the severity of the affliction, the manner of administration and the judgment of the prescribing physician.

The therapy can be repeated intermittently while symptoms detectable or even when they are not detectable. The therapy can be provided alone or in combination with other drugs. In the case of autoimmune disorders, the drugs that can be used in combination with CLASP-2 or fragments thereof include, but are not limited to, steroid and non-steroid immunosuppressive agents.

5.10.3. Toxicity

Preferably, a therapeutically effective dose of the proteins described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

5.11. Binding Assays

CLASP-2 polypeptides can be used to screen for molecules that bind to CLASP-2 or for molecules to which CLASP-2 binds. The binding of CLASP-2 by the molecule can activate (agonist), increase, inhibit (antagonist), or decrease activity of the CLASP-2 or the molecule bound. Examples of such molecules include antibodies, oligonucleotides, proteins (e.g., receptors), or small molecules. Preferably, the molecule is closely related to the natural ligand of CLASP-2, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely-related to the natural receptor to which CLASP-2 binds, or at least, a fragment of the receptor capable of being bound by CLASP-2 (e.g., active site). In either case, the molecule can be rationally designed using known techniques.

Preferably, the screening for these molecules involves producing appropriate cells which express CLASP-2, either as a secreted protein or on the cell membrane. Preferred cells include cells from mammals, yeast, *Drosophila*, or *E. coli*. Cells expressing CLASP-2 (or cell membrane containing the expressed polypeptide) are then preferably contacted with a test compound potentially containing the molecule to observe binding, stimulation, or inhibition of activity of either CLASP-2 or the molecule.

The assay can simply test binding of a candidate compound to CLASP-2, where binding is detected by a label, or in an assay involving competition with a labeled competitor. Further, the assay can test whether the candidate compound results in a signal generated by binding to CLASP-2.

Alternatively, the assay can be carried out using cell-free preparations, polypeptide affixed to a solid support, chemical libraries, or natural product mixtures. The assay can also simply comprise the steps of mixing a candidate compound with a solution containing CLASP-2, measuring CLASP-2 activity or binding, and comparing the CLASP-2 activity or binding to a standard. Preferably, an ELISA assay can measure CLASP-2 level or activity in a sample (e.g., biological sample) using a monoclonal or polyclonal antibody. The antibody can measure CLASP-2 level or activity by either binding, directly or indirectly, to CLASP-2 or by competing with CLASP-2 for a substrate.

In another aspect of the invention, the CLASP-2 polypeptides, or fragments thereof, can be used as "bait proteins" in a two-hybrid assay (see, e.g., U.S. Pat. No. 5,283,317; Zervos et al., 1993, Cell 72: 223-232; Madura et al., 1993, J. Biol. Chem. 268: 12046-12054; Bartel et al., 1993, Biotechniques 14: 920-924; Iwabuchi et al., 1993, Oncogene 8: 1693-1696; and Brent WO 94/10300), to identify other proteins, which bind to or interact with CLASP-2 ("CLASP-2-binding proteins" or "CLASP-2-bp") and modulate CLASP-2 polypeptide activity. Such CLASP-2-binding proteins are also likely to be involved in the propagation of signals by the CLASP-2 polypeptides as, for example, upstream or downstream elements of the CLASP-2 pathway.

All of these above assays can be used as diagnostic or prognostic markers. The molecules discovered using these assays can be used to treat disease or to bring about a particular result in a patient by activating or inhibiting the CLASP-2 molecule. Moreover, the assays can discover agents which can inhibit or enhance the production of CLASP-2 from suitably manipulated cells or tissues.

Therefore, the invention includes a method of identifying compounds or agents that bind to CLASP-2 polypeptides comprising the steps of: (a) contacting a CLASP-2 polypeptide with a compound or agent under conditions which allow binding of the compound to the CLASP-2 polypeptide to form a complex and (b) determining if binding has occurred. Moreover, the invention includes a method of identifying agonists or antagonists comprising the steps of: (a) incubating a candidate compound with CLASP-2, (b) assaying a biological activity, and (b) determining if a biological activity of CLASP-2 has been altered.

Several methods of automating assays have been developed in recent years so as to permit screening of tens of thousands of compounds in a short period. See, e.g., Fodor et al., 1991, Science 251: 767-773, and other descriptions of chemical diversity libraries, which describe means for testing of binding affinity by a plurality of compounds.

5.12. Other Uses of CLASP Polynucleotides and Polypeptides

The polynucleotides, polypeptides, polypeptide homologues, modulators, and antibodies described herein can be used in one or more of the following methods: a) drug screening assays; b) diagnostic assays particularly in disease identification, allelic screening and pharmocogenetic testing; and c) pharmacogenomics. A CLASP-2 polypeptide of the invention has one or more of the activities described herein and can thus be used to, for example, modulate an immune response in an immune cell, for example by binding to a CLASP binding partner making it unavailable for binding to the naturally present CLASP polypeptide.

In one embodiment, these CLASP-2 binding partners can be tyrosine kinases (e.g., lyn, lck, fyn, ZAP-70m SyK, and CSK). In another embodiment, these CLASP-2 binding partners can be tyrosine phosphatases (e.g., EZRIN, SHP-1, SHP-2 and PTP36). In another embodiment, these CLASP-2 target molecules can be adaptor proteins (e.g., NCK, CBL, SHC, LNK, SLP-76, HS1, SIT, VAV, GrB2, and BRDG1. In another embodiment, these CLASP-2 binding partners can be cytoskeletal associated proteins such as ankyrin, spectrin, talin, ezrin, tropomyosin, myosin, plectin, syndecans, paralemmin, Band 3 protein, cytoskeletal protein 4.1, and PTP36. In a further embodiment, CLASP-2 binding partners can be members of the integrin family. The isolated nucleic acid molecules of the invention can be used to express CLASP-2 polypeptide (e.g., via a recombinant expression vector in a host cell or in gene therapy applications), to detect CLASP-2 mRNA (e.g., in a biological sample) or a naturally occurring or recombinantly generated genetic mutation in an CLASP-2 gene, and to modulate CLASP-2 activity, as described further below. In addition, the CLASP-2 polypeptides can be used to screen drugs or compounds which modulate CLASP-2 polypeptide activity as well as to treat disorders characterized by insufficient production of CLASP-2 polypeptide or production of CLASP-2 polypeptide forms which have decreased activity compared to wild type CLASP-2. Moreover, the anti-CLASP-2 antibodies of the invention can be used to detect and isolate an CLASP-2 polypeptide, particularly fragments of CLASP-2 present in a biological sample, and to modulate CLASP-2 polypeptide activity.

5.13. Diagnostic Assays

The invention further provides a method for detecting the presence of CLASP, or fragment thereof, in a biological sample. Usually the biological sample contains lymphocytes (e.g., from blood). The method involves contacting the biological sample with a compound or an agent capable of detecting CLASP polypeptide or mRNA such that the presence of CLASP is detected in the biological sample.

A preferred agent for detecting CLASP-2 mRNA is a directly or indirectly labeled nucleic acid probe capable of hybridizing to CLASP-2 mRNA. The nucleic acid probe can be, for example, the full-length CLASP-2 cDNA of SEQ ID NO: 1, or a portion thereof, such as an oligonucleotide of at least 15, 30, 50, 100, 250 or 500 nucleotides in length and sufficient to specifically hybridize under stringent conditions to CLASP-2 mRNA.

A preferred agent for detecting CLASP-2 polypeptide is a directly or indirectly labeled antibody capable of binding to a CLASP-2 polypeptide. Antibodies can be polyclonal, or more preferably, monoclonal. An intact antibody, or a fragment thereof (e.g., Fab or F(ab)$_2$) can be used. The term "directly or indirectly", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The detection method of the invention can be used to detect CLASP-2 mRNA or polypeptide in a biological sample in vitro as well as in vivo. For example, in vitro techniques for detection of CLASP-2 mRNA include Northern hybridizations and in situ hybridizations. In vitro techniques for detection of CLASP-2 polypeptide include enzyme linked immunosorbent assays (ELISAs), Western blots, immunoprecipitations and immunofluorescence. Alternatively, CLASP-2 polypeptide can be detected in vivo in a subject by introducing into the subject a labeled anti-CLASP-2 antibody. For example, the antibody can be labeled with a radioactive marker whose presence and location in a subject can be detected by standard imaging techniques. Particularly useful are methods which detect the allelic variant of CLASP-2 expressed in a subject and methods which detect fragments of an CLASP-2 polypeptide in a sample.

The invention also encompasses kits for detecting the presence of CLASP-2 in a biological sample. For example, the kit can comprise a directly or indirectly labeled compound or agent capable of detecting CLASP-2 polypeptide or mRNA in a biological sample; means for determining the amount of CLASP-2 in the sample; and means for comparing the amount of CLASP-2 in the sample with a standard. The compound or agent can be packaged in a suitable container. The kit can further comprise instructions for using the kit to detect CLASP-2 mRNA or polypeptide.

The methods of the invention can also be used to detect naturally occurring genetic mutations in an CLASP-2 gene, thereby determining if a subject with the mutated gene is at risk for a disorder characterized by aberrant or abnormal CLASP-2 nucleic acid expression or CLASP-2 polypeptide activity as described herein. In preferred embodiments, the methods include detecting, in a sample of cells from the subject, the presence or absence of a genetic mutation characterized by at least one of an alteration affecting the integrity of a gene encoding an CLASP-2 polypeptide, or the misexpression of the CLASP-2 gene.

5.14. Biological Activities of CLASP-2

As described herein, CLASP polypeptides mediates a variety of cell functions in lymphocytes and other cells. As described herein, a variety of assays are useful for detecting or quantitating CLASP activity, or for identifying agents (including polynucleotides, polypeptides, and antibodies of the invention) that modulate CLASP activity (i.e., biological activity, e.g., binding) or expression. Such agents are useful for treatment of diseases and conditions associated with aberrant CLASP expression or activity. Further, following the guidance provided herein, other CLASP-mediated activities can be identified by those of skill using routine assays, such as those described below.

Exemplary assays for CLASP function (or modulation of function) include assays for modulation of an in vitro or in vivo cell response (e.g., an immune response such as lymphocyte activation, antibody production, inflammation) by detecting a change in an activity (e.g., cytokine production, calcium flux, tyrosine phosphorylation, regulation of early activation markers, cell metabolism, proliferation, and the like, as described below) of cells in vitro or in vivo. In one embodiment, the cells are lymphocytes.

In one assay, for example, recombinant CLASP-2 protein, peptides, or antibodies corresponding to the CLASP-2 extracellular domain can be mixed directly with T and B cells. Cytokine production by these cells can then be measured and the degree of modulation of the immune response quantitated. Alternatively, antigen-presenting B cells are mixed with untransfected T cells or T cells that have been transfected with CLASP-2 isoforms. Cytokine production (or calcium flux or other assays in §5.14.3) is be measured at the appropriate time to determine the effect of CLASP-2 on such an immune response. In a similar assay, B cells transfected with CLASP-2 constructs are tested for their ability to stimulate a T cell to generate an immune response. Transfected constructs in any of these cases could encode, for example, full or partial length CLASP-2 sequences, or antisense constructs to inhibit translation of endogenous CLASP-2 gene. Any of the examples described herein can be used to stimulate an immune response in the presence or absence of CLASP-2 isoforms or antibodies and assay the resulting effects on immune response by the methods listed in §5.14.3.

5.14.1 Methods for Generating an Immune Response In Vitro

In various assays, an effect of an agent on immune cells is detected using an in vitro assay. The degree of an immune response can be measured or quantitated by a number of standard assays including those described below.

In one assay, human peripheral blood mononuclear cells (PBMC), human T cell clones (e.g., Jurkat E6, ATCC TIB-152), EBV-transformed B cell clones (e.g., 9D10, ATCC CRL-8752), antigen-specific T cell clones or lines can be used to examine immune responses in vitro. Activation, enhanced activation or inhibition of activation of these cells or cell lines can be used for the evaluation of potential CLASP therapeutics. Standard methods by which hematopoietic cells are stimulated to undergo activation characteristic of an immune response are, for example:

A) Antigen specific stimulation of immune responses. Either pre-immunized or naïve mouse splenocytes can be generated by standard procedures. In addition, antigen-specific T cell clones and hybridomas (e.g., MBP-specific), and numerous B cell lymphoma cell lines (e.g., CH27), have been previously characterized are available for the assays discussed below. Antigen specific splenocytes or B-cells can be mixed with specific T-cells in the presence of antigen to generate an immune response. This can be performed in the presence or absence of CLASP-2 to assay whether CLASP-2 modulates the immune response as measured by any of the assays in section 5.14.2.

B) Non-specific T cell activation. The following methods can be used to activate T cells in the absence of antigen: 1) cross-linking T cell receptor (TCR) by addition of antibodies against receptor activation molecules (e.g., TCR, CD3, or CD2) together with antibodies against co-stimulator molecules, for example anti-CD28; 2) activating cell surface receptors in a non-specific fashion using lectins such as concanavalin A (con A) and phytohemagglutinin (PHA); 3) mimicking cell surface receptor-mediated activation using pharmacological agents that activate protein kinase C (e.g., phorbol esters) and increase cytoplasmic $Ca^{2+}$ (e.g., ionomycin).

C) Non-specific B cell activation: 1) application of antibodies against cell surface molecules such as IgM, CD20, or CD21. 2) Lipopolysaccharide (LPS), phorbol esters, calcium ionophores and ionomycin can also be used to by-pass receptor triggering.

D) Mixed lymphocyte reaction (MLR). Mix donor PBMC with recipient PBMC to activate lymphocytes by presentation of mismatched tissue antigens, which occurs in all cases except identical twins.

E) Generation of a specific T cell clone or line that recognizes a particular antigen. A standard approach is to generate tetanus toxin-specific T cells from a donor that has recently been boosted with tetanus toxin. Major histocompatability complex- (MHC-) matched antigen presenting cells and a source of tetanus toxin are used to maintain antigen specificity of the cell line or T cell clone (Lanzavecchia, A., et al., 1983, Eur. J. Immun. 13: 733-738).

The anticipated mechanism of action of a CLASP polypeptide or polynucleotide should define the appropriate assay to use to investigate its potential enhancement or inhibition of lymphocyte activation. For example, soluble proteins containing the CLASP extracellular domain may interfere with the interaction between T cells and antigen presenting cells. Such interaction plays a role in the MLR and in antigen-specific T cell activation, but not in non-specific T or B cell activation. The assays described above have the advantage of several possible detection methods for quantitation.

5.14.2. Methods for Generating an Immune Response In Vivo

In various assays, an effect of an agent on immune cells is detected using an in vivo assay. The degree of an immune response can be measured or quantitated by a number of standard assays including those described below.

(A) Animal Model for Transplantation Rejection: Ectopic Heart Transplantation

In one embodiment, a standard animal model for graft versus host rejection is ectopic heart transplantation (Fulmer et al., 1963, Am. J. Anat. 113: 273-281). This method involves using BALB/C mice (either sex, and range from 1-9 months) for transplanting cardiac tissue into a surgically-created pocket on the dorsum for both ears made by slitting the skin over the auricular artery at the base of the ear. Small curved forceps are forced into the slit, bluntly dissecting between the skin and the cartilage plate. Donor tissue is eased into the base of the pocket near the distal edge of the ear. The auricular artery is used to seal off the opening of the pocket. Within 10 to 14 days pulsatile activity of the transplant should be observed. Gross appearance of the graft, patterns of vacuolar supply to the graft area and pulsatile activity can be easily observed utilizing transilluminated light during the first three weeks post-transplantation. Follow-up can continue for for several months.

(B) Animal model for Autoimmune Disease: Induction of Collagen Induced Arthritis (CIA)

Collagen Induced Arthritis (CIA) is a standard model for studying progression and immune (Courtenay et al., 1980, Nature 283: 666 and Wooley et al., 1981, J. Exp. Med. 154: 688). DBA/a mice can be used as an assay for the in vivo relevance of CLASP-2 in vitro testing potential immune therapeutics. In vivo experiments will be performed to examine the ability of potential therapeutics to prevent CIA. We will use 3-5 mice per group to statistically justify our results.

Once a titer of the potency of collagen type II (CII) is obtained therapeutics can be tested. In one embodiment, three mice will be immunized with three different concentrations of CII 50, 200, and 400 μg per animal (Nabozny et al., 1996, J. Exp. Med., 183: 27-37). To induce CIA, animals can be immunized with an appropriate concentration of CII, determined as described above. One half of a 1:1 ratio of antigen:CFA can be injected at the base of the tail and the remainder equally divided in each hind footpad. Mice can be carefully monitored every day for the onset and progression of CIA throughout the experiment until its termination 12 weeks post-immunization with CII. The pieces of heart transplanted can be approximately 3×3 mm in size. The severity of arthritis can be assessed following standard procedures known to one of skill in the art.

5.14.3 Assay Quantitation (A) Tyrosine Phosphorylation

Tyrosine phosphorylation of early response proteins such as HS1, PLC-r, ZAP-76, and Vav is an early biochemical event following T cell activation. The tyrosine phosphorylated proteins can be detected by Western blot using antibodies against phosphorylated tyrosine residues. Tyrosine phosphorylation of these early response proteins can be used as a standard assay for T cell activation (J. Biol. Chem., 1997, 272(23): 14562-14570). Any change in the phosphorylation pattern of these or related proteins when immune responses are generated in the presence of CLASP is indicative of a CLASP modulation of this response.

(B) Intracellular Calcium Flux

The kinetics of intracellular $Ca^{2+}$ concentrations are measured over time after stimulation of cells preloaded with a calcium sensitive dye. Upon binding the $Ca^{2+}$ indicator dye, Fluor-4 (Molecular Probes), exhibits an increase in fluorescence level using flow cytometry, solution fluorometry, and confocal microscopy. Any change in the level or timing of calcium flux when immune responses are generated in the presence of CLASP is indicative of a CLASP modulation of this response (C) Regulation of Early Activation Markers Increased and diminished expression/regulation of early lymphocyte activation marker levels such as CD69, IL-2R, MHC class II, B7, and TCR are commonly measured with fluorescently labeled antibodies using flow cytometry. All antibodies are commercially available. Any change in the expression levels of lymphocyte activation markers when immune responses are generated in the presence of CLASP is indicative of a CLASP modulation of this response.

(D) Increased Metabolic Activity/Acid Release

Activation of most known signal transduction pathways trigger increases in acidic metabolites. This reproducible biological event is measured as the rate of acid release using a microphysiometer (Molecular Devices), can be used as an early activation marker when comparing the treatment of cells with potential biological therapeutics (McConnell, H. M. et al., 1992, Science 257: 1906-1912 and McConnell, H. M., 1995, Proc. Natl. Acad. Sci. 92: 2750-2754). Any statistically significant increase or decrease in acid release of CLASP-treated sample, as compared to control sample (no treatment), suggest and effect of CLASP on biological function.

(E) Cell Proliferation/Cell Viability Assays (1) $^3$H-thimidine Incorporation

Exposure of lymphocytes to antigen or mitogen in vitro induces DNA synthesis and cellular proliferation. The measurement of mitotic activity by $^3$H-thimidine incorporation into newly synthesized DNA is one of the most frequently used assays to quantitative T cell activation. Depending on the cell population and form of stimulation used to activate the T cells, mitotic activity can be measured within 24-72 hrs. in vitro, post $^3$H-thimidine pulse (Mishell, B. B. and S. M. Shiigi, 1980, Selected Methods in Cellular Immunology, W.H. Freeman and Company and Dutton, R. W. and Pearce, J. D., 1962, Nature 194: 93). Any statistically significant increase or decrease in CPM of CLASP-treated sample, as compared to control sample (no treatment), suggest and effect of CLASP on biological function.

(2) MTS [5-(3-carboxymethoxyphenyl)-2-(4,5-dimethylthiazolyl)-3(4-sulfophenyl)tetrazolium, inner salt] is a colorimetric method for determining the number of viable cells in proliferation or cytotoxicity assays (Barltrop, J. A. et al., 1991, Bioorg. & Med. Chem. Lett. 1: 611). 1-5 days after lymphocyte activation, MTS tetrazolium compound, Owen's reagent, is bioreduced by cells into a colored formazan product that is soluble in tissue culture media. Color intensity is read at 490 nm minus 650 nm using a microplate reader. Any statistically significant increase or decrease in color intensity of CLASP-treated sample, as compared to control sample (no treatment), can suggest an effect of CLASP on biological function (Mosmann, T., 1983, J. Immunol. Methods 65: 55 and Barltrop, J. A. et al. (1991)).

(3) Bromodeoxyuridine (BrdU), a thymidine analogue, readily incorporates into cells undergoing DNA synthesis. BrdU-pulsed cells are labeled with an enzyme-conjugated anti-BrdU antibody (Gratzner, H. G., 1982, Science 218: 474-475.). A colorimetric, soluble substrate is used to visualize proliferating cells that have incorporated BrdU. Reaction is stopped with sulfuric acid and plate is read at 450 nm using a microplate reader. Any statistically significant increase or decrease in color intensity of CLASP-treated sample, as compared to control sample (no treatment), suggest an effect of CLASP on biological function.

(F) Apoptosis by Annexin V

Programmed cell death or apoptosis is an early event in a cascade of catabolic reactions leading to cell death. A lose in the integrity of the cell membrane allows for the binding of fluorescently conjugated phosphatidylserine. Stained cells can be measured by fluorescence microscopy and flow cytometry (Vermes, I., 1995, J. Immunol. Methods. 180: 39-52). In one embodiment, any statistically significant increase or decrease in apoptotic cell number of CLASP-treated sample, as compared to control sample (no treatment), suggest an effect of CLASP on biological function. For evaluating apoptosis in situ, assays for evaluating cell death in tissue samples can also be used in vivo studies.

(G) Quantitation of Cytokine Production

Cell supernatants harvested after cell stimulation for 16-48 hrs are stored at −80° C. until assayed or directly tested for cytokine production. Multiple cytokine assays can be performed on each sample. IL-2, IL-3, IFN-γ and other cytokine ELISA Assays are available for mouse, rat, and human (Endogen, Inc. and BioSource). Cytokine production is measured using a standard two-antibody sandwich ELISA protocol as described by the manufacturer. The presence of horseradish peroxidase is detected with 3,3'5,5' tertamethyl benziidine (TMB) substrate and the reaction is stopped with sulfuric acid. The absorbency at 450 nm is measured using a microplate reader. Any statistically significant increase or decrease in color intensity of CLASP-treated sample, as compared to control sample (no treatment), suggest an effect of CLASP on biological function.

(H) NF-AT can be Visualized by Immunostaining

T cell activation requires the import of nuclear factor of activated T cells (NFAT) to the nucleus. This translocation of NF-AT can be visualized by immunostaining with anti-NF-AT antibody (Cell 1998, 93: 851-861). Therefore, NF-AT nuclear translocation has been used to assay T cell activation. Similarly, NF-AT/luciferase reporter assays have been used as a standard measurement of T cell activation (MCB 1996, 12: 7151-7160).

(I) ELISA for Collagen Type II (CII)-Specific Antibodies (See Above for Related In Vivo Assay)

C(II) titers from serum of animals immunized with CLASP-2 can be measured and compared. Both TH1-dependent IgG2a and TH2-dependent IgG1 and IgE CII-specific antibody isotypes will be measured by ELISA. Mouse blood will be obtained by orbital bleed one and two months post-immunization with CII. Samples will be allowed to coagulate and centrifuge to obtain sera, and stored at −80° C. until assayed by ELISA. Coat ELISA plates with CII and dilute sera. HRP conjugated goat, isotype specific antibody. Plates are then expose to TMB substrate and read at 450 nm using a microplate reader (Nabozny et al., 1996, J. Exp. Med. 183: 27-37). Any change in the levels of Collagen specific antibodies by colorimetric test when immune responses are generated in the presence of CLASP is indicative of a CLASP modulation of this response.

(J) Antibody Production by ELISPOT Assay

A solid-phase enzyme-linked immunospot (ELISPOT) assay for the quantification of isotype-specific antibody secreting cells (Czerkinsky et al., 1983, J Immunol. Methods. 65: 109-121). Both human and mouse B cells can be tested for isotype and antigen specific antibody production. Although based on a standard ELISA, this technique becomes more sensitive by detecting antibody secretion from single cells. Any change in ELISPOT levels when immune responses are generated in the presence of CLASP is indicative of a CLASP modulation of this response.

(K) Cellular Degranulation Following IgE Cross-Linking.

Two cell lines have been obtained from ATCC (MEG01 and HEL-17.92), both of which express the human FCεR1 receptor. FCεR1 is the high affinity receptor for IgE complexes, which when coupled to biotin can be cross-linked with avidin to induce degranulation and histamine release of lymphocytes. Following acylatation of the sample, histamine is quantified with an enzyme immunoassay competition assay (Immunotech). Histamine release. A statistically significant increase or decrease in histamine concentration of a CLASP-2 treated sample, as compared to control sample (no treatment), suggest an effect of CLASP-2 on biological function. Any change in frequency of degranulation or histamine levels when immune responses are generated in the presence of CLASP is indicative of a CLASP modulation of this response.

(L) Cellular Phenotyping of Lymphocytes by Flow Cytometry and Immunocytochemistry Determining the tissue distribution of lymphocytes following a pathological disorder can aid in identifying specific organ, tissue and lymphocyte involved in an immune response. Cellular phenotyping of lymphocyte trafficking is generally performed with by flow cytometry and Immunocytochemistry. There are several cluster determination (CD) molecules that are routinely used to identify phenotype, activation kinetics, and regulation events of cells. Any change in levels or distribution of CD molecules when immune responses are generated in the presence of CLASP is indicative of a CLASP modulation of this response.

(M) Structure/Function Assays: Homotypic and/or Heterotypic, Calcium-Dependant Cell Adhesion L929 cells can be transfected with CLASP and Neomycin. G418-resistant clones can be screened for CLASP-expression with anti-CLASP peptide-specific antibodies. These CLASP-expressing clones can then be used to test for homotypic and/or heterotypic calcium dependent cell adhesion using the "cell aggregation assay" described for cadherin molecules (Murphy-Erdosh, C. et al., 1995, J. Cell Biol. 129: 1379-1390). Any change in the levels of cellular aggregation when immune responses are generated in the presence of CLASP-2 is indicative of a CLASP-2 modulation of this response.

\*\*\*

The following cDNA clones described in the Specification and further described in the Examples below have been deposited with the American Type Culture Collection, 10801 University Boulevard, Manassas, Va. 20110-2209 under the Budapest Treaty on Mar. 24, 2000 and given the Accession Nos. indicated:

hCLASP-2A 3' clone (AVC-PD1) ATCC accession number PTA-1563 hCLASP-2A 5' clone (AVC-PD2) ATCC accession number PTA-1562 hCLASP-2B clone (AVC-PD12) ATCC accession number PTA-1573

The following cDNA clones described in the Specification and further described in the Examples below have been deposited with the American Type Culture Collection, 10801 University Boulevard, Manassas, Va. 20110-2209 under the Budapest Treaty on Oct. 17, 2000 and given the Accession Nos. indicated:

hCLASP-2 clone hC2GR3.3 (AVC-PD14) ATCC Accession No. PTA-2611 hCLASP-2 clone hC2RT (AVC-PD19) ATCC Accession No. PTA-2614

\*\*\*

6. EXAMPLES

Example 1

Cloning of CLASP-2

The cloning of the CLASP gene family has not been a straightforward process. The cloning of each CLASP family member required the use of multiple techniques and resources. CLASP-2 was cloned in the following manner: an expressed sequence tag or EST clone (IMAGE clone 815795, derived from human germinal B cells) was identified based on a BLAST search of human GenBank human EST database using CLASP-1 sequences. IMAGE clone 815795 was sequenced completely. A polynucleotide probe prepared from 815975 sequence was labeled with $^{32}$P-dCTP and used to screen human cDNA libraries including Jurkat (Stratagene) and Ramos B cell cDNA library (James Boulter, UCLA). The screening methods employed were as described in Maniatis et al., 1989, Molecular Cloning A Laboratory Manual, Cold Spring Harbor Laboratory, New York. Several clones were identified and clone C9, with an insert of 3,752 base pairs, was sequenced (ABI dye-sequencing system, PE Applied Biosystems; Perkin-Elmer Corporation, 761 Main Avenue, Norwalk, Conn., U.S.A.). A 5' probe was prepared from C9 sequence and used to rescreen the cDNA libraries.

Several clones were isolated, but could not be excised from the phage (Stratagene, CA) without deleting the insert. To circumvent this problem, anchor PCR was performed using M13F primer and CLASP-2 primer (C96AS). The PCR fragment was cloned using the pGEM-T system (Promega), although initial attempts were unsuccessful. The isolated sequence encompassed additional but incomplete cDNA sequence and was determined to carry at least one mutation that may have allowed it to be propagated in bacteria. Commercial libraries from multiple tissue sources including human placenta, B cell, T cell and peripheral blood were exhaustively screened and re-screened resulting in the acquisition of only partial cDNAs. Generation of cDNA libraries using oligo dT or CLASP-specific primers also resulted in the acquisition of partial cDNAs. Genomic libraries were screened to obtain a portion of the genomic locus for each of the CLASP genes, and a genomic walk was initiated to obtain 5' exons and extend the cDNA sequence.

To obtain additional 5' CLASP-2 sequence, portions of the cDNA and genomic sequence from a BAC (Bacterial Artificial Chromosome) genomic library were compared to the NCBI database by BLAST. A genomic clone (Genbank identifier: gi9988160) comprising random, shotgun genomic sequence was identified. Using TFASTX (Pearson and Lipman, PNAS (1988) 85:2444-2448), the amino-terminal sequence of human CLASP4 was compared to 6 frame translation of gi9988160. Areas of gi9988160 that encoded amino acids with high similarity to CLASP4 amino acid sequence were used to design CLASP-2-specific oligonucleotides for RTPCR (reverse transcriptase polymerase chain reaction according to manufacturers instructions: Reverse transcriptase Gibco/BRL, Taq Polymerase from Sigma). Using oligonucleotides hC2gS5 (nucleotides −66 to −44 in Table 4 and C2AS18 (reverse complement of nucleotides 2120 to 2140 in Table 4 an RTPCR product of approximately 2.2 kb was generated, sequenced (dideoxynucleotide termination sequencing, Beckman Coulter CEQ2000) and shown to be additional human CLASP-2 5' sequence. Further complicating the cloning full-length CLASP cDNA products was the difficulty to clone (and subclone) certain CLASP cDNA products. Standard isolation of some of the CLASP cDNAs from a pure phage population following screening of commercially available cDNA libraries ("ZAP-out" procedure, Stratagene) resulted in no bacterial colonies. Similarly, certain RT-PCR products could not be cloned into standard plasmid vectors. No colonies were isolated by cloning these fragments into vectors lacking promoters, reverse orientations, low copy vectors, or by growth at altered temperatures or levels of antibiotic for plasmid selection (examples: CLASP-7-HC7gS6 to HC7gAS1 and HC7gS3 to HC7AS14; CLASP-4-C4P2 to hC4ASTM and C4P2 to HC4AS3'; CLASP-1-hC1S5' to hC1AS3'Kpn and C1S7 to hC1AS3'Kpn; see Primer Table below). One possibility is that sequences contained within certain regions of CLASP cDNAs are bactericidal and therefore not amenable to cloning. To circumvent these problems direct sequencing of RT-PCR products was performed.

PRIMER TABLE

| CLASP gene | Sense Primer | Sense sequence | Antisense Primer | Antisense sequence |
|---|---|---|---|---|
| CLASP-7 | HC7gS5 | AGGCCTTGTCTCTGTTTACCTG (SEQ ID NO:140) | HC7gASI | TGTCATGTACTGCACTCGCACAGC (SEQ ID NO:145) |
| CLASP-7 | HC7gS3 | ACAGGAACCTGCTGTACGTGTAC (SEQ ID NO:141) | HC7AS14 | TCGTGGCTGCACAGGATGCGGGTG (SEQ ID NO:146) |
| CLASP-4 | C4P2 | GACCCATTAGGAGGTCTAC (SEQ ID NO:142) | HC4AS3' | CGGGATCCATTGTCACCGTACATCTGC (SEQ ID NO:147) |
| CLASP-4 | C4P2 | GACCCATTAGGAGGTCTAC (SEQ ID NO:142) | HC4AS3' | CGGGATCCATTGTCACCGTACATCTGC (SEQ ID NO:147) |
| CLASP-1 | hC1S5' | TATGTCTCAGTCACCTACCTG (SEQ ID NO:143) | HC1AS3'Kpn | CTTGGTACCACTTCAGCACTAGATGAGATG (SEQ ID NO:148) |
| CLASP-1 | C1S7 | TCAAGACCAGGGCATGCAAG (SEQ ID NO:144 | HC1AS3'Kpn | CTTGGTACCACTTCAGCACTAGATGAGATG (SEQ ID NO:148) |

In-frame stop codons were not present suggesting that the cDNA was not full length. To obtain the 5' terminus of CLASP-2 5' RACE was employed. Antisense oligonucleotides directed against the 5' end of the longest CLASP-2 sequence were generated:

Primers used for human CLASP-2 5' RACE

| primer | sequence(5' TO 3') | nucleotide position |
|---|---|---|
| HC2RACE1 | AAGAGCAGCATCTCCCGTAAACAGTC (SEQ ID NO:149) | −15 to 11 |
| HC2RACE2 | TAACAAGCTCTGTGCTTCCTCTTCCG (SEQ ID NO:150) | 414 to 443 |
| HC2RACE3 | ACCACTTTGTTCGGAAGCTGTCGAAACTC (SEQ ID NO:151) | 512 to 540 |
| HC2RACE4 | TTTGTACAGCCAGCCATGCTTGGTGATC (SEQ ID NO:152) | 634 to 661 |

RACE was carried out using Generacer kit (Invitrogen) according to manufacturers specifications using polyA selected mRNA from 9D10 B cell tissue culture line. The sequence of the oligonucleotides presented is the reverse complement (i.e., antisense) of the CLASP1 cDNA at the indicated position based upon numbering in Table 4.

The full length cDNA (presented in Table 4) is therefore a compilation of cDNA from cDNA libraries, RTPCR products and 5' RACE products.

Example 2

Tissue and Cell Line Expression of the CLASP-2 Gene

Multiple Tissue Northern Blots were Purchased from Clontech; Hybridization procedures were followed according to manufacturer's procedures and recommendations. Human T cell line (Jurkat), human myelomonocyte cells (MV4-11), B cells (9D10), monocytes (THP-1), mouse T cells (3A9), mouse B cells (CH27), human promyelocyte (HL60) and human kidney epithelial cells (293 cell line) were maintained as cultured cell lines. For Multiple Cell Northerns, RNA was prepared from cell suspensions using the GIBCO-BRL Trizol system. All steps were performed according to the manufacturer's procedures and recommendations. RNA concentrations were determined by the 260 nm/280 nm light absorption of the RNA solution. 20 µg RNA was ethanol precipitated and resuspended in formamide/formaldehyde buffer and incubated for 15' at 65° C. to eliminate putative secondary structures. RNA samples were run over night on a 1.1% agarose gel containing 1.5% formaldehyde (both gel and running buffer were 20 mM sodium phosphate, pH 7.5). To visualize RNA after gel migration, approx. 0.5 µg ethidium bromide was added to each sample prior to the run together with RNA loading buffer. RNA in the gel was then visualized by 260 nm wavelength light. After soaking the gel for 15' in deionized water to reduce the concentration of ethidium bromide in the gel, the RNA was transferred onto Amersham Hybond-N plus membrane by capillary blotting in 20×SSC buffer for 5 hours. Subsequent to blotting, the membrane was washed in 5×SSC for 3' and RNA was crosslinked to the membrane by UV light (Stratagene Stratalinker).

A probe which recognizes CLASP-2 isoforms A, B, C, and D (probe HC2.2) was used. Probe HC2.2 encompasses nucleotides 3920 to 4650 (731 bp long) of CLASP-2A. The HC2.2 probe was prepared using standard labeling kits and desalted using pasteur pipette G-50 Sephadex column in TEN (10 mM Tris-HCl, pH 8.0, 1 mM EDTA, and 100 mM NaCl).

Hybridizations of $^{32}$P dCTP labeled DNA probes to the membrane bound RNAs (multiple tissue and multiple cells) were carried out in CLONTECH EXPRESSHYB solution, at 68° C. and for 1-2 hours. Blots were washed 2 times in 2×SSC 0.1% SDS for 10' each at 50° C. and then twice in 0.2×SSC 0.1% SDS for 10' each at 50° C., followed by a 5' wash in 2×SSC at 50° C. Exposure to KODAK BIOMAX MS film was carried out at minus 80° C. using amplifying screens. Typical exposure times were 10 to 36 hours.

Example 3

Southern Analysis of CLASP-2

BAC DNA was prepared from *E. coli* over night cultures using the QIAGEN DNA preparation system. All preps were performed according to the manufacturer's procedures, including the modifications for low copy number DNA constructs. Genomic DNA was prepared from HeLa cells (ATCC #CCL-17) using the methods described by Sambrook, Fritsch and Maniatis (1989); DNA concentrations were determined by the 260 nm light absorption of the DNA solution, and aliquots corresponding to 20 microgram (µg) genomic. DNA or 2 µg for BAC DNA were used for restriction enzyme digests with Eco RI or HinD III (genomic DNA) or Eco RI and Pst I (BAC DNA). Digests were carried out in 150 microliter volume for 4 hours at 37° C. Digested DNA was ethanol precipitated and the pellet was resuspended in 20 microliter deionized water prior to migration over a 1.2% agarose gel at 35 V over night. Running buffer was TAE, and the gel contained 0.1 µg ethidium bromide/ml to visualize DNA.

Subsequent to gel separation, DNA was visualized by 260 nm wavelength light. The gel was then washed twice for 20' in denaturing buffer (0.5M NaCl, 0.4 N NaOH) and twice in neutralization buffer (1.5 M NaCl, 0.5 M TRIS pH 8.0). DNA was transferred from the gel onto AMERSHAM HYBOND N membrane by capillary blotting in 20×SSC for 5 hours. The DNA was crosslinked to the membrane by UV light using a Stratagene Stratalinker.

A probe, HC2.1, which recognizes CLASP-2, was used. Probe HC2.1 encompasses nucleotides 325 to 1126 (802 bp long) of CLASP-2A. The HC2.1 probe was prepared using standard labeling kits and desalted using pasteur pipette G-50 Sephadex column in TEN (10 mM Tris-HCl, pH 8.0, 1 mM EDTA, and 100 mM Nacl). Hybridizations of $^{32}$P dCTP labeled DNA against DNA immobilized onto the membrane were carried out at 65° C. overnight in modified CHURCH hybridization solution (7% SDS, 0.5 M sodiumphosphate, 1 mM EDTA). Membranes were then exposed to KODAK BIOMAX MS film at minus 80° C. Typical exposure times were 12 hours for genomic DNA southern analysis and 3 hours for BAC DNA Southern analysis.

The genomic DNA southern analysis revealed two fragments (~4.5 kb and 1.85 kb) in the Eco RI digested DNA but three fragments in BACs 4 and 6 DNA. The two major bands are identical in both genomic and BAC DNA (FIG. 7).

Example 4

CLASP-2 Genomic Cloning

Genomic clones of human CLASP-2 were obtained using the Release I high density filters from Genome Systems Inc (cat # FBAC-4434). Two rounds of screening were completed. The first round of screening was carried out using a probe corresponding to nucleotides 3830 to 4558 of the human CLASP-2 cDNA by standard protocols specific by Genome Systems. This screen identified two genomic clones, referred to as AVC BAC4 and 7. A second round of screening using a probe that corresponded to nucleotides 1208 to 1604 of human CLASP-2 cDNA identified clone AVC BAC26. All the clones were partially sequenced to authenticate that they were indeed CLASP-2 genomic clones, to verify exon sequences, and to identify exon/intron boundaries. Oligonucleotides for sequencing the BACs were based upon human CLASP-2 cDNA sequence. Sense and antisense sequencing oligonucleotides were designed along the length of the human CLASP-2 cDNA spaced approximately every 200 nucleotides to ensure a high density of coverage of the corresponding genomic regions. Sequencing reactions with primers and BAC DNA were carried out by standard PCR sequencing using Big Dye termination sequencing mix (ABI). Results from sequence reactions were analyzed using Sequencher software (Genecodes). The results are summarized in FIG. 6.

Example 5

Expression of Recombinant CLASP-2A Polypeptide in Bacterial Cells

Portions of hCLASP-2 were cloned into the GST expression vector pGEX (Pharmacia). These include the region spanning the potential Cadherin processing site through 200 amino acids of the predicted extracellular domain (nucleotide 866-1459; GST-EC12; 55 kD fusion) and a portion of the intracellular domain (nucleotide 3230-4065; GST-cyto; 57 kD fusion). These regions were amplified using primers at the limits of these sequences on either cDNA clones or cDNA generated from Jurkat or Human Peripheral Blood RNA. Amplified DNA sequences were digested with restriction enzymes for cloning in-frame into GST expression vectors. Fusion proteins were expressed by IPTG induction in DH5α and purified according to instructions from Pharmacia using glutathione-Sepharose (Pharmacia). SDS-PAGE gel stained with Coomassie Blue showing induced and uninduced expression of the GST-CLASP-2-cyto construct is shown in FIG. 8. These recombinant proteins were expressed in DH5α and purified according to instructions from Pharmacia using glutathione-Sepharose. Such recombinant proteins were used to generate antibodies (Josman laboratories) using a AVC Rapid Immunization Protocol.

The full length CLASP can easily be expressed from either the beginning of the hCLASP-2 sequence (in frame with nucleotide 2) or from the first or second methionine (nucleotide 278 or nucleotide 476, underlined in FIG. 1) through to the stop codon (nucleotide 4058). Assuming that the GST moiety has a weight of 26 kD, the total predicted sizes are 180, 168, and 164.5 kD respectively. Alternatively, other bacterial expression systems such as 6CLASP HIS tags, Calmodulin binding protein, maltose binding protein can also be used in a similar manner.

Example 6

Expression of Recombinant CLASP-2A Polypeptide in Mammalian Cells

Example 6A

Secreted Fusions

Several portions of the predicted extracellular domain were constructed as hIgG fusions using the CD5gamma-1 expression vector (kindly provided by B. Seed, Harvard University). Polypeptides were cloned into this vector in frame with a CD5 leader sequence that directs the fusion protein into the secretory pathway and in frame with a C-terminal hIgG(Fc) protein. This fusion can be secreted from cell lines such as 293 (Hsieh, J-C., 1999, Nature 398: 431-436). Sense primers with hCLASP-2 sequences beginning at nucleotide 866 and antisense primers at nucleotide 1459 (EC12-IgG), nucleotide 2389 (ECC-IgG) and nucleotide 2857 (ECM-IgG) were used to amplify portions of the extracellular domain for insertion into this vector. Recombinant vectors were purified by Maxiprep (Qiagen) and transfected into 293 EBNA-T cells (kindly provided by B. Seed, Harvard University) by calcium phosphate techniques (Sambrook and Maniatis). After 2-7 days, secreted expression was analyzed by an ELISA against the hIgG fusion using a goat F(ab')2 anti human IgG(Fc) antibody (Jackson Immunolabs) and Protein-A-HRP (Pierce). Intracellular expression was monitored by immunofluorescence microscopy with a FITC labeled goat anti Human IgG(Fc) antibody (Caltag).

Example 6B

Intracellular Fusions

Similar methods have been used to construct fusions for expression of full length hCLASP-2 isoforms as well as truncated C-terminal forms in other cell lines such as Jurkat. Recombinant hCLASP-2 fragments were either isolated by digestion of cDNA clones or amplified by primers flanking specific regions. These can be cloned into expression vectors such as pBJ1-neo (Mark Davis, Stanford University), Peak12 (B. Seed, Harvard University), and pDsRed1-N1 (Clontech). pBJ1-neo and Peak12 allow untagged expression of recombinant proteins and pDsRed1-N1 will allow either untagged or a C-terminal Red fluorescent protein tag. These can be used to generate protein or for expression of various forms for functional analyses.

Example 7

Antisense Inhibition of CLASP-2 Expression

Example 7A

Inhibition of CLASP-2 Expression In Vitro

In this example, inhibition of CLASP-2 expression is examined using an in vitro cell-free expression system. To identify the useful antisense oligonucleotides, a series of antisense phosphorothioate oligonucleotides (PS-ODNs), which span portion CLASP-2 sequence, can be systematically assayed for the ability to block CLASP-2 expression in vitro.

For inhibition of CLASP-2 expression in vitro, a CLASP-2 transcription/expression plasmid can be used according to standard methodology for in vitro transcription and translation of sense CLASP-2 RNA. Coupled transcription-translation reactions can be performed with a reticulocyte lysate system (Promega TNT™) according to standard conditions. Each coupled transcription/translation reaction can include CLASP-2 RNA transcribed from the expression plasmid, and a test antisense polynucleotide at a range of standard test concentrations, as well as the luciferase transcription/translation internal control to normalize each reaction (see, e.g., Sambrook et al., supra, Ausubel et al., supra). The translation reaction can also be performed with sense CLASP-2 RNA that is synthesized in vitro in a separate reaction and then added to the translation reaction. $^{35}$S-Met is included in the reaction to label the translation products. The negative control is performed without added PS-ODN or a sense PS-ODN.

The labeled translation products can be separated by gel electrophoresis and quantitated after exposing the gel to a phosphorimager screen. The amount of CLASP-2 protein expressed in the presence of CLASP-2 specific PS-ODNs can be normalized to the co-expressed luciferase control.

Example 7B

Inhibition of CLASP-2 Expression Ex Vivo

A. Reagents

Cells: Jurkat, Clone E6-1 ATCC TIB-152; 9D10 ATCC CRL8752; additional cells from the ATCC or NCI.

Media and solutions: RPMI 1640 medium, BioWhitaker; DMEM/M199 medium, BioWhitaker; EMEM, BioWhitaker; Fetal Bovine Serum, Summit (stored frozen at −20° C., stored thawed at 4° C.); Trypsin-EDTA, GIBCO (stored frozen at −20° C., stored thawed 4° C.; Isoton II (stored at RT); DMSO (stored at RT); oligonucleotides (see Table 1 and FIG. 3, stored in solution at −20° C.); PBS ($Ca^{2+}/Mg^{2+}$ free); TE; 10 mM Tris-HCL, pH 8.0; 1 mM EDTA.

To prepare oligonucleotide stocks: Oligonucleotide nucleotides (PS-ODNs) can dissolved in the appropriate amount of TE to make a concentrated stock solution (1-20 mM).

B. Treatment of Cells Ex Vivo with Antisense CLASP-2 Oligonucleotides

Stock cultures of cells in log-phase growth (in T75 flask) can be used. Jurkat, and 9D10 cells are used in this assay. Jurkat and 9D10 are suspension cultures and are passed through dilutions in media. Cell density is measured using a Coulter counter or hemacytometer.

For 6-well dishes, $1.1 \times 10^5$ cells total per well, 2 ml/well is added. The amount of cells can be scaled up or down proportionally for 12-well, 100 mm, or 150 mm dishes. For example, for 12-well dishes, use $4.6 \times 10^4$ cells in 2 ml media; for 100 mm dishes use $6 \times 10^5$ cells in 10 ml media; for 150 mm dishes use $1.7 \times 10^6$ cells in 35 ml media.

An appropriate number of cells (as described in step 2 above) are collected, centrifuged and resuspended in media containing a range of ODN concentrations. The cells are treated in single, duplicate, or triplicate wells. Control wells are treated with TE or sense ODNs diluted in media.

The suspension cultures are washed and resuspended daily with PS-ODN media.

Suspension cultures are grown for 2-4 days. Cells are washed with PBS and density measured using a Coulter counter or a hemocytometer. If necessary, the cells are replated at $1.1 \times 10^5$ cells per well, 2 ml media per well, and fed with PS-ODN as described above.

Samples of the cells can also be harvested for analysis to determine the effects of CLASP-2 antisense ODNs. Samples are harvested for RNA and analyzed by either Northern analysis or RT-PCR for the presence of CLASP-2 mRNA. Functional consequences of CLASP-2 antisense ODNs can be analyzed by measuring the ability of Jurkat and 9D10 cells to be activated. Jurkat cells are activated by exposure to anti-CD3 and anti-CD28 crosslinking antibodies, and 9D10 cells are activated by exposure to anti-IgM crosslinking antibody or *P. aeruginosa* lipopolysaccharide. A hallmark of activation, calcium influx, can be measured by flow cytometry. Additionally, ELISA assays can be used to measure Interleukin-2 production from Jurkat cells and secreted IgM can be measured using standard assays from 9D10.

Table 5 below shows exemplary oligonucleotides for this assay:

TABLE 5

| Oligo | Sequence 5'-3' | length | notes/comments |
|---|---|---|---|
| 1 | GAAGGCGATCATCACGT GGCCTTCCATCGC (SEQ ID NO:109) | 30-mer | encompasses nucleotides 473-502 and spans the putative initiator methionine (underlined). The function of HC2A, 2B, 2C, and 2E isoforms can be eliminated by this oligonucleotide. |
| 2 | GCTTCAAGTAATGACTGG TGCAGAACATCTG (SEQ ID NO:110) | 31-mer | Oligonucleotide that should recognize HC2A, 2B, 2D, 2E, and 2F. Encompasses nucleotides 2121-2151. Can be eliminate function of these CLASP-2 isoforms. |
| 3 | GCTCCTCCTCAGGCAGGC GCTATGGCTGTGG (SEQ ID NO:111) | 34-mer | oligonucleotide specific for HC2C based upon a specific exon found at nucleotide 2927. Can eliminate only HC2D function. |
| 4 | GTAGGCCCGGTGCAGCGT GTCATACAGATGG (SEQ ID NO:112) | 31-mer | oligonucleotide specific for HC2B, 2C, 2D and 2E based upon specific exon sequence found at nucleotide 3153. Can eliminate function of these CLASP-2 isoforms. |
| 5 | GCAATGTCTGAGACTTTC GATCATGAACTATG (SEQ ID NO:113) | 32-mer | oligonucleotide specific for HC2A, 2B, 2E, and 2F. Encompasses nucleotides 1987-2018. Can eliminate function of these CLASP-2 isoforms. |
| 6 | CAGGAGCTGGTTCTTAAA (SEQ ID NO:114) | 18-mer | oligonucleotide specific for HC2A, 2D and 2E. Encompasses nucleotides 2219-2224. Can eliminate function of these CLASP-2 isoforms |

Table 5 legend. All nucleotide numeration are relative to Human CLASP-2A (HC2A). See FIG. 2A.

Example 8

Example 8A

Synthesis of Carboxyl-Termini PDZ-Ligand Peptides

The GST-PDZ fusion proteins are made following standard procedures. An exemplary GST-PDZ fusion protein was constructed as follows: A 572 bp fragment encoding two PDZ domains of the human neDLG gene (Genbank Accession No. U49089.1) was amplified from total Jurkat RNA by RT-PCR according to standard protocols (Sambrook, Fritsch, and Maniatis, 1989, Molecular Cloning—A Laboratory Manual. Cold Spring Harbor Press.) using primers flanked by restriction endonuclease sites for cloning. Fragments were purified by Sephaglas (Pharmacia), digested with the appropriate enzymes, and ligated into the GST expression vector pGEX-3X (Pharmacia) cut with similar enzymes. Recombinant constructs were confirmed by sequencing. Fusion proteins were expressed by IPTG induction in DH5α and purified using glutathione-Sepharose (Pharmacia) according to instructions from Pharmacia. Excess glutathione was removed using a PD10 desalting column (Pharmacia) and samples were diaconcentrated by placing the protein in dialysis tubing (14,000 MW cutoff) and laying the tubing on polyethylene glycol (3350; Sigma) until volume had been reduced by approximately 50%. Glycerol was then added to 35% final concentration and samples were stored at −20° C. These recombinant proteins have been used to generate antibodies (Josman laboratories) by standard protocols and for biochemical studies describe herein.

Synthetic peptides corresponding to the carboxyl-terminus of a protein of interest are synthesized by standard resin-based chemistry (e.g., FMOC), labeled with biotin at the amino-terminus when indicated, and cleaved from the resin using a halide containing acid (e.g., trifluoroacetic acid). The synthetic peptides are then purified by reverse phase high performance liquid chromatography (HPLC) and the identity of the peptides are confirmed by mass spectrometry.

Example 8B

Measurement of CLASP-2 Peptide Binding to PDZ Domain-Containing Proteins

The binding of a biotinylated carboxyl-terminal peptide to a GST-PDZ fusion protein is measured as follows:
(1) GST fusion protein containing one or more PDZ domain(s) is coated onto a protein-binding surface. The protein-binding surface is the surface of a polystyrene plate, which in some cases has been pre-treated by coating with 5 µg/ml of goat-anti-GST polyclonal antibody followed by blocking with excess bovine serum albumin (BSA). The concentration of GST fusion protein used is 5-10 µg/ml and the reaction of the GST fusion protein with the plate is carried out in PBS for 1-16 hours at 4° C. If not already blocked, the plate is then blocked with BSA (2% in PBS, 2 hours, 4° C.)
(2) The plate is washed with PBS.
(3) The biotinylated peptide (generally 0.2-20 µM) is then added to the plate and allowed to react in PBS/2% BSA buffer with the GST fusion protein for 10 minutes at 4° C. followed by 20 minutes at 25° C. In cases where competition between a labeled (biotinylated) and unlabeled (non-biotinylated) peptide is performed, the unlabeled peptide is added immediately prior to adding the labeled peptide.
(4) The plate is washed with PBS.
(5) 0.5 µg/ml steptavidin-HRP conjugate is added to the plate in PBS/2% BSA buffer and allowed to react for 20 minutes at 4° C.
(6) The plate is washed 5× with detergent (tween 20) containing solution.
(7) The plate is developed by addition of HRP-substrate solution for 20 minutes at room temperature.
(8) The reaction of the HRP and its substrate is terminated by addition of 1 M sulfuric acid.
(9) The optical density of each well of the plate is read at 450 nm.

In cases where measurement of the apparent affinity of PDZ-ligand interaction is desired, the above procedure is carried out with multiple concentrations of the labeled peptide being used in a single experiment. A plot of binding versus peptide concentration added is then fit to the equation:

$$\text{Binding [peptide]} = \text{Saturation Binding} \times ([\text{peptide}] / ([\text{peptide}] + K_d))$$

where "Binding [peptide]" is the binding of a given concentration of peptide to the GST-PDZ fusion protein minus binding to the GST alone control, "Kd" is the apparent affinity of the binding reaction, and "Saturation Binding" is computed to allow the best fit of the data to the above equation. The term apparent affinity is used because the reaction may not reach equilibrium during the duration of the binding reaction in which case the apparent affinity would underestimate the actual affinity (i.e., actual Kd<observed Kd).

Example 9

Expression of Human CLASP-2 in Activated T-Cells

General Experimental Design

The expression profiles of human CLASP-2 in T cells upon T cell activation was determined by Northern analysis. Jurkat E6 lymphoblasts were activated by treatment with anti-CD28, PMA, and Ionomycin. Subsequently, total RNA was extracted from cell aliquots harvested at 0, 1, 2, 4, 8, and 14 hours post activation. The RNA concentration of each preparation was determined by the absorption at 260 nm using a spectrophotometer and concentrations of the different RNA preparations were adjusted such that equal quantities of each RNA preparation could be subjected to Northern analysis. Even gel loading was monitored by ethidium bromide staining of the formaldehyde-agarose gel. Northern membranes were hybridized to radioactively labeled probes corresponding to portions of human CLASP-2 and human beta-actin. Expression levels of CLASP-2 at different time points post T-cell activation are proportional to the radioactive signal generated by hybridization by the CLASP-2 specific radioactively labeled probe that remained bound to the Northern membrane under stringent washing conditions. The entire experiment was done in duplicate.

Jurkat E6 Cell Activation

Jurkat E6 cells were maintained and tested in complete IMDM medium supplemented with 2 mM glutamine, 10 mM HEPES, 100 u/mL penicillin, 100 µg/mL streptomycin, 0.1 mM nonessential amino acids, 1 mM sodium pyruvate (Gibco/BRL), 50 µM beta mercaptoethanol (Sigma), and 10% fetal calf serum (Gemini). T cells were activated as described per Fraser et al., using 0.1 g/mL mouse anti-human CD28 monoclonal antibody (PharMingen International catalog number 33741A), 50 ng/mL PMA (Sigma), and 1 µM ionomycin (Calbiochem). Following incubation at 37° C. and 5.0% v/v $CO_2$, $0.5 \times 10^6$ cells were harvested by centrifugation at 500×g for 10 minutes (min) at room temperature at 0, 1, 2, 4, 8 and 14 hours post activation and subjected to RNA extraction.

For RNA preparation, probe labeling and Northern analysis protocols, see methods and procedures described in Example 2 above. The CLASP-2 specific probe encompassing nucleotides 5352 to 5922 was generated by PCR from a plasmid containing cloned CLASP-2 cDNA sequences using primers C2S12 and C2AS21.

Hybridization, Washing, and Exposure

Blots were washed twice in 2×SSC 0.1% SDS for 10 min each at 60° C. and then twice in 0.2×SSC 0.1% SDS for 10 min each at 60° C., followed by a 5' wash in 2×SSC at 60° C. Exposure to KODAK BIOMAX MS film was carried out at minus 80° C. using amplifying screens. Typically, exposure times were 10 to 36 hours. Signal intensities on Northern membranes were quantified by the use of a phosphor imager system (STORM, Molecular Dynamics). Signals were counted in the "volume report" mode.

Results

CLASP-2 expression levels as determined by Northern analysis (FIG. 11) slightly decrease at 1 hour post activation. The maximum decrease of approximately 36% is seen at 2 hours post activation. Expression levels augment again at 4 hours post activation but do not attain the level that is seen before activation (0 hours). Intensities of CLASP-2-specific signals on the Northern blot were quantified by phosphor imager analysis. Rectangles were drawn around the areas of CLASP-2-specific signal and total quantity of signal was determined by the "volume report" mode; phosphor imager quantification results of two entirely independent experiments are shown in the diagram (green bars corresponds to Northern blot shown). The above result suggests, that transcriptional control of CLASP-2 expression and T-cell activation are functionally linked to each other.

Example 10

Chromosomal Location of CLASP-2 and Possible Disease Associations

CLASP-2 cDNA sequences have been mapped to the genomic clone (GI:9926440, GI:9988160) by use of sequence homology bioinformatics tools BLAST.

Clone (GI:9926440, GI:9988160) has previously been mapped to the chromosomal location 13q12-q13. The literature research reports that the mutations, deletions, rearrangements, disomies and/or breakpoints (in general: chromosomal aberations) in below listed genes make the genes strong candidates for the onset of the listed diseases/disorders. Because the CLASP-2 gene is localized in the chromosome location 13q12-q13, abnormal CLASP-2 gene regulation or deletion, rearrangement and/or mutations in CLASP-2 locus might be directly or indirectly associated with the onset of the listed diseases. Further, CLASP-2 gene can be used as a genetic probe to detect the abnormality in regions of these below listed genes and as a diagnostic marker for the related disease/disorders.

| CANDIDATE GENES | LOCUS | RELATED DISEASE/DISORDERS |
|---|---|---|
| IPF1: Insulin promoter factor1 | 13q12.1 | MODY4: non insulin-dependent juvenile type, Defect in pancreatic islet development and insulin transcription. |
| BRCA2 | 13q12.3 | BCLL2: B cell lymphoma, deletion encompassing BRCA2 causes B cell lymphoma. BRCA2 is one of the responsible genes for DNA repairing in S phase. |
| | 13q13.1-q14.3 | Deletion of these locus causes MDS6: Myelo dysplastic syndrome type 6 including AML. |

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications and patent documents cited above are hereby incorporated by reference in their entirety for all purposes to the same extent as if each were so individually denoted. Without wishing to exclude incorporating the remainder of the following patent applications, the following sections of the following patent applications are explicitly incorporated by reference herein: FIGS. 1-8, Table 2, the sequence listing and Examples 1-6 on pages 109-120 of U.S. patent Ser. No. 09/737,246, filed Dec. 13, 2000 (abandoned); FIGS. 1-8, Table 2, the sequence listing and Examples 1-6 on pages 108-119 of U.S. patent Ser No. 09/736,969, filed May 7, 2001 (abandoned); FIGS. 1-8, Table 2, the sequence listing and Examples 1-4 on pages 106-111 of U.S. patent Ser. No. 09/736,960 filed Dec. 13, 2000 (abandoned); FIGS. 1-7, Table 2, the sequence listing and Examples 1-4 on pages 106-111 of U.S. patent Ser. No. 09/736,968, filed Dec. 13, 2000 (abandoned); FIGS. 1-9, Table 2, the sequence listing, and Examples 1-7 on pages 106-130 of U.S. patent Ser. No. 09/978,244 filed Oct. 15, 2001 (abandoned); and FIGS. 1-9, Table 2 and 3, the sequence listing and Examples 1-7 on pages 108-132 of PCT application Ser. No. US02/24482 now published as WO03/025120.

SEQUENCE LISTING

```
<160> NUMBER OF SEQ ID NOS: 152

<210> SEQ ID NO 1
<211> LENGTH: 4807
<212> TYPE: DNA
<213> ORGANISM: Homo sapiens
<220> FEATURE:
<221> NAME/KEY: CDS
<222> LOCATION: (2)..(4060)
<223> OTHER INFORMATION: Human cadherin-like asymmetry protein 2A
      (CLASP-2A)

<400> SEQUENCE: 1
```

```
a gtt tta cac cat cac caa aac cca gaa ttt tat gat gag att aaa ata        49
  Val Leu His His His Gln Asn Pro Glu Phe Tyr Asp Glu Ile Lys Ile
    1               5                  10                  15 gag ttg ccc act cag ctg cat gaa aag cac cac ctg ttg ctc aca ttc          97
Glu Leu Pro Thr Gln Leu His Glu Lys His His Leu Leu Leu Thr Phe
                20                  25                  30 ttc cat gtc agc tgt gac aac tca agt aaa gga agc acg aag aag agg         145
Phe His Val Ser Cys Asp Asn Ser Ser Lys Gly Ser Thr Lys Lys Arg
            35                  40                  45 gat gtc gtt gaa acc caa gtt ggc tac tcc tgg ctt ccc ctc ctg aaa         193
Asp Val Val Glu Thr Gln Val Gly Tyr Ser Trp Leu Pro Leu Leu Lys
        50                  55                  60 gac gga agg gtg gtg aca agc gag cag cac atc ccg gtc tcg gcg aac         241
Asp Gly Arg Val Val Thr Ser Glu Gln His Ile Pro Val Ser Ala Asn
 65                  70                  75                  80 ctt cct tcg ggc tat ctt ggc tac caa gag ctt ggg atg ggc agg cat         289
Leu Pro Ser Gly Tyr Leu Gly Tyr Gln Glu Leu Gly Met Gly Arg His
                85                  90                  95 tat ggt ccg gaa att aaa tgg gta gat gga ggc aag cca ctg ctg aaa         337
Tyr Gly Pro Glu Ile Lys Trp Val Asp Gly Gly Lys Pro Leu Leu Lys
            100                 105                 110 att tcc act cat ctg gtt tct aca gtg tat act cag gat cag cat tta         385
Ile Ser Thr His Leu Val Ser Thr Val Tyr Thr Gln Asp Gln His Leu
        115                 120                 125 cat aat ttt ttc cag tac tgt cag aaa acc gaa tct gga gcc caa gcc         433
His Asn Phe Phe Gln Tyr Cys Gln Lys Thr Glu Ser Gly Ala Gln Ala
130                 135                 140 tta gga aac gaa ctt gta aag tac ctt aag agt ctg cat gcg atg gaa         481
Leu Gly Asn Glu Leu Val Lys Tyr Leu Lys Ser Leu His Ala Met Glu
145                 150                 155                 160 ggc cac gtg atg atc gcc ttc ttg ccc act atc cta aac cag ctg ttc         529
Gly His Val Met Ile Ala Phe Leu Pro Thr Ile Leu Asn Gln Leu Phe
                165                 170                 175 cga gtc ctc acc aga gcc aca cag gaa gaa gtc gcg gtt aac gtg act         577
Arg Val Leu Thr Arg Ala Thr Gln Glu Glu Val Ala Val Asn Val Thr
            180                 185                 190 cgg gtc att att cat gtg gtt gcc cag tgc cat gag gaa gga ttg gag         625
Arg Val Ile Ile His Val Val Ala Gln Cys His Glu Glu Gly Leu Glu
        195                 200                 205 agc cac ttg agg tca tat gtt aag tac gcg tat aag gct gag cca tat         673
Ser His Leu Arg Ser Tyr Val Lys Tyr Ala Tyr Lys Ala Glu Pro Tyr
    210                 215                 220 gtt gcc tct gaa tac aag aca gtg cat gaa gaa ctg acc aaa tcc atg         721
Val Ala Ser Glu Tyr Lys Thr Val His Glu Glu Leu Thr Lys Ser Met
225                 230                 235                 240 acc acg att ctc aag cct tct gcc gat ttc ctc acc agc aac aaa cta         769
Thr Thr Ile Leu Lys Pro Ser Ala Asp Phe Leu Thr Ser Asn Lys Leu
                245                 250                 255 ctg agg tac tca tgg ttt ttc ttt gat gta ctg atc aaa tct atg gct         817
Leu Arg Tyr Ser Trp Phe Phe Phe Asp Val Leu Ile Lys Ser Met Ala
            260                 265                 270 cag cat ttg ata gag aac tcc aaa gtt aag ttg ctg cga aac cag aga         865
Gln His Leu Ile Glu Asn Ser Lys Val Lys Leu Leu Arg Asn Gln Arg
        275                 280                 285 ttt cct gca tcc tat cat cat gca gcg gaa acc gtt gta aat atg ctg         913
Phe Pro Ala Ser Tyr His His Ala Ala Glu Thr Val Val Asn Met Leu
    290                 295                 300 atg cca cac atc act cag aag ttt gga gat aat cca gag gca tct aag        961
Met Pro His Ile Thr Gln Lys Phe Gly Asp Asn Pro Glu Ala Ser Lys
305                 310                 315                 320
```

```
                                                               -continued aac gcg aat cat agc ctt gct gtc ttc atc aag aga tgt ttc acc ttc     1009
Asn Ala Asn His Ser Leu Ala Val Phe Ile Lys Arg Cys Phe Thr Phe
            325                 330                 335 atg gac agg ggc ttt gtc ttc aag cag atc aac aac tac att agc tgt     1057
Met Asp Arg Gly Phe Val Phe Lys Gln Ile Asn Asn Tyr Ile Ser Cys
        340                 345                 350 ttt gct cct gga gac cca aag acc ctc ttt gaa tac aag ttt gaa ttt     1105
Phe Ala Pro Gly Asp Pro Lys Thr Leu Phe Glu Tyr Lys Phe Glu Phe
            355                 360                 365 ctc cgt gta gtg tgc aac cat gaa cat tat att ccg ttg aac tta cca     1153
Leu Arg Val Val Cys Asn His Glu His Tyr Ile Pro Leu Asn Leu Pro
370                 375                 380 atg cca ttt gga aaa ggc agg att caa aga tac caa gac ctc cag ctt     1201
Met Pro Phe Gly Lys Gly Arg Ile Gln Arg Tyr Gln Asp Leu Gln Leu
385                 390                 395                 400 gac tac tca tta aca gat gag ttc tgc aga aac cac ttc ttg gtg gga     1249
Asp Tyr Ser Leu Thr Asp Glu Phe Cys Arg Asn His Phe Leu Val Gly
            405                 410                 415 ctg tta ctg agg gag gtg ggg aca gcc ctc cag gag ttc cgg gag gtc     1297
Leu Leu Leu Arg Glu Val Gly Thr Ala Leu Gln Glu Phe Arg Glu Val
        420                 425                 430 cgt ctg atc gcc atc agt gtg ctc aag aac ctg ctg ata aag cat tct     1345
Arg Leu Ile Ala Ile Ser Val Leu Lys Asn Leu Leu Ile Lys His Ser
            435                 440                 445 ttt gat gac aga tat gct tca agg agc cat cag gca agg ata gcc acc     1393
Phe Asp Asp Arg Tyr Ala Ser Arg Ser His Gln Ala Arg Ile Ala Thr
450                 455                 460 ctc tac ctg cct ctg ttt ggt ctg ctg att gaa aac gtc cag cgg atc     1441
Leu Tyr Leu Pro Leu Phe Gly Leu Leu Ile Glu Asn Val Gln Arg Ile
465                 470                 475                 480 aat gtg agg gat gtg tca ccc ttc cct gtg aac gcg ggc atg acc gtg     1489
Asn Val Arg Asp Val Ser Pro Phe Pro Val Asn Ala Gly Met Thr Val
            485                 490                 495 aag gat gaa tcc ctg gct cta cca gct gtg aat ccg ctg gtg acg ccg     1537
Lys Asp Glu Ser Leu Ala Leu Pro Ala Val Asn Pro Leu Val Thr Pro
        500                 505                 510 cag aag gga agc acc ctg gac aac agc ctg cac aag gac ctg ctg ggc     1585
Gln Lys Gly Ser Thr Leu Asp Asn Ser Leu His Lys Asp Leu Leu Gly
            515                 520                 525 gcc atc tcc ggc att gct tct cca tat aca acc tca act cca aac atc     1633
Ala Ile Ser Gly Ile Ala Ser Pro Tyr Thr Thr Ser Thr Pro Asn Ile
530                 535                 540 aac agt gtg aga aat gct gat tcg aga gga tct ctc ata agc aca gat     1681
Asn Ser Val Arg Asn Ala Asp Ser Arg Gly Ser Leu Ile Ser Thr Asp
545                 550                 555                 560 tcg ggt aac agc ctt cca gaa agg aat agt gag aag agc aat tcc ctg     1729
Ser Gly Asn Ser Leu Pro Glu Arg Asn Ser Glu Lys Ser Asn Ser Leu
            565                 570                 575 gat aag cac caa caa agt agc aca ttg gga aat tcc gtg gtt cgc tgt     1777
Asp Lys His Gln Gln Ser Ser Thr Leu Gly Asn Ser Val Val Arg Cys
        580                 585                 590 gat aaa ctt gac cag tct gag att aag agc cta ctg atg tgt ttc ctc     1825
Asp Lys Leu Asp Gln Ser Glu Ile Lys Ser Leu Leu Met Cys Phe Leu
            595                 600                 605 tac atc tta aag agc atg tct gat gat gct ttg ttt aca tat tgg aac     1873
Tyr Ile Leu Lys Ser Met Ser Asp Asp Ala Leu Phe Thr Tyr Trp Asn
610                 615                 620 aag gct tca aca tct gaa ctt atg gat ttt ttt aca ata tct gaa gtc     1921
Lys Ala Ser Thr Ser Glu Leu Met Asp Phe Phe Thr Ile Ser Glu Val
```

```
                625                 630                 635                 640
tgc ctg cac cag ttc cag tac atg ggg aag cga tac ata gcc agg aac        1969
Cys Leu His Gln Phe Gln Tyr Met Gly Lys Arg Tyr Ile Ala Arg Asn
                    645                 650                 655 cag gag ggg ttg gga ccc ata gtt cat gat cga aag tct cag aca ttg        2017
Gln Glu Gly Leu Gly Pro Ile Val His Asp Arg Lys Ser Gln Thr Leu
            660                 665                 670 cct gtt tcc cgt aac aga aca gga atg atg cat gcc aga ttg cag cag        2065
Pro Val Ser Arg Asn Arg Thr Gly Met Met His Ala Arg Leu Gln Gln
        675                 680                 685 ctg ggc agc ctg gat aac tct ctc act ttt aac cac agc tat ggc cac        2113
Leu Gly Ser Leu Asp Asn Ser Leu Thr Phe Asn His Ser Tyr Gly His
    690                 695                 700 tcg gac gca gat gtt ctg cac cag tca tta ctt gaa gcc aac att gct        2161
Ser Asp Ala Asp Val Leu His Gln Ser Leu Leu Glu Ala Asn Ile Ala
705                 710                 715                 720 act gag gtt tgc ctg aca gct ctg gac acg ctt tct cta ttt aca ttg        2209
Thr Glu Val Cys Leu Thr Ala Leu Asp Thr Leu Ser Leu Phe Thr Leu
                    725                 730                 735 gcg ttt aag aac cag ctc ctg gcc gac cat gga cat aat cct ctc atg        2257
Ala Phe Lys Asn Gln Leu Leu Ala Asp His Gly His Asn Pro Leu Met
            740                 745                 750 aaa aaa gtt ttt gat gtc tac ctg tgt ttt ctt caa aaa cat cag tct        2305
Lys Lys Val Phe Asp Val Tyr Leu Cys Phe Leu Gln Lys His Gln Ser
        755                 760                 765 gaa acg gct tta aaa aat gtc ttc act gcc tta agg tcc tta att tat        2353
Glu Thr Ala Leu Lys Asn Val Phe Thr Ala Leu Arg Ser Leu Ile Tyr
    770                 775                 780 aag ttt ccc tca aca ttc tat gaa ggg aga gcg gac atg tgt gcg gct        2401
Lys Phe Pro Ser Thr Phe Tyr Glu Gly Arg Ala Asp Met Cys Ala Ala
785                 790                 795                 800 ctg tgt tac gag att ctc aag tgc tgt aac tcc aag ctg agc tcc atc        2449
Leu Cys Tyr Glu Ile Leu Lys Cys Cys Asn Ser Lys Leu Ser Ser Ile
                    805                 810                 815 agg acg gag gcc tcc cag ctg ctc tac ttc ctg atg agg aac aac ttt        2497
Arg Thr Glu Ala Ser Gln Leu Leu Tyr Phe Leu Met Arg Asn Asn Phe
            820                 825                 830 gat tac act gga aag aag tcc ttt gtc cgg aca cat ttg caa gtc atc        2545
Asp Tyr Thr Gly Lys Lys Ser Phe Val Arg Thr His Leu Gln Val Ile
        835                 840                 845 ata tct gtc agc cag ctg ata gca gac gtt gtt ggc att ggg gaa acc        2593
Ile Ser Val Ser Gln Leu Ile Ala Asp Val Val Gly Ile Gly Glu Thr
    850                 855                 860 aga ttc cag cag tcc ctg tcc atc atc aac aac tgt gcc aac agt gac        2641
Arg Phe Gln Gln Ser Leu Ser Ile Ile Asn Asn Cys Ala Asn Ser Asp
865                 870                 875                 880 cgg ctt att aag cac acc agc ttc tcc tct gat gtg aag gac tta acc        2689
Arg Leu Ile Lys His Thr Ser Phe Ser Ser Asp Val Lys Asp Leu Thr
                    885                 890                 895 aaa agg ata cgc acg gtg cta atg gcc acc gcc cag atg aag gag cat        2737
Lys Arg Ile Arg Thr Val Leu Met Ala Thr Ala Gln Met Lys Glu His
            900                 905                 910 gag aac gac cca gag atg ctg gtg gac ctc cag tac agc ctg gcc aaa        2785
Glu Asn Asp Pro Glu Met Leu Val Asp Leu Gln Tyr Ser Leu Ala Lys
        915                 920                 925 tcc tat gcc agc acg ccc gag ctc agg aag acg tgg ctc gac agc atg        2833
Ser Tyr Ala Ser Thr Pro Glu Leu Arg Lys Thr Trp Leu Asp Ser Met
    930                 935                 940 gcc agg atc cat gtc aaa aat ggc gat ctc tca gag gca gca atg tgc        2881
```

```
Ala Arg Ile His Val Lys Asn Gly Asp Leu Ser Glu Ala Ala Met Cys
945                 950                 955                 960 tat gtc cac gta aca gcc cta gtg gca gaa tat ctc aca cgg aaa ggc    2929
Tyr Val His Val Thr Ala Leu Val Ala Glu Tyr Leu Thr Arg Lys Gly
                965                 970                 975 gtg ttt aga caa gga tgc acc gcc ttc agg gtc att acc cca aac atc    2977
Val Phe Arg Gln Gly Cys Thr Ala Phe Arg Val Ile Thr Pro Asn Ile
            980                 985                 990 gac gag gag gcc tcc atg atg gaa gac gtg ggg atg cag gat gtc cat    3025
Asp Glu Glu Ala Ser Met Met Glu Asp Val Gly Met Gln Asp Val His
        995                 1000                1005 ttc aac gag gat gtg ctg atg gag ctc ctt gag cag tgc gca gat gga    3073
Phe Asn Glu Asp Val Leu Met Glu Leu Leu Glu Gln Cys Ala Asp Gly
    1010                1015                1020 ctc tgg aaa gcc gag cgc tac gag ctc atc gcc gac atc tac aaa ctt    3121
Leu Trp Lys Ala Glu Arg Tyr Glu Leu Ile Ala Asp Ile Tyr Lys Leu
1025                1030                1035                1040 atc atc ccc att tat gag aag cgg agg gat ttc ttt gaa gat gaa gat    3169
Ile Ile Pro Ile Tyr Glu Lys Arg Arg Asp Phe Phe Glu Asp Glu Asp
                1045                1050                1055 gga aag gag tat att tac aag gaa ccc aaa ctc aca ccg ctg tcg gaa    3217
Gly Lys Glu Tyr Ile Tyr Lys Glu Pro Lys Leu Thr Pro Leu Ser Glu
            1060                1065                1070 att tct cag aga ctc ctt aaa ctg tac tcg gat aaa ttt ggt tct gaa    3265
Ile Ser Gln Arg Leu Leu Lys Leu Tyr Ser Asp Lys Phe Gly Ser Glu
        1075                1080                1085 aat gtc aaa atg ata cag gat tct ggc aag gtc aac cct aag gat ctg    3313
Asn Val Lys Met Ile Gln Asp Ser Gly Lys Val Asn Pro Lys Asp Leu
    1090                1095                1100 gat tct aag tat gca tac atc cag gtg act cac gtc atc ccc ttc ttt    3361
Asp Ser Lys Tyr Ala Tyr Ile Gln Val Thr His Val Ile Pro Phe Phe
1105                1110                1115                1120 gac gaa aaa gag ttg caa gaa agg aaa aca gag ttt gag aga tcc cac    3409
Asp Glu Lys Glu Leu Gln Glu Arg Lys Thr Glu Phe Glu Arg Ser His
                1125                1130                1135 aac atc cgc cgc ttc atg ttt gag atg cca ttt acg cag acc ggg aag    3457
Asn Ile Arg Arg Phe Met Phe Glu Met Pro Phe Thr Gln Thr Gly Lys
            1140                1145                1150 agg cag ggc ggg gtg gaa gag cag tgc aaa cgg cgc acc atc ctg aca    3505
Arg Gln Gly Gly Val Glu Glu Gln Cys Lys Arg Arg Thr Ile Leu Thr
        1155                1160                1165 gcc ata cac tgc ttc cct tat gtg aag aag cgc atc cct gtc atg tac    3553
Ala Ile His Cys Phe Pro Tyr Val Lys Lys Arg Ile Pro Val Met Tyr
    1170                1175                1180 cag cac cac act gac ctg aac ccc atc gag gtg gcc att gac gag atg    3601
Gln His His Thr Asp Leu Asn Pro Ile Glu Val Ala Ile Asp Glu Met
1185                1190                1195                1200 agt aag aag gtg gcg gag ctc cgg cag ctg tgc tcc tcg gcc gag gtg    3649
Ser Lys Lys Val Ala Glu Leu Arg Gln Leu Cys Ser Ser Ala Glu Val
                1205                1210                1215 gac atg atc aaa ctg cag ctc aaa ctc cag ggc agc gtg agt gtt cag    3697
Asp Met Ile Lys Leu Gln Leu Lys Leu Gln Gly Ser Val Ser Val Gln
            1220                1225                1230 gtc aat gct ggc cca cta gca tat gcg cga gct ttc tta gat gat aca    3745
Val Asn Ala Gly Pro Leu Ala Tyr Ala Arg Ala Phe Leu Asp Asp Thr
        1235                1240                1245 aac aca aag cga tat cct gac aat aaa gtg aag ctg ctt aag gaa gtt    3793
Asn Thr Lys Arg Tyr Pro Asp Asn Lys Val Lys Leu Leu Lys Glu Val
    1250                1255                1260
```

```
ttc agg caa ttt gtg gaa gct tgc ggt caa gcc tta gcg gta aac gaa    3841
Phe Arg Gln Phe Val Glu Ala Cys Gly Gln Ala Leu Ala Val Asn Glu
1265                1270                1275                1280 cgt ctg att aaa gaa gac cag ctc gag tat cag gaa gaa atg aaa gcc    3889
Arg Leu Ile Lys Glu Asp Gln Leu Glu Tyr Gln Glu Glu Met Lys Ala
        1285                1290                1295 aac tac agg gaa atg gcg aag gag ctt tct gaa atc atg cat gag cag    3937
Asn Tyr Arg Glu Met Ala Lys Glu Leu Ser Glu Ile Met His Glu Gln
            1300                1305                1310 atc tgc ccc ctg gag gag aag acg agc gtc tta ccg aat tcc ctt cac    3985
Ile Cys Pro Leu Glu Glu Lys Thr Ser Val Leu Pro Asn Ser Leu His
                1315                1320                1325 atc ttc aac gcc atc agt ggg act cca aca agc aca atg gtt cac ggg    4033
Ile Phe Asn Ala Ile Ser Gly Thr Pro Thr Ser Thr Met Val His Gly
            1330                1335                1340 atg acc agc tcg tct tcg gtc gtg tga ttacatctca tggcccgtgt          4080
Met Thr Ser Ser Ser Ser Val Val
1345                1350 gtggggactt gctttgtcat ttgcaaactc aggatgcttt ccaaagccaa tcactgggga   4140
gaccgagcac agggaggacc aaggggaagg ggagagaaag gaaataaaga caacgttat    4200 ttcttaacag actttctata ggagttgtaa gaaggtgcac atatttttt aaatctcact    4260 ggcaatattc aaagttttca ttgtgtctta acaaaggtgt ggtagacact cttgagctgg   4320
acttagattt tattcttcct tgcagagtag tgttagaata gatggcctac agaaaaaaaa   4380
ggttctggga tctacatggc agggagggct gcactgacat tgatgcctgg gggacctttt   4440
gcctcgactc gtgccggaaa tctgatcgta atcagggtac agaacttact agttttgtct   4500
aggagtatgt tgtatgacta ggatttgtgc tattatctca ttcaacaaca tagagcaaga   4560
atagtgagct aactgagcta gacactcaat taatccgcta ctggcttcaa gtcagaactt   4620
tgtcattaat catcgactcc gggacggtca tatatgtatt acatttctac attttaata   4680 ctcacatggg cttatgcatt aagtttaatt gtgataaatt tgtgctggtc cagtatatgc   4740
aatacacttt aatggtttat tcttgtcata aaaatgtgca atatggagat gtatacaagt   4800
ctttact                                                            4807

<210> SEQ ID NO 2
<211> LENGTH: 1352
<212> TYPE: PRT
<213> ORGANISM: Homo sapiens
<223> OTHER INFORMATION: Human cadherin-like asymmetry protein 2A

<400> SEQUENCE: 2

Val Leu His His His Gln Asn Pro Glu Phe Tyr Asp Glu Ile Lys Ile
1               5                   10                  15

Glu Leu Pro Thr Gln Leu His Glu Lys His His Leu Leu Leu Thr Phe
            20                  25                  30

Phe His Val Ser Cys Asp Asn Ser Ser Lys Gly Ser Thr Lys Lys Arg
        35                  40                  45

Asp Val Val Glu Thr Gln Val Gly Tyr Ser Trp Leu Pro Leu Leu Lys
    50                  55                  60

Asp Gly Arg Val Val Thr Ser Glu Gln His Ile Pro Val Ser Ala Asn
65                  70                  75                  80

Leu Pro Ser Gly Tyr Leu Gly Tyr Gln Glu Leu Gly Met Gly Arg His
                85                  90                  95

Tyr Gly Pro Glu Ile Lys Trp Val Asp Gly Gly Lys Pro Leu Leu Lys
            100                 105                 110
```

```
Ile Ser Thr His Leu Val Ser Thr Val Tyr Thr Gln Asp Gln His Leu
        115                 120                 125

His Asn Phe Phe Gln Tyr Cys Gln Lys Thr Glu Ser Gly Ala Gln Ala
130                 135                 140

Leu Gly Asn Glu Leu Val Lys Tyr Leu Lys Ser Leu His Ala Met Glu
145                 150                 155                 160

Gly His Val Met Ile Ala Phe Leu Pro Thr Ile Leu Asn Gln Leu Phe
                165                 170                 175

Arg Val Leu Thr Arg Ala Thr Gln Glu Glu Val Ala Val Asn Val Thr
            180                 185                 190

Arg Val Ile Ile His Val Val Ala Gln Cys His Glu Glu Gly Leu Glu
            195                 200                 205

Ser His Leu Arg Ser Tyr Val Lys Tyr Ala Tyr Lys Ala Glu Pro Tyr
        210                 215                 220

Val Ala Ser Glu Tyr Lys Thr Val His Glu Glu Leu Thr Lys Ser Met
225                 230                 235                 240

Thr Thr Ile Leu Lys Pro Ser Ala Asp Phe Leu Thr Ser Asn Lys Leu
                245                 250                 255

Leu Arg Tyr Ser Trp Phe Phe Phe Asp Val Leu Ile Lys Ser Met Ala
            260                 265                 270

Gln His Leu Ile Glu Asn Ser Lys Val Lys Leu Leu Arg Asn Gln Arg
        275                 280                 285

Phe Pro Ala Ser Tyr His His Ala Ala Glu Thr Val Val Asn Met Leu
    290                 295                 300

Met Pro His Ile Thr Gln Lys Phe Gly Asp Asn Pro Glu Ala Ser Lys
305                 310                 315                 320

Asn Ala Asn His Ser Leu Ala Val Phe Ile Lys Arg Cys Phe Thr Phe
                325                 330                 335

Met Asp Arg Gly Phe Val Phe Lys Gln Ile Asn Asn Tyr Ile Ser Cys
            340                 345                 350

Phe Ala Pro Gly Asp Pro Lys Thr Leu Phe Glu Tyr Lys Phe Glu Phe
        355                 360                 365

Leu Arg Val Val Cys Asn His Glu His Tyr Ile Pro Leu Asn Leu Pro
    370                 375                 380

Met Pro Phe Gly Lys Gly Arg Ile Gln Arg Tyr Gln Asp Leu Gln Leu
385                 390                 395                 400

Asp Tyr Ser Leu Thr Asp Glu Phe Cys Arg Asn His Phe Leu Val Gly
                405                 410                 415

Leu Leu Leu Arg Glu Val Gly Thr Ala Leu Gln Glu Phe Arg Glu Val
            420                 425                 430

Arg Leu Ile Ala Ile Ser Val Leu Lys Asn Leu Leu Ile Lys His Ser
        435                 440                 445

Phe Asp Asp Arg Tyr Ala Ser Arg Ser His Gln Ala Arg Ile Ala Thr
    450                 455                 460

Leu Tyr Leu Pro Leu Phe Gly Leu Leu Ile Glu Asn Val Gln Arg Ile
465                 470                 475                 480

Asn Val Arg Asp Val Ser Pro Phe Pro Val Asn Ala Gly Met Thr Val
                485                 490                 495

Lys Asp Glu Ser Leu Ala Leu Pro Ala Val Asn Pro Leu Val Thr Pro
            500                 505                 510

Gln Lys Gly Ser Thr Leu Asp Asn Ser Leu His Lys Asp Leu Leu Gly
        515                 520                 525
```

-continued

```
Ala Ile Ser Gly Ile Ala Ser Pro Tyr Thr Ser Thr Pro Asn Ile
    530                 535                 540
Asn Ser Val Arg Asn Ala Asp Ser Arg Gly Ser Leu Ile Ser Thr Asp
545                 550                 555                 560
Ser Gly Asn Ser Leu Pro Glu Arg Asn Ser Glu Lys Ser Asn Ser Leu
                565                 570                 575
Asp Lys His Gln Gln Ser Ser Thr Leu Gly Asn Ser Val Val Arg Cys
            580                 585                 590
Asp Lys Leu Asp Gln Ser Glu Ile Lys Ser Leu Leu Met Cys Phe Leu
        595                 600                 605
Tyr Ile Leu Lys Ser Met Ser Asp Asp Ala Leu Phe Thr Tyr Trp Asn
    610                 615                 620
Lys Ala Ser Thr Ser Glu Leu Met Asp Phe Phe Thr Ile Ser Glu Val
625                 630                 635                 640
Cys Leu His Gln Phe Gln Tyr Met Gly Lys Arg Tyr Ile Ala Arg Asn
                645                 650                 655
Gln Glu Gly Leu Gly Pro Ile Val His Asp Arg Lys Ser Gln Thr Leu
            660                 665                 670
Pro Val Ser Arg Asn Arg Thr Gly Met Met His Ala Arg Leu Gln Gln
        675                 680                 685
Leu Gly Ser Leu Asp Asn Ser Leu Thr Phe Asn His Ser Tyr Gly His
    690                 695                 700
Ser Asp Ala Asp Val Leu His Gln Ser Leu Leu Glu Ala Asn Ile Ala
705                 710                 715                 720
Thr Glu Val Cys Leu Thr Ala Leu Asp Thr Leu Ser Leu Phe Thr Leu
                725                 730                 735
Ala Phe Lys Asn Gln Leu Leu Ala Asp His Gly His Asn Pro Leu Met
            740                 745                 750
Lys Lys Val Phe Asp Val Tyr Leu Cys Phe Leu Gln Lys His Gln Ser
        755                 760                 765
Glu Thr Ala Leu Lys Asn Val Phe Thr Ala Leu Arg Ser Leu Ile Tyr
    770                 775                 780
Lys Phe Pro Ser Thr Phe Tyr Glu Gly Arg Ala Asp Met Cys Ala Ala
785                 790                 795                 800
Leu Cys Tyr Glu Ile Leu Lys Cys Cys Asn Ser Lys Leu Ser Ser Ile
                805                 810                 815
Arg Thr Glu Ala Ser Gln Leu Leu Tyr Phe Leu Met Arg Asn Asn Phe
            820                 825                 830
Asp Tyr Thr Gly Lys Lys Ser Phe Val Arg Thr His Leu Gln Val Ile
        835                 840                 845
Ile Ser Val Ser Gln Leu Ile Ala Asp Val Val Gly Ile Gly Glu Thr
    850                 855                 860
Arg Phe Gln Gln Ser Leu Ser Ile Ile Asn Asn Cys Ala Asn Ser Asp
865                 870                 875                 880
Arg Leu Ile Lys His Thr Ser Phe Ser Ser Asp Val Lys Asp Leu Thr
                885                 890                 895
Lys Arg Ile Arg Thr Val Leu Met Ala Thr Ala Gln Met Lys Glu His
            900                 905                 910
Glu Asn Asp Pro Glu Met Leu Val Asp Leu Gln Tyr Ser Leu Ala Lys
        915                 920                 925
Ser Tyr Ala Ser Thr Pro Glu Leu Arg Lys Thr Trp Leu Asp Ser Met
    930                 935                 940
Ala Arg Ile His Val Lys Asn Gly Asp Leu Ser Glu Ala Ala Met Cys
```

```
                945                 950                 955                 960
Tyr Val His Val Thr Ala Leu Val Ala Glu Tyr Leu Thr Arg Lys Gly
                965                 970                 975
Val Phe Arg Gln Gly Cys Thr Ala Phe Arg Val Ile Thr Pro Asn Ile
                980                 985                 990
Asp Glu Glu Ala Ser Met Met Glu Asp Val Gly Met Gln Asp Val His
                995                1000                1005
Phe Asn Glu Asp Val Leu Met Glu Leu Leu Glu Gln Cys Ala Asp Gly
               1010                1015                1020
Leu Trp Lys Ala Glu Arg Tyr Glu Leu Ile Ala Asp Ile Tyr Lys Leu
1025                1030                1035                1040
Ile Ile Pro Ile Tyr Glu Lys Arg Arg Asp Phe Phe Glu Asp Glu Asp
               1045                1050                1055
Gly Lys Glu Tyr Ile Tyr Lys Glu Pro Lys Leu Thr Pro Leu Ser Glu
               1060                1065                1070
Ile Ser Gln Arg Leu Leu Lys Leu Tyr Ser Asp Lys Phe Gly Ser Glu
               1075                1080                1085
Asn Val Lys Met Ile Gln Asp Ser Gly Lys Val Asn Pro Lys Asp Leu
               1090                1095                1100
Asp Ser Lys Tyr Ala Tyr Ile Gln Val Thr His Val Ile Pro Phe Phe
1105                1110                1115                1120
Asp Glu Lys Glu Leu Gln Glu Arg Lys Thr Glu Phe Glu Arg Ser His
               1125                1130                1135
Asn Ile Arg Arg Phe Met Phe Glu Met Pro Phe Thr Gln Thr Gly Lys
               1140                1145                1150
Arg Gln Gly Gly Val Glu Glu Gln Cys Lys Arg Arg Thr Ile Leu Thr
               1155                1160                1165
Ala Ile His Cys Phe Pro Tyr Val Lys Lys Arg Ile Pro Val Met Tyr
               1170                1175                1180
Gln His His Thr Asp Leu Asn Pro Ile Glu Val Ala Ile Asp Glu Met
1185                1190                1195                1200
Ser Lys Lys Val Ala Glu Leu Arg Gln Leu Cys Ser Ser Ala Glu Val
               1205                1210                1215
Asp Met Ile Lys Leu Gln Leu Lys Leu Gln Gly Ser Val Ser Val Gln
               1220                1225                1230
Val Asn Ala Gly Pro Leu Ala Tyr Ala Arg Ala Phe Leu Asp Asp Thr
               1235                1240                1245
Asn Thr Lys Arg Tyr Pro Asp Asn Lys Val Lys Leu Leu Lys Glu Val
               1250                1255                1260
Phe Arg Gln Phe Val Glu Ala Cys Gly Gln Ala Leu Ala Val Asn Glu
1265                1270                1275                1280
Arg Leu Ile Lys Glu Asp Gln Leu Glu Tyr Gln Glu Glu Met Lys Ala
               1285                1290                1295
Asn Tyr Arg Glu Met Ala Lys Glu Leu Ser Glu Ile Met His Glu Gln
               1300                1305                1310
Ile Cys Pro Leu Glu Glu Lys Thr Ser Val Leu Pro Asn Ser Leu His
               1315                1320                1325
Ile Phe Asn Ala Ile Ser Gly Thr Pro Thr Ser Thr Met Val His Gly
               1330                1335                1340
Met Thr Ser Ser Ser Ser Val Val
1345                1350

<210> SEQ ID NO 3
```

```
<211> LENGTH: 3705
<212> TYPE: DNA
<213> ORGANISM: Homo sapiens
<220> FEATURE:
<221> NAME/KEY: CDS
<222> LOCATION: (1)..(3702)
<223> OTHER INFORMATION: Human cadherin-like asymmetry protein 2B
      (CLASP-2B)

<400> SEQUENCE: 3 gcg atg gaa ggc cac gtg atg atc gcc ttc ttg ccc act atc cta aac      48
Ala Met Glu Gly His Val Met Ile Ala Phe Leu Pro Thr Ile Leu Asn
 1               5                  10                  15 cag ctg ttc cga gtc ctc acc aga gcc aca cag gaa gaa gtc gcg gtt      96
Gln Leu Phe Arg Val Leu Thr Arg Ala Thr Gln Glu Glu Val Ala Val
             20                  25                  30 aac gtg act cgg gtc att att cat gtg gtt gcc cag tgc cat gag gaa     144
Asn Val Thr Arg Val Ile Ile His Val Val Ala Gln Cys His Glu Glu
         35                  40                  45 gga ttg gag agc cac ttg agg tca tat gtt aag tac gcg tat aag gct     192
Gly Leu Glu Ser His Leu Arg Ser Tyr Val Lys Tyr Ala Tyr Lys Ala
     50                  55                  60 gag cca tat gtt gcc tct gaa tac aag aca gtg cat gaa gaa ctg acc     240
Glu Pro Tyr Val Ala Ser Glu Tyr Lys Thr Val His Glu Glu Leu Thr
 65                  70                  75                  80 aaa tcc atg acc acg att ctc aag cct tct gcc gat ttc ctc acc agc     288
Lys Ser Met Thr Thr Ile Leu Lys Pro Ser Ala Asp Phe Leu Thr Ser
                 85                  90                  95 aac aaa cta ctg agg tac tca tgg ttt ttc ttt gat gta ctg atc aaa     336
Asn Lys Leu Leu Arg Tyr Ser Trp Phe Phe Phe Asp Val Leu Ile Lys
            100                 105                 110 tct atg gct cag cat ttg ata gag aac tcc aaa gtt aag ttg ctg cga     384
Ser Met Ala Gln His Leu Ile Glu Asn Ser Lys Val Lys Leu Leu Arg
        115                 120                 125 aac cag aga ttt cct gca tcc tat cat cat gca gcg gaa acc gtt gta     432
Asn Gln Arg Phe Pro Ala Ser Tyr His His Ala Ala Glu Thr Val Val
    130                 135                 140 aat atg ctg atg cca cac atc act cag aag ttt gga gat aat cca gag     480
Asn Met Leu Met Pro His Ile Thr Gln Lys Phe Gly Asp Asn Pro Glu
145                 150                 155                 160 gca tct aag aac gcg aat cat agc ctt gct gtc ttc atc aag aga tgt     528
Ala Ser Lys Asn Ala Asn His Ser Leu Ala Val Phe Ile Lys Arg Cys
                165                 170                 175 ttc acc ttc atg gac agg ggc ttt gtc ttc aag cag atc aac aac tac     576
Phe Thr Phe Met Asp Arg Gly Phe Val Phe Lys Gln Ile Asn Asn Tyr
            180                 185                 190 att agc tgt ttt gct cct gga gac cca aag acc ctc ttt gaa tac aag     624
Ile Ser Cys Phe Ala Pro Gly Asp Pro Lys Thr Leu Phe Glu Tyr Lys
        195                 200                 205 ttt gaa ttt ctc cgt gta gtg tgc aac cat gaa cat tat att ccg ttg     672
Phe Glu Phe Leu Arg Val Val Cys Asn His Glu His Tyr Ile Pro Leu
    210                 215                 220 aac tta cca atg cca ttt gga aaa ggc agg att caa aga tac caa gac     720
Asn Leu Pro Met Pro Phe Gly Lys Gly Arg Ile Gln Arg Tyr Gln Asp
225                 230                 235                 240 ctc cag ctt gac tac tca tta aca gat gag ttc tgc aga aac cac ttc     768
Leu Gln Leu Asp Tyr Ser Leu Thr Asp Glu Phe Cys Arg Asn His Phe
                245                 250                 255 ttg gtg gga ctg tta ctg agg gag gtg ggg aca gcc ctc cag gag ttc     816
Leu Val Gly Leu Leu Leu Arg Glu Val Gly Thr Ala Leu Gln Glu Phe
            260                 265                 270
```

```
cgg gag gtc cgt ctg atc gcc atc agt gtg ctc aag aac ctg ctg ata     864
Arg Glu Val Arg Leu Ile Ala Ile Ser Val Leu Lys Asn Leu Leu Ile
        275                 280                 285 aag cat tct ttt gat gac aga tat gct tca agg agc cat cag gca agg     912
Lys His Ser Phe Asp Asp Arg Tyr Ala Ser Arg Ser His Gln Ala Arg
290                 295                 300 ata gcc acc ctc tac ctg cct ctg ttt ggt ctg ctg att gaa aac gtc     960
Ile Ala Thr Leu Tyr Leu Pro Leu Phe Gly Leu Leu Ile Glu Asn Val
305                 310                 315                 320 cag cgg atc aat gtg agg gat gtg tca ccc ttc cct gtg aac gcg ggc    1008
Gln Arg Ile Asn Val Arg Asp Val Ser Pro Phe Pro Val Asn Ala Gly
            325                 330                 335 atg acc gtg aag gat gaa tcc ctg gct cta cca gct gtg aat ccg ctg    1056
Met Thr Val Lys Asp Glu Ser Leu Ala Leu Pro Ala Val Asn Pro Leu
        340                 345                 350 gtg acg ccg cag aag gga agc acc ctg gac aac agc ctg cac aag gac    1104
Val Thr Pro Gln Lys Gly Ser Thr Leu Asp Asn Ser Leu His Lys Asp
    355                 360                 365 ctg ctg ggc gcc atc tcc ggc att gct tct cca tat aca acc tca act    1152
Leu Leu Gly Ala Ile Ser Gly Ile Ala Ser Pro Tyr Thr Thr Ser Thr
370                 375                 380 cca aac atc aac agt gtg aga aat gct gat tcg aga gga tct ctc ata    1200
Pro Asn Ile Asn Ser Val Arg Asn Ala Asp Ser Arg Gly Ser Leu Ile
385                 390                 395                 400 agc aca gat tcg ggt aac agc ctt cca gaa agg aat agt gag aag agc    1248
Ser Thr Asp Ser Gly Asn Ser Leu Pro Glu Arg Asn Ser Glu Lys Ser
            405                 410                 415 aat tcc ctg gat aag cac caa caa agt agc aca ttg gga aat tcc gtg    1296
Asn Ser Leu Asp Lys His Gln Gln Ser Ser Thr Leu Gly Asn Ser Val
        420                 425                 430 gtt cgc tgt gat aaa ctt gac cag tct gag att aag agc cta ctg atg    1344
Val Arg Cys Asp Lys Leu Asp Gln Ser Glu Ile Lys Ser Leu Leu Met
    435                 440                 445 tgt ttc ctc tac atc tta aag agc atg tct gat gat gct ttg ttt aca    1392
Cys Phe Leu Tyr Ile Leu Lys Ser Met Ser Asp Asp Ala Leu Phe Thr
450                 455                 460 tat tgg aac aag gct tca aca tct gaa ctt atg gat ttt ttt aca ata    1440
Tyr Trp Asn Lys Ala Ser Thr Ser Glu Leu Met Asp Phe Phe Thr Ile
465                 470                 475                 480 tct gaa gtc tgc ctg cac cag ttc cag tac atg ggg aag cga tac ata    1488
Ser Glu Val Cys Leu His Gln Phe Gln Tyr Met Gly Lys Arg Tyr Ile
            485                 490                 495 gcc agg aac cag gag ggg ttg gga ccc ata gtt cat gat cga aag tct    1536
Ala Arg Asn Gln Glu Gly Leu Gly Pro Ile Val His Asp Arg Lys Ser
        500                 505                 510 cag aca ttg cct gtt tcc cgt aac aga aca gga atg atg cat gcc aga    1584
Gln Thr Leu Pro Val Ser Arg Asn Arg Thr Gly Met Met His Ala Arg
    515                 520                 525 ttg cag cag ctg ggc agc ctg gat aac tct ctc act ttt aac cac agc    1632
Leu Gln Gln Leu Gly Ser Leu Asp Asn Ser Leu Thr Phe Asn His Ser
530                 535                 540 tat ggc cac tcg gac gca gat gtt ctg cac cag tca tta ctt gaa gcc    1680
Tyr Gly His Ser Asp Ala Asp Val Leu His Gln Ser Leu Leu Glu Ala
545                 550                 555                 560 aac att gct act gag gtt tgc ctg aca gct ctg gac acg ctt tct cta    1728
Asn Ile Ala Thr Glu Val Cys Leu Thr Ala Leu Asp Thr Leu Ser Leu
            565                 570                 575 ttt aca ttg gcg ttt aag ctc ctg gcc gac cat gga cat aat cct ctc    1776
Phe Thr Leu Ala Phe Lys Leu Leu Ala Asp His Gly His Asn Pro Leu
        580                 585                 590
```

```
                                                        -continued atg aaa aaa gtt ttt gat gtc tac ctg tgt ttt ctt caa aaa cat cag        1824
Met Lys Lys Val Phe Asp Val Tyr Leu Cys Phe Leu Gln Lys His Gln
    595                 600                 605 tct gaa acg gct tta aaa aat gtc ttc act gcc tta agg tcc tta att        1872
Ser Glu Thr Ala Leu Lys Asn Val Phe Thr Ala Leu Arg Ser Leu Ile
610                 615                 620 tat aag ttt ccc tca aca ttc tat gaa ggg aga gcg gac atg tgt gcg        1920
Tyr Lys Phe Pro Ser Thr Phe Tyr Glu Gly Arg Ala Asp Met Cys Ala
625                 630                 635                 640 gct ctg tgt tac gag att ctc aag tgc tgt aac tcc aag ctg agc tcc        1968
Ala Leu Cys Tyr Glu Ile Leu Lys Cys Cys Asn Ser Lys Leu Ser Ser
                645                 650                 655 atc agg acg gag gcc tcc cag ctg ctc tac ttc ctg atg agg aac aac        2016
Ile Arg Thr Glu Ala Ser Gln Leu Leu Tyr Phe Leu Met Arg Asn Asn
            660                 665                 670 ttt gat tac act gga aag aag tcc ttt gtc cgg aca cat ttg caa gtc        2064
Phe Asp Tyr Thr Gly Lys Lys Ser Phe Val Arg Thr His Leu Gln Val
        675                 680                 685 atc ata tct gtc agc cag ctg ata gca gac gtt gtt ggc att ggg gaa        2112
Ile Ile Ser Val Ser Gln Leu Ile Ala Asp Val Val Gly Ile Gly Glu
    690                 695                 700 acc aga ttc cag cag tcc ctg tcc atc atc aac aac tgt gcc aac agt        2160
Thr Arg Phe Gln Gln Ser Leu Ser Ile Ile Asn Asn Cys Ala Asn Ser
705                 710                 715                 720 gac cgg ctt att aag cac acc agc ttc tcc tct gat gtg aag gac tta        2208
Asp Arg Leu Ile Lys His Thr Ser Phe Ser Ser Asp Val Lys Asp Leu
                725                 730                 735 acc aaa agg ata cgc acg gtg cta atg gcc acc gcc cag atg aag gag        2256
Thr Lys Arg Ile Arg Thr Val Leu Met Ala Thr Ala Gln Met Lys Glu
            740                 745                 750 cat gag aac gac cca gag atg ctg gtg gac ctc cag tac agc ctg gcc        2304
His Glu Asn Asp Pro Glu Met Leu Val Asp Leu Gln Tyr Ser Leu Ala
        755                 760                 765 aaa tcc tat gcc agc acg ccc gag ctc agg aag acg tgg ctc gac agc        2352
Lys Ser Tyr Ala Ser Thr Pro Glu Leu Arg Lys Thr Trp Leu Asp Ser
    770                 775                 780 atg gcc agg atc cat gtc aaa aat ggc gat ctc tca gag gca gca atg        2400
Met Ala Arg Ile His Val Lys Asn Gly Asp Leu Ser Glu Ala Ala Met
785                 790                 795                 800 tgc tat gtc cac gta aca gcc cta gtg gca gaa tat ctc aca cgg aaa        2448
Cys Tyr Val His Val Thr Ala Leu Val Ala Glu Tyr Leu Thr Arg Lys
                805                 810                 815 ggc gtg ttt aga caa gga tgc acc gcc ttc agg gtc att acc cca aac        2496
Gly Val Phe Arg Gln Gly Cys Thr Ala Phe Arg Val Ile Thr Pro Asn
            820                 825                 830 atc gac gag gag gcc tcc atg atg gaa gac gtg ggg atg cag gat gtc        2544
Ile Asp Glu Glu Ala Ser Met Met Glu Asp Val Gly Met Gln Asp Val
        835                 840                 845 cat ttc aac gag gat gtg ctg atg gag ctc ttg gag cag tgc gca gat        2592
His Phe Asn Glu Asp Val Leu Met Glu Leu Leu Glu Gln Cys Ala Asp
    850                 855                 860 gga ctc tgg aaa gcc gag cgc tac gag ctc atc gcc gac atc tac aaa        2640
Gly Leu Trp Lys Ala Glu Arg Tyr Glu Leu Ile Ala Asp Ile Tyr Lys
865                 870                 875                 880 ctt atc atc ccc att tat gag aag cgg agg gat ttt gag agg ctg gcc        2688
Leu Ile Ile Pro Ile Tyr Glu Lys Arg Arg Asp Phe Glu Arg Leu Ala
                885                 890                 895 cat ctg tat gac acg ctg cac cgg gcc tac agc aaa gtg acc gag gtc        2736
His Leu Tyr Asp Thr Leu His Arg Ala Tyr Ser Lys Val Thr Glu Val
```

```
                           900             905             910
atg cac tcg ggc cgc agg ctt ctg ggg acc tac ttc cgg gta gcc ttc      2784
Met His Ser Gly Arg Arg Leu Leu Gly Thr Tyr Phe Arg Val Ala Phe
            915                 920                 925 ttc ggg cag gga ttc ttt gaa gat gaa gat gga aag gag tat att tac      2832
Phe Gly Gln Gly Phe Phe Glu Asp Glu Asp Gly Lys Glu Tyr Ile Tyr
930                 935                 940 aag gaa ccc aaa ctc aca ccg ctg tcg gaa att tct cag aga ctc ctt      2880
Lys Glu Pro Lys Leu Thr Pro Leu Ser Glu Ile Ser Gln Arg Leu Leu
945                 950                 955                 960 aaa ctg tac tcg gat aaa ttt ggt tct gaa aat gtc aaa atg ata cag      2928
Lys Leu Tyr Ser Asp Lys Phe Gly Ser Glu Asn Val Lys Met Ile Gln
            965                 970                 975 gat tct ggc aag gtc aac cct aag gat ctg gat tct aag tat gca tac      2976
Asp Ser Gly Lys Val Asn Pro Lys Asp Leu Asp Ser Lys Tyr Ala Tyr
            980                 985                 990 atc cag gtg act cac gtc atc ccc ttc ttt gac gaa aaa gag ttg caa      3024
Ile Gln Val Thr His Val Ile Pro Phe Phe Asp Glu Lys Glu Leu Gln
            995                 1000                1005 gaa agg aaa aca gag ttt gag aga tcc cac aac atc cgc cgc ttc atg      3072
Glu Arg Lys Thr Glu Phe Glu Arg Ser His Asn Ile Arg Arg Phe Met
    1010                1015                1020 ttt gag atg cca ttt acg cag acc ggg aag agg cag ggc ggg gtg gaa      3120
Phe Glu Met Pro Phe Thr Gln Thr Gly Lys Arg Gln Gly Gly Val Glu
1025                1030                1035                1040 gag cag tgc aaa cgg cgc acc atc ctg aca gcc ata cac tgc ttc cct      3168
Glu Gln Cys Lys Arg Arg Thr Ile Leu Thr Ala Ile His Cys Phe Pro
                1045                1050                1055 tat gtg aag aag cgc atc cct gtc atg tac cag cac cac act gac ctg      3216
Tyr Val Lys Lys Arg Ile Pro Val Met Tyr Gln His His Thr Asp Leu
                1060                1065                1070 aac ccc atc gag gtg gcc att gac gag atg agt aag aag gtg gcg gag      3264
Asn Pro Ile Glu Val Ala Ile Asp Glu Met Ser Lys Lys Val Ala Glu
                1075                1080                1085 ctc cgg cag ctg tgc tcc tcg gcc gag gtg gac atg atc aaa ctg cag      3312
Leu Arg Gln Leu Cys Ser Ser Ala Glu Val Asp Met Ile Lys Leu Gln
    1090                1095                1100 ctc aaa ctc cag ggc agc gtg agt gtt cag gtc aat gct ggc cca cta      3360
Leu Lys Leu Gln Gly Ser Val Ser Val Gln Val Asn Ala Gly Pro Leu
1105                1110                1115                1120 gca tat gcg cga gct ttc tta gat gat aca aac aca aag cga tat cct      3408
Ala Tyr Ala Arg Ala Phe Leu Asp Asp Thr Asn Thr Lys Arg Tyr Pro
                1125                1130                1135 gac aat aaa gtg aag ctg ctt aag gaa gtt ttc agg caa ttt gtg gaa      3456
Asp Asn Lys Val Lys Leu Leu Lys Glu Val Phe Arg Gln Phe Val Glu
                1140                1145                1150 gct tgc ggt caa gcc tta gcg gta aac gaa cgt ctg att aaa gaa gac      3504
Ala Cys Gly Gln Ala Leu Ala Val Asn Glu Arg Leu Ile Lys Glu Asp
                1155                1160                1165 cag ctc gag tat cag gaa gaa atg aaa gcc aac tac agg gaa atg gcg      3552
Gln Leu Glu Tyr Gln Glu Glu Met Lys Ala Asn Tyr Arg Glu Met Ala
    1170                1175                1180 aag gag ctt tct gaa atc atg cat gag cag atc tgc ccc ctg gag gag      3600
Lys Glu Leu Ser Glu Ile Met His Glu Gln Ile Cys Pro Leu Glu Glu
1185                1190                1195                1200 aag acg agc gtc tta ccg aat tcc ctt cac atc ttc aac gcc atc agt      3648
Lys Thr Ser Val Leu Pro Asn Ser Leu His Ile Phe Asn Ala Ile Ser
                1205                1210                1215 ggg act cca aca agc aca atg gtt cac ggg atg acc agc tcg tct tcg      3696
```

```
Gly Thr Pro Thr Ser Thr Met Val His Gly Met Thr Ser Ser Ser Ser
            1220                1225                1230 gtc gtg tga                                                          3705
Val Val
```

<210> SEQ ID NO 4
<211> LENGTH: 1234
<212> TYPE: PRT
<213> ORGANISM: Homo sapiens
<223> OTHER INFORMATION: Human cadherin-like asymmetry protein 2B

<400> SEQUENCE: 4

```
Ala Met Glu Gly His Val Met Ile Ala Phe Leu Pro Thr Ile Leu Asn
  1               5                  10                  15

Gln Leu Phe Arg Val Leu Thr Arg Ala Thr Gln Glu Glu Val Ala Val
             20                  25                  30

Asn Val Thr Arg Val Ile Ile His Val Ala Gln Cys His Glu Glu
         35                  40                  45

Gly Leu Glu Ser His Leu Arg Ser Tyr Val Lys Tyr Ala Tyr Lys Ala
     50                  55                  60

Glu Pro Tyr Val Ala Ser Glu Tyr Lys Thr Val His Glu Glu Leu Thr
 65                  70                  75                  80

Lys Ser Met Thr Thr Ile Leu Lys Pro Ser Ala Asp Phe Leu Thr Ser
                 85                  90                  95

Asn Lys Leu Leu Arg Tyr Ser Trp Phe Phe Phe Asp Val Leu Ile Lys
            100                 105                 110

Ser Met Ala Gln His Leu Ile Glu Asn Ser Lys Val Lys Leu Leu Arg
        115                 120                 125

Asn Gln Arg Phe Pro Ala Ser Tyr His His Ala Ala Glu Thr Val Val
    130                 135                 140

Asn Met Leu Met Pro His Ile Thr Gln Lys Phe Gly Asp Asn Pro Glu
145                 150                 155                 160

Ala Ser Lys Asn Ala Asn His Ser Leu Ala Val Phe Ile Lys Arg Cys
                165                 170                 175

Phe Thr Phe Met Asp Arg Gly Phe Val Phe Lys Gln Ile Asn Asn Tyr
            180                 185                 190

Ile Ser Cys Phe Ala Pro Gly Asp Pro Lys Thr Leu Phe Glu Tyr Lys
        195                 200                 205

Phe Glu Phe Leu Arg Val Val Cys Asn His Glu His Tyr Ile Pro Leu
    210                 215                 220

Asn Leu Pro Met Pro Phe Gly Lys Gly Arg Ile Gln Arg Tyr Gln Asp
225                 230                 235                 240

Leu Gln Leu Asp Tyr Ser Leu Thr Asp Glu Phe Cys Arg Asn His Phe
                245                 250                 255

Leu Val Gly Leu Leu Leu Arg Glu Val Gly Thr Ala Leu Gln Glu Phe
            260                 265                 270

Arg Glu Val Arg Leu Ile Ala Ile Ser Val Leu Lys Asn Leu Leu Ile
        275                 280                 285

Lys His Ser Phe Asp Asp Arg Tyr Ala Ser Arg Ser His Gln Ala Arg
    290                 295                 300

Ile Ala Thr Leu Tyr Leu Pro Leu Phe Gly Leu Leu Ile Glu Asn Val
305                 310                 315                 320

Gln Arg Ile Asn Val Arg Asp Val Ser Pro Phe Pro Val Asn Ala Gly
                325                 330                 335

Met Thr Val Lys Asp Glu Ser Leu Ala Leu Pro Ala Val Asn Pro Leu
```

-continued

```
              340                 345                 350
Val Thr Pro Gln Lys Gly Ser Thr Leu Asp Asn Ser Leu His Lys Asp
              355                 360                 365
Leu Leu Gly Ala Ile Ser Gly Ile Ala Ser Pro Tyr Thr Thr Ser Thr
              370                 375                 380
Pro Asn Ile Asn Ser Val Arg Asn Ala Asp Ser Arg Gly Ser Leu Ile
385               390                 395                 400
Ser Thr Asp Ser Gly Asn Ser Leu Pro Glu Arg Asn Ser Glu Lys Ser
                  405                 410                 415
Asn Ser Leu Asp Lys His Gln Gln Ser Ser Thr Leu Gly Asn Ser Val
              420                 425                 430
Val Arg Cys Asp Lys Leu Asp Gln Ser Glu Ile Lys Ser Leu Leu Met
              435                 440                 445
Cys Phe Leu Tyr Ile Leu Lys Ser Met Ser Asp Asp Ala Leu Phe Thr
              450                 455                 460
Tyr Trp Asn Lys Ala Ser Thr Ser Glu Leu Met Asp Phe Phe Thr Ile
465               470                 475                 480
Ser Glu Val Cys Leu His Gln Phe Gln Tyr Met Gly Lys Arg Tyr Ile
                  485                 490                 495
Ala Arg Asn Gln Glu Gly Leu Gly Pro Ile Val His Asp Arg Lys Ser
              500                 505                 510
Gln Thr Leu Pro Val Ser Arg Asn Arg Thr Gly Met Met His Ala Arg
              515                 520                 525
Leu Gln Gln Leu Gly Ser Leu Asp Asn Ser Leu Thr Phe Asn His Ser
              530                 535                 540
Tyr Gly His Ser Asp Ala Asp Val Leu His Gln Ser Leu Leu Glu Ala
545               550                 555                 560
Asn Ile Ala Thr Glu Val Cys Leu Thr Ala Leu Asp Thr Leu Ser Leu
                  565                 570                 575
Phe Thr Leu Ala Phe Lys Leu Leu Ala Asp His Gly His Asn Pro Leu
              580                 585                 590
Met Lys Lys Val Phe Asp Val Tyr Leu Cys Phe Leu Gln Lys His Gln
              595                 600                 605
Ser Glu Thr Ala Leu Lys Asn Val Phe Thr Ala Leu Arg Ser Leu Ile
              610                 615                 620
Tyr Lys Phe Pro Ser Thr Phe Tyr Glu Gly Arg Ala Asp Met Cys Ala
625               630                 635                 640
Ala Leu Cys Tyr Glu Ile Leu Lys Cys Cys Asn Ser Lys Leu Ser Ser
                  645                 650                 655
Ile Arg Thr Glu Ala Ser Gln Leu Leu Tyr Phe Leu Met Arg Asn Asn
              660                 665                 670
Phe Asp Tyr Thr Gly Lys Lys Ser Phe Val Arg Thr His Leu Gln Val
              675                 680                 685
Ile Ile Ser Val Ser Gln Leu Ile Ala Asp Val Val Gly Ile Gly Glu
              690                 695                 700
Thr Arg Phe Gln Gln Ser Leu Ser Ile Ile Asn Asn Cys Ala Asn Ser
705               710                 715                 720
Asp Arg Leu Ile Lys His Thr Ser Phe Ser Ser Asp Val Lys Asp Leu
                  725                 730                 735
Thr Lys Arg Ile Arg Thr Val Leu Met Ala Thr Ala Gln Met Lys Glu
              740                 745                 750
His Glu Asn Asp Pro Glu Met Leu Val Asp Leu Gln Tyr Ser Leu Ala
              755                 760                 765
```

-continued

```
Lys Ser Tyr Ala Ser Thr Pro Glu Leu Arg Lys Thr Trp Leu Asp Ser
    770                 775                 780

Met Ala Arg Ile His Val Lys Asn Gly Asp Leu Ser Glu Ala Ala Met
785                 790                 795                 800

Cys Tyr Val His Val Thr Ala Leu Val Ala Glu Tyr Leu Thr Arg Lys
                805                 810                 815

Gly Val Phe Arg Gln Gly Cys Thr Ala Phe Arg Val Ile Thr Pro Asn
            820                 825                 830

Ile Asp Glu Glu Ala Ser Met Met Glu Asp Val Gly Met Gln Asp Val
        835                 840                 845

His Phe Asn Glu Asp Val Leu Met Glu Leu Leu Glu Gln Cys Ala Asp
    850                 855                 860

Gly Leu Trp Lys Ala Glu Arg Tyr Glu Leu Ile Ala Asp Ile Tyr Lys
865                 870                 875                 880

Leu Ile Ile Pro Ile Tyr Glu Lys Arg Arg Asp Phe Glu Arg Leu Ala
                885                 890                 895

His Leu Tyr Asp Thr Leu His Arg Ala Tyr Ser Lys Val Thr Glu Val
            900                 905                 910

Met His Ser Gly Arg Arg Leu Leu Gly Thr Tyr Phe Arg Val Ala Phe
        915                 920                 925

Phe Gly Gln Gly Phe Phe Glu Asp Glu Asp Gly Lys Glu Tyr Ile Tyr
    930                 935                 940

Lys Glu Pro Lys Leu Thr Pro Leu Ser Glu Ile Ser Gln Arg Leu Leu
945                 950                 955                 960

Lys Leu Tyr Ser Asp Lys Phe Gly Ser Glu Asn Val Lys Met Ile Gln
                965                 970                 975

Asp Ser Gly Lys Val Asn Pro Lys Asp Leu Asp Ser Lys Tyr Ala Tyr
            980                 985                 990

Ile Gln Val Thr His Val Ile Pro Phe Phe Asp Glu Lys Glu Leu Gln
        995                 1000                1005

Glu Arg Lys Thr Glu Phe Glu Arg Ser His Asn Ile Arg Arg Phe Met
    1010                1015                1020

Phe Glu Met Pro Phe Thr Gln Thr Gly Lys Arg Gln Gly Gly Val Glu
1025                1030                1035                1040

Glu Gln Cys Lys Arg Arg Thr Ile Leu Thr Ala Ile His Cys Phe Pro
                1045                1050                1055

Tyr Val Lys Lys Arg Ile Pro Val Met Tyr Gln His His Thr Asp Leu
            1060                1065                1070

Asn Pro Ile Glu Val Ala Ile Asp Glu Met Ser Lys Lys Val Ala Glu
        1075                1080                1085

Leu Arg Gln Leu Cys Ser Ser Ala Glu Val Asp Met Ile Lys Leu Gln
    1090                1095                1100

Leu Lys Leu Gln Gly Ser Val Ser Val Gln Val Asn Ala Gly Pro Leu
1105                1110                1115                1120

Ala Tyr Ala Arg Ala Phe Leu Asp Asp Thr Asn Thr Lys Arg Tyr Pro
                1125                1130                1135

Asp Asn Lys Val Lys Leu Leu Lys Glu Val Phe Arg Gln Phe Val Glu
            1140                1145                1150

Ala Cys Gly Gln Ala Leu Ala Val Asn Glu Arg Leu Ile Lys Glu Asp
        1155                1160                1165

Gln Leu Glu Tyr Gln Glu Glu Met Lys Ala Asn Tyr Arg Glu Met Ala
    1170                1175                1180
```

```
Lys Glu Leu Ser Glu Ile Met His Glu Gln Ile Cys Pro Leu Glu Glu
1185                1190                1195                1200

Lys Thr Ser Val Leu Pro Asn Ser Leu His Ile Phe Asn Ala Ile Ser
                1205                1210                1215

Gly Thr Pro Thr Ser Thr Met Val His Gly Met Thr Ser Ser Ser
            1220                1225                1230

Val Val

<210> SEQ ID NO 5
<211> LENGTH: 1250
<212> TYPE: DNA
<213> ORGANISM: Homo sapiens
<220> FEATURE:
<221> NAME/KEY: CDS
<222> LOCATION: (2)..(784)
<223> OTHER INFORMATION: Human cadherin-like asymmetry protein 2C
      (CLASP-2C)

<400> SEQUENCE: 5 g ttt aga caa gga tgc acc gcc ttc agg gtc att acc cca aac atc gac     49
  Phe Arg Gln Gly Cys Thr Ala Phe Arg Val Ile Thr Pro Asn Ile Asp
  1               5                   10                  15 gag gag gcc tcc atg atg gaa gac gtg ggg atg cag gat gtc cat ttc      97
Glu Glu Ala Ser Met Met Glu Asp Val Gly Met Gln Asp Val His Phe
            20                  25                  30 aac gag gat gtg ctg atg gag ctc ctt gag cag tgc gca gat gga ctc     145
Asn Glu Asp Val Leu Met Glu Leu Leu Glu Gln Cys Ala Asp Gly Leu
        35                  40                  45 tgg aaa gcc gag cgc tac gag ctc atc gcc gac atc tac aaa ctt atc     193
Trp Lys Ala Glu Arg Tyr Glu Leu Ile Ala Asp Ile Tyr Lys Leu Ile
    50                  55                  60 atc ccc att tat gag aag cgg agg gat ttt gag agg ctg gcc cat ctg     241
Ile Pro Ile Tyr Glu Lys Arg Arg Asp Phe Glu Arg Leu Ala His Leu
65                  70                  75                  80 tat gac acg ctg cac cgg gcc tac agc aaa gtg acc gag gtc atg cac     289
Tyr Asp Thr Leu His Arg Ala Tyr Ser Lys Val Thr Glu Val Met His
                85                  90                  95 tcg ggc cgc agg ctt ctg ggg acc tac ttc cgg gta gcc ttc ttc ggg     337
Ser Gly Arg Arg Leu Leu Gly Thr Tyr Phe Arg Val Ala Phe Phe Gly
            100                 105                 110 cag gga ttc ttt gaa gat gaa gat gga aag gag tat att tac aag gaa     385
Gln Gly Phe Phe Glu Asp Glu Asp Gly Lys Glu Tyr Ile Tyr Lys Glu
        115                 120                 125 ccc aaa ctc aca ccg ctg tcg gaa att tct cag aga ctc ctt aaa ctg     433
Pro Lys Leu Thr Pro Leu Ser Glu Ile Ser Gln Arg Leu Leu Lys Leu
    130                 135                 140 tac tcg gat aaa ttt ggt tct gaa aat gtc aaa atg aca cag gat tct     481
Tyr Ser Asp Lys Phe Gly Ser Glu Asn Val Lys Met Thr Gln Asp Ser
145                 150                 155                 160 ggc aag gtc aac cct aag gat ctg gat tct aag tat gca tac atc cag     529
Gly Lys Val Asn Pro Lys Asp Leu Asp Ser Lys Tyr Ala Tyr Ile Gln
                165                 170                 175 gtg act cac gtc atc ccc ttc ttt gac gaa aaa gag ttg caa gaa agg     577
Val Thr His Val Ile Pro Phe Phe Asp Glu Lys Glu Leu Gln Glu Arg
            180                 185                 190 aaa aca gag ttt gag aga tcc cac aac atc cgc cgc ttc atg ttt gag     625
Lys Thr Glu Phe Glu Arg Ser His Asn Ile Arg Arg Phe Met Phe Glu
        195                 200                 205 atg cca ttt acg cag acc ggg aag agg cag ggc ggg gtg gaa gag cag     673
Met Pro Phe Thr Gln Thr Gly Lys Arg Gln Gly Gly Val Glu Glu Gln
    210                 215                 220
```

```
tgc aaa cgg cgc acc atc ctg aca gcc ata cac tgc ttc cct tat gtg       721
Cys Lys Arg Arg Thr Ile Leu Thr Ala Ile His Cys Phe Pro Tyr Val
225                 230                 235                 240 aag aag cgc atc cct ttc atg tac cag cac cac act gac ctg aac ccc       769
Lys Lys Arg Ile Pro Phe Met Tyr Gln His His Thr Asp Leu Asn Pro
                245                 250                 255 atc gag gtc cat tga cgagatgagt aagaaggtgg cggagctccg gcagctgtgc       824
Ile Glu Val His
            260 tcctcggccg aggtggacat gatcaaactg cagctcaaac tccagggcag cgtgagtgtt     884 caggtcaatg ctggcccact agcatatgcg cgagctttct tagatgatac aaacacaaag     944 cgatatcctg acaataaagt gaagctgctt aaggaagttt tcaggcaatt tgtggaagct    1004 tgcggtcaag ccttagcggt aaacgaacgt ctgattaaag aagaccagct cgagtatcag    1064 gaagaaatga agccaactca agggaaatg gcgaaggagc tttctgaaat catgcatgag     1124 cagatctgcc ccctggagga aagacgagc gtcttaccga attcccttca catcttcaac     1184 gccatcagtg ggactccaac aagcacaatg gttcacggga tgaccagctc gtcttcggtc    1244 gtgtga                                                               1250
```

<210> SEQ ID NO 6
<211> LENGTH: 260
<212> TYPE: PRT
<213> ORGANISM: Homo sapiens
<223> OTHER INFORMATION: Human cadherin-like asymmetry protein 2C

<400> SEQUENCE: 6

```
Phe Arg Gln Gly Cys Thr Ala Phe Arg Val Ile Thr Pro Asn Ile Asp
 1               5                  10                  15

Glu Glu Ala Ser Met Met Glu Asp Val Gly Met Gln Asp Val His Phe
                20                  25                  30

Asn Glu Asp Val Leu Met Glu Leu Leu Glu Gln Cys Ala Asp Gly Leu
            35                  40                  45

Trp Lys Ala Glu Arg Tyr Glu Leu Ile Ala Asp Ile Tyr Lys Leu Ile
    50                  55                  60

Ile Pro Ile Tyr Glu Lys Arg Arg Asp Phe Glu Arg Leu Ala His Leu
65                  70                  75                  80

Tyr Asp Thr Leu His Arg Ala Tyr Ser Lys Val Thr Glu Val Met His
                85                  90                  95

Ser Gly Arg Arg Leu Leu Gly Thr Tyr Phe Arg Val Ala Phe Phe Gly
            100                 105                 110

Gln Gly Phe Phe Glu Asp Glu Asp Gly Lys Glu Tyr Ile Tyr Lys Glu
        115                 120                 125

Pro Lys Leu Thr Pro Leu Ser Glu Ile Ser Gln Arg Leu Leu Lys Leu
    130                 135                 140

Tyr Ser Asp Lys Phe Gly Ser Glu Asn Val Lys Met Thr Gln Asp Ser
145                 150                 155                 160

Gly Lys Val Asn Pro Lys Asp Leu Asp Ser Lys Tyr Ala Tyr Ile Gln
                165                 170                 175

Val Thr His Val Ile Pro Phe Phe Asp Glu Lys Glu Leu Gln Glu Arg
            180                 185                 190

Lys Thr Glu Phe Glu Arg Ser His Asn Ile Arg Arg Phe Met Phe Glu
        195                 200                 205

Met Pro Phe Thr Gln Thr Gly Lys Arg Gln Gly Gly Val Glu Glu Gln
    210                 215                 220
```

```
Cys Lys Arg Arg Thr Ile Leu Thr Ala Ile His Cys Phe Pro Tyr Val
225                 230                 235                 240

Lys Lys Arg Ile Pro Phe Met Tyr Gln His His Thr Asp Leu Asn Pro
            245                 250                 255

Ile Glu Val His
            260

<210> SEQ ID NO 7
<211> LENGTH: 5862
<212> TYPE: DNA
<213> ORGANISM: Homo sapiens
<220> FEATURE:
<221> NAME/KEY: CDS
<222> LOCATION: (1)..(4602)
<223> OTHER INFORMATION: Human cadherin-like asymmetry protein 2D
      (CLASP-2D) KIAA1058

<400> SEQUENCE: 7 gca tct gga aat ctt gac aaa aat gcc aga ttt tct gcc atc tac agg      48
Ala Ser Gly Asn Leu Asp Lys Asn Ala Arg Phe Ser Ala Ile Tyr Arg
 1               5                  10                  15 caa gac agc aat aag cta tcc aat gat gac atg ctc aag tta ctt gca     96
Gln Asp Ser Asn Lys Leu Ser Asn Asp Asp Met Leu Lys Leu Leu Ala
                20                  25                  30 gac ttt cgg aaa cct gag aag atg gct aag ctc cca gtg att tta ggc    144
Asp Phe Arg Lys Pro Glu Lys Met Ala Lys Leu Pro Val Ile Leu Gly
            35                  40                  45 aat cta gac att aca att gat aat gtt tcc tca gac ttc cct aat tat    192
Asn Leu Asp Ile Thr Ile Asp Asn Val Ser Ser Asp Phe Pro Asn Tyr
        50                  55                  60 gtt aat tca tca tac att ccc aca aaa caa ttt gaa acc tgc agt aaa    240
Val Asn Ser Ser Tyr Ile Pro Thr Lys Gln Phe Glu Thr Cys Ser Lys
 65                  70                  75                  80 act ccc atc acg ttt gaa gtg gag gaa ttt gtg ccc tgc ata cca aaa    288
Thr Pro Ile Thr Phe Glu Val Glu Glu Phe Val Pro Cys Ile Pro Lys
                 85                  90                  95 cac act cag cct tac acc atc tac acc aat cac ctt tac gtt tat cct    336
His Thr Gln Pro Tyr Thr Ile Tyr Thr Asn His Leu Tyr Val Tyr Pro
            100                 105                 110 aag tac ttg aaa tac gac agt cag aag tct ttt gcc aag gct aga aat    384
Lys Tyr Leu Lys Tyr Asp Ser Gln Lys Ser Phe Ala Lys Ala Arg Asn
        115                 120                 125 att gcg att tgc att gaa ttc aaa gat tca gat gag gaa gac tct cag    432
Ile Ala Ile Cys Ile Glu Phe Lys Asp Ser Asp Glu Glu Asp Ser Gln
    130                 135                 140 ccc ctt aag tgc att tat ggc aga cct ggt ggg cca gtt ttc aca aga    480
Pro Leu Lys Cys Ile Tyr Gly Arg Pro Gly Gly Pro Val Phe Thr Arg
145                 150                 155                 160 agc gcc ttt gct gca gtt tta cac cat cac caa aac cca gaa ttt tat    528
Ser Ala Phe Ala Ala Val Leu His His His Gln Asn Pro Glu Phe Tyr
                165                 170                 175 gat gag att aaa ata gag ttg ccc act cag ctg cat gaa aag cac cac    576
Asp Glu Ile Lys Ile Glu Leu Pro Thr Gln Leu His Glu Lys His His
            180                 185                 190 ctg ttg ctc aca ttc ttc cat gtc agc tgt gac aac tca agt aaa gga    624
Leu Leu Leu Thr Phe Phe His Val Ser Cys Asp Asn Ser Ser Lys Gly
        195                 200                 205 agc acg aag aag agg gat gtc gtt gaa acc caa gtt ggc tac tcc tgg    672
Ser Thr Lys Lys Arg Asp Val Val Glu Thr Gln Val Gly Tyr Ser Trp
    210                 215                 220
```

```
                                    -continued ctt ccc ctc ctg aaa gac gga agg gtg gtg aca agc gag cag cac atc         720
Leu Pro Leu Leu Lys Asp Gly Arg Val Val Thr Ser Glu Gln His Ile
225                 230                 235                 240 ccg gtc tcg gcg aac ctt cct tcg ggc tat ctt ggc tac cag gag ctt         768
Pro Val Ser Ala Asn Leu Pro Ser Gly Tyr Leu Gly Tyr Gln Glu Leu
                245                 250                 255 ggg atg ggc agg cat tat ggt ccg gaa att aaa tgg gta gat gga ggc         816
Gly Met Gly Arg His Tyr Gly Pro Glu Ile Lys Trp Val Asp Gly Gly
            260                 265                 270 aag cca ctg ctg aaa att tcc act cat ctg gtt tct aca gtg tat act         864
Lys Pro Leu Leu Lys Ile Ser Thr His Leu Val Ser Thr Val Tyr Thr
        275                 280                 285 cag gat cag cat tta cat aat ttt ttc cag tac tgt cag aaa acc gaa         912
Gln Asp Gln His Leu His Asn Phe Phe Gln Tyr Cys Gln Lys Thr Glu
290                 295                 300 tct gga gcc caa gcc tta gga aac gaa ctt gta aag tac ctt aag agt         960
Ser Gly Ala Gln Ala Leu Gly Asn Glu Leu Val Lys Tyr Leu Lys Ser
305                 310                 315                 320 ctg cat gcg atg gaa ggc cac gtg atg atc gcc ttc ttg ccc act atc        1008
Leu His Ala Met Glu Gly His Val Met Ile Ala Phe Leu Pro Thr Ile
                325                 330                 335 cta aac cag ctg ttc cga gtc ctc acc aga gcc aca cag gaa gaa gtc        1056
Leu Asn Gln Leu Phe Arg Val Leu Thr Arg Ala Thr Gln Glu Glu Val
            340                 345                 350 gcg gtt aac gtg act cgg gtc att att cat gtg gtt gcc cag tgc cat        1104
Ala Val Asn Val Thr Arg Val Ile Ile His Val Val Ala Gln Cys His
        355                 360                 365 gag gaa gga ttg gag agc cac ttg agg tca tat gtt aag tac gcg tat        1152
Glu Glu Gly Leu Glu Ser His Leu Arg Ser Tyr Val Lys Tyr Ala Tyr
370                 375                 380 aag gct gag cca tat gtt gcc tct gaa tac aag aca gtg cat gaa gaa        1200
Lys Ala Glu Pro Tyr Val Ala Ser Glu Tyr Lys Thr Val His Glu Glu
385                 390                 395                 400 ctg acc aaa tcc atg acc acg att ctc aag cct tct gcc gat ttc ctc        1248
Leu Thr Lys Ser Met Thr Thr Ile Leu Lys Pro Ser Ala Asp Phe Leu
                405                 410                 415 acc agc aac aaa cta ctg aag tac tca tgg ttt ttc ttt gat gta ctg        1296
Thr Ser Asn Lys Leu Leu Lys Tyr Ser Trp Phe Phe Phe Asp Val Leu
            420                 425                 430 atc aaa tct atg gct cag cat ttg ata gag aac tcc aaa gtt aag ttg        1344
Ile Lys Ser Met Ala Gln His Leu Ile Glu Asn Ser Lys Val Lys Leu
        435                 440                 445 ctg cga aac cag aga ttt cct gca tcc tat cat cat gca gtg gaa acc        1392
Leu Arg Asn Gln Arg Phe Pro Ala Ser Tyr His His Ala Val Glu Thr
450                 455                 460 gtt gta aat atg ctg atg cca cac atc act cag aag ttt cga gat aat        1440
Val Val Asn Met Leu Met Pro His Ile Thr Gln Lys Phe Arg Asp Asn
465                 470                 475                 480 cca gag gca tct aag aac gcg aat cat agc ctt gct gtc ttc atc aag        1488
Pro Glu Ala Ser Lys Asn Ala Asn His Ser Leu Ala Val Phe Ile Lys
                485                 490                 495 aga tgt ttc acc ttc atg gac agg ggc ttt gtc ttc aag cag atc aac        1536
Arg Cys Phe Thr Phe Met Asp Arg Gly Phe Val Phe Lys Gln Ile Asn
            500                 505                 510 aac tac att agc tgt ttt gct cct gga gac cca aag acc ctc ttt gaa        1584
Asn Tyr Ile Ser Cys Phe Ala Pro Gly Asp Pro Lys Thr Leu Phe Glu
        515                 520                 525 tac aag ttt gaa ttt ctc cgt gta gtg tgc aac cat gaa cat tat att        1632
Tyr Lys Phe Glu Phe Leu Arg Val Val Cys Asn His Glu His Tyr Ile
530                 535                 540
```

```
ccg ttg aac tta cca atg cca ttt gga aaa ggc agg att caa aga tac      1680
Pro Leu Asn Leu Pro Met Pro Phe Gly Lys Gly Arg Ile Gln Arg Tyr
545                 550                 555                 560 caa gac ctc cag ctt gac tac tca tta aca gat gag ttc tgc aga aac      1728
Gln Asp Leu Gln Leu Asp Tyr Ser Leu Thr Asp Glu Phe Cys Arg Asn
                565                 570                 575 cac ttc ttg gtg gga ctg tta ctg agg gag gtg ggg aca gcc ctc cag      1776
His Phe Leu Val Gly Leu Leu Leu Arg Glu Val Gly Thr Ala Leu Gln
            580                 585                 590 gag ttc cgg gag gtc cgt ctg atc gcc atc agt gtg ctc aag aac ctg      1824
Glu Phe Arg Glu Val Arg Leu Ile Ala Ile Ser Val Leu Lys Asn Leu
        595                 600                 605 ctg ata aag cat tct ttt gat gac aga tat gct tca agg agc cat cag      1872
Leu Ile Lys His Ser Phe Asp Asp Arg Tyr Ala Ser Arg Ser His Gln
    610                 615                 620 gca agg ata gcc acc ctc tac ctg cct ctg ttt ggt ctg ctg att gaa      1920
Ala Arg Ile Ala Thr Leu Tyr Leu Pro Leu Phe Gly Leu Leu Ile Glu
625                 630                 635                 640 aac gtc cag cgg atc aat gtg agg gat gtg tca ccc ttc cct gtg aac      1968
Asn Val Gln Arg Ile Asn Val Arg Asp Val Ser Pro Phe Pro Val Asn
                645                 650                 655 gcg ggc atg act gtg aag gat gaa tcc ctg gct cta cca gct gtg aat      2016
Ala Gly Met Thr Val Lys Asp Glu Ser Leu Ala Leu Pro Ala Val Asn
            660                 665                 670 ccg ctg gtg acg ccg cag aag gga agc acc ctg gac aac agc ctg cac      2064
Pro Leu Val Thr Pro Gln Lys Gly Ser Thr Leu Asp Asn Ser Leu His
        675                 680                 685 aag gac ctg ctg ggc gcc atc tcc ggc att gct tct cca tat aca acc      2112
Lys Asp Leu Leu Gly Ala Ile Ser Gly Ile Ala Ser Pro Tyr Thr Thr
    690                 695                 700 tca act cca aac atc aac agt gtg aga aat gct gat tcg aga gga tct      2160
Ser Thr Pro Asn Ile Asn Ser Val Arg Asn Ala Asp Ser Arg Gly Ser
705                 710                 715                 720 ctc ata agc aca gat tcg ggt aac agc ctt cca gaa agg aat agt gag      2208
Leu Ile Ser Thr Asp Ser Gly Asn Ser Leu Pro Glu Arg Asn Ser Glu
                725                 730                 735 aag agc aat tcc ctg gat aag cac caa caa agt agc aca ttg gga aat      2256
Lys Ser Asn Ser Leu Asp Lys His Gln Gln Ser Ser Thr Leu Gly Asn
            740                 745                 750 tcc gtg gtt cgc tgt gat aaa ctt gac cag tct gag att aag agc cta      2304
Ser Val Val Arg Cys Asp Lys Leu Asp Gln Ser Glu Ile Lys Ser Leu
        755                 760                 765 ctg atg tgt ttc ctc tac atc tta aag agc atg tct gat gat gct ttg      2352
Leu Met Cys Phe Leu Tyr Ile Leu Lys Ser Met Ser Asp Asp Ala Leu
    770                 775                 780 ttt aca tat tgg aac aag gct tca aca tct gaa ctt atg gat ttt ttt      2400
Phe Thr Tyr Trp Asn Lys Ala Ser Thr Ser Glu Leu Met Asp Phe Phe
785                 790                 795                 800 aca ata tct gaa gtc tgc ctg cac cag ttc cag tac atg ggg aag cga      2448
Thr Ile Ser Glu Val Cys Leu His Gln Phe Gln Tyr Met Gly Lys Arg
                805                 810                 815 tac ata gcc aga aca gga atg atg cat gcc aga ttg cag cag ctg ggc      2496
Tyr Ile Ala Arg Thr Gly Met Met His Ala Arg Leu Gln Gln Leu Gly
            820                 825                 830 agc ctg gat aac tct ctc act ttt aac cac agc tat ggc cac tcg gac      2544
Ser Leu Asp Asn Ser Leu Thr Phe Asn His Ser Tyr Gly His Ser Asp
        835                 840                 845 gca gat gtt ctg cac cag tca tta ctt gaa gcc aac att gct act gag      2592
Ala Asp Val Leu His Gln Ser Leu Leu Glu Ala Asn Ile Ala Thr Glu
```

```
                                                          -continued 850                855                860
gtt tgc ctg aca gct ctg gac acg ctt tct cta ttt aca ttg gcg ttt      2640
Val Cys Leu Thr Ala Leu Asp Thr Leu Ser Leu Phe Thr Leu Ala Phe
865                870                875                880 aag aac cag ctc ctg gcc gac cat gga cat aat cct ctc atg aaa aaa      2688
Lys Asn Gln Leu Leu Ala Asp His Gly His Asn Pro Leu Met Lys Lys
                885                890                895 gtt ttt gat gtc tac ctg tgt ttt ctt caa aaa cat cag tct gaa acg      2736
Val Phe Asp Val Tyr Leu Cys Phe Leu Gln Lys His Gln Ser Glu Thr
        900                905                910 gct tta aaa aat gtc ttc act gcc tta agg tcc tta att tat aag ttt      2784
Ala Leu Lys Asn Val Phe Thr Ala Leu Arg Ser Leu Ile Tyr Lys Phe
            915                920                925 ccc tca aca ttc tat gaa ggg aga gcg gac atg tgt gcg gct ctg tgt      2832
Pro Ser Thr Phe Tyr Glu Gly Arg Ala Asp Met Cys Ala Ala Leu Cys
                930                935                940 tac gag att ctc aag tgc tgt aac tcc aag ctg agc tcc atc agg acg      2880
Tyr Glu Ile Leu Lys Cys Cys Asn Ser Lys Leu Ser Ser Ile Arg Thr
945                950                955                960 gag gcc tcc cag ctg ctc tac ttc ctg atg agg aac aac ttt gat tac      2928
Glu Ala Ser Gln Leu Leu Tyr Phe Leu Met Arg Asn Asn Phe Asp Tyr
                965                970                975 act gga aag aag tcc ttt gtc cgg aca cat ttg caa gtc atc ata tct      2976
Thr Gly Lys Lys Ser Phe Val Arg Thr His Leu Gln Val Ile Ile Ser
        980                985                990 gtc agc cag ctg ata gca gac gtt gtt ggc att ggg gga acc aga ttc      3024
Val Ser Gln Leu Ile Ala Asp Val Val Gly Ile Gly Gly Thr Arg Phe
            995                1000               1005 cag cag tcc ctg tcc atc atc aac aac tgt gcc aac agt gac cgg ctt      3072
Gln Gln Ser Leu Ser Ile Ile Asn Asn Cys Ala Asn Ser Asp Arg Leu
    1010               1015               1020 att aag cac acc agc ttc tcc tct gat gtg aag gac tta acc aaa agg      3120
Ile Lys His Thr Ser Phe Ser Ser Asp Val Lys Asp Leu Thr Lys Arg
1025               1030               1035               1040 ata cgc acg gtg cta atg gcc acc gcc cag atg aag gag cat gag aac      3168
Ile Arg Thr Val Leu Met Ala Thr Ala Gln Met Lys Glu His Glu Asn
                1045               1050               1055 gac cca gag atg ctg gtg gac ctc cag tac agc ctg gcc aaa tcc tat      3216
Asp Pro Glu Met Leu Val Asp Leu Gln Tyr Ser Leu Ala Lys Ser Tyr
        1060               1065               1070 gcc agc acg ccc gag ctc agg aag acg tgg ctc gac agc atg gcc agg      3264
Ala Ser Thr Pro Glu Leu Arg Lys Thr Trp Leu Asp Ser Met Ala Arg
            1075               1080               1085 atc cat gtc aaa aat ggc gat ctc tca gag gca gca atg tgc tat gtc      3312
Ile His Val Lys Asn Gly Asp Leu Ser Glu Ala Ala Met Cys Tyr Val
    1090               1095               1100 cac gta aca gcc cta gtg gca gaa tat ctc aca cgg aaa gaa gca gtc      3360
His Val Thr Ala Leu Val Ala Glu Tyr Leu Thr Arg Lys Glu Ala Val
1105               1110               1115               1120 cag tgg gag ccg ccc ctt ctc ccc cac agc cat agc gcc tgc ctg agg      3408
Gln Trp Glu Pro Pro Leu Leu Pro His Ser His Ser Ala Cys Leu Arg
                1125               1130               1135 agg agc cgg gga ggc gtg ttt aga caa gga tgc acc gcc ttc agg gtc      3456
Arg Ser Arg Gly Gly Val Phe Arg Gln Gly Cys Thr Ala Phe Arg Val
        1140               1145               1150 att acc cca aac atc gac gag gag gcc tcc atg atg gaa gac gtg ggg      3504
Ile Thr Pro Asn Ile Asp Glu Glu Ala Ser Met Met Glu Asp Val Gly
            1155               1160               1165 atg cag gat gtc cat ttc aac gag gat gtg ctg atg gag ctc ctt gag      3552
```

```
                Met Gln Asp Val His Phe Asn Glu Asp Val Leu Met Glu Leu Leu Glu
                    1170                1175                1180 cag tgc gca gat gga ctc tgg aaa gcc gag cgc tac gag ctc att gcc          3600
Gln Cys Ala Asp Gly Leu Trp Lys Ala Glu Arg Tyr Glu Leu Ile Ala
1185                1190                1195                1200 gac atc tac aaa ctt atc atc ccc att tat gag aag cgg agg gat ttt          3648
Asp Ile Tyr Lys Leu Ile Ile Pro Ile Tyr Glu Lys Arg Arg Asp Phe
                1205                1210                1215 gag agg ctg gcc cat ctg tat gac acg ctg cac cgg gcc tac agc aaa          3696
Glu Arg Leu Ala His Leu Tyr Asp Thr Leu His Arg Ala Tyr Ser Lys
            1220                1225                1230 gtg acc gag gtc atg cac tcg ggc cgc agg ctt ctg ggg acc tac ttc          3744
Val Thr Glu Val Met His Ser Gly Arg Arg Leu Leu Gly Thr Tyr Phe
        1235                1240                1245 cgg gta gcc ttc ttc ggg cag gca gcg caa tac cag ttt aca gac agt          3792
Arg Val Ala Phe Phe Gly Gln Ala Ala Gln Tyr Gln Phe Thr Asp Ser
    1250                1255                1260 gaa aca gat gtg gag gga ttc ttt gaa gat gaa gat gga aag gag tat          3840
Glu Thr Asp Val Glu Gly Phe Phe Glu Asp Glu Asp Gly Lys Glu Tyr
1265                1270                1275                1280 att tac aag gaa ccc aaa ctc aca ccg ctg tcg gaa att tct cag aga          3888
Ile Tyr Lys Glu Pro Lys Leu Thr Pro Leu Ser Glu Ile Ser Gln Arg
                1285                1290                1295 ctc ctt aaa ctg tac tcg gat aaa ttt ggt tct gaa aat gtc aaa atg          3936
Leu Leu Lys Leu Tyr Ser Asp Lys Phe Gly Ser Glu Asn Val Lys Met
            1300                1305                1310 ata cag gat tct ggc aag gtc aac cct aag gat ctg gat tct aag tat          3984
Ile Gln Asp Ser Gly Lys Val Asn Pro Lys Asp Leu Asp Ser Lys Tyr
        1315                1320                1325 gcc tac atc cag gtg act cac gtc atc ccc ttc ttt gac gaa aaa gag          4032
Ala Tyr Ile Gln Val Thr His Val Ile Pro Phe Phe Asp Glu Lys Glu
    1330                1335                1340 ttg caa gaa agg aaa aca gag ttt gag aga tcc cac aac atc cgc cgc          4080
Leu Gln Glu Arg Lys Thr Glu Phe Glu Arg Ser His Asn Ile Arg Arg
1345                1350                1355                1360 ttc atg ttt gag atg cca ttt acg cag acc ggg aag agg cag ggc ggg          4128
Phe Met Phe Glu Met Pro Phe Thr Gln Thr Gly Lys Arg Gln Gly Gly
                1365                1370                1375 gtg gaa gag cag tgc aaa cgg cgc acc atc ctg aca gcc ata cac tgc          4176
Val Glu Glu Gln Cys Lys Arg Arg Thr Ile Leu Thr Ala Ile His Cys
            1380                1385                1390 ttc cct tat gtg aag aag cgc atc cct gtc atg tac cag cac cac act          4224
Phe Pro Tyr Val Lys Lys Arg Ile Pro Val Met Tyr Gln His His Thr
        1395                1400                1405 gac ctg aac ccc atc gag gtg gcc att gac gag atg agt aag aag gtg          4272
Asp Leu Asn Pro Ile Glu Val Ala Ile Asp Glu Met Ser Lys Lys Val
    1410                1415                1420 gcg gag ctc cgg cag ctg tgc tcc tcg gcc gag gtg gac atg atc aaa          4320
Ala Glu Leu Arg Gln Leu Cys Ser Ser Ala Glu Val Asp Met Ile Lys
1425                1430                1435                1440 ctg cag ctc aaa ctc cag ggc agc gtg agt gtt cag gtc aat gct ggc          4368
Leu Gln Leu Lys Leu Gln Gly Ser Val Ser Val Gln Val Asn Ala Gly
                1445                1450                1455 cca cta gca tat gcg cga gct ttc tta gat gat aca aac aca aag cga          4416
Pro Leu Ala Tyr Ala Arg Ala Phe Leu Asp Asp Thr Asn Thr Lys Arg
            1460                1465                1470 tat cct gac aat aaa gtg aag ctg ctt aag gaa gtt ttc agg caa ttt          4464
Tyr Pro Asp Asn Lys Val Lys Leu Leu Lys Glu Val Phe Arg Gln Phe
        1475                1480                1485
```

-continued

```
gtg gaa gct tgc ggt caa gcc tta gcg gta aac gaa cgt ctg att aaa       4512
Val Glu Ala Cys Gly Gln Ala Leu Ala Val Asn Glu Arg Leu Ile Lys
    1490                1495                1500 gaa gac cag ctc gag tat cag gaa gaa atg aaa gcc aac tac agg gaa       4560
Glu Asp Gln Leu Glu Tyr Gln Glu Glu Met Lys Ala Asn Tyr Arg Glu
1505                1510                1515                1520 atg gcg aag gag ctt tct gaa atc atg cat gag cag ctg gga               4602
Met Ala Lys Glu Leu Ser Glu Ile Met His Glu Gln Leu Gly
                1525                1530 tgatctgccc cctggaggag aagacgagcg tcttaccgaa ttcccttcac atcttcaacg     4662
ccatcagtgg gactccaaca agcacaatgg ttcacgggat gaccagctcg tcttcggtcg     4722
tgtgattaca tctcatggcc cgtgtgtggg gacttgcttt gtcatttgca aactcaggat     4782
gctttccaaa gccaatcact ggggagaccc agcacaggga ggaccagggg aaggggagag     4842
aaaggaaata agaacaacg ttatttctta acagactttc tataggagtt gtaagaaggt      4902
gcacatattt ttttaaatct cactggcaat attcaaagtt ttcattgtgt cttaacaaag     4962
gtgtggtaga cactcttgag ctggacttag attttattct tccttgcaga gtagtgttag     5022
aatagatggc ctacagaaaa aaaaggttct gggatctaca tggcagggag ggctgcactg     5082
acattgatgc ctgggggacc ttttgcctcg aggctgagct ggaaaatctt gaaatatt       5142
tttttttcct gtggcacatt caggttgaat acaagaacta ttttgtgac tagttttga      5202
tgacctaagg gaactgacca ttgtaatttt tgtaccagtg aaccaggaga tttagtgctt     5262
ttatattcat ttccttgcat ttaagaaaat atgaaagctt aaggaattat gtgagcttaa     5322
aactagtcaa gcagtttaga accaaaggcc tatattaata accgcaacta tgctgaaaag    5382
tacaaagtag tacagtatat tgttatgtac atatcattgt taatacagtc ctggcattct     5442
gtacatatat gtattacatt tctacatttt taatactcac atgggcttat gcattaagtt    5502
taattgtgat aaatttgtgc tgttccagta tatgcaatac actttaatgt tttattcttg    5562
tacataaaaa tgtgcaatat ggagatgtat acagtcttta ctatattagg tttataaaca    5622
gttttaagaa tttcatccct ttgccaaaat ggtggagtat gtaattggta aatcataaat    5682
cctgtggtga atggtggtgt actttaaagc tgtcaccatg ttatattttc ttttaagaca    5742
ttaatttagt aatttatat ttgggaaaat aaaggttttt aatttatttt aactggaatc     5802
actgccctgc tgtaattaaa cattctgtac cacatctgta ttaaaagac attgctgacc    5862
```

<210> SEQ ID NO 8
<211> LENGTH: 1534
<212> TYPE: PRT
<213> ORGANISM: Homo sapiens
<223> OTHER INFORMATION: Human cadherin-like asymmetry protein 2D

<400> SEQUENCE: 8

```
Ala Ser Gly Asn Leu Asp Lys Asn Ala Arg Phe Ser Ala Ile Tyr Arg
  1               5                  10                  15

Gln Asp Ser Asn Lys Leu Ser Asn Asp Asp Met Leu Lys Leu Leu Ala
                 20                  25                  30

Asp Phe Arg Lys Pro Glu Lys Met Ala Lys Leu Pro Val Ile Leu Gly
             35                  40                  45

Asn Leu Asp Ile Thr Ile Asp Asn Val Ser Ser Asp Phe Pro Asn Tyr
         50                  55                  60

Val Asn Ser Ser Tyr Ile Pro Thr Lys Gln Phe Glu Thr Cys Ser Lys
 65                  70                  75                  80

Thr Pro Ile Thr Phe Glu Val Glu Glu Phe Val Pro Cys Ile Pro Lys
```

```
                    85                  90                  95
His Thr Gln Pro Tyr Thr Ile Tyr Thr Asn His Leu Tyr Val Tyr Pro
            100                 105                 110

Lys Tyr Leu Lys Tyr Asp Ser Gln Lys Ser Phe Ala Lys Ala Arg Asn
            115                 120                 125

Ile Ala Ile Cys Ile Glu Phe Lys Asp Ser Asp Glu Asp Ser Gln
            130                 135                 140

Pro Leu Lys Cys Ile Tyr Gly Arg Pro Gly Pro Val Phe Thr Arg
145                 150                 155                 160

Ser Ala Phe Ala Ala Val Leu His His His Gln Asn Pro Glu Phe Tyr
                165                 170                 175

Asp Glu Ile Lys Ile Glu Leu Pro Thr Gln Leu His Glu Lys His His
            180                 185                 190

Leu Leu Leu Thr Phe Phe His Val Ser Cys Asp Asn Ser Ser Lys Gly
            195                 200                 205

Ser Thr Lys Lys Arg Asp Val Val Glu Thr Gln Val Gly Tyr Ser Trp
            210                 215                 220

Leu Pro Leu Leu Lys Asp Gly Arg Val Val Thr Ser Glu Gln His Ile
225                 230                 235                 240

Pro Val Ser Ala Asn Leu Pro Ser Gly Tyr Leu Gly Tyr Gln Glu Leu
                245                 250                 255

Gly Met Gly Arg His Tyr Gly Pro Glu Ile Lys Trp Val Asp Gly Gly
            260                 265                 270

Lys Pro Leu Leu Lys Ile Ser Thr His Leu Val Ser Thr Val Tyr Thr
            275                 280                 285

Gln Asp Gln His Leu His Asn Phe Phe Gln Tyr Cys Gln Lys Thr Glu
            290                 295                 300

Ser Gly Ala Gln Ala Leu Gly Asn Glu Leu Val Lys Tyr Leu Lys Ser
305                 310                 315                 320

Leu His Ala Met Glu Gly His Val Met Ile Ala Phe Leu Pro Thr Ile
                325                 330                 335

Leu Asn Gln Leu Phe Arg Val Leu Thr Arg Ala Thr Gln Glu Glu Val
            340                 345                 350

Ala Val Asn Val Thr Arg Val Ile Ile His Val Val Ala Gln Cys His
            355                 360                 365

Glu Glu Gly Leu Glu Ser His Leu Arg Ser Tyr Val Lys Tyr Ala Tyr
            370                 375                 380

Lys Ala Glu Pro Tyr Val Ala Ser Glu Tyr Lys Thr Val His Glu Glu
385                 390                 395                 400

Leu Thr Lys Ser Met Thr Thr Ile Leu Lys Pro Ser Ala Asp Phe Leu
                405                 410                 415

Thr Ser Asn Lys Leu Leu Lys Tyr Ser Trp Phe Phe Phe Asp Val Leu
            420                 425                 430

Ile Lys Ser Met Ala Gln His Leu Ile Glu Asn Ser Lys Val Lys Leu
            435                 440                 445

Leu Arg Asn Gln Arg Phe Pro Ala Ser Tyr His His Ala Val Glu Thr
450                 455                 460

Val Val Asn Met Leu Met Pro His Ile Thr Gln Lys Phe Arg Asp Asn
465                 470                 475                 480

Pro Glu Ala Ser Lys Asn Ala Asn His Ser Leu Ala Val Phe Ile Lys
                485                 490                 495

Arg Cys Phe Thr Phe Met Asp Arg Gly Phe Val Phe Lys Gln Ile Asn
            500                 505                 510
```

-continued

Asn Tyr Ile Ser Cys Phe Ala Pro Gly Asp Pro Lys Thr Leu Phe Glu
            515                 520                 525

Tyr Lys Phe Glu Phe Leu Arg Val Val Cys Asn His Glu His Tyr Ile
    530                 535                 540

Pro Leu Asn Leu Pro Met Pro Phe Gly Lys Gly Arg Ile Gln Arg Tyr
545                 550                 555                 560

Gln Asp Leu Gln Leu Asp Tyr Ser Leu Thr Asp Glu Phe Cys Arg Asn
                565                 570                 575

His Phe Leu Val Gly Leu Leu Leu Arg Glu Val Gly Thr Ala Leu Gln
            580                 585                 590

Glu Phe Arg Glu Val Arg Leu Ile Ala Ile Ser Val Leu Lys Asn Leu
        595                 600                 605

Leu Ile Lys His Ser Phe Asp Asp Arg Tyr Ala Ser Arg Ser His Gln
    610                 615                 620

Ala Arg Ile Ala Thr Leu Tyr Leu Pro Leu Phe Gly Leu Leu Ile Glu
625                 630                 635                 640

Asn Val Gln Arg Ile Asn Val Arg Asp Val Ser Pro Phe Pro Val Asn
                645                 650                 655

Ala Gly Met Thr Val Lys Asp Glu Ser Leu Ala Leu Pro Ala Val Asn
            660                 665                 670

Pro Leu Val Thr Pro Gln Lys Gly Ser Thr Leu Asp Asn Ser Leu His
        675                 680                 685

Lys Asp Leu Leu Gly Ala Ile Ser Gly Ile Ala Ser Pro Tyr Thr Thr
    690                 695                 700

Ser Thr Pro Asn Ile Asn Ser Val Arg Asn Ala Asp Ser Arg Gly Ser
705                 710                 715                 720

Leu Ile Ser Thr Asp Ser Gly Asn Ser Leu Pro Glu Arg Asn Ser Glu
                725                 730                 735

Lys Ser Asn Ser Leu Asp Lys His Gln Gln Ser Ser Thr Leu Gly Asn
            740                 745                 750

Ser Val Val Arg Cys Asp Lys Leu Asp Gln Ser Glu Ile Lys Ser Leu
        755                 760                 765

Leu Met Cys Phe Leu Tyr Ile Leu Lys Ser Met Ser Asp Asp Ala Leu
    770                 775                 780

Phe Thr Tyr Trp Asn Lys Ala Ser Thr Ser Glu Leu Met Asp Phe Phe
785                 790                 795                 800

Thr Ile Ser Glu Val Cys Leu His Gln Phe Gln Tyr Met Gly Lys Arg
                805                 810                 815

Tyr Ile Ala Arg Thr Gly Met Met His Ala Arg Leu Gln Gln Leu Gly
            820                 825                 830

Ser Leu Asp Asn Ser Leu Thr Phe Asn His Ser Tyr Gly His Ser Asp
        835                 840                 845

Ala Asp Val Leu His Gln Ser Leu Leu Glu Ala Asn Ile Ala Thr Glu
    850                 855                 860

Val Cys Leu Thr Ala Leu Asp Thr Leu Ser Leu Phe Thr Leu Ala Phe
865                 870                 875                 880

Lys Asn Gln Leu Leu Ala Asp His Gly His Asn Pro Leu Met Lys Lys
                885                 890                 895

Val Phe Asp Val Tyr Leu Cys Phe Leu Gln Lys His Gln Ser Glu Thr
            900                 905                 910

Ala Leu Lys Asn Val Phe Thr Ala Leu Arg Ser Leu Ile Tyr Lys Phe
        915                 920                 925

-continued

```
Pro Ser Thr Phe Tyr Glu Gly Arg Ala Asp Met Cys Ala Ala Leu Cys
    930                 935                 940

Tyr Glu Ile Leu Lys Cys Cys Asn Ser Lys Leu Ser Ser Ile Arg Thr
945                 950                 955                 960

Glu Ala Ser Gln Leu Leu Tyr Phe Leu Met Arg Asn Asn Phe Asp Tyr
                965                 970                 975

Thr Gly Lys Lys Ser Phe Val Arg Thr His Leu Gln Val Ile Ile Ser
            980                 985                 990

Val Ser Gln Leu Ile Ala Asp Val Gly Ile Gly Gly Thr Arg Phe
        995                 1000                1005

Gln Gln Ser Leu Ser Ile Ile Asn Asn Cys Ala Asn Ser Asp Arg Leu
    1010                1015                1020

Ile Lys His Thr Ser Phe Ser Ser Asp Val Lys Asp Leu Thr Lys Arg
1025                1030                1035                1040

Ile Arg Thr Val Leu Met Ala Thr Ala Gln Met Lys Glu His Glu Asn
                1045                1050                1055

Asp Pro Glu Met Leu Val Asp Leu Gln Tyr Ser Leu Ala Lys Ser Tyr
            1060                1065                1070

Ala Ser Thr Pro Glu Leu Arg Lys Thr Trp Leu Asp Ser Met Ala Arg
        1075                1080                1085

Ile His Val Lys Asn Gly Asp Leu Ser Glu Ala Ala Met Cys Tyr Val
    1090                1095                1100

His Val Thr Ala Leu Val Ala Glu Tyr Leu Thr Arg Lys Glu Ala Val
1105                1110                1115                1120

Gln Trp Glu Pro Pro Leu Leu Pro His Ser His Ser Ala Cys Leu Arg
                1125                1130                1135

Arg Ser Arg Gly Gly Val Phe Arg Gln Gly Cys Thr Ala Phe Arg Val
            1140                1145                1150

Ile Thr Pro Asn Ile Asp Glu Glu Ala Ser Met Met Glu Asp Val Gly
        1155                1160                1165

Met Gln Asp Val His Phe Asn Glu Asp Val Leu Met Glu Leu Leu Glu
    1170                1175                1180

Gln Cys Ala Asp Gly Leu Trp Lys Ala Glu Arg Tyr Glu Leu Ile Ala
1185                1190                1195                1200

Asp Ile Tyr Lys Leu Ile Ile Pro Ile Tyr Glu Lys Arg Arg Asp Phe
                1205                1210                1215

Glu Arg Leu Ala His Leu Tyr Asp Thr Leu His Arg Ala Tyr Ser Lys
            1220                1225                1230

Val Thr Glu Val Met His Ser Gly Arg Arg Leu Leu Gly Thr Tyr Phe
        1235                1240                1245

Arg Val Ala Phe Phe Gly Gln Ala Ala Gln Tyr Gln Phe Thr Asp Ser
    1250                1255                1260

Glu Thr Asp Val Glu Gly Phe Phe Glu Asp Glu Asp Gly Lys Glu Tyr
1265                1270                1275                1280

Ile Tyr Lys Glu Pro Lys Leu Thr Pro Leu Ser Glu Ile Ser Gln Arg
                1285                1290                1295

Leu Leu Lys Leu Tyr Ser Asp Lys Phe Gly Ser Glu Asn Val Lys Met
            1300                1305                1310

Ile Gln Asp Ser Gly Lys Val Asn Pro Lys Asp Leu Asp Ser Lys Tyr
        1315                1320                1325

Ala Tyr Ile Gln Val Thr His Val Ile Pro Phe Phe Asp Glu Lys Glu
    1330                1335                1340

Leu Gln Glu Arg Lys Thr Glu Phe Glu Arg Ser His Asn Ile Arg Arg
```

-continued

```
                1345                1350                1355                1360
Phe Met Phe Glu Met Pro Phe Thr Gln Thr Gly Lys Arg Gln Gly Gly
            1365                1370                1375

Val Glu Glu Gln Cys Lys Arg Arg Thr Ile Leu Thr Ala Ile His Cys
        1380                1385                1390

Phe Pro Tyr Val Lys Lys Arg Ile Pro Val Met Tyr Gln His His Thr
    1395                1400                1405

Asp Leu Asn Pro Ile Glu Val Ala Ile Asp Glu Met Ser Lys Lys Val
        1410                1415                1420

Ala Glu Leu Arg Gln Leu Cys Ser Ser Ala Glu Val Asp Met Ile Lys
1425                1430                1435                1440

Leu Gln Leu Lys Leu Gln Gly Ser Val Ser Val Gln Val Asn Ala Gly
            1445                1450                1455

Pro Leu Ala Tyr Ala Arg Ala Phe Leu Asp Asp Thr Asn Thr Lys Arg
        1460                1465                1470

Tyr Pro Asp Asn Lys Val Lys Leu Leu Lys Glu Val Phe Arg Gln Phe
    1475                1480                1485

Val Glu Ala Cys Gly Gln Ala Leu Ala Val Asn Glu Arg Leu Ile Lys
        1490                1495                1500

Glu Asp Gln Leu Glu Tyr Gln Glu Met Lys Ala Asn Tyr Arg Glu
1505                1510                1515                1520

Met Ala Lys Glu Leu Ser Glu Ile Met His Glu Gln Leu Gly
            1525                1530

<210> SEQ ID NO 9
<211> LENGTH: 3642
<212> TYPE: DNA
<213> ORGANISM: Homo sapiens
<220> FEATURE:
<221> NAME/KEY: CDS
<222> LOCATION: (1)..(3642)
<223> OTHER INFORMATION: Human cadherin-like asymmetry protein 2E (CLASP
      2E)

<400> SEQUENCE: 9 gcg atg gaa ggc cac gtg atg atc gcc ttc ttg ccc act atc cta aac        48
Ala Met Glu Gly His Val Met Ile Ala Phe Leu Pro Thr Ile Leu Asn
  1               5                  10                  15 cag ctg ttc cga gtc ctc acc aga gcc aca cag gaa gaa gtc gcg gtt        96
Gln Leu Phe Arg Val Leu Thr Arg Ala Thr Gln Glu Glu Val Ala Val
             20                  25                  30 aac gtg act cgg gtc att att cat gtg gtt gcc cag tgc cat gag gaa       144
Asn Val Thr Arg Val Ile Ile His Val Val Ala Gln Cys His Glu Glu
         35                  40                  45 gga ttg gag agc cac ttg agg tca tat gtt aag tac gcg tat aag gct       192
Gly Leu Glu Ser His Leu Arg Ser Tyr Val Lys Tyr Ala Tyr Lys Ala
     50                  55                  60 gag cca tat gtt gcc tct gaa tac aag aca gtg cat gaa gaa ctg acc       240
Glu Pro Tyr Val Ala Ser Glu Tyr Lys Thr Val His Glu Glu Leu Thr
 65                  70                  75                  80 aaa tcc atg acc acg att ctc aag cct tct gcc gat ttc ctc acc agc       288
Lys Ser Met Thr Thr Ile Leu Lys Pro Ser Ala Asp Phe Leu Thr Ser
                 85                  90                  95 aac aaa cta ctg agg tac tca tgg ttt ttc ttt gat gta ctg atc aaa       336
Asn Lys Leu Leu Arg Tyr Ser Trp Phe Phe Phe Asp Val Leu Ile Lys
            100                 105                 110 tct atg gct cag cat ttg ata gag aac tcc aaa gtt aag ttg ctg cga       384
Ser Met Ala Gln His Leu Ile Glu Asn Ser Lys Val Lys Leu Leu Arg
        115                 120                 125
```

-continued

| | |
|---|---|
| aac cag aga ttt cct gca tcc tat cat cat gca gcg gaa acc gtt gta<br>Asn Gln Arg Phe Pro Ala Ser Tyr His His Ala Ala Glu Thr Val Val<br>130                          135                        140 | 432 |
| aat atg ctg atg cca cac atc act cag aag ttt gga gat aat cca gag<br>Asn Met Leu Met Pro His Ile Thr Gln Lys Phe Gly Asp Asn Pro Glu<br>145                          150                        155                        160 | 480 |
| gca tct aag aac gcg aat cat agc ctt gct gtc ttc atc aag aga tgt<br>Ala Ser Lys Asn Ala Asn His Ser Leu Ala Val Phe Ile Lys Arg Cys<br>                        165                        170                        175 | 528 |
| ttc acc ttc atg gac agg ggc ttt gtc ttc aag cag atc aac aac tac<br>Phe Thr Phe Met Asp Arg Gly Phe Val Phe Lys Gln Ile Asn Asn Tyr<br>                          180                        185                        190 | 576 |
| att agc tgt ttt gct cct gga gac cca aag acc ctc ttt gaa tac aag<br>Ile Ser Cys Phe Ala Pro Gly Asp Pro Lys Thr Leu Phe Glu Tyr Lys<br>                    195                        200                        205 | 624 |
| ttt gaa ttt ctc cgt gta gtg tgc aac cat gaa cat tat att ccg ttg<br>Phe Glu Phe Leu Arg Val Val Cys Asn His Glu His Tyr Ile Pro Leu<br>210                          215                        220 | 672 |
| aac tta cca atg cca ttt gga aaa ggc agg att caa aga tac caa gac<br>Asn Leu Pro Met Pro Phe Gly Lys Gly Arg Ile Gln Arg Tyr Gln Asp<br>225                          230                        235                        240 | 720 |
| ctc cag ctt gac tac tca tta aca gat gag ttc tgc aga aac cac ttc<br>Leu Gln Leu Asp Tyr Ser Leu Thr Asp Glu Phe Cys Arg Asn His Phe<br>                        245                        250                        255 | 768 |
| ttg gtg gga ctg tta ctg agg gag gtg ggg aca gcc ctc cag gag ttc<br>Leu Val Gly Leu Leu Leu Arg Glu Val Gly Thr Ala Leu Gln Glu Phe<br>                    260                        265                        270 | 816 |
| cgg gag gtc cgt ctg atc gcc atc agt gtg ctc aag aac ctg ctg ata<br>Arg Glu Val Arg Leu Ile Ala Ile Ser Val Leu Lys Asn Leu Leu Ile<br>275                          280                        285 | 864 |
| aag cat tct ttt gat gac aga tat gct tca agg agc cat cag gca agg<br>Lys His Ser Phe Asp Asp Arg Tyr Ala Ser Arg Ser His Gln Ala Arg<br>                        290                        295                        300 | 912 |
| ata gcc acc ctc tac ctg cct ctg ttt ggt ctg ctg att gaa aac gtc<br>Ile Ala Thr Leu Tyr Leu Pro Leu Phe Gly Leu Leu Ile Glu Asn Val<br>305                          310                        315                        320 | 960 |
| cag cgg atc aat gtg agg gat gtg tca ccc ttc cct gtg aac gcg ggc<br>Gln Arg Ile Asn Val Arg Asp Val Ser Pro Phe Pro Val Asn Ala Gly<br>                        325                        330                        335 | 1008 |
| atg acc gtg aag gat gaa tcc ctg gct cta cca gct gtg aat ccg ctg<br>Met Thr Val Lys Asp Glu Ser Leu Ala Leu Pro Ala Val Asn Pro Leu<br>                    340                        345                        350 | 1056 |
| gtg acg ccg cag aag gga agc acc ctg gac aac agc ctg cac aag gac<br>Val Thr Pro Gln Lys Gly Ser Thr Leu Asp Asn Ser Leu His Lys Asp<br>                        355                        360                        365 | 1104 |
| ctg ctg ggc gcc atc tcc ggc att gct tct cca tat aca acc tca act<br>Leu Leu Gly Ala Ile Ser Gly Ile Ala Ser Pro Tyr Thr Thr Ser Thr<br>370                          375                        380 | 1152 |
| cca aac atc aac agt gtg aga aat gct gat tcg aga gga tct ctc ata<br>Pro Asn Ile Asn Ser Val Arg Asn Ala Asp Ser Arg Gly Ser Leu Ile<br>385                          390                        395                        400 | 1200 |
| agc aca gat tcg ggt aac agc ctt cca gaa agg aat agt gag aag agc<br>Ser Thr Asp Ser Gly Asn Ser Leu Pro Glu Arg Asn Ser Glu Lys Ser<br>                    405                        410                        415 | 1248 |
| aat tcc ctg gat aag cac caa caa agt agc aca ttg gga aat tcc gtg<br>Asn Ser Leu Asp Lys His Gln Gln Ser Ser Thr Leu Gly Asn Ser Val<br>                        420                        425                        430 | 1296 |
| gtt cgc tgt gat aaa ctt gac cag tct gag att aag agc cta ctg atg<br>Val Arg Cys Asp Lys Leu Asp Gln Ser Glu Ile Lys Ser Leu Leu Met | 1344 |

-continued

```
              435                 440                 445
tgt ttc ctc tac atc tta aag agc atg tct gat gat gct ttg ttt aca    1392
Cys Phe Leu Tyr Ile Leu Lys Ser Met Ser Asp Asp Ala Leu Phe Thr
    450                 455                 460 tat tgg aac aag gct tca aca tct gaa ctt atg gat ttt ttt aca ata    1440
Tyr Trp Asn Lys Ala Ser Thr Ser Glu Leu Met Asp Phe Phe Thr Ile
465                 470                 475                 480 tct gaa gtc tgc ctg cac cag ttc cag tac atg ggg aag cga tac ata    1488
Ser Glu Val Cys Leu His Gln Phe Gln Tyr Met Gly Lys Arg Tyr Ile
                485                 490                 495 gcc agg aac cag gag ggg ttg gga ccc ata gtt cat gat cga aag tct    1536
Ala Arg Asn Gln Glu Gly Leu Gly Pro Ile Val His Asp Arg Lys Ser
            500                 505                 510 cag aca ttg cct gtt tcc cgt aac aga aca gga atg atg cat gcc aga    1584
Gln Thr Leu Pro Val Ser Arg Asn Arg Thr Gly Met Met His Ala Arg
        515                 520                 525 ttg cag cag ctg ggc agc ctg gat aac tct ctc act ttt aac cac agc    1632
Leu Gln Gln Leu Gly Ser Leu Asp Asn Ser Leu Thr Phe Asn His Ser
    530                 535                 540 tat ggc cac tcg gac gca gat gtt ctg cac cag tca tta ctt gaa gcc    1680
Tyr Gly His Ser Asp Ala Asp Val Leu His Gln Ser Leu Leu Glu Ala
545                 550                 555                 560 aac att gct act gag gtt tgc ctg aca gct ctg gac acg ctt tct cta    1728
Asn Ile Ala Thr Glu Val Cys Leu Thr Ala Leu Asp Thr Leu Ser Leu
                565                 570                 575 ttt aca ttg gcg ttt aag aac cag ctc ctg gcc gac cat gga cat aat    1776
Phe Thr Leu Ala Phe Lys Asn Gln Leu Leu Ala Asp His Gly His Asn
            580                 585                 590 cct ctc atg aaa aaa gtt ttt gat gtc tac ctg tgt ttt ctt caa aaa    1824
Pro Leu Met Lys Lys Val Phe Asp Val Tyr Leu Cys Phe Leu Gln Lys
        595                 600                 605 cat cag tct gaa acg gct tta aaa aat gtc ttc act gcc tta agg tcc    1872
His Gln Ser Glu Thr Ala Leu Lys Asn Val Phe Thr Ala Leu Arg Ser
    610                 615                 620 tta att tat aag ttt ccc tca aca ttc tat gaa ggg aga gcg gac atg    1920
Leu Ile Tyr Lys Phe Pro Ser Thr Phe Tyr Glu Gly Arg Ala Asp Met
625                 630                 635                 640 tgt gcg gct ctg tgt tac gag att ctc aag tgc tgt aac tcc aag ctg    1968
Cys Ala Ala Leu Cys Tyr Glu Ile Leu Lys Cys Cys Asn Ser Lys Leu
                645                 650                 655 agc tcc atc agg acg gag gcc tcc cag ctg ctc tac ttc ctg atg agg    2016
Ser Ser Ile Arg Thr Glu Ala Ser Gln Leu Leu Tyr Phe Leu Met Arg
            660                 665                 670 aac aac ttt gat tac act gga aag aag tcc ttt gtc cgg aca cat ttg    2064
Asn Asn Phe Asp Tyr Thr Gly Lys Lys Ser Phe Val Arg Thr His Leu
        675                 680                 685 caa gtc atc ata tct gtc agc cag ctg ata gca gac gtt gtt ggc att    2112
Gln Val Ile Ile Ser Val Ser Gln Leu Ile Ala Asp Val Val Gly Ile
    690                 695                 700 ggg gaa acc aga ttc cag cag tcc ctg tcc atc atc aac aac tgt gcc    2160
Gly Glu Thr Arg Phe Gln Gln Ser Leu Ser Ile Ile Asn Asn Cys Ala
705                 710                 715                 720 aac agt gac cgg ctt att aag cac acc agc ttc tcc tct gat gtg aag    2208
Asn Ser Asp Arg Leu Ile Lys His Thr Ser Phe Ser Ser Asp Val Lys
                725                 730                 735 gac tta acc aaa agg ata cgc acg gtg cta atg gcc acc gcc cag atg    2256
Asp Leu Thr Lys Arg Ile Arg Thr Val Leu Met Ala Thr Ala Gln Met
            740                 745                 750 aag gag cat gag aac gac cca gag atg ctg gtg gac ctc cag tac agc    2304
```

-continued

```
                    Lys Glu His Glu Asn Asp Pro Glu Met Leu Val Asp Leu Gln Tyr Ser
                                    755                 760                 765 ctg gcc aaa tcc tat gcc agc acg ccc gag ctc agg aag acg tgg ctc              2352
Leu Ala Lys Ser Tyr Ala Ser Thr Pro Glu Leu Arg Lys Thr Trp Leu
        770                 775                 780 gac agc atg gcc agg atc cat gtc aaa aat ggc gat ctc tca gag gca              2400
Asp Ser Met Ala Arg Ile His Val Lys Asn Gly Asp Leu Ser Glu Ala
785                 790                 795                 800 gca atg tgc tat gtc cac gta aca gcc cta gtg gca gaa tat ctc aca              2448
Ala Met Cys Tyr Val His Val Thr Ala Leu Val Ala Glu Tyr Leu Thr
                805                 810                 815 cgg aaa ggc gtg ttt aga caa gga tgc acc gcc ttc agg gtc att acc              2496
Arg Lys Gly Val Phe Arg Gln Gly Cys Thr Ala Phe Arg Val Ile Thr
        820                 825                 830 cca aac atc gac gag gag gcc tcc atg atg gaa gac gtg ggg aaa gcc              2544
Pro Asn Ile Asp Glu Glu Ala Ser Met Met Glu Asp Val Gly Lys Ala
                835                 840                 845 gag cgc tac gag ctc atc gcc gac atc tac aaa ctt atc atc ccc att              2592
Glu Arg Tyr Glu Leu Ile Ala Asp Ile Tyr Lys Leu Ile Ile Pro Ile
    850                 855                 860 tat gag aag cgg agg gat ttt gag agg ctg gcc cat ctg tat gac acg              2640
Tyr Glu Lys Arg Arg Asp Phe Glu Arg Leu Ala His Leu Tyr Asp Thr
865                 870                 875                 880 ctg cac cgg gcc tac agc aaa gtg acc gag gtc atg cac tcg ggc cgc              2688
Leu His Arg Ala Tyr Ser Lys Val Thr Glu Val Met His Ser Gly Arg
                885                 890                 895 agg ctt ctg ggg acc tac ttc cgg gta gcc ttc ttc ggg cag gga ttc              2736
Arg Leu Leu Gly Thr Tyr Phe Arg Val Ala Phe Phe Gly Gln Gly Phe
        900                 905                 910 ttt gaa gat gaa gat gga aag gag tat att tac aag gaa ccc aaa ctc              2784
Phe Glu Asp Glu Asp Gly Lys Glu Tyr Ile Tyr Lys Glu Pro Lys Leu
                915                 920                 925 aca ccg ctg tcg gaa att tct cag aga ctc ctt aaa ctg tac tcg gat              2832
Thr Pro Leu Ser Glu Ile Ser Gln Arg Leu Leu Lys Leu Tyr Ser Asp
    930                 935                 940 aaa ttt ggt tct gaa aat gtc aaa atg ata cag gat tct ggc aag gtc              2880
Lys Phe Gly Ser Glu Asn Val Lys Met Ile Gln Asp Ser Gly Lys Val
945                 950                 955                 960 aac cct aag gat ctg gat tct aag tat gca tac atc cag gtg act cac              2928
Asn Pro Lys Asp Leu Asp Ser Lys Tyr Ala Tyr Ile Gln Val Thr His
                965                 970                 975 gtc atc ccc ttc ttt gac gaa aaa gag ttg caa gaa agg aaa aca gag              2976
Val Ile Pro Phe Phe Asp Glu Lys Glu Leu Gln Glu Arg Lys Thr Glu
        980                 985                 990 ttt gag aga tcc cac aac atc cgc cgc ttc atg ttt gag atg cca ttt              3024
Phe Glu Arg Ser His Asn Ile Arg Arg Phe Met Phe Glu Met Pro Phe
                995                 1000                1005 acg cag acc ggg aag agg cag ggc ggg gtg gaa gag cag tgc aaa cgg              3072
Thr Gln Thr Gly Lys Arg Gln Gly Gly Val Glu Glu Gln Cys Lys Arg
    1010                1015                1020 cgc acc atc ctg aca gcc ata cac tgc ttc cct tat gtg aag aag cgc              3120
Arg Thr Ile Leu Thr Ala Ile His Cys Phe Pro Tyr Val Lys Lys Arg
1025                1030                1035                1040 atc cct gtc atg tac cag cac cac act gac ctg aac ccc atc gag gtg              3168
Ile Pro Val Met Tyr Gln His His Thr Asp Leu Asn Pro Ile Glu Val
                1045                1050                1055 gcc att gac gag atg agt aag aag gtg gcg gag ctc cgg cag ctg tgc              3216
Ala Ile Asp Glu Met Ser Lys Lys Val Ala Glu Leu Arg Gln Leu Cys
        1060                1065                1070
```

-continued

| | |
|---|---|
| tcc tcg gcc gag gtg gac atg atc aaa ctg cag ctc aaa ctc cag ggc<br>Ser Ser Ala Glu Val Asp Met Ile Lys Leu Gln Leu Lys Leu Gln Gly<br>     1075                   1080                   1085 | 3264 |
| agc gtg agt gtt cag gtc aat gct ggc cca cta gca tat gcg cga gct<br>Ser Val Ser Val Gln Val Asn Ala Gly Pro Leu Ala Tyr Ala Arg Ala<br>1090                     1095                   1100 | 3312 |
| ttc tta gat gat aca aac aca aag cga tat cct gac aat aaa gtg aag<br>Phe Leu Asp Asp Thr Asn Thr Lys Arg Tyr Pro Asp Asn Lys Val Lys<br>1105                     1110                   1115                   1120 | 3360 |
| ctg ctt aag gaa gtt ttc agg caa ttt gtg gaa gct tgc ggt caa gcc<br>Leu Leu Lys Glu Val Phe Arg Gln Phe Val Glu Ala Cys Gly Gln Ala<br>     1125                   1130                   1135 | 3408 |
| tta gcg gta aac gaa cgt ctg att aaa gaa gac cag ctc gag tat cag<br>Leu Ala Val Asn Glu Arg Leu Ile Lys Glu Asp Gln Leu Glu Tyr Gln<br>               1140                   1145                   1150 | 3456 |
| gaa gaa atg aaa gcc aac tac agg gaa atg gcg aag gag ctt tct gaa<br>Glu Glu Met Lys Ala Asn Tyr Arg Glu Met Ala Lys Glu Leu Ser Glu<br>           1155                   1160                   1165 | 3504 |
| atc atg cat gag cag atc tgc ccc ctg gag gag aag acg agc gtc tta<br>Ile Met His Glu Gln Ile Cys Pro Leu Glu Glu Lys Thr Ser Val Leu<br>1170                     1175                   1180 | 3552 |
| ccg aat tcc ctt cac atc ttc aac gcc atc agt ggg act cca aca agc<br>Pro Asn Ser Leu His Ile Phe Asn Ala Ile Ser Gly Thr Pro Thr Ser<br>1185                   1190                   1195                   1200 | 3600 |
| aca atg gtt cac ggg atg acc agc tcg tct tcg gtc gtg tga<br>Thr Met Val His Gly Met Thr Ser Ser Ser Ser Val Val<br>           1205                   1210 | 3642 |

<210> SEQ ID NO 10
<211> LENGTH: 1213
<212> TYPE: PRT
<213> ORGANISM: Homo sapiens
<223> OTHER INFORMATION: Human cadherin-like asymmetry protein 2E (CLASP

<400> SEQUENCE: 10

```
Ala Met Glu Gly His Val Met Ile Ala Phe Leu Pro Thr Ile Leu Asn
  1               5                  10                  15

Gln Leu Phe Arg Val Leu Thr Arg Ala Thr Gln Glu Glu Val Ala Val
             20                  25                  30

Asn Val Thr Arg Val Ile Ile His Val Val Ala Gln Cys His Glu Glu
         35                  40                  45

Gly Leu Glu Ser His Leu Arg Ser Tyr Val Lys Tyr Ala Tyr Lys Ala
     50                  55                  60

Glu Pro Tyr Val Ala Ser Glu Tyr Lys Thr Val His Glu Glu Leu Thr
 65                  70                  75                  80

Lys Ser Met Thr Thr Ile Leu Lys Pro Ser Ala Asp Phe Leu Thr Ser
                 85                  90                  95

Asn Lys Leu Leu Arg Tyr Ser Trp Phe Phe Phe Asp Val Leu Ile Lys
            100                 105                 110

Ser Met Ala Gln His Leu Ile Glu Asn Ser Lys Val Lys Leu Leu Arg
        115                 120                 125

Asn Gln Arg Phe Pro Ala Ser Tyr His His Ala Ala Glu Thr Val Val
    130                 135                 140

Asn Met Leu Met Pro His Ile Thr Gln Lys Phe Gly Asp Asn Pro Glu
145                 150                 155                 160

Ala Ser Lys Asn Ala Asn His Ser Leu Ala Val Phe Ile Lys Arg Cys
                165                 170                 175

Phe Thr Phe Met Asp Arg Gly Phe Val Phe Lys Gln Ile Asn Asn Tyr
```

-continued

```
                180                 185                 190
Ile Ser Cys Phe Ala Pro Gly Asp Pro Lys Thr Leu Phe Glu Tyr Lys
        195                 200                 205

Phe Glu Phe Leu Arg Val Val Cys Asn His Glu His Tyr Ile Pro Leu
210                 215                 220

Asn Leu Pro Met Pro Phe Gly Lys Gly Arg Ile Gln Arg Tyr Gln Asp
225                 230                 235                 240

Leu Gln Leu Asp Tyr Ser Leu Thr Asp Glu Phe Cys Arg Asn His Phe
                245                 250                 255

Leu Val Gly Leu Leu Arg Glu Val Gly Thr Ala Leu Gln Glu Phe
                260                 265                 270

Arg Glu Val Arg Leu Ile Ala Ile Ser Val Leu Lys Asn Leu Leu Ile
                275                 280                 285

Lys His Ser Phe Asp Asp Arg Tyr Ala Ser Arg Ser His Gln Ala Arg
        290                 295                 300

Ile Ala Thr Leu Tyr Leu Pro Leu Phe Gly Leu Ile Glu Asn Val
305                 310                 315                 320

Gln Arg Ile Asn Val Arg Asp Val Ser Pro Phe Pro Val Asn Ala Gly
                325                 330                 335

Met Thr Val Lys Asp Glu Ser Leu Ala Leu Pro Ala Val Asn Pro Leu
                340                 345                 350

Val Thr Pro Gln Lys Gly Ser Thr Leu Asp Asn Ser Leu His Lys Asp
                355                 360                 365

Leu Leu Gly Ala Ile Ser Gly Ile Ala Ser Pro Tyr Thr Thr Ser Thr
        370                 375                 380

Pro Asn Ile Asn Ser Val Arg Asn Ala Asp Ser Arg Gly Ser Leu Ile
385                 390                 395                 400

Ser Thr Asp Ser Gly Asn Ser Leu Pro Glu Arg Asn Ser Glu Lys Ser
                405                 410                 415

Asn Ser Leu Asp Lys His Gln Gln Ser Ser Thr Leu Gly Asn Ser Val
                420                 425                 430

Val Arg Cys Asp Lys Leu Asp Gln Ser Glu Ile Lys Ser Leu Leu Met
        435                 440                 445

Cys Phe Leu Tyr Ile Leu Lys Ser Met Ser Asp Asp Ala Leu Phe Thr
        450                 455                 460

Tyr Trp Asn Lys Ala Ser Thr Ser Glu Leu Met Asp Phe Thr Ile
465                 470                 475                 480

Ser Glu Val Cys Leu His Gln Phe Gln Tyr Met Gly Lys Arg Tyr Ile
                485                 490                 495

Ala Arg Asn Gln Glu Gly Leu Gly Pro Ile Val His Asp Arg Lys Ser
                500                 505                 510

Gln Thr Leu Pro Val Ser Arg Asn Arg Thr Gly Met Met His Ala Arg
        515                 520                 525

Leu Gln Gln Leu Gly Ser Leu Asp Asn Ser Leu Thr Phe Asn His Ser
        530                 535                 540

Tyr Gly His Ser Asp Ala Asp Val Leu His Gln Ser Leu Leu Glu Ala
545                 550                 555                 560

Asn Ile Ala Thr Glu Val Cys Leu Thr Ala Leu Asp Thr Leu Ser Leu
                565                 570                 575

Phe Thr Leu Ala Phe Lys Asn Gln Leu Leu Ala Asp His Gly His Asn
                580                 585                 590

Pro Leu Met Lys Lys Val Phe Asp Val Tyr Leu Cys Phe Leu Gln Lys
        595                 600                 605
```

```
His Gln Ser Glu Thr Ala Leu Lys Asn Val Phe Thr Ala Leu Arg Ser
    610                 615                 620

Leu Ile Tyr Lys Phe Pro Ser Thr Phe Tyr Glu Gly Arg Ala Asp Met
625                 630                 635                 640

Cys Ala Ala Leu Cys Tyr Glu Ile Leu Lys Cys Cys Asn Ser Lys Leu
                645                 650                 655

Ser Ser Ile Arg Thr Glu Ala Ser Gln Leu Leu Tyr Phe Leu Met Arg
            660                 665                 670

Asn Asn Phe Asp Tyr Thr Gly Lys Lys Ser Phe Val Arg Thr His Leu
        675                 680                 685

Gln Val Ile Ile Ser Val Ser Gln Leu Ile Ala Asp Val Val Gly Ile
    690                 695                 700

Gly Glu Thr Arg Phe Gln Gln Ser Leu Ser Ile Ile Asn Asn Cys Ala
705                 710                 715                 720

Asn Ser Asp Arg Leu Ile Lys His Thr Ser Phe Ser Ser Asp Val Lys
                725                 730                 735

Asp Leu Thr Lys Arg Ile Arg Thr Val Leu Met Ala Thr Ala Gln Met
            740                 745                 750

Lys Glu His Glu Asn Asp Pro Glu Met Leu Val Asp Leu Gln Tyr Ser
        755                 760                 765

Leu Ala Lys Ser Tyr Ala Ser Thr Pro Glu Leu Arg Lys Thr Trp Leu
    770                 775                 780

Asp Ser Met Ala Arg Ile His Val Lys Asn Gly Asp Leu Ser Glu Ala
785                 790                 795                 800

Ala Met Cys Tyr Val His Val Thr Ala Leu Val Ala Glu Tyr Leu Thr
                805                 810                 815

Arg Lys Gly Val Phe Arg Gln Gly Cys Thr Ala Phe Arg Val Ile Thr
            820                 825                 830

Pro Asn Ile Asp Glu Glu Ala Ser Met Met Glu Asp Val Gly Lys Ala
        835                 840                 845

Glu Arg Tyr Glu Leu Ile Ala Asp Ile Tyr Lys Leu Ile Ile Pro Ile
    850                 855                 860

Tyr Glu Lys Arg Arg Asp Phe Glu Arg Leu Ala His Leu Tyr Asp Thr
865                 870                 875                 880

Leu His Arg Ala Tyr Ser Lys Val Thr Glu Val Met His Ser Gly Arg
                885                 890                 895

Arg Leu Leu Gly Thr Tyr Phe Arg Val Ala Phe Phe Gly Gln Gly Phe
            900                 905                 910

Phe Glu Asp Glu Asp Gly Lys Glu Tyr Ile Tyr Lys Glu Pro Lys Leu
        915                 920                 925

Thr Pro Leu Ser Glu Ile Ser Gln Arg Leu Leu Lys Leu Tyr Ser Asp
    930                 935                 940

Lys Phe Gly Ser Glu Asn Val Lys Met Ile Gln Asp Ser Gly Lys Val
945                 950                 955                 960

Asn Pro Lys Asp Leu Asp Ser Lys Tyr Ala Tyr Ile Gln Val Thr His
                965                 970                 975

Val Ile Pro Phe Phe Asp Glu Lys Glu Leu Gln Glu Arg Lys Thr Glu
            980                 985                 990

Phe Glu Arg Ser His Asn Ile Arg Arg Phe Met Phe Glu Met Pro Phe
        995                 1000                1005

Thr Gln Thr Gly Lys Arg Gln Gly Gly Val Glu Glu Gln Cys Lys Arg
    1010                1015                1020
```

```
Arg Thr Ile Leu Thr Ala Ile His Cys Phe Pro Tyr Val Lys Lys Arg
1025                1030                1035                1040

Ile Pro Val Met Tyr Gln His His Thr Asp Leu Asn Pro Ile Glu Val
            1045                1050                1055

Ala Ile Asp Glu Met Ser Lys Lys Val Ala Glu Leu Arg Gln Leu Cys
        1060                1065                1070

Ser Ser Ala Glu Val Asp Met Ile Lys Leu Gln Leu Lys Leu Gln Gly
    1075                1080                1085

Ser Val Ser Val Gln Val Asn Ala Gly Pro Leu Ala Tyr Ala Arg Ala
   1090                1095                1100

Phe Leu Asp Asp Thr Asn Thr Lys Arg Tyr Pro Asp Asn Lys Val Lys
1105                1110                1115                1120

Leu Leu Lys Glu Val Phe Arg Gln Phe Val Glu Ala Cys Gly Gln Ala
                1125                1130                1135

Leu Ala Val Asn Glu Arg Leu Ile Lys Glu Asp Gln Leu Glu Tyr Gln
            1140                1145                1150

Glu Glu Met Lys Ala Asn Tyr Arg Glu Met Ala Lys Glu Leu Ser Glu
        1155                1160                1165

Ile Met His Glu Gln Ile Cys Pro Leu Glu Glu Lys Thr Ser Val Leu
    1170                1175                1180

Pro Asn Ser Leu His Ile Phe Asn Ala Ile Ser Gly Thr Pro Thr Ser
1185                1190                1195                1200

Thr Met Val His Gly Met Thr Ser Ser Ser Ser Val Val
                1205                1210

<210> SEQ ID NO 11
<211> LENGTH: 69
<212> TYPE: DNA
<213> ORGANISM: Artificial Sequence
<220> FEATURE:
<223> OTHER INFORMATION: Description of Artificial Sequence: Insertion
      of 69 nucleotides at position 2927 in human CLASP-2A
      found in human CLASP-2D

<400> SEQUENCE: 11
aagcagtcca gtgggagccg ccccttctcc cccacagcca tagcgcctgc ctgaggagga        60
gccggggag                                                                69

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Amino acids
      encoded by insertion of 69 nucleotides at position
      2927 of human CLASP-2A found in human CLASP-2D.

<400> SEQUENCE: 12

Ala Val Gln Trp Glu Pro Pro Leu Leu Pro His Ser His Ser Ala Cys
  1               5                  10                  15

Leu Arg Arg Ser Arg Gly
            20

<210> SEQ ID NO 13
<211> LENGTH: 165
<212> TYPE: DNA
<213> ORGANISM: Artificial Sequence
<220> FEATURE:
<223> OTHER INFORMATION: Description of Artificial Sequence: Insertion
      at position 3153, entire sequence insertion in human
      CLASP-2D, portion of insertion in human CLASP-2B,
```

-continued 2C and 2E

<400> SEQUENCE: 13

```
tgagaggctg gcccatctgt atgacacgct gcaccgggcc tacagcaaag tgaccgaggt    60
catgcactcg ggccgcaggc ttctggggac ctacttccgg gtagccttct tcgggcaggc   120
agcgcaatac cagtttacag acagtgaaac agatgtggag ggatt                   165
```

<210> SEQ ID NO 14
<211> LENGTH: 54
<212> TYPE: PRT
<213> ORGANISM: Artificial Sequence
<220> FEATURE:
<223> OTHER INFORMATION: Description of Artificial Sequence: Amino acids encoded by entire insertion at position 3153 of human CLASP-2A found in human CLASP-2D

<400> SEQUENCE: 14

```
Glu Arg Leu Ala His Leu Tyr Asp Thr Leu His Arg Ala Tyr Ser Lys
 1               5                  10                  15
Val Thr Glu Val Met His Ser Gly Arg Arg Leu Leu Gly Thr Tyr Phe
            20                  25                  30
Arg Val Ala Phe Phe Gly Gln Ala Ala Gln Tyr Gln Phe Thr Asp Ser
        35                  40                  45
Glu Thr Asp Val Glu Gly
     50
```

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: Amino acids encoded by insertion at position 3153 of human CLASP-2A found in human CLASP-2B, 2C and 2E

<400> SEQUENCE: 15

```
Glu Arg Leu Ala His Leu Tyr Asp Thr Leu His Arg Ala Tyr Ser Lys
 1               5                  10                  15
Val Thr Glu Val Met His Ser Gly Arg Arg Leu Leu Gly Thr Tyr Phe
            20                  25                  30
Arg Val Ala Phe Phe Gly Gln Gly
        35                  40
```

<210> SEQ ID NO 16
<211> LENGTH: 3614
<212> TYPE: DNA
<213> ORGANISM: Homo sapiens
<220> FEATURE:
<221> NAME/KEY: CDS
<222> LOCATION: (3)..(2864)
<223> OTHER INFORMATION: Human cadherin-like asymmetry protein 2A-80 (CLASP-2A-80)

<400> SEQUENCE: 16

```
tc cag ctt gac tac tca tta aca gat gag ttc tgc aga aac cac ttc      47
   Gln Leu Asp Tyr Ser Leu Thr Asp Glu Phe Cys Arg Asn His Phe
    1               5                  10                  15
ttg gtg gga ctg tta ctg agg gag gtg ggg aca gcc ctc cag gag ttc     95
Leu Val Gly Leu Leu Leu Arg Glu Val Gly Thr Ala Leu Gln Glu Phe
            20                  25                  30
cgg gag gtc cgt ctg atc gcc atc agt gtg ctc aag aac ctg ctg ata    143
Arg Glu Val Arg Leu Ile Ala Ile Ser Val Leu Lys Asn Leu Leu Ile
        35                  40                  45
```

-continued

| | |
|---|---|
| aag cat tct ttt gat gac aga tat gct tca agg agc cat cag gca agg<br>Lys His Ser Phe Asp Asp Arg Tyr Ala Ser Arg Ser His Gln Ala Arg<br>        50                     55                   60 | 191 |
| ata gcc acc ctc tac ctg cct ctg ttt ggt ctg ctg att gaa aac gtc<br>Ile Ala Thr Leu Tyr Leu Pro Leu Phe Gly Leu Leu Ile Glu Asn Val<br>65                    70                     75 | 239 |
| cag cgg atc aat gtg agg gat gtg tca ccc ttc cct gtg aac gcg ggc<br>Gln Arg Ile Asn Val Arg Asp Val Ser Pro Phe Pro Val Asn Ala Gly<br>80                      85                              95 | 287 |
| atg acc gtg aag gat gaa tcc ctg gct cta cca gct gtg aat ccg ctg<br>Met Thr Val Lys Asp Glu Ser Leu Ala Leu Pro Ala Val Asn Pro Leu<br>               100                    105                110 | 335 |
| gtg acg ccg cag aag gga agc acc ctg gac aac agc ctg cac aag gac<br>Val Thr Pro Gln Lys Gly Ser Thr Leu Asp Asn Ser Leu His Lys Asp<br>        115                    120                125 | 383 |
| ctg ctg ggc gcc atc tcc ggc att gct tct cca tat aca acc tca act<br>Leu Leu Gly Ala Ile Ser Gly Ile Ala Ser Pro Tyr Thr Thr Ser Thr<br>    130                    135                140 | 431 |
| cca aac atc aac agt gtg aga aat gct gat tcg aga gga tct ctc ata<br>Pro Asn Ile Asn Ser Val Arg Asn Ala Asp Ser Arg Gly Ser Leu Ile<br>145                    150                155 | 479 |
| agc aca gat tcg ggt aac agc ctt cca gaa agg aat agt gag aag agc<br>Ser Thr Asp Ser Gly Asn Ser Leu Pro Glu Arg Asn Ser Glu Lys Ser<br>160                    165                170                175 | 527 |
| aat tcc ctg gat aag cac caa caa agt agc aca ttg gga aat tcc gtg<br>Asn Ser Leu Asp Lys His Gln Gln Ser Ser Thr Leu Gly Asn Ser Val<br>               180                    185                190 | 575 |
| gtt cgc tgt gat aaa ctt gac cag tct gag att aag agc cta ctg atg<br>Val Arg Cys Asp Lys Leu Asp Gln Ser Glu Ile Lys Ser Leu Leu Met<br>        195                    200                205 | 623 |
| tgt ttc ctc tac atc tta aag agc atg tct gat gat gct ttg ttt aca<br>Cys Phe Leu Tyr Ile Leu Lys Ser Met Ser Asp Asp Ala Leu Phe Thr<br>    210                    215                220 | 671 |
| tat tgg aac aag gct tca aca tct gaa ctt atg gat ttt ttt aca ata<br>Tyr Trp Asn Lys Ala Ser Thr Ser Glu Leu Met Asp Phe Phe Thr Ile<br>225                    230                235 | 719 |
| tct gaa gtc tgc ctg cac cag ttc cag tac atg ggg aag cga tac ata<br>Ser Glu Val Cys Leu His Gln Phe Gln Tyr Met Gly Lys Arg Tyr Ile<br>240                    245                250                255 | 767 |
| gcc agg aac cag gag ggg ttg gga ccc ata gtt cat gat cga aag tct<br>Ala Arg Asn Gln Glu Gly Leu Gly Pro Ile Val His Asp Arg Lys Ser<br>               260                    265                270 | 815 |
| cag aca ttg cct gtt tcc cgt aac aga aca gga atg atg cat gcc aga<br>Gln Thr Leu Pro Val Ser Arg Asn Arg Thr Gly Met Met His Ala Arg<br>        275                    280                285 | 863 |
| ttg cag cag ctg ggc agc ctg gat aac tct ctc act ttt aac cac agc<br>Leu Gln Gln Leu Gly Ser Leu Asp Asn Ser Leu Thr Phe Asn His Ser<br>    290                    295                300 | 911 |
| tat ggc cac tcg gac gca gat gtt ctg cac cag tca tta ctt gaa gcc<br>Tyr Gly His Ser Asp Ala Asp Val Leu His Gln Ser Leu Leu Glu Ala<br>305                    310                315 | 959 |
| aac att gct act gag gtt tgc ctg aca gct ctg gac acg ctt tct cta<br>Asn Ile Ala Thr Glu Val Cys Leu Thr Ala Leu Asp Thr Leu Ser Leu<br>320                    325                330                335 | 1007 |
| ttt aca ttg gcg ttt aag aac cag ctc ctg gcc gac cat gga cat aat<br>Phe Thr Leu Ala Phe Lys Asn Gln Leu Leu Ala Asp His Gly His Asn<br>               340                    345                350 | 1055 |
| cct ctc atg aaa aaa gtt ttt gat gtc tac ctg tgt ttt ctt caa aaa<br>Pro Leu Met Lys Lys Val Phe Asp Val Tyr Leu Cys Phe Leu Gln Lys | 1103 |

-continued

```
                   355                 360                 365
cat cag tct gaa acg gct tta aaa aat gtc ttc act gcc tta agg tcc     1151
His Gln Ser Glu Thr Ala Leu Lys Asn Val Phe Thr Ala Leu Arg Ser
            370                 375                 380 tta att tat aag ttt ccc tca aca ttc tat gaa ggg aga gcg gac atg     1199
Leu Ile Tyr Lys Phe Pro Ser Thr Phe Tyr Glu Gly Arg Ala Asp Met
385                 390                 395 tgt gcg gct ctg tgt tac gag att ctc aag tgc tgt aac tcc aag ctg     1247
Cys Ala Ala Leu Cys Tyr Glu Ile Leu Lys Cys Cys Asn Ser Lys Leu
400                 405                 410                 415 agc tcc atc agg acg gag gcc tcc cag ctg ctc tac ttc ctg atg agg     1295
Ser Ser Ile Arg Thr Glu Ala Ser Gln Leu Leu Tyr Phe Leu Met Arg
            420                 425                 430 aac aac ttt gat tac act gga aag aag tcc ttt gtc cgg aca cat ttg     1343
Asn Asn Phe Asp Tyr Thr Gly Lys Lys Ser Phe Val Arg Thr His Leu
            435                 440                 445 caa gtc atc ata tct gtc agc cag ctg ata gca gac gtt gtt ggc att     1391
Gln Val Ile Ile Ser Val Ser Gln Leu Ile Ala Asp Val Val Gly Ile
            450                 455                 460 ggg gaa acc aga ttc cag cag tcc ctg tcc atc atc aac aac tgt gcc     1439
Gly Glu Thr Arg Phe Gln Gln Ser Leu Ser Ile Ile Asn Asn Cys Ala
            465                 470                 475 aac agt gac cgg ctt att aag cac acc agc ttc tcc tct gat gtg aag     1487
Asn Ser Asp Arg Leu Ile Lys His Thr Ser Phe Ser Ser Asp Val Lys
480                 485                 490                 495 gac tta acc aaa agg ata cgc acg gtg cta atg gcc acc gcc cag atg     1535
Asp Leu Thr Lys Arg Ile Arg Thr Val Leu Met Ala Thr Ala Gln Met
            500                 505                 510 aag gag cat gag aac gac cca gag atg ctg gtg gac ctc cag tac agc     1583
Lys Glu His Glu Asn Asp Pro Glu Met Leu Val Asp Leu Gln Tyr Ser
            515                 520                 525 ctg gcc aaa tcc tat gcc agc acg ccc gag ctc agg aag acg tgg ctc     1631
Leu Ala Lys Ser Tyr Ala Ser Thr Pro Glu Leu Arg Lys Thr Trp Leu
            530                 535                 540 gac agc atg gcc agg atc cat gtc aaa aat ggc gat ctc tca gag gca     1679
Asp Ser Met Ala Arg Ile His Val Lys Asn Gly Asp Leu Ser Glu Ala
545                 550                 555 gca atg tgc tat gtc cac gta aca gcc cta gtg gca gaa tat ctc aca     1727
Ala Met Cys Tyr Val His Val Thr Ala Leu Val Ala Glu Tyr Leu Thr
560                 565                 570                 575 cgg aaa ggc gtg ttt aga caa gga tgc acc gcc ttc agg gtc att acc     1775
Arg Lys Gly Val Phe Arg Gln Gly Cys Thr Ala Phe Arg Val Ile Thr
            580                 585                 590 cca aac atc gac gag gag gcc tcc atg atg gaa gac gtg ggg atg cag     1823
Pro Asn Ile Asp Glu Glu Ala Ser Met Met Glu Asp Val Gly Met Gln
            595                 600                 605 gat gtc cat ttc aac gag gat gtg ctg atg gag ctc ctt gag cag tgc     1871
Asp Val His Phe Asn Glu Asp Val Leu Met Glu Leu Leu Glu Gln Cys
            610                 615                 620 gca gat gga ctc tgg aaa gcc gag cgc tac gag ctc atc gcc gac atc     1919
Ala Asp Gly Leu Trp Lys Ala Glu Arg Tyr Glu Leu Ile Ala Asp Ile
625                 630                 635 tac aaa ctt atc atc ccc att tat gag aag cgg agg gat ttc ttt gaa     1967
Tyr Lys Leu Ile Ile Pro Ile Tyr Glu Lys Arg Arg Asp Phe Phe Glu
640                 645                 650                 655 gat gaa gat gga aag gag tat att tac aag gaa ccc aaa ctc aca ccg     2015
Asp Glu Asp Gly Lys Glu Tyr Ile Tyr Lys Glu Pro Lys Leu Thr Pro
            660                 665                 670 ctg tcg gaa att tct cag aga ctc ctt aaa ctg tac tcg gat aaa ttt     2063
```

```
                Leu Ser Glu Ile Ser Gln Arg Leu Leu Lys Leu Tyr Ser Asp Lys Phe
                                675                 680                 685 ggt tct gaa aat gtc aaa atg ata cag gat tct ggc aag gtc aac cct       2111
Gly Ser Glu Asn Val Lys Met Ile Gln Asp Ser Gly Lys Val Asn Pro
            690                 695                 700 aag gat ctg gat tct aag tat gca tac atc cag gtg act cac gtc atc       2159
Lys Asp Leu Asp Ser Lys Tyr Ala Tyr Ile Gln Val Thr His Val Ile
705                 710                 715 ccc ttc ttt gac gaa aaa gag ttg caa gaa agg aaa aca gag ttt gag       2207
Pro Phe Phe Asp Glu Lys Glu Leu Gln Glu Arg Lys Thr Glu Phe Glu
720                 725                 730                 735 aga tcc cac aac atc cgc cgc ttc atg ttt gag atg cca ttt acg cag       2255
Arg Ser His Asn Ile Arg Arg Phe Met Phe Glu Met Pro Phe Thr Gln
                740                 745                 750 acc ggg aag agg cag ggc ggg gtg gaa gag cag tgc aaa cgg cgc acc       2303
Thr Gly Lys Arg Gln Gly Gly Val Glu Glu Gln Cys Lys Arg Arg Thr
            755                 760                 765 atc ctg aca gcc ata cac tgc ttc cct tat gtg aag aag cgc atc cct       2351
Ile Leu Thr Ala Ile His Cys Phe Pro Tyr Val Lys Lys Arg Ile Pro
770                 775                 780 gtc atg tac cag cac cac act gac ctg aac ccc atc gag gtg gcc att       2399
Val Met Tyr Gln His His Thr Asp Leu Asn Pro Ile Glu Val Ala Ile
785                 790                 795 gac gag atg agt aag aag gtg gcg gag ctc cgg cag ctg tgc tcc tcg       2447
Asp Glu Met Ser Lys Lys Val Ala Glu Leu Arg Gln Leu Cys Ser Ser
800                 805                 810                 815 gcc gag gtg gac atg atc aaa ctg cag ctc aaa ctc cag ggc agc gtg       2495
Ala Glu Val Asp Met Ile Lys Leu Gln Leu Lys Leu Gln Gly Ser Val
                820                 825                 830 agt gtt cag gtc aat gct ggc cca cta gca tat gcg cga gct ttc tta       2543
Ser Val Gln Val Asn Ala Gly Pro Leu Ala Tyr Ala Arg Ala Phe Leu
            835                 840                 845 gat gat aca aac aca aag cga tat cct gac aat aaa gtg aag ctg ctt       2591
Asp Asp Thr Asn Thr Lys Arg Tyr Pro Asp Asn Lys Val Lys Leu Leu
850                 855                 860 aag gaa gtt ttc agg caa ttt gtg gaa gct tgc ggt caa gcc tta gcg       2639
Lys Glu Val Phe Arg Gln Phe Val Glu Ala Cys Gly Gln Ala Leu Ala
865                 870                 875 gta aac gaa cgt ctg att aaa gaa gac cag ctc gag tat cag gaa gaa       2687
Val Asn Glu Arg Leu Ile Lys Glu Asp Gln Leu Glu Tyr Gln Glu Glu
880                 885                 890                 895 atg aaa gcc aac tac agg gaa atg gcg aag gag ctt tct gaa atc atg       2735
Met Lys Ala Asn Tyr Arg Glu Met Ala Lys Glu Leu Ser Glu Ile Met
                900                 905                 910 cat gag cag atc tgc ccc ctg gag gag aag acg agc gtc tta ccg aat       2783
His Glu Gln Ile Cys Pro Leu Glu Glu Lys Thr Ser Val Leu Pro Asn
            915                 920                 925 tcc ctt cac atc ttc aac gcc atc agt ggg act cca aca agc aca atg       2831
Ser Leu His Ile Phe Asn Ala Ile Ser Gly Thr Pro Thr Ser Thr Met
930                 935                 940 gtt cac ggg atg acc agc tcg tct tcg gtc gtg tgattacatc tcatggcccg     2884
Val His Gly Met Thr Ser Ser Ser Val Val
        945                 950 tgtgtgggga cttgctttgt catttgcaaa ctcaggatgc tttccaaagc caatcactgg     2944
ggagaccgag cacagggagg accaagggga aggggagaga aaggaaataa agaacaacgt     3004
tatttcttaa cagactttct ataggagttg taagaaggtg cacatatttt tttaaatctc     3064
actggcaata ttcaaagttt tcattgtgtc ttaacaaagg tgtggtagac actcttgagc     3124
```

-continued

```
tggacttaga ttttattctt ccttgcagag tagtgttaga atagatggcc tacagaaaaa   3184
aaaggttctg ggatctacat ggcagggagg gctgcactga cattgatgcc tgggggacct   3244
tttgcctcga ctcgtgccgg aaatctgatc gtaatcaggg tacagaactt actagttttg   3304
tctaggagta tgttgtatga ctaggatttg tgctattatc tcattcaaca acatagagca   3364
agaatagtga gctaactgag ctagacactc aattaatccg ctactggctt caagtcagaa   3424
ctttgtcatt aatcatcgac tccgggacgg tcatatatgt attacatttc tacattttta   3484
atactcacat gggcttatgc attaagttta attgtgataa atttgtgctg gtccagtata   3544
tgcaatacac tttaatggtt tattcttgtc ataaaaatgt gcaatatgga gatgtataca   3604
agtctttact                                                          3614
```

<210> SEQ ID NO 17
<211> LENGTH: 954
<212> TYPE: PRT
<213> ORGANISM: Homo sapiens
<223> OTHER INFORMATION: Human cadherin-like asymmetry protein 2A-80

<400> SEQUENCE: 17

```
Gln Leu Asp Tyr Ser Leu Thr Asp Glu Phe Cys Arg Asn His Phe Leu
  1               5                  10                  15

Val Gly Leu Leu Arg Glu Val Gly Thr Ala Leu Gln Glu Phe Arg
             20                  25                  30

Glu Val Arg Leu Ile Ala Ile Ser Val Leu Lys Asn Leu Leu Ile Lys
         35                  40                  45

His Ser Phe Asp Asp Arg Tyr Ala Ser Arg Ser His Gln Ala Arg Ile
     50                  55                  60

Ala Thr Leu Tyr Leu Pro Leu Phe Gly Leu Leu Ile Glu Asn Val Gln
 65                  70                  75                  80

Arg Ile Asn Val Arg Asp Val Ser Pro Phe Pro Val Asn Ala Gly Met
                 85                  90                  95

Thr Val Lys Asp Glu Ser Leu Ala Leu Pro Ala Val Asn Pro Leu Val
            100                 105                 110

Thr Pro Gln Lys Gly Ser Thr Leu Asp Asn Ser Leu His Lys Asp Leu
        115                 120                 125

Leu Gly Ala Ile Ser Gly Ile Ala Ser Pro Tyr Thr Thr Ser Thr Pro
    130                 135                 140

Asn Ile Asn Ser Val Arg Asn Ala Asp Ser Arg Gly Ser Leu Ile Ser
145                 150                 155                 160

Thr Asp Ser Gly Asn Ser Leu Pro Glu Arg Asn Ser Glu Lys Ser Asn
                165                 170                 175

Ser Leu Asp Lys His Gln Gln Ser Ser Thr Leu Gly Asn Ser Val Val
            180                 185                 190

Arg Cys Asp Lys Leu Asp Gln Ser Glu Ile Lys Ser Leu Leu Met Cys
        195                 200                 205

Phe Leu Tyr Ile Leu Lys Ser Met Ser Asp Asp Ala Leu Phe Thr Tyr
    210                 215                 220

Trp Asn Lys Ala Ser Thr Ser Glu Leu Met Asp Phe Phe Thr Ile Ser
225                 230                 235                 240

Glu Val Cys Leu His Gln Phe Gln Tyr Met Gly Lys Arg Tyr Ile Ala
                245                 250                 255

Arg Asn Gln Glu Gly Leu Gly Pro Ile Val His Asp Arg Lys Ser Gln
            260                 265                 270

Thr Leu Pro Val Ser Arg Asn Arg Thr Gly Met Met His Ala Arg Leu
```

-continued

```
                275                 280                 285
Gln Gln Leu Gly Ser Leu Asp Asn Ser Leu Thr Phe Asn His Ser Tyr
            290                 295                 300

Gly His Ser Asp Ala Asp Val Leu His Gln Ser Leu Leu Glu Ala Asn
305                 310                 315                 320

Ile Ala Thr Glu Val Cys Leu Thr Ala Leu Asp Thr Leu Ser Leu Phe
                325                 330                 335

Thr Leu Ala Phe Lys Asn Gln Leu Leu Ala Asp His Gly His Asn Pro
            340                 345                 350

Leu Met Lys Lys Val Phe Asp Val Tyr Leu Cys Phe Leu Gln Lys His
            355                 360                 365

Gln Ser Glu Thr Ala Leu Lys Asn Val Phe Thr Ala Leu Arg Ser Leu
        370                 375                 380

Ile Tyr Lys Phe Pro Ser Thr Phe Tyr Glu Gly Arg Ala Asp Met Cys
385                 390                 395                 400

Ala Ala Leu Cys Tyr Glu Ile Leu Lys Cys Cys Asn Ser Lys Leu Ser
                405                 410                 415

Ser Ile Arg Thr Glu Ala Ser Gln Leu Leu Tyr Phe Leu Met Arg Asn
            420                 425                 430

Asn Phe Asp Tyr Thr Gly Lys Lys Ser Phe Val Arg Thr His Leu Gln
            435                 440                 445

Val Ile Ile Ser Val Ser Gln Leu Ile Ala Asp Val Val Gly Ile Gly
        450                 455                 460

Glu Thr Arg Phe Gln Gln Ser Leu Ser Ile Ile Asn Asn Cys Ala Asn
465                 470                 475                 480

Ser Asp Arg Leu Ile Lys His Thr Ser Phe Ser Ser Asp Val Lys Asp
                485                 490                 495

Leu Thr Lys Arg Ile Arg Thr Val Leu Met Ala Thr Ala Gln Met Lys
            500                 505                 510

Glu His Glu Asn Asp Pro Glu Met Leu Val Asp Leu Gln Tyr Ser Leu
            515                 520                 525

Ala Lys Ser Tyr Ala Ser Thr Pro Glu Leu Arg Lys Thr Trp Leu Asp
        530                 535                 540

Ser Met Ala Arg Ile His Val Lys Asn Gly Asp Leu Ser Glu Ala Ala
545                 550                 555                 560

Met Cys Tyr Val His Val Thr Ala Leu Val Ala Glu Tyr Leu Thr Arg
                565                 570                 575

Lys Gly Val Phe Arg Gln Gly Cys Thr Ala Phe Arg Val Ile Thr Pro
            580                 585                 590

Asn Ile Asp Glu Glu Ala Ser Met Met Glu Asp Val Gly Met Gln Asp
            595                 600                 605

Val His Phe Asn Glu Asp Val Leu Met Glu Leu Leu Glu Gln Cys Ala
        610                 615                 620

Asp Gly Leu Trp Lys Ala Glu Arg Tyr Glu Leu Ile Ala Asp Ile Tyr
625                 630                 635                 640

Lys Leu Ile Ile Pro Ile Tyr Glu Lys Arg Arg Asp Phe Phe Glu Asp
                645                 650                 655

Glu Asp Gly Lys Glu Tyr Ile Tyr Lys Glu Pro Lys Leu Thr Pro Leu
            660                 665                 670

Ser Glu Ile Ser Gln Arg Leu Leu Lys Leu Tyr Ser Asp Lys Phe Gly
            675                 680                 685

Ser Glu Asn Val Lys Met Ile Gln Asp Ser Gly Lys Val Asn Pro Lys
        690                 695                 700
```

```
Asp Leu Asp Ser Lys Tyr Ala Tyr Ile Gln Val Thr His Val Ile Pro
705                 710                 715                 720

Phe Phe Asp Glu Lys Glu Leu Gln Glu Arg Lys Thr Glu Phe Glu Arg
                725                 730                 735

Ser His Asn Ile Arg Arg Phe Met Phe Glu Met Pro Phe Thr Gln Thr
            740                 745                 750

Gly Lys Arg Gln Gly Gly Val Glu Glu Gln Cys Lys Arg Arg Thr Ile
        755                 760                 765

Leu Thr Ala Ile His Cys Phe Pro Tyr Val Lys Lys Arg Ile Pro Val
770                 775                 780

Met Tyr Gln His His Thr Asp Leu Asn Pro Ile Glu Val Ala Ile Asp
785                 790                 795                 800

Glu Met Ser Lys Lys Val Ala Glu Leu Arg Gln Leu Cys Ser Ser Ala
                805                 810                 815

Glu Val Asp Met Ile Lys Leu Gln Leu Lys Leu Gln Gly Ser Val Ser
            820                 825                 830

Val Gln Val Asn Ala Gly Pro Leu Ala Tyr Ala Arg Ala Phe Leu Asp
        835                 840                 845

Asp Thr Asn Thr Lys Arg Tyr Pro Asp Asn Lys Val Lys Leu Leu Lys
850                 855                 860

Glu Val Phe Arg Gln Phe Val Glu Ala Cys Gly Gln Ala Leu Ala Val
865                 870                 875                 880

Asn Glu Arg Leu Ile Lys Glu Asp Gln Leu Glu Tyr Gln Glu Met
                885                 890                 895

Lys Ala Asn Tyr Arg Glu Met Ala Lys Glu Leu Ser Glu Ile Met His
            900                 905                 910

Glu Gln Ile Cys Pro Leu Glu Glu Lys Thr Ser Val Leu Pro Asn Ser
        915                 920                 925

Leu His Ile Phe Asn Ala Ile Ser Gly Thr Pro Thr Ser Thr Met Val
    930                 935                 940

His Gly Met Thr Ser Ser Ser Val Val
945                 950

<210> SEQ ID NO 18
<211> LENGTH: 526
<212> TYPE: DNA
<213> ORGANISM: Homo sapiens
<220> FEATURE:
<221> NAME/KEY: CDS
<222> LOCATION: (1)..(525)
<223> OTHER INFORMATION: Human cadherin-like asymmetry protein 2F
      (CLASP-2F)

<400> SEQUENCE: 18 gct gat tcg aga gga tct ctc ata agc aca gat tcg ggt aac agc ctt      48
Ala Asp Ser Arg Gly Ser Leu Ile Ser Thr Asp Ser Gly Asn Ser Leu
1               5                   10                  15 cca gaa agg aat agt gag aag agc aat tcc ctg gat aag cac caa caa      96
Pro Glu Arg Asn Ser Glu Lys Ser Asn Ser Leu Asp Lys His Gln Gln
            20                  25                  30 agc agc aca ttg gga aat tcc gtg gtt cgc tgt gat aaa ctt gac cag     144
Ser Ser Thr Leu Gly Asn Ser Val Val Arg Cys Asp Lys Leu Asp Gln
        35                  40                  45 tct gag att aag agc cta ctg atg tgt ttc ctc tac atc tta aag agc     192
Ser Glu Ile Lys Ser Leu Leu Met Cys Phe Leu Tyr Ile Leu Lys Ser
    50                  55                  60 atg tct gat gat gct ttg ttt aca tat tgg aac aag gct tca aca tct     240
Met Ser Asp Asp Ala Leu Phe Thr Tyr Trp Asn Lys Ala Ser Thr Ser
65                  70                  75                  80 gaa ctt atg gat ttt ttt aca ata tct gaa gtc tgc ctg cac cag ttc     288
```

```
                                                  -continued

Glu Leu Met Asp Phe Phe Thr Ile Ser Glu Val Cys Leu His Gln Phe
                 85                  90                  95
cag tac atg ggg aag cga tac ata gcc agt gtg aga aag ata tca agt      336
Gln Tyr Met Gly Lys Arg Tyr Ile Ala Ser Val Arg Lys Ile Ser Ser
            100                 105                 110
gtg ctt gga att tct gta gac aat ggc tat ggc cac tcg gac gca gat      384
Val Leu Gly Ile Ser Val Asp Asn Gly Tyr Gly His Ser Asp Ala Asp
        115                 120                 125
gtt ctg cac cag tca tta ctt gaa gcc aac att gct act gag gtt tgc      432
Val Leu His Gln Ser Leu Leu Glu Ala Asn Ile Ala Thr Glu Val Cys
    130                 135                 140
ctg aca gct ctg gac acg ctt tct cta ttt aca ttg gcg ttt aag aac      480
Leu Thr Ala Leu Asp Thr Leu Ser Leu Phe Thr Leu Ala Phe Lys Asn
145                 150                 155                 160
cag ctc ctg gcc gac cat gga cat aat cct ctc atg aaa aaa aaa a       526
Gln Leu Leu Ala Asp His Gly His Asn Pro Leu Met Lys Lys Lys
                165                 170                 175

<210> SEQ ID NO 19
<211> LENGTH: 175
<212> TYPE: PRT
<213> ORGANISM: Homo sapiens
<223> OTHER INFORMATION: Human cadherin-like asymmetry protein 2F

<400> SEQUENCE: 19

Ala Asp Ser Arg Gly Ser Leu Ile Ser Thr Asp Ser Gly Asn Ser Leu
 1               5                  10                  15

Pro Glu Arg Asn Ser Glu Lys Ser Asn Ser Leu Asp Lys His Gln Gln
            20                  25                  30

Ser Ser Thr Leu Gly Asn Ser Val Val Arg Cys Asp Lys Leu Asp Gln
        35                  40                  45

Ser Glu Ile Lys Ser Leu Leu Met Cys Phe Leu Tyr Ile Leu Lys Ser
    50                  55                  60

Met Ser Asp Asp Ala Leu Phe Thr Tyr Trp Asn Lys Ala Ser Thr Ser
65                  70                  75                  80

Glu Leu Met Asp Phe Phe Thr Ile Ser Glu Val Cys Leu His Gln Phe
                85                  90                  95

Gln Tyr Met Gly Lys Arg Tyr Ile Ala Ser Val Arg Lys Ile Ser Ser
            100                 105                 110

Val Leu Gly Ile Ser Val Asp Asn Gly Tyr Gly His Ser Asp Ala Asp
        115                 120                 125

Val Leu His Gln Ser Leu Leu Glu Ala Asn Ile Ala Thr Glu Val Cys
    130                 135                 140

Leu Thr Ala Leu Asp Thr Leu Ser Leu Phe Thr Leu Ala Phe Lys Asn
145                 150                 155                 160

Gln Leu Leu Ala Asp His Gly His Asn Pro Leu Met Lys Lys Lys
                165                 170                 175

<210> SEQ ID NO 20
<211> LENGTH: 738
<212> TYPE: PRT
<213> ORGANISM: Rattus norvegicus
<220> FEATURE:
<223> OTHER INFORMATION: Rat TRG protein

<400> SEQUENCE: 20

Lys Leu Ser Arg Gly His Ser Pro Leu Met Lys Lys Val Phe Asp Val
 1               5                  10                  15

Tyr Leu Cys Phe Leu Gln Lys His Gln Ser Glu Met Ala Leu Lys Asn
            20                  25                  30

Val Phe Thr Ala Leu Arg Ser Leu Ile Tyr Lys Phe Pro Ser Thr Phe
        35                  40                  45
```

-continued

Tyr Glu Gly Arg Ala Asp Met Cys Ala Ser Leu Cys Tyr Glu Val Leu
 50                  55                  60

Lys Cys Cys Asn Ser Lys Leu Ser Ser Ile Arg Thr Glu Ala Ser Gln
 65                  70                  75                  80

Leu Leu Tyr Phe Leu Met Arg Asn Asn Phe Asp Tyr Thr Gly Lys Lys
                 85                  90                  95

Ser Phe Val Arg Thr His Leu Gln Val Ile Ile Ser Leu Ser Gln Leu
                100                 105                 110

Ile Ala Asp Val Val Gly Ile Gly Gly Thr Arg Phe Gln Gln Ser Leu
                115                 120                 125

Ser Ile Ile Asn Asn Cys Ala Asn Ser Asp Arg Leu Ile Lys His Thr
    130                 135                 140

Ser Phe Ser Ser Asp Val Lys Asp Leu Thr Lys Arg Ile Arg Thr Val
145                 150                 155                 160

Leu Met Ala Thr Ala Gln Met Lys Glu His Glu Asn Asp Pro Glu Met
                165                 170                 175

Leu Val Asp Leu Gln Tyr Ser Leu Ala Lys Ser Tyr Ala Ser Thr Pro
                180                 185                 190

Glu Leu Arg Lys Thr Trp Leu Asp Ser Met Ala Arg Ile His Val Lys
            195                 200                 205

Asn Gly Asp Leu Ser Glu Ala Ala Met Cys Tyr Val His Val Thr Ala
    210                 215                 220

Leu Val Ala Glu Tyr Leu Thr Arg Lys Glu Ala Asp Leu Ala Leu Gln
225                 230                 235                 240

Arg Glu Pro Pro Val Phe Pro Tyr Ser His Thr Ser Cys Gln Arg Lys
                245                 250                 255

Ser Arg Gly Gly Met Phe Arg Gln Gly Cys Thr Ala Phe Arg Val Ile
            260                 265                 270

Thr Pro Asn Ile Asp Glu Glu Ala Ser Met Met Glu Asp Val Gly Met
        275                 280                 285

Gln Asp Val His Phe Asn Glu Asp Val Leu Met Glu Leu Leu Glu Gln
    290                 295                 300

Cys Ala Asp Gly Leu Trp Lys Ala Glu Arg Leu Arg Ala Gly Leu Leu
305                 310                 315                 320

Thr Ser Ile Asn Ser Ser Pro Ser Met Lys Ser Gly Gly Thr Leu
                325                 330                 335

Glu Thr Thr His Leu Tyr Asp Thr Leu His Arg Pro Tyr Ser Lys Val
            340                 345                 350

Thr Glu Val Ile Thr Arg Ala Ala Gly Ser Trp Asp Leu Leu Pro Gly
        355                 360                 365

Gly Leu Phe Gly Gln Gly Phe Phe Glu Asp Glu Asp Gly Lys Glu Tyr
    370                 375                 380

Ile Tyr Lys Glu Pro Lys Leu Thr Pro Leu Ser Glu Ile Ser Gln Arg
385                 390                 395                 400

Leu Leu Lys Leu Tyr Ser Asp Lys Phe Gly Ser Glu Asn Val Lys Met
                405                 410                 415

Ile Gln Asp Ser Gly Lys Val Asn Pro Lys Asp Leu Asp Ser Lys Phe
            420                 425                 430

Ala Tyr Ile Gln Val Thr His Val Thr Pro Phe Phe Asp Glu Lys Glu
        435                 440                 445

Leu Gln Glu Arg Lys Thr Glu Phe Glu Arg Cys His Asn Ile Arg Arg
    450                 455                 460

Phe Met Phe Glu Met Pro Phe Thr Gln Thr Gly Lys Arg Gln Gly Gly

```
                465                 470                 475                 480
Val Glu Glu Gln Cys Lys Arg Arg Thr Ile Leu Thr Ala Ile His Cys
                    485                 490                 495

Phe Pro Tyr Val Lys Lys Arg Ile Pro Val Met Tyr Gln His His Thr
                500                 505                 510

Asp Leu Asn Pro Ile Glu Val Ala Ile Asp Glu Met Ser Lys Lys Val
                515                 520                 525

Ala Glu Leu His Gln Leu Cys Ser Ser Ala Glu Val Asp Met Ile Lys
            530                 535                 540

Leu Gln Leu Lys Leu Gln Gly Ser Val Ser Val Gln Val Asn Ala Gly
545                 550                 555                 560

Pro Leu Ala Tyr Ala Arg Ala Phe Leu Asp Asp Thr Asn Thr Lys Arg
                565                 570                 575

Tyr Pro Asp Asn Lys Val Lys Leu Leu Lys Glu Val Phe Arg Gln Phe
                580                 585                 590

Val Glu Ala Cys Gly Gln Ala Leu Ala Val Asn Glu Arg Leu Ile Lys
                595                 600                 605

Glu Asp Gln Leu Glu Tyr Gln Glu Met Lys Ala Asn Tyr Arg Glu
            610                 615                 620

Ile Arg Lys Glu Leu Ser Asp Ile Ile Val Pro Arg Ile Cys Pro Gly
625                 630                 635                 640

Glu Asp Lys Arg Ala Thr Lys Phe Pro Ala His Leu Gln Arg His Gln
                645                 650                 655

Arg Asp Thr Asn Lys His Ser Gly Ser Arg Val Asp Gln Phe Ile Leu
                660                 665                 670

Ser Cys Val Thr Leu Pro His Glu Pro His Val Gly Thr Cys Phe Val
                675                 680                 685

Met Cys Lys Leu Arg Thr Thr Phe Arg Ala Asn His Trp Phe Cys Gln
            690                 695                 700

Ala Gln Glu Glu Ala Met Gly Asn Gly Arg Glu Lys Glu Pro Trp Thr
705                 710                 715                 720

Val Ile Phe Asn Ser Arg Phe Tyr Arg Ser Trp Gly Lys Val His Ile
                725                 730                 735

Phe Phe

<210> SEQ ID NO 21
<211> LENGTH: 1214
<212> TYPE: PRT
<213> ORGANISM: Homo sapiens
<220> FEATURE:
<223> OTHER INFORMATION: Human CLASP-4 protein

<400> SEQUENCE: 21

Met Glu Ile Gln Val Leu Ile Arg Phe Leu Ser Val Ile Leu Met Gln
1               5                   10                  15

Leu Phe Trp Val Leu Pro Asn Met Ile His Glu Asp Val Pro Ile
                20                  25                  30

Ser Cys Pro Met Val Leu Phe His Ile Val Ser Lys Cys His Glu Glu
            35                  40                  45

Gly Leu Asp Ser Tyr Leu Ser Ser Phe Ile Lys Tyr Ser Phe Arg Pro
        50                  55                  60

Gly Lys Pro Ser Ala Pro Gln Ala Pro Leu Ile His Glu Thr Leu Ala
65                  70                  75                  80

Thr Met Met Ile Ala Leu Leu Lys Gln Ser Ala Asp Phe Leu Ala Ile
                85                  90                  95
```

-continued

```
Asn Lys Leu Leu Lys Tyr Ser Trp Phe Phe Glu Ile Ile Ala Lys
            100                 105                 110
Ser Met Ala Thr Tyr Leu Leu Glu Glu Asn Lys Ile Lys Leu Thr His
        115                 120                 125
Gly Gln Arg Phe Pro Lys Ala Tyr His His Ala Leu His Ser Leu Phe
    130                 135                 140
Leu Ala Ile Thr Ile Val Glu Ser Gln Tyr Ala Glu Ile Pro Lys Glu
145                 150                 155                 160
Ser Arg Asn Val Asn Tyr Ser Leu Ala Ser Phe Leu Lys Cys Cys Leu
                165                 170                 175
Thr Leu Met Asp Arg Gly Phe Val Phe Asn Leu Ile Asn Asp Tyr Ile
            180                 185                 190
Ser Gly Phe Ser Pro Lys Asp Pro Lys Val Leu Ala Glu Tyr Lys Phe
        195                 200                 205
Glu Phe Leu Gln Thr Ile Cys Asn His Glu His Tyr Ile Pro Leu Asn
    210                 215                 220
Leu Pro Met Ala Phe Ala Lys Pro Lys Leu Gln Arg Val Gln Asp Ser
225                 230                 235                 240
Asn Leu Glu Tyr Ser Leu Ser Asp Glu Tyr Cys Lys His His Phe Leu
                245                 250                 255
Val Gly Leu Leu Leu Arg Glu Thr Ser Ile Ala Leu Gln Asp Asn Tyr
            260                 265                 270
Glu Ile Arg Tyr Thr Ala Ile Ser Val Ile Lys Asn Leu Leu Ile Lys
        275                 280                 285
His Ala Phe Asp Thr Arg Tyr Gln His Lys Asn Gln Gln Ala Lys Ile
    290                 295                 300
Ala Gln Leu Tyr Leu Pro Phe Val Gly Leu Leu Glu Asn Ile Gln
305                 310                 315                 320
Arg Leu Ala Gly Arg Asp Thr Leu Tyr Ser Cys Ala Ala Met Pro Asn
                325                 330                 335
Ser Ala Ser Arg Asp Glu Phe Pro Cys Gly Phe Thr Ser Pro Ala Asn
            340                 345                 350
Arg Gly Ser Leu Ser Thr Asp Lys Asp Thr Ala Tyr Gly Ser Phe Gln
        355                 360                 365
Asn Gly His Gly Ile Lys Arg Glu Asp Ser Arg Gly Ser Leu Ile Pro
    370                 375                 380
Glu Gly Ala Thr Gly Phe Pro Asp Gln Gly Asn Thr Gly Glu Asn Thr
385                 390                 395                 400
Arg Gln Ser Ser Thr Arg Ser Ser Val Ser Gln Tyr Asn Arg Leu Asp
                405                 410                 415
Gln Tyr Glu Ile Arg Ser Leu Leu Met Cys Tyr Leu Tyr Ile Val Lys
            420                 425                 430
Met Ile Ser Glu Asp Thr Leu Leu Thr Tyr Trp Asn Lys Val Ser Pro
        435                 440                 445
Gln Glu Leu Ile Asn Ile Leu Ile Leu Glu Val Cys Leu Phe His
    450                 455                 460
Phe Arg Tyr Met Gly Lys Arg Asn Ile Ala Arg Val His Asp Ala Trp
465                 470                 475                 480
Leu Ser Lys His Phe Gly Ile Asp Arg Lys Ser Gln Thr Met Pro Ala
                485                 490                 495
Leu Arg Asn Arg Ser Gly Val Met Gln Ala Arg Leu Gln His Leu Ser
            500                 505                 510
```

```
Ser Leu Glu Ser Ser Phe Thr Leu Asn His Ser Ser Thr Thr Thr Glu
            515                 520                 525

Ala Asp Ile Phe His Gln Ala Leu Leu Glu Gly Asn Thr Ala Thr Glu
            530                 535                 540

Val Ser Leu Thr Val Leu Asp Thr Ile Ser Phe Phe Thr Gln Cys Phe
545                 550                 555                 560

Lys Thr His Phe Leu Asn Asn Asp Gly His Asn Pro Leu Met Lys Lys
            565                 570                 575

Val Phe Asp Ile His Leu Ala Phe Leu Lys Asn Gly Gln Ser Glu Val
            580                 585                 590

Ser Leu Lys His Val Phe Ala Ser Leu Arg Ala Phe Ile Ser Lys Phe
            595                 600                 605

Pro Ser Ala Phe Phe Lys Gly Arg Val Asn Met Cys Ala Ala Phe Cys
            610                 615                 620

Tyr Glu Val Leu Lys Cys Cys Thr Ser Lys Ile Ser Thr Arg Asn
625                 630                 635                 640

Glu Ala Ser Ala Leu Leu Tyr Leu Leu Met Arg Asn Asn Phe Glu Tyr
            645                 650                 655

Thr Lys Arg Lys Thr Phe Leu Arg Thr His Leu Gln Ile Ile Ala
            660                 665                 670

Val Ser Gln Leu Ile Ala Asp Val Ala Leu Ser Gly Gly Ser Arg Phe
            675                 680                 685

Gln Glu Ser Leu Phe Ile Ile Asn Asn Phe Ala Asn Ser Asp Arg Pro
            690                 695                 700

Met Leu Ala Arg Ala Phe Pro Ala Glu Val Lys Asp Leu Thr Lys Arg
705                 710                 715                 720

Ile Arg Thr Val Leu Met Ala Thr Ala Gln Met Lys Glu His Glu Lys
            725                 730                 735

Asp Pro Glu Met Leu Ile Asp Leu Gln Tyr Ser Leu Ala Lys Ser Tyr
            740                 745                 750

Ala Ser Thr Pro Glu Leu Arg Lys Thr Trp Leu Asp Ser Met Ala Lys
            755                 760                 765

Ile His Val Lys Asn Gly Asp Phe Ser Glu Ala Ala Met Cys Tyr Val
            770                 775                 780

His Val Ala Ala Leu Val Ala Glu Phe Leu His Arg Lys Lys Leu Phe
785                 790                 795                 800

Pro Asn Gly Cys Ser Ala Phe Lys Lys Ile Thr Pro Asn Ile Asp Glu
            805                 810                 815

Glu Gly Ala Met Lys Glu Asp Ala Gly Met Met Asp Val His Tyr Ser
            820                 825                 830

Glu Glu Val Leu Leu Glu Leu Leu Glu Gln Cys Val Asn Gly Leu Trp
            835                 840                 845

Lys Ala Glu Arg Tyr Glu Ile Ile Ser Glu Ile Ser Lys Leu Ile Gly
            850                 855                 860

Pro Ile Tyr Glu Asn Arg Arg Glu Phe Glu Asn Leu Thr Gln Val Tyr
865                 870                 875                 880

Arg Thr Leu His Gly Ala Tyr Thr Lys Ile Leu Glu Val Met His Thr
            885                 890                 895

Lys Lys Arg Leu Leu Gly Thr Phe Phe Arg Val Ala Phe Tyr Gly Gln
            900                 905                 910

Ser Phe Phe Glu Glu Glu Asp Gly Lys Glu Tyr Ile Tyr Lys Glu Pro
            915                 920                 925

Lys Leu Thr Gly Leu Ser Glu Ile Ser Leu Arg Leu Val Lys Leu Tyr
```

-continued

```
                930                 935                 940
Gly Glu Lys Phe Gly Thr Glu Asn Val Lys Ile Ile Gln Asp Ser Asp
945                 950                 955                 960

Lys Val Asn Ala Lys Glu Leu Asp Pro Lys Tyr Ala His Ile Gln Val
                965                 970                 975

Thr Tyr Val Lys Pro Tyr Phe Asp Asp Lys Glu Leu Thr Glu Arg Lys
            980                 985                 990

Thr Glu Phe Glu Arg Asn His Asn Ile Ser Arg Phe Val Phe Glu Ala
            995                 1000                1005

Pro Tyr Thr Leu Ser Gly Lys Lys Gln Gly Cys Ile Glu Gln Cys
    1010                1015                1020

Lys Arg Arg Thr Ile Leu Thr Thr Ser Asn Ser Phe Pro Tyr Val Lys
1025                1030                1035                1040

Lys Arg Ile Pro Ile Asn Cys Glu Gln Gln Ile Asn Leu Lys Pro Ile
                1045                1050                1055

Asp Gly Ala Thr Asp Glu Ile Lys Asp Lys Thr Ala Glu Leu Gln Lys
            1060                1065                1070

Leu Cys Ser Ser Thr Asp Val Asp Met Ile Gln Leu Gln Leu Lys Leu
    1075                1080                1085

Gln Gly Trp Val Ser Val Gln Val Asn Ala Gly Pro Leu Ala Tyr Ala
    1090                1095                1100

Arg Ala Phe Leu Asn Asp Ser Gln Ala Ser Lys Tyr Pro Pro Lys Lys
1105                1110                1115                1120

Val Ser Glu Leu Lys Asp Met Phe Arg Lys Phe Ile Gln Ala Cys Ser
            1125                1130                1135

Ile Ala Leu Glu Leu Asn Glu Arg Leu Ile Lys Glu Asp Gln Val Glu
            1140                1145                1150

Tyr His Glu Gly Leu Lys Ser Asn Phe Arg Asp Met Val Lys Glu Leu
            1155                1160                1165

Ser Asp Ile Ile His Glu Gln Ile Leu Gln Glu Asp Thr Met His Ser
    1170                1175                1180

Pro Trp Met Ser Asn Thr Leu His Val Phe Cys Ala Ile Ser Gly Thr
1185                1190                1195                1200

Ser Ser Asp Arg Gly Tyr Gly Ser Pro Arg Tyr Ala Glu Val
            1205                1210

<210> SEQ ID NO 22
<211> LENGTH: 1288
<212> TYPE: PRT
<213> ORGANISM: Homo sapiens
<220> FEATURE:
<223> OTHER INFORMATION: Human CLASP-1 protein

<400> SEQUENCE: 22

Met Ser Phe Leu Pro Ile Ile Leu Asn Gln Leu Phe Lys Val Leu Val
1               5                   10                  15

Gln Asn Glu Glu Asp Glu Ile Thr Thr Thr Val Thr Arg Val Leu Pro
            20                  25                  30

Asp Ile Val Ala Lys Cys His Glu Gln Leu Asp His Ser Val Gln
        35                  40                  45

Ser Tyr Ile Lys Phe Val Phe Lys Thr Arg Ala Cys Lys Glu Arg Pro
    50                  55                  60

Val His Glu Asp Leu Ala Lys Asn Val Thr Gly Leu Leu Lys Ser Asn
65                  70                  75                  80

Asp Ser Pro Thr Val Lys His Val Leu Lys His Ser Trp Phe Phe Phe
```

-continued

```
                85                  90                  95
Ala Ile Ile Leu Lys Ser Met Ala Gln His Leu Ile Asp Thr Asn Lys
            100                 105                 110
Ile Gln Leu Pro Arg Pro Gln Arg Phe Pro Glu Ser Tyr Gln Asn Glu
            115                 120                 125
Leu Asp Asn Leu Val Met Val Leu Ser Asp His Val Ile Trp Lys Tyr
            130                 135                 140
Lys Asp Ala Leu Glu Glu Thr Arg Arg Ala Thr His Ser Val Ala Arg
145                 150                 155                 160
Phe Leu Lys Arg Cys Phe Thr Phe Met Asp Arg Gly Cys Val Phe Lys
                165                 170                 175
Met Val Asn Asn Tyr Ile Ser Met Phe Ser Ser Gly Asp Leu Lys Thr
            180                 185                 190
Leu Cys Gln Tyr Lys Phe Asp Phe Leu Gln Glu Val Cys Gln His Glu
            195                 200                 205
His Phe Ile Pro Leu Cys Leu Pro Ile Arg Ser Ala Asn Ile Pro Asp
    210                 215                 220
Pro Leu Thr Pro Ser Glu Ser Thr Gln Glu Leu His Ala Ser Asp Met
225                 230                 235                 240
Pro Glu Tyr Ser Val Thr Asn Glu Phe Cys Arg Lys His Phe Leu Ile
                245                 250                 255
Gly Ile Leu Leu Arg Glu Val Gly Phe Ala Leu Gln Glu Asp Gln Asp
                260                 265                 270
Val Arg His Leu Ala Leu Ala Val Leu Lys Asn Leu Met Ala Lys His
            275                 280                 285
Ser Phe Asp Asp Arg Tyr Arg Glu Pro Arg Lys Gln Ala Gln Ile Ala
    290                 295                 300
Ser Leu Tyr Met Pro Leu Tyr Gly Met Leu Leu Asp Asn Met Pro Arg
305                 310                 315                 320
Ile Tyr Leu Lys Asp Leu Tyr Pro Phe Thr Val Asn Thr Ser Asn Gln
                325                 330                 335
Gly Ser Arg Asp Asp Leu Ser Thr Asn Gly Gly Phe Gln Ser Gln Thr
            340                 345                 350
Ala Ile Lys His Ala Asn Ser Val Asp Thr Ser Phe Ser Lys Asp Val
            355                 360                 365
Leu Asn Ser Ile Ala Ala Phe Ser Ser Ile Ala Ile Ser Thr Val Asn
    370                 375                 380
His Ala Asp Ser Arg Ala Ser Leu Ala Ser Leu Asp Ser Asn Pro Ser
385                 390                 395                 400
Thr Asn Glu Lys Ser Ser Glu Lys Thr Asp Asn Cys Glu Lys Ile Pro
                405                 410                 415
Arg Pro Leu Ala Leu Ile Gly Ser Thr Leu Arg Phe Asp Arg Leu Asp
            420                 425                 430
Gln Ala Glu Thr Arg Ser Leu Leu Met Cys Phe Leu His Ile Met Lys
            435                 440                 445
Thr Ile Ser Tyr Glu Thr Leu Ile Ala Tyr Trp Gln Arg Ala Pro Ser
    450                 455                 460
Pro Glu Val Ser Asp Phe Phe Ser Ile Leu Asp Val Cys Leu Gln Asn
465                 470                 475                 480
Phe Arg Tyr Leu Gly Lys Arg Asn Ile Ile Arg Lys Ile Ala Ala Ala
                485                 490                 495
Phe Lys Phe Val Gln Ser Thr Gln Asn Asn Gly Thr Leu Lys Gly Ser
            500                 505                 510
```

```
Asn Pro Ser Cys Gln Thr Ser Gly Leu Leu Ala Gln Trp Met His Ser
            515                 520                 525
Thr Ser Arg His Glu Gly His Lys Gln His Arg Ser Gln Thr Leu Pro
        530                 535                 540
Ile Ile Arg Gly Lys Asn Ala Leu Ser Asn Pro Lys Leu Leu Gln Met
545                 550                 555                 560
Leu Asp Asn Thr Met Thr Ser Asn Ser Asn Glu Ile Asp Ile Val His
                565                 570                 575
His Val Asp Thr Glu Ala Asn Ile Ala Thr Glu Gly Cys Leu Thr Ile
            580                 585                 590
Leu Asp Leu Val Ser Leu Phe Thr Gln Thr His Gln Arg Gln Leu Gln
        595                 600                 605
Gln Cys Asp Cys Gln Asn Ser Leu Met Lys Arg Gly Phe Asp Thr Tyr
    610                 615                 620
Met Leu Phe Phe Gln Val Asn Gln Ser Ala Thr Ala Leu Lys His Val
625                 630                 635                 640
Phe Ala Ser Leu Arg Leu Phe Val Cys Lys Phe Pro Ser Ala Phe Phe
                645                 650                 655
Gln Gly Pro Ala Asp Leu Cys Gly Ser Phe Cys Tyr Glu Val Leu Lys
            660                 665                 670
Cys Cys Asn His Arg Ser Arg Ser Thr Gln Thr Glu Ala Ser Ala Leu
        675                 680                 685
Leu Tyr Leu Phe Met Arg Lys Asn Phe Glu Phe Asn Lys Gln Lys Ser
    690                 695                 700
Ile Val Arg Ser His Leu Gln Leu Ile Lys Ala Val Ser Gln Leu Ile
705                 710                 715                 720
Ala Asp Ala Gly Ile Gly Gly Ser Arg Phe Gln His Ser Leu Ala Ile
                725                 730                 735
Thr Asn Asn Phe Ala Asn Gly Asp Lys Gln Met Lys Asn Ser Asn Phe
            740                 745                 750
Pro Ala Glu Val Lys Asp Leu Thr Lys Arg Ile Arg Thr Val Leu Met
        755                 760                 765
Ala Thr Ala Gln Met Lys Glu His Glu Lys Asp Pro Glu Met Leu Val
    770                 775                 780
Asp Leu Gln Tyr Ser Leu Ala Asn Ser Tyr Ala Ser Thr Pro Glu Leu
785                 790                 795                 800
Arg Arg Thr Trp Leu Glu Ser Met Ala Lys Ile His Ala Arg Asn Gly
                805                 810                 815
Asp Leu Ser Glu Ala Ala Met Cys Tyr Ile His Ile Ala Ala Leu Ile
            820                 825                 830
Ala Glu Tyr Leu Lys Arg Lys Gly Tyr Trp Lys Val Glu Lys Ile Cys
        835                 840                 845
Thr Ala Ser Leu Leu Ser Glu Asp Thr His Pro Cys Asp Ser Asn Ser
    850                 855                 860
Leu Leu Thr Thr Pro Ser Gly Ser Met Phe Ser Met Gly Trp Pro
865                 870                 875                 880
Ala Phe Leu Ser Ile Thr Pro Asn Ile Lys Glu Glu Gly Ala Ala Lys
                885                 890                 895
Glu Asp Ser Gly Met His Asp Thr Pro Tyr Asn Glu Asn Ile Leu Val
            900                 905                 910
Glu Gln Leu Tyr Met Cys Gly Glu Phe Leu Trp Lys Ser Glu Arg Tyr
        915                 920                 925
```

```
Glu Leu Ile Ala Asp Val Asn Lys Pro Ile Ile Ala Val Phe Glu Lys
        930                 935                 940

Gln Arg Asp Phe Lys Lys Leu Ser Asp Leu Tyr Tyr Asp Ile His Arg
945                 950                 955                 960

Ser Tyr Leu Lys Val Ala Glu Val Val Asn Ser Glu Lys Arg Leu Phe
                965                 970                 975

Gly Arg Tyr Tyr Arg Val Ala Phe Tyr Gly Gln Gly Phe Phe Glu Glu
            980                 985                 990

Glu Glu Gly Lys Glu Tyr Ile Tyr Lys Glu Pro Lys Leu Thr Gly Leu
        995                 1000                1005

Ser Glu Ile Ser Gln Arg Leu Leu Lys Leu Tyr Ala Asp Lys Phe Gly
    1010                1015                1020

Ala Asp Asn Val Lys Ile Ile Gln Asp Ser Asn Lys Val Asn Pro Lys
1025                1030                1035                1040

Asp Leu Asp Pro Lys Tyr Ala Tyr Ile Gln Val Thr Tyr Val Thr Pro
                1045                1050                1055

Phe Phe Glu Glu Lys Glu Ile Glu Asp Arg Lys Thr Asp Phe Glu Met
            1060                1065                1070

His His Asn Ile Asn Arg Phe Val Phe Glu Thr Pro Phe Thr Leu Ser
        1075                1080                1085

Gly Lys Lys His Gly Gly Val Ala Glu Gln Cys Lys Arg Arg Thr Ile
    1090                1095                1100

Leu Thr Thr Ser His Leu Phe Pro Tyr Val Lys Lys Arg Ile Gln Val
1105                1110                1115                1120

Ile Ser Gln Ser Ser Thr Glu Leu Asn Pro Ile Glu Val Ala Ile Asp
                1125                1130                1135

Glu Met Ser Arg Lys Val Ser Glu Leu Asn Gln Leu Cys Thr Met Glu
            1140                1145                1150

Glu Val Asp Met Ile Ser Leu Gln Leu Lys Leu Gln Gly Ser Val Ser
        1155                1160                1165

Val Lys Val Asn Ala Gly Pro Met Ala Tyr Ala Arg Ala Phe Leu Glu
    1170                1175                1180

Glu Thr Asn Ala Lys Lys Tyr Pro Asp Asn Gln Val Lys Leu Leu Lys
1185                1190                1195                1200

Glu Ile Phe Arg Gln Phe Ala Asp Ala Cys Gly Gln Ala Leu Asp Val
                1205                1210                1215

Asn Glu Arg Leu Ile Lys Glu Asp Gln Leu Glu Tyr Gln Glu Glu Leu
            1220                1225                1230

Arg Ser His Tyr Lys Asp Met Leu Ser Glu Leu Ser Thr Val Met Asn
        1235                1240                1245

Glu Gln Ile Thr Gly Arg Asp Asp Leu Ser Lys Arg Gly Val Asp Gln
    1250                1255                1260

Thr Cys Thr Arg Val Ile Ser Lys Ala Thr Pro Ala Leu Pro Thr Val
1265                1270                1275                1280

Ser Ile Ser Ser Ser Ala Glu Val
                1285

<210> SEQ ID NO 23
<211> LENGTH: 1220
<212> TYPE: PRT
<213> ORGANISM: Homo sapiens
<220> FEATURE:
<223> OTHER INFORMATION: Human CLASP-3 protein

<400> SEQUENCE: 23
```

-continued

```
Gly Pro Gly Pro Ala Arg Ser Thr Val Ser Ile Ser Leu Ile Ser Asn
  1               5                  10                  15

Ser Ala Arg Val Asn Arg Ser Arg Ser Leu Ser Asn Ser Asn Pro Asp
                 20                  25                  30

Ile Ser Gly Thr Pro Thr Ser Pro Asp Asp Glu Val Arg Ser Ile Ile
             35                  40                  45

Gly Ser Lys Gly Leu Asp Arg Ser Asn Ser Trp Val Asn Thr Gly Gly
         50                  55                  60

Pro Lys Ala Ala Pro Trp Gly Ser Asn Pro Ser Pro Ser Ala Glu Ser
 65                  70                  75                  80

Thr Gln Ala Met Asp Arg Ser Cys Asn Arg Met Ser Ser His Thr Glu
                 85                  90                  95

Thr Ser Ser Phe Leu Gln Thr Leu Thr Gly Arg Leu Pro Thr Lys Lys
             100                 105                 110

Leu Phe His Glu Glu Leu Ala Leu Gln Trp Val Val Cys Ser Gly Ser
         115                 120                 125

Val Arg Glu Ser Ala Leu Gln Gln Ala Trp Phe Phe Phe Glu Leu Met
     130                 135                 140

Val Lys Ser Met Val His His Leu Tyr Phe Asn Asp Lys Leu Glu Ala
145                 150                 155                 160

Pro Arg Lys Ser Arg Phe Pro Glu Arg Phe Met Asp Asp Ile Ala Ala
                165                 170                 175

Leu Val Ser Thr Ile Ala Ser Asp Ile Val Ser Arg Phe Gln Lys Asp
            180                 185                 190

Thr Glu Met Val Glu Arg Leu Asn Thr Ser Leu Ala Phe Phe Leu Asn
        195                 200                 205

Asp Leu Leu Ser Val Met Asp Arg Gly Phe Val Phe Ser Leu Ile Lys
    210                 215                 220

Ser Cys Tyr Lys Gln Val Ser Ser Lys Leu Tyr Ser Leu Pro Asn Pro
225                 230                 235                 240

Ser Val Leu Val Ser Leu Arg Leu Asp Phe Leu Arg Ile Ile Cys Ser
                245                 250                 255

His Glu His Tyr Val Thr Leu Asn Leu Pro Cys Ser Leu Leu Thr Pro
            260                 265                 270

Pro Ala Ser Pro Ser Pro Ser Val Ser Ser Ala Thr Ser Gln Ser Ser
        275                 280                 285

Gly Phe Ser Thr Asn Val Gln Asp Gln Lys Ile Ala Asn Met Phe Glu
    290                 295                 300

Leu Ser Val Pro Phe Arg Gln Gln His Tyr Leu Ala Gly Leu Val Leu
305                 310                 315                 320

Thr Glu Leu Ala Val Ile Leu Asp Pro Asp Ala Glu Gly Leu Phe Gly
                325                 330                 335

Leu His Lys Lys Val Ile Asn Met Val His Asn Leu Leu Ser Ser His
            340                 345                 350

Asp Ser Asp Pro Arg Tyr Ser Asp Pro Gln Ile Lys Ala Arg Val Ala
        355                 360                 365

Met Leu Tyr Leu Pro Leu Ile Gly Ile Ile Met Glu Thr Val Pro Gln
    370                 375                 380

Leu Tyr Asp Phe Thr Glu Thr His Asn Gln Arg Gly Arg Pro Ile Cys
385                 390                 395                 400

Ile Ala Thr Asp Asp Tyr Glu Ser Glu Ser Gly Ser Met Ile Ser Gln
                405                 410                 415

Thr Val Ala Met Ala Ile Ala Gly Thr Ser Val Pro Gln Leu Thr Arg
```

-continued

```
                420                 425                 430
Pro Gly Ser Phe Leu Leu Thr Ser Thr Ser Gly Arg Gln His Thr Thr
            435                 440                 445
Phe Ser Ala Glu Ser Ser Arg Ser Leu Leu Ile Cys Leu Leu Trp Val
        450                 455                 460
Leu Lys Asn Ala Asp Glu Thr Val Leu Gln Lys Trp Phe Thr Asp Leu
465                 470                 475                 480
Ser Val Leu Gln Leu Asn Arg Leu Leu Asp Leu Leu Tyr Leu Cys Val
                485                 490                 495
Ser Cys Phe Glu Tyr Lys Gly Lys Val Phe Glu Arg Met Asn Ser
            500                 505                 510
Leu Thr Phe Lys Lys Ser Lys Asp Met Arg Ala Lys Leu Glu Glu Ala
        515                 520                 525
Ile Leu Gly Ser Ile Gly Ala Arg Gln Glu Met Val Arg Arg Ser Arg
        530                 535                 540
Gly Gln Leu Glu Arg Ser Pro Ser Gly Ser Ala Phe Gly Ser Gln Glu
545                 550                 555                 560
Asn Leu Arg Trp Arg Lys Asp Met Thr His Trp Arg Gln Asn Thr Glu
                565                 570                 575
Lys Leu Asp Lys Ser Arg Ala Glu Ile Glu His Glu Ala Leu Ile Asp
            580                 585                 590
Gly Asn Leu Ala Thr Glu Ala Asn Leu Ile Ile Leu Asp Thr Leu Glu
        595                 600                 605
Ile Val Val Gln Thr Val Ser Val Thr Glu Ser Lys Glu Ser Ile Leu
        610                 615                 620
Gly Gly Val Leu Lys Val Leu Leu His Ser Met Ala Cys Asn Gln Ser
625                 630                 635                 640
Ala Val Tyr Leu Gln His Cys Phe Ala Thr Gln Arg Ala Leu Val Ser
                645                 650                 655
Lys Phe Pro Glu Leu Leu Phe Glu Glu Thr Glu Gln Cys Ala Asp
            660                 665                 670
Leu Cys Leu Arg Leu Leu Arg His Cys Ser Ser Ser Ile Gly Thr Ile
        675                 680                 685
Arg Ser His Pro Ser Ala Ser Leu Tyr Leu Leu Met Arg Gln Asn Phe
        690                 695                 700
Glu Ile Gly Asn Asn Phe Ala Arg Val Lys Met Gln Val Pro Met Ser
705                 710                 715                 720
Leu Ser Ser Leu Val Gly Thr Ser Gln Asn Phe Asn Glu Glu Phe Leu
                725                 730                 735
Arg Arg Ser Leu Lys Thr Ile Leu Thr Tyr Ala Glu Glu Asp Leu Glu
            740                 745                 750
Leu Arg Glu Thr Thr Phe Pro Asp Gln Val Gln Asp Leu Val Phe Asn
        755                 760                 765
Leu His Met Ile Leu Ser Asp Thr Val Lys Met Lys Glu His Gln Glu
        770                 775                 780
Asp Pro Glu Met Leu Ile Asp Leu Met Tyr Arg Ile Ala Lys Gly Tyr
785                 790                 795                 800
Gln Thr Ser Pro Asp Leu Arg Leu Thr Trp Leu Gln Asn Met Ala Gly
                805                 810                 815
Lys His Ser Glu Arg Ser Asn His Ala Glu Ala Gln Cys Leu Val
            820                 825                 830
His Ser Ala Ala Leu Val Ala Glu Tyr Leu Ser Met Leu Glu Asp Arg
        835                 840                 845
```

-continued

```
Lys Tyr Leu Pro Val Gly Cys Val Thr Phe Gln Asn Ile Ser Ser Asn
    850                 855                 860

Val Leu Glu Glu Ser Ala Val Ser Asp Asp Val Val Ser Pro Asp Glu
865                 870                 875                 880

Glu Gly Ile Cys Ser Gly Lys Tyr Phe Thr Glu Ser Gly Leu Val Gly
            885                 890                 895

Leu Leu Glu Gln Ala Ala Ser Phe Ser Met Ala Gly Met Tyr Glu
        900                 905                 910

Ala Val Asn Glu Val Tyr Lys Val Leu Ile Pro Ile His Glu Ala Asn
    915                 920                 925

Arg Asp Ala Lys Lys Leu Ser Thr Ile His Gly Lys Leu Gln Glu Ala
930                 935                 940

Phe Ser Lys Ile Val His Gln Ser Thr Gly Trp Glu Arg Met Phe Gly
945                 950                 955                 960

Thr Tyr Phe Arg Val Gly Phe Tyr Gly Thr Lys Phe Gly Asp Leu Asp
            965                 970                 975

Glu Gln Glu Phe Val Tyr Lys Glu Pro Ala Ile Thr Lys Leu Ala Glu
        980                 985                 990

Ile Ser His Arg Leu Glu Gly Phe Tyr Gly Glu Arg Phe Gly Glu Asp
    995                 1000                1005

Val Val Glu Val Ile Lys Asp Ser Asn Pro Val Asp Lys Cys Lys Leu
1010                1015                1020

Asp Pro Asn Lys Ala Tyr Ile Gln Ile Thr Tyr Val Glu Pro Tyr Phe
1025                1030                1035                1040

Asp Thr Tyr Glu Met Lys Asp Arg Ile Thr Tyr Phe Asp Lys Asn Tyr
            1045                1050                1055

Asn Leu Arg Arg Phe Met Tyr Cys Thr Pro Phe Thr Leu Asp Gly Arg
        1060                1065                1070

Ala His Gly Glu Leu His Glu Gln Phe Lys Arg Lys Thr Ile Leu Thr
    1075                1080                1085

Thr Ser His Ala Phe Pro Tyr Ile Lys Thr Arg Val Asn Val Thr His
1090                1095                1100

Lys Glu Glu Ile Ile Leu Thr Pro Ile Glu Val Ala Ile Glu Asp Met
1105                1110                1115                1120

Gln Lys Lys Thr Gln Glu Leu Ala Phe Ala Thr His Gln Asp Pro Ala
            1125                1130                1135

Asp Pro Lys Met Leu Gln Met Val Leu Gln Gly Ser Val Gly Thr Thr
        1140                1145                1150

Val Asn Gln Gly Pro Leu Glu Val Ala Gln Val Phe Leu Ser Glu Ile
    1155                1160                1165

Pro Ser Asp Pro Lys Leu Phe Arg His His Asn Lys Leu Arg Leu Cys
1170                1175                1180

Phe Lys Asp Phe Thr Lys Arg Cys Glu Asp Ala Leu Arg Lys Asn Lys
1185                1190                1195                1200

Ser Leu Ile Gly Pro Val Gln Lys Glu Tyr Gln Arg Glu Leu Gly Lys
            1205                1210                1215

Leu Ser Ser Pro
    1220

<210> SEQ ID NO 24
<211> LENGTH: 987
<212> TYPE: PRT
<213> ORGANISM: Homo sapiens
<220> FEATURE:
```

<223> OTHER INFORMATION: Human CLASP-5 protein

<400> SEQUENCE: 24

```
Met Asn Ala Asp Thr Ala Pro Thr Ser Pro Cys Pro Ser Ile Ser Ser
  1               5                  10                  15

Gln Asn Ser Ser Cys Ser Ser Phe Gln Asp Gln Lys Ile Ala Ser
             20                  25                  30

Met Phe Asp Arg Thr Ser Arg Val Pro Ala Ser Ser Thr Ser Ser Pro
             35                  40                  45

Gly Leu Leu Phe Thr Glu Leu Ala Ala Leu Asp Ala Glu Gly Glu
     50                  55                  60

Gly Ile Ser Glu Val Gln Arg Lys Ala Val Ser Ala Ile His Ser Leu
 65                  70                  75                  80

Leu Ser Ser His Asp Leu Asp Pro Arg Cys Val Lys Pro Glu Val Lys
                 85                  90                  95

Val Lys Ile Ala Ala Leu Tyr Leu Pro Leu Val Gly Ile Ile Leu Asp
                100                 105                 110

Ala Leu Pro Gln Leu Cys Asp Phe Thr Val Ala Asp Thr Arg Arg Tyr
            115                 120                 125

Arg Thr Ser Gly Ser Asp Glu Glu Gln Glu Gly Ala Gly Ala Ile Thr
        130                 135                 140

Gln Asn Val Ala Leu Ala Ile Ala Gly Asn Asn Phe Asn Leu Lys Thr
145                 150                 155                 160

Ser Gly Ile Val Leu Ser Ser Leu Pro Tyr Lys Gln Tyr Asn Met Leu
                165                 170                 175

Asn Ala Asp Thr Thr Arg Asn Leu Met Ile Cys Phe Leu Trp Ile Met
            180                 185                 190

Lys Asn Ala Asp Gln Ser Leu Ile Arg Lys Trp Ile Ala Asp Leu Pro
        195                 200                 205

Ser Thr Gln Leu Asn Arg Ile Leu Asp Leu Leu Phe Ile Cys Val Leu
    210                 215                 220

Cys Phe Glu Tyr Lys Gly Lys Gln Ser Ser Asp Lys Val Ser Thr Gln
225                 230                 235                 240

Val Leu Gln Lys Ser Arg Asp Val Lys Ala Arg Leu Glu Glu Ala Leu
                245                 250                 255

Leu Arg Gly Glu Gly Ala Arg Gly Glu Met Met Arg Arg Arg Ala Pro
            260                 265                 270

Gly Asn Asp Arg Phe Pro Gly Leu Asn Glu Asn Leu Arg Trp Lys Lys
        275                 280                 285

Glu Gln Thr His Trp Arg Gln Ala Asn Glu Lys Leu Asp Lys Thr Lys
    290                 295                 300

Ala Glu Leu Asp Gln Glu Ala Leu Ile Ser Gly Asn Leu Ala Thr Glu
305                 310                 315                 320

Ala His Leu Ile Ile Leu Asp Met Gln Glu Asn Ile Ile Gln Ala Ser
                325                 330                 335

Ser Ala Leu Asp Cys Lys Asp Ser Leu Leu Gly Gly Val Leu Arg Val
            340                 345                 350

Leu Val Asn Ser Leu Asn Cys Asp Gln Ser Thr Thr Tyr Leu Thr His
        355                 360                 365

Cys Phe Ala Thr Leu Arg Ala Leu Ile Ala Lys Phe Gly Asp Leu Leu
    370                 375                 380

Phe Glu Glu Glu Val Glu Gln Cys Phe Asp Leu Cys His Gln Val Leu
385                 390                 395                 400
```

```
His His Cys Ser Ser Met Asp Val Thr Arg Ser Gln Ala Cys Ala
                405                 410                 415

Thr Leu Tyr Leu Leu Met Arg Phe Ser Phe Gly Ala Thr Ser Asn Phe
            420                 425                 430

Ala Arg Val Lys Met Gln Val Thr Met Ser Leu Ala Ser Leu Val Gly
            435                 440                 445

Arg Ala Pro Asp Phe Asn Glu Glu His Leu Arg Arg Ser Leu Arg Thr
        450                 455                 460

Ile Leu Ala Tyr Ser Glu Glu Asp Thr Ala Met Gln Met Thr Pro Phe
465                 470                 475                 480

Pro Thr Gln Val Glu Glu Leu Leu Cys Asn Leu Asn Ser Ile Leu Tyr
                485                 490                 495

Asp Thr Val Lys Met Arg Glu Phe Gln Glu Asp Pro Glu Met Leu Met
                500                 505                 510

Asp Leu Met Tyr Arg Ile Ala Lys Ser Tyr Gln Ala Ser Pro Asp Leu
            515                 520                 525

Arg Leu Thr Trp Leu Gln Asn Met Ala Glu Lys His Thr Lys Lys Lys
        530                 535                 540

Cys Tyr Thr Glu Ala Ala Met Cys Leu Val His Ala Ala Ala Leu Val
545                 550                 555                 560

Ala Glu Tyr Leu Ser Met Leu Glu Asp His Ser Tyr Leu Pro Val Gly
                565                 570                 575

Ser Val Ser Phe Gln Asn Ile Ser Ser Asn Val Leu Glu Glu Ser Val
            580                 585                 590

Val Ser Glu Asp Thr Leu Ser Pro Asp Glu Asp Gly Val Cys Ala Gly
        595                 600                 605

Gln Tyr Phe Thr Glu Ser Gly Leu Val Gly Leu Leu Gln Ala Ala
            610                 615                 620

Glu Leu Phe Ser Thr Gly Gly Leu Tyr Glu Thr Val Asn Glu Val Tyr
625                 630                 635                 640

Lys Leu Val Ile Pro Ile Leu Glu Ala His Arg Glu Phe Arg Lys Leu
                645                 650                 655

Thr Leu Thr His Ser Lys Leu Gln Arg Ala Phe Asp Ser Ile Val Asn
                660                 665                 670

Lys Asp His Lys Arg Met Phe Gly Thr Tyr Phe Arg Val Gly Phe Phe
            675                 680                 685

Gly Ser Lys Phe Gly Asp Leu Asp Glu Gln Glu Phe Val Tyr Lys Glu
        690                 695                 700

Pro Ala Ile Thr Lys Leu Pro Glu Ile Ser His Arg Leu Glu Ala Phe
705                 710                 715                 720

Tyr Gly Gln Cys Phe Gly Ala Glu Phe Val Glu Val Ile Lys Asp Ser
                725                 730                 735

Thr Pro Val Asp Lys Thr Lys Leu Asp Pro Asn Lys Ala Tyr Ile Gln
            740                 745                 750

Ile Thr Phe Val Glu Pro Tyr Phe Asp Glu Tyr Glu Met Lys Asp Arg
        755                 760                 765

Val Thr Tyr Phe Glu Lys Asn Phe Asn Leu Arg Arg Phe Met Tyr Thr
    770                 775                 780

Thr Pro Phe Thr Leu Glu Gly Arg Pro Arg Gly Glu Leu His Glu Gln
785                 790                 795                 800

Tyr Arg Arg Asn Thr Val Leu Thr Thr Met His Ala Phe Pro Tyr Ile
                805                 810                 815

Lys Thr Arg Ile Ser Val Ile Gln Lys Glu Glu Phe Val Leu Thr Pro
```

```
                        820                 825                 830
Ile Glu Val Ala Ile Glu Asp Met Lys Lys Thr Leu Gln Leu Ala
        835                 840                 845

Val Ala Ile Asn Gln Glu Pro Pro Asp Ala Lys Met Leu Gln Met Val
    850                 855                 860

Leu Gln Gly Ser Val Gly Ala Thr Val Asn Gln Gly Pro Leu Glu Val
865                 870                 875                 880

Ala Gln Val Phe Leu Ala Glu Ile Pro Ala Asp Pro Lys Leu Tyr Arg
                885                 890                 895

His His Asn Lys Leu Arg Leu Cys Phe Lys Glu Phe Ile Met Arg Cys
            900                 905                 910

Gly Glu Ala Val Glu Lys Asn Lys Arg Leu Ile Thr Ala Asp Gln Arg
        915                 920                 925

Glu Tyr Gln Gln Glu Leu Lys Lys Asn Tyr Asn Lys Leu Lys Glu Asn
    930                 935                 940

Leu Arg Pro Met Ile Glu Arg Lys Ile Pro Glu Leu Tyr Lys Pro Ile
945                 950                 955                 960

Phe Arg Val Glu Ser Gln Lys Arg Asp Ser Phe His Arg Ser Ser Phe
                965                 970                 975

Arg Lys Cys Glu Thr Gln Leu Ser Gln Gly Ser
            980                 985

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: CLASP/DOCK
      motifs A and B from CLASP-1

<400> SEQUENCE: 25

Tyr Arg Val Ala Phe Tyr Gly Gln Gly Phe Phe Glu Glu Glu Glu Gly
 1               5                  10                  15

Lys Glu Tyr Ile Tyr Lys Glu Pro
            20

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: CLASP/DOCK
      motifs A and B from CLASP-2D KIAA1058

<400> SEQUENCE: 26

Phe Arg Val Ala Phe Phe Gly Gln Ala Ala Gln Tyr Gln Phe Thr Asp
 1               5                  10                  15

Ser Glu Thr Asp Val Glu Gly Phe Phe Glu Asp Glu Asp Gly Lys Glu
            20                  25                  30

Tyr Ile Tyr Lys Glu Pro
        35

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: CLASP/DOCK
      motif B from CLASP-2

<400> SEQUENCE: 27
```

```
Phe Glu Asp Glu Asp Gly Lys Glu Tyr Ile Tyr Lys Glu Pro
 1               5                   10
```

<210> SEQ ID NO 28
<211> LENGTH: 24
<212> TYPE: PRT
<213> ORGANISM: Artificial Sequence
<220> FEATURE:
<223> OTHER INFORMATION: Description of Artificial Sequence: CLASP/DOCK
       motifs A and B from CLASP-6

<400> SEQUENCE: 28

```
Phe Arg Val Ala Phe Phe Gly Gln Gly Phe Phe Glu Asp Glu Asp Gly
 1               5                   10                  15

Lys Glu Tyr Ile Tyr Lys Glu Pro
            20
```

<210> SEQ ID NO 29
<211> LENGTH: 24
<212> TYPE: PRT
<213> ORGANISM: Artificial Sequence
<220> FEATURE:
<223> OTHER INFORMATION: Description of Artificial Sequence: CLASP/DOCK
       motifs A and B from CLASP-4

<400> SEQUENCE: 29

```
Phe Arg Val Ala Phe Tyr Gly Gln Ser Phe Phe Glu Glu Glu Asp Gly
 1               5                   10                  15

Lys Glu Tyr Ile Tyr Lys Glu Pro
            20
```

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: CLASP/DOCK
       motifs A and B from DOCK180

<400> SEQUENCE: 30

```
Phe Ala Val Gly Tyr Tyr Gly Gln Gly Phe Pro Thr Phe Leu Arg Gly
 1               5                   10                  15

Lys Val Phe Ile Tyr Arg Gly Lys Glu Tyr Glu Arg Arg Glu Asp
            20                  25                  30
```

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: CLASP/DOCK
       motifs A and B from DOCK2

<400> SEQUENCE: 31

```
Phe Ala Val Gly Tyr Tyr Gly Gln Gly Phe Pro Ser Phe Leu Arg Asn
 1               5                   10                  15

Lys Val Phe Ile Tyr Arg Gly Lys Glu Tyr Glu Arg Arg Glu Asp
            20                  25                  30
```

<210> SEQ ID NO 32
<211> LENGTH: 24
<212> TYPE: PRT
<213> ORGANISM: Artificial Sequence
<220> FEATURE:
<223> OTHER INFORMATION: Description of Artificial Sequence: CLASP/DOCK

```
                    motifs A and B from DOCK3

<400> SEQUENCE: 32

Phe Arg Val Gly Phe Tyr Gly Arg Lys Phe Pro Phe Leu Arg Asn
  1               5                  10                  15

Lys Glu Tyr Val Cys Arg Gly His
              20

<210> SEQ ID NO 33
<211> LENGTH: 24
<212> TYPE: PRT
<213> ORGANISM: Artificial Sequence
<220> FEATURE:
<223> OTHER INFORMATION: Description of Artificial Sequence: CLASP/DOCK
      motifs A and B from KIAA0716

<400> SEQUENCE: 33

Phe Arg Val Gly Phe Tyr Gly Lys Lys Phe Pro Phe Leu Arg Asn
  1               5                  10                  15

Lys Glu Phe Val Cys Arg Gly His
              20

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: CLASP/DOCK
      motifs A and B from CLASP-3

<400> SEQUENCE: 34

Phe Arg Val Gly Phe Tyr Gly Thr Lys Phe Gly Asp Leu Asp Glu Gln
  1               5                  10                  15

Glu Phe Val Tyr Lys Glu Pro
              20

<210> SEQ ID NO 35
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motif C from rat TRG

<400> SEQUENCE: 35

Pro Lys Leu Thr Pro Leu Ser Glu Ile Ser Gln Arg Leu Leu Lys Leu
  1               5                  10                  15

Tyr Ser Asp Lys Phe Gly Ser Glu Asn Val Lys Met Ile Gln Asp Ser
                 20                  25                  30

Gly Lys Val Asn Pro Lys Asp Leu Asp Ser Lys Phe Ala Tyr Ile Gln
              35                  40                  45

Val Thr His Val Thr Pro Phe Phe Asp Glu Lys Glu
           50                  55                  60

<210> SEQ ID NO 36
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motif C from CLASP-1

<400> SEQUENCE: 36

Pro Lys Leu Thr Gly Leu Ser Glu Ile Ser Gln Arg Leu Leu Lys Leu
```

```
                1               5                  10                 15
Tyr Ala Asp Lys Phe Gly Ala Asp Asn Val Lys Ile Ile Gln Asp Ser
                    20                  25                  30

Asn Lys Val Asn Pro Lys Asp Leu Asp Pro Lys Tyr Ala Tyr Ile Gln
            35                  40                  45

Val Thr Tyr Val Thr Pro Phe Phe Glu Glu Lys Glu
        50                  55                  60

<210> SEQ ID NO 37
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motif C from CLASP-2

<400> SEQUENCE: 37

Pro Lys Leu Thr Pro Leu Ser Glu Ile Ser Gln Arg Leu Leu Lys Leu
1               5                   10                  15

Tyr Ser Asp Lys Phe Gly Ser Glu Asn Val Lys Met Thr Gln Asp Ser
                    20                  25                  30

Gly Lys Val Asn Pro Lys Asp Leu Asp Ser Lys Tyr Ala Tyr Ile Gln
            35                  40                  45

Val Thr His Val Ile Pro Phe Phe Asp Glu Lys Glu
        50                  55                  60

<210> SEQ ID NO 38
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motif C from CLASP-4

<400> SEQUENCE: 38

Pro Lys Leu Thr Gly Leu Ser Glu Ile Ser Leu Arg Leu Val Lys Leu
1               5                   10                  15

Tyr Gly Glu Lys Phe Gly Thr Glu Asn Val Lys Ile Ile Gln Asp Ser
                    20                  25                  30

Asp Lys Val Asn Ala Lys Glu Leu Asp Pro Lys Tyr Ala His Ile Gln
            35                  40                  45

Val Thr Tyr Val Lys Pro Tyr Phe Asp Lys Glu
        50                  55                  60

<210> SEQ ID NO 39
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motif C from CLASP-3

<400> SEQUENCE: 39

Pro Ala Ile Thr Lys Leu Ala Glu Ile Ser His Arg Leu Glu Gly Phe
1               5                   10                  15

Tyr Gly Glu Arg Phe Gly Glu Asp Val Val Glu Val Ile Lys Asp Ser
                    20                  25                  30

Asn Pro Val Asp Lys Cys Lys Leu Asp Pro Asn Lys Ala Tyr Ile Gln
            35                  40                  45

Ile Thr Tyr Val Glu Pro Tyr Phe Asp Thr Tyr Glu
        50                  55                  60
```

<210> SEQ ID NO 40
<211> LENGTH: 54
<212> TYPE: PRT
<213> ORGANISM: Artificial Sequence
<220> FEATURE:
<223> OTHER INFORMATION: Description of Artificial Sequence: CLASP/DOCK
motif C from KIAA0716

<400> SEQUENCE: 40

His Asp Tyr Glu Arg Leu Glu Ala Phe Gln Gln Arg Met Leu Asn Glu
1               5                   10                  15

Phe Pro His Ala Ile Ala Met Gln His Ala Asn Gln Pro Asp Glu Thr
            20                  25                  30

Ile Phe Gln Ala Glu Ala Gln Tyr Leu Gln Ile Tyr Ala Val Thr Pro
        35                  40                  45

Ile Pro Glu Ser Gln Glu
    50

<210> SEQ ID NO 41
<211> LENGTH: 54
<212> TYPE: PRT
<213> ORGANISM: Artificial Sequence
<220> FEATURE:
<223> OTHER INFORMATION: Description of Artificial Sequence: CLASP/DOCK
motif C from DOCK3

<400> SEQUENCE: 41

His Asp Tyr Glu Arg Leu Glu Ala Phe Gln Gln Arg Met Leu Ser Glu
1               5                   10                  15

Phe Pro Gln Ala Val Ala Met Gln His Pro Asn His Pro Asp Asp Ala
            20                  25                  30

Ile Leu Gln Cys Asp Ala Gln Tyr Leu Gln Ile Tyr Ala Val Thr Pro
        35                  40                  45

Ile Pro Asp Tyr Val Asp
    50

<210> SEQ ID NO 42
<211> LENGTH: 46
<212> TYPE: PRT
<213> ORGANISM: Artificial Sequence
<220> FEATURE:
<223> OTHER INFORMATION: Description of Artificial Sequence: CLASP/DOCK
motif C from DOCK2

<400> SEQUENCE: 42

Phe Gln Met Gln Leu Met Thr Gln Phe Pro Asn Ala Glu Lys Met Asn
1               5                   10                  15

Thr Thr Ser Ala Pro Gly Asp Asp Val Lys Asn Ala Pro Gly Gln Tyr
            20                  25                  30

Ile Gln Cys Phe Thr Val Gln Pro Val Leu Asp Glu His Pro
        35                  40                  45

<210> SEQ ID NO 43
<211> LENGTH: 53
<212> TYPE: PRT
<213> ORGANISM: Artificial Sequence
<220> FEATURE:
<223> OTHER INFORMATION: Description of Artificial Sequence: CLASP/DOCK
motif C from DOCK180

<400> SEQUENCE: 43

Glu Tyr Glu Arg Arg Glu Asp Phe Gln Met Gln Leu Met Thr Gln Phe

```
                1               5                  10                  15
Pro Asn Ala Glu Lys Met Asn Thr Thr Ser Ala Pro Gly Asp Asp Val
                    20                  25                  30

Lys Asn Ala Pro Gly Gln Tyr Ile Gln Cys Phe Thr Val Gln Pro Val
            35                  40                  45

Leu Asp Glu His Pro
        50

<210> SEQ ID NO 44
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-1

<400> SEQUENCE: 44

Arg Thr Ile Leu Thr Thr Ser His Leu Phe Pro Tyr Val Lys Lys Arg
  1               5                  10                  15

Ile Gln Val Ile Ser Gln Ser Ser Thr Glu Leu Asn Pro Ile Glu Val
                20                  25                  30

Ala Ile Asp Glu Met Ser Arg Lys Val Ser Glu Leu Asn
            35                  40                  45

<210> SEQ ID NO 45
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from rat TRG

<400> SEQUENCE: 45

Arg Thr Ile Leu Thr Ala Ile His Cys Phe Pro Tyr Val Lys Lys Arg
  1               5                  10                  15

Ile Pro Val Met Tyr Gln His His Thr Asp Leu Asn Pro Ile Glu Val
                20                  25                  30

Ala Ile Asp Glu Met Ser Lys Lys Val Ala Glu Leu His
            35                  40                  45

<210> SEQ ID NO 46
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-2D KIAA1058

<400> SEQUENCE: 46

Arg Thr Ile Leu Thr Ala Ile His Cys Phe Pro Tyr Val Lys Lys Arg
  1               5                  10                  15

Ile Pro Val Met Tyr Gln His His Thr Asp Leu Asn Pro Ile Glu Val
                20                  25                  30

Ala Ile Asp Glu Met Ser Lys Lys Val Ala Glu Leu Arg
            35                  40                  45

<210> SEQ ID NO 47
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-2
```

<400> SEQUENCE: 47

Arg Thr Ile Leu Thr Ala Ile His Cys Phe Pro Tyr Val Lys Lys Arg
1               5                   10                  15

Ile Pro Val Met Tyr Gln His His Thr Asp Leu Asn Pro Ile Glu Val
            20                  25                  30

Ala Ile Asp Glu Met Ser Lys Lys Val Ala Glu Leu Arg
        35                  40                  45

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-6

<400> SEQUENCE: 48

Arg Thr Ile Leu Thr Ala Ile His Cys Phe Pro Tyr Val Lys Lys Arg
1               5                   10                  15

Ile Pro Phe Met Tyr Gln His His Thr Asp Leu Asn Pro Ile Glu Val
            20                  25                  30

His Asp Glu Met Ser Lys Lys Val Ala Glu Leu Arg
        35                  40

<210> SEQ ID NO 49
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-4

<400> SEQUENCE: 49

Arg Thr Ile Leu Thr Thr Ser Asn Ser Phe Pro Tyr Val Lys Lys Arg
1               5                   10                  15

Ile Pro Ile Asn Cys Glu Gln Gln Ile Asn Leu Lys Pro Ile Asp Val
            20                  25                  30

Ala Thr Asp Glu Ile Lys Asp Lys Thr Ala Glu Leu Gln
        35                  40                  45

<210> SEQ ID NO 50
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from CLASP-3

<400> SEQUENCE: 50

Lys Thr Ile Leu Thr Thr Ser His Ala Phe Pro Tyr Ile Lys Thr Arg
1               5                   10                  15

Val Asn Val Thr His Lys Glu Glu Ile Ile Leu Thr Pro Ile Glu Val
            20                  25                  30

Ala Ile Glu Asp Met Gln Lys Lys Thr Gln Glu Leu Ala
        35                  40                  45

<210> SEQ ID NO 51
<211> LENGTH: 45
<212> TYPE: PRT
<213> ORGANISM: Artificial Sequence
<220> FEATURE:
<223> OTHER INFORMATION: Description of Artificial Sequence: CLASP/DOCK

```
                         motifs D and E from CLASP-5

<400> SEQUENCE: 51

Asn Thr Val Leu Thr Thr Met His Ala Phe Pro Tyr Ile Lys Thr Arg
 1               5                  10                  15

Ile Ser Val Ile Gln Lys Glu Glu Phe Val Leu Thr Pro Ile Glu Val
                20                  25                  30

Ala Ile Glu Asp Met Lys Lys Lys Thr Leu Gln Leu Ala
        35                  40                  45

<210> SEQ ID NO 52
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from KIAA0716

<400> SEQUENCE: 52

Arg Thr Ser Leu Tyr Leu Val Gln Ser Leu Pro Gly Ile Ser Arg Trp
 1               5                  10                  15

Phe Glu Val Glu Lys Arg Glu Val Val Glu Met Ser Pro Leu Glu Asn
                20                  25                  30

Ala Ile Glu Val Leu Glu Asn Lys Asn Gln Gln Leu Lys
        35                  40                  45

<210> SEQ ID NO 53
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from DOCK2

<400> SEQUENCE: 53

Arg Thr Ser Phe Val Thr Ala Tyr Lys Leu Pro Gly Ile Leu Arg Trp
 1               5                  10                  15

Phe Glu Val Val His Met Ser Gln Thr Thr Ile Ser Pro Leu Glu Asn
                20                  25                  30

Ala Ile Glu Thr Met Ser Thr Ala Asn Glu Lys Ile Leu
        35                  40                  45

<210> SEQ ID NO 54
<211> LENGTH: 45
<212> TYPE: PRT
<213> ORGANISM: Artificial Sequence
<220> FEATURE:
<223> OTHER INFORMATION: Description of Artificial Sequence: CLASP/DOCK
      motifs D and E from DOCK3

<400> SEQUENCE: 54

Arg Thr Thr Leu Thr Leu Thr His Ser Leu Pro Gly Ile Ser Arg Trp
 1               5                  10                  15

Phe Glu Val Glu Arg Arg Glu Leu Val Glu Val Ser Pro Leu Glu Asn
                20                  25                  30

Ala Ile Gln Val Val Glu Asn Lys Asn Gln Glu Leu Arg
        35                  40                  45

<210> SEQ ID NO 55
<211> LENGTH: 45
<212> TYPE: PRT
<213> ORGANISM: Artificial Sequence
<220> FEATURE:
```

<223> OTHER INFORMATION: Description of Artificial Sequence: CLASP/DOCK
      motifs D and E from DOCK180

<400> SEQUENCE: 55

Arg Thr Ser Phe Val Thr Ala Tyr Lys Leu Pro Gly Ile Leu Arg Trp
1               5                   10                  15

Phe Glu Val Val His Met Ser Gln Thr Thr Ile Ser Pro Leu Glu Asn
                20                  25                  30

Ala Ile Glu Thr Met Ser Thr Ala Asn Glu Lys Ile Leu
        35                  40              45

<210> SEQ ID NO 56
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-1

<400> SEQUENCE: 56

Ser Leu Gln Leu Lys Leu Gln Gly Ser Val Ser Val Lys Val Asn Ala
1               5                   10                  15

Gly Pro Met Ala Tyr Ala Arg Ala Phe Leu Glu Glu Thr Asn Ala Lys
                20                  25                  30

Lys Tyr Pro Asp Asn Gln Val Lys Leu Leu Lys Glu Ile Phe Arg Gln
            35                  40                  45

Phe Ala Asp Ala Cys Gly Gln Ala Leu Asp
        50                  55

<210> SEQ ID NO 57
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from rat TRG

<400> SEQUENCE: 57

Lys Leu Gln Leu Lys Leu Gln Gly Ser Val Ser Val Gln Val Asn Ala
1               5                   10                  15

Gly Pro Leu Ala Tyr Ala Arg Ala Phe Leu Asp Asp Thr Asn Thr Lys
                20                  25                  30

Arg Tyr Pro Asp Asn Lys Val Lys Leu Leu Lys Glu Val Phe Arg Gln
            35                  40                  45

Phe Val Glu Ala Cys Gly Gln Ala Leu Ala
        50                  55

<210> SEQ ID NO 58
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-2D KIAA1058

<400> SEQUENCE: 58

Lys Leu Gln Leu Lys Leu Gln Gly Ser Val Ser Val Gln Val Asn Ala
1               5                   10                  15

Gly Pro Leu Ala Tyr Ala Arg Ala Phe Leu Asp Asp Thr Asn Thr Lys
                20                  25                  30

Arg Tyr Pro Asp Asn Lys Val Lys Leu Leu Lys Glu Val Phe Arg Gln
            35                  40                  45

```
Phe Val Glu Ala Cys Gly Gln Ala Leu Ala
     50                  55

<210> SEQ ID NO 59
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-2

<400> SEQUENCE: 59

Lys Leu Gln Leu Lys Leu Gln Gly Ser Val Ser Val Gln Val Asn Ala
 1               5                  10                  15

Gly Pro Leu Ala Tyr Ala Arg Ala Phe Leu Asp Asp Thr Asn Thr Lys
             20                  25                  30

Arg Tyr Pro Asp Asn Lys Val Lys Leu Leu Lys Glu Val Phe Arg Gln
         35                  40                  45

Phe Val Glu Ala Cys Gly Gln Ala Leu Ala
     50                  55

<210> SEQ ID NO 60
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-6

<400> SEQUENCE: 60

Lys Leu Gln Leu Lys Leu Gln Gly Ser Val Ser Val Gln Val Asn Ala
 1               5                  10                  15

Gly Pro Leu Ala Tyr Ala Arg Ala Phe Leu Asp Asp Thr Asn Thr Lys
             20                  25                  30

Arg Tyr Pro Asp Asn Lys Val Lys Leu Leu Lys Glu Val Phe Arg Gln
         35                  40                  45

Phe Val Glu Ala Cys Gly Gln Ala Leu Ala
     50                  55

<210> SEQ ID NO 61
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-3

<400> SEQUENCE: 61

Met Leu Gln Met Val Leu Gln Gly Ser Val Gly Thr Thr Val Asn Gln
 1               5                  10                  15

Gly Pro Leu Glu Val Ala Gln Val Phe Leu Ser Glu Ile Pro Ser Asp
             20                  25                  30

Pro Lys Leu Phe Arg His His Asn Lys Leu Arg Leu Cys Phe Lys Asp
         35                  40                  45

Phe Thr Lys Arg Cys Glu Asp Ala Leu Arg
     50                  55

<210> SEQ ID NO 62
<211> LENGTH: 58
<212> TYPE: PRT
<213> ORGANISM: Artificial Sequence
<220> FEATURE:
```

```
<223> OTHER INFORMATION: Description of Artificial Sequence: CLASP/DOCK
      motifs F and G from CLASP-4

<400> SEQUENCE: 62

Gln Leu Gln Leu Lys Leu Gln Gly Cys Val Ser Val Gln Val Asn Ala
1               5                   10                  15

Gly Pro Leu Ala Tyr Ala Arg Ala Phe Leu Asn Asp Ser Gln Ala Ser
            20                  25                  30

Lys Tyr Pro Pro Lys Lys Val Ser Glu Leu Lys Asp Met Phe Arg Lys
        35                  40                  45

Phe Ile Gln Ala Cys Ser Ile Ala Leu Glu
    50                  55

<210> SEQ ID NO 63
<211> LENGTH: 58
<212> TYPE: PRT
<213> ORGANISM: Artificial Sequence
<220> FEATURE:
<223> OTHER INFORMATION: Description of Artificial Sequence: CLASP/DOCK
      motifs F and G from CLASP-5

<400> SEQUENCE: 63

Met Leu Gln Met Val Leu Gln Gly Ser Val Gly Ala Thr Val Asn Gln
1               5                   10                  15

Gly Pro Leu Glu Val Ala Gln Val Phe Leu Ala Glu Ile Pro Ala Asp
            20                  25                  30

Pro Lys Leu Tyr Arg His His Asn Lys Leu Arg Leu Cys Phe Lys Glu
        35                  40                  45

Phe Ile Met Arg Cys Gly Glu Ala Val Glu
    50                  55

<210> SEQ ID NO 64
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motifs F and G from KIAA0716

<400> SEQUENCE: 64

Pro Leu Thr Met Cys Leu Asn Gly Val Ile Asp Ala Ala Val Asn Gly
1               5                   10                  15

Gly Val Ser Arg Tyr Gln Glu Ala Phe Phe Val Lys Glu Tyr Ile Leu
            20                  25                  30

Ser His Pro Glu Asp Gly Glu Lys Ile Ala Arg Leu Arg Glu Leu Met
        35                  40                  45

Leu Glu Gln Ala Gln Ile Leu Glu Phe Gly Leu Ala
    50                  55                  60

<210> SEQ ID NO 65
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motifs F and G from DOCK2

<400> SEQUENCE: 65

Pro Leu Ser Met Leu Leu Asn Gly Ile Val Asp Pro Ala Val Met Gly
1               5                   10                  15

Gly Phe Ala Lys Tyr Glu Lys Ala Phe Phe Thr Glu Glu Tyr Val Arg
            20                  25                  30
```

Asp His Pro Glu Asp Gln Asp Lys Leu Thr His Leu Lys Asp Leu Ile
         35                  40                  45

Ala Trp Gln Ile Pro Phe Leu Gly Ala Gly Ile Lys
     50                  55                  60

<210> SEQ ID NO 66
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motifs F and G  from DOCK3

<400> SEQUENCE: 66

Leu Leu Ser Met Cys Leu Asn Gly Val Ile Asp Ala Ala Val Asn Gly
 1               5                  10                  15

Gly Ile Ala Arg Tyr Gln Glu Ala Phe Phe Asp Lys Asp Tyr Ile Asn
             20                  25                  30

Lys His Pro Gly Asp Ala Glu Lys Ile Thr Gln Leu Lys Glu Leu Met
         35                  40                  45

Gln Glu Gln Val His Val Leu Gly Val Gly Leu Ala
     50                  55                  60

<210> SEQ ID NO 67
<211> LENGTH: 60
<212> TYPE: PRT
<213> ORGANISM: Artificial Sequence
<220> FEATURE:
<223> OTHER INFORMATION: Description of Artificial Sequence: CLASP/DOCK
      motifs F and G from DOCK180

<400> SEQUENCE: 67

Pro Leu Ser Met Leu Leu Asn Gly Ile Val Asp Pro Ala Val Met Gly
 1               5                  10                  15

Gly Phe Ala Lys Tyr Glu Lys Ala Phe Phe Thr Glu Glu Tyr Val Arg
             20                  25                  30

Asp His Pro Glu Ala His Glu Lys Ile Glu Lys Leu Lys Asp Leu Ile
         35                  40                  45

Ala Trp Gln Ile Pro Phe Leu Ala Glu Gly Ile Arg
     50                  55                  60

<210> SEQ ID NO 68
<211> LENGTH: 683
<212> TYPE: DNA
<213> ORGANISM: Artificial Sequence
<220> FEATURE:
<223> OTHER INFORMATION: Description of Artificial Sequence: Ref 1.1
      sequence of bacterial artificial chromosome BAC4
      using primer HC2AS2
<220> FEATURE:
<221> NAME/KEY: modified_base
<222> LOCATION: (1)..(683)
<223> OTHER INFORMATION: n is g, a, c, or t

<400> SEQUENCE: 68
tttctacagn gtntactcag gtatgtgctc cttcaacaaa attagcagtt gctgctctgt      60
gacaaagttt gcaccatttt gcaagaagaa aaaaatccta atgtgttata ttactatatt    120
tttactctat agatcttttt ctaaagaaag aaagtacaac tgaagtgctt atatgtattc    180
atataaatga ctagtacaag catcattttg caacagattt ccccttttcat tggaggatct    240 tcttgatgtt atttgtacac gatcaatttt tagtcttaat aagatgaggc tgggtgtggt    300

```
ggctcacacc tgtaatccta gcattttgga ggccaaggtg ggcagatcac tttagcccag      360
gggtttgaga ccagcctggc caacatggca aaaccttgtc tctacaaaaa tacnaaaatt      420
atccaggcat ggtgatgtgt gcctgtagtc ccaactncct aggaggctag ggtaggggg       480 atttgcaaga ggctgggagg gtcaaagccc naantgagcc attggtncat gtcacttgga      540
ccccaagcnn ggggnganca agagcaaagg actnntgtnn tttanaaaaa aaaccgggct      600
accatacnna ccaacccncn nacctacccn acctttccan nttaaaanaa ggctttgnct      660
tgcanaggaa aancaaaatn ncc                                              683

<210> SEQ ID NO 69
<211> LENGTH: 673
<212> TYPE: DNA
<213> ORGANISM: Artificial Sequence
<220> FEATURE:
<223> OTHER INFORMATION: Description of Artificial Sequence: Ref 1.2
      sequence of bacterial artificial chromosome BAC26
      using primer HC2AS2
<220> FEATURE:
<221> NAME/KEY: modified_base
<222> LOCATION: (1)..(673)
<223> OTHER INFORMATION: n = g, a, c, or t

<400> SEQUENCE: 69
tctggtttct acagtgtata ctnaggtatg tgctccttna acaaaattag cagttgctgc       60
tctgtgacaa agtttgcacc attttgcaag aagaaaaaaa tcctaatgtg ttatattact      120
atatttttac tctatagatc tttttctaaa gaaagaaagt acaactgaag tgcttatatg      180
tattcatata aatgactagt acaagcatca ttttgcaaca gatttcccct ttcattggag      240
gatcttcttg atgttatttg tacacgatca atttttagtc ttaataagat gaggctgggt      300
gtggtggctc acacctgtaa tcctagcatt ttggaggcca aggtgggcag atcactttag      360
cccaggggtt tgagaccagc ctggccaaca tggcaaaacc ttgtctctac aaaaatacaa      420
aaattatcca ggcatggtga tgtgtgcctg tagtcccagc tacctaggag gctagggtag      480
ggggattgca agaggctngg aggtcaaggc ccgcagtgag ccatggtcat gtcactgcac      540
ccccagccag ggccgacagg agcaagactn ttgtntcaaa aaaaaacagn aaccaacanc      600
caacaacaac aacnaccttt cngcaaaana agcttgctnc aangaaacca aaatgncttc      660
ttnttttccc ccn                                                         673

<210> SEQ ID NO 70
<211> LENGTH: 1034
<212> TYPE: DNA
<213> ORGANISM: Artificial Sequence
<220> FEATURE:
<223> OTHER INFORMATION: Description of Artificial Sequence: Ref 1.3
      sequence of bacterial artificial chromosome BAC6
      using primer HC2AS2
<220> FEATURE:
<221> NAME/KEY: modified_base
<222> LOCATION: (1)..(1034)
<223> OTHER INFORMATION: n = g, a, c, or t

<400> SEQUENCE: 70
agnnnnnccc nctacnccac ttttaaccct ttgaaaacac agtgtttnct caantatgcg       60
ctccttcaca tattagcagt tgctgctctg tgacatagtt gcaccattnt gcaagaagaa      120
aaaatcctaa gtgtnatatc actatatnnn tactctatag atcttntcta aagaaagaaa      180
gtcaactgat gtgcttatat gtatncatat aaatgactag tacatgcatc attttgcaac      240
agatntctcc tcacattgga ggatcttctn gangnattcg acacgatnan tattagtctn      300
```

```
aataagatga ngctggtgtg gnggtacact gnatctagca tntggangca tgtggcagac    360
acttanccnc ggtngagaca gctgtcactg ncnaactgtc tctntaaanc aaanctccg     420 cnggngatgg gctgagccag tcctagnngc tagntagnga tgnngagntg tngcacgncg    480
agngagcatg ntctgtactg actcatcagg cgncnacacg ntctgttcna aaacatacca   540
cacacactcn cacctncgca aaattgctct nnaaanatgc ttntttcaca cngntncaat    600
cnctatatnn tcttctattc tncnacgtnt nattannatc ttncnctgca naacnatncg   660
nccacctnna nnaccttang cttngtttca cgcttatagc tccctacac ntnncagcnn    720 ttncnngtga agggccnccc gaatctacga ncatactctc tccgtatatn gcctcggtca    780
ncgccatctg ctgtntnctc ntcnctngcn nttnancngt ncgctatctc tnnnccggat    840
ccncnccata tnntnnctct acttanagcg taanntntnc ncncactant cacaacttnt    900
ncntnnaact ctatctnctc ctctctacca cctcacttac tacctnttca cncantctcc    960
ttcnctntcc actgatctcc acatagctgc tntactcgcc antttatcat atncacacnc   1020
tctacgctnn ntnt                                                     1034
```

<210> SEQ ID NO 71
<211> LENGTH: 644
<212> TYPE: DNA
<213> ORGANISM: Artificial Sequence
<220> FEATURE:
<223> OTHER INFORMATION: Description of Artificial Sequence: Ref 2.1
      sequence of bacterial artificial chromosome BAC4
      using primer HC2S1
<220> FEATURE:
<221> NAME/KEY: modified_base
<222> LOCATION: (1)..(644)
<223> OTHER INFORMATION: n = g, a, c, or t

<400> SEQUENCE: 71

```
cttgtattna aagagggtct gcaggaagaa gtgtgtagtc ataaatacct cactggatat    60
tttatacagg attctaaaaa acctattagc aatagtatgc tagaaatagt cattagcttc    120
ttgaccttct tagaactgca cactctattg cactgtacag atttcaggat ggctgcaggg    180
attgatttga aaactaagga cacatttcaa taaacaatgt cttcaattga ttttaggc     240 tcctcctact tcaatgaagg acttcaggta gcttataatt acagacacag gctcaataca    300
ataaaaaaat tagtaaggca gagctttaaa aaaaaaaag gaaaagata attctaccag    360 agaaaggcta catggtgact tctgttacca gtaacaaccc ccgcactacc tttgggtctc    420
caggagcaaa acagctaatg tagttgttga tctgcttgaa gacaaagccc ctgtccatga    480
aggtgaaaca tctctgtgga ggaaaacaag caaaaaagtt atttcaggtc caaacatttc    540
ggaaatttgg attcaaagca ggcatttatt gctaataagt ttatccactg acataaaaaa    600
catgccttca acattgccag agcacctact ctattntagt cncn                    644
```

<210> SEQ ID NO 72
<211> LENGTH: 725
<212> TYPE: DNA
<213> ORGANISM: Artificial Sequence
<220> FEATURE:
<223> OTHER INFORMATION: Description of Artificial Sequence: Ref 3.1
      sequence of bacterial artificial chromosome BAC4
      using primer C96AS
<220> FEATURE:
<221> NAME/KEY: modified_base
<222> LOCATION: (1)..(725)
<223> OTHER INFORMATION: n = g, a, c, or t

<400> SEQUENCE: 72

```
aatcagcaga ccaaacagag gcaggtagag ggtggctatc cttgcctgat ggctctgaaa        60
agaagacaca catggtaagt ttgacccagg attctgagaa ccgaactaag ttggtgctga       120
ccatctcctt tatttggatc cttcctataa agacagatat ttgattttag tcccaaaata       180
gagcaaaatc ttagtgctgt taccatgaat tttctaactg attactttct ttacaccact       240
taaaataaag gacattatca atgcacattc cttccattgg ggaccactca cccttgaagc       300
atatctgtca tcaaaagaat gctttatcag caggttcttg agcacactga tggcgatcag       360
acggacctcc cggaactcct ggagggctgt ccccacctcc ctnagtaaca gtcccaccaa       420
gaagtggttt ctgcagaact catctgttaa tgagtagtca agctgggagg tctgaaatga       480
ggatagaaac tactttgngt taggaaagat gcaatgctct tttgaataaa acaaacaaac       540
caaacnaaca aaaaaaaaac taagacccat ccttntgnat ttcaagccca ccctggggtn       600
ggtcaaagag atgatcagna ntttggcntt naaatgaaga aagaaataaa ttntccaggg       660
gntgttctnc ttttagcac anggagggat nttaantgaa aaccaattta aatccaattn       720
aggng                                                                   725
```

<210> SEQ ID NO 73
<211> LENGTH: 689
<212> TYPE: DNA
<213> ORGANISM: Artificial Sequence
<220> FEATURE:
<223> OTHER INFORMATION: Description of Artificial Sequence: Ref 4.1
 sequence of bacterial artificial chromosome BAC4
 using primer C2AS5
<220> FEATURE:
<221> NAME/KEY: modified_base
<222> LOCATION: (1)..(689)
<223> OTHER INFORMATION: n = g, a, c, or t

<400> SEQUENCE: 73

```
ttcctttctg caaggctgtt cccgaatctg tgcttatgag agatcctctc gaatcagcat        60
ttctcacact gttgatgttt ggagttgagg ttgtatatgg agaagctaaa tggaaatcaa       120
gccaacaata aagttttatt aagacagaac aaaataaaga tgagtactga actttaaggg       180
aaattgcttt tattgcactt attttttctg ttaggaagtt ggctcaagag ttgcattcca       240
ttacttcacc tttaaagaac caggtcatat acaatgagat aaaagaaac tagtctgaaa       300
cattcagatg taaacatcaa ttcacttgtt agaaaccacc tttgatcgct aaagactaaa       360
tgcatacctg tttcagaatg tgatagaatg aagacttaaa aaaattaaaa gataaatcca       420
cctacaacta tcaaatcaca aaattaaacc acacaacaaa cttgtagcat tcaaactggt       480
aataaacact gaggagccta cccaactctg aggggtgtca tggggtattt taaattttcg       540
aggagaacac agtgatatgt gacctcagcc agaagctgct gtttnagcag caggttggtg       600
ctatgctcct ttttgaagac atatttgtga agctgggtat tttgggggc ctgcttatga       660
taaaanggca aggtnttcaa tgnaggggn                                         689
```

<210> SEQ ID NO 74
<211> LENGTH: 680
<212> TYPE: DNA
<213> ORGANISM: Artificial Sequence
<220> FEATURE:
<223> OTHER INFORMATION: Description of Artificial Sequence: Ref 4.2
 sequence of bacterial artificial chromosome BAC26
 using primer C2AS5
<220> FEATURE:
<221> NAME/KEY: modified_base
<222> LOCATION: (1)..(680)
<223> OTHER INFORMATION: n = a, g, c, or t

<400> SEQUENCE: 74

```
ttcctttctg gaaggctgtt acccgaatct gtgcttatga gagatcctct cgaatcagca      60
tttctcacac tgttgatgtt tggagttgag gttgtatatg gagaagctaa atggaaatca     120
agccaacaat aaagttttat taagacagaa caaaataaag atgagtactg aactttaagg     180
gaaattgctt ttattgcact tatttttct gttaggaagt tggctcaaga gttgcattcc      240
attacttcac ctttaaagaa ccaggtcata tacaatgaga taaaagaaa ctagtctgaa      300
acattcagat gtaaacatca attcacttgt tagaaaccac ctttgatcgc taaagactaa    360
atgcatacct gtttcagaat gtgatagaat gaagacttaa aaaaattaaa agataaatcc   420
acctacaact atcaaatcac aaaattaaac cncacaacaa acttgtagca ttcaaactgg   480
taataaaaca ctgaggagcc tacccaactt tgaggggtgt caatgggtn ttttaaatt     540
tttcgnggga nancccagtg ntatggtgac cttcacccaa gaagcttgtt tgtttnacca   600
agcnaggttg nnctntgctc cttttagaa nacnntattt tnnnaaatnc tggnttttt     660
nngnggcccc ctncnttnnt                                                680
```

<210> SEQ ID NO 75
<211> LENGTH: 686
<212> TYPE: DNA
<213> ORGANISM: Artificial Sequence
<220> FEATURE:
<223> OTHER INFORMATION: Description of Artificial Sequence: Ref 5.1 sequence of bacterial artificial chromosome BAC4 using primer C2S6
<220> FEATURE:
<221> NAME/KEY: modified_base
<222> LOCATION: (1)..(686)
<223> OTHER INFORMATION: n = g, c, a, or t

<400> SEQUENCE: 75

```
ttcctggata aggtaattgc ttttacccaa cacaaatgtt tcttataatc aatggattta     60
gcccaaagta aacgtacttc atgttctagt gccttttaag tgtgaccttt tgttttttc    120
taaaccaccc ggctgacctg gagtaggtga tgagagcttt aaggttgggg cccattcctt   180
gaagtgctct gattcctgtt tccagtacct cagatcctgg gcaggtttg cagtggagcg    240
tcttgagtga atggctctgg tgggttgaac ggggagggac tcaaaatgct gcccatctca   300
atttcctgta gtcttttat ttatttattt attttttgag acagagtctc gctctgtcgc   360
ccaggctgga gtacagcggc acgatctcaa ttnactgcaa cctccgcctc ctgggttcaa   420
acgactcctc tgcctcagcc tcccagcag ctgggaccac aggcacaagc caccaccgcc   480
cggctaattt tttgtnttt tagtagagat ggggtttcac catatttggc caggctgggc   540
tcaaactcct gacctcgtca tccgcncct cggnctncca aagtgcttgg gattncaggc   600
ngtgagccca cttacacctn gggcaattcc ctgtnagtct tttttaccag agacaccatc   660
attcaacaca gcttttccac ccacaa                                        686
```

<210> SEQ ID NO 76
<211> LENGTH: 672
<212> TYPE: DNA
<213> ORGANISM: Artificial Sequence
<220> FEATURE:
<223> OTHER INFORMATION: Description of Artificial Sequence: Ref 5.2 sequence of bacterial artificial chromosome BAC26 using primer C2S6
<220> FEATURE:

```
<221> NAME/KEY: modified_base
<222> LOCATION: (1)..(672)
<223> OTHER INFORMATION: n = g, a, c, or t

<400> SEQUENCE: 76
tgagaagagc aatttcctgg ataaggtaat tgcttttacc caacacaaat gtttcttata    60
atcaatggat ttagcccaaa gtaaacgtac ttcatgttct agtgcctttt aagtgtgacc   120
ttttgttttt ttctaaacca cccggctgac ctggagtagg tgatgagagc tttaaggttg   180
gggcccattc cttgaagtgc tctgattcct gtttccagta cctcagatcc tgggcagggt   240
ttgcagtgga gcgtcttgag tgaatggctc tggtgggttg aacggggagg gactcaaaat   300
gctgcccatc tcaatttcct gtagtctttt tatttattta tttattttt gagacagagt    360 ctcgctctgt cgcccaggct ggagtacagc ggcacgatct caattcactg caacctccgn   420
ctccctgggt tcaaacgact cctctgnctn agnctcccag cagcctggga accacaggct   480
cangccacca cgcccggcta attnttgtaa ttttnagtaa naaattgggg gttctcacca   540
tnttggccca agncttgggc ctaaaaacct tnctnaccnt cgncattcnc ncccnaccn    600 tgggcnctnc tcaaangngc ttggggattt ancannggcn ttaacccccc ntatcaccgt   660
ggnccttaat tt                                                       672

<210> SEQ ID NO 77
<211> LENGTH: 700
<212> TYPE: DNA
<213> ORGANISM: Artificial Sequence
<220> FEATURE:
<223> OTHER INFORMATION: Description of Artificial Sequence: Ref 6.1
      sequence of bacterial artificial chromosome BAC4
      using primer C2S7
<220> FEATURE:
<221> NAME/KEY: modified_base
<222> LOCATION: (1)..(700)
<223> OTHER INFORMATION: n = g, a, c, or t

<400> SEQUENCE: 77
nagngnnggt ttnagncgtt tgaagcctgn nacgnggtgn gtgctngaac tctgtgggct     60
ttcaggtact ggggtatctg ggagcctgct gtttgcattg ctagtgcatc agaccagggc   120
tttttcctcc ctgtagctgc tacttataca catagctcta actgagatga ttctccagac   180
aactgatgca gagcagcaaa agcttctgcc gttctcccct tctaggagtg tctcctttct    240
ttggaaagag atcatgaggg gctagattgt aatgaagtga ggctcagtgc ttgagcacat    300
ccggtaaaag ttcaatatat tggtcataa agtttctcat tctttatagc agttaatttc    360
tctggctcat gagttttctt agttttaatc tgacttttaa attaatgtct ccagcaccag    420
tcatatcccc agggcaaact caaaggcatg agaggccaga ctcgggtcct ggtcatagca    480
acccctgtct agggccttgg tccctgcctc cgcttgtgtg ctgtggcgca ggtcctatgg    540
gcccttagga aacaggacca ccctgtcgca ccccctacag agaccagcca agtttgacat    600
tagatcaccg tagcaatgtn tgcaaattcc agtttcttgc taaaacaggt taagccttgc    660
agccacttta tctgtaactg gcngaggttt tgacataaaa                         700

<210> SEQ ID NO 78
<211> LENGTH: 676
<212> TYPE: DNA
<213> ORGANISM: Artificial Sequence
<220> FEATURE:
<223> OTHER INFORMATION: Description of Artificial Sequence: Ref 7.1
      sequence of bacterial artificial chromosome BAC4
      using primer C2S8
```

```
<220> FEATURE:
<221> NAME/KEY: modified_base
<222> LOCATION: (1)..(676)
<223> OTHER INFORMATION: n = g, a, c, or t

<400> SEQUENCE: 78
ctctcgacac gctgtttcta ttaacattgg cgtttaaggt ttgtatcaat ttgctgttcg      60
nggttctagt tttacctttc acattcattc tgcttggtaa gctcagtgag cacaaactta     120
ctatgttgca ttttttacttc agcaattatt tttgtccctg taaggaaacc attaatcttt    180
aaattccttt aatgaaatca ttccacagtg aatggcttga atgccctgaa ataaaattta     240
actggtcagt gtgtgctgcg cgcttgggta tggtggaaac acggtctctg gaggcagtta     300
actcttggct cgaaccttga ggatggtgaa tataggcacc taatcaggca tttctgcctt     360
gaatatcttt aaatatatcc aaatgttata gcgtttaatt agatttttat gtagaaagga     420
gcaataaaca caagacacat gttttcagtt ttttatctgt tactgcatta aatgataaaa     480
acgttttgga gatagaaaat gaaggggtt ttttttttgt cttgttttaa agttttagca      540
aataatattc aagtaggtgg agatggactc ttcaccactc tcctgttttt aggaacccaa     600
tacttttttca ttcttgctaa atgattactt ccatttctag catagaaaag gagaaaattg    660
gaatgagtgt ttatat                                                     676

<210> SEQ ID NO 79
<211> LENGTH: 686
<212> TYPE: DNA
<213> ORGANISM: Artificial Sequence
<220> FEATURE:
<223> OTHER INFORMATION: Description of Artificial Sequence: Ref 8.1
      sequence of bacterial artificial chromosome BAC4
      using primer C2S9
<220> FEATURE:
<221> NAME/KEY: modified_base
<222> LOCATION: (1)..(686)
<223> OTHER INFORMATION: n = a, c, g, or t

<400> SEQUENCE: 79
cgctttnaaa tnccagccgc tactgcgggg cgntnaattc gaaacgtgtt gttntctgtg     60
atgcctggct ctgattgtgt gggattggtc atcagtggcg gttggcagnt ggggttcatg     120
gaagcggcca tggggactga tggcaggccc ttggattgcc accgcagagc ctggcagtgt     180
ctttggtctg cattcctacc ggcgaagtct catttcacct cacgtgttat ctcttggaaa     240
gcattccttt agcgggctgt gtctacccct ccatcctctc gtccaaactc ccctccttc     300
tctgttctgt ctccttccca tcctcttctc cccagttctt cttcctatgt tccttcctca    360
gtggtttctc ttcctctgtt tgactttcca aggtcatttt gactgttcct gctcccaact    420
acaaagatac taaaatctca cctaaccact cttcttcttt cttaatgaaa gaatgttttc     480
agtccatccc aaatttgtgt ggacttcaca aaccttctct aaaatggagc ttttctctt     540
cctactcttg actagntggt aaacgctcca tgttcttggc cagaactccc tggtgagtag    600
cgtcactccc actttcctgt gcagaaccaa gcctcctaga aaactccttt gcanctgagt    660
gggttgggac acgcccttttn tttggg                                        686

<210> SEQ ID NO 80
<211> LENGTH: 680
<212> TYPE: DNA
<213> ORGANISM: Artificial Sequence
<220> FEATURE:
<223> OTHER INFORMATION: Description of Artificial Sequence: Ref 9.1
      sequence of bacterial artificial chromosome BAC4
``` using primer C2AS10
<220> FEATURE:
<221> NAME/KEY: modified_base
<222> LOCATION: (1)..(680)
<223> OTHER INFORMATION: n = g, a, t, or c

<400> SEQUENCE: 80

```
tttanaccna tntatccgng tcagttanag gagtctctga gaaatttccg acagcggtgt      60
gagtttgggt tccttgtaaa tatactcctt tccatcttca tcttcaaaga atccctgtga     120
cataaagcac aattagagct atccctgaac gtaagcccag ggcttaccac ctaggaagcg     180
ttcttttatt acaaggggga aaaaaaggaa tgggtctaaa aatccagctg aaatgggctt     240
tctgaatgag aaagaaaatg ctaataacat gaagtctagg tgcaaaggta aggaaaaac      300
acaacattgc aaacttattc aagaatgcag tcattaagtg ttgagtgaaa tgaaagatt      360
tggatacaag actaagctgt cccagggaag tctaatggga gtcaagcctg tttcactttc     420
ccaagaagca gaactcacta naaaatgatg agcagcccac gacaggcagg ctcagaagtg     480
gacatgcctc ccttctcctg atggctncca tgcacacagg attttatggc atgaactgaa     540
gcgtttgggg gtctggagta agtttagtaa aagttaggta aagcttgtat aaattgtatt     600
tttgctttac ccgatgagaa aaaaaatatt naagacctgg tagcttcaat attcaagaaa     660
aatattttc atntcacccg                                                  680
```

<210> SEQ ID NO 81
<211> LENGTH: 619
<212> TYPE: DNA
<213> ORGANISM: Artificial Sequence
<220> FEATURE:
<223> OTHER INFORMATION: Description of Artificial Sequence: Ref 10.1
      sequence of bacterial artificial chromosome BAC4
      using primer C2S11
<220> FEATURE:
<221> NAME/KEY: modified_base
<222> LOCATION: (1)..(619)
<223> OTHER INFORMATION: n = g, a, c, or t

<400> SEQUENCE: 81

```
ngnangtgga gccncgancc aggacaatc tnaacctnct taaactgtac tcggatnaat       60
ttggttctga aaatgtcaaa atgatacagg attctggcaa ggtattgacc atgtttggan    120
aagtttcata gcaatgtaat gttgtgatnc gattacatat natatatttt taaatgtnta    180
tagaaaaaaa cacangaaaa atattaagga ttgttggccc gtgagtggca ggtgtatntt    240
cttnctgatc ctttagngct ttccattaca tgcntgacat taaaaaaanc tttatcgcct    300
aattttttgaa acatctaatt ttacaaaata attaaccgtn tggccangna tattntcatt   360
tttaggncca gctatttaga aactctgaca naaatgaggg gctgtggctt ncctncctnn    420
acttgnccct ctttcnngna tgtaccacat gaacttgncn cctctttcnn ctnaccgggt    480
ggcatgttan aggacaggtt gaaaccncan tngggcngga nttnggtnna attgggacac    540
aatggtacna ngctctatng gaatngaaac tctcccnacn nncngtgnnc cntggggaaa    600
atgngncnna ttcattttn                                                  619
```

<210> SEQ ID NO 82
<211> LENGTH: 597
<212> TYPE: DNA
<213> ORGANISM: Artificial Sequence
<220> FEATURE:
<223> OTHER INFORMATION: Description of Artificial Sequence: Ref 11.1
      sequence of bacterial artificial chromosome BAC4
      using primer C2S12

```
<220> FEATURE:
<221> NAME/KEY: modified_base
<222> LOCATION: (1)..(597)
<223> OTHER INFORMATION: n = g, a, c, or t

<400> SEQUENCE: 82
agnanngttn ngcagctgca nntctggacc canaggccgc angggcacga gccnggacac    60
gctcggcaaa gagctgtcca gagggattca gaagcttcag gactggaagg gtctttcgag   120
ctcagttagc cacccccaca cccatttcag tttcacattt atctagtgct tccttttgaa   180
tacttgggat gtttttctgt tgatctgttg gcacttcctt cttccacaag accagaagct   240
catatccaat ctaaggtcac ttaccttct gagaatctga tgaaaatggc gtgccttatg   300
tgcctagatg cttttgcaca cagtctaagg tgacttatgg actccaggtc cagcagccac   360
acccagtcct gggtctccgc acagggaggg accgtcttc acacacctgt ctcaggttct   420
agcattgggc tgcttcagcg gtctcaggct gtgagtaaat gggatgtgag cttggatcgc   480
cccacgctgt tgncccccgg ggggcttggc cagctggcca cttngaaatg cctccttttg   540
cccaggaaag ctcactgcat ttcaatgggg nttntccacg aagttcanct ttangggg    597

<210> SEQ ID NO 83
<211> LENGTH: 634
<212> TYPE: DNA
<213> ORGANISM: Artificial Sequence
<220> FEATURE:
<223> OTHER INFORMATION: Description of Artificial Sequence: Ref 12.1
      sequence of bacterial artificial chromosome BAC4
      using primer C2S13
<220> FEATURE:
<221> NAME/KEY: modified_base
<222> LOCATION: (1)..(634)
<223> OTHER INFORMATION: n = a, c, g, or t

<400> SEQUENCE: 83
agnaaggtnn ctcantnaan ncagcgtgag ngttcaggtg agccaggcac agcaggccgg    60
agggcagcag gggacgtcct tgcccctggg tgacttgaga gtcgtttcca ctaacaaggt   120
ctacttgaga gcctcggttt accaagtgat ccctgctccc ttcccccaac gtntgtgaca   180
tttctcctga tatcagaggg ggaggaaacc tcatgatccc tgccccccgc cccatgagga   240
ctgactgtgg ggacaaagag ccagatctca tagactaccc tgatttgtca gtatttgggg   300
aattctgggt gcctgattag aagcatcaag actcttctaa atncaaagaa gtgtggagag   360
cagtagattt tcctataaaa ctggtgttgc tggtttctat gaaaattgga tccaaaaaaa   420
gtccttaagt ttaccctctt aatggnatct tttgattaat ggaattcatt attttaatat   480
agcccaatca atccaatttt tctttattgg tagcattttt atgttctctt taaaaaaatc   540
ttggnctacc tccaaaattt cacagatgtt ctcctagggt tttcctcctt ttggttcaag   600
catcccattc aangtcttgc agtccattct gggg                               634

<210> SEQ ID NO 84
<211> LENGTH: 567
<212> TYPE: DNA
<213> ORGANISM: Artificial Sequence
<220> FEATURE:
<223> OTHER INFORMATION: Description of Artificial Sequence: Ref 13.1
      sequence of bacterial artificial chromosome BAC4
      using primer C2S14
<220> FEATURE:
<221> NAME/KEY: modified_base
<222> LOCATION: (1)..(567)
<223> OTHER INFORMATION: n = a, g, c, or t
```

```
<400> SEQUENCE: 84
gacttanatt tattcttcct tgcagagtag tgttagaata gatggcctac agaaaaaaaa      60
ggttctggga tctacatggc agggagggct gcactgacat tgatgcctgg gggacctttt     120
gcctcgaggc tgagctggaa atcttgaaa atatttttt tttcctgtgg cacattcagg       180
ttgaatacaa gaactatttt tgtgactatg tttttgatga cctaagggaa ctgaccattg     240
taatttttgt accantgaac cangagattt aagtgctttt atattcattt ccttgcattt     300
aagaaaatat gaaagcttaa ggaattatgt gagcttaaaa ctagtcaagc antttagaac     360
caaaggccta tnttnataac cgcaactatg ctnaaaagna caaagtagta cagnatattg     420
ntatgtacat atcatttggt aatacacncc nggcnttctg tacatatatg tattacattt     480
ctacnttttt aatactcccn tgggcttatg ccnttaaggt taanttgnga taaatttngg     540
ctgttccngt ntatncnata ncctttt                                         567

<210> SEQ ID NO 85
<211> LENGTH: 662
<212> TYPE: DNA
<213> ORGANISM: Artificial Sequence
<220> FEATURE:
<223> OTHER INFORMATION: Description of Artificial Sequence: Ref 14.1
      sequence of bacterial artificial chromosome BAC4
      using primer C2AS15
<220> FEATURE:
<221> NAME/KEY: modified_base
<222> LOCATION: (1)..(662)
<223> OTHER INFORMATION: n = a, c, g, t

<400> SEQUENCE: 85
atgagaatgt aatacatata tgtacagaat gccaggactg tattaacaat gatatgtaca      60
taacaatata ctgtactact tgtactttt cagcatagtt gcggttatta atataggcct     120
ttggttctaa actgcttgac tagttttaag ctcacataat tccttaagct ttcatatttt     180
cttaaatgca aggaaatgaa tataaaagca ctaaatctcc tggttcactg gtacaaaaat     240
tacaatggtc agttcccttta ggtcatcaaa aactagtcac aaaaatagtt cttgtattca     300
acctgaatgt gccacaggaa aaaaaaaata ttttcaagat tttccagctc agcctcgagg     360
caaaaggccc ccaggcatca atgtcagngc agccctcctg ccatgtagat cccagaacct     420 ttttttctg taggccatct attctaacac tactctgcag ggagaataaa atctaaagnc     480
cagctcaaga gtgctaccac acctttgtta agacacaatg aaaactttgg atattggcag     540
gngagattta aaaaaaaatg tgccctttct taccactcct atagnaaagt ctggttaaga     600
aataaccgtt ggtctttatt ttccttttnt ttccccttcc cttgggncctt cctggggctc     660 gg                                                                    662

<210> SEQ ID NO 86
<211> LENGTH: 19
<212> TYPE: PRT
<213> ORGANISM: Artificial Sequence
<220> FEATURE:
<223> OTHER INFORMATION: Description of Artificial Sequence: KV1.3
      inhibitor

<400> SEQUENCE: 86

Thr Thr Asn Asn Asn Pro Asn Ser Ala Val Asn Ile Lys Lys Ile Phe
  1               5                  10                  15

Thr Asp Val
```

<210> SEQ ID NO 87
<211> LENGTH: 4898
<212> TYPE: DNA
<213> ORGANISM: Homo sapiens
<220> FEATURE:
<221> NAME/KEY: CDS
<222> LOCATION: (567)..(4148)
<223> OTHER INFORMATION: Human CLASP-2

<400> SEQUENCE: 87

```
aattgtaata cgactcacta tagggcgaat tgggtaccgg gccccccctc gaggtcgacg      60
gtatcgataa gcttgatatc gaattcggca cgagttttac accatcacca aaacccagaa    120 tttatgatg agattaaaat agagttgccc actcagctgc atgaaaagca ccacctgttg     180
ctcacattct tccatgtcag ctgtgacaac tcaagtaaag gaagcacgaa gaagagggat    240
gtcgttgaaa cccaagttgg ctactcctgg cttcccctcc tgaaagacgg aagggtggtg    300
acaagcgagc agcacatccc ggtctcggcg aaccttcctt cgggctatct tggctaccaa    360
gagcttggga tgggcaggca ttatggtccg gaaattaaat gggtagatgg aggcaagcca    420
ctgctgaaaa tttccactca tctggtttct acagggatac tcaggatcag catttacata    480 atttttttcca gtactgtcag aaaaccgaat ctggagccca agccttagga aacgaacttg    540
taaagtacct taagagtctg catgcg atg gaa ggc cac gtg atg atc gcc ttc     593
                                Met Glu Gly His Val Met Ile Ala Phe
                                  1               5 ttg ccc act atc cta aac cag ctg ttc cga gtc ctc acc aga gcc aca        641
Leu Pro Thr Ile Leu Asn Gln Leu Phe Arg Val Leu Thr Arg Ala Thr
 10                  15                  20                  25 cag gaa gaa gtc gcg gtt aac gtg act cgg gtc att att cat gtg gtt        689
Gln Glu Glu Val Ala Val Asn Val Thr Arg Val Ile Ile His Val Val
             30                  35                  40 gcc cag tgc cat gag gaa gga ttg gag agc cac ttg agg tca tat gtt        737
Ala Gln Cys His Glu Glu Gly Leu Glu Ser His Leu Arg Ser Tyr Val
         45                  50                  55 aag tac gcg tat aag gct gag cca tat gtt gcc tct gaa tac aag aca        785
Lys Tyr Ala Tyr Lys Ala Glu Pro Tyr Val Ala Ser Glu Tyr Lys Thr
     60                  65                  70 gtg cat gaa gaa ctg acc aaa tcc atg acc acg att ctc aag cct tct        833
Val His Glu Glu Leu Thr Lys Ser Met Thr Thr Ile Leu Lys Pro Ser
 75                  80                  85 gcc gat ttc ctc acc agc aac aaa cta ctg agg tac tca tgg ttt ttc        881
Ala Asp Phe Leu Thr Ser Asn Lys Leu Leu Arg Tyr Ser Trp Phe Phe
 90                  95                 100                 105 ttt gat gta ctg atc aaa tct atg gct cag cat ttg ata gag aac tcc        929
Phe Asp Val Leu Ile Lys Ser Met Ala Gln His Leu Ile Glu Asn Ser
            110                 115                 120 aaa gtt aag ttg ctg cga aac cag aga ttt cct gca tcc tat cat cat        977
Lys Val Lys Leu Leu Arg Asn Gln Arg Phe Pro Ala Ser Tyr His His
        125                 130                 135 gca gcg gaa acc gtt gta aat atg ctg atg cca cac atc act cag aag       1025
Ala Ala Glu Thr Val Val Asn Met Leu Met Pro His Ile Thr Gln Lys
    140                 145                 150 ttt gga gat aat cca gag gca tct aag aac gcg aat cat agc ctt gct       1073
Phe Gly Asp Asn Pro Glu Ala Ser Lys Asn Ala Asn His Ser Leu Ala
155                 160                 165 gtc ttc atc aag aga tgt ttc acc ttc atg gac agg ggc ttt gtc ttc       1121
Val Phe Ile Lys Arg Cys Phe Thr Phe Met Asp Arg Gly Phe Val Phe
170                 175                 180                 185 aag cag atc aac aac tac att agc tgt ttt gct cct gga gac cca aag       1169
Lys Gln Ile Asn Asn Tyr Ile Ser Cys Phe Ala Pro Gly Asp Pro Lys
```

```
                        190                 195                 200
acc ctc ttt gaa tac aag ttt gaa ttt ctc cgt gta gtg tgc aac cat        1217
Thr Leu Phe Glu Tyr Lys Phe Glu Phe Leu Arg Val Val Cys Asn His
            205                 210                 215 gaa cat tat att ccg ttg aac tta cca atg cca ttt gga aaa ggc agg        1265
Glu His Tyr Ile Pro Leu Asn Leu Pro Met Pro Phe Gly Lys Gly Arg
            220                 225                 230 att caa aga tac caa gac ctc cag ctt gac tac tca tta aca gat gag        1313
Ile Gln Arg Tyr Gln Asp Leu Gln Leu Asp Tyr Ser Leu Thr Asp Glu
235                 240                 245 ttc tgc aga aac cac ttc ttg gtg gga ctg tta ctg agg gag gtg ggg        1361
Phe Cys Arg Asn His Phe Leu Val Gly Leu Leu Leu Arg Glu Val Gly
250                 255                 260                 265 aca gcc ctc cag gag ttc cgg gag gtc cgt ctg atc gcc atc agt gtg        1409
Thr Ala Leu Gln Glu Phe Arg Glu Val Arg Leu Ile Ala Ile Ser Val
                270                 275                 280 ctc aag aac ctg ctg ata aag cat tct ttt gat gac aga tat gct tca        1457
Leu Lys Asn Leu Leu Ile Lys His Ser Phe Asp Asp Arg Tyr Ala Ser
            285                 290                 295 agg agc cat cag gca agg ata gcc acc ctc tac ctg cct ctg ttt ggt        1505
Arg Ser His Gln Ala Arg Ile Ala Thr Leu Tyr Leu Pro Leu Phe Gly
            300                 305                 310 ctg ctg att gaa aac gtc cag cgg atc aat gtg agg gat gtg tca ccc        1553
Leu Leu Ile Glu Asn Val Gln Arg Ile Asn Val Arg Asp Val Ser Pro
315                 320                 325 ttc cct gtg aac gcg ggc atg acc gtg aag gat gaa tcc ctg gct cta        1601
Phe Pro Val Asn Ala Gly Met Thr Val Lys Asp Glu Ser Leu Ala Leu
330                 335                 340                 345 cca gct gtg aat ccg ctg gtg acg ccg cag aag gga agc acc ctg gac        1649
Pro Ala Val Asn Pro Leu Val Thr Pro Gln Lys Gly Ser Thr Leu Asp
                350                 355                 360 aac agc ctg cac aag gac ctg ctg ggc gcc atc tcc ggc att gct tct        1697
Asn Ser Leu His Lys Asp Leu Leu Gly Ala Ile Ser Gly Ile Ala Ser
            365                 370                 375 cca tat aca acc tca act cca aac atc aac agt gtg aga aat gct gat        1745
Pro Tyr Thr Thr Ser Thr Pro Asn Ile Asn Ser Val Arg Asn Ala Asp
            380                 385                 390 tcg aga gga tct ctc ata agc aca gat tcg ggt aac agc ctt cca gaa        1793
Ser Arg Gly Ser Leu Ile Ser Thr Asp Ser Gly Asn Ser Leu Pro Glu
395                 400                 405 agg aat agt gag aag agc aat tcc ctg gat aag cac caa caa agt agc        1841
Arg Asn Ser Glu Lys Ser Asn Ser Leu Asp Lys His Gln Gln Ser Ser
410                 415                 420                 425 aca ttg gga aat tcc gtg gtt cgc tgt gat aaa ctt gac cag tct gag        1889
Thr Leu Gly Asn Ser Val Val Arg Cys Asp Lys Leu Asp Gln Ser Glu
                430                 435                 440 att aag agc cta ctg atg tgt ttc ctc tac atc tta aag agc atg tct        1937
Ile Lys Ser Leu Leu Met Cys Phe Leu Tyr Ile Leu Lys Ser Met Ser
            445                 450                 455 gat gat gct ttg ttt aca tat tgg aac aag gct tca aca tct gaa ctt        1985
Asp Asp Ala Leu Phe Thr Tyr Trp Asn Lys Ala Ser Thr Ser Glu Leu
            460                 465                 470 atg gat ttt ttt aca ata tct gaa gtc tgc ctg cac cag ttc cag tac        2033
Met Asp Phe Phe Thr Ile Ser Glu Val Cys Leu His Gln Phe Gln Tyr
475                 480                 485 atg ggg aag cga tac ata gcc agg aac cag gag ggg ttg gga ccc ata        2081
Met Gly Lys Arg Tyr Ile Ala Arg Asn Gln Glu Gly Leu Gly Pro Ile
490                 495                 500                 505 gtt cat gat cga aag tct cag aca ttg cct gtt tcc cgt aac aga aca        2129
```

```
Val His Asp Arg Lys Ser Gln Thr Leu Pro Val Ser Arg Asn Arg Thr
            510                 515                 520 gga atg atg cat gcc aga ttg cag cag ctg ggc agc ctg gat aac tct     2177
Gly Met Met His Ala Arg Leu Gln Gln Leu Gly Ser Leu Asp Asn Ser
        525                 530                 535 ctc act ttt aac cac agc tat ggc cac tcg gac gca gat gtt ctg cac     2225
Leu Thr Phe Asn His Ser Tyr Gly His Ser Asp Ala Asp Val Leu His
            540                 545                 550 cag tca tta ctt gaa gcc aac att gct act gag gtt tgc ctg aca gct     2273
Gln Ser Leu Leu Glu Ala Asn Ile Ala Thr Glu Val Cys Leu Thr Ala
    555                 560                 565 ctg gac acg ctt tct cta ttt aca ttg gcg ttt aag aac cag ctc ctg     2321
Leu Asp Thr Leu Ser Leu Phe Thr Leu Ala Phe Lys Asn Gln Leu Leu
570                 575                 580                 585 gcc gac cat gga cat aat cct ctc atg aaa aaa gtt ttt gat gtc tac     2369
Ala Asp His Gly His Asn Pro Leu Met Lys Lys Val Phe Asp Val Tyr
            590                 595                 600 ctg tgt ttt ctt caa aaa cat cag tct gaa acg gct tta aaa aat gtc     2417
Leu Cys Phe Leu Gln Lys His Gln Ser Glu Thr Ala Leu Lys Asn Val
        605                 610                 615 ttc act gcc tta agg tcc tta att tat aag ttt ccc tca aca ttc tat     2465
Phe Thr Ala Leu Arg Ser Leu Ile Tyr Lys Phe Pro Ser Thr Phe Tyr
            620                 625                 630 gaa ggg aga gcg gac atg tgt gcg gct ctg tgt tac gag att ctc aag     2513
Glu Gly Arg Ala Asp Met Cys Ala Ala Leu Cys Tyr Glu Ile Leu Lys
    635                 640                 645 tgc tgt aac tcc aag ctg agc tcc atc agg acg gag gcc tcc cag ctg     2561
Cys Cys Asn Ser Lys Leu Ser Ser Ile Arg Thr Glu Ala Ser Gln Leu
650                 655                 660                 665 ctc tac ttc ctg atg agg aac aac ttt gat tac act gga aag aag tcc     2609
Leu Tyr Phe Leu Met Arg Asn Asn Phe Asp Tyr Thr Gly Lys Lys Ser
            670                 675                 680 ttt gtc cgg aca cat ttg caa gtc atc ata tct gtc agc cag ctg ata     2657
Phe Val Arg Thr His Leu Gln Val Ile Ile Ser Val Ser Gln Leu Ile
        685                 690                 695 gca gac gtt gtt ggc att ggg gaa acc aga ttc cag cag tcc ctg tcc     2705
Ala Asp Val Val Gly Ile Gly Glu Thr Arg Phe Gln Gln Ser Leu Ser
            700                 705                 710 atc atc aac aac tgt gcc aac agt gac cgg ctt att aag cac acc agc     2753
Ile Ile Asn Asn Cys Ala Asn Ser Asp Arg Leu Ile Lys His Thr Ser
    715                 720                 725 ttc tcc tct gat gtg aag gac tta acc aaa agg ata cgc acg gtg cta     2801
Phe Ser Ser Asp Val Lys Asp Leu Thr Lys Arg Ile Arg Thr Val Leu
730                 735                 740                 745 atg gcc acc gcc cag atg aag gag cat gag aac gac cca gag atg ctg     2849
Met Ala Thr Ala Gln Met Lys Glu His Glu Asn Asp Pro Glu Met Leu
            750                 755                 760 gtg gac ctc cag tac agc ctg gcc aaa tcc tat gcc agc acg ccc gag     2897
Val Asp Leu Gln Tyr Ser Leu Ala Lys Ser Tyr Ala Ser Thr Pro Glu
        765                 770                 775 ctc agg aag acg tgg ctc gac agc atg gcc agg atc cat gtc aaa aat     2945
Leu Arg Lys Thr Trp Leu Asp Ser Met Ala Arg Ile His Val Lys Asn
            780                 785                 790 ggc gat ctc tca gag gca gca atg tgc tat gtc cac gta aca gcc cta     2993
Gly Asp Leu Ser Glu Ala Ala Met Cys Tyr Val His Val Thr Ala Leu
    795                 800                 805 gtg gca gaa tat ctc aca cgg aaa ggc gtg ttt aga caa gga tgc acc     3041
Val Ala Glu Tyr Leu Thr Arg Lys Gly Val Phe Arg Gln Gly Cys Thr
810                 815                 820                 825
```

```
gcc ttc agg gtc att acc cca aac atc gac gag gag gcc tcc atg atg    3089
Ala Phe Arg Val Ile Thr Pro Asn Ile Asp Glu Glu Ala Ser Met Met
            830                 835                 840 gaa gac gtg ggg atg cag gat gtc cat ttc aac gag gat gtg ctg atg    3137
Glu Asp Val Gly Met Gln Asp Val His Phe Asn Glu Asp Val Leu Met
            845                 850                 855 gag ctc ctt gag cag tgc gca gat gga ctc tgg aaa gcc gag cgc tac    3185
Glu Leu Leu Glu Gln Cys Ala Asp Gly Leu Trp Lys Ala Glu Arg Tyr
            860                 865                 870 gag ctc atc gcc gac atc tac aaa ctt atc atc ccc att tat gag aag    3233
Glu Leu Ile Ala Asp Ile Tyr Lys Leu Ile Ile Pro Ile Tyr Glu Lys
            875                 880                 885 cgg agg gat ttc ttt gaa gat gaa gat gga aag gag tat att tac aag    3281
Arg Arg Asp Phe Phe Glu Asp Glu Asp Gly Lys Glu Tyr Ile Tyr Lys
890                 895                 900                 905 gaa ccc aaa ctc aca ccg ctg tcg gaa att tct cag aga ctc ctt aaa    3329
Glu Pro Lys Leu Thr Pro Leu Ser Glu Ile Ser Gln Arg Leu Leu Lys
            910                 915                 920 ctg tac tcg gat aaa ttt ggt tct gaa aat gtc aaa atg ata cag gat    3377
Leu Tyr Ser Asp Lys Phe Gly Ser Glu Asn Val Lys Met Ile Gln Asp
            925                 930                 935 tct ggc aag gtc aac cct aag gat ctg gat tct aag tat gca tac atc    3425
Ser Gly Lys Val Asn Pro Lys Asp Leu Asp Ser Lys Tyr Ala Tyr Ile
            940                 945                 950 cag gtg act cac gtc atc ccc ttc ttt gac gaa aaa gag ttg caa gaa    3473
Gln Val Thr His Val Ile Pro Phe Phe Asp Glu Lys Glu Leu Gln Glu
            955                 960                 965 agg aaa aca gag ttt gag aga tcc cac aac atc cgc cgc ttc atg ttt    3521
Arg Lys Thr Glu Phe Glu Arg Ser His Asn Ile Arg Arg Phe Met Phe
970                 975                 980                 985 gag atg cca ttt acg cag acc ggg aag agg cag ggc ggg gtg gaa gag    3569
Glu Met Pro Phe Thr Gln Thr Gly Lys Arg Gln Gly Gly Val Glu Glu
            990                 995                 1000 cag tgc aaa cgg cgc acc atc ctg aca gcc ata cac tgc ttc cct tat    3617
Gln Cys Lys Arg Arg Thr Ile Leu Thr Ala Ile His Cys Phe Pro Tyr
            1005                1010                1015 gtg aag aag cgc atc cct gtc atg tac cag cac cac act gac ctg aac    3665
Val Lys Lys Arg Ile Pro Val Met Tyr Gln His His Thr Asp Leu Asn
            1020                1025                1030 ccc atc gag gtg gcc att gac gag atg agt aag aag gtg gcg gag ctc    3713
Pro Ile Glu Val Ala Ile Asp Glu Met Ser Lys Lys Val Ala Glu Leu
            1035                1040                1045 cgg cag ctg tgc tcc tcg gcc gag gtg gac atg atc aaa ctg cag ctc    3761
Arg Gln Leu Cys Ser Ser Ala Glu Val Asp Met Ile Lys Leu Gln Leu
1050                1055                1060                1065 aaa ctc cag ggc agc gtg agt gtt cag gtc aat gct ggc cca cta gca    3809
Lys Leu Gln Gly Ser Val Ser Val Gln Val Asn Ala Gly Pro Leu Ala
            1070                1075                1080 tat gcg cga gct ttc tta gat gat aca aac aca aag cga tat cct gac    3857
Tyr Ala Arg Ala Phe Leu Asp Asp Thr Asn Thr Lys Arg Tyr Pro Asp
            1085                1090                1095 aat aaa gtg aag ctg ctt aag gaa gtt ttc agg caa ttt gtg gaa gct    3905
Asn Lys Val Lys Leu Leu Lys Glu Val Phe Arg Gln Phe Val Glu Ala
            1100                1105                1110 tgc ggt caa gcc tta gcg gta aac gaa cgt ctg att aaa gaa gac cag    3953
Cys Gly Gln Ala Leu Ala Val Asn Glu Arg Leu Ile Lys Glu Asp Gln
            1115                1120                1125 ctc gag tat cag gaa gaa atg aaa gcc aac tac agg gaa atg gcg aag    4001
Leu Glu Tyr Gln Glu Glu Met Lys Ala Asn Tyr Arg Glu Met Ala Lys
1130                1135                1140                1145
```

-continued

```
gag ctt tct gaa atc atg cat gag cag atc tgc ccc ctg gag gag aag       4049
Glu Leu Ser Glu Ile Met His Glu Gln Ile Cys Pro Leu Glu Glu Lys
            1150                1155                1160 acg agc gtc tta ccg aat tcc ctt cac atc ttc aac gcc atc agt ggg       4097
Thr Ser Val Leu Pro Asn Ser Leu His Ile Phe Asn Ala Ile Ser Gly
        1165                1170                1175 act cca aca agc aca atg gtt cac ggg atg acc agc tcg tct tcg gtc       4145
Thr Pro Thr Ser Thr Met Val His Gly Met Thr Ser Ser Ser Ser Val
        1180                1185                1190 gtg tgattacatc tcatggcccg tgtgtgggga cttgctttgt catttgcaaa            4198
Val ctcaggatgc tttccaaagc caatcactgg ggagaccgag cacagggagg accaagggga     4258
aggggagaga aggaaataa agaacaacgt tatttcttaa cagactttct ataggagttg      4318
taagaaggtg cacatatttt tttaaatctc actggcaata ttcaaagttt tcattgtgtc     4378
ttaacaaagg tgtggtagac actcttgagc tggacttaga ttttattctt ccttgcagag     4438
tagtgttaga atagatggcc tacagaaaaa aaaggttctg ggatctacat ggcagggagg     4498
gctgcactga cattgatgcc tgggggacct tttgcctcga ctcgtgccgg aaatctgatc     4558
gtaatcaggg tacagaactt actagttttg tctaggagta tgttgtatga ctaggatttg     4618
tgctattatc tcattcaaca acatagagca agaatagtga gctaactgag ctagacactc     4678
aattaatccg ctactggctt caagtcagaa ctttgtcatt aatcatcgac tccgggacgg     4738
tcatatatgt attacatttc tacatttta atactcacat gggcttatgc attaagttta      4798
attgtgataa atttgtgctg gtccagtata tgcaatacac tttaatggtt tattcttgtc     4858
ataaaaatgt gcaatatgga gatgtataca agtctttact                          4898
```

<210> SEQ ID NO 88
<211> LENGTH: 1194
<212> TYPE: PRT
<213> ORGANISM: Homo sapiens
<223> OTHER INFORMATION: Human CLASP-2

<400> SEQUENCE: 88

```
Met Glu Gly His Val Met Ile Ala Phe Leu Pro Thr Ile Leu Asn Gln
 1               5                   10                  15

Leu Phe Arg Val Leu Thr Arg Ala Thr Gln Glu Glu Val Ala Val Asn
                20                  25                  30

Val Thr Arg Val Ile Ile His Val Val Ala Gln Cys His Glu Glu Gly
            35                  40                  45

Leu Glu Ser His Leu Arg Ser Tyr Val Lys Tyr Ala Tyr Lys Ala Glu
        50                  55                  60

Pro Tyr Val Ala Ser Glu Tyr Lys Thr Val His Glu Glu Leu Thr Lys
 65                  70                  75                  80

Ser Met Thr Thr Ile Leu Lys Pro Ser Ala Asp Phe Leu Thr Ser Asn
                85                  90                  95

Lys Leu Leu Arg Tyr Ser Trp Phe Phe Phe Asp Val Leu Ile Lys Ser
                100                 105                 110

Met Ala Gln His Leu Ile Glu Asn Ser Lys Val Lys Leu Leu Arg Asn
            115                 120                 125

Gln Arg Phe Pro Ala Ser Tyr His His Ala Ala Glu Thr Val Val Asn
        130                 135                 140

Met Leu Met Pro His Ile Thr Gln Lys Phe Gly Asp Asn Pro Glu Ala
145                 150                 155                 160
```

-continued

```
Ser Lys Asn Ala Asn His Ser Leu Ala Val Phe Ile Lys Arg Cys Phe
            165                 170                 175

Thr Phe Met Asp Arg Gly Phe Val Phe Lys Gln Ile Asn Asn Tyr Ile
        180                 185                 190

Ser Cys Phe Ala Pro Gly Asp Pro Lys Thr Leu Phe Glu Tyr Lys Phe
    195                 200                 205

Glu Phe Leu Arg Val Val Cys Asn His Glu His Tyr Ile Pro Leu Asn
210                 215                 220

Leu Pro Met Pro Phe Gly Lys Gly Arg Ile Gln Arg Tyr Gln Asp Leu
225                 230                 235                 240

Gln Leu Asp Tyr Ser Leu Thr Asp Glu Phe Cys Arg Asn His Phe Leu
            245                 250                 255

Val Gly Leu Leu Leu Arg Glu Val Gly Thr Ala Leu Gln Glu Phe Arg
        260                 265                 270

Glu Val Arg Leu Ile Ala Ile Ser Val Leu Lys Asn Leu Leu Ile Lys
    275                 280                 285

His Ser Phe Asp Asp Arg Tyr Ala Ser Arg Ser His Gln Ala Arg Ile
290                 295                 300

Ala Thr Leu Tyr Leu Pro Leu Phe Gly Leu Leu Ile Glu Asn Val Gln
305                 310                 315                 320

Arg Ile Asn Val Arg Asp Val Ser Pro Phe Pro Val Asn Ala Gly Met
            325                 330                 335

Thr Val Lys Asp Glu Ser Leu Ala Leu Pro Ala Val Asn Pro Leu Val
        340                 345                 350

Thr Pro Gln Lys Gly Ser Thr Leu Asp Asn Ser Leu His Lys Asp Leu
    355                 360                 365

Leu Gly Ala Ile Ser Gly Ile Ala Ser Pro Tyr Thr Thr Ser Thr Pro
370                 375                 380

Asn Ile Asn Ser Val Arg Asn Ala Asp Ser Arg Gly Ser Leu Ile Ser
385                 390                 395                 400

Thr Asp Ser Gly Asn Ser Leu Pro Glu Arg Asn Ser Glu Lys Ser Asn
            405                 410                 415

Ser Leu Asp Lys His Gln Gln Ser Ser Thr Leu Gly Asn Ser Val Val
        420                 425                 430

Arg Cys Asp Lys Leu Asp Gln Ser Glu Ile Lys Ser Leu Leu Met Cys
    435                 440                 445

Phe Leu Tyr Ile Leu Lys Ser Met Ser Asp Asp Ala Leu Phe Thr Tyr
450                 455                 460

Trp Asn Lys Ala Ser Thr Ser Glu Leu Met Asp Phe Phe Thr Ile Ser
465                 470                 475                 480

Glu Val Cys Leu His Gln Phe Gln Tyr Met Gly Lys Arg Tyr Ile Ala
            485                 490                 495

Arg Asn Gln Glu Gly Leu Gly Pro Ile Val His Asp Arg Lys Ser Gln
        500                 505                 510

Thr Leu Pro Val Ser Arg Asn Arg Thr Gly Met Met His Ala Arg Leu
    515                 520                 525

Gln Gln Leu Gly Ser Leu Asp Asn Ser Leu Thr Phe Asn His Ser Tyr
530                 535                 540

Gly His Ser Asp Ala Asp Val Leu His Gln Ser Leu Leu Glu Ala Asn
545                 550                 555                 560

Ile Ala Thr Glu Val Cys Leu Thr Ala Leu Asp Thr Leu Ser Leu Phe
            565                 570                 575

Thr Leu Ala Phe Lys Asn Gln Leu Leu Ala Asp His Gly His Asn Pro
```

-continued

```
                    580                 585                 590
Leu Met Lys Lys Val Phe Asp Val Tyr Leu Cys Phe Leu Gln Lys His
            595                 600                 605
Gln Ser Glu Thr Ala Leu Lys Asn Val Phe Thr Ala Leu Arg Ser Leu
            610                 615                 620
Ile Tyr Lys Phe Pro Ser Thr Phe Tyr Glu Gly Arg Ala Asp Met Cys
625                 630                 635                 640
Ala Ala Leu Cys Tyr Glu Ile Leu Lys Cys Cys Asn Ser Lys Leu Ser
                    645                 650                 655
Ser Ile Arg Thr Glu Ala Ser Gln Leu Leu Tyr Phe Leu Met Arg Asn
            660                 665                 670
Asn Phe Asp Tyr Thr Gly Lys Lys Ser Phe Val Arg Thr His Leu Gln
            675                 680                 685
Val Ile Ile Ser Val Ser Gln Leu Ile Ala Asp Val Val Gly Ile Gly
            690                 695                 700
Glu Thr Arg Phe Gln Gln Ser Leu Ser Ile Ile Asn Asn Cys Ala Asn
705                 710                 715                 720
Ser Asp Arg Leu Ile Lys His Thr Ser Phe Ser Ser Asp Val Lys Asp
                    725                 730                 735
Leu Thr Lys Arg Ile Arg Thr Val Leu Met Ala Thr Ala Gln Met Lys
            740                 745                 750
Glu His Glu Asn Asp Pro Glu Met Leu Val Asp Leu Gln Tyr Ser Leu
            755                 760                 765
Ala Lys Ser Tyr Ala Ser Thr Pro Glu Leu Arg Lys Thr Trp Leu Asp
            770                 775                 780
Ser Met Ala Arg Ile His Val Lys Asn Gly Asp Leu Ser Glu Ala Ala
785                 790                 795                 800
Met Cys Tyr Val His Val Thr Ala Leu Val Ala Glu Tyr Leu Thr Arg
                    805                 810                 815
Lys Gly Val Phe Arg Gln Gly Cys Thr Ala Phe Arg Val Ile Thr Pro
            820                 825                 830
Asn Ile Asp Glu Glu Ala Ser Met Met Glu Asp Val Gly Met Gln Asp
            835                 840                 845
Val His Phe Asn Glu Asp Val Leu Met Glu Leu Leu Glu Gln Cys Ala
            850                 855                 860
Asp Gly Leu Trp Lys Ala Glu Arg Tyr Glu Leu Ile Ala Asp Ile Tyr
865                 870                 875                 880
Lys Leu Ile Ile Pro Ile Tyr Glu Lys Arg Arg Asp Phe Phe Glu Asp
                    885                 890                 895
Glu Asp Gly Lys Glu Tyr Ile Tyr Lys Glu Pro Lys Leu Thr Pro Leu
            900                 905                 910
Ser Glu Ile Ser Gln Arg Leu Leu Lys Leu Tyr Ser Asp Lys Phe Gly
            915                 920                 925
Ser Glu Asn Val Lys Met Ile Gln Asp Ser Gly Lys Val Asn Pro Lys
            930                 935                 940
Asp Leu Asp Ser Lys Tyr Ala Tyr Ile Gln Val Thr His Val Ile Pro
945                 950                 955                 960
Phe Phe Asp Glu Lys Glu Leu Gln Glu Arg Lys Thr Glu Phe Glu Arg
                    965                 970                 975
Ser His Asn Ile Arg Arg Phe Met Phe Glu Met Pro Phe Thr Gln Thr
            980                 985                 990
Gly Lys Arg Gln Gly Gly Val Glu Glu Gln Cys Lys Arg Arg Thr Ile
            995                 1000                1005
```

```
Leu Thr Ala Ile His Cys Phe Pro Tyr Val Lys Lys Arg Ile Pro Val
    1010                1015                1020

Met Tyr Gln His His Thr Asp Leu Asn Pro Ile Glu Val Ala Ile Asp
1025                1030                1035                1040

Glu Met Ser Lys Lys Val Ala Glu Leu Arg Gln Leu Cys Ser Ser Ala
            1045                1050                1055

Glu Val Asp Met Ile Lys Leu Gln Leu Lys Leu Gln Gly Ser Val Ser
            1060                1065                1070

Val Gln Val Asn Ala Gly Pro Leu Ala Tyr Ala Arg Ala Phe Leu Asp
        1075                1080                1085

Asp Thr Asn Thr Lys Arg Tyr Pro Asp Asn Lys Val Lys Leu Leu Lys
    1090                1095                1100

Glu Val Phe Arg Gln Phe Val Glu Ala Cys Gly Gln Ala Leu Ala Val
1105                1110                1115                1120

Asn Glu Arg Leu Ile Lys Glu Asp Gln Leu Glu Tyr Gln Gly Glu Met
                1125                1130                1135

Lys Ala Asn Tyr Arg Glu Met Ala Lys Glu Leu Ser Glu Ile Met His
            1140                1145                1150

Glu Gln Ile Cys Pro Leu Glu Glu Lys Thr Ser Val Leu Pro Asn Ser
        1155                1160                1165

Leu His Ile Phe Asn Ala Ile Ser Gly Thr Pro Thr Ser Thr Met Val
    1170                1175                1180

His Gly Met Thr Ser Ser Ser Ser Val Val
1185                1190

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Furin
      cleavage consensus sequence

<400> SEQUENCE: 89

Arg Lys Gln Arg
  1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence:
      Human CLASP-2 predicted cleavage site by homology

<400> SEQUENCE: 90

Arg Asn Gln Arg
  1

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Conserved
      consensus motif E
<220> FEATURE:
<221> NAME/KEY: MOD_RES
<222> LOCATION: (3)
<223> OTHER INFORMATION: Xaa = any amino acid
<220> FEATURE:
<221> NAME/KEY: MOD_RES
```

```
<222> LOCATION: (6)
<223> OTHER INFORMATION: Xaa = any amino acid

<400> SEQUENCE: 91

Pro Glu Xaa Ala Ile Xaa Met
  1               5

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Conserved
      consensus motif F
<220> FEATURE:
<221> NAME/KEY: MOD_RES
<222> LOCATION: (1)..(15)
<223> OTHER INFORMATION: Xaa is any amino acid.

<400> SEQUENCE: 92

Leu Xaa Met Xaa Leu Gly Xaa Val Xaa Xaa Xaa Val Asn Xaa Gly
  1               5                  10                  15

<210> SEQ ID NO 93
<211> LENGTH: 125
<212> TYPE: DNA
<213> ORGANISM: Artificial Sequence
<220> FEATURE:
<223> OTHER INFORMATION: Description of Artificial Sequence: CLASP-2C
      exon not found in CLASP-2A
<220> FEATURE:
<221> NAME/KEY: misc_feature
<222> LOCATION: (1)..(125)
<223> OTHER INFORMATION: N is A, C, G, or T.

<400> SEQUENCE: 93
agggattttg agaggctggc ccatctgtat gacacgctgc accgggccta cagcaaagtg      60
accgaggtca tgcactcggg ccgcagttnc tggggaccta cttccgggta gccttcttcg     120
ggcag                                                                 125

<210> SEQ ID NO 94
<211> LENGTH: 44
<212> TYPE: PRT
<213> ORGANISM: Artificial Sequence
<220> FEATURE:
<223> OTHER INFORMATION: Description of Artificial Sequence: Amino acids
      encoded by CLASP-2C exon not found in CLASP-2A

<400> SEQUENCE: 94

Arg Asp Phe Glu Arg Leu Ala His Leu Tyr Asp Thr Leu His Arg Ala
  1               5                  10                  15

Tyr Ser Lys Val Thr Glu Val Met His Ser Gly Arg Arg Leu Leu Gly
             20                  25                  30

Thr Tyr Phe Arg Val Ala Phe Phe Gly Gln Gly Phe
         35                  40

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Exemplary
      probe/primer F1

<400> SEQUENCE: 95
cccagatttt tatgatgag                                                   19
```

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Exemplary
      probe/primer R1

<400> SEQUENCE: 96
gataatgaca aagttctgac                                              20

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Exemplary
      probe/primer F2

<400> SEQUENCE: 97
ctggaaatct tgacaaaaat gc                                           22

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Exemplary
      probe/primer R2

<400> SEQUENCE: 98
gtctttttaa tacagatgtg g                                            21

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Exemplary
      probe/primer F3

<400> SEQUENCE: 99
gagaggctgg cccatctgta tg                                           22

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Exemplary
      probe/primer R3

<400> SEQUENCE: 100
atcttcaaag aatccctgcc                                              20

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Exemplary
      probe/primer F4

<400> SEQUENCE: 101
gaagcagtcc agtgggagcc g                                            21

```
<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Exemplary
      probe/primer R4

<400> SEQUENCE: 102
gcctccccgg ctcctcctca gg                                               22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Exemplary
      probe/primer R5

<400> SEQUENCE: 103
cctccacatc tgtttcactg tc                                               22

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Exemplary
      probe/primer F5

<400> SEQUENCE: 104
ctccatgatg gaagacgtgg g                                                21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Exemplary
      probe/primer R6

<400> SEQUENCE: 105
gatgagctcg tagcgctcgg c                                                21

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Exemplary
      probe/primer F6

<400> SEQUENCE: 106
cattggcgtt taagctcctg                                                  20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Exemplary
      probe/primer F7

<400> SEQUENCE: 107
ggacccatag ttcatgatcg                                                  20
```

```
<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Exemplary
      probe/primer R4

<400> SEQUENCE: 108
cttcatcttc aagaaatccc tc                                               22

<210> SEQ ID NO 109
<211> LENGTH: 30
<212> TYPE: DNA
<213> ORGANISM: Artificial Sequence
<220> FEATURE:
<223> OTHER INFORMATION: Description of Artificial Sequence: Antisense
      oligo 1

<400> SEQUENCE: 109
gaaggcgatc atcacgtggc cttccatcgc                                       30

<210> SEQ ID NO 110
<211> LENGTH: 31
<212> TYPE: DNA
<213> ORGANISM: Artificial Sequence
<220> FEATURE:
<223> OTHER INFORMATION: Description of Artificial Sequence: Antisense
      oligo 2

<400> SEQUENCE: 110
gcttcaagta atgactggtg cagaacatct g                                     31

<210> SEQ ID NO 111
<211> LENGTH: 31
<212> TYPE: DNA
<213> ORGANISM: Artificial Sequence
<220> FEATURE:
<223> OTHER INFORMATION: Description of Artificial Sequence: Antisense
      oligo 3

<400> SEQUENCE: 111
gctcctcctc aggcaggcgc tatggctgtg g                                     31

<210> SEQ ID NO 112
<211> LENGTH: 31
<212> TYPE: DNA
<213> ORGANISM: Artificial Sequence
<220> FEATURE:
<223> OTHER INFORMATION: Description of Artificial Sequence: Antisense
      oligo 4

<400> SEQUENCE: 112
gtaggcccgg tgcagcgtgt catacagatg g                                     31

<210> SEQ ID NO 113
<211> LENGTH: 32
<212> TYPE: DNA
<213> ORGANISM: Artificial Sequence
<220> FEATURE:
<223> OTHER INFORMATION: Description of Artificial Sequence: Antisense
      oligo 5

<400> SEQUENCE: 113
gcaatgtctg agactttcga tcatgaacta tg                                    32

<210> SEQ ID NO 114
```

```
<211> LENGTH: 18
<212> TYPE: DNA
<213> ORGANISM: Artificial Sequence
<220> FEATURE:
<223> OTHER INFORMATION: Description of Artificial Sequence: Antisense
      oligo 6

<400> SEQUENCE: 114
caggagctgg ttcttaaa                                                       18

<210> SEQ ID NO 115
<211> LENGTH: 81
<212> TYPE: DNA
<213> ORGANISM: Homo sapiens
<220> FEATURE:
<223> OTHER INFORMATION: Exon 1A

<400> SEQUENCE: 115 gcagggaaa aacctggccc catgattcac ttacttccca ccggatctct cccatgacac          60
gtgaggatta ttacaattta a                                                  81

<210> SEQ ID NO 116
<211> LENGTH: 118
<212> TYPE: DNA
<213> ORGANISM: Homo sapiens
<220> FEATURE:
<223> OTHER INFORMATION: Exon 1B

<400> SEQUENCE: 116
ttatcccttt actacttgcg aagtgagttc ggtagatggg agtggagaag agaaccttag         60
aatcattgtt tagtcttcat ctttcacagc tcaggctgaa ggcctttcct tgctgaga         118

<210> SEQ ID NO 117
<211> LENGTH: 42
<212> TYPE: DNA
<213> ORGANISM: Homo sapiens
<220> FEATURE:
<223> OTHER INFORMATION: Exon 1C

<400> SEQUENCE: 117
gcggcagagc gtgtctgagg tggtgcgcgg ctccgtgctc ct                            42

<210> SEQ ID NO 118
<211> LENGTH: 6791
<212> TYPE: DNA
<213> ORGANISM: Homo sapiens
<220> FEATURE:
<221> NAME/KEY: CDS
<222> LOCATION: (102)..(6044)
<223> OTHER INFORMATION: Human CLASP-2 gene

<400> SEQUENCE: 118
ggcaaagcca aagctaattg agcaagctaa ttgagccact cgactatgaa aatgtcatcg         60
tccagaagaa gactcagatc ctgaacgact gtttacggga g atg ctg ctc ttc cct       116
                                              Met Leu Leu Phe Pro
                                                1               5 tac gat gac ttt cag acg gcc atc ctg aga cga cag ggt cga tac ata         164
Tyr Asp Asp Phe Gln Thr Ala Ile Leu Arg Arg Gln Gly Arg Tyr Ile
            10                  15                  20 tgc tca aca gtg cct gcg aag gcg gaa gag gaa gca cag agc ttg ttt         212
Cys Ser Thr Val Pro Ala Lys Ala Glu Glu Glu Ala Gln Ser Leu Phe
        25                  30                  35 gtt aca gag tgc atc aaa acc tat aac tct gac tgg cat ctt gtg aac         260
Val Thr Glu Cys Ile Lys Thr Tyr Asn Ser Asp Trp His Leu Val Asn
```

```
                    40                    45                        50
tat aaa tat gaa gat tac tca gga gag ttt cga cag ctt ccg aac aaa       308
Tyr Lys Tyr Glu Asp Tyr Ser Gly Glu Phe Arg Gln Leu Pro Asn Lys
         55                   60                       65 gtg gtc aag ttg gat aaa ctt cca gtt cat gtc tat gaa gtt gac gag       356
Val Val Lys Leu Asp Lys Leu Pro Val His Val Tyr Glu Val Asp Glu
 70                   75                       80                85 gag gtc gac aaa gat gag gat gct gcc tcc ctt ggt tcc cag aag ggt       404
Glu Val Asp Lys Asp Glu Asp Ala Ala Ser Leu Gly Ser Gln Lys Gly
                     90                       95                  100 ggg atc acc aag cat ggc tgg ctg tac aaa ggc aac atg aac agt gcc       452
Gly Ile Thr Lys His Gly Trp Leu Tyr Lys Gly Asn Met Asn Ser Ala
                105                      110                 115 atc agc gtg acc atg agg tca ttt aag aga cga ttt ttc cac ctg att       500
Ile Ser Val Thr Met Arg Ser Phe Lys Arg Arg Phe Phe His Leu Ile
            120                      125                 130 caa ctt ggc gat gga tcc tat aat ttg aat ttt tat aaa gat gaa aag       548
Gln Leu Gly Asp Gly Ser Tyr Asn Leu Asn Phe Tyr Lys Asp Glu Lys
135                      140                 145 atc tcc aaa gaa cca aaa gga tca ata ttt ctg gat tcc tgt atg ggt       596
Ile Ser Lys Glu Pro Lys Gly Ser Ile Phe Leu Asp Ser Cys Met Gly
150                  155                 160                  165 gtc gtt cag aac aac aaa gtc agg cgt ttt gct ttt gag ctc aag atg       644
Val Val Gln Asn Asn Lys Val Arg Arg Phe Ala Phe Glu Leu Lys Met
                 170                 175                 180 cag gac aaa agt agt tat ctc ttg gca gca gac agt gaa gtg gaa atg       692
Gln Asp Lys Ser Ser Tyr Leu Leu Ala Ala Asp Ser Glu Val Glu Met
             185                 190                 195 gaa gaa tgg atc aca att cta aat aag atc ctc cag ctc aac ttt gaa       740
Glu Glu Trp Ile Thr Ile Leu Asn Lys Ile Leu Gln Leu Asn Phe Glu
         200                 205                 210 gct gca atg caa gaa aag cga aat ggc gac tct cac gaa gat gat gaa       788
Ala Ala Met Gln Glu Lys Arg Asn Gly Asp Ser His Glu Asp Asp Glu
     215                 220                 225 caa agc aaa ttg gaa ggt tct ggt tcc ggt tta gat agc tac ctg ccg       836
Gln Ser Lys Leu Glu Gly Ser Gly Ser Gly Leu Asp Ser Tyr Leu Pro
230                 235                 240                 245 gaa ctt gcc aag agt gca aga gaa gca gaa atc aaa cta aaa agt gaa       884
Glu Leu Ala Lys Ser Ala Arg Glu Ala Glu Ile Lys Leu Lys Ser Glu
             250                 255                 260 agc aga gtc aaa ctt ttt tat ttg gac cca gat gcc cag aag ctt gac       932
Ser Arg Val Lys Leu Phe Tyr Leu Asp Pro Asp Ala Gln Lys Leu Asp
         265                 270                 275 ttc tca tca gct gag cca gaa gtg aag tca ttt gaa gag aag ttt gga       980
Phe Ser Ser Ala Glu Pro Glu Val Lys Ser Phe Glu Glu Lys Phe Gly
     280                 285                 290 aaa agg atc ctt gtc aag tgc aat gat tta tct ttc aat ttg caa tgc      1028
Lys Arg Ile Leu Val Lys Cys Asn Asp Leu Ser Phe Asn Leu Gln Cys
295                 300                 305 tgt gtt gcc gaa aat gaa gaa gga ccc act aca aat gtt gaa cct ttc      1076
Cys Val Ala Glu Asn Glu Glu Gly Pro Thr Thr Asn Val Glu Pro Phe
310                 315                 320                 325 ttt gtt act cta tcc ctg ttt gac ata aaa tac aac cgg aag att tct      1124
Phe Val Thr Leu Ser Leu Phe Asp Ile Lys Tyr Asn Arg Lys Ile Ser
             330                 335                 340 gcc gat ttc cac gta gac ctg aac cat ttc tca gtg agg caa atg ctc      1172
Ala Asp Phe His Val Asp Leu Asn His Phe Ser Val Arg Gln Met Leu
         345                 350                 355 gcc acc acg tcc ccg gcg ctg atg aat ggc agt ggg cag agc cca tct      1220
```

```
                Ala Thr Thr Ser Pro Ala Leu Met Asn Gly Ser Gly Gln Ser Pro Ser
                            360                 365                 370 gtc ctc aag ggc atc ctt cat gaa gcc gcc atg cag tat ccg aag cag              1268
Val Leu Lys Gly Ile Leu His Glu Ala Ala Met Gln Tyr Pro Lys Gln
        375                 380                 385 gga ata ttt tca gtc act tgt cct cat cca gat ata ttt ctt gtg gcc              1316
Gly Ile Phe Ser Val Thr Cys Pro His Pro Asp Ile Phe Leu Val Ala
390                 395                 400                 405 aga att gaa aaa gtc ctt cag ggg agc atc aca cat tgc gct gag cca              1364
Arg Ile Glu Lys Val Leu Gln Gly Ser Ile Thr His Cys Ala Glu Pro
                410                 415                 420 tat atg aaa agt tca gac tct tct aag gtg gcc cag aag gtg ctg aag              1412
Tyr Met Lys Ser Ser Asp Ser Ser Lys Val Ala Gln Lys Val Leu Lys
            425                 430                 435 aat gcc aag cag gca tgc caa aga cta gga cag tat aga atg cca ttt              1460
Asn Ala Lys Gln Ala Cys Gln Arg Leu Gly Gln Tyr Arg Met Pro Phe
        440                 445                 450 gct tgg gca gca agg aca ttg ttt aag gat gca tct gga aat ctt gac              1508
Ala Trp Ala Ala Arg Thr Leu Phe Lys Asp Ala Ser Gly Asn Leu Asp
    455                 460                 465 aaa aat gcc aga ttt tct gcc atc tac agg caa gac agc aat aag cta              1556
Lys Asn Ala Arg Phe Ser Ala Ile Tyr Arg Gln Asp Ser Asn Lys Leu
470                 475                 480                 485 tcc aat gat gac atg ctc aag tta ctt gca gac ttt cgg aaa cct gag              1604
Ser Asn Asp Asp Met Leu Lys Leu Leu Ala Asp Phe Arg Lys Pro Glu
                490                 495                 500 aag atg gct aag ctc cca gtg att tta ggc aat cta gac att aca att              1652
Lys Met Ala Lys Leu Pro Val Ile Leu Gly Asn Leu Asp Ile Thr Ile
            505                 510                 515 gat aat gtt tcc tca gac ttc cct aat tat gtt aat tca tca tac att              1700
Asp Asn Val Ser Ser Asp Phe Pro Asn Tyr Val Asn Ser Ser Tyr Ile
        520                 525                 530 ccc aca aaa caa ttt gaa acc tgc agt aaa act ccc atc acg ttt gaa              1748
Pro Thr Lys Gln Phe Glu Thr Cys Ser Lys Thr Pro Ile Thr Phe Glu
    535                 540                 545 gtg gag gaa ttt gtg ccc tgc ata cca aaa cac act cag cct tac acc              1796
Val Glu Glu Phe Val Pro Cys Ile Pro Lys His Thr Gln Pro Tyr Thr
550                 555                 560                 565 atc tac acc aat cac ctt tac gtt tat cct aag tac ttg aaa tac gac              1844
Ile Tyr Thr Asn His Leu Tyr Val Tyr Pro Lys Tyr Leu Lys Tyr Asp
                570                 575                 580 agt cag aag tct ttt gcc aag gct aga aat att gcg att tgc att gaa              1892
Ser Gln Lys Ser Phe Ala Lys Ala Arg Asn Ile Ala Ile Cys Ile Glu
            585                 590                 595 ttc aaa gat tca gat gag gaa gac tct cag ccc ctt aag tgc att tat              1940
Phe Lys Asp Ser Asp Glu Glu Asp Ser Gln Pro Leu Lys Cys Ile Tyr
        600                 605                 610 ggc aga cct ggt ggg cca gtt ttc aca aga agc gcc ttt gct gca gtt              1988
Gly Arg Pro Gly Gly Pro Val Phe Thr Arg Ser Ala Phe Ala Ala Val
    615                 620                 625 tta cac cat cac caa aac cca gaa ttt tat gat gag att aaa ata gag              2036
Leu His His His Gln Asn Pro Glu Phe Tyr Asp Glu Ile Lys Ile Glu
630                 635                 640                 645 ttg ccc act cag ctg cat gaa aag cac cac ctg ttg ctc aca ttc ttc              2084
Leu Pro Thr Gln Leu His Glu Lys His His Leu Leu Leu Thr Phe Phe
                650                 655                 660 cat gtc agc tgt gac aac tca agt aaa gga agc acg aag aag agg gat              2132
His Val Ser Cys Asp Asn Ser Ser Lys Gly Ser Thr Lys Lys Arg Asp
            665                 670                 675
```

```
gtc gtt gaa acc caa gtt ggc tac tcc tgg ctt ccc ctc ctg aaa gac    2180
Val Val Glu Thr Gln Val Gly Tyr Ser Trp Leu Pro Leu Leu Lys Asp
            680                 685                 690 gga agg gtg gtg aca agc gag cag cac atc ccg gtc tcg gcg tac ctt    2228
Gly Arg Val Val Thr Ser Glu Gln His Ile Pro Val Ser Ala Tyr Leu
695                 700                 705 cct tcg ggc cat ctt ggc tac caa gag ctt ggg atg ggc agg cat tat    2276
Pro Ser Gly His Leu Gly Tyr Gln Glu Leu Gly Met Gly Arg His Tyr
710                 715                 720                 725 ggt ccg gaa att aaa tgg gta gat gga ggc aag cca ctg ctg aaa att    2324
Gly Pro Glu Ile Lys Trp Val Asp Gly Gly Lys Pro Leu Leu Lys Ile
            730                 735                 740 tcc act cat ctg gtt tct aca gtg tat act cag gat cag cat tta cat    2372
Ser Thr His Leu Val Ser Thr Val Tyr Thr Gln Asp Gln His Leu His
            745                 750                 755 aat ttt ttc cag tac tgt cag aaa acc gaa tct gga gcc caa gcc tta    2420
Asn Phe Phe Gln Tyr Cys Gln Lys Thr Glu Ser Gly Ala Gln Ala Leu
            760                 765                 770 gga aac gaa ctt gta aag tac ctt aag agt ctg cat gcg atg gaa ggc    2468
Gly Asn Glu Leu Val Lys Tyr Leu Lys Ser Leu His Ala Met Glu Gly
775                 780                 785 cac gtg atg atc gcc ttc ttg ccc act atc cta aac cag ctg ttc cga    2516
His Val Met Ile Ala Phe Leu Pro Thr Ile Leu Asn Gln Leu Phe Arg
790                 795                 800                 805 gtc ctc acc aga gcc aca cag gaa gaa gtc gcg gtt aac gtg act cgg    2564
Val Leu Thr Arg Ala Thr Gln Glu Glu Val Ala Val Asn Val Thr Arg
            810                 815                 820 gtc att att cat gtg gtt gcc cag tgc cat gag gaa gga ttg gag agc    2612
Val Ile Ile His Val Val Ala Gln Cys His Glu Glu Gly Leu Glu Ser
            825                 830                 835 cac ttg agg tca tat gtt aag tac gcg tat aag gct gag cca tat gtt    2660
His Leu Arg Ser Tyr Val Lys Tyr Ala Tyr Lys Ala Glu Pro Tyr Val
            840                 845                 850 gcc tct gaa tac aag aca gtg cat gaa gaa ctg acc aaa tcc atg acc    2708
Ala Ser Glu Tyr Lys Thr Val His Glu Glu Leu Thr Lys Ser Met Thr
855                 860                 865 acg att ctc aag cct tct gcc gat ttc ctc acc agc aac aaa cta ctg    2756
Thr Ile Leu Lys Pro Ser Ala Asp Phe Leu Thr Ser Asn Lys Leu Leu
870                 875                 880                 885 agg tac tca tgg ttt ttc ttt gat gta ctg atc aaa tct atg gct cag    2804
Arg Tyr Ser Trp Phe Phe Phe Asp Val Leu Ile Lys Ser Met Ala Gln
            890                 895                 900 cat ttg ata gag aac tcc aaa gtt aag ttg ctg cga aac cag aga ttt    2852
His Leu Ile Glu Asn Ser Lys Val Lys Leu Leu Arg Asn Gln Arg Phe
            905                 910                 915 cct gca tcc tat cat cat gca gcg gaa acc gtt gta aat atg ctg atg    2900
Pro Ala Ser Tyr His His Ala Ala Glu Thr Val Val Asn Met Leu Met
            920                 925                 930 cca cac atc act cag aag ttt gga gat aat cca gag gca tct aag aac    2948
Pro His Ile Thr Gln Lys Phe Gly Asp Asn Pro Glu Ala Ser Lys Asn
935                 940                 945 gcg aat cat agc ctt gct gtc ttc atc aag aga tgt ttc acc ttc atg    2996
Ala Asn His Ser Leu Ala Val Phe Ile Lys Arg Cys Phe Thr Phe Met
950                 955                 960                 965 gac agg ggc ttt gtc ttc aag cag atc aac aac tac att agc tgt ttt    3044
Asp Arg Gly Phe Val Phe Lys Gln Ile Asn Asn Tyr Ile Ser Cys Phe
            970                 975                 980 gct cct gga gac cca aag acc ctc ttt gaa tac aag ttt gaa ttt ctc    3092
Ala Pro Gly Asp Pro Lys Thr Leu Phe Glu Tyr Lys Phe Glu Phe Leu
            985                 990                 995
```

```
cgt gta gtg tgc aac cat gaa cat tat att ccg ttg aac tta cca atg       3140
Arg Val Val Cys Asn His Glu His Tyr Ile Pro Leu Asn Leu Pro Met
        1000                1005                1010 cca ttt gga aaa ggc agg att caa aga tac caa gac ctc cag ctt gac       3188
Pro Phe Gly Lys Gly Arg Ile Gln Arg Tyr Gln Asp Leu Gln Leu Asp
    1015                1020                1025 tac tca tta aca gat gag ttc tgc aga aac cac ttc ttg gtg gga ctg       3236
Tyr Ser Leu Thr Asp Glu Phe Cys Arg Asn His Phe Leu Val Gly Leu
1030                1035                1040                1045 tta ctg agg gag gtg ggg aca gcc ctc cag gag ttc cgg gag gtc cgt       3284
Leu Leu Arg Glu Val Gly Thr Ala Leu Gln Glu Phe Arg Glu Val Arg
                1050                1055                1060 ctg atc gcc atc agt gtg ctc aag aac ctg ctg ata aag cat tct ttt       3332
Leu Ile Ala Ile Ser Val Leu Lys Asn Leu Leu Ile Lys His Ser Phe
            1065                1070                1075 gat gac aga tat gct tca agg agc cat cag gca agg ata gcc acc ctc       3380
Asp Asp Arg Tyr Ala Ser Arg Ser His Gln Ala Arg Ile Ala Thr Leu
        1080                1085                1090 tac ctg cct ctg ttt ggt ctg ctg att gaa aac gtc cag cgg atc aat       3428
Tyr Leu Pro Leu Phe Gly Leu Leu Ile Glu Asn Val Gln Arg Ile Asn
    1095                1100                1105 gtg agg gat gtg tca ccc ttc cct gtg aac gcg ggc atg acc gtg aag       3476
Val Arg Asp Val Ser Pro Phe Pro Val Asn Ala Gly Met Thr Val Lys
1110                1115                1120                1125 gat gaa tcc ctg gct cta cca gct gtg aat ccg ctg gtg acg ccg cag       3524
Asp Glu Ser Leu Ala Leu Pro Ala Val Asn Pro Leu Val Thr Pro Gln
                1130                1135                1140 aag gga agc acc ctg gac aac agc ctg cac aag gac ctg ctg ggc gcc       3572
Lys Gly Ser Thr Leu Asp Asn Ser Leu His Lys Asp Leu Leu Gly Ala
            1145                1150                1155 atc tcc ggc att gct tct cca tat aca acc tca act cca aac atc aac       3620
Ile Ser Gly Ile Ala Ser Pro Tyr Thr Thr Ser Thr Pro Asn Ile Asn
        1160                1165                1170 agt gtg aga aat gct gat tcg aga gga tct ctc ata agc aca gat tcg       3668
Ser Val Arg Asn Ala Asp Ser Arg Gly Ser Leu Ile Ser Thr Asp Ser
    1175                1180                1185 ggt aac agc ctt cca gaa agg aat agt gag aag agc aat tcc ctg gat       3716
Gly Asn Ser Leu Pro Glu Arg Asn Ser Glu Lys Ser Asn Ser Leu Asp
1190                1195                1200                1205 aag cac caa caa agt agc aca ttg gga aat tcc gtg gtt cgc tgt gat       3764
Lys His Gln Gln Ser Ser Thr Leu Gly Asn Ser Val Val Arg Cys Asp
                1210                1215                1220 aaa ctt gac cag tct gag att aag agc cta ctg atg tgt ttc ctc tac       3812
Lys Leu Asp Gln Ser Glu Ile Lys Ser Leu Leu Met Cys Phe Leu Tyr
            1225                1230                1235 atc tta aag agc atg tct gat gat gct ttg ttt aca tat tgg aac aag       3860
Ile Leu Lys Ser Met Ser Asp Asp Ala Leu Phe Thr Tyr Trp Asn Lys
        1240                1245                1250 gct tca aca tct gaa ctt atg gat ttt ttt aca ata tct gaa gtc tgc       3908
Ala Ser Thr Ser Glu Leu Met Asp Phe Phe Thr Ile Ser Glu Val Cys
    1255                1260                1265 ctg cac cag ttc cag tac atg ggg aag cga tac ata gcc agg aac cag       3956
Leu His Gln Phe Gln Tyr Met Gly Lys Arg Tyr Ile Ala Arg Asn Gln
1270                1275                1280                1285 gag ggg ttg gga ccc ata gtt cat gat cga aag tct cag aca ttg cct       4004
Glu Gly Leu Gly Pro Ile Val His Asp Arg Lys Ser Gln Thr Leu Pro
                1290                1295                1300 gtt tcc cgt aac aga aca gga atg atg cat gcc aga ttg cag cag ctg       4052
Val Ser Arg Asn Arg Thr Gly Met Met His Ala Arg Leu Gln Gln Leu
```

-continued

| | |
|---|---|
| ggc agc ctg gat aac tct ctc act ttt aac cac agc tat ggc cac tcg<br>Gly Ser Leu Asp Asn Ser Leu Thr Phe Asn His Ser Tyr Gly His Ser<br>1320              1325              1330 | 4100 |
| gac gca gat gtt ctg cac cag tca tta ctt gaa gcc aac att gct act<br>Asp Ala Asp Val Leu His Gln Ser Leu Leu Glu Ala Asn Ile Ala Thr<br>1335              1340              1345 | 4148 |
| gag gtt tgc ctg aca gct ctg gac acg ctt tct cta ttt aca ttg gcg<br>Glu Val Cys Leu Thr Ala Leu Asp Thr Leu Ser Leu Phe Thr Leu Ala<br>1350            1355              1360              1365 | 4196 |
| ttt aag aac cag ctc ctg gcc gac cat gga cat aat cct ctc atg aaa<br>Phe Lys Asn Gln Leu Leu Ala Asp His Gly His Asn Pro Leu Met Lys<br>1370            1375              1380 | 4244 |
| aaa gtt ttt gat gtc tac ctg tgt ttt ctt caa aaa cat cag tct gaa<br>Lys Val Phe Asp Val Tyr Leu Cys Phe Leu Gln Lys His Gln Ser Glu<br>1385            1390              1395 | 4292 |
| acg gct tta aaa aat gtc ttc act gcc tta agg tcc tta att tat aag<br>Thr Ala Leu Lys Asn Val Phe Thr Ala Leu Arg Ser Leu Ile Tyr Lys<br>1400            1405              1410 | 4340 |
| ttt ccc tca aca ttc tat gaa ggg aga gcg gac atg tgt gcg gct ctg<br>Phe Pro Ser Thr Phe Tyr Glu Gly Arg Ala Asp Met Cys Ala Ala Leu<br>1415            1420              1425 | 4388 |
| tgt tac gag att ctc aag tgc tgt aac tcc aag ctg agc tcc atc agg<br>Cys Tyr Glu Ile Leu Lys Cys Cys Asn Ser Lys Leu Ser Ser Ile Arg<br>1430            1435              1440              1445 | 4436 |
| acg gag gcc tcc cag ctg ctc tac ttc ctg atg agg aac aac ttt gat<br>Thr Glu Ala Ser Gln Leu Leu Tyr Phe Leu Met Arg Asn Asn Phe Asp<br>1450            1455              1460 | 4484 |
| tac act gga aag aag tcc ttt gtc cgg aca cat ttg caa gtc atc ata<br>Tyr Thr Gly Lys Lys Ser Phe Val Arg Thr His Leu Gln Val Ile Ile<br>1465            1470              1475 | 4532 |
| tct gtc agc cag ctg ata gca gac gtt gtt ggc att ggg gaa acc aga<br>Ser Val Ser Gln Leu Ile Ala Asp Val Val Gly Ile Gly Glu Thr Arg<br>1480            1485              1490 | 4580 |
| ttc cag cag tcc ctg tcc atc atc aac aac tgt gcc aac agt gac cgg<br>Phe Gln Gln Ser Leu Ser Ile Ile Asn Asn Cys Ala Asn Ser Asp Arg<br>1495            1500              1505 | 4628 |
| ctt att aag cac acc agc ttc tcc tct gat gtg aag gac tta acc aaa<br>Leu Ile Lys His Thr Ser Phe Ser Ser Asp Val Lys Asp Leu Thr Lys<br>1510            1515              1520              1525 | 4676 |
| agg ata cgc acg gtg cta atg gcc acc gcc cag atg aag gag cat gag<br>Arg Ile Arg Thr Val Leu Met Ala Thr Ala Gln Met Lys Glu His Glu<br>1530            1535              1540 | 4724 |
| aac gac cca gag atg ctg gtg gac ctc cag tac agc ctg gcc aaa tcc<br>Asn Asp Pro Glu Met Leu Val Asp Leu Gln Tyr Ser Leu Ala Lys Ser<br>1545            1550              1555 | 4772 |
| tat gcc agc acg ccc gag ctc agg aag acg tgg ctc gac agc atg gcc<br>Tyr Ala Ser Thr Pro Glu Leu Arg Lys Thr Trp Leu Asp Ser Met Ala<br>1560            1565              1570 | 4820 |
| agg atc cat gtc aaa aat ggc gat ctc tca gag gca gca atg tgc tat<br>Arg Ile His Val Lys Asn Gly Asp Leu Ser Glu Ala Ala Met Cys Tyr<br>1575            1580              1585 | 4868 |
| gtc cac gta aca gcc cta gtg gca gaa tat ctc aca cgg aaa ggc gtg<br>Val His Val Thr Ala Leu Val Ala Glu Tyr Leu Thr Arg Lys Gly Val<br>1590            1595              1600              1605 | 4916 |
| ttt aga caa gga tgc acc gcc ttc agg gtc att acc cca aac atc gac<br>Phe Arg Gln Gly Cys Thr Ala Phe Arg Val Ile Thr Pro Asn Ile Asp<br>1610            1615              1620 | 4964 |
| gag gag gcc tcc atg atg gaa gac gtg ggg atg cag gat gtc cat ttc | 5012 |

```
                Glu Glu Ala Ser Met Met Glu Asp Val Gly Met Gln Asp Val His Phe
                        1625                1630                1635 aac gag gat gtg ctg atg gag ctc ctt gag cag tgc gca gat gga ctc        5060
Asn Glu Asp Val Leu Met Glu Leu Leu Glu Gln Cys Ala Asp Gly Leu
        1640                1645                1650 tgg aaa gcc gag cgc tac gag ctc atc gcc gac atc tac aaa ctt atc        5108
Trp Lys Ala Glu Arg Tyr Glu Leu Ile Ala Asp Ile Tyr Lys Leu Ile
    1655                1660                1665 atc ccc att tat gag aag cgg agg gat ttc ttt gaa gat gaa gat gga        5156
Ile Pro Ile Tyr Glu Lys Arg Arg Asp Phe Phe Glu Asp Glu Asp Gly
1670                1675                1680                1685 aag gag tat att tac aag gaa ccc aaa ctc aca ccg ctg tcg gaa att        5204
Lys Glu Tyr Ile Tyr Lys Glu Pro Lys Leu Thr Pro Leu Ser Glu Ile
                1690                1695                1700 tct cag aga ctc ctt aaa ctg tac tcg gat aaa ttt ggt tct gaa aat        5252
Ser Gln Arg Leu Leu Lys Leu Tyr Ser Asp Lys Phe Gly Ser Glu Asn
            1705                1710                1715 gtc aaa atg ata cag gat tct ggc aag gtc aac cct aag gat ctg gat        5300
Val Lys Met Ile Gln Asp Ser Gly Lys Val Asn Pro Lys Asp Leu Asp
        1720                1725                1730 tct aag tat gca tac atc cag gtg act cac gtc atc ccc ttc ttt gac        5348
Ser Lys Tyr Ala Tyr Ile Gln Val Thr His Val Ile Pro Phe Phe Asp
1735                1740                1745 gaa aaa gag ttg caa gaa agg aaa aca gag ttt gag aga tcc cac aac        5396
Glu Lys Glu Leu Gln Glu Arg Lys Thr Glu Phe Glu Arg Ser His Asn
1750                1755                1760                1765 atc cgc cgc ttc atg ttt gag atg cca ttt acg cag acc ggg aag agg        5444
Ile Arg Arg Phe Met Phe Glu Met Pro Phe Thr Gln Thr Gly Lys Arg
                1770                1775                1780 cag ggc ggg gtg gaa gag cag tgc aaa cgg cgc acc atc ctg aca gcc        5492
Gln Gly Gly Val Glu Glu Gln Cys Lys Arg Arg Thr Ile Leu Thr Ala
            1785                1790                1795 ata cac tgc ttc cct tat gtg aag aag cgc atc cct gtc atg tac cag        5540
Ile His Cys Phe Pro Tyr Val Lys Lys Arg Ile Pro Val Met Tyr Gln
        1800                1805                1810 cac cac act gac ctg aac ccc atc gag gtg gcc att gac gag atg agt        5588
His His Thr Asp Leu Asn Pro Ile Glu Val Ala Ile Asp Glu Met Ser
1815                1820                1825 aag aag gtg gcg gag ctc cgg cag ctg tgc tcc tcg gcc gag gtg gac        5636
Lys Lys Val Ala Glu Leu Arg Gln Leu Cys Ser Ser Ala Glu Val Asp
1830                1835                1840                1845 atg atc aaa ctg cag ctc aaa ctc cag ggc agc gtg agt gtt cag gtc        5684
Met Ile Lys Leu Gln Leu Lys Leu Gln Gly Ser Val Ser Val Gln Val
                1850                1855                1860 aat gct ggc cca cta gca tat gcg cga gct ttc tta gat gat aca aac        5732
Asn Ala Gly Pro Leu Ala Tyr Ala Arg Ala Phe Leu Asp Asp Thr Asn
            1865                1870                1875 aca aag cga tat cct gac aat aaa gtg aag ctg ctt aag gaa gtt ttc        5780
Thr Lys Arg Tyr Pro Asp Asn Lys Val Lys Leu Leu Lys Glu Val Phe
        1880                1885                1890 agg caa ttt gtg gaa gct tgc ggt caa gcc tta gcg gta aac gaa cgt        5828
Arg Gln Phe Val Glu Ala Cys Gly Gln Ala Leu Ala Val Asn Glu Arg
1895                1900                1905 ctg att aaa gaa gac cag ctc gag tat cag gaa gaa atg aaa gcc aac        5876
Leu Ile Lys Glu Asp Gln Leu Glu Tyr Gln Glu Glu Met Lys Ala Asn
1910                1915                1920                1925 tac agg gaa atg gcg aag gag ctt tct gaa atc atg cat gag cag atc        5924
Tyr Arg Glu Met Ala Lys Glu Leu Ser Glu Ile Met His Glu Gln Ile
                1930                1935                1940
```

-continued

| | |
|---|---|
| tgc ccc ctg gag gag aag acg agc gtc tta ccg aat tcc ctt cac atc<br>Cys Pro Leu Glu Glu Lys Thr Ser Val Leu Pro Asn Ser Leu His Ile<br>       1945             1950                 1955 | 5972 |
| ttc aac gcc atc agt ggg act cca aca agc aca atg gtt cac ggg atg<br>Phe Asn Ala Ile Ser Gly Thr Pro Thr Ser Thr Met Val His Gly Met<br>       1960             1965                1970 | 6020 |
| acc agc tcg tct tcg gtc gtg tga ttacatctca tggcccgtgt gtggggactt<br>Thr Ser Ser Ser Ser Val Val<br>  1975              1980 | 6074 |
| gctttgtcat ttgcaaactc aggatgcttt ccaaagccaa tcactgggga gaccgagcac | 6134 |
| agggaggacc aaggggaagg ggagagaaag gaaataaaga acaacgttat ttcttaacag | 6194 |
| actttctata ggagttgtaa aaggtgcac atattttttt aaatctcact ggcaatattc | 6254 |
| aaagttttca ttgtgtctta acaaaggtgt ggtagacact cttgagctgg acttagattt | 6314 |
| tattcttcct tgcagagtag tgttagaata gatggcctac agaaaaaaaa ggttctggga | 6374 |
| tctacatggc agggagggct gcactgacat tgatgcctgg gggacctttt gcctcgactc | 6434 |
| gtgccggaaa tctgatcgta atcagggtac agaacttact agttttgtct aggagtatgt | 6494 |
| tgtatgacta ggatttgtgc tattatctca ttcaacaaca tagagcaaga atagtgagct | 6554 |
| aactgagcta gacactcaat taatccgcta ctggcttcaa gtcagaactt tgtcattaat | 6614 |
| catcgactcc gggacggtca tatatgtatt acatttctac attttaata ctcacatggg | 6674 |
| cttatgcatt aagtttaatt gtgataaatt tgtgctggtc cagtatatgc aatacacttt | 6734 |
| aatggtttat tcttgtcata aaaatgtgca atatggagat gtatacaagt ctttact | 6791 |

<210> SEQ ID NO 119
<211> LENGTH: 1980
<212> TYPE: PRT
<213> ORGANISM: Homo sapiens
<223> OTHER INFORMATION: Human CLASP-2 gene

<400> SEQUENCE: 119

Met Leu Leu Phe Pro Tyr Asp Asp Phe Gln Thr Ala Ile Leu Arg Arg
  1               5                 10               15

Gln Gly Arg Tyr Ile Cys Ser Thr Val Pro Ala Lys Ala Glu Glu Glu
             20                 25               30

Ala Gln Ser Leu Phe Val Thr Glu Cys Ile Lys Thr Tyr Asn Ser Asp
        35                 40               45

Trp His Leu Val Asn Tyr Lys Tyr Glu Asp Tyr Ser Gly Glu Phe Arg
 50                55                60

Gln Leu Pro Asn Lys Val Val Lys Leu Asp Lys Leu Pro Val His Val
65                70               75              80

Tyr Glu Val Asp Glu Glu Val Asp Lys Asp Gly Asp Ala Ala Ser Leu
             85                90              95

Gly Ser Gln Lys Gly Gly Ile Thr Lys His Gly Trp Leu Tyr Lys Gly
          100                105              110

Asn Met Asn Ser Ala Ile Ser Val Thr Met Arg Ser Phe Lys Arg Arg
       115               120              125

Phe Phe His Leu Ile Gln Leu Gly Asp Gly Ser Tyr Asn Leu Asn Phe
   130               135               140

Tyr Lys Asp Glu Lys Ile Ser Lys Glu Pro Lys Gly Ser Ile Phe Leu
145               150               155             160

Asp Ser Cys Met Gly Val Val Gln Asn Asn Lys Val Arg Arg Phe Ala
          165                170              175

Phe Glu Leu Lys Met Gln Asp Lys Ser Ser Tyr Leu Leu Ala Ala Asp

-continued

```
                180                 185                 190
Ser Glu Val Glu Met Glu Trp Ile Thr Ile Leu Asn Lys Ile Leu
        195                 200                 205
Gln Leu Asn Phe Glu Ala Ala Met Gln Glu Lys Arg Asn Gly Asp Ser
    210                 215                 220
His Glu Asp Asp Glu Gln Ser Lys Leu Glu Gly Ser Gly Ser Gly Leu
225                 230                 235                 240
Asp Ser Tyr Leu Pro Glu Leu Ala Lys Ser Ala Arg Glu Ala Glu Ile
                245                 250                 255
Lys Leu Lys Ser Glu Ser Arg Val Lys Leu Phe Tyr Leu Asp Pro Asp
            260                 265                 270
Ala Gln Lys Leu Asp Phe Ser Ser Ala Glu Pro Glu Val Lys Ser Phe
        275                 280                 285
Glu Glu Lys Phe Gly Lys Arg Ile Leu Val Lys Cys Asn Asp Leu Ser
    290                 295                 300
Phe Asn Leu Gln Cys Cys Val Ala Glu Asn Glu Glu Gly Pro Thr Thr
305                 310                 315                 320
Asn Val Glu Pro Phe Phe Val Thr Leu Ser Leu Phe Asp Ile Lys Tyr
                325                 330                 335
Asn Arg Lys Ile Ser Ala Asp Phe His Val Asp Leu Asn His Phe Ser
            340                 345                 350
Val Arg Gln Met Leu Ala Thr Thr Ser Pro Ala Leu Met Asn Gly Ser
        355                 360                 365
Gly Gln Ser Pro Ser Val Leu Lys Gly Ile Leu His Glu Ala Ala Met
    370                 375                 380
Gln Tyr Pro Lys Gln Gly Ile Phe Ser Val Thr Cys Pro His Pro Asp
385                 390                 395                 400
Ile Phe Leu Val Ala Arg Ile Glu Lys Val Leu Gln Gly Ser Ile Thr
                405                 410                 415
His Cys Ala Glu Pro Tyr Met Lys Ser Ser Asp Ser Ser Lys Val Ala
            420                 425                 430
Gln Lys Val Leu Lys Asn Ala Lys Gln Ala Cys Gln Arg Leu Gly Gln
        435                 440                 445
Tyr Arg Met Pro Phe Ala Trp Ala Ala Arg Thr Leu Phe Lys Asp Ala
    450                 455                 460
Ser Gly Asn Leu Asp Lys Asn Ala Arg Phe Ser Ala Ile Tyr Arg Gln
465                 470                 475                 480
Asp Ser Asn Lys Leu Ser Asn Asp Met Leu Lys Leu Leu Ala Asp
                485                 490                 495
Phe Arg Lys Pro Glu Lys Met Ala Lys Leu Pro Val Ile Leu Gly Asn
            500                 505                 510
Leu Asp Ile Thr Ile Asp Asn Val Ser Ser Asp Phe Pro Asn Tyr Val
        515                 520                 525
Asn Ser Ser Tyr Ile Pro Thr Lys Gln Phe Glu Thr Cys Ser Lys Thr
    530                 535                 540
Pro Ile Thr Phe Glu Val Glu Glu Phe Val Pro Cys Ile Pro Lys His
545                 550                 555                 560
Thr Gln Pro Tyr Thr Ile Tyr Thr Asn His Leu Tyr Val Tyr Pro Lys
                565                 570                 575
Tyr Leu Lys Tyr Asp Ser Gln Lys Ser Phe Ala Lys Ala Arg Asn Ile
            580                 585                 590
Ala Ile Cys Ile Glu Phe Lys Asp Ser Asp Glu Glu Asp Ser Gln Pro
        595                 600                 605
```

```
Leu Lys Cys Ile Tyr Gly Arg Pro Gly Gly Pro Val Phe Thr Arg Ser
    610                 615                 620

Ala Phe Ala Ala Val Leu His His Gln Asn Pro Glu Phe Tyr Asp
625                 630                 635                 640

Glu Ile Lys Ile Glu Leu Pro Thr Gln Leu His Glu Lys His His Leu
                    645                 650                 655

Leu Leu Thr Phe Phe His Val Ser Cys Asp Asn Ser Ser Lys Gly Ser
                660                 665                 670

Thr Lys Lys Arg Asp Val Val Glu Thr Gln Val Gly Tyr Ser Trp Leu
            675                 680                 685

Pro Leu Leu Lys Asp Gly Arg Val Val Thr Ser Glu Gln His Ile Pro
        690                 695                 700

Val Ser Ala Tyr Leu Pro Ser Gly His Leu Tyr Gln Glu Leu Gly
705                 710                 715                 720

Met Gly Arg His Tyr Gly Pro Glu Ile Lys Trp Val Asp Gly Gly Lys
                    725                 730                 735

Pro Leu Leu Lys Ile Ser Thr His Leu Val Ser Thr Val Tyr Thr Gln
                740                 745                 750

Asp Gln His Leu His Asn Phe Phe Gln Tyr Cys Gln Lys Thr Glu Ser
            755                 760                 765

Gly Ala Gln Ala Leu Gly Asn Glu Leu Val Lys Tyr Leu Lys Ser Leu
        770                 775                 780

His Ala Met Glu Gly His Val Met Ile Ala Phe Leu Pro Thr Ile Leu
785                 790                 795                 800

Asn Gln Leu Phe Arg Val Leu Thr Arg Ala Thr Gln Glu Glu Val Ala
                    805                 810                 815

Val Asn Val Thr Arg Val Ile Ile His Val Val Ala Gln Cys His Glu
                820                 825                 830

Glu Gly Leu Glu Ser His Leu Arg Ser Tyr Val Lys Tyr Ala Tyr Lys
            835                 840                 845

Ala Glu Pro Tyr Val Ala Ser Glu Tyr Lys Thr Val His Glu Glu Leu
        850                 855                 860

Thr Lys Ser Met Thr Thr Ile Leu Lys Pro Ser Ala Asp Phe Leu Thr
865                 870                 875                 880

Ser Asn Lys Leu Leu Arg Tyr Ser Trp Phe Phe Phe Asp Val Leu Ile
                    885                 890                 895

Lys Ser Met Ala Gln His Leu Ile Glu Asn Ser Lys Val Lys Leu Leu
                900                 905                 910

Arg Asn Gln Arg Phe Pro Ala Ser Tyr His His Ala Ala Glu Thr Val
            915                 920                 925

Val Asn Met Leu Met Pro His Ile Thr Gln Lys Phe Gly Asp Asn Pro
        930                 935                 940

Glu Ala Ser Lys Asn Ala Asn His Ser Leu Ala Val Phe Ile Lys Arg
945                 950                 955                 960

Cys Phe Thr Phe Met Asp Arg Gly Phe Val Phe Lys Gln Ile Asn Asn
                    965                 970                 975

Tyr Ile Ser Cys Phe Ala Pro Gly Asp Pro Lys Thr Leu Phe Glu Tyr
                980                 985                 990

Lys Phe Glu Phe Leu Arg Val Val Cys Asn His Glu His Tyr Ile Pro
            995                 1000                1005

Leu Asn Leu Pro Met Pro Phe Gly Lys Gly Arg Ile Gln Arg Tyr Gln
    1010                1015                1020
```

```
Asp Leu Gln Leu Asp Tyr Ser Leu Thr Asp Glu Phe Cys Arg Asn His
1025                1030                1035                1040

Phe Leu Val Gly Leu Leu Arg Glu Val Gly Thr Ala Leu Gln Glu
            1045                1050                1055

Phe Arg Glu Val Arg Leu Ile Ala Ile Ser Val Leu Lys Asn Leu Leu
                1060                1065                1070

Ile Lys His Ser Phe Asp Asp Arg Tyr Ala Ser Arg Ser His Gln Ala
    1075                1080                1085

Arg Ile Ala Thr Leu Tyr Leu Pro Leu Phe Gly Leu Leu Ile Glu Asn
    1090                1095                1100

Val Gln Arg Ile Asn Val Arg Asp Val Ser Pro Phe Pro Val Asn Ala
1105                1110                1115                1120

Gly Met Thr Val Lys Asp Glu Ser Leu Ala Leu Pro Ala Val Asn Pro
                1125                1130                1135

Leu Val Thr Pro Gln Lys Gly Ser Thr Leu Asp Asn Ser Leu His Lys
            1140                1145                1150

Asp Leu Leu Gly Ala Ile Ser Gly Ile Ala Ser Pro Tyr Thr Thr Ser
                1155                1160                1165

Thr Pro Asn Ile Asn Ser Val Arg Asn Ala Asp Ser Arg Gly Ser Leu
1170                1175                1180

Ile Ser Thr Asp Ser Gly Asn Ser Leu Pro Glu Arg Asn Ser Glu Lys
1185                1190                1195                1200

Ser Asn Ser Leu Asp Lys His Gln Gln Ser Ser Thr Leu Gly Asn Ser
                1205                1210                1215

Val Val Arg Cys Asp Lys Leu Asp Gln Ser Glu Ile Lys Ser Leu Leu
                1220                1225                1230

Met Cys Phe Leu Tyr Ile Leu Lys Ser Met Ser Asp Asp Ala Leu Phe
                1235                1240                1245

Thr Tyr Trp Asn Lys Ala Ser Thr Ser Glu Leu Met Asp Phe Phe Thr
                1250                1255                1260

Ile Ser Glu Val Cys Leu His Gln Phe Gln Tyr Met Gly Lys Arg Tyr
1265                1270                1275                1280

Ile Ala Arg Asn Gln Glu Gly Leu Gly Pro Ile Val His Asp Arg Lys
                1285                1290                1295

Ser Gln Thr Leu Pro Val Ser Arg Asn Arg Thr Gly Met Met His Ala
                1300                1305                1310

Arg Leu Gln Gln Leu Gly Ser Leu Asp Asn Ser Leu Thr Phe Asn His
        1315                1320                1325

Ser Tyr Gly His Ser Asp Ala Asp Val Leu His Gln Ser Leu Leu Glu
    1330                1335                1340

Ala Asn Ile Ala Thr Glu Val Cys Leu Thr Ala Leu Asp Thr Leu Ser
1345                1350                1355                1360

Leu Phe Thr Leu Ala Phe Lys Asn Gln Leu Leu Ala Asp His Gly His
            1365                1370                1375

Asn Pro Leu Met Lys Lys Val Phe Asp Val Tyr Leu Cys Phe Leu Gln
            1380                1385                1390

Lys His Gln Ser Glu Thr Ala Leu Lys Asn Val Phe Thr Ala Leu Arg
    1395                1400                1405

Ser Leu Ile Tyr Lys Phe Pro Ser Thr Phe Tyr Glu Gly Arg Ala Asp
    1410                1415                1420

Met Cys Ala Ala Leu Cys Tyr Glu Ile Leu Lys Cys Cys Asn Ser Lys
1425                1430                1435                1440

Leu Ser Ser Ile Arg Thr Glu Ala Ser Gln Leu Leu Tyr Phe Leu Met
```

-continued

```
                1445                1450                1455
Arg Asn Asn Phe Asp Tyr Thr Gly Lys Lys Ser Phe Val Arg Thr His
        1460                1465                1470
Leu Gln Val Ile Ile Ser Val Ser Gln Leu Ile Ala Asp Val Val Gly
        1475                1480                1485
Ile Gly Glu Thr Arg Phe Gln Gln Ser Leu Ser Ile Ile Asn Asn Cys
        1490                1495                1500
Ala Asn Ser Asp Arg Leu Ile Lys His Thr Ser Phe Ser Ser Asp Val
1505                1510                1515                1520
Lys Asp Leu Thr Lys Arg Ile Arg Thr Val Leu Met Ala Thr Ala Gln
            1525                1530                1535
Met Lys Glu His Glu Asn Asp Pro Glu Met Leu Val Asp Leu Gln Tyr
            1540                1545                1550
Ser Leu Ala Lys Ser Tyr Ala Ser Thr Pro Glu Leu Arg Lys Thr Trp
            1555                1560                1565
Leu Asp Ser Met Ala Arg Ile His Val Lys Asn Gly Asp Leu Ser Glu
        1570                1575                1580
Ala Ala Met Cys Tyr Val His Val Thr Ala Leu Val Ala Glu Tyr Leu
1585                1590                1595                1600
Thr Arg Lys Gly Val Phe Arg Gln Gly Cys Thr Ala Phe Arg Val Ile
            1605                1610                1615
Thr Pro Asn Ile Asp Glu Glu Ala Ser Met Met Glu Asp Val Gly Met
        1620                1625                1630
Gln Asp Val His Phe Asn Glu Asp Val Leu Met Glu Leu Leu Glu Gln
        1635                1640                1645
Cys Ala Asp Gly Leu Trp Lys Ala Glu Arg Tyr Glu Leu Ile Ala Asp
        1650                1655                1660
Ile Tyr Lys Leu Ile Ile Pro Ile Tyr Glu Lys Arg Arg Asp Phe Phe
1665                1670                1675                1680
Glu Asp Glu Asp Gly Lys Glu Tyr Ile Tyr Lys Glu Pro Lys Leu Thr
            1685                1690                1695
Pro Leu Ser Glu Ile Ser Gln Arg Leu Leu Lys Leu Tyr Ser Asp Lys
        1700                1705                1710
Phe Gly Ser Glu Asn Val Lys Met Ile Gln Asp Ser Gly Lys Val Asn
        1715                1720                1725
Pro Lys Asp Leu Asp Ser Lys Tyr Ala Tyr Ile Gln Val Thr His Val
        1730                1735                1740
Ile Pro Phe Phe Asp Glu Lys Glu Leu Gln Glu Arg Lys Thr Glu Phe
1745                1750                1755                1760
Glu Arg Ser His Asn Ile Arg Arg Phe Met Phe Glu Met Pro Phe Thr
            1765                1770                1775
Gln Thr Gly Lys Arg Gln Gly Gly Val Glu Glu Gln Cys Lys Arg Arg
            1780                1785                1790
Thr Ile Leu Thr Ala Ile His Cys Phe Pro Tyr Val Lys Lys Arg Ile
            1795                1800                1805
Pro Val Met Tyr Gln His His Thr Asp Leu Asn Pro Ile Glu Val Ala
        1810                1815                1820
Ile Asp Glu Met Ser Lys Lys Val Ala Glu Leu Arg Gln Leu Cys Ser
1825                1830                1835                1840
Ser Ala Glu Val Asp Met Ile Lys Leu Gln Leu Lys Leu Gln Gly Ser
            1845                1850                1855
Val Ser Val Gln Val Asn Ala Gly Pro Leu Ala Tyr Ala Arg Ala Phe
        1860                1865                1870
```

```
Leu Asp Asp Thr Asn Thr Lys Arg Tyr Pro Asp Asn Lys Val Lys Leu
    1875                1880                1885

Leu Lys Glu Val Phe Arg Gln Phe Val Glu Ala Cys Gly Gln Ala Leu
    1890                1895                1900

Ala Val Asn Glu Arg Leu Ile Lys Glu Asp Gln Leu Glu Tyr Gln Glu
1905                1910                1915                1920

Glu Met Lys Ala Asn Tyr Arg Glu Met Ala Lys Glu Leu Ser Glu Ile
                1925                1930                1935

Met His Glu Gln Ile Cys Pro Leu Glu Glu Lys Thr Ser Val Leu Pro
        1940                1945                1950

Asn Ser Leu His Ile Phe Asn Ala Ile Ser Gly Thr Pro Thr Ser Thr
    1955                1960                1965

Met Val His Gly Met Thr Ser Ser Ser Ser Val Val
    1970                1975                1980

<210> SEQ ID NO 120
<211> LENGTH: 179
<212> TYPE: DNA
<213> ORGANISM: Homo sapiens
<220> FEATURE:
<223> OTHER INFORMATION: CLASP-2 exon 1

<400> SEQUENCE: 120
tgtcttgctt atcttttcgc cctccaggca aagccaaagc taattgagcc actcgactat    60
gaaaatgtca tcgtccagaa gaagactcag atcctgaacg actgtttacg ggagatgctg   120 ctcttcccett acgatgactt tcaggtaagt aacgttatgt ttctatccgt agaaccacg    179

<210> SEQ ID NO 121
<211> LENGTH: 183
<212> TYPE: DNA
<213> ORGANISM: Homo sapiens
<220> FEATURE:
<223> OTHER INFORMATION: CLASP-2 exon 2

<400> SEQUENCE: 121
ttacccaagg ctttcctcc tgttttgtt tccagacggc atcctgaga cgacagggtc        60 gatacatatg ctcaacagtg cctgcgaagg cggaagagga agcacagagc ttgtttgtta   120
cagaggtaag gctctttcct gcattaattt acattttgaa gtcattttcc cctaactgcc   180
tcc                                                                  183

<210> SEQ ID NO 122
<211> LENGTH: 151
<212> TYPE: DNA
<213> ORGANISM: Homo sapiens
<220> FEATURE:
<223> OTHER INFORMATION: CLASP-2 exon 3

<400> SEQUENCE: 122
ttttctattt ttaaaatccc ccttcaatag tgcatcaaaa cctataactc tgactggcat     60
cttgtgaact ataaatatga agattactca ggagagtttc gacagcttcc gaagtgagta   120
agctatatta tacacatagg gaaaagtctt t                                   151

<210> SEQ ID NO 123
<211> LENGTH: 147
<212> TYPE: DNA
<213> ORGANISM: Homo sapiens
<220> FEATURE:
<223> OTHER INFORMATION: CLASP-2 exon 4
```

<400> SEQUENCE: 123

```
ctaaaacaaa ttttctttgt tgtttttata gcaaagtggt caagttggat aaacttccag    60
ttcatgtcta tgaagttgac gaggaggtcg acaaagatga ggtgggatac ctgcttgctg   120
ttgcttctct tttcactcta gatttaa                                        147
```

<210> SEQ ID NO 124
<211> LENGTH: 176
<212> TYPE: DNA
<213> ORGANISM: Homo sapiens
<220> FEATURE:
<223> OTHER INFORMATION: Exon 5

<400> SEQUENCE: 124

```
ggaggttgac tgctggtgtt ttccttctct cctaggatgc tgcctcccct ggttcccaga    60
agggtgggat caccaagcat ggctggctgt acaaaggcaa catgaacagt gccatcagcg   120
tgaccatgag ggtgaggacg cacatcactt tgccctcccc tctcacaagc cctttc        176
```

<210> SEQ ID NO 125
<211> LENGTH: 206
<212> TYPE: DNA
<213> ORGANISM: Homo sapiens
<220> FEATURE:
<223> OTHER INFORMATION: Exon 6

<400> SEQUENCE: 125

```
tgaaagaata gctgtgtgta tattttctc tcagtcattt aagagacgat ttttccacct    60
gattcaactt ggcgatggat cctataattt gaatttttat aaagatgaaa agatctccaa   120
agaaccaaaa ggatcaatat ttctggattc ctgtatgggt gtcgttcagg taaatatgaa   180
aagagtttta ccattatgtt ttctta                                         206
```

<210> SEQ ID NO 126
<211> LENGTH: 246
<212> TYPE: DNA
<213> ORGANISM: Homo sapiens
<220> FEATURE:
<223> OTHER INFORMATION: Exon 7

<400> SEQUENCE: 126

```
aagtatgtct gtttatcctt ttttcatttc agaacaacaa agtcaggcgt tttgcttttg    60
agctcaagat gcaggacaaa agtagttatc tcttggcagc agacagtgaa gtggaaatgg   120
aagaatggat cacaattcta ataagatcc tccagctcaa ctttgaagct gcaatgcaag   180
aaaagcgaaa tggcgactct cacgaaggta gataggcttg gcttccccca ggcacataca   240
cactct                                                               246
```

<210> SEQ ID NO 127
<211> LENGTH: 144
<212> TYPE: DNA
<213> ORGANISM: Homo sapiens
<220> FEATURE:
<223> OTHER INFORMATION: Exon 8

<400> SEQUENCE: 127

```
attacaagtg attccgataa tctgttttgc cattttagat gatgaacaaa gcaaattgga    60
aggttctggt tccggtttag atagctacct gccggaactt gccaaggtaa catcgtctta   120
tatcttctgc tcttcgttga atgc                                           144
```

```
<210> SEQ ID NO 128
<211> LENGTH: 152
<212> TYPE: DNA
<213> ORGANISM: Homo sapiens
<220> FEATURE:
<223> OTHER INFORMATION: Exon 9

<400> SEQUENCE: 128
gattgtgtta aatgtaattt tcatgtatct tgttatcaga gtgcaagaga agcagaaatc      60
aaactaaaaa gtgaaagcag agtcaaactt ttttatttgg acccagatgc ccaggtaaga     120
actatctaaa tgtttaatat ttaaaaccaa at                                   152

<210> SEQ ID NO 129
<211> LENGTH: 222
<212> TYPE: DNA
<213> ORGANISM: Homo sapiens
<220> FEATURE:
<223> OTHER INFORMATION: Exon 10

<400> SEQUENCE: 129
cataacttat ttatatgttt acattttctt ttaaagaagc ttgacttctc atcagctgag      60
ccagaagtga agtcatttga agagaagttt ggaaaaagga tccttgtcaa gtgcaatgat    120
ttatctttca atttgcaatg ctgtgttgcc gaaaatgaag aaggacccac tacaaatgta    180
atttttcatt ttaaaaataa acattaaaaa aaaaatagcc ag                        222

<210> SEQ ID NO 130
<211> LENGTH: 289
<212> TYPE: DNA
<213> ORGANISM: Homo sapiens
<220> FEATURE:
<223> OTHER INFORMATION: Exon 11

<400> SEQUENCE: 130
ccatggtgat cattggattg ttttgttttg ttcaggttga acctttcttt gttactctat      60
ccctgtttga cataaaatac aaccggaaga tttctgccga tttccacgta gacctgaacc    120
atttctcagt gaggcaaatg ctcgccacca cgtccccggc gctgatgaat ggcagtgggc    180
agagcccatc tgtcctcaag ggcatccttc atgaagccgc catgcagtat ccgaagcagg    240
tggggagtat gagcccagca ttcccactac tcagactcac tttgcatgc                289

<210> SEQ ID NO 131
<211> LENGTH: 205
<212> TYPE: DNA
<213> ORGANISM: Homo sapiens
<220> FEATURE:
<223> OTHER INFORMATION: Exon 12

<400> SEQUENCE: 131
gaattctgct tactgaagaa aattgtttgc ctcctaggga atattttcag tcacttgtcc      60
tcatccagat atatttcttg tggccagaat tgaaaaagtc cttcagggga gcatcacaca    120
ttgcgctgag ccatatatga aaagttcaga ctcttctaag gtatgaatgg cttttacgct    180
ttggggtggt aaaaagcaat ctgaa                                           205

<210> SEQ ID NO 132
<211> LENGTH: 166
<212> TYPE: DNA
<213> ORGANISM: Homo sapiens
<220> FEATURE:
<223> OTHER INFORMATION: Exon 13
```

```
<400> SEQUENCE: 132
cagtatctca tagctttatt ctcatgtctt caaggtggcc cagaaggtgc tgaagaatgc      60
caagcaggca tgccaaagac taggacagta tagaatgcca tttgcttggg cagcaaggta     120
aggaacacct tttataccct ttaaatcgat atagataggt gcatgg                    166

<210> SEQ ID NO 133
<211> LENGTH: 159
<212> TYPE: DNA
<213> ORGANISM: Homo sapiens
<220> FEATURE:
<223> OTHER INFORMATION: Exon 14

<400> SEQUENCE: 133
gaaacccagt ttagaaatgt tgcttttgcca tttcaggaca ttgtttaagg atgcatctgg     60
aaatcttgac aaaaatgcca gattttctgc catctacagg caagacagca ataagctatc    120
caatgatgac atgctcaagt tacttgcaga cttttcggaa                           159

<210> SEQ ID NO 134
<211> LENGTH: 43545
<212> TYPE: DNA
<213> ORGANISM: Homo sapiens
<220> FEATURE:
<223> OTHER INFORMATION: Genomic DNA at the CLASP-2 locus.

<400> SEQUENCE: 134
taccaagggc aactctggca caccctaaag tctggaaagg ggacatagct agtcagggat      60
gacccgagaa atgactggaa gctccaccag aatgcagagc ttcctttgtg cttaaataac    120
tgaacaagca tcactctgtg tagcaggaca ccacccagca ttttttgtcc ctttggaaac    180
aactcttatt tctgtttctt tgtgatacca aaactagcat actctaattg tagaaaatac    240
aaaacataga gtagaacata ctaagttctt tatcttaaga aatggcattt gtgtatgaga    300
atgtcttgct tatcttttcg ccctccaggc aaagccaaag ctaattgagc cactcgacta    360
tgaaaatgtc atcgtccaga agaagactca gatcctgaac gactgtttac gggagatgct    420
gctcttccct tacgatgact ttcaggtaag taacgttatg tttctatccg tagaaccacg    480
tgtttgatct taacaagcag tattttcta tgtattgatt tattgtttgg ttagttaatt     540
attattatta ttattttttt tgagacacag tcttgctctg tcacgcaggc ttgagtgcag    600
tggtgccatc ttggctcaac ggcaacctcc gcctcctggg ttcaagcatt tctcctgcct    660
cagcctctca agtaactggg attacaggcg tgtgccacca tgcctggcta attttgtct     720 ttgtattaga gacagggttt tgccacgtgt gccagggtcg tcccaaactc ctggccttaa    780
gtgatctatc tgccttggcc tctcaaaatg ttgggattat aggcatgagc cactgtgccc    840
ggcctaatta tggtttttaa aagatgaaaa taagatgtta tttaagaaag aaaagttatt    900
ttatattctt ccaagcatcc ttcatgagtt gataattttt aatggtatta tttttgcata    960
ttaattataa gtatgccaaa atgtgtgtgt gtgtgtgtgt gtgtgtgtgt gtgtgtatct   1020
tgaataaaag tgctatactc tgtctgggct gatttagtgg gcacaagtgc ctttctgtct   1080
tttgagattt gttttgattt agattttttg gccaagtacc ttagaatctt aatgatgggc   1140
tttgctgggg agcagtggga gatttcgtca tgccttttt taggatggca tttgggagcc   1200
tgccttcaga ggccctgcac tctgtgtggg ctcccagcaa agcgttcaag gttagccaag   1260
aatggcctga agtttacctc tgtagtgtaa tgtgggtgct gttccttgga agaaatgtgg   1320
```

-continued

| | |
|---|---|
| aggactcagc acagctcctg ctgtgtgccg ctctttcagg ctatggcctg tggttaagag | 1380 |
| actaacaaga agctgtgagg ctgttgagga atgagaatga cattcttcct ccaggaaacc | 1440 |
| cggtggtgtt aaatgccttg cagcgagcca ccttggtcca tttggaggtt ctggttactt | 1500 |
| tccttgctct cctgggacct gatcctggca cttctttctc ctctcctttg atgctcttag | 1560 |
| ttggacactt ctctacctga tgctgttacc atttaagccc tgtcttttgt gaatcgagct | 1620 |
| gcctttttt tttaagcttc actgattctt tgttgtttga ttccaaaagt gttacatcca | 1680 |
| tgtacaaaaa gataaatgag agggaaatat tgaaataatt gacatgaaaa gcctccccac | 1740 |
| gccttctaat cccatcccac agaacatgac ttaactgtat acagtctgt gcatacttgt | 1800 |
| ctttagaaac ttccatgtta atagaaattg ttaaattacg atccttgaag gttttttccc | 1860 |
| accaaattta agcgactcca gcttacaaca gaggtgagaa ttttcacaaa tgttcactct | 1920 |
| ttctaacttg ttagagatac ctgggcccca aatgattat tctttagctc tgtcctgcat | 1980 |
| aaaaggaatg cccatgggaa tgaaattgac cattcgtgtg gtgttgctac caaagtaaca | 2040 |
| ggtaaatggg ttgaggtcat gccaaacaat accatgcttt gcatacttca tttcatgact | 2100 |
| aaactgcatg ggaacggact aataaatgag aacctctgaa tgatgccttt tgcctgtgat | 2160 |
| ttggcaacaa atgaaaagca aaatcaaatg attataaatt gtactgcatg ttgacaagat | 2220 |
| tttcctgtag tgttgtctga ggaagctaaa ggttatctca aatttctctc aacatgaagt | 2280 |
| atgtgttctt cttggtatta attaaagtaa caactttttt gagtttgcaa cctagaatga | 2340 |
| aaaattctat ttgtatgact gagataaaat tgcttaagaa acaaccaaag aaacgagata | 2400 |
| cagttagttg agtgtcatct ttatcccagg gaacaggtat ctggatgttt aagcagttgc | 2460 |
| agaatcagac agtttaaact ttgagaaaac ttctgtgtcc cctttgcttt taactactct | 2520 |
| ggtgatagca ggcacaaata ttctaggaaa ggcaaagaac tcactagcat tttgttggct | 2580 |
| aaggtgatga gcaaatatta ttttctgttt ggggagaagt tttcctagag atttaggagc | 2640 |
| ttgaattgga gctttaatcc tcatcacagg aattgtgatg ggccccagtg aagtttgggt | 2700 |
| acaattattt gttttcttat agactcccac tttcttatca ggtaaagcca tgtactctgt | 2760 |
| gctttcttgt taaattgtct cagtgatgtt attaactgtc taattagctg gatgagtgaa | 2820 |
| aggtcttaac agtgccacag attctttcta tctgtgtttt cttaggcaga ataagagcag | 2880 |
| aattattgta ttattagagg cagagggaac aaattagatt ggggaaagtg ttttatttca | 2940 |
| tatggaaaag taataccaag ttggttagga aatggcagca gcaaaacgca tgctgagggg | 3000 |
| tgatttactg cacttaaata atttagcagt ataagttaac tattaaaata atagaacttg | 3060 |
| gtgtccattt ctgccaaata tatttgaaat gacaatttac taaaatataa gcatggatag | 3120 |
| tggtgatgct tgtgtacatt tttcaagtag gcacatgttg atcttgagcc tttactggtc | 3180 |
| agatcctaaa ggcatctaca tgttctctaa aaatgagttg tgtcaagaaa agatttgcgg | 3240 |
| gttgcatgta gttgcctgag gatgacagaa gagtagttac tacaacagca gcaaagaaga | 3300 |
| gagacatgaa gtaaacgtgg attttaaaa atcaaaagaa taggccaggc gcactggctc | 3360 |
| atgcctgtaa tcccagcact tgggaggcc gaggtgggca gatcacaagg tcaggagttt | 3420 |
| gagaccagcc tggccaatat ggtgaaaccc catctctacc agaaaataca aaattagcca | 3480 |
| ggcatggtgg tgcatgcctg taatcccagc tactcgggag gctgaggcag gagaatctct | 3540 |
| tgaaaccagg agacagaggt tgcagtaagc tgagatcgtg ccactgcatt ccagcctggg | 3600 |
| cgacagagtg agactccatc tcaaaacaaa caaaaaatca aataatagt tcccagccat | 3660 |
| caggttattg atgaagtagg ctgggcacgg tggctcacac ctgtaatccc agcacattgg | 3720 |

```
gagtccgagg caggtggatc acctgaggtc aggtgtttga daccagcctg gccaacatgg    3780
caaaaccccg tctctactaa aaatacaaaa attagccagg catggtggtg ggcacctata    3840
atcccagcta cttgggaggc tgaggcaaga gaatcgcttg aacctgggag gtggaggttg    3900
cagtgagcca agatcgcgcc attgcactcc agcctggggg acaagaggaa aactccatct    3960
caaaaaaaaa aagggaatat taatgaagta aagtacatgt gatctgccat ggccagggac    4020
aggaatgcca tggggcctgc agccgtcact agctgatggc ccttcttttt gcagaatcag    4080
atcctgtcgc ttggggatct ctgccatctg tgctttggct tcatggttct ccttgccagc    4140
agcatcttct cttctagatc tttcctaccc tttagagacc acttgaaatc ccatattgtc    4200
tgaagctatt taagtccaca gaaacttttc cccccactgt ctcaattcct ttcctactgc    4260
ctgtctgcac cgtgcacata aacacttgag tatgtggtct tggctgttca cgacctactt    4320
cttaggcttc ttgcacgcag gcatcccgcc ccgtgctgtg gtcctgagaa gggctggctt    4380
tgagcctctg ttctcccacc cacctgccca cctacacatg cacaaaatcc ctttcttgct    4440
aggtgctagg gttgaatacc cattgcttac cttactaata gtaaaatttt tacaagcatt    4500
aggttatttt ctttgattca tcaagtaaat attaatactg tttggaacat gtgatagtcc    4560
cagcgactag atttgtaaaa atatttgcag gatcaatgat ttggtttggc agaagtaggt    4620
aatttctaaa attaaaaaat gcaggtaaaa cagggactgg agaggagtat ttttcctag     4680
tgattaataa acctttatt ttcttattgt tttgttgtct tacccagttt atttggcgta    4740
aatctgagaa cttactttt ccatgagcaa agttagaggt aaactttaac aagcagttag    4800
acagaggtaa tgacctttag attaaaaggt tttaggtcaa gctgtataag ttgacttgtc    4860
gcttaagaca tgatgagcct ctgtttaact gaaagtcaag cccaggacgc ctgccttttc    4920
catcaaagac atgggatttg ggtggcagct gactattgat ttccaatgac gattcttctt    4980
caagtggagg tcttttttacc agatggtcct gttggtgggg acattgttaa ccctgcgatt    5040
aaccgacggc atcttcatct ggcttttaag ctccttgtat cctgacttgt tacacagctt    5100
acttatgctt gtgcgactat gtaaagtgac agtatatgag aaaggtagtg agtagtaaga    5160
atgttgggag acaatttaag ctaccattca tatttcataa aaattagact tttgtgtctg    5220
gtgtaaacaa acagaggaca gagcttgtat gaaaggataa aagagcgtta agggttacac    5280
gtccattagg ataaaaaaac tagaatattt cttctgaaa cctgaagccc aggccgggca    5340
tggtggctca cgcctgtaat ctcagcactt tgggaggttg agatgggaga ttgtttgagc    5400
ccaggagttt gagaccagcc tgggcaacat ggtgaaaccc catctctatt taaagaataa    5460
ggctgggtgt ggtggctcac acctgtaatc ctagtgcttt gggagtgtga ggcaggtgga    5520
ttgcttgagt tcaggagttt gagaccagcc tgggcaacat ggtgaaaccc catctgtact    5580
aaaaatacaa aaattaggcg ggtgtggtgg cgcccgcctg tagtcccagc tactcaggag    5640
gctgaagcat gacaatcact tgaacttggg aggcagaggt tgcagtgagc cgagatcatg    5700
ccactgcact ccagcctggg tgacagagag agactccgtc tcaaaaaaat taaaaaatta    5760
ggctgggcgc agtggctcac gcctgtaatc ccagcacttt gggaggccga ggtgggcaga    5820
tcacgaggtc aggagattga gaccatcctg gctaacacgg tgaaacccg tctctactaa    5880
aaatacaaaa aattagttgg gcatggtggc aggcgcctgt agtcccagct gctcgggagg    5940
ctgaggcaga gaatggcgt gaacccggga ggcggagctg gcagtgagct gagattgcgc    6000
cactgcactc cagactgggc gacagagcga gacctgtctc aaaaaataaa ataaaataaa    6060
```

```
ataaataaaa aaattaaaaa gaaaagaaa aggaaacctt aagcctagtt attgaggtag      6120
acaggatgct acccctgccc tgtcatttta tttaaaagaa gcatttaagc ctaatgaaca      6180
cgagcagttc taatgtccgt tggaggggag gtagcattca cagttcatag attcatttag      6240
caattactga ttgagcatct tctgtgtgtc tagttatcta tgctcttagg cgctgggat      6300 gtggcagtga acaagaacag atgtaaatga caagagatgg atggtggtga tggttgcaca      6360
attgtgtgaa tgtacttaat gccactgaac tgtatactta aaaatgttca aaatggctgg      6420
gcatggtggc tcacgcctgt aatcccagca ctttgggagg ccgaggcggg tggatcacct      6480
gagattagga gttcgagacc agcctgatca acatggagaa accccgtctc tactaaaaat      6540
acaaaattaa ccgagcgtgg tggcgcatgc ctgtaatccc agctactcgg gaggctgaga      6600
caggagaatc gcttgaaccc gggtggcgga ggttgcagtg agccgagatc ccgccattgc      6660
actccagcct gggcaacaga gcaagactcc atctcaaaaa aaaaagtttc aaatggtaaa      6720
tttatgcata ttttaccaga ataaaaaaag gcagttaaga caagtaagat gctgtgtcat      6780
ggggctagat caagcactta ggggtggggt gttagggact ttgaacgggg cctctaccct      6840
gcgggaaggg ctgagctgga gggatctgtg gccccctgat caagaaagaa gcaggagctg      6900
taacccagcc tggctttgga acttgaggct gcccagtgga atctgttgtg tgtgacggaa      6960
ggaggcagct gcactggatg ggagaaactg gagggactct gtggctgcca gggccagctg      7020
cagggcacac agctgcactc tgaggctggc acctgcctcc ttcacttacc caaggctttt      7080
cctcctgttt ttgtttccag acggccatcc tgagacgaca gggtcgatac atatgctcaa      7140
cagtgcctgc gaaggcggaa gaggaagcac agagcttgtt tgttacagag gtaaggctct      7200
ttcctgcatt aatttacatt ttgaagtcat tttcccctaa ctgcctcctt ttctttaaat      7260
ttcaaaattg tcaaggaagt gtcaaagggg taattgtatt tctatgatgg aagttcaaat      7320
agaataatgt gaattttca gactctgaaa cttggacaga aatgtccaca ggggctattt       7380
cttttttaca ttttttattat ttttaaaact ttatttattt ggaggggct atatctgact      7440 acaaaaagtg aattccacag aatttatctc atggacttaa aataagcagt aacttgtaaa      7500
tgaattcact ggaaatctgt gggaggtctt gttattgata ctgttttttaa gggtgacaca      7560 cacatttatg tatcatttat ttcatttata catttatatt tgcaagttat ttttgactag      7620
tattcatgaa gtactagctg ataataagca gggtctatcg ctagtcaata tatattatta      7680
tatatattga ttactatata tattcctaat caagatacat tgattaatat tattttttgtt     7740 tgaaaatgca aataaaatta tcttatggaa gaaagataaa ttatttactt ttttattttt     7800 attttattt tttgagacag agtcttgctc tgttgtctaa gctagagtgc tgtggagcaa       7860
tcttggctca ctgcaacctc tgcctctcct gggttcaagt ggtctcctg cctcagcctc        7920 ccaagtagct gggattacag gcgtgcacca ccacgcctgg ctaacctttg tattttagt       7980 agggacaggg tttcagcctg ttagtcaggc tggtctcaga ctcctgacct caagtgatct      8040
gcccgccttg gcctcccaaa gtgctaggat tactggcatg agccactgtg cctggccaga      8100
aagagaaatt attacaattt aggttgtttg ctttagtttt tccccttgga gtgtttgttt     8160
tttcctccag gtaattttag gtaggaagga ataattagat gttttaattt gtttctttta     8220
agtgcacctt catttaaaaa taatgatttt ttttttaatcc tggttttttct agttgatatt    8280 tagatcataa atatgctcat caataaaatt gcttactata aggaagctat aaatactctt      8340
ataaagacca attaaataac aatatttaat ttccattgag attttttgaaa aattaaatat    8400 aaaattaaaa aattttttaag tgtgttccct catctttctg aagaagtaac ttcctgtctt     8460
```

```
acctcctttg ccactatatt agtaaactta attccagaca aatacagcca gatatgtttg    8520
tgaatgtagt tataaatgtc ttttaaggc aggtagtggc aaactatgac ctgcaagcaa    8580
aatccagcct gtagccaatt tttgtaaata aagttttatt gtaaagcagc caagcacatt    8640
tgtttacata ttgcctatgg ctactgtcac catgcaactc aaagttaagt agagataata    8700
tgaccctcaa agctgaaaat atttatgatc ttgccttta cacaaaaagt ttgttgacct    8760
atgttttaaa gcatgtggca aaattattaa ttgctaactc agttctccca gttgattaaa    8820
aaaatatggt tttttgaggg agaactctcc attaagttat ttaatcactg caggttgagc    8880
aatagctgct tcatcctatg ctgctggagc caacataact aaacactttt gggacccttc    8940
cacttgggtg gagtgaacat cacttcctct tcatcctctg atccagggaa tgacctaatg    9000
gcttaaaaca aagcaaaaca aagcagaaaa aaacttcaaa aaccttcag tgtaacttca    9060 aaatattatt gaatttcacc agtttgaaat gttaatcgta taatcagtca gtcacattcc    9120 tgtcttttg aaggtacagt tctcaggatc tggctttctg atggaactcc ttatctccta    9180
gactttctgc atcccagag gggtgggggt tgcttgccta attctgtgct tctgctttgg    9240
aatttagcca atgcctgcta tgtagatggt caacactggc ttgttaaatc aatgaatctc    9300
taaatactta gccaggttca ctgtggagtt ttttttgtt ttttttttt tttgtatgtg    9360 cgattcctta aattataaa tatgaaca taataaactg taattatttt ccccattttg    9420
cctaaggtat taaaatcttg gccaggcgca gtggctcacg cctgtaatcc cagtactttg    9480
ggaggccgag gcgggtggat cacgaggtca ggagttcgag accagcctga ccaacattgt    9540
gaaaccctgt ctctactaaa aatacaaaaa gtagccaggc gtcgtggtgt cgcctgtaa    9600 tcccagctac tcgggaggct gaggtaggag aatcgcttga acccgggagg cagaggttgc    9660
agtgagccaa gattgcacca ctgcactcca gcctgggtaa cagagcaaga ttccgtctta    9720 aaaaaaata aataaataaa taaaaatctg gctccattc ataaatgcat ttataatata    9780
caaatttatg ctggtttatt tagttttaa ttgggcaggt acatttata cttcagaata    9840 gttttaatgt cctgcaggag acttggtggt acaatttcag ttctagagct tgttgaaaaa    9900
ccgctgtagc tcttttgaaga aataggatc acacccacaa gaccacgtcg tacatagtca    9960
ggcctgacta cttagctgtg ccagtggacc taggggcagt agtgggaaaa tccaaaacta    10020
tggattattc tgaaatctga ctggttttgg aatgaaattt tgagtgtgaa tgtatgatac    10080
tcaaaatgtg aaaatgcttt gagaaatcta aaaaaatcat tttcaaggat aaaatagcat    10140
tttaaaatat tcttaactac agagtaaaaa aatcaaaaag tttgccagct ccaaaatctg    10200
actttgcgct tagcccttct ctgccattta ttccacctct cagaataatt ttaaaaactt    10260
acattacctt cacatcacac atcacaccct tgccagtaaa gtgcttattg tagagcctgg    10320
cacaaaataa gcacttgctg ctgttgtaat tcttactttc atgagtttgg aggtggaggg    10380
gagtttgctt cagaagacct tcaggcatgg cctgtgacac agatagaaag gttgacagta    10440
gaaacgatga agtgaaagaa gcagaataga gacgttgttc atgttagtta cagccagagc    10500
caaataaact agataaggca taaatacatt tatcgaccta tgttttcatt gattcactca    10560
tgcttttttt ccacccacac tgaagtctgc acataaatag tcaagtgctg actgacaga    10620 agatcatttg aactaagctg attttaacta aaattcttta gcttttgatt ttgactcatt    10680
catatttgaa gatctggtgg atgtggcatt ataatcttag gctttatgca ctattggagg    10740
atcttcatgg gtggatgaac gacggacacc aggctggccc attgaatctg tcatgtggcg    10800
```

```
aggtagtttg aatgcagtct gtgtaggtga ggtcactaat agaatccttg gcagtggaag    10860
actacattaa acattctgta cacacacaca gatgaaaatg tcatggtgct aatattaatt    10920
ggaatgcata tgtttcttcc taattatttc actcttttcc ttatgaatgg aaagaaaaac    10980
tgagggcaga tttatatggt aatattaact aacagagcta gctagttcta atattagtaa    11040
ataccatgaa ggcgtcttta agttcacgca tcctattcac ttttatgtca tagtagaggc    11100
cacatggctt tttaagaacc aggtgcttac tctgaaatag tccattgtta agtaaatgtc    11160
acaaggttag gtgaagttgt ctccttgtaa aacctgctct cagatcatta atgatgataa    11220
cttaaagtga tactacccc aagggtaatg tttcagtggt tcaaagtctc aagcttcaca    11280
ggaatctctg gtggtggaat tcaggcatt agctcgttga tgggaaaaaa ttttttgat    11340 gtttctatgg gtatgccttc acaaactttc ccaagtgttt tccaaaaatc acgtctttct    11400 gtttttatt ttctattttt aaaatccccc ttcaatagtg catcaaaacc tataactctg    11460
actggcatct tgtgaactat aaatatgaag attactcagg agagtttcga cagcttccga    11520
agtgagtaag ctatattata cacatagggga aaagtctttg tacttgaaat gcttgggggg    11580
aggtatgtaa cttcatatgc aatcagagta attgaggaaa atatttttag atggtttatg    11640
tgtatgtggt gtaactattg tttacagggc ctttgattgt aagactcaaa catgctactt    11700
tggtattgat aggtagtaat aaacatgtgg atggtttaat tatgtccagt ggttcttttc    11760
agggtaccac tgataaataa ataggtgaaa tttttcact acaaaatata aacaaacaa     11820 aacgtaagtg tactgaaata tgctgcagtg catttttcc ttgaaaagaa tattttgaag    11880
aagataatta taaagagcat tttacattga ataaatttta tgttttaaa aaaagtaaat    11940 caagaaacaa gcattttccc agttaaattt tttttttatc tcctttaatg tattaactta    12000
ttctagacta taccaaaagc aagtgtattt agattgaata gttgtggcca aagtgaatcg    12060
cggtagctag gtattgcctt gacagactat cttttataaa aggttccatt gtgtgttgct    12120
ttaaaggaat acctgagact gggtaatttc taaagaaaag agatttattt atttattttt    12180
atttatttag ttttgagaca gagtcttgct ctgtcaccca ggctggaata caatgacacg    12240
atctctgctc actgcaacct ccacctccca agttcaagca actctcccgc tcagcctcc    12300 cgagttgctg ggattacagc cacttgccac cacgcccggc taattttgta ttttagtag    12360 agacagggtt tcaccgtgtt ggccaggctg gtctcgaact cctgaactca ggtgatccac    12420
ctgcctctgc ctcccaaagt gctgggatta caagcattag ccaccgagac tagccaagaa    12480
aagagattta tttcgcttat agttctgcag gttgtacaag aagcatagca ctggcttctg    12540
ctcagcttct gttgaagact tttgtgctgc ttcaaaacat gatggaaaag gtcaaaggga    12600
aagttggcac ttgtgaaaag agaccaaaga ggaggaggaa actcacttta taacaaccca    12660
ttctcttggg tactaatcca tttcagcaac aagtaatccc atcttgccag gaacaagaat    12720
tcactcatta ctgtgagaac agcaccaagc ctctcatgat ggatctgccc cataacccac    12780
taggcccaat tatgcaacaa cggggaccaa atttcaatct gagttttggt gggaataaaa    12840
accatatcca aaccatagca gttggcaaat tgaattatac ttgatttttgg gaaaattgaa    12900 agcaaatagt gatggattat gttttaaaac taaccatcac caatgaaaat attacttgag    12960
acctgattaa tgtattttc tttgcgtttg ttacatcttt gagctggaac cttttatgcg    13020
gttctcagta gacctagctg tttgttttc ctccttgtgt ggctttgcca ctccttaaga    13080
atgttcggcc aattcccga ttgcctcttt ttaaacctca gccaggaaca ctccctccta    13140
gtattatctt ctccagatgg gtagccctt agttctatat ttacccaatc ctcccttagg    13200
```

```
gatttttaa ttcttcccat tggattggct taacccatct tgttgatcc tcttgttcat    13260 agtctcaggg ttgaaagata tcagactatg tcatgtcgta tacttactat ctaatagact    13320
gctggtacat tttctctctt ggcattaatg agaatttcca aatgtgtgat gagaaagaga    13380
gggagaattg taacagtggt gaagaacaca gattctgtgt tctgcctcag acgactctgc    13440
cgtctgtcag cctgatttc ctcatctgtt aaatggcctt aacaacagtc accatgatta    13500
aaggattaaa tgagagggca catgagaagt gcgcagggcc tagcacgtca tacccattga    13560
gtaaatgtaa gctgcttatt ggtattggtg tcttgttttt gttgtggtta ataccatcat    13620
tgttaatcgg tttcaacgca acaactcaat cttcctttt ttcctcataa actttgtatt    13680
aaaagttatt ctaccaagtc tttgtttatt aaaaactaat ccactttctt atttttagta    13740
tgcctgctaa ctccccagaa gctatgctgt cttttccaca tagcttttg gagctttctt    13800 actcaagtct cttggcttac ccaccttgaa aagcaagggc atagatggtt ttattctttg    13860
tctgaataaa gaagctgggc catctttgga tttagtaaag gccgggccct atgatggagg    13920
aagaaatgca aagcctcttc cttgactagg catttctaaa acaaattttc tttgttgttt    13980
ttatagcaaa gtggtcaagt tggataaact tccagttcat gtctatgaag ttgacgagga    14040
ggtcgacaaa gatgaggtgg gatacctgct tgctgttgct tctcttttca ctctagattt    14100
aaacatcaat tttacagact tagaagatta gttagaaaat taccgacatt tagccaaaac    14160
aggcattgga gtgttacatg aaacgggaat aattttttaa aaatgttatt gattgattgg    14220
aataaggtct ctgtttcaac tttactgctt agcatttcat gttctcttgg ttgtgtttat    14280
ttgttctgag atcattttca aagacttgga tcagatctgg ctacattgtt aaaagatatc    14340
aagatgactt agaccttgaa tttaggttgt ttttcaacag atctcgaaac agctgccagc    14400
cagtagattt aaatggctat ttcttcaatg attgctttta gtgaagtctg atttgatcaa    14460
gcccactccc cctattccta gaggaaagct catggctaaa gaactatata agggagtag    14520 ggcattgaga tgagtctgcc cactgagtga gggaaacctc acaagaagac aatgcccatc    14580
tctgcatttc tcatcctccc cattgattgt taagtgtccc attgtgagtt taggttttc    14640 cttctttaaa aaaattgtca gctgagctat aacattagcc actcattaag caatgtgcat    14700
gtagcaaatt atttttattc cccccatcac tttatctctc ctttctgtat tgcctcaatt    14760
tcctcccttg ctttattcac cttttccctga actaagcctc tgggaaggtt tccaggaatg    14820
tgcatgtgct tttgtcctct gactatagg gagtgtcatt tgaaaacatt ttttcgtgaa    14880
accaggcaag accttccaac gtgagtggtc agttgaggta tgtcctttt ggtccttttg    14940 tggctcatta aacactgaca aataaaaatt tggacaggag ctagctttgc ctttaatgga    15000
ataaagtttt cagaaatgta ggcgggtctc tctctttcac cgctaagtgg acttttatgt    15060
gacttgtagg cattggtgtc aatgggtgct tcagtaaagg ggcaatggac aacttggcac    15120
aaagggaatg accttcccat tgaccaaact cacagcaagc aacccaggta ataacgggag    15180
gttgactgct ggtgtttttcc ttctctccta ggatgctgcc tcccttggtt cccagaaggg    15240
tgggatcacc aagcatggct ggctgtacaa aggcaacatg aacagtgcca tcagcgtgac    15300
catgagggtg aggacgcaca tcactttgcc ctcccctctc acaagcctt tctgccatag    15360 agctcgagaa caatgctcaa gatgaatgcg catgctgttc ttccccacaa aagggacatt    15420
gtctgattcc taggatgctc ccctggtgat agcaccccca ttggcacagc ctcatccacc    15480
cactttccct cactgtcttc tgaccaccag cataaggaga ccatccctgg gctggtgtga    15540
```

-continued

```
aggtgcagac actgacatag gctttcttct ctgtaataac tgaaaagtgc tctttggtac    15600
ctcacagaat gtcaccaagg ggctatctgt catgccaatc ctgagcactt ctgtggaggt    15660
gtactgcagc aaagtcaagt aaagcaaaaa ttgaggacga gaaaagaaaa tagttgcata    15720
gaagagaagg ttgcagacag agaagtcaaa ccaatagaag aagctattca ggagaaaagt    15780
gggaccagag gaacatcagg attaataaca aagggaagag aaacaaggga gtcagggaga    15840
taaaaattaa ggaggaaatg tgactgtcat taccctaagg ctggaaaatc attcagcgtc    15900
atgaggcaaa aaatagttcc cattctgtga gcaagaaacc ctggggattt tagagaaagt    15960
ttctgtcctt ctgtgctgca tcccaaattg gaagtccctg cactgctttt gggtagttat    16020
gtaaaatctc tgattccgtg ggtgagaaaa atgacccatg gatattaggg gaaccacctc    16080
ctcagaactg agatgcagtg agcttcttag atgggatggg gagtcttgac cccacagtga    16140
cctggagcat cagctagagt gagaacggaa acaggtttta tgtatgtatg tagtcataag    16200
tgggttattg atagagattg tgaccctctt cattttgaaa gaatagctgt gtgtatattt    16260
ttctctcagt catttaagag acgattttc cacctgattc aacttggcga tggatcctat    16320
aatttgaatt tttataaaga tgaaaagatc tccaaagaac caaaaggatc aatatttctg    16380
gattcctgta tgggtgtcgt tcaggtaaat atgaaaagag ttttaccatt atgttttctt    16440
atctgcagta gtgcttatgt gtaaattagc agatttaagc aaacacttcc aaaaatggca    16500
atatgcatgg tagaaatata acatataact ttaaatgagg caagccttgt ttttcatcat    16560
tgtagaagat ggaagggata atgtagaggc agaattatgc tgtggcaggc aggagcactc    16620
tggctcggcc actttatagc tgcgtgacct ttaacaggct acttaattca gataatgaga    16680
atgtttcttt aatacggcaa atgagtacat tggatgaatc agtgcaggaa atatttaaa    16740 acacttcata gtatctcagt ggtgattttt atcgctagca ttgtagtacc agtggcggtg    16800
tagatcagta aagagattag gtttcagcgc agattgagtt caaatccctg ctcctccact    16860
taccaactgt gtaaccttgg agatgttatt taacctctct gtacctcagt ttcttcattt    16920
gttaaataag gataatggca gtaccaaata tggttactga gagggttcat tcattacaca    16980
tgtaaaaagc ttagaacagt gccaacaaat ggtaagcatt tggtcagtat tagatagttt    17040
tgttatcata gggctgttgt acttttatat catagggctt atgtacttat cctttaaaat    17100
tattgttaat taaagataac acatgaatgt atttttcttg taaaaaatca gccaatacag    17160
ataaagtgaa agtccttctg gactcctccc ctccttcagt gtctcttttc tgaggggagc    17220
tactaccagt tttgcatgca tccttctgta gcttttagc attgtctttg gaagagagtt    17280
gtcaatttcc ctgtccatca tctgtccatc catccatcca tccatccatc tgtccacccc    17340
tccattcatc cagccttgcc actttcaagg aagatttaag gcagcagctt ataagcatac    17400
acaggacatg ggatagcata aatttaaagt ggggggtgaaa gcagaaagat gaacagggga    17460
ttgggataag ggtgagagaa aatagagtta aggagaaagc gtatgttttg aagatctaac    17520
acctgctgtg ggtgggccac cacctgggct ctatgctttc tcacttggag acctgtttag    17580
tcacgcaatt cacagtgcac atgagataaa ggcatgatgc ctgttagtc gactctagaa    17640 gcacccctga ctttaaaaag aagttaaagc aaaactaaat gtatttggca acctcatttt    17700
ttaaagtagg aagtaattat ttttgtttta taagagagtt ttgctgcctg tttctggccc    17760
agggacagat gtttataagt acaactgccc tgagctatca attagtctcc ggggtgcatt    17820
tcaaaatcta aggttctgac ttcaatggaa gtctcttcct tcaaattgtc tttgcagatg    17880
cagctgatgg tgtttttcatt taataaagtg tatccaaggc ttcaaaaaag taaaataatt    17940
```

```
tgtttttatc tgtgtctgtt tgtaaactaa gcatcaaaag ttgtgattta agtgttttta    18000
aaaattatta cttatggata ttataaaaaa attagttgac tggtgctgtg aattaaaaaa    18060
agtgcctaaa ctaaaaaatt ttgaagcatt ttagaaccct tgaaatttat tatacttatt    18120
ttgcagatga gaaaactgag gctcagaaac agaaatttag aattgaggcc taatgttttt    18180
ttctccactt ttaactttct cttttcatga ttgtgagtat gcagggaaag gaggagagaa    18240
aattcatttt gtttcaagcc tttgacttct tccctggttc ttgccttgaa gtttaagtgg    18300
aatccaaagt ggcaattact gagcccacag cagacagtct gtgcacaaga gtgtgtggct    18360
ttgccaaggg gagcacttga cttttgcattt ctaagaactg tgctgcagaa tcacagagac    18420
tttttgggagg gttgccctgt ccctgagacc tccaccaagg aactcttaga gagagtgtgg    18480
ataacccagt aggattttag tggctatgcg gggggctgtc ctgctggctc aggttagtgg    18540
gagtgtttga tttcatatcg ctcagcctgt ccttacaggg gatcttgtgc catgatcctc    18600
agagctgaac ctctgtctac tgcggccaac ctggggagat tttgctccct ggaggacatc    18660
ttggaatgtc tgaagactgg catctattgg cttaaggcca taaatttcgc taaacattgt    18720
acaatgcatg gaccagccac tcacaacaaa gaattggctg cccaagtgtc agtagtaccg    18780
agattgagaa atcctggcct agtgcatgtt catcttccgt ctgttactgc acatggacta    18840
ctgttcttgt tctgtgagcc agtcaccctc ttgcaggcat gaaaactgga ggcatgaggc    18900
aaggccacgg acagggagtc caaatacctt ttgggattca taaaggatgg gaaagttcca    18960
gataagtaag ccaaacatag taatagataa tggttggctt ttaaaaatgt aataccatac    19020
actacttcat taaaaaaata ggagctgaag aaatatgaaa attttacatg aaatttcatt    19080
tattcaacaa atattttcta aatacccact atgtgcaagt cactgtagag tccatagaga    19140
ctaaggatgt gtagcactga caaaaatggg agcactgagg aggtttcatt ccactgcagg    19200
gacacacagt gaatcagatg agtatgtaaa gcaggtaatg agtcagaagg aaaaataaag    19260
cttgcagaaa gtgaagcagg gaaggtggac ggtaatggga tttcatgggg gggggctttc    19320
atgaggaggg ggcaagctat ttaaaatagc ttggttctaa atgccaatga gatatcactc    19380
accaacaaga gagagtaatt atttttaaagc agttctaatt cttttaaagt atgtctgttt    19440
atcctttttt catttcagaa caacaaagtc aggcgttttg cttttgagct caagatgcag    19500
gacaaaagta gttatctctt ggcagcagac agtgaagtgg aaatggaaga atggatcaca    19560
attctaaata agatcctcca gctcaacttt gaagctgcaa tgcaagaaaa gcgaaatggc    19620
gactctcacg aaggtagata ggcttggctt ccccccaggca catacacact ctgtgggtgt    19680
ctttattttt gccaggtggg tataagaagg agacctgtgt tacacaagta catgagaggt    19740
gggacggata ggagctcttt acaaatatcc tgtcagcaaa ggttttgtca cattataact    19800
tacttccctg acatttcgta tatggaaatc atgtaatggg aagaaccaaa gctttggagg    19860
cagaaaggga gacctgggtt tgagtgccat aaatactgta tttcagctgt gtagccctgg    19920
gtaaacaact tatgttttct gagcctcagt tgactcacct ataaaatggg aataaacatg    19980
aaaattgctg ggaagatggg aagtgtaaat aagaaaatga atctcaagta tctggcatag    20040
aattttactg tattataaaa tattagtaat aattagaatg catgggagcc tcagattaaa    20100
ttggtgagaa aaatctggct atgttcttga caattcatgt tttacttcaa cccttaggtg    20160
attcccaacc ctggcttccc cttagaagta cctgggagct ttttaaaaat accatttacc    20220
tggtcccaca aaagattctg atttagttgg tctggggtgg agcctgggca ggtctgactt    20280
```

```
ttagggggtc tcatggacgt gtccatgtgg gctgttgttc atagctagtg tcagttctaa    20340
ttggacggtg tccatgctat accagctgct cagtgttttg actttcatca ctgagcctgt    20400
ggatcagtat ttttcaaag cacccaagt gtttcccagg agcatccaga gtggggaacc     20460
actgtgttca tttgaaggca cctaagagaa acggccttcc tcctcctgtt tcaaatgaaa    20520
tgctatgaat tacaagtgat tccgataatc tgttttgcca ttttagatga tgaacaaagc    20580
aaattggaag gttctggttc cggtttagat agctacctgc cggaacttgc caaggtaaca    20640
tcgtcttata tcttctgctc ttcgttgaat gctgttgaag tatgtctcat ttcactggtt    20700
tgtccagaat ggaatctgtt gaaatcataa aaattacatt gtgattaccc tctctttttt    20760
ctgacctgat tacgaggtga cgtgtactca tgcagtatga tttcaggtct gtcttctaaa    20820
aagtacccta caaagcattc tccttttatt attattttaa gtgttttttt ccctgataat    20880
gcttaacact gcatcacagg tactgaagaa ataactgaaa tatgcaggca gatgttctca    20940
taatagcatc gtactttcta tgttgataca tgtgctctcc cttactcagg gtaatagaca    21000
cggttccaaa gaggaaggac ctggtaatct tgccacgaaa cccgggggtt gcctgagtta    21060
cagaaattgt ttcgggtcac tcttactgga aaaaaaataa gctattcctg tgtcttacaa    21120
ttttgagaaa tttaaaagtt actgaaaagc acaaagaaaa gcaaatcaac catactgcta    21180
cttcccagat taaatatcta ttatgatgtt gccttttag cttccatatt cttaaaagat    21240
ataaaacatc ggttatagtt gaagttcttt ttaaacactg tccttattcc cattctcttc    21300
ttctcccaca accccaatca gaaacaagca ctattaaaag ttttactttc attttttatat   21360
ctttacaaat aaatctatca taatgatata tacagtatga tttagtatgt ttaaaaatgt    21420
tttataaatg ctaacatacc atatgtattc tgcactttaa aaaattttta aatttacccc    21480
tttttatttgt actatataga cttttttattt tagctgttct attattttca ttttttttcta  21540
ttataaacaa agctacaatg actgtccttg tacttgtgtc cttgtgtgta tctgaatgat    21600
tctttcttaa atgagagaaa tatctttgtc ttctctagcc ctttgcactc ttactctgtt    21660
actgcccttc tattcttttt tgatactaga gtgaaatggc gacccctccac acccacatct    21720
taaacactat aatagaaaca tggtttatct atataggatt ataaatagac cagcattcag    21780
cattgacctt tatttaagaa caacatggct gttctcaagt gtaaaatctc cctccctggc    21840
tagggcttta gagcattgtt tttcttagg acttgactgc taccacagta tcttttagc     21900
acctgcctat taaagctaat tttagtgcca ccattgtaaa ccacctccta gtctgggaag    21960
agttttggct tgtgtgtttg tgttatgaat gtctgtgtat catattttgc attgagattt    22020
gcttttttgt ttctggatgt ttgggggttc ataatttctc aaaacaaaat atttgtgccc    22080
atttgggttt tagtttgttg cagcaggtaa tatatgtgat gccatctaga attcagaaag    22140
taaccttctg cacttactgg gtgaacggaa tggatcccta ggagaagatt catgttattt    22200
gagcctaatg ttgattaatt aaaaatctat gcttttttcct atgaggatat acaggaacgg    22260
tccctccctt ctcttactac ccagccaata taattcagta ttgtttgatc ccaagaccta    22320
gggagatttt ttaagatata catatatta atataaatgt atacatttat gtatatatac    22380
ttttttataa gtataattgt atatttttgtc atttaaaata tttggaacta ttttttaaact  22440
atgggttaca agttaggtta agccatttta gttggtgaaa tcagtttgat ttcaaccccct  22500
gcttcttttt gttttgtttc tatttagttt tttattcttt ttattgaggt ataatttgca    22560
atagcagaat gctcaaacat gaattgtaga gctcactgga gttcgcattt gtacactgat    22620
ataagcagcc ctcaggctag cttgtacctg agaccctctt tattttgacc tccatcaccg    22680
```

```
tagattagtt ttgactttc tagaccttcc tgtgaatgga cttatacatg tactctttgt    22740
gtcaggctta tttagctaaa catgtgattc actttaagaa gttttttta ggtcgggcat     22800
agtggctcat gcctgtaatc ccagcacttt gggaggctga ggtgagcgga tcttttgagg    22860
ttaggagttc aagaccagcc ttgccaacat ggtataaaac cctgtctcta ctagaaatac    22920
aaaaattagc taggcgtggt ggcaggtgcc tgtaatccca gctacttggg aggctgaggc    22980
aggagaatca tttgaacctg gaaggcagag attgcagtga gctgagatca tgccactgca    23040
ctctagcctg ggtgacagag caagactgtg tctcaaaaaa aaaaaagggg tccgttttaa    23100
tgaaataaaa tggaatggag aatatgaaag tacactgccc ttaataatga cattattttt    23160
tatataaaat actgtcatta ttattttggt ggcacctgcc accatgccta gctaattttt    23220
gtatttctag tagagacagg gttttatacc atgttggcga ggctggtctt gaactcctaa    23280
cctcaaaaga tccacccacc tcagcctccc aaagtgctga gattacaggc atgagccact    23340
acgcccgacc tgaaaaaaaa ctttttaaag tgaattacat aattttttac ataaaataat    23400
gtcattatta agggcaatgt actatttata catatagtgt gtatgtgtgt cttgcatagt    23460
gatataaaag atatttgttt ttcttagtgt gctattatgt atatttattt actttcattg    23520
gtatataatg tacctatttt gggagttcat gtgatacttt gatatctgta tacaatgtgt    23580
gatgatcaaa tcaggataat tgggatagcc atcacctcaa acatttatct ttgtgttggg    23640
aatttgaaac atttcttacc aggagtcatg gtcaaaacct gaaaaatgaa tccttgttag    23700
aggcttttac tctttcccc tggctttcag gtgttttaca aatacttta tttaggaagg      23760
tagaaaggtg gaaagtaatt ttttgaaggg gaaaagaatg aagaaaatgg agatgagtta    23820
ttcactcagc acatgggtat ctgtgggctt tgccttttaa agcccagctt ggtgtcagtg    23880
tgagcagccc aggcagtaag gggagacctg tgttccccat ccccagcctt gagcaaaaat    23940
gcagttttgg ctgtttatca tccccttca gggtgtctga actatttgca ccggttgaga     24000
aggcaaagaa gttgacctga taactgttgg tcatcccatt aggaaggatg gattccatgg    24060
ttacagaatc agagactgaa gtatgcagag ggaggggtgg ggagagagaa ctgtgcaagg    24120
agtttaccca gggtatgaag aggtaaagag gtcagtatca gggaaggaag gtgcaagaaa    24180
gggtcaggct gggaggctgg gccacagttc agtaagatta caaagaaggg cctagaacaa    24240
tgagggcagg cagaaggtgg ctgaaggtgt aatttcatgg caggttcctt ttctaatcag    24300
ctcctctaac ctccttcatc ctgttgcccc ggcttttgtt ttccactgtg actaagacat    24360
agccaaacag gatatgaccg acaggaagtt gtttcagtgc aaaaataact gatgtctcat    24420
tctggaatat tatggaaggg ctcattactt acagtgtgag tgatgtaaac ccaggttttc    24480
agaattttt gtataatctt ggagcttatg tttgtacatt tagtactgaa catctgtatt     24540
gttttcttat tagagaacac actgtattta ccctaaaact ggttcttttc ctccatattgt   24600
ctattatgga accaaacaat tttattgta aatgtaacag tgtgtagcat cagtcttata     24660
aatattttag tttgatacac aaaccgtagt tcaagttagt taattgattt cttccctaga    24720
aagtcaagga gtaacataat caggttataa acttcattac tagttattta ataatttatt    24780
tctctggtta catttatatc ttaggtgaca tcagaacata tatgtcacct ccttaaagat    24840
agtgtgaaga aaacccacct tatgttttct tccacagctt ttctgtttgt gagctttat    24900
ttttgtactc aaagaatagc atccaacttt tactttggtt tccccatgtg gttctgaaag    24960
agaagtagaa tttcttctaa atccggaatt gctcacatcc ttttacctttt taactttgtt   25020
```

-continued

```
ttaagcaaat gaacttattg ttccaggtaa atcttccaca gttgcatgca ggggaaagta    25080
tgatgtctca gactttatag tctcatggag atggagtgag gatcaagggc catgctcagc    25140
agaacttgtc aggacccagc agtttcacgg acaccttttc ttaattttta aaccaagtct    25200
ataataagtg ctttcttccc tagattccaa tccagaaaac aatatcattg cactattata    25260
caaaggagct ggctaggctt gtgtctgtgg ggtcagctgg tgttgcattt ctgggcctcc    25320
tttgtgaaga ggatgaactg atggtcctga gaagttaggt gtcttggaag tagtggaaat    25380
aaatcatgat aactctttaa attaaagatt atatattttg gcctcaaaac attttgcaaa    25440
gtcctcctat tccaacccaa tctgtttaaa tgacccaaca ttcaacacat tgtttctgat    25500
aattcatcct cagaataaga tgctgttggc cataatcttt gtctctagat tgttttatct    25560
actcgcaaat aaatttaaga cacagagtat gcctaaagcc tacagcagac tttctggaaa    25620
ctcttgaatg tttggtccat aactacttct taagacaaag aagaaaacct tgtcagggtg    25680
tgtcattagt gcttgaatgt agggtttaca ggatggggtg gggtggggga atcgcccttg    25740
gtttagatga atcattcttt tccttgtctt ctcagcaaac accagtttct acagagaaca    25800
gctctgccat tgtgcatttt ctgtctccat tttcctctca ttctcctctc cacgaaaccc    25860
agagtagtca gtgggctttg gcaggaaag tggcaacagg gtgtctgggg aaaagccagt     25920
tggctcttct taccatcaca atatagactg accacaggtt attttaagag cagagctggt    25980
ttccatcact ctgagaagtg ctcaactaca gactttggga tgatatttgt tatagctgta    26040
ttttctccac tcttagattg tgaaagtaca tattacaagt atttatttta ttatctttac    26100
taaaatttta attaaaaaga agcgtgcttg ccgcaataag taaaaatacc caaagttgtt    26160
taaagaaaag ttcaccttttt cccttcatcc tccattccca cattcctgag aacactgaag   26220
ttaataaccg gttgcaattc ccctttcacc aaactgattg ctcatagaaa tatagataaa    26280
catatgtaag gtttttaagt ttttttaata aaaatatgtt catgatatat acattattct    26340
gaaattttct gtatcactta aaaatatttc atagatgtcc ctctgggcca gtggaagatc    26400
tggttccccc ttacatacat atcagcaagc tgcatgatat ttcaactatt gctactgcac    26460
agtttattca gccatctccc tattaatgaa catttaaggt ttttttttca gttttttagcc   26520
tctacaaaca gtacacaata aacaacatga cattaaatac ttgtgctctt atttcagtag    26580
gagaaattcc ccaatgtgga atttttaagt caaagtttat tgtgttttta atgctttaaa    26640
cattgccagg ttaccgtccc aaaaggctat aacaattcac atttctgttt ctctgcatct    26700
tcaccagacg agtgtaaaat ggtatttttac tgtgctttca tttatatttt gctggttatt   26760
agtgatattt ttcatatttt catatatttta tttgccattt gtgttttttc ttcctgactt   26820
gcttgttcac attgtttacc ttgttttctt ctgtcttgtg tagtgtaata gtttagactc    26880
tgaagccagg caacctgagt tagaagccag gcctctattt catgatgtag gtctttgggc    26940
aaagtaccta acattcatgc cttagtgttt tctcttttaa tgagcaggga taataatagt    27000
acctgcctcc taaggttgta taaaattaaa atgggcactt agggtaatat ctagcaggta    27060
gatattggct attatcaata gtagctctta tcgttactat tcttccagat actgtttcct    27120
gactctgggg caaagtcctg ctaccctgaa accacatttt tctacctctt agattttact    27180
tggtaattcc atcagccact gttgggcatc ctctgtgttt aatgcatcat cttagacctt    27240
aggagggatg ggaggaactt aagaagccg aatttgcttt ttatttatct tgtagcagag     27300
caatagatgt atattaggta gattacaagc ttttaggtta ttttgcatc taaagctgtc     27360
ccttctttc caataaatga tgtctgtggt aaagaatata tctgttgggt gttagtgaca     27420
```

```
aaatcagaat gctttgtgtc tattttggct agtagttaat tgttttctt ttattgtgtc    27480 tgcattccta tttgttcttt aattataccg agctcattag cagttattct tgctttattc    27540
atttcttatc tcctagcata gtcagctcaa gacaacaagc atctttcaga aagccactag    27600
gaattgcatc tacattaaga acccactcct ctgctctagc gtctgagaac ataacacagt    27660
atttgccttt gttgaagggc tcaagcggac gattcagaag tagaatagat aactgttggt    27720
ggtggcttgc agcacctagt actgatggtt tgttaggaa acaccacagg cagtatacaa    27780
tgtaaagcaa gttctttggg ttcagttaaa tagattccac ttgcacgtgt tctcactctt    27840
ttggtgtgaa aaattaggaa aggtgatagg caggatagaa taaaatgaag tggtcccatc    27900
tcccatatgg agagcgcctg cctccaccac agacacatgt tttgccctgg aagcataaac    27960
agaagattgc aggaacgccc cttcacctcc atagccttca ggctcccatc gatagcatca    28020
agataaactt ggtgtggcaa cagacttgag ccatcatctt gtttaacatt tttacctgga    28080
agtgaaaatg gaatccagag aggctaagta gcttgcacag ctacttaatt gaactagaac    28140
cagaacccag tttcttagta ttctggtgcc cattttatat aaacatagac agctgatcat    28200
ggtagtttgg atcattgcta aagacctatt atatacaaca atcgtatggc taagaagatt    28260
aagatgctta ttttctcgtt atccatgatt agaaatgtaa taagagactt tgttctgtca    28320
ccaacagaag agacaagacg ccttttctgc tgtggttgtg agtgcccat caagtgctga    28380 gatgtgactc atgtctttgg ggaaagtagc agatgagaga gtacattcta ttccgactcc    28440
atagacttaa ctgtggagac tgagagtagt ggagagctca gactgacaag aagaacagaa    28500
tatagactta gaggcaccag gcatgaaaaa tcataaagat ggagatgact tctatcttgt    28560
gaatgtctga aaagcctctc tctctttctg ttcccaaatc cttcatctcc agccctcatc    28620
tctgccacca tctgtcggtt ttcttccgtg gcctctcttc tgtccacctc ttcaatgttg    28680
ggcccccagg attttgtctt cagactcact ttcaccctct ccctcaggac atctcatcca    28740
ctcccaaggc tggaactcca gccttcctct cagccttgcg cttaagtttc atccctttag    28800
ctgtctattg gatgtttcca gttggaaatt ccacaggcat ctctacccag gcgtctctac    28860
acaaagatga taaaaatatt atcatctttt tggcagattt gttttcctg agttttctgt    28920 cgtgttcatg gattcaccat tcagcaggct gcccaagcta gaaatgtggg atttgttaat    28980
cggccctgct gtgagactgg gaggctggtg tgataaccca agaaagacat tgtgggcctc    29040
tgggtcttat cctttttaac ccattgcctc agccctgccc gagtgatgct tctgaaatgt    29100
ggaactcatt ttattctctt acctaaaagg ttgcaggata ttttagattc tgaatgaaat    29160
ccccaatcct tttttttttt ttttaagtga agcaagttt attaagaaag taagaaata    29220 aagaatggct atgccattgg caaagcagcc ctgtgggctg ctggttgccc attttatgt    29280 ttttttcttg atgatatgct aaacaagggg tgggaaatcc ccaatccttg gcattcaaat    29340
cccagactca tttcttttca cttttttttt ttaatcatgc cctgcctttc agttatgatg    29400
agtgacttgg tcattgctca ggtgtgactt gtccctttgc acctgctgtg ccttctccta    29460
gaatgcgctt ttctcctttc ctggccaagt gttcttgtcc ttcaaatgg gccttccctt    29520 gggaggtggt ttctgacgac cacccctag tccaagtcag ctcccactgt actttaaact    29580
ttctcttgtc ttccttatta cctgttgata tgctctctcc ccacctggtg ttccttggga    29640
ctagggactt ccttcattca catttcacat aacttgaggg cctggctcat aagaggtgct    29700
taatgaatat ttattgaatt aattagcatc ttgtccttca agatcagcca tcattttctc    29760
```

```
tatctcatca ttcaaaatat attccttcct cttccccttc ttgcacccag tcacagactg    29820
gactctatta aatcctgtct atcatctggg ctcatttcca tcctcagtgt ctgtctgtgc    29880
atccttttca ttcagccagg gatgttcagc tcgattctgc cccttcattc caagcctgtc    29940
ccatattcca ttactttatg aagcctttct tgacacacag atgcttaatt attctctttt    30000
gctttctttg tgttgacttt gactctgcca ctggttgtga gcttcagaag ggcagggatc    30060
tcaccttcac ttcttttcc tcctagtgct ttctttgtgt gctgcacact ccctggcaca     30120
cacagcggct ctccaacacg aggcagagct ttccagcagc ctcaaccttc aggactgggc    30180
agcttttaaa tgtatttggg cacctttgca agaaaaggat gtgttaaat gtaattttca     30240 tgtatcttgt tatcagagtg caagagaagc agaaatcaaa ctgaaaagtg aaagcagagt    30300
caaacttttt tatttggacc cagatgccca ggtaagaact atctaaatgt ttaatattta    30360
aaaccaaatg tgggagagaa aatcatcgat gggcttattt gtttatttgt ttgctttgtt    30420
tattttggaa aaacaagcaa ataactata gaaaatttgg ggaaaagagg aaaaataaaa     30480
atgtataatc ttatcaccat agcattacta ttgtgaatat ttgatattca atagatgttt    30540
gaaaattggg agagatttat tgaaagacat tctcaagttc acaaagaaca tctaatttac    30600
ctgttaaaat aaccatcaga aacaacagg tatcactgca gttgcctggg agtcagtgat     30660
aattcccgac tagcccaggc tcaggctcaa atacaaacct tttccattta actctaacga    30720
taagtacttt tctgtttcct cacaaacctc ataaccatac gtatgtgtgt ttatatgtct    30780 atattttta tttgcttta agaagttttt gtttatcatt gtaaaatata cataatataa       30840
aatttaccat tttaaccatt tttaagtgta cggttcagtg cattaaata cattctcatt      30900 gttgtacaac cattaccacc atccatttcc agaacttctt cattttccca cacgaaaact    30960
ttgtatcaaa tgataaccttc ctttccttc ttcccccatc cctagtaac ctctgttcta     31020 ctctgtgaac ctgcctattt taggaacctc ataaatgtgg aatcatacag tatttgtcct    31080
ttgtttctgg cttcttaaac ttaacatgtt ttcaaggtca atccatgttg tagcatgtgt    31140
cagaatttcc ttcctttctg tggctgaata ttccattgta tgtatatact catttata      31200 tatccttgta aatctgttga tggacacttg gttggatact tgatggacat tggttttgtt    31260
gttcatgatc ataattttca agctctgtat tttttcagtt catccattga gtaggtatac    31320
catcatgtct tttttttttt gtctttttt ttttttttt tttgaggcag agtcttgctc      31380
tgtcgcccag gctggagtgc agtggtgcaa tctcggctca ctgcaagctc cgcctcctgg    31440
gttcacacca ttctcctgcc tcagcctcag cctcccgagt agctgggacc acaggtgccc    31500
actaccacac ctggctaatt ttttgtatt ttttgtagag acggggtctc actgggttag      31560
ccaggatggt ctcgatctcc tgacctggtg agccgccagc ctcggcctcc caaagtgctg    31620
gaattacagg cgtgagccac cgtgcccggc ccatgtcttt gaccattgtt ataaactatg    31680
tgtgtaacta ctataaacca tagaaaccga ttatataata gcaacactat tgtgagtaaa    31740
taagtgtata tagcttttcc atatttatt ccgtttcctt tggatgcatt tatgatgttt      31800
ttttaaaata agagcataac ttatttatat gtttacttt tcttttaaag aagcttgact      31860
tctcatcagc tgagccagaa gtgaagtcat ttgaagagaa gtttggaaaa aggatccttg    31920
tcaagtgcaa tgatttatct ttcaatttgc aatgctgtgt tgccgaaaat gaagaaggac    31980
ccactacaaa tgtaattttt catttaaaa ataaacatta aaaaaaaat aggcagaggt       32040 ttcagatgta cctttacagt gcagcctgga taagaaatcc tagtccctgg tatcaaagag    32100
gtgcagtgtt tggatcagga tatggaggtt gttagcctgc aaggacagga tgttcgtgat    32160
```

```
ggaagatgag ggtggcaggt ttgtgctcag ctttccagga gacagagttc atcttagatg   32220
cttcagggaa cgcaactgtg ttttctatgg aacatacatt acgtagcaaa acacataaag   32280
gtaaaataat tgttttgttt gtttcctaaa atgttttata agctaattct ctgtatgcag   32340
aaggatgaga ctgtttagta gtaatttatg gcaacagtcc taaataggtc ttgtcatttc   32400
tcttttgata gcaacattct tttgtccctg tttgagccat ggtgatcatt ggattgtttt   32460
gttttgttca ggttgaacct ttctttgtta ctctatccct gtttgacata aaatacaacc   32520
ggaagatttc tgccgatttc cacgtagacc tgaaccattt ctcagtgagg caaatgctcg   32580
ccaccacgtc cccggcgctg atgaatggca gtgggcagag cccatctgtc ctcaagggca   32640
tccttcatga agccgccatg cagtatccga agcaggtggg gagtatgagc ccagcattcc   32700
cactactcag actcactttg catgctacct aaatgcacca aaaatgctca aattagacct   32760
tgtaatgcac aagtggggtc attagactct taattaatag tatttattat tagacagtaa   32820
aagcaagctg agaaataagt ggcttttaat ttcctttctt ctttctaaaa gttctcctag   32880
ttacctccct caccaaatag acttttttgag cagatgatga actgtttgtc agctaactag   32940
tttggcactg ggtgcttttt actagttgtc ctgtttcact gttctttgct gtttaatgtt   33000
catgggattt gtttaacgta gctgtgaatt ctgcttactg aagaaaattg tttgcctcct   33060
agggaatatt ttcagtcact tgtcctcatc cagatatatt tcttgtggcc agaattgaaa   33120
aagtccttca ggggagcatc acacattgcg ctgagccata tatgaaaagt tcagactctt   33180
ctaaggtatg aatggctttt acgctttggg gtggtaaaaa gcaatctgaa aagaggcctt   33240
tatgtgatac tataaatcct taatgaaatc aaacataagc catatttata ctctaaaaga   33300
tgtagaatat gctacctgta tttactctga actttatgtc ttgattttga aggaaatgta   33360
gtcctatgtg taaataaaat gatccacttg actagacagt tctgacatcc taaaataatt   33420
tgcaaaggaa ttaccagctt aatagtaaac tttctgtgtt agaaggtaca tgtatgatat   33480
tcaaatagag tttcttctat ctgttaattt gcctcttggg ttctgaaatt ctattttggt   33540
ccacttacac ttatatatga ggctggagac caggagatgc ccttggctca gatgacctgg   33600
ccagcagtgt cagtgattca ggtccacttg gttttgcta gaaggggcag gttttaggt   33660 ggaagatgga agaaaacat acatgatgta tgtttggttt ttttcaaagt agtgttcatt   33720
acttgggaag tgcctaggca tggacatacc atagaattat taaatattag aggtcatcta   33780
gtccaagatg tgctttcata tttcaggaca ctgaggctca ccaaggctta gtgatctgct   33840
cagtgtctca tggctggagc tgccagggg cacttgactg ccacttcgta gcaccttgtg   33900
ctacctggtt agtgtaatct gttaagtgct attatccttg ccagtttttac atattttttag   33960 ttatttaaaa aaaaaattgt gtggtcatct gagaggcctg aattcactga caaggactgg   34020
tcagcagtag gagtggatac cccagaggct gtgagtgaag tttactaagt tggattcaga   34080
gcttcctatc ttcacctcta tgggcgccca tgcatcacag ctgtgtccac aggatgcacg   34140
atggccattg agaaatggat tttggagtca aagacctgg gtgctgcatg cttaactcat   34200
ctgggtcctt tggacaaatc acatcacctc tcatggcctc catatgttcc ttctgtgcat   34260
gaaggatgat gttacttctt gcctctgcct tcctcatagg gacagtgtta ggatcaaaca   34320
gatcatgtat gagtcagtgc tgtgggcacc ataaatcaca gaaagcccag aagacatcgt   34380
catttattac agccccagtc aagtaaaagc ccatttaccc aggcacattg gttccaacag   34440
taagcctttt tggctgatga aagctgtgta aagtttggtc tctggagaga agctgtttta   34500
```

-continued

```
ttttttttaaa ccaagtctgt aaaaccttgg atgagaagct cttttagctc ttttatgttt    34560
tgatcaataa tcaatgaagg cccaatataa gatctcctcc cccgaccgtg tatgcaacac    34620
atttccaagg cccatccaca gcaactttgt tacttctgcc tgccgcatgc atggtttgaa    34680
atttggcagc tcatattggt gtaaaaatca catatcactg taggctaaac ttacctctgc    34740
acactcctcc atgtccactg agcatctgct gaagtctgct ttttcttcat ttttttatgg    34800
aatgtaaagc tcatccatgt gtacattatt catgcattta cttttctgcc acctccaaag    34860
cattcaatta aagcaggaat taaggctcaa ctatcttact ttagcacagt tttggcagag    34920
atgttacagt gagatgattt ttttctgtct gtcaaagttg tttcttcatg ttttccaaga    34980
tggtctagaa catcatttag agtaaatttt cattttggag gaaatttta tgaaaagtct     35040
ctgtaggtat ctcctgtgaa tagaggtttt aaaaagaaaa agaaggggaa aaaagcccaa    35100
agggaaaaaa taagtttctt actctgactt tcacacatac tgtgttctat ttgctcccctt   35160
catatgtccg agagctaagt cctcattcac tgcagaaaag gcttattgat gttttatgtt    35220
ttagctttaa attttatgaa attactgcat tttactccac aacatattca tcattgttag    35280
aaccaaaaaa tcttgaacct gaaatgtttt aagtaaattg accctgcagc taggtaggcc    35340
attgtacccc ataactcata cacctaagac cccactaagt cgccccaccc agggaggcaa    35400
gaacatacct cattggagaa gggggggaggt cctagatgat tccctgacat ctcttccaat   35460
taggatgtat tttccaggtt actcatgaag gcagcagttc ctacagcatg attatggtag    35520
gattataaag ttttgcaact gaaagggatc atgaaaagta tagcctagcc cccatttttca   35580
ggtgtggata gtggagctca gagaggtttg atggcctaca gagtcataca gctggattca    35640
gtgtgactta gagacagaca gctctgtcat ctagatcctt ctggatcctt ctagatcctt    35700
cctgtggctg atggtacaca cagatcaccg gaggtcttgt cagaacgcac gttctgatcc    35760
aggaagtttg gggcaaggcc tgagactctg catttctaca gtgatgctga tgctatagca    35820
cactttggtt ttggagtaca tttcccaaaa ttggtttgac tttgatatac ttatgtaaaa    35880
gacccttcag taaaaaaaaa aaaaaaaaaa ttaagtaatg taaaagaccc ttcactgtaa    35940
ctctgagaca atcaaacttt gcattgatga caaagcacta tcacagtaca gacaaatttg    36000
gaaaaattaa gcattatctt ttttagcaat aggggtatag atgattaata ataggtctgc    36060
cttaggctaa aagcaaataa gcttcattgt acactgtgaa ttaatcaatc aatcaacaac    36120
aaaccaaaat tgatcattag gaagtagaaa tagcagtaat tcatgtttag aaagcaagaa    36180
tatagcattg agaaccccag cctaactgaa gtcagtatct taatatctta tcccttatat    36240
tgtgggaatc agcataagct agtgcgcttt aggagctgtg aaagcttagt attttaatta    36300
gtgttctcat ttcaatccta ataatgtgat atattttgat atggatacca aatagtaatt    36360
attaataact cagtagactt ataataagta gcacttagtc ataaagatgt atgaaaacct    36420
ctgaaacagc atgtttgttg cccgtaaaga ccaaagaaga gacatggatt ttggaaagtc    36480
ttcgttctgt attctttgag aatcactgct agagaatgcg ttaaataaag tactctgcac    36540
agagtgtgaa tccagccata ttcattactg tatgatgtgc ttttctatgc atccaatgct    36600
atggtaagga cttatttagt gagcatgtaa ggatggctct tgaggtcaca gttctttcag    36660
tgagatgcag tatctcatag ctttattctc atgtcttcaa ggtggcccag aaggtgctga    36720
agaatgccaa gcaggcatgc caaagactag gacagtatag aatgccattt gcttgggcag    36780
caaggtaagg aacaccttt ataccttta aatcgatata gataggtgca tggatgggtc     36840
aataggccta ttctgtttgt tgttcagaga caaagaggat ttgaatgtgt aaaactgaga    36900
```

```
aatacataag cccagatttt gaaaaaatca tttggtagag tcacagagag gatagacact   36960
gtctggagaa gtgctacctg gaactggcag ggtgcacggt agtgttagct gcagagctgg   37020
gattcaagga cccaaccaca tgcctccagc tggaagtcag ggcaatccag tgaggcctgg   37080
ggtgatcttt atctcttgac tctacttgtt aagcatttga cttgtgtata ttgtttccta   37140
agcacaagcc attggctgga actgttttct atgtaaattg atttagttgt cctcatcccc   37200
atagatgttt tccatgtttt tagataatga gatttctgtt ggctatagcc aatggaataa   37260
taattagact tctcatagaa actagactta aataatgaat tgattttggt gttttggaaa   37320
cccagtttag aaatgttgct ttgccatttc aggacattgt ttaaggatgc atctggaaat   37380
cttgacaaaa atgccagatt ttctgccatc tacaggcaag acagcaataa gctatccaat   37440
gatgacatgc tcaagttact tgcagacttt cggaagtgag tttcaaggtc ttatttccac   37500
acctgaaaaa tagaagctgt gtagtgggga gggaggaaca ggggagcagt cacttaggtt   37560
gctcgattta gacatcagag gggatggcaa atgagcgtga agcatttcct caaacccttg   37620
agaagaaaga tggggtgaaa atcagaagaa taaccagtta atttgaattc tgtagaggat   37680
gttttgggtg gtgctgtgaa gggtggactg ggtaaggatg agcctatggt ggggaggaaa   37740
cagttgagga accttgtcaa gaggtgagaa aggactcagc aaagccactg caagtgcaaa   37800
caggaagaag gggacaaatt caagtcgtgc caaagagata cgatgactgg gtcttggctt   37860
ggggtggtaa tagtctaaga taaataactt gcaaggtttc taacttggaa gtttctggca   37920
ccagttgttg cttagcttgt ggcagcattg ctccactctg cctctggcct cacatggtcc   37980
tcttcctgtg tgtctctgtc taaattccct tcttagaaca ctagtgataa agcatcaggg   38040
ccaagcctag tgacctcatc ttaactgatt gcatctgcag agaccctgtt tccaaatagg   38100
tcacatttat aggtacaaag ggttgggact tcaccatgct tttggaggac acaattcaac   38160
ccataacaat gaggcaaaga gggagcaagg aatgtgtgca acatcacagg gccggcagct   38220
tccccaagtc agtctcaccc gagggtctgt gttcttaacc tctatgctgt tttgctgcta   38280
catcctaaag agttcactct gaacctttga aactgatttt ctttgctagg gagatgggtc   38340
ttagaatttt tctggggaaa ttctgggaat gtgaaagagc tgagggcgct agaagatgtg   38400
aagtgaaaag aatagctgag agccaaatgc taactattct atgccaaagg tatccttgtt   38460
ttttttttt tttgtgcata tcaaaatagc aatcttatca gtttgtctag aactcaagaa   38520
tgattgctta gctttcttta accttatttt accttttttct tatctgtctt cagtagtagg   38580
aatagaaacg atatgagtca tagaaacagg ctcaataagt tctgaaaaca cagagacgtg   38640
ttcctaatca gaatccaatc acgtccatgt cagcaggcgg cttcagcctt cacagcgacg   38700
tgaaatccct tgtcaagagg ctcaaaaagg tagaaaggat tctcaaggtc tctttcagtt   38760
atgtgattat acagtttttg actgtcttga tgtttcccct gtttggagct ttaatgagaa   38820
gtgcaacctc agttttgcta acatgcagct aaggttggcc tgttcagcaa agcagtgtgc   38880
atgcccgctg ggctgatttg gaatgaacct ttcacagctc acgtagggaa ttggagaagg   38940
gggagaggag gatactggtg aaggatgagg cctgctgggt tagccttcca gggttcctgg   39000
accatatagg tgccccaaat tcccagtcac tatctgacag ttttatgacc tggtaaggac   39060
acaggtcttg gccagggagt gcccctggat ccctatgaat ctgttattca tgaaagacta   39120
aataaaagaa tagtacccta tttttacttt taaatcatag aggttcttta gtttacaaac   39180
ataatacatg ttcattttag aaattttgag aaatacagaa gaataaaagg atgaaaaaag   39240
```

```
gtttactact agttttaacc ttcgtggtga acttttggag aactttttt tttttttga    39300
gatggagtct cactctgtcc ctcaggctgg cgtacagtag cacgatttca gctcactgca  39360
acctccgcct cccgagttca agcgattctc ctgcctcagc ctcccaagta gctgggacta  39420
taggcgccca ccactacgcc tggctaattt ttgtatttt agtagagatg gggtttcacc   39480
atattggcca ggctgatctc aaactgctga ccttgtgatc tgcccgcctc agcctcccaa  39540
agtgctggga ttacaggcat gagccaccgt gcccagccta ggggggaaca tttttttta   39600
cgttttattc ctttacattt tattttagtt tatcttatgt agctatgatc atactaaata  39660
tgtaatattt ccctgcacaa ctcaagtatt ttctgaaagt gttatatata cattttata   39720
gacatcattt ttaatgcata aatattataa tagtccattg agatagacca tagattattt  39780
aactcttccc ccattttttg acttttttt tttttccga gatggagtct cgctctgtcg    39840
ccaggctgga gtgcagtggc accatctcag ctcactgcaa cctccgcctc caggttcaa   39900
gcaattctcc tgcctcagcc tcctgagtag ctgggactcc tgagtagctg agtagcgcat  39960
gctgccacgc cccgctaatt tttttttt tttttttt ttttgtatt ttagtagaga       40020
tactaaatat ctcaccatct tgcccaggct ggtctcaaac tcctgacctc aggcaatctg  40080
cccgcctcag cttcccaaag tgctgggatt acaggtgtga gccaccatgc ccagccattt  40140
tttgacttt aatgtgtttc tgattttca gaattatacc tataagccac agttagaatc    40200
tttaaaaaa tcttctctat tggtagtggg taatatatta tcatacatac tatattatca   40260
tatagtaatt attgtcattt tttgagtttc aagaaaattt cattcttact aattttttca  40320
aaaaccagtc acctttagtt ggatagattt caatattttc cttcgctcaa ctaccatgca  40380
actcttaata accatgaggt gggtctgcgt gtacttagga aagtgaatac actatattat  40440
taaggaagaa aaaatatatc tgtattacta tatttttga aagaaaatat atatttctttt  40500
tgtatgtaaa tgaagaaatg gataagcaag tagctatcta gatggaaaga taggcataaa  40560
aatagctatt taggatatat gccaaataat catggttatc tctgagggat gggttgatgg  40620
gtgatatttc accttccact ttataacatt ctgtcatttt tatatgaact tttaaaaaac  40680
taacactttt atattcagac aaaacaaaca atgaagtttt ttatatgtga tggaggttgg  40740
agccctgtct cagaagttac ttcctaggct ggttagcttg agacttcccc acagtggcgg  40800
ctcctcaggg gcagccccag tgcatggtcc tgtcttcagt ggaggctggg gagtggggct  40860
tcacatggtc actaatttga aagtgatggg agcagaaagc ctgtggccag gcagaaagga  40920
gcccagggaa aaccaagtgt gagttctctt ctgcacacca cttcttcatg catgtgctca  40980
gcaggagggc attggtgtga agggtgtgct ccaggtggcc agttagagac ccagaaacct  41040
gaaaacaggg atccgatggt gacagcatag aagacacagc aggataagtg aggccacgct  41100
cctcaataag tattcaaaga aactttggtg cccactcccc gtattcttca aacagagtt   41160
aggggacgtg gaggattcct ttttcatttt ttaaaaatct ttgcattgct attttcttt   41220
cctctgtata ttttacagga ataatctca tgtcagtggc ctgggcaccg gcttggatcc   41280
aaagctattt ttctacccc catgattgtc tcaaatgtt atttaataat gcatgaaaaa    41340
aatttcttca cgctgtctca gtcttaacaa aacagctgcc aaagctcata agccactttc  41400
cttttccct tgcaataatt acccaggat atgttcaag atttagtaag aaagcgattc     41460
tgtccgatag atgatattgc taacattta taagaagaga gacttggtac tttgtatttg   41520
atttgttcat ggtggtatct catggataag atggtatctc atcttttcca acttctgcag  41580
gaaatgcgaa gacatgaagg caaagtataa aaatagaacg ttttctttaa aacgtagacc  41640
```

```
tttttaatgg tactacgttg gatagtttag gtaataatac tactaaagtt tttgcgtatg    41700
cagcttaatg tgtctgtgtt tatttgtaca ctcatcttct ttgcatccag gttttacagt    41760
cttaccccga tttcgctctg gttacactgc actcaagcca agtagggctg cttgactttc    41820
tctaaaccca ctggggactt ccctctgcca tgcttttctc tctgcccaaa ttgtgtcccc    41880
ttcctgcctc atcaagcagc acataaatca caaacacatg cagcatacac acttcccctt    41940
ttcctttgtc tttctcaggg aactctactc atctttcaaa gcccagtctg tggctcactt    42000
ctgtgctggg agtcctggag gcggttactt ggcttctctg cctgagccgc ctcctctttt    42060
taagggtgga taataacagc ccctgccccc taaaaccgtg gtggggaata aatgcaaaag    42120
gcattaaggt gatttctccc accatgaata ctgatctcat cccgtgttcc ctctcgatag    42180
atctagatac tctgccttct ggtagaggtt tgtacatact ctgtgaaagt gattgccctc    42240
atatgccgta agtagcttac agtgtctact ggacttttgg cttcttgagg aaagaaatta    42300
tgtcttgttt gcattcctcc atggtcctga gtacatacat tgcagcatat cctaagcact    42360
tgataaatgc ttattgaatt ttcttcttag acataaactc agtggttttt gttgaaacaa    42420
aaatatctca aatttctttc aatcatatat agttgttttt ttttaagtga caccaaagct    42480
tttagggaat atttcctttc acaaaacaca gttagaagat taaactcacc accaatagca    42540
gtccaaacat acctgtattg ccagctaatc attttaacga gccaatacag gaagtcagga    42600
agggaagacc ggctgcagaa acacttagat aaggacccca aatctgttgg catgggagga    42660
ctgctagttg atgataccat tcccatttcc tctgtgggaa ttgttgagtc agcagaaatg    42720
gatgggcagt gggaagggaa aattttccta agagagagtt tgagcctcac ttctacattc    42780
acacagagac aggagcagtt cccagaggcc aggcatcctg caagtgtctg tattgcatgc    42840
ttacttaatt cgtgtaattt taagatgagt tttcatgttc aaggattatt ttataaattt    42900
tgcatagaat ataggtactc tttagcaaaa caaagcaaaa aaaccaaaac tattctcagt    42960
catgaaagaa ttcagtttgt gtaacacgca cacaaccacc actttggaag tgcataaaaa    43020
ggcagtaaaa tctttattgc ctgtgagtgt ttgatgtcta ataaaccaga ttcaacataa    43080
accataaact tttgaaatgg gtttgagatt gggttttttaa aaacttaaag ctggcaaaaa    43140
aaaaaacaac ttttaaaagc ccatgtgcta cataatatgg aactaaactc agaaatgtgc    43200
ttggaaacac atggaaagaa cgtctttaca gaagcagcaa ctagaagtaa aatctctcag    43260
cagagggagg aaatagaata agaaataact atagttaggc acagaaggac acaatacact    43320
ataggaagat ttccagtgaa gatcatttaa ttaaaatatg ttgcttagaa acgtatttta    43380
attgtgttcc acctctctca aaaatttata tgtggaggat gttggagtga tcttaaaaat    43440
ggtgatgaag atgcctgttc attcataggt ggaaataatt aggaggggggt gaaatccatt    43500
acccttgcat acttacttat atttaaaagt ataatttgta ataaa                    43545
```

<210> SEQ ID NO 135
<211> LENGTH: 2008
<212> TYPE: PRT
<213> ORGANISM: Homo sapiens
<220> FEATURE:
<223> OTHER INFORMATION: Clasp-4 amino acid sequence

<400> SEQUENCE: 135

```
Met Phe Pro Met Glu Asp Ile Ser Ile Ser Val Ile Gly Arg Gln Arg
  1               5                  10                  15

Arg Thr Val Gln Ser Thr Val Pro Glu Asp Ala Glu Lys Arg Ala Gln
```

-continued

```
              20                  25                  30
Ser Leu Phe Val Lys Glu Cys Ile Lys Thr Tyr Ser Thr Asp Trp His
         35                  40                  45

Val Val Asn Tyr Lys Tyr Glu Asp Phe Ser Gly Asp Phe Arg Met Leu
         50                  55                  60

Pro Cys Lys Ser Leu Arg Pro Glu Lys Ile Pro Asn His Val Phe Glu
 65                  70                  75                  80

Ile Asp Glu Asp Cys Glu Lys Asp Glu Ser Ser Ser Leu Cys Ser
                 85                  90                  95

Gln Lys Gly Gly Val Ile Lys Gln Gly Trp Leu His Lys Ala Asn Val
                100                 105                 110

Asn Ser Thr Ile Thr Val Thr Met Lys Val Phe Lys Arg Arg Tyr Phe
            115                 120                 125

Tyr Leu Thr Gln Leu Pro Asp Gly Ser Tyr Ile Leu Asn Ser Tyr Lys
            130                 135                 140

Asp Glu Lys Asn Ser Lys Glu Ser Lys Gly Cys Ile Tyr Leu Asp Ala
145                 150                 155                 160

Cys Ile Asp Val Val Gln Cys Pro Lys Met Arg Arg His Ala Phe Glu
                165                 170                 175

Leu Lys Met Leu Asp Lys Tyr Ser His Tyr Leu Ala Ala Glu Thr Glu
            180                 185                 190

Gln Glu Met Glu Glu Trp Leu Ile Thr Leu Lys Lys Ile Ile Gln Ile
            195                 200                 205

Asn Thr Asp Ser Leu Val Gln Glu Lys Glu Thr Val Glu Thr Ala
    210                 215                 220

Gln Asp Asp Glu Thr Ser Ser Gln Gly Lys Ala Glu Asn Ile Met Ala
225                 230                 235                 240

Ser Leu Glu Arg Ser Met His Pro Glu Leu Met Lys Tyr Gly Arg Glu
                245                 250                 255

Thr Glu Gln Leu Asn Lys Leu Ser Arg Gly Asp Gly Arg Gln Asn Leu
            260                 265                 270

Phe Ser Phe Asp Ser Glu Val Gln Arg Leu Asp Phe Ser Gly Ile Glu
        275                 280                 285

Pro Asp Ile Lys Pro Phe Glu Glu Lys Cys Asn Lys Arg Phe Leu Val
290                 295                 300

Asn Cys His Asp Leu Thr Phe Asn Ile Leu Gly Gln Ile Gly Asp Asn
305                 310                 315                 320

Ala Lys Gly Pro Pro Thr Asn Val Glu Pro Phe Phe Ile Asn Leu Ala
                325                 330                 335

Leu Phe Asp Val Lys Asn Asn Cys Lys Ile Ser Ala Asp Phe His Val
            340                 345                 350

Asp Leu Asn Pro Pro Ser Val Arg Glu Met Leu Trp Gly Ser Ser Thr
        355                 360                 365

Gln Leu Ala Ser Asp Gly Ser Pro Lys Gly Ser Ser Pro Glu Ser Tyr
        370                 375                 380

Ile His Gly Ile Ala Glu Ser Gln Leu Arg Tyr Ile Gln Gln Gly Ile
385                 390                 395                 400

Phe Ser Val Thr Asn Pro His Pro Glu Ile Phe Leu Val Ala Arg Ile
                405                 410                 415

Glu Lys Val Leu Gln Gly Asn Ile Thr His Cys Ala Glu Pro Tyr Ile
            420                 425                 430

Lys Asn Ser Asp Pro Val Lys Thr Ala Gln Lys Val His Arg Thr Ala
435                 440                 445
```

```
Lys Gln Val Cys Ser Arg Leu Gly Gln Tyr Arg Met Pro Phe Ala Trp
    450                 455                 460

Ala Ala Arg Pro Ile Phe Lys Asp Thr Gln Gly Ser Leu Asp Leu Asp
465                 470                 475                 480

Gly Arg Phe Ser Pro Leu Tyr Lys Gln Asp Ser Ser Lys Leu Ser Ser
                485                 490                 495

Glu Asp Ile Leu Lys Leu Leu Ser Glu Tyr Lys Pro Glu Lys Thr
                500                 505                 510

Lys Leu Gln Ile Ile Pro Gly Gln Leu Asn Ile Thr Val Glu Cys Val
            515                 520                 525

Pro Val Asp Leu Ser Asn Cys Ile Thr Ser Ser Tyr Val Pro Leu Lys
    530                 535                 540

Pro Phe Glu Lys Asn Cys Gln Asn Ile Thr Val Glu Val Glu Glu Phe
545                 550                 555                 560

Val Pro Glu Met Thr Lys Tyr Cys Tyr Pro Phe Thr Ile Tyr Lys Asn
                565                 570                 575

His Leu Tyr Val Tyr Pro Leu Gln Leu Lys Tyr Asp Ser Gln Lys Thr
            580                 585                 590

Phe Ala Lys Ala Arg Asn Ile Ala Val Cys Val Glu Phe Arg Asp Ser
    595                 600                 605

Asp Glu Ser Asp Ala Ser Ala Leu Lys Cys Ile Tyr Gly Lys Pro Ala
610                 615                 620

Gly Ser Val Phe Thr Thr Asn Ala Tyr Ala Val Val Ser His His Asn
625                 630                 635                 640

Gln Asn Pro Glu Phe Tyr Asp Glu Ile Lys Ile Glu Leu Pro Ile His
                645                 650                 655

Leu His Gln Lys His His Leu Leu Phe Thr Phe Tyr His Val Ser Cys
            660                 665                 670

Glu Ile Asn Thr Lys Gly Thr Thr Lys Lys Gln Asp Thr Val Glu Thr
            675                 680                 685

Pro Val Gly Phe Ala Trp Val Pro Leu Leu Lys Asp Gly Arg Ile Ile
    690                 695                 700

Thr Phe Glu Gln Gln Leu Pro Val Ser Ala Asn Leu Pro Pro Gly Tyr
705                 710                 715                 720

Leu Asn Leu Asn Asp Ala Glu Ser Arg Arg Gln Cys Asn Val Asp Ile
                725                 730                 735

Lys Trp Val Asp Gly Ala Lys Pro Leu Leu Lys Phe Lys Ser His Leu
            740                 745                 750

Glu Ser Thr Ile Tyr Thr Gln Asp Leu His Val His Lys Phe Phe His
            755                 760                 765

His Cys Gln Leu Ile Gln Ser Gly Ser Lys Glu Val Pro Gly Glu Leu
    770                 775                 780

Ile Lys Tyr Leu Lys Cys Leu His Ala Met Glu Ile Gln Val Met Ile
785                 790                 795                 800

Gln Phe Leu Pro Val Ile Leu Met Gln Leu Phe Arg Val Leu Thr Asn
                805                 810                 815

Met Thr His Glu Asp Asp Val Pro Ile Asn Cys Thr Met Val Leu Leu
            820                 825                 830

His Ile Val Ser Lys Cys His Glu Glu Gly Leu Asp Ser Tyr Leu Arg
    835                 840                 845

Ser Phe Ile Lys Tyr Ser Phe Arg Pro Glu Lys Pro Ser Ala Pro Gln
850                 855                 860
```

```
Ala Gln Leu Ile His Glu Thr Leu Ala Thr Thr Met Ile Ala Ile Leu
865                 870                 875                 880

Lys Gln Ser Ala Asp Phe Leu Ser Ile Asn Lys Leu Leu Lys Tyr Ser
                885                 890                 895

Trp Phe Phe Phe Glu Ile Ile Ala Lys Ser Met Ala Thr Tyr Leu Leu
            900                 905                 910

Glu Glu Asn Lys Ile Lys Leu Pro Arg Gly Gln Arg Phe Pro Glu Thr
        915                 920                 925

Tyr His His Val Leu His Ser Leu Leu Leu Ala Ile Ile Pro His Val
    930                 935                 940

Thr Ile Arg Tyr Ala Glu Ile Pro Asp Glu Ser Arg Asn Val Asn Tyr
945                 950                 955                 960

Ser Leu Ala Ser Phe Leu Lys Arg Cys Leu Thr Leu Met Asp Arg Gly
                965                 970                 975

Phe Ile Phe Asn Leu Ile Asn Asp Tyr Ile Ser Gly Phe Ser Pro Lys
            980                 985                 990

Asp Pro Lys Val Leu Ala Glu Tyr Lys Phe Glu Phe Leu Gln Thr Ile
        995                 1000                1005

Cys Asn His Glu His Tyr Ile Pro Leu Asn Leu Pro Met Ala Phe Ala
    1010                1015                1020

Lys Pro Lys Leu Gln Arg Val Gln Asp Ser Asn Leu Glu Tyr Ser Leu
1025                1030                1035                1040

Ser Asp Glu Tyr Cys Lys His His Phe Leu Val Gly Leu Leu Leu Arg
                1045                1050                1055

Glu Thr Ser Ile Ala Leu Gln Asp Asn Tyr Glu Ile Arg Tyr Thr Ala
            1060                1065                1070

Ile Ser Val Ile Lys Asn Leu Leu Ile Lys His Ala Phe Asp Thr Arg
        1075                1080                1085

Tyr Gln His Lys Asn Gln Gln Ala Lys Ile Ala Gln Leu Tyr Leu Pro
    1090                1095                1100

Phe Val Gly Leu Leu Leu Glu Asn Ile Gln Arg Leu Ala Gly Arg Asp
1105                1110                1115                1120

Thr Leu Tyr Ser Cys Ala Ala Met Pro Asn Ser Ala Ser Arg Asp Glu
                1125                1130                1135

Phe Pro Cys Gly Phe Thr Ser Pro Ala Asn Arg Gly Ser Leu Ser Thr
            1140                1145                1150

Asp Lys Asp Thr Ala Tyr Gly Ser Phe Gln Asn Gly His Gly Ile Lys
        1155                1160                1165

Arg Glu Asp Ser Arg Gly Ser Leu Ile Pro Glu Gly Ala Thr Gly Phe
    1170                1175                1180

Pro Asp Gln Gly Asn Thr Gly Glu Asn Thr Arg Gln Ser Ser Thr Arg
1185                1190                1195                1200

Ser Ser Val Ser Gln Tyr Asn Arg Leu Asp Gln Tyr Glu Ile Arg Ser
                1205                1210                1215

Leu Leu Met Cys Tyr Leu Tyr Ile Val Lys Met Ile Ser Glu Asp Thr
            1220                1225                1230

Leu Leu Thr Tyr Trp Asn Lys Val Ser Pro Gln Glu Leu Ile Asn Ile
        1235                1240                1245

Leu Ile Leu Leu Glu Val Cys Leu Phe His Phe Arg Tyr Met Gly Lys
    1250                1255                1260

Arg Asn Ile Ala Arg Val His Asp Ala Trp Leu Ser Lys His Phe Gly
1265                1270                1275                1280

Ile Asp Arg Lys Ser Gln Thr Met Pro Ala Leu Arg Asn Arg Ser Gly
```

-continued

```
                1285                1290                1295
Val Met Gln Ala Arg Leu Gln His Leu Ser Ser Leu Glu Ser Ser Phe
        1300                1305                1310
Thr Leu Asn His Ser Ser Thr Thr Thr Glu Ala Asp Ile Phe His Gln
    1315                1320                1325
Ala Leu Leu Glu Gly Asn Thr Ala Thr Glu Val Ser Leu Thr Val Leu
        1330                1335                1340
Asp Thr Ile Ser Phe Phe Thr Gln Cys Phe Lys Thr Gln Leu Leu Asn
1345                1350                1355                1360
Asn Asp Gly His Asn Pro Leu Met Lys Lys Val Phe Asp Ile His Leu
            1365                1370                1375
Ala Phe Leu Lys Asn Gly Gln Ser Glu Val Ser Leu Lys His Val Phe
        1380                1385                1390
Ala Ser Leu Arg Ala Phe Ile Ser Lys Phe Pro Ser Ala Phe Phe Lys
        1395                1400                1405
Gly Arg Val Asn Met Cys Ala Ala Phe Cys Tyr Glu Val Leu Lys Cys
    1410                1415                1420
Cys Thr Ser Lys Ile Ser Ser Thr Arg Asn Glu Ala Ser Ala Leu Leu
1425                1430                1435                1440
Tyr Leu Leu Met Arg Asn Asn Phe Glu Tyr Thr Lys Arg Lys Thr Phe
            1445                1450                1455
Leu Arg Thr His Leu Gln Ile Ile Ile Ala Val Ser Gln Leu Ile Ala
            1460                1465                1470
Asp Val Ala Leu Ser Gly Gly Ser Arg Phe Gln Glu Ser Leu Phe Ile
        1475                1480                1485
Ile Asn Asn Phe Ala Asn Ser Asp Arg Pro Met Lys Ala Thr Ala Phe
        1490                1495                1500
Pro Ala Glu Val Lys Asp Leu Thr Lys Arg Ile Arg Thr Val Leu Met
1505                1510                1515                1520
Ala Thr Ala Gln Met Lys Glu His Glu Lys Asp Pro Glu Met Leu Ile
        1525                1530                1535
Asp Leu Gln Tyr Ser Leu Ala Lys Ser Tyr Ala Ser Thr Pro Glu Leu
            1540                1545                1550
Arg Lys Thr Trp Leu Asp Ser Met Ala Lys Ile His Val Lys Asn Gly
        1555                1560                1565
Asp Phe Ser Glu Ala Ala Met Cys Tyr Val His Val Ala Ala Leu Val
    1570                1575                1580
Ala Glu Phe Leu His Arg Lys Lys Leu Phe Pro Asn Gly Cys Ser Ala
1585                1590                1595                1600
Phe Lys Lys Ile Thr Pro Asn Ile Asp Glu Glu Gly Ala Met Lys Glu
            1605                1610                1615
Asp Ala Gly Met Met Asp Val His Tyr Ser Glu Glu Val Leu Leu Glu
        1620                1625                1630
Leu Leu Glu Gln Cys Val Asp Gly Leu Trp Lys Ala Glu Arg Tyr Glu
    1635                1640                1645
Ile Ile Ser Glu Ile Ser Lys Leu Ile Val Pro Ile Tyr Glu Lys Arg
    1650                1655                1660
Arg Glu Phe Glu Lys Leu Thr Gln Val Tyr Arg Thr Leu His Gly Ala
1665                1670                1675                1680
Tyr Thr Lys Ile Leu Glu Val Met His Thr Lys Lys Arg Leu Leu Gly
            1685                1690                1695
Thr Phe Phe Arg Val Ala Phe Tyr Gly Gln Ser Phe Phe Glu Glu Glu
        1700                1705                1710
```

```
Asp Gly Lys Glu Tyr Ile Tyr Lys Glu Pro Lys Leu Thr Gly Leu Ser
            1715                1720                1725

Glu Ile Ser Leu Arg Leu Val Lys Leu Tyr Gly Glu Lys Phe Gly Thr
        1730                1735                1740

Glu Asn Val Lys Ile Ile Gln Asp Ser Asp Lys Val Asn Ala Lys Glu
1745                1750                1755                1760

Leu Asp Pro Lys Tyr Ala His Ile Gln Val Thr Tyr Val Lys Pro Tyr
            1765                1770                1775

Phe Asp Asp Lys Glu Leu Thr Glu Arg Lys Thr Glu Phe Glu Arg Asn
        1780                1785                1790

His Asn Ile Ser Arg Phe Val Phe Glu Ala Pro Tyr Thr Leu Ser Gly
        1795                1800                1805

Lys Lys Gln Gly Cys Ile Glu Glu Gln Cys Lys Arg Arg Thr Ile Leu
    1810                1815                1820

Thr Thr Ser Asn Ser Phe Pro Tyr Val Lys Lys Arg Ile Pro Ile Asn
1825                1830                1835                1840

Cys Glu Gln Gln Ile Asn Leu Lys Pro Ile Asp Gly Ala Thr Asp Glu
        1845                1850                1855

Ile Lys Asp Lys Thr Ala Glu Leu Gln Lys Leu Cys Ser Ser Thr Asp
            1860                1865                1870

Val Asp Met Ile Gln Leu Gln Leu Lys Leu Gln Gly Trp Val Ser Val
        1875                1880                1885

Gln Val Asn Ala Gly Pro Leu Ala Tyr Ala Arg Ala Phe Leu Asn Asp
    1890                1895                1900

Ser Gln Ala Ser Lys Tyr Pro Pro Lys Lys Val Ser Glu Leu Lys Asp
1905                1910                1915                1920

Met Phe Arg Lys Phe Ile Gln Ala Cys Ser Ile Ala Leu Glu Leu Asn
            1925                1930                1935

Glu Arg Leu Ile Lys Glu Asp Gln Val Glu Tyr His Glu Gly Leu Lys
        1940                1945                1950

Ser Asn Phe Arg Asp Met Val Lys Glu Leu Ser Asp Ile Ile His Glu
    1955                1960                1965

Gln Ile Leu Gln Glu Asp Thr Met His Ser Pro Trp Met Ser Asn Thr
1970                1975                1980

Leu His Val Phe Cys Ala Ile Ser Gly Thr Ser Ser Asp Arg Gly Tyr
1985                1990                1995                2000

Gly Ser Pro Arg Tyr Ala Glu Val
            2005

<210> SEQ ID NO 136
<211> LENGTH: 2015
<212> TYPE: PRT
<213> ORGANISM: Homo sapiens
<220> FEATURE:
<223> OTHER INFORMATION: CLASP-5 amino acid sequence

<400> SEQUENCE: 136

Met Thr His Leu Asn Ser Leu Asp Val Gln Leu Ala Gln Glu Leu Gly
  1               5                   10                  15

Asp Phe Thr Asp Asp Leu Asp Val Val Phe Thr Pro Lys Glu Cys
            20                  25                  30

Arg Thr Leu Gln Pro Ser Leu Pro Glu Glu Gly Val Glu Leu Asp Pro
        35                  40                  45

His Val Arg Asp Cys Val Gln Thr Tyr Ile Arg Glu Trp Leu Ile Val
    50                  55                  60
```

-continued

```
Asn Arg Lys Asn Gln Gly Ser Pro Glu Ile Cys Gly Phe Lys Lys Thr
 65                  70                  75                  80

Gly Ser Arg Lys Asp Phe His Lys Thr Leu Pro Lys Gln Thr Phe Glu
             85                  90                  95

Ser Glu Thr Leu Glu Cys Ser Glu Pro Ala Ala Gln Ala Gly Pro Arg
        100                 105                 110

His Leu Asn Val Leu Cys Asp Val Ser Gly Lys Gly Pro Val Thr Ala
             115                 120                 125

Cys Asp Phe Asp Leu Arg Ser Leu Gln Pro Asp Lys Arg Leu Glu Asn
130                 135                 140

Leu Leu Gln Gln Val Ser Ala Glu Asp Phe Glu Lys Gln Asn Glu Glu
145                 150                 155                 160

Ala Arg Arg Thr Asn Arg Gln Ala Glu Leu Phe Ala Leu Tyr Pro Ser
                 165                 170                 175

Val Asp Glu Glu Asp Ala Val Glu Ile Arg Pro Val Pro Glu Cys Pro
             180                 185                 190

Lys Glu His Leu Gly Asn Arg Ile Leu Val Lys Leu Leu Thr Leu Lys
        195                 200                 205

Phe Glu Ile Glu Ile Glu Pro Leu Phe Ala Ser Ile Ala Leu Tyr Asp
210                 215                 220

Val Lys Glu Arg Lys Lys Ile Ser Glu Asn Phe His Cys Asp Leu Asn
225                 230                 235                 240

Ser Asp Gln Phe Lys Gly Phe Leu Arg Ala His Thr Pro Ser Val Ala
                 245                 250                 255

Ala Ser Ser Gln Ala Arg Ser Ala Val Phe Ser Val Thr Tyr Pro Ser
             260                 265                 270

Ser Asp Ile Tyr Leu Val Val Lys Ile Glu Lys Val Leu Gln Gln Gly
        275                 280                 285

Asp Ile Gly Asp Cys Ala Glu Pro Tyr Thr Val Ile Lys Glu Ser Asp
290                 295                 300

Gly Gly Lys Ser Lys Glu Lys Ile Glu Lys Leu Lys Leu Gln Ala Glu
305                 310                 315                 320

Ser Phe Cys Gln Arg Leu Gly Lys Tyr Arg Met Pro Phe Ala Trp Ala
                 325                 330                 335

Pro Ile Ser Leu Ser Ser Phe Asn Val Ser Thr Leu Glu Arg Glu
             340                 345                 350

Val Thr Asp Val Asp Ser Val Val Gly Arg Ser Pro Val Gly Glu Arg
        355                 360                 365

Arg Thr Leu Ala Gln Ser Arg Arg Leu Ser Glu Arg Ala Leu Ser Leu
370                 375                 380

Glu Glu Asn Gly Val Gly Ser Asn Phe Lys Thr Ser Thr Leu Ser Val
385                 390                 395                 400

Ser Ser Phe Phe Lys Gln Glu Gly Asp Arg Leu Ser Asp Glu Asp Leu
                 405                 410                 415

Phe Lys Phe Leu Ala Asp Tyr Lys Arg Ser Ser Ser Leu Gln Arg Arg
             420                 425                 430

Val Lys Ser Ile Pro Gly Leu Leu Arg Leu Glu Ile Ser Thr Ala Pro
        435                 440                 445

Glu Ile Ile Asn Cys Cys Leu Thr Pro Glu Met Leu Pro Val Lys Pro
450                 455                 460

Phe Pro Glu Asn Arg Thr Arg Pro His Lys Glu Ile Leu Glu Phe Pro
465                 470                 475                 480
```

-continued

```
Thr Arg Glu Val Tyr Val Pro His Thr Val Arg Asn Leu Leu Tyr
            485                 490                 495

Val Tyr Pro Gln Arg Leu Asn Phe Val Asn Lys Leu Ala Ser Ala Arg
                500                 505                 510

Asn Ile Thr Ile Lys Ile Gln Phe Met Cys Gly Glu Asp Ala Ser Asn
            515                 520                 525

Ala Met Pro Val Ile Phe Gly Lys Ser Ser Gly Pro Glu Phe Leu Gln
        530                 535                 540

Glu Val Tyr Thr Ala Val Thr Tyr His Asn Lys Ser Pro Asp Phe Tyr
545                 550                 555                 560

Glu Glu Val Lys Ile Lys Leu Pro Ala Lys Leu Thr Val Asn His His
                565                 570                 575

Leu Leu Phe Thr Phe Tyr His Ile Ser Cys Gln Gln Lys Gln Gly Ala
                580                 585                 590

Ser Val Glu Thr Leu Leu Gly Tyr Ser Trp Leu Pro Ile Leu Leu Asn
            595                 600                 605

Glu Arg Leu Gln Thr Gly Ser Tyr Cys Leu Pro Val Ala Leu Glu Lys
        610                 615                 620

Leu Pro Pro Asn Tyr Ser Met His Ser Ala Lys Val Pro Leu Gln
625                 630                 635                 640

Asn Pro Pro Ile Lys Trp Ala Glu Gly His Lys Gly Val Phe Asn Ile
                645                 650                 655

Glu Val Gln Ala Val Ser Ser Val His Thr Gln Asp Asn His Leu Glu
            660                 665                 670

Lys Phe Phe Thr Leu Cys His Ser Leu Glu Ser Gln Val Thr Phe Pro
        675                 680                 685

Ile Arg Val Leu Asp Gln Lys Ile Ser Glu Met Ala Leu Glu His Glu
    690                 695                 700

Leu Lys Leu Ser Ile Ile Cys Leu Asn Ser Ser Arg Leu Glu Pro Leu
705                 710                 715                 720

Val Leu Phe Leu His Leu Val Leu Asp Lys Leu Phe Gln Leu Ser Val
                725                 730                 735

Gln Pro Met Val Ile Ala Gly Gln Thr Ala Asn Phe Ser Gln Phe Ala
            740                 745                 750

Phe Glu Ser Val Val Ala Ile Ala Asn Ser Leu His Asn Ser Lys Asp
        755                 760                 765

Leu Ser Lys Asp Gln His Gly Arg Asn Cys Leu Leu Ala Ser Tyr Val
    770                 775                 780

His Tyr Val Phe Arg Leu Pro Glu Val Gln Arg Asp Val Pro Lys Ser
785                 790                 795                 800

Gly Ala Pro Thr Ala Leu Leu Asp Pro Arg Ser Tyr His Thr Tyr Gly
                805                 810                 815

Arg Thr Ser Ala Ala Ala Val Ser Ser Lys Leu Leu Gln Ala Arg Val
            820                 825                 830

Met Ser Ser Ser Asn Pro Asp Leu Ala Gly Thr His Ser Ala Ala Asp
        835                 840                 845

Glu Glu Val Lys Asn Ile Met Ser Ser Lys Ile Ala Asp Arg Asn Cys
    850                 855                 860

Ser Arg Met Ser Tyr Tyr Cys Ser Gly Ser Ser Asp Ala Pro Ser Ser
865                 870                 875                 880

Pro Ala Ala Pro Arg Pro Ala Ser Lys Lys His Phe His Glu Glu Leu
                885                 890                 895

Ala Leu Gln Met Val Val Ser Thr Gly Met Val Lys Ser Met Ala Gln
```

-continued

```
                900                 905                 910
His Val His Asn Met Asp Lys Arg Asp Ser Phe Arg Arg Thr Arg Phe
        915                 920                 925

Ser Asp Arg Phe Met Asp Asp Ile Thr Thr Ile Val Asn Val Val Thr
930                 935                 940

Ser Glu Ile Ala Ala Leu Leu Val Lys Pro Gln Lys Glu Asn Glu Gln
945                 950                 955                 960

Ala Glu Lys Met Asn Ile Ser Leu Ala Phe Phe Leu Tyr Asp Leu Leu
            965                 970                 975

Ser Leu Met Asp Arg Gly Phe Val Phe Asn Leu Ile Arg His Tyr Cys
        980                 985                 990

Ser Gln Leu Ser Ala Lys Leu Ser Asn Leu Pro Thr Leu Ile Ser Met
    995                 1000                1005

Arg Leu Glu Phe Leu Arg Ile Leu Cys Ser His Glu His Tyr Leu Asn
    1010                1015                1020

Leu Asn Leu Phe Phe Met Asn Ala Asp Thr Ala Pro Thr Ser Pro Cys
1025                1030                1035                1040

Pro Ser Ile Ser Ser Gln Asn Ser Ser Ser Cys Ser Ser Phe Gln Asp
            1045                1050                1055

Gln Lys Ile Ala Ser Met Phe Asp Leu Thr Ser Glu Tyr Arg Gln Gln
            1060                1065                1070

His Phe Leu Thr Gly Leu Leu Phe Thr Glu Leu Ala Ala Ala Leu Asp
        1075                1080                1085

Ala Glu Gly Glu Gly Ile Ser Lys Val Gln Arg Lys Ala Val Ser Ala
    1090                1095                1100

Ile His Ser Leu Leu Ser Ser His Asp Leu Asp Pro Arg Cys Val Lys
1105                1110                1115                1120

Pro Glu Val Lys Val Lys Ile Ala Ala Leu Tyr Leu Pro Leu Val Gly
            1125                1130                1135

Ile Ile Leu Asp Ala Leu Pro Gln Leu Cys Asp Phe Thr Val Ala Asp
            1140                1145                1150

Thr Arg Arg Tyr Arg Thr Ser Gly Ser Asp Glu Glu Gln Glu Gly Ala
        1155                1160                1165

Gly Ala Ile Asn Gln Asn Val Ala Leu Ala Ile Ala Gly Asn Asn Phe
    1170                1175                1180

Asn Leu Lys Thr Ser Gly Ile Val Leu Ser Ser Leu Pro Tyr Lys Gln
1185                1190                1195                1200

Tyr Asn Met Leu Asn Ala Asp Thr Thr Arg Asn Leu Met Ile Cys Phe
            1205                1210                1215

Leu Trp Ile Met Lys Asn Ala Asp Gln Ser Leu Ile Arg Lys Trp Ile
            1220                1225                1230

Ala Asp Leu Pro Ser Thr Gln Leu Asn Arg Ile Leu Asp Leu Leu Phe
        1235                1240                1245

Ile Cys Val Leu Cys Phe Glu Tyr Lys Gly Lys Gln Ser Ser Asp Lys
    1250                1255                1260

Val Ser Thr Gln Val Leu Gln Lys Ser Arg Asp Val Lys Ala Arg Leu
1265                1270                1275                1280

Glu Glu Ala Leu Leu Arg Gly Glu Gly Ala Arg Gly Glu Met Met Arg
            1285                1290                1295

Arg Arg Ala Pro Gly Asn Asp Arg Phe Pro Gly Leu Asn Glu Asn Leu
            1300                1305                1310

Arg Trp Lys Lys Glu Gln Thr His Trp Arg Gln Ala Asn Glu Lys Leu
        1315                1320                1325
```

-continued

```
Asp Lys Thr Lys Ala Glu Leu Asp Gln Glu Ala Leu Ile Ser Gly Asn
    1330                1335                1340

Leu Ala Thr Glu Ala His Leu Ile Ile Leu Asp Met Gln Glu Asn Ile
1345                1350                1355                1360

Ile Gln Ala Ser Ser Ala Leu Asp Cys Lys Asp Ser Leu Leu Gly Gly
                1365                1370                1375

Val Leu Arg Val Leu Val Asn Ser Leu Asn Cys Asp Gln Ser Thr Thr
            1380                1385                1390

Tyr Leu Thr His Cys Phe Ala Thr Leu Arg Ala Leu Ile Ala Lys Phe
        1395                1400                1405

Gly Asp Leu Leu Phe Glu Glu Glu Val Glu Gln Cys Phe Asp Leu Cys
    1410                1415                1420

His Gln Val Leu His His Cys Ser Ser Ser Met Asp Val Thr Arg Ser
1425                1430                1435                1440

Gln Ala Cys Ala Thr Leu Tyr Leu Leu Met Arg Phe Ser Phe Gly Ala
                1445                1450                1455

Thr Ser Asn Phe Ala Arg Val Lys Met Gln Val Thr Met Ser Leu Ala
            1460                1465                1470

Ser Leu Val Gly Arg Ala Pro Asp Phe Asn Glu Glu His Leu Arg Arg
        1475                1480                1485

Ser Leu Arg Thr Ile Leu Ala Tyr Ser Glu Glu Asp Thr Ala Met Gln
    1490                1495                1500

Met Thr Pro Phe Pro Thr Gln Val Glu Glu Leu Leu Cys Asn Leu Asn
1505                1510                1515                1520

Ser Ile Leu Tyr Asp Thr Val Lys Met Arg Glu Phe Gln Glu Asp Pro
                1525                1530                1535

Glu Met Leu Met Asp Leu Met Tyr Arg Ile Ala Lys Ser Tyr Gln Ala
            1540                1545                1550

Ser Pro Asp Leu Arg Leu Thr Trp Leu Gln Asn Met Ala Glu Lys His
        1555                1560                1565

Thr Lys Lys Lys Cys Tyr Thr Glu Ala Ala Met Cys Leu Val His Ala
    1570                1575                1580

Ala Ala Leu Val Ala Glu Tyr Leu Ser Met Leu Glu Asp His Ser Tyr
1585                1590                1595                1600

Leu Pro Val Gly Ser Val Ser Phe Gln Asn Ile Ser Ser Asn Val Leu
                1605                1610                1615

Glu Glu Ser Val Val Ser Glu Asp Thr Leu Ser Pro Asp Glu Asp Gly
            1620                1625                1630

Val Cys Ala Gly Gln Tyr Phe Thr Glu Ser Gly Leu Val Gly Leu Leu
        1635                1640                1645

Glu Gln Ala Ala Glu Leu Phe Ser Thr Gly Gly Leu Tyr Glu Thr Val
    1650                1655                1660

Asn Glu Val Tyr Lys Leu Val Ile Pro Ile Leu Glu Ala His Arg Glu
1665                1670                1675                1680

Phe Arg Lys Leu Thr Leu Thr His Ser Lys Leu Gln Arg Ala Phe Asp
                1685                1690                1695

Ser Ile Val Asn Lys Asp His Lys Arg Met Phe Gly Thr Tyr Phe Arg
            1700                1705                1710

Val Gly Phe Phe Gly Ser Lys Phe Gly Asp Leu Asp Glu Gln Glu Phe
        1715                1720                1725

Val Tyr Lys Glu Pro Ala Ile Thr Lys Leu Pro Glu Ile Ser His Arg
    1730                1735                1740
```

```
Leu Glu Ala Phe Tyr Gly Gln Cys Phe Gly Ala Glu Phe Val Glu Val
1745                1750                1755                1760

Ile Lys Asp Ser Thr Pro Val Asp Lys Thr Lys Leu Asp Pro Asn Lys
            1765                1770                1775

Ala Tyr Ile Gln Ile Thr Phe Val Glu Pro Tyr Phe Asp Glu Tyr Glu
            1780                1785                1790

Met Lys Asp Arg Val Thr Tyr Phe Glu Lys Asn Phe Asn Leu Arg Arg
            1795                1800                1805

Phe Met Tyr Thr Thr Pro Phe Thr Leu Glu Gly Arg Pro Arg Gly Glu
        1810                1815                1820

Leu His Glu Gln Tyr Arg Arg Asn Thr Val Leu Thr Thr Met His Ala
1825                1830                1835                1840

Phe Pro Tyr Ile Lys Thr Arg Ile Ser Val Ile Gln Lys Glu Glu Phe
                1845                1850                1855

Val Leu Thr Pro Ile Glu Val Ala Ile Glu Asp Met Lys Lys Lys Thr
            1860                1865                1870

Leu Gln Leu Ala Val Ala Ile Asn Gln Glu Pro Pro Asp Ala Lys Met
        1875                1880                1885

Leu Gln Met Val Leu Gln Gly Ser Val Gly Ala Thr Val Asn Gln Gly
    1890                1895                1900

Pro Leu Glu Val Ala Gln Val Phe Leu Ala Glu Ile Pro Ala Asp Pro
1905                1910                1915                1920

Lys Leu Tyr Arg His His Asn Lys Leu Arg Leu Cys Phe Lys Glu Phe
                1925                1930                1935

Ile Met Arg Cys Gly Glu Ala Val Glu Lys Asn Lys Arg Leu Ile Thr
            1940                1945                1950

Ala Asp Gln Arg Glu Tyr Gln Gln Glu Leu Lys Lys Asn Tyr Asn Lys
            1955                1960                1965

Leu Lys Glu Asn Leu Arg Pro Met Ile Glu Arg Lys Ile Pro Glu Leu
        1970                1975                1980

Tyr Lys Pro Ile Phe Arg Val Glu Ser Gln Lys Arg Asp Ser Phe His
1985                1990                1995                2000

Arg Ser Ser Phe Arg Lys Cys Glu Thr Gln Leu Ser Gln Gly Ser
            2005                2010                2015

<210> SEQ ID NO 137
<211> LENGTH: 2090
<212> TYPE: PRT
<213> ORGANISM: Homo sapiens
<220> FEATURE:
<223> OTHER INFORMATION: CLASP-3 amino acid sequence

<400> SEQUENCE: 137

Met Ala Glu Arg Arg Ala Phe Ala Gln Lys Ile Ser Arg Thr Val Ala
1               5                   10                  15

Ala Glu Val Arg Lys Gln Ile Ser Gly Gln Tyr Ser Gly Ser Pro Gln
            20                  25                  30

Leu Leu Lys Asn Leu Asn Ile Val Gly Asn Ile Ser His His Thr Thr
        35                  40                  45

Val Pro Leu Thr Glu Ala Val Asp Pro Val Asp Leu Glu Asp Tyr Leu
    50                  55                  60

Ile Thr His Pro Leu Ala Val Asp Ser Gly Pro Leu Arg Asp Leu Ile
65                  70                  75                  80

Glu Phe Pro Pro Asp Asp Ile Glu Val Val Tyr Ser Pro Arg Asp Cys
                85                  90                  95
```

-continued

```
Arg Thr Leu Val Ser Ala Val Pro Glu Glu Ser Glu Met Asp Pro His
            100                 105                 110

Val Arg Asp Cys Ile Arg Ser Tyr Thr Glu Asp Trp Ala Ile Val Ile
            115                 120                 125

Arg Lys Tyr His Lys Leu Gly Thr Gly Phe Asn Pro Asn Thr Leu Asp
        130                 135                 140

Lys Gln Lys Glu Arg Gln Lys Gly Leu Pro Lys Gln Val Phe Glu Ser
145                 150                 155                 160

Asp Glu Ala Pro Asp Gly Asn Ser Tyr Gln Asp Gln Asp Leu
                165                 170                 175

Lys Arg Arg Ser Met Ser Ile Asp Asp Thr Pro Arg Gly Ser Trp Ala
            180                 185                 190

Cys Ser Ile Phe Asp Leu Lys Asn Ser Leu Pro Asp Ala Leu Leu Pro
        195                 200                 205

Asn Leu Leu Asp Arg Thr Pro Asn Glu Glu Ile Asp Arg Gln Asn Asp
    210                 215                 220

Asp Gln Arg Lys Ser Asn Arg His Lys Glu Leu Phe Ala Leu His Pro
225                 230                 235                 240

Ser Pro Asp Glu Glu Pro Ile Glu Arg Leu Ser Val Pro Asp Ile
                245                 250                 255

Pro Lys Glu His Phe Gly Gln Arg Leu Leu Val Lys Cys Leu Ser Leu
            260                 265                 270

Lys Phe Glu Ile Glu Ile Glu Pro Ile Phe Ala Ser Leu Ala Leu Tyr
        275                 280                 285

Asp Val Lys Glu Lys Lys Lys Ile Ser Glu Asn Phe Tyr Phe Asp Leu
    290                 295                 300

Asn Ser Glu Gln Met Lys Gly Leu Leu Arg Pro His Val Pro Pro Ala
305                 310                 315                 320

Ala Ile Thr Thr Leu Ala Arg Ser Ala Ile Phe Ser Ile Thr Tyr Pro
                325                 330                 335

Ser Gln Asp Val Phe Leu Val Ile Lys Leu Glu Lys Val Leu Gln Gln
            340                 345                 350

Gly Asp Ile Gly Glu Cys Ala Glu Pro Tyr Met Ile Phe Lys Glu Ala
        355                 360                 365

Asp Ala Thr Lys Asn Lys Glu Lys Leu Glu Lys Leu Lys Ser Gln Ala
    370                 375                 380

Asp Gln Phe Cys Gln Arg Leu Gly Lys Tyr Arg Met Pro Phe Ala Trp
385                 390                 395                 400

Thr Ala Ile His Leu Met Asn Ile Val Ser Ser Ala Gly Ser Leu Glu
                405                 410                 415

Arg Asp Ser Thr Glu Val Glu Ile Ser Thr Gly Glu Lys Gly Ser
            420                 425                 430

Trp Ser Glu Arg Arg Asn Ser Ser Ile Val Gly Arg Ser Leu Glu
        435                 440                 445

Arg Thr Thr Ser Gly Asp Asp Ala Cys Asn Leu Thr Ser Phe Arg Pro
    450                 455                 460

Ala Thr Leu Thr Val Thr Asn Phe Phe Lys Gln Glu Gly Asp Arg Leu
465                 470                 475                 480

Ser Asp Glu Asp Leu Tyr Lys Phe Leu Ala Asp Met Arg Arg Pro Ser
                485                 490                 495

Ser Val Leu Arg Arg Leu Arg Pro Ile Thr Ala Gln Leu Lys Ile Asp
            500                 505                 510

Ile Ser Pro Ala Pro Glu Asn Pro His Tyr Cys Leu Thr Pro Glu Leu
```

-continued

```
            515                 520                 525
Leu Gln Val Lys Leu Tyr Pro Asp Ser Arg Val Arg Pro Thr Arg Glu
            530                 535                 540
Ile Leu Glu Phe Pro Ala Arg Asp Val Tyr Val Pro Asn Thr Thr Tyr
545                 550                 555                 560
Arg Asn Leu Leu Tyr Ile Tyr Pro Gln Ser Leu Asn Phe Ala Asn Arg
                565                 570                 575
Gln Gly Ser Ala Arg Asn Ile Thr Val Lys Val Gln Phe Met Tyr Gly
                580                 585                 590
Glu Asp Pro Ser Asn Ala Met Pro Val Ile Phe Gly Lys Ser Ser Cys
                595                 600                 605
Ser Glu Phe Ser Lys Glu Ala Tyr Thr Ala Val Tyr His Asn Arg
    610                 615                 620
Ser Pro Asp Phe His Glu Glu Ile Lys Val Lys Leu Pro Ala Thr Leu
625                 630                 635                 640
Thr Asp His His His Leu Leu Phe Thr Phe Tyr His Val Ser Cys Gln
                645                 650                 655
Gln Lys Gln Asn Thr Pro Leu Glu Thr Pro Val Gly Tyr Thr Trp Ile
                660                 665                 670
Pro Met Leu Gln Asn Gly Arg Leu Lys Thr Gly Gln Phe Cys Leu Pro
                675                 680                 685
Val Ser Leu Glu Lys Pro Pro Gln Ala Tyr Ser Val Leu Ser Pro Glu
690                 695                 700
Val Pro Leu Pro Gly Met Lys Trp Val Asp Asn His Lys Gly Val Phe
705                 710                 715                 720
Asn Val Glu Val Val Ala Val Ser Ser Ile His Thr Gln Asp Pro Tyr
                725                 730                 735
Leu Asp Lys Phe Phe Ala Leu Val Asn Ala Leu Asp Glu His Leu Phe
                740                 745                 750
Pro Val Arg Ile Gly Asp Met Arg Ile Met Glu Asn Asn Leu Glu Asn
                755                 760                 765
Glu Leu Lys Ser Ser Ile Ser Ala Leu Asn Ser Ser Gln Leu Glu Pro
    770                 775                 780
Val Val Arg Phe Leu His Leu Leu Asp Lys Leu Ile Leu Val
785                 790                 795                 800
Ile Arg Pro Pro Val Ile Ala Gly Gln Ile Val Asn Leu Gly Gln Ala
                805                 810                 815
Ser Phe Glu Ala Met Ala Ser Ile Ile Asn Arg Leu His Lys Asn Leu
                820                 825                 830
Glu Gly Asn His Asp Gln His Gly Arg Asn Ser Leu Leu Ala Ser Tyr
                835                 840                 845
Ile His Tyr Val Phe Arg Leu Pro Asn Thr Tyr Pro Asn Ser Ser Ser
    850                 855                 860
Pro Gly Pro Gly Gly Leu Gly Gly Ser Val His Tyr Ala Thr Met Ala
865                 870                 875                 880
Arg Ser Ala Val Arg Pro Ala Ser Leu Asn Leu Asn Arg Ser Arg Ser
                885                 890                 895
Leu Ser Asn Ser Asn Pro Asp Ile Ser Gly Thr Pro Thr Ser Pro Asp
                900                 905                 910
Asp Glu Val Arg Ser Ile Ile Gly Ser Lys Gly Leu Asp Arg Ser Asn
                915                 920                 925
Ser Trp Val Asn Thr Gly Gly Pro Lys Ala Ala Pro Trp Gly Ser Asn
    930                 935                 940
```

```
Pro Ser Pro Ser Ala Glu Ser Thr Gln Ala Met Asp Arg Ser Cys Asn
945                 950                 955                 960

Arg Met Ser Ser His Thr Glu Thr Ser Ser Phe Leu Gln Thr Leu Thr
            965                 970                 975

Gly Arg Leu Pro Thr Lys Lys Leu Phe His Glu Glu Leu Ala Leu Gln
        980                 985                 990

Trp Val Val Cys Ser Gly Ser Val Arg Glu Ser Ala Leu Gln Gln Ala
            995                 1000                1005

Trp Phe Phe Phe Glu Leu Met Val Lys Ser Met Val His His Leu Tyr
    1010                1015                1020

Phe Asn Asp Lys Leu Glu Ala Pro Arg Lys Ser Arg Phe Pro Glu Arg
1025                1030                1035                1040

Phe Met Asp Asp Ile Ala Ala Leu Val Ser Thr Ile Ala Ser Asp Ile
                1045                1050                1055

Val Ser Arg Phe Gln Lys Asp Thr Glu Met Val Glu Arg Leu Asn Thr
            1060                1065                1070

Ser Leu Ala Phe Phe Leu Asn Asp Leu Leu Ser Val Met Asp Arg Gly
        1075                1080                1085

Phe Val Phe Ser Leu Ile Lys Ser Cys Tyr Lys Gln Val Ser Ser Lys
    1090                1095                1100

Leu Tyr Ser Leu Pro Asn Pro Ser Val Leu Val Ser Leu Arg Leu Asp
1105                1110                1115                1120

Phe Leu Arg Ile Ile Cys Ser His Glu His Tyr Val Thr Leu Asn Leu
                1125                1130                1135

Pro Cys Ser Leu Leu Thr Pro Pro Ala Ser Pro Ser Pro Ser Val Ser
            1140                1145                1150

Ser Ala Thr Ser Gln Ser Ser Gly Phe Ser Thr Asn Val Gln Asp Gln
        1155                1160                1165

Lys Ile Ala Asn Met Phe Glu Leu Ser Val Pro Phe Arg Gln Gln His
    1170                1175                1180

Tyr Leu Ala Gly Leu Val Leu Thr Glu Leu Ala Val Ile Leu Asp Pro
1185                1190                1195                1200

Asp Ala Glu Gly Leu Phe Gly Leu His Lys Lys Val Ile Asn Met Val
                1205                1210                1215

His Asn Leu Leu Ser Ser His Asp Ser Asp Pro Arg Tyr Ser Asp Pro
            1220                1225                1230

Gln Ile Lys Ala Arg Val Ala Met Leu Tyr Leu Pro Leu Ile Gly Ile
        1235                1240                1245

Ile Met Glu Thr Val Pro Gln Leu Tyr Asp Phe Thr Glu Thr His Asn
    1250                1255                1260

Gln Arg Gly Arg Pro Ile Cys Ile Ala Thr Asp Asp Tyr Glu Ser Glu
1265                1270                1275                1280

Ser Gly Ser Met Ile Ser Gln Thr Val Ala Met Ala Ile Ala Gly Thr
                1285                1290                1295

Ser Val Pro Gln Leu Thr Arg Pro Gly Ser Phe Leu Leu Thr Ser Thr
            1300                1305                1310

Ser Gly Arg Gln His Thr Thr Phe Ser Ala Glu Ser Ser Arg Ser Leu
        1315                1320                1325

Leu Ile Cys Leu Leu Trp Val Leu Lys Asn Ala Asp Glu Thr Val Leu
    1330                1335                1340

Gln Lys Trp Phe Thr Asp Leu Ser Val Leu Gln Leu Asn Arg Leu Leu
1345                1350                1355                1360
```

-continued

```
Asp Leu Leu Tyr Leu Cys Val Ser Cys Phe Glu Tyr Lys Gly Lys Lys
            1365                1370                1375
Val Phe Glu Arg Met Asn Ser Leu Thr Phe Lys Lys Ser Lys Asp Met
        1380                1385                1390
Arg Ala Lys Leu Glu Glu Ala Ile Leu Gly Ser Ile Gly Ala Arg Gln
    1395                1400                1405
Glu Met Val Arg Arg Ser Arg Gly Gln Leu Glu Arg Ser Pro Ser Gly
1410                1415                1420
Ser Ala Phe Gly Ser Gln Glu Asn Leu Arg Trp Arg Lys Asp Met Thr
1425                1430                1435                1440
His Trp Arg Gln Asn Thr Glu Lys Leu Asp Lys Ser Arg Ala Glu Ile
            1445                1450                1455
Glu His Glu Ala Leu Ile Asp Gly Asn Leu Ala Thr Glu Ala Asn Leu
        1460                1465                1470
Ile Ile Leu Asp Thr Leu Glu Ile Val Val Gln Thr Val Ser Val Thr
    1475                1480                1485
Glu Ser Lys Glu Ser Ile Leu Gly Gly Val Leu Lys Val Leu Leu His
    1490                1495                1500
Ser Met Ala Cys Asn Gln Ser Ala Val Tyr Leu Gln His Cys Phe Ala
1505                1510                1515                1520
Thr Gln Arg Ala Leu Val Ser Lys Phe Pro Glu Leu Leu Phe Glu Glu
            1525                1530                1535
Glu Thr Glu Gln Cys Ala Asp Leu Cys Leu Arg Leu Leu Arg His Cys
        1540                1545                1550
Ser Ser Ser Ile Gly Thr Ile Arg Ser His Pro Ser Ala Ser Leu Tyr
    1555                1560                1565
Leu Leu Met Arg Gln Asn Phe Glu Ile Gly Asn Asn Phe Ala Arg Val
    1570                1575                1580
Lys Met Gln Val Pro Met Ser Leu Ser Ser Leu Val Gly Thr Ser Gln
1585                1590                1595                1600
Asn Phe Asn Glu Glu Phe Leu Arg Arg Ser Leu Lys Thr Ile Leu Thr
            1605                1610                1615
Tyr Ala Glu Glu Asp Leu Glu Leu Arg Glu Thr Thr Phe Pro Asp Gln
        1620                1625                1630
Val Gln Asp Leu Val Phe Asn Leu His Met Ile Leu Ser Asp Thr Val
    1635                1640                1645
Lys Met Lys Glu His Gln Glu Asp Pro Glu Met Leu Ile Asp Leu Met
1650                1655                1660
Tyr Arg Ile Ala Lys Gly Tyr Gln Thr Ser Pro Glu Arg Leu Thr Trp
1665                1670                1675                1680
Leu Gln Asn Met Ala Gly Lys His Ser Glu Arg Ser Asn His Ala Glu
            1685                1690                1695
Ala Ala Gln Cys Leu Val His Ser Ala Ala Leu Val Ala Glu Tyr Leu
        1700                1705                1710
Ser Met Leu Glu Asp Arg Lys Tyr Leu Pro Val Gly Cys Val Thr Phe
    1715                1720                1725
Gln Asn Ile Ser Ser Asn Val Leu Glu Glu Ser Ala Val Ser Asp Asp
    1730                1735                1740
Val Val Ser Pro Asp Glu Glu Gly Ile Cys Ser Gly Lys Tyr Phe Thr
1745                1750                1755                1760
Glu Ser Gly Leu Val Gly Leu Leu Glu Gln Ala Ala Ala Ser Phe Ser
            1765                1770                1775
Met Ala Gly Met Tyr Glu Ala Val Asn Glu Val Tyr Lys Val Leu Ile
```

```
                      1780                1785                1790
Pro Ile His Glu Ala Asn Arg Asp Ala Lys Lys Leu Ser Thr Ile His
     1795                1800                1805
Gly Lys Leu Gln Glu Ala Phe Ser Lys Ile Val His Gln Ser Thr Gly
     1810                1815                1820
Trp Glu Arg Met Phe Gly Thr Tyr Phe Arg Val Gly Phe Tyr Gly Thr
1825                1830                1835                1840
Lys Phe Gly Asp Leu Asp Glu Gln Glu Phe Val Tyr Lys Glu Pro Ala
             1845                1850                1855
Ile Thr Lys Leu Ala Glu Ile Ser His Arg Leu Glu Gly Phe Tyr Gly
         1860                1865                1870
Glu Arg Phe Gly Glu Asp Val Val Glu Val Ile Lys Asp Ser Asn Pro
     1875                1880                1885
Val Asp Lys Cys Lys Leu Asp Pro Asn Lys Ala Tyr Ile Gln Ile Thr
     1890                1895                1900
Tyr Val Glu Pro Tyr Phe Asp Thr Tyr Glu Met Lys Asp Arg Ile Thr
1905                1910                1915                1920
Tyr Phe Asp Lys Asn Tyr Asn Leu Arg Arg Phe Met Tyr Cys Thr Pro
             1925                1930                1935
Phe Thr Leu Asp Gly Arg Ala His Gly Glu Leu His Glu Gln Phe Lys
         1940                1945                1950
Arg Lys Thr Ile Leu Thr Thr Ser His Ala Phe Pro Tyr Ile Lys Thr
     1955                1960                1965
Arg Val Asn Val Thr His Lys Glu Glu Ile Ile Leu Thr Pro Ile Glu
     1970                1975                1980
Val Ala Ile Glu Asp Met Gln Lys Lys Thr Gln Glu Leu Ala Phe Ala
1985                1990                1995                2000
Thr His Gln Asp Pro Ala Asp Pro Lys Met Leu Gln Met Val Leu Gln
             2005                2010                2015
Gly Ser Val Gly Thr Thr Val Asn Gln Gly Pro Leu Glu Val Ala Gln
         2020                2025                2030
Val Phe Leu Ser Glu Ile Pro Ser Asp Pro Lys Leu Phe Arg His His
     2035                2040                2045
Asn Lys Leu Arg Leu Cys Phe Lys Asp Phe Thr Lys Arg Cys Glu Asp
     2050                2055                2060
Ala Leu Arg Lys Asn Lys Ser Leu Ile Gly Pro Val Gln Lys Glu Tyr
2065                2070                2075                2080
Gln Arg Glu Leu Gly Lys Leu Ser Ser Pro
             2085                2090

<210> SEQ ID NO 138
<211> LENGTH: 2047
<212> TYPE: PRT
<213> ORGANISM: Homo sapiens
<220> FEATURE:
<223> OTHER INFORMATION: CLASP-7 amino acid sequence

<400> SEQUENCE: 138

Met Ala Ala Ser Glu Arg Arg Ala Phe Ala His Lys Ile Asn Arg Thr
  1               5                  10                  15
Val Ala Ala Glu Val Arg Lys Gln Val Ser Arg Glu Arg Ser Gly Ser
             20                  25                  30
Pro His Ser Ser Arg Arg Cys Ser Ser Ser Leu Gly Val Pro Leu Thr
         35                  40                  45
Glu Val Val Glu Pro Leu Asp Phe Glu Asp Val Leu Leu Ser Arg Pro
```

-continued

```
            50                  55                  60
Pro Asp Ala Glu Pro Gly Pro Leu Arg Asp Leu Val Glu Phe Pro Ala
 65                  70                  75                  80

Asp Asp Leu Glu Leu Leu Leu Gln Pro Arg Glu Cys Arg Thr Thr Glu
                 85                  90                  95

Pro Gly Ile Pro Lys Asp Glu Lys Leu Asp Ala Gln Val Arg Ala Ala
            100                 105                 110

Val Glu Met Tyr Ile Glu Asp Trp Val Ile Val His Arg Arg Tyr Gln
            115                 120                 125

Tyr Leu Ser Ala Ala Tyr Ser Pro Val Thr Thr Asp Thr Gln Arg Glu
130                 135                 140

Arg Gln Lys Gly Leu Pro Arg Gln Val Phe Glu Gln Asp Ala Ser Gly
145                 150                 155                 160

Asp Glu Arg Ser Gly Pro Glu Asp Ser Asn Asp Ser Arg Arg Gly Ser
                165                 170                 175

Gly Ser Pro Glu Asp Thr Pro Arg Ser Ser Gly Ala Ser Ser Ile Phe
            180                 185                 190

Asp Leu Arg Asn Leu Ala Ala Asp Ser Leu Leu Pro Ser Leu Leu Glu
            195                 200                 205

Arg Ala Ala Pro Glu Asp Val Asp Arg Arg Asn Glu Thr Leu Arg Arg
210                 215                 220

Gln His Arg Pro Pro Ala Leu Leu Thr Leu Tyr Pro Ala Pro Asp Glu
225                 230                 235                 240

Asp Glu Ala Val Glu Arg Cys Ser Arg Pro Glu Pro Arg Glu His
                245                 250                 255

Phe Gly Gln Arg Ile Leu Val Lys Cys Leu Ser Leu Lys Phe Glu Ile
            260                 265                 270

Glu Ile Glu Pro Ile Phe Gly Ile Leu Ala Leu Tyr Asp Val Arg Glu
            275                 280                 285

Lys Lys Lys Ile Ser Glu Asn Phe Tyr Phe Asp Leu Asn Ser Asp Ser
290                 295                 300

Met Lys Gly Leu Leu Arg Ala His Gly Thr His Pro Ala Ile Ser Thr
305                 310                 315                 320

Leu Ala Arg Ser Ala Ile Phe Ser Val Thr Tyr Pro Ser Pro Asp Ile
                325                 330                 335

Phe Leu Val Ile Lys Leu Glu Lys Val Leu Gln Gln Gly Asp Ile Ser
            340                 345                 350

Glu Cys Cys Glu Pro Tyr Met Val Leu Lys Glu Val Asp Thr Ala Lys
            355                 360                 365

Asn Lys Glu Lys Leu Glu Lys Leu Arg Leu Ala Ala Glu Gln Phe Cys
370                 375                 380

Thr Arg Leu Gly Arg Tyr Arg Met Pro Phe Ala Trp Thr Ala Val His
385                 390                 395                 400

Leu Ala Asn Ile Val Ser Ser Ala Gly Gln Leu Asp Arg Asp Ser Asp
                405                 410                 415

Ser Glu Gly Glu Arg Arg Pro Ala Trp Thr Asp Arg Arg Arg Gly
            420                 425                 430

Pro Gln Asp Arg Ala Ser Ser Gly Asp Asp Ala Cys Ser Phe Ser Gly
            435                 440                 445

Phe Arg Pro Ala Thr Leu Thr Val Thr Asn Phe Phe Lys Gln Glu Ala
450                 455                 460

Glu Arg Leu Ser Asp Glu Asp Leu Phe Lys Phe Leu Ala Asp Met Arg
465                 470                 475                 480
```

-continued

```
Arg Pro Ser Ser Leu Leu Arg Arg Leu Arg Pro Val Thr Ala Gln Leu
                485                 490                 495

Lys Ile Asp Ile Ser Pro Ala Pro Glu Asn Pro His Phe Cys Leu Ser
                500                 505                 510

Pro Glu Leu Leu His Ile Lys Pro Tyr Pro Asp Pro Arg Gly Arg Pro
                515                 520                 525

Thr Lys Glu Ile Leu Glu Phe Pro Ala Arg Glu Val Tyr Ala Pro His
                530                 535                 540

Thr Ser Tyr Arg Asn Leu Leu Tyr Val Tyr Pro His Ser Leu Asn Phe
545                 550                 555                 560

Ser Ser Arg Gln Gly Ser Val Arg Asn Leu Ala Val Arg Val Gln Tyr
                565                 570                 575

Met Thr Gly Glu Asp Pro Ser Gln Ala Leu Pro Val Ile Phe Gly Lys
                580                 585                 590

Ser Ser Cys Ser Glu Phe Thr Arg Glu Ala Phe Thr Pro Val Val Tyr
                595                 600                 605

His Asn Lys Ser Pro Glu Phe Tyr Glu Glu Phe Lys Leu His Leu Pro
                610                 615                 620

Ala Cys Val Thr Glu Asn His His Leu Leu Phe Thr Phe Tyr His Val
625                 630                 635                 640

Ser Cys Gln Pro Arg Pro Gly Thr Ala Leu Glu Thr Pro Val Gly Phe
                645                 650                 655

Thr Trp Ile Pro Leu Leu Gln His Gly Arg Leu Arg Thr Gly Pro Phe
                660                 665                 670

Cys Leu Pro Val Ser Val Asp Gln Pro Pro Ser Tyr Ser Val Leu
                675                 680                 685

Thr Pro Asp Val Ala Leu Pro Gly Met Arg Trp Val Asp Gly His Lys
                690                 695                 700

Gly Val Phe Ser Val Glu Leu Thr Ala Val Ser Ser Val His Pro Gln
705                 710                 715                 720

Asp Pro Tyr Leu Asp Lys Phe Phe Thr Leu Val His Val Leu Glu Glu
                725                 730                 735

Gly Ala Phe Pro Phe Arg Leu Lys Asp Thr Val Leu Ser Glu Gly Asn
                740                 745                 750

Val Glu Gln Glu Leu Arg Ala Ser Leu Ala Ala Leu Arg Leu Ala Ser
                755                 760                 765

Pro Glu Pro Leu Val Ala Phe Ser His His Val Leu Asp Lys Leu Val
                770                 775                 780

Arg Leu Val Ile Arg Pro Pro Ile Ile Ser Gly Gln Ile Val Asn Leu
785                 790                 795                 800

Gly Arg Gly Ala Phe Glu Ala Met Ala His Val Val Ser Leu Val His
                805                 810                 815

Arg Ser Leu Glu Ala Ala Gln Asp Ala Arg Gly His Cys Pro Gln Leu
                820                 825                 830

Ala Ala Tyr Val His Tyr Ala Phe Arg Leu Pro Gly Thr Glu Pro Ser
                835                 840                 845

Leu Pro Asp Gly Ala Pro Pro Val Thr Val Gln Ala Ala Thr Leu Ala
                850                 855                 860

Arg Gly Ser Gly Arg Pro Ala Ser Leu Tyr Leu Ala Arg Ser Lys Ser
865                 870                 875                 880

Ile Ser Ser Ser Asn Pro Asp Leu Ala Val Ala Pro Gly Ser Val Asp
                885                 890                 895
```

-continued

Asp Glu Val Ser Arg Ile Leu Ala Ser Lys Leu Leu His Glu Glu Leu
        900                 905                 910

Ala Leu Gln Trp Val Val Ser Ser Ala Val Arg Glu Ala Ile Leu
        915                 920                 925

Gln His Ala Trp Phe Phe Gln Leu Met Val Lys Ser Met Ala Leu
        930                 935                 940

His Leu Leu Leu Gly Gln Arg Leu Asp Thr Pro Arg Lys Leu Arg Phe
945                 950                 955                 960

Pro Gly Arg Phe Leu Asp Asp Ile Thr Ala Leu Val Gly Ser Val Gly
                965                 970                 975

Leu Glu Val Ile Thr Arg Val His Lys Asp Val Glu Leu Ala Glu His
            980                 985                 990

Leu Asn Ala Ser Leu Ala Phe Phe Leu Ser Asp Leu Leu Ser Leu Val
        995                 1000                1005

Asp Arg Gly Phe Val Phe Ser Leu Val Arg Ala His Tyr Lys Gln Val
    1010                1015                1020

Ala Thr Arg Leu Gln Ser Ser Pro Asn Pro Ala Ala Leu Leu Thr Leu
1025                1030                1035                1040

Arg Met Glu Phe Thr Arg Ile Leu Cys Ser His Glu His Tyr Val Thr
            1045                1050                1055

Leu Asn Leu Pro Cys Cys Pro Leu Ser Pro Pro Ala Ser Pro Ser Pro
        1060                1065                1070

Ser Val Ser Ser Thr Thr Ser Gln Ser Thr Phe Ser Ser Gln Ala
        1075                1080                1085

Pro Asp Pro Lys Val Thr Ser Met Phe Glu Leu Ser Gly Pro Phe Arg
    1090                1095                1100

Gln Gln His Phe Leu Ala Gly Leu Leu Leu Thr Glu Leu Ala Leu Ala
1105                1110                1115                1120

Leu Glu Pro Glu Ala Glu Gly Ala Phe Leu Leu His Lys Lys Ala Ile
            1125                1130                1135

Ser Ala Val His Ser Leu Leu Cys Gly His Asp Thr Asp Pro Arg Tyr
        1140                1145                1150

Ala Glu Ala Thr Val Lys Ala Arg Val Ala Glu Leu Tyr Leu Pro Leu
    1155                1160                1165

Leu Ser Ile Ala Arg Asp Thr Leu Pro Arg Leu His Asp Phe Ala Glu
    1170                1175                1180

Gly Pro Gly Gln Arg Ser Arg Leu Ala Ser Met Leu Asp Ser Asp Thr
1185                1190                1195                1200

Glu Gly Glu Gly Asp Ile Ala Gly Thr Ile Asn Pro Ser Val Ala Met
            1205                1210                1215

Ala Ile Ala Gly Gly Pro Leu Ala Pro Gly Ser Arg Ala Ser Ile Ser
        1220                1225                1230

Gln Gly Pro Pro Thr Ala Ser Arg Ala Gly Cys Ala Leu Ser Ala Glu
    1235                1240                1245

Ser Ser Arg Thr Leu Leu Ala Cys Val Leu Trp Val Leu Lys Asn Thr
    1250                1255                1260

Glu Pro Ala Leu Leu Gln Arg Trp Ala Thr Asp Leu Thr Leu Pro Gln
1265                1270                1275                1280

Leu Gly Arg Leu Leu Asp Leu Leu Tyr Leu Cys Leu Ala Ala Phe Glu
            1285                1290                1295

Tyr Lys Gly Lys Lys Ala Phe Glu Arg Ile Asn Ser Leu Thr Phe Lys
        1300                1305                1310

Lys Ser Leu Asp Met Lys Ala Arg Leu Glu Glu Ala Ile Leu Gly Thr

-continued

```
        1315                1320                1325
Ile Gly Ala Arg Gln Glu Met Val Arg Arg Ser Arg Glu Arg Ser Pro
    1330                1335                1340
Phe Gly Asn Pro Glu Asn Val Arg Trp Arg Lys Ser Val Thr His Trp
1345                1350                1355                1360
Lys Gln Thr Ser Asp Arg Val Asp Lys Thr Lys Asp Glu Met Glu His
                1365                1370                1375
Glu Ala Leu Val Glu Gly Asn Leu Ala Thr Glu Ala Ser Leu Val Val
            1380                1385                1390
Leu Asp Thr Leu Glu Ile Ile Val Gln Thr Val Met Leu Ser Glu Ala
        1395                1400                1405
Arg Glu Ser Val Leu Gly Ala Val Leu Lys Val Val Leu Tyr Ser Leu
    1410                1415                1420
Gly Ser Ala Gln Ser Ala Leu Phe Leu Gln His Gly Leu Ala Thr Gln
1425                1430                1435                1440
Arg Ala Leu Val Ser Lys Phe Pro Glu Leu Leu Phe Glu Glu Asp Thr
                1445                1450                1455
Glu Leu Cys Ala Asp Leu Cys Leu Arg Leu Leu Arg His Cys Gly Ser
            1460                1465                1470
Arg Ile Ser Thr Ile Arg Thr His Ala Ser Ala Ser Leu Tyr Leu Leu
        1475                1480                1485
Met Arg Gln Asn Phe Glu Ile Gly His Asn Phe Ala Arg Val Lys Met
    1490                1495                1500
Gln Val Thr Met Ser Leu Ser Ser Leu Val Gly Thr Thr Gln Asn Phe
1505                1510                1515                1520
Ser Glu Glu His Leu Arg Arg Ser Leu Lys Thr Ile Leu Thr Tyr Ala
                1525                1530                1535
Glu Glu Asp Met Gly Leu Arg Asp Ser Thr Phe Ala Glu Gln Val Gln
            1540                1545                1550
Asp Leu Met Phe Asn Leu His Met Ile Leu Thr Asp Thr Val Lys Met
        1555                1560                1565
Lys Glu His Gln Glu Asp Pro Glu Met Leu Ile Asp Leu Met Tyr Arg
    1570                1575                1580
Ile Ala Arg Gly Tyr Gln Gly Ser Pro Asp Leu Arg Leu Thr Trp Leu
1585                1590                1595                1600
Gln Asn Met Ala Gly Lys His Ala Glu Leu Gly Asn His Ala Glu Ala
                1605                1610                1615
Ala Gln Cys Met Val His Ala Ala Ala Leu Val Ala Glu Tyr Leu Ala
            1620                1625                1630
Leu Leu Glu Asp Gln Arg His Leu Pro Val Gly Cys Val Ser Phe Gln
        1635                1640                1645
Asn Ile Ser Ser Asn Val Leu Glu Glu Ser Ala Ile Ser Asp Asp Ile
    1650                1655                1660
Leu Ser Pro Asp Glu Glu Gly Phe Cys Ser Gly Lys His Phe Thr Glu
1665                1670                1675                1680
Leu Gly Leu Val Gly Leu Leu Glu Gln Ala Ala Gly Tyr Phe Thr Met
                1685                1690                1695
Gly Gly Leu Tyr Glu Ala Val Asn Glu Val Tyr Lys Asn Leu Ile Pro
            1700                1705                1710
Ile Leu Glu Ala His Arg Asp Tyr Lys Lys Leu Ala Ala Val His Gly
        1715                1720                1725
Lys Leu Gln Glu Ala Phe Thr Lys Ile Met His Gln Ser Ser Gly Trp
    1730                1735                1740
```

```
Glu Arg Val Phe Gly Thr Tyr Phe Arg Val Gly Phe Tyr Ala His
1745                1750                1755                1760

Phe Gly Asp Leu Asp Glu Gln Glu Phe Val Tyr Lys Glu Pro Ser Ile
            1765                1770                1775

Thr Lys Leu Ala Glu Ile Ser His Arg Leu Glu Glu Phe Tyr Thr Glu
        1780                1785                1790

Arg Phe Gly Asp Asp Val Val Glu Ile Ile Lys Asp Ser Tyr Pro Val
    1795                1800                1805

Asp Lys Ser Lys Leu Asp Ser Gln Lys Ala Tyr Ile Gln Ile Thr Tyr
1810                1815                1820

Val Glu Pro Tyr Phe Asp Thr Tyr Glu Leu Lys Asp Arg Val Thr Tyr
1825                1830                1835                1840

Phe Asp Arg Asn Tyr Gly Leu Arg Thr Phe Leu Phe Cys Thr Pro Phe
            1845                1850                1855

Thr Pro Asp Gly Arg Ala His Gly Glu Leu Pro Glu Gln His Lys Arg
        1860                1865                1870

Lys Thr Leu Leu Ser Thr Asp His Ala Phe Pro Tyr Ile Lys Thr Arg
    1875                1880                1885

Ile Arg Val Cys His Arg Glu Glu Thr Val Leu Thr Pro Val Glu Val
1890                1895                1900

Ala Ile Glu Asp Met Gln Lys Lys Thr Arg Glu Leu Ala Phe Ala Thr
1905                1910                1915                1920

Glu Gln Asp Pro Pro Asp Ala Lys Met Leu Gln Met Val Leu Gln Gly
            1925                1930                1935

Ser Val Gly Pro Thr Val Asn Gln Gly Pro Leu Glu Val Ala Gln Val
        1940                1945                1950

Phe Leu Ala Glu Ile Pro Glu Asp Pro Lys Leu Phe Arg His His Asn
    1955                1960                1965

Lys Leu Arg Leu Cys Phe Lys Asp Phe Cys Lys Lys Cys Glu Asp Ala
1970                1975                1980

Leu Arg Lys Asn Lys Ala Leu Ile Gly Pro Asp Gln Lys Glu Tyr His
1985                1990                1995                2000

Arg Glu Leu Glu Arg Asn Tyr Cys Arg Leu Arg Glu Ala Leu Gln Pro
            2005                2010                2015

Leu Leu Thr Gln Arg Leu Pro Gln Leu Met Ala Pro Thr Pro Pro Gly
        2020                2025                2030

Leu Arg Asn Ser Leu Asn Arg Ala Ser Phe Arg Lys Ala Asp Leu
    2035                2040                2045

<210> SEQ ID NO 139
<211> LENGTH: 2180
<212> TYPE: PRT
<213> ORGANISM: Homo sapiens
<220> FEATURE:
<223> OTHER INFORMATION: CLASP-1 amino acid sequence

<400> SEQUENCE: 139

Met Ser Phe Arg Gly Lys Val Phe Lys Arg Glu Pro Ser Glu Phe Trp
1               5                   10                  15

Lys Lys Arg Arg Thr Val Arg Arg Val Ile Gln Glu Glu Phe His Arg
            20                  25                  30

Phe Ser Ser Gln Glu Lys Pro Arg Leu Leu Glu Pro Leu Asp Tyr Glu
        35                  40                  45

Thr Val Ile Glu Glu Leu Glu Lys Thr Tyr Arg Asn Asp Pro Leu Gln
    50                  55                  60
```

```
Asp Leu Leu Phe Phe Pro Ser Asp Asp Phe Ser Ala Ala Thr Val Ser
 65                  70                  75                  80

Trp Asp Ile Arg Thr Leu Tyr Ser Thr Val Pro Glu Asp Ala Glu His
             85                  90                  95

Lys Ala Glu Asn Leu Leu Val Lys Glu Ala Cys Lys Phe Tyr Ser Ser
            100                 105                 110

Gln Trp His Val Val Asn Tyr Lys Tyr Glu Gln Tyr Ser Gly Asp Ile
        115                 120                 125

Arg Gln Leu Pro Arg Ala Glu Tyr Lys Pro Glu Lys Leu Pro Ser His
    130                 135                 140

Ser Phe Glu Ile Asp His Glu Asp Ala Asp Lys Asp Glu Asp Thr Thr
145                 150                 155                 160

Ser His Ser Ser Lys Gly Gly Gly Ala Gly Gly Thr Gly Val
            165                 170                 175

Phe Lys Ser Gly Trp Leu Tyr Lys Gly Asn Phe Asn Ser Thr Val Asn
            180                 185                 190

Asn Thr Val Thr Val Arg Ser Phe Lys Lys Arg Tyr Phe Gln Leu Thr
        195                 200                 205

Gln Leu Pro Asp Asn Ser Tyr Ile Met Asn Phe Tyr Lys Asp Glu Lys
    210                 215                 220

Ile Ser Lys Glu Pro Lys Gly Cys Ile Phe Leu Asp Ser Cys Thr Gly
225                 230                 235                 240

Val Val Gln Asn Asn Arg Leu Arg Lys Tyr Ala Phe Glu Leu Lys Met
            245                 250                 255

Asn Asp Leu Thr Tyr Phe Val Leu Ala Ala Glu Thr Glu Ser Asp Met
        260                 265                 270

Asp Glu Trp Ile His Thr Leu Asn Arg Ile Leu Gln Ile Ser Pro Glu
    275                 280                 285

Gly Pro Leu Gln Gly Arg Arg Ser Thr Glu Leu Thr Asp Leu Gly Leu
290                 295                 300

Asp Ser Leu Asp Asn Ser Val Thr Cys Glu Cys Thr Pro Glu Glu Thr
305                 310                 315                 320

Asp Ser Ser Glu Asn Asn Leu His Ala Asp Phe Ala Lys Tyr Leu Thr
            325                 330                 335

Glu Thr Glu Asp Thr Val Lys Thr Thr Arg Asn Met Glu Arg Leu Asn
        340                 345                 350

Leu Phe Ser Leu Asp Pro Asp Ile Asp Thr Leu Lys Leu Gln Lys Lys
    355                 360                 365

Asp Leu Leu Glu Pro Glu Ser Val Ile Lys Pro Phe Glu Lys Ala
370                 375                 380

Ala Lys Arg Ile Met Ile Ile Cys Lys Ala Leu Asn Ser Asn Leu Gln
385                 390                 395                 400

Gly Cys Val Thr Glu Asn Glu Asn Asp Pro Ile Thr Asn Ile Glu Pro
            405                 410                 415

Phe Phe Val Ser Val Ala Leu Tyr Asp Leu Arg Asp Ser Arg Lys Ile
        420                 425                 430

Ser Ala Asp Phe His Val Asp Leu Asn His Ala Ala Val Arg Gln Met
    435                 440                 445

Leu Leu Gly Ala Ser Val Ala Leu Glu Asn Gly Asn Ile Asp Thr Ile
450                 455                 460

Thr Pro Arg Gln Ser Glu Glu Pro His Ile Lys Gly Leu Pro Glu Glu
465                 470                 475                 480
```

-continued

```
Trp Leu Lys Phe Pro Lys Gln Ala Val Phe Ser Val Ser Asn Pro His
            485                 490                 495

Ser Glu Ile Val Leu Val Ala Lys Ile Glu Lys Val Leu Met Gly Asn
        500                 505                 510

Ile Ala Ser Gly Ala Glu Pro Tyr Ile Lys Asn Pro Asp Ser Asn Lys
        515                 520                 525

Tyr Ala Gln Lys Ile Leu Lys Ser Asn Arg Gln Phe Cys Ser Lys Leu
        530                 535                 540

Gly Lys Tyr Arg Arg Ala Phe Ala Trp Ala Val Arg Ser Val Phe Lys
545                 550                 555                 560

Asp Asn Gln Gly Asn Val Asp Arg Asp Ser Arg Phe Ser Pro Leu Phe
                565                 570                 575

Arg Gln Glu Ser Ser Lys Ile Ser Thr Glu Asp Leu Val Lys Leu Val
                580                 585                 590

Ser Asp Tyr Arg Arg Ala Asp Arg Ile Ser Lys Met Gln Thr Ile Pro
                595                 600                 605

Gly Ser Leu Asp Ile Ala Val Asp Asn Val Pro Leu Glu His Pro Asn
            610                 615                 620

Cys Val Thr Ser Ser Phe Ile Pro Val Lys Pro Phe Asn Met Met Ala
625                 630                 635                 640

Gln Thr Glu Pro Thr Val Glu Val Glu Phe Val Tyr Asp Ser Thr
                    645                 650                 655

Lys Tyr Cys Arg Pro Tyr Arg Val Tyr Lys Asn Gln Ile Tyr Ile Tyr
                660                 665                 670

Pro Lys His Leu Lys Tyr Asp Ser Gln Lys Cys Phe Asn Lys Ala Arg
            675                 680                 685

Asn Ile Thr Val Cys Ile Glu Phe Lys Asn Ser Asp Glu Glu Ser Ala
            690                 695                 700

Lys Pro Leu Lys Cys Ile Tyr Gly Lys Pro Glu Gly Pro Leu Phe Thr
705                 710                 715                 720

Ser Ala Ala Tyr Thr Ala Val Leu His His Ser Gln Asn Pro Asp Phe
                725                 730                 735

Ser Asp Glu Val Lys Ile Glu Leu Pro Thr Gln Leu His Glu Lys His
                740                 745                 750

His Ile Leu Phe Ser Phe Tyr His Val Thr Cys Asp Ile Asn Ala Lys
            755                 760                 765

Ala Asn Ala Lys Lys Lys Glu Ala Leu Glu Thr Ser Val Gly Tyr Ala
        770                 775                 780

Trp Leu Pro Leu Met Lys His Asp Gln Ile Ala Ser Gln Glu Tyr Asn
785                 790                 795                 800

Ile Pro Ile Ala Thr Ser Leu Pro Pro Asn Tyr Leu Ser Phe Gln Asp
                805                 810                 815

Ser Ala Ser Gly Lys His Gly Gly Ser Asp Ile Lys Trp Val Asp Gly
                820                 825                 830

Gly Lys Pro Leu Phe Lys Val Ser Thr Phe Val Val Ser Thr Val Asn
            835                 840                 845

Thr Gln Asp Pro His Val Asn Ala Phe Phe Gln Glu Cys Gln Lys Arg
            850                 855                 860

Glu Lys Asp Met Ser Gln Ser Pro Thr Ser Asn Phe Ile Arg Ser Cys
865                 870                 875                 880

Lys Asn Leu Leu Asn Val Glu Lys Ile His Ala Ile Met Ser Phe Leu
                885                 890                 895

Pro Ile Ile Leu Asn Gln Leu Phe Lys Val Leu Val Gln Asn Glu Glu
```

-continued

```
                900                 905                 910
Asp Glu Ile Thr Thr Thr Val Thr Arg Val Leu Pro Asp Ile Val Ala
            915                 920                 925
Lys Cys His Glu Glu Gln Leu Asp His Ser Val Gln Ser Tyr Ile Lys
        930                 935                 940
Phe Val Phe Lys Thr Arg Ala Cys Lys Glu Arg Pro Val His Glu Asp
945                 950                 955                 960
Leu Ala Lys Asn Val Thr Gly Leu Leu Lys Ser Asn Asp Ser Pro Thr
                965                 970                 975
Val Lys His Val Leu Lys His Ser Trp Phe Phe Ala Ile Ile Leu
            980                 985                 990
Lys Ser Met Ala Gln His Leu Ile Asp Thr Asn Lys Ile Gln Leu Pro
        995                 1000                1005
Arg Pro Gln Arg Phe Pro Glu Ser Tyr Gln Asn Glu Leu Asp Asn Leu
    1010                1015                1020
Val Met Val Leu Ser Asp His Val Ile Trp Lys Tyr Lys Asp Ala Leu
1025                1030                1035                1040
Glu Glu Thr Arg Arg Ala Thr His Ser Val Ala Arg Phe Leu Lys Arg
                1045                1050                1055
Cys Phe Thr Phe Met Asp Arg Gly Cys Val Phe Lys Met Val Asn Asn
            1060                1065                1070
Tyr Ile Ser Met Phe Ser Ser Gly Asp Leu Lys Thr Leu Cys Gln Tyr
        1075                1080                1085
Lys Phe Asp Phe Leu Gln Glu Val Cys Gln His Glu His Phe Ile Pro
    1090                1095                1100
Leu Cys Leu Pro Ile Arg Ser Ala Asn Ile Pro Asp Pro Leu Thr Pro
1105                1110                1115                1120
Ser Glu Ser Thr Gln Glu Leu His Ala Ser Asp Met Pro Glu Tyr Ser
                1125                1130                1135
Val Thr Asn Glu Phe Cys Arg Lys His Phe Leu Ile Gly Ile Leu Leu
            1140                1145                1150
Arg Glu Val Gly Phe Ala Leu Gln Glu Asp Gln Asp Val Arg His Leu
        1155                1160                1165
Ala Leu Ala Val Leu Lys Asn Leu Met Ala Lys His Ser Phe Asp Asp
    1170                1175                1180
Arg Tyr Arg Glu Pro Arg Lys Gln Ala Gln Ile Ala Ser Leu Tyr Met
1185                1190                1195                1200
Pro Leu Tyr Gly Met Leu Leu Asp Asn Met Pro Arg Ile Tyr Leu Lys
                1205                1210                1215
Asp Leu Tyr Pro Phe Thr Val Asn Thr Ser Asn Gln Gly Ser Arg Asp
            1220                1225                1230
Asp Leu Ser Thr Asn Gly Gly Phe Gln Ser Gln Thr Ala Ile Lys His
        1235                1240                1245
Ala Asn Ser Val Asp Thr Ser Phe Ser Lys Asp Val Leu Asn Ser Ile
    1250                1255                1260
Ala Ala Phe Ser Ser Ile Ala Ile Ser Thr Val Asn His Ala Asp Ser
1265                1270                1275                1280
Arg Ala Ser Leu Ala Ser Leu Asp Ser Asn Pro Ser Thr Asn Glu Lys
                1285                1290                1295
Ser Ser Glu Lys Thr Asp Asn Cys Glu Lys Ile Pro Arg Pro Leu Ala
            1300                1305                1310
Leu Ile Gly Ser Thr Leu Arg Phe Asp Arg Leu Asp Gln Ala Glu Thr
        1315                1320                1325
```

-continued

Arg Ser Leu Leu Met Cys Phe Leu His Ile Met Lys Thr Ile Ser Tyr
    1330                1335                1340

Glu Thr Leu Ile Ala Tyr Trp Gln Arg Ala Pro Ser Pro Glu Val Ser
1345                1350                1355                1360

Asp Phe Phe Ser Ile Leu Asp Val Cys Leu Gln Asn Phe Arg Tyr Leu
            1365                1370                1375

Gly Lys Arg Asn Ile Ile Arg Lys Ile Ala Ala Phe Lys Phe Val
        1380                1385                1390

Gln Ser Thr Gln Asn Asn Gly Thr Leu Lys Gly Ser Asn Pro Ser Cys
    1395                1400                1405

Gln Thr Ser Gly Leu Leu Ala Gln Trp Met His Ser Thr Ser Arg His
    1410                1415                1420

Glu Gly His Lys Gln His Arg Ser Gln Thr Leu Pro Ile Ile Arg Gly
1425                1430                1435                1440

Lys Asn Ala Leu Ser Asn Pro Lys Leu Leu Gln Met Leu Asp Asn Thr
            1445                1450                1455

Met Thr Ser Asn Ser Asn Glu Ile Asp Ile Val His His Val Asp Thr
        1460                1465                1470

Glu Ala Asn Ile Ala Thr Glu Gly Cys Leu Thr Ile Leu Asp Leu Val
        1475                1480                1485

Ser Leu Phe Thr Gln Thr His Gln Arg Gln Leu Gln Gln Cys Asp Cys
    1490                1495                1500

Gln Asn Ser Leu Met Lys Arg Gly Phe Asp Thr Tyr Met Leu Phe Phe
1505                1510                1515                1520

Gln Val Asn Gln Ser Ala Thr Ala Leu Lys His Val Phe Ala Ser Leu
            1525                1530                1535

Arg Leu Phe Val Cys Lys Phe Pro Ser Ala Phe Phe Gln Gly Pro Ala
        1540                1545                1550

Asp Leu Cys Gly Ser Phe Cys Tyr Glu Val Leu Lys Cys Cys Asn His
    1555                1560                1565

Arg Ser Arg Ser Thr Gln Thr Glu Ala Ser Ala Leu Leu Tyr Leu Phe
    1570                1575                1580

Met Arg Lys Asn Phe Glu Phe Asn Lys Gln Lys Ser Ile Val Arg Ser
1585                1590                1595                1600

His Leu Gln Leu Ile Lys Ala Val Ser Gln Leu Ile Ala Asp Ala Gly
            1605                1610                1615

Ile Gly Gly Ser Arg Phe Gln His Ser Leu Ala Ile Thr Asn Asn Phe
        1620                1625                1630

Ala Asn Gly Asp Lys Gln Met Lys Asn Ser Asn Phe Pro Ala Glu Val
    1635                1640                1645

Lys Asp Leu Thr Lys Arg Ile Arg Thr Val Leu Met Ala Thr Ala Gln
    1650                1655                1660

Met Lys Glu His Glu Lys Asp Pro Glu Met Leu Val Asp Leu Gln Tyr
1665                1670                1675                1680

Ser Leu Ala Asn Ser Tyr Ala Ser Thr Pro Glu Leu Arg Arg Thr Trp
            1685                1690                1695

Leu Glu Ser Met Ala Lys Ile His Ala Arg Asn Gly Asp Leu Ser Glu
        1700                1705                1710

Ala Ala Met Cys Tyr Ile His Ile Ala Ala Leu Ile Ala Glu Tyr Leu
    1715                1720                1725

Lys Arg Lys Gly Tyr Trp Lys Val Glu Lys Ile Cys Thr Ala Ser Leu
    1730                1735                1740

-continued

```
Leu Ser Glu Asp Thr His Pro Cys Asp Ser Asn Ser Leu Leu Thr Thr
1745                1750                1755                1760

Pro Ser Gly Gly Ser Met Phe Ser Met Gly Trp Pro Ala Phe Leu Ser
            1765                1770                1775

Ile Thr Pro Asn Ile Lys Glu Glu Gly Ala Ala Lys Glu Asp Ser Gly
            1780                1785                1790

Met His Asp Thr Pro Tyr Asn Glu Asn Ile Leu Val Glu Gln Leu Tyr
        1795                1800                1805

Met Cys Gly Glu Phe Leu Trp Lys Ser Glu Arg Tyr Glu Leu Ile Ala
    1810                1815                1820

Asp Val Asn Lys Pro Ile Ile Ala Val Phe Glu Lys Gln Arg Asp Phe
1825                1830                1835                1840

Lys Lys Leu Ser Asp Leu Tyr Tyr Asp Ile His Arg Ser Tyr Leu Lys
            1845                1850                1855

Val Ala Glu Val Val Asn Ser Glu Lys Arg Leu Phe Gly Arg Tyr Tyr
            1860                1865                1870

Arg Val Ala Phe Tyr Gly Gln Gly Phe Phe Glu Glu Glu Gly Lys
        1875                1880                1885

Glu Tyr Ile Tyr Lys Glu Pro Lys Leu Thr Gly Leu Ser Glu Ile Ser
    1890                1895                1900

Gln Arg Leu Leu Lys Leu Tyr Ala Asp Lys Phe Gly Ala Asp Asn Val
1905                1910                1915                1920

Lys Ile Ile Gln Asp Ser Asn Lys Val Asn Pro Lys Asp Leu Asp Pro
            1925                1930                1935

Lys Tyr Ala Tyr Ile Gln Val Thr Tyr Val Thr Pro Phe Phe Glu Glu
            1940                1945                1950

Lys Glu Ile Glu Asp Arg Lys Thr Asp Phe Glu Met His His Asn Ile
        1955                1960                1965

Asn Arg Phe Val Phe Glu Thr Pro Phe Thr Leu Ser Gly Lys Lys His
    1970                1975                1980

Gly Gly Val Ala Glu Gln Cys Lys Arg Arg Thr Ile Leu Thr Thr Ser
1985                1990                1995                2000

His Leu Phe Pro Tyr Val Lys Lys Arg Ile Gln Val Ile Ser Gln Ser
            2005                2010                2015

Ser Thr Glu Leu Asn Pro Ile Glu Val Ala Ile Asp Glu Met Ser Arg
            2020                2025                2030

Lys Val Ser Glu Leu Asn Gln Leu Cys Thr Met Glu Glu Val Asp Met
        2035                2040                2045

Ile Ser Leu Gln Leu Lys Leu Gln Gly Ser Val Ser Val Lys Val Asn
    2050                2055                2060

Ala Gly Pro Met Ala Tyr Ala Arg Ala Phe Leu Glu Glu Thr Asn Ala
2065                2070                2075                2080

Lys Lys Tyr Pro Asp Asn Gln Val Lys Leu Leu Lys Glu Ile Phe Arg
            2085                2090                2095

Gln Phe Ala Asp Ala Cys Gly Gln Ala Leu Asp Val Asn Glu Arg Leu
            2100                2105                2110

Ile Lys Glu Asp Gln Leu Glu Tyr Gln Glu Glu Leu Arg Ser His Tyr
        2115                2120                2125

Lys Asp Met Leu Ser Glu Leu Ser Thr Val Met Asn Glu Gln Ile Thr
    2130                2135                2140

Gly Arg Asp Asp Leu Ser Lys Arg Gly Val Asp Gln Thr Cys Thr Arg
2145                2150                2155                2160

Val Ile Ser Lys Ala Thr Pro Ala Leu Pro Thr Val Ser Ile Ser Ser
```

Ser Ala Glu Val
    2180

<210> SEQ ID NO 140
<211> LENGTH: 22
<212> TYPE: DNA
<213> ORGANISM: Homo sapiens

<400> SEQUENCE: 140
aggccttgtc tctgtttacc tg                                              22

<210> SEQ ID NO 141
<211> LENGTH: 23
<212> TYPE: DNA
<213> ORGANISM: Homo sapiens

<400> SEQUENCE: 141
acaggaacct gctgtacgtg tac                                             23

<210> SEQ ID NO 142
<211> LENGTH: 19
<212> TYPE: DNA
<213> ORGANISM: Homo sapiens

<400> SEQUENCE: 142
gacccattag gaggtctac                                                  19

<210> SEQ ID NO 143
<211> LENGTH: 21
<212> TYPE: DNA
<213> ORGANISM: Homo sapiens

<400> SEQUENCE: 143
tatgtctcag tcacctacct g                                               21

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: C1S7 primer

<400> SEQUENCE: 144
tcaagaccag ggcatgcaag                                                 20

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: HC7gAS1
      antisense primer

<400> SEQUENCE: 145
tgtcatgtac tgcactcgca cagc                                            24

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: HC7AS14
      antisense primer

```
<400> SEQUENCE: 146
tcgtggctgc acaggatgcg ggtg                                        24

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: HC4AS3'
      antisense primer

<400> SEQUENCE: 147
cgggatccat tgtcaccgta catctgc                                     27

<210> SEQ ID NO 148
<211> LENGTH: 30
<212> TYPE: DNA
<213> ORGANISM: Artificial Sequence
<220> FEATURE:
<223> OTHER INFORMATION: Description of Artificial Sequence: HC1AS3'Kpn
      antisense primer

<400> SEQUENCE: 148
cttggtacca cttcagcact agatgagatg                                  30

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: HC2RACE1
      primer

<400> SEQUENCE: 149
aagagcagca tctcccgtaa acagtc                                      26

<210> SEQ ID NO 150
<211> LENGTH: 26
<212> TYPE: DNA
<213> ORGANISM: Artificial Sequence
<220> FEATURE:
<223> OTHER INFORMATION: Description of Artificial Sequence: HC2RACE2
      Primer

<400> SEQUENCE: 150
taacaagctc tgtgcttcct cttccg                                      26

<210> SEQ ID NO 151
<211> LENGTH: 29
<212> TYPE: DNA
<213> ORGANISM: Artificial Sequence
<220> FEATURE:
<223> OTHER INFORMATION: Description of Artificial Sequence: HC2RACE3
      PRIMER

<400> SEQUENCE: 151
accactttgt tcggaagctg tcgaaactc                                   29

<210> SEQ ID NO 152
<211> LENGTH: 28
<212> TYPE: DNA
<213> ORGANISM: Artificial Sequence
<220> FEATURE:
```

-continued

```
<223> OTHER INFORMATION: Description of Artificial Sequence: HC2RACE4
      Primer

<400> SEQUENCE: 152
tttgtacagc cagccatgct tggtgatc                                              28
```

What is claimed is:

1. An isolated cadherin-like asymmetry protein 2 (CLASP-2) polynucleotide, wherein said polynucleotide comprises a nucleic acid encoding SEQ ID NO:2.

2. The polynucleotide of claim 1, wherein said polypeptide specifically binds to a PSD-95, Dlg, and Zo-1 domain (PDZ domain) of postsynaptic density protein of 95 kDa (PSD95), discs large 1 protein (DLG1) or neuroendocrine DLG (neDLG).

3. The polynucleotide of claim 2, wherein said polypeptide has a binding affinity of at least $10^4$ $M^{-1}$ for binding PSD95, DLG1 or neDLG.

4. The isolated polynucleotide of claim 1, comprising the cDNA coding sequence of ATCC Deposit Nos. PTA-1562 and PTA-1563 and PTA-1573.

5. A vector comprising the polynucleotide of claim 1.

6. An expression vector comprising the polynucleotide of claim 1 in which the nucleotide sequence of the polynucleotide is operatively linked with a regulatory sequence that controls expression of the polynucleotide in a host cell.

7. A host cell comprising the polynucleotide of claim 1, or progeny of the host cell, wherein the host cell is an isolated cell or a prokaryotic cell or a yeast cell.

8. The host cell of claim 7 which is a eukaryote.

9. A method for producing a polypeptide comprising:
   (a) culturing the host cell of claim 7 under conditions such that the polypeptide is expressed; and
   (b) recovering the polypeptide from the cultured host cell or its cultured medium.

10. A host cell comprising the polynucleotide of claim 1, or progeny of the host cell, wherein the host cell is an isolated cell or a prokaryotic cell or a yeast cell, and wherein the nucleotide sequence of the polynucleotide is operatively linked with a regulatory sequence that controls expression of the polynucleotide.

11. The polynucleotide of claim 1 that is RNA.

12. An isolated cadherin-like asymmetry protein 2 (CLASP-2) polynucleotide comprising SEQ ID NO: 1.

13. An isolated DNA that encodes a cadherin-like asymmetry protein 2 (CLASP-2) protein of-SEQ ID NO: 2.

* * * * *